US007491718B2

(12) United States Patent
Comess et al.

(10) Patent No.: US 7,491,718 B2

(45) Date of Patent: Feb. 17, 2009

(54) SULFONAMIDES HAVING ANTIANGIOGENIC AND ANTICANCER ACTIVITY

(75) Inventors: Kenneth M. Comess, Winnetka, IL (US); Scott A. Erickson, Zion, IL (US); Jack Henkin, Highland Park, IL (US); Douglas M. Kalvin, Buffalo Grove, IL (US); Megumi Kawai, Libertyville, IL (US); Ki H. Kim, Vista, CA (US); Nwe Y. BaMaung, Niles, IL (US); Chang Hoon Park, Libertyville, IL (US); George S. Sheppard, Wilmette, IL (US); Anil Vasudevan, Gurnee, IL (US); Jieyi Wang, Lake Bluff, IL (US); David M. Barnes, Lake Villa, IL (US); Steve D. Fidanze, Grayslake, IL (US); Lawrence Kolaczkowski, Gurnee, IL (US); Robert A. Mantei, Franklin, WI (US); David C. Park, Urbana, IL (US); William J. Sanders, Fox Lake, IL (US); Jason S. Tedrow, Evanston, IL (US); Gary T. Wang, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 447 days.

(21) Appl. No.: 10/681,784

(22) Filed: Oct. 8, 2003

(65) Prior Publication Data

US 2004/0167128 A1 Aug. 26, 2004

Related U.S. Application Data

(60) Provisional application No. 60/416,793, filed on Oct. 8, 2002.

(51) Int. Cl.

| | |
|---|---|
| ***A61K 31/435*** | (2006.01) |
| ***A61K 31/535*** | (2006.01) |
| ***A61K 31/4965*** | (2006.01) |
| ***A61K 31/415*** | (2006.01) |
| ***A61K 31/40*** | (2006.01) |
| ***A61K 31/425*** | (2006.01) |
| ***C07D 265/30*** | (2006.01) |
| ***C07D 241/04*** | (2006.01) |
| ***C07D 279/12*** | (2006.01) |
| ***C07D 277/02*** | (2006.01) |
| ***C07D 263/02*** | (2006.01) |
| ***C07C 255/03*** | (2006.01) |
| *A61K 31/42* | (2006.01) |

(52) U.S. Cl. .................................................. 514/227.8

(58) Field of Classification Search ................. 544/162, 544/382, 59; 546/310; 548/194, 233, 328.1, 548/530; 514/227.8, 237, 255.01, 35, 398, 514/423, 370, 374; 558/413, 414

See application file for complete search history.

(56) References Cited

U.S. PATENT DOCUMENTS

| | | | | |
|---|---|---|---|---|
| 2,335,221 | A | 11/1943 | Ewins et al. | |
| 3,162,684 | A * | 12/1964 | Frick et al. | 564/92 |
| 5,929,097 | A | 7/1999 | Levin et al. | |
| 6,207,704 | B1 | 3/2001 | Liu et al. | 514/475 |
| 6,335,334 | B1 | 1/2002 | Schindler et al. | |
| 2004/0019113 | A1* | 1/2004 | Jozefiak et al. | 514/602 |

FOREIGN PATENT DOCUMENTS

| | | |
|---|---|---|
| AT | 272 351 | 8/2004 |
| DE | 686 644 | 1/1940 |
| JP | 2001-240581 | 9/2001 |
| WO | 98/16503 | 4/1998 |
| WO | 98/16506 | 4/1998 |
| WO | 98/16514 | 4/1998 |
| WO | 98/16520 | 4/1998 |

OTHER PUBLICATIONS

Griffith et al., "Methionine aminopeptidase (type 2) is the common target for angiogenesis inhibitors AGM-1470 and ovalicin," Chemistry & Biology 4(5):461-471 (1997).

Hodgson et al., "Reactions of Aromatic Nitro-compounds with Alkaline Sulphides." J. Chem. Soc. 1187 (1949).

Showalter et al., "Concise syntheses of the novel 1*H*-pyrrolo[3,2-*g*]quinazoline ring system and its [2,3-*f*] angular isomer," J. Org. Chem. 61:1155-1158 (1996).

Sin et al., "The anti-angiogenic agent fumagillin covalently binds and inhbits the methionine aminopeptidase, MetAP-2," Proc. Natl. Acad. Sci. USA 94:6099-6103 (1997).

Tilley et al., "Synthesis of 5-alkoxyanthranilic acids," Org. Prep. Proc. Int. 13(3-4):189-196 (1981).

Tomioka et al., "Studies on aromatic nitro compounds. V. A simple one-pot preparation of o-aminoaroylnitriles from some aromatic nitro compounds," Chem. Pharm. Bull. 33(4):1360-1366 (1985).

J. Med. Chem. 33(5):1312-1329 (1990) XP002271724.

J. Org. Chem. 53(7):1380-1383 (1988) XP002271725.

Bull. Chem. Soc. Jpn. 40:2844-2847 (1967) XP002271726.

J. Chem. Soc. Perkin Trans. I 1602-1605 (1973) XP002271727.

Synthesis, 4:280-282 (1989) XP002271728.

Chem. Ber. 76:128-134 (1943) XP002271729.

J. Am. Chem. Soc. 67:1711 (1945) XP002271730.

Nippon Kagaku Kaishi 723-727 (1978) XP002271731.

J. Chem. Soc. 961-966 (1950) XP002271732.

Synthesis 6:487-489 (1981) XP002271733.

J. Med. Chem. 24(9):1097-1099 (1981) XP002271734.

(Continued)

*Primary Examiner*—James O. Wilson
*Assistant Examiner*—Ebenezer Sackey
(74) *Attorney, Agent, or Firm*—B. Gregory Donner

(57) ABSTRACT

Compounds having methionine aminopeptidase-2 inhibitory (MetAP2) are described. Also described are pharmaceutical compositions comprising the compounds, methods of treatment using the compounds, methods of inhibiting angiogenesis, and methods of treating cancer.

3 Claims, No Drawings

OTHER PUBLICATIONS

Heterocycl. Chem. 30(6):1613-1622 (1993) XP002271736.
Chem. Heterocycl. Compd. 8:557-561 (1972) XP002271737.
Chem. Heterocycl. Compd. 7:964-967 (1971) XP002271738.
Chem. Heterocycl. Compd. 8:1212-1215 (1972) XP002271739.
Chem. Pharm. Bull. 41(5):894-906 (1993) XP002271740.
J. Org Chem. 38:1512-1517 (1973) XP002271741.
J. Chem. Soc. Perkin Trans. I 2313-2318 (1973) XP002271742.
Tetrahedron 44(5):1465-1476 (1988) XP002271743.
J. Am. Chem. Soc. 109(21):6491-6502 (1987) XP002271744.
JP 2001-240581 XP002271745.
Proceedings of the National Academy of Sciences of the United States of America 99(15):10066-10071 (2002) XP002271723.

* cited by examiner

SULFONAMIDES HAVING ANTIANGIOGENIC AND ANTICANCER ACTIVITY

This application is claims priority to U.S. Provisional Patent Application Ser. No. 60/416,793, filed on Oct. 8, 2002.

TECHNICAL FIELD

The present invention relates to compounds having methionine aminopeptidase-2 inhibitory (MetAP2) activity useful for treating cancer and other conditions which arise from or are exacerbated by angiogenesis, pharmaceutical compositions comprising the compounds, methods of treatment using the compounds, methods of inhibiting angiogenesis, and methods of treating cancer.

BACKGROUND OF THE INVENTION

Angiogenesis is the fundamental process by which new blood vessels are formed and is essential to a variety of normal body activities (such as reproduction, development, and wound repair). Although the process is not completely understood, it is believed to involve a complex interplay of molecules which both stimulate and inhibit the growth of endothelial cells, the primary cells of the capillary blood vessels. Under normal conditions these molecules appear to maintain the microvasculature in a quiescent state (i.e., one of no capillary growth) for prolonged periods that may last for weeks, or in some cases, decades. However, when necessary, such as during wound repair, these same cells can undergo rapid proliferation and turnover within as little as five days.

Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exacerbate an existing pathological condition.

As the literature has established a causal link between inhibition of MetAP2 and the resultant inhibition of endothelial cell proliferation and angiogenesis (see *Proc. Natl. Acad. Sci. USA* 94: 6099-6103 (1997) and *Chemistry and Biology*, 4(6): 461-471 (1997)), it can be inferred that compounds which inhibit MetAP2 could serve as angiogenesis inhibitors.

SUMMARY OF THE INVENTION

According to the principle embodiment of the present invention compound of formula (I)

(I)

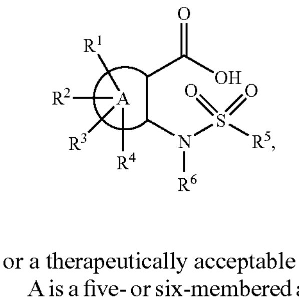

or a therapeutically acceptable salt thereof, wherein

A is a five- or six-membered aromatic or non-aromatic ring containing from zero to three atoms selected from the group consisting of nitrogen, oxygen, and sulfur; wherein the five- or six-membered ring is optionally fused to a second five-, six-, or seven-membered aromatic or non-aromatic ring containing from zero to three atoms selected from the group consisting of nitrogen, oxygen, and sulfur;

$R^1$, $R^2$ and $R^3$ are independently selected from the group consisting of hydrogen, alkenyl, alkoxy, alkoxyalkyl, alkoxycarbonyl, alkoxycarbonylalkyl, alkyl, alkylcarbonyloxy, alkylidene, alkylsulfanyl, alkylsulfanylalkyl, alkylsulfonyl, alkylsulfonylalkyl, amino, aminoalkyl, aminoalkenyl, aminoalkoxy, aminocarbonylalkenyl, aryl, carboxyalkenyl, carboxyalkyl, cyano, cycloalkyl, (cycloalkyl)alkyl, halo, haloalkoxy, haloalkyl, (heterocycle)alkyl, hydroxy, hydroxyalkyl, nitro;

$R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}N$—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl ($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle;

$R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}N$—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl ($R_{c5}$)N—, $R_{e5}R_{f5}$Nalkyl($R_{c5}$)Ncarbonyl, $R_{e5}R_{f5}$Nalkyl($R_{c5}$) Ncarbonylalkenyl, $R_{e4}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl ($R_{e5}$)Ncarbonyl($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each indepen- 27dently selected from the group consisting of hydrogen, alkoxyalkyl, alkyl, alkylcarbonyl, aminoalkyl, cycloalkyl, (cycloalkyl)alkyl, heterocycle and phenyl;

$R^6$ is selected from the group consisting of hydrogen, alkyl, alkylsulfanylalkyl, aryl, and arylalkyl; and provided that when A is phenyl, at least one of $R^1$, $R^2$, $R^3$ and $R^4$ is other than, hydrogen, $C_1$ alkyl or halo.

According to another embodiment of the present invention there is disclosed a method of inhibiting methionine aminopeptidase-2 comprising administering to a patient in need of such treatment a therapeutically effective amount of a compound of formula (I), or a therapeutically acceptable salt thereof.

According to another embodiment of the present invention there is disclosed a method of treating cancer comprising administering to a patient in need of such treatment a therapeutically effective amount of a compound of formula (I), or a therapeutically acceptable salt thereof.

According to another embodiment of the present invention there is disclosed a method of treating cancer comprising administering to a patient in need of such treatment a therapeutically effective amount of a compound of formula (IV), or a therapeutically acceptable salt thereof.

According to another embodiment of the present invention there is disclosed a pharmaceutical composition comprising a compound of claim 1 or a therapeutically acceptable salt thereof in combination with a therapeutically acceptable carrier.

According to another embodiment of the present invention there is disclosed a pharmaceutical composition comprising a compound of claim 6 or a therapeutically acceptable salt thereof in combination with a therapeutically acceptable carrier.

DETAILED DESCRIPTION OF THE INVENTION

According to another embodiment of the present invention there is disclosed a compound of formula (II)

(II)

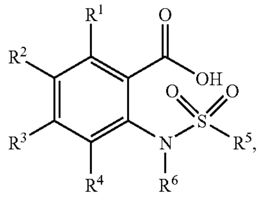

or a therapeutically acceptable salt thereof, wherein $R^1$, $R^2$ and $R^3$ are independently selected from the group consisting of hydrogen, alkenyl, alkoxy, alkoxyalkyl, alkoxycarbonyl, alkoxycarbonylalkyl, alkyl, alkylcarbonyloxy, alkylidene, alkylsulfanyl, alkylsulfanylalkyl, alkylsulfonyl, alkylsulfonylalkyl, amino, aminoalkyl, aminoalkenyl, aminoalkoxy, aminocarbonylalkenyl, aryl, carboxyalkenyl, carboxyalkyl, cyano, cycloalkyl, (cycloalkyl)alkyl, halo, haloalkoxy, haloalkyl, (heterocycle)alkyl, hydroxy, hydroxyalkyl, nitro; or $R^1$ and $R^2$ together with the carbon atoms to which they are attached, form a five-, six-, or seven-membered saturated or unsaturated carbocyclic ring which can be optionally substituted with 1 or 2 substituents independently selected from the group consisting of alkoxy, alkyl, amino, halo, and haloalkyl; or $R^2$ and $R^3$ together with the carbon atoms to which they are attached, form a five-, six-, or seven-membered saturated or unsaturated carbocyclic ring which can be optionally substituted with 1 or 2 substituents independently selected from the group consisting of alkoxy, alkyl, amino, halo, and haloalkyl; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}N$—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{e4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl ($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}N$—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl; $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{c5}$) Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e4}R_{f5}$Nalkoxycarbonyl ($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$) N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; $R^6$ is selected from the group consisting of hydrogen, alkyl, alkylsulfanylalkyl, aryl, and arylalkyl; and provided that at least one of $R^1$, $R^2$, $R^3$ and $R^4$ is other than hydrogen, $C_1$ alkyl or halo.

According to another embodiment of the present invention there is disclosed a compound of formula (III)

(III)

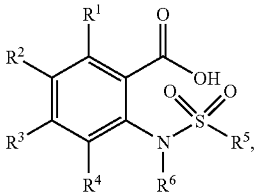

or a therapeutically acceptable salt thereof, wherein $R^1$ is selected from the group consisting of hydrogen, $C_1$-$C_4$ alkyl, $C_2$-$C_4$ alkenyl, $C_2$-$C_4$ alkoxy, halo, haloalkyl, haloakoxy, $R_aR_bN$— and $R_aR_b$Nalkoxy, wherein $R_a$ and $R_b$ are each independently selected from the group consisting of hydrogen and alkyl; $R^2$ is selected from the group consisting of alkoxy, alkoxyalkyl, $C_1$-$C_{10}$ alkyl, alkylsulfanyl, alkylsulfanylalkyl, alkylsulfonyl, alkylsulfonylalkyl, amino, aminoalkyl, cycloalkyl, (cycloalkyl)alkyl, halo, haloalkoxy, and haloalkyl; $R^3$ is selected from the group consisting of hydrogen, alkyl and halogen; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}N$—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}N$—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{c5}$)Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; and $R^6$ is selected from the group consisting of hydrogen, alkyl, alkylsulfanylalkyl, aryl, and arylalkyl.

According to another embodiment of the present invention there is disclosed a compound of formula (III) or a therapeutically acceptable salt thereof, wherein $R^1$ is hydrogen, $R^2$ is selected from the group consisting of alkoxy, alkoxyalkyl, $C_1$-$C_{10}$ alkyl, alkylsulfanyl, alkylsulfanylalkyl, alkylsulfonyl, alkylsulfonylalkyl, amino, aminoalkyl, cycloalkyl, (cycloalkyl)alkyl, halo, haloalkoxy, and haloalkyl; $R^3$ and $R^6$ are each hydrogen; $R^5$ is aryl and $R^4$ is as defined in formula (III).

According to another embodiment of the present invention there is disclosed a compound of formula (III) or a therapeutically acceptable salt thereof, wherein $R^1$ is hydrogen; $R^2$ is selected from the group consisting of alkoxy, alkoxyalkyl, $C_1$-$C_3$ alkyl, alkylsulfanyl, alkylsulfanylalkyl, alkylsulfonyl, alkylsulfonylalkyl, amino, aminoalkyl, halo, haloalkoxy, and haloalkyl; $R^3$ and $R^6$ are each hydrogen; $R^5$ is aryl and $R^4$ is as defined in formula (III).

According to another embodiment of the present invention there is disclosed a compound of formula (III) or a therapeutically acceptable salt thereof, wherein $R^1$ is hydrogen; $R^2$ is selected from the group consisting of alkoxy, alkoxyalkyl, $C_1$-$C_3$ alkyl, amino, aminoalkyl, halo, haloalkoxy, and haloalkyl; $R^3$ and $R^6$ are each hydrogen; $R^5$ is aryl and $R^4$ is as defined in formula (III).

According to another embodiment of the present invention there is disclosed a compound of formula (IV)

(IV)

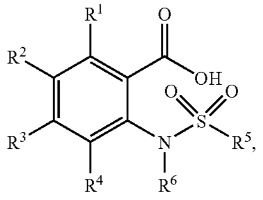

or a therapeutically acceptable salt thereof, wherein $R^1$ and $R^2$, together with the carbon atoms to which they are attached, form a five-, six-, or seven-membered saturated or unsaturated carbocyclic ring which can be optionally substituted with one or two substituents independently selected from the group consisting of alkoxy, alkyl, amino, halo, and haloalkyl; $R^3$ is selected from the group consisting of hydrogen, alkyl and halogen; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}N$—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}N$—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e4}R_{f5}$Nalkyl($R_{c5}$)Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; and $R^6$ is selected from the group consisting of hydrogen, alkyl, alkylsulfanylalkyl, aryl, and arylalkyl.

According to another embodiment of the present invention there is disclosed a compound of formula (IV); or a therapeutically acceptable salt thereof, wherein $R^1$ and $R^2$, together with the carbon atoms to which they are attached, form a five-, six-, or seven-membered saturated or unsaturated carbocyclic ring which can be optionally substituted with one or two substituents independently selected from the group consisting of alkoxy, alkyl, amino, halo, and haloalkyl; $R^3$ and $R^6$ are both hydrogen; $R^5$ is aryl and $R^4$ is as defined in formula (IV).

According to another embodiment of the present invention there is disclosed a compound of formula (IV)

(IV)

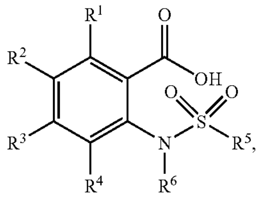

or a therapeutically acceptable salt thereof, wherein $R^1$ and $R^2$, together with the carbon atoms to which they are attached, form a six membered monounsaturated carbocyclic ring which can be optionally substituted with one or two substituents independently selected from the group consisting of alkoxy, alkyl, amino, halo, and haloalkyl; $R^3$ is selected from the group consisting of hydrogen, alkyl and halogen; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}N$—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}N$—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{c5}$)Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; and $R^6$ is selected from the group consisting of hydrogen, alkyl, alkylsulfanylalkyl, aryl, and arylalkyl.

According to another embodiment of the present invention there is disclosed a compound of formula (IV) or a therapeutically acceptable salt thereof, wherein $R^1$ and $R^2$, together with the carbon atoms to which they are attached, form a six membered monounsaturated carbocyclic ring which can be optionally substituted with one or two substituents independently selected from the group consisting of alkoxy, alkyl, amino, halo, and haloalkyl; $R^3$ and $R^6$ are hydrogen, $R^5$ is aryl and $R^4$ is as defined in formula (IV).

According to another embodiment of the present invention there is disclosed a compound of formula (V)

(V)

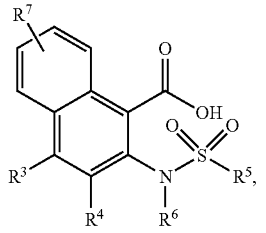

or a therapeutically acceptable salt thereof, wherein $R^3$ is selected from the group consisting of hydrogen, alkyl and halogen; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}$N—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl ($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}$N—, $R_{c5}R_{d5}$Nalkyl, $R_{c5}R_{d5}$Nalkenyl, $R_{c5}R_{f5}$Nalkynyl, $R_{c5}R_{f5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl ($R_{c5}$)N—, $R_{e5}R_{f5}$Nalkyl($R_{c5}$)Ncarbonyl, $R_{e5}R_{f5}$Nalkyl($R_{c5}$) Ncarbonylalkenyl, $R_{e5}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl ($R_{e5}$)Ncarbonyl($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; $R^6$ is selected from the group consisting of hydrogen, alkyl, alkylsulfanylalkyl, aryl, and arylalkyl; and $R^7$ is selected from the group consisting of hydrogen, $C_1$-$C_3$ alkyl, $C_2$-$C_3$ alkenyl, $C_2$-$C_3$ alkoxy, halo, haloalkyl, haloakoxy, $R_aR_b$N— and $R_aR_b$Nalkoxy, wherein $R_a$ and $R_b$ are each independently selected from the group consisting of hydrogen and alkyl.

According to another embodiment of the present invention there is disclosed a compound of formula (V)

(V)

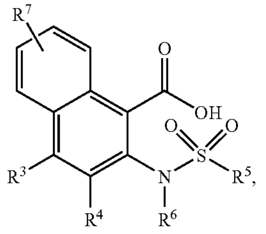

or a therapeutically acceptable salt thereof, wherein $R^3$ and $R^6$ are hydrogen, $R^5$ is aryl and $R^4$ is as defined in formula (V).

According to another embodiment of the present invention there is disclosed a compound of formula (VI)

(VI)

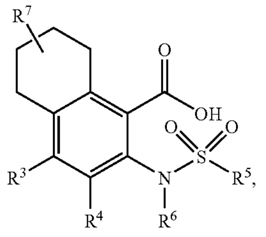

or a therapeutically acceptable salt thereof, wherein $R^3$ is selected from the group consisting of hydrogen, alkyl and halogen; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}N$—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl ($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}N$—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{e5}$) Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e5}R_{f5}$Nalkoxycarbonyl ($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$) N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; $R^6$ is selected from the group consisting of hydrogen, alkyl, alkylsulfanylalkyl, aryl, and arylalkyl; and $R^7$ is selected from the group consisting of hydrogen, $C_1$-$C_3$ alkyl, $C_2$-$C_3$ alkenyl, $C_2$-$C_3$ alkoxy, halo, haloalkyl, haloakoxy, $R_aR_bN$— and $R_aR_b$Nalkoxy, wherein $R_a$ and $R_b$ are each independently selected from the group consisting of hydrogen and alkyl.

According to another embodiment of the present invention there is disclosed a compound of formula (VI)

(VI)

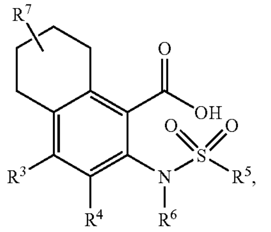

or a therapeutically acceptable salt thereof, wherein $R^3$ and $R^6$ are hydrogen, $R^5$ is aryl and $R^4$ is as defined in formula (VI).

According to another embodiment of the present invention there is disclosed a compound of formula (VII)

(VII)

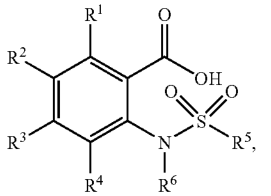

or a therapeutically acceptable salt thereof, wherein $R^1$ is selected from the group consisting of hydrogen, $C_1$-$C_4$ alkyl, $C_2$-$C_4$ alkenyl, $C_2$-$C_4$ alkoxy, halo, haloalkyl, haloakoxy, $R_aR_bN$— and $R_aR_b$Nalkoxy, wherein $R_a$ and $R_b$ are each independently selected from the group consisting of hydrogen and alkyl; $R^2$ and $R^3$, together with the carbon atoms to which they are attached, form a five-, six-, or seven-membered saturated or unsaturated carbocyclic ring which can be optionally substituted with one or two substituents independently selected from the group consisting of alkoxy, alkyl, amino, halo, and haloalkyl; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}N$—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$) Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl ($R_{c4}$)N—, $R_{c4}R_{f4}$Nalkylsulfanyl, $R_{c4}R_{d4}$Nalkylsulfinyl, $R_{c4}R_{d4}$Nalkylsulfonyl, $R_{g4}R_{j4}$Nalkyl($R_{e4}$)Ncarbonyl($R_{c4}$) N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of, alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}N$—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{c5}$)Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; and $R^6$ is selected from the group consisting of hydrogen, alkyl, alkylsulfanylalkyl, aryl, and arylalkyl.

According to another embodiment of the present invention there is disclosed a compound of formula (VIIa)

(VIIa)

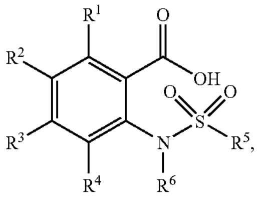

or a therapeutically acceptable salt thereof, wherein $R^1$ is selected from the group consisting of hydrogen, $C_1$-$C_4$ alkyl, $C_2$-$C_4$ alkenyl, $C_2$-$C_4$ alkoxy, halo, haloalkyl, haloakoxy, $R_aR_bN$— and $R_aR_b$Nalkoxy, wherein $R_a$ and $R_b$ are each independently selected from the group consisting of hydrogen and alkyl; $R^2$ and $R^3$, together with the carbon atoms to which they are attached, form a five or six-membered saturated carbocyclic ring which can be optionally substituted with one or two substituents independently selected from the group consisting of alkoxy, alkyl, amino, halo, and haloalkyl; $R^5$ is aryl; $R^6$ is hydrogen; and $R^4$ is as defined in formula (VII).

According to another embodiment of the present invention there is disclosed a compound of formula (VIb)

(VIIb)

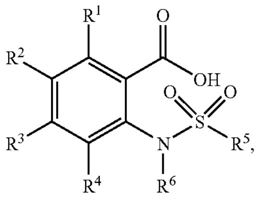

or a therapeutically acceptable salt thereof, wherein $R^1$ is selected from the group consisting of hydrogen, $C_1$-$C_4$ alkyl, $C_2$-$C_4$ alkenyl, $C_2$-$C_4$ alkoxy, halo, haloalkyl, haloakoxy, $R_aR_bN$— and $R_aR_b$Nalkoxy, wherein $R_a$ and $R_b$ are each independently selected from the group consisting of hydrogen and alkyl; $R^2$ and $R^3$, together with the carbon atoms to which they are attached, form a six-membered unsaturated carbocyclic ring which can be optionally substituted with one or two substituents independently selected from the group consisting of alkoxy, alkyl, amino, halo, and haloalkyl; $R^5$ is aryl; $R^6$ is hydrogen; and $R^4$ is as defined in formula (VII).

According to another embodiment of the present invention there is disclosed a compound of formula (VIIc)

(VIIc)

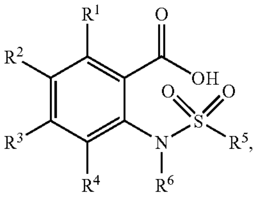

or a therapeutically acceptable salt thereof, wherein $R^1$ is selected from the group consisting of hydrogen, $C_1$-$C_4$ alkyl, $C_2$-$C_4$ alkenyl, $C_2$-$C_4$ alkoxy, halo, haloalkyl, haloakoxy, $R_aR_bN$— and $R_aR_b$Nalkoxy, wherein $R_a$ and $R_b$ are each independently selected from the group consisting of hydrogen and alkyl; $R^2$ and $R^3$, together with the carbon atoms to which they are attached, form a six-membered monounsaturated carbocyclic ring which can be optionally substituted with one or two substituents independently selected from the group consisting of alkoxy, alkyl, amino, halo, and haloalkyl; $R^5$ is aryl; $R^6$ is hydrogen; and $R^4$ is as defined in formula (VII).

According to another embodiment of the present invention there is disclosed a method of inhibiting angiogenesis comprising administering to a patient in need of such treatment a therapeutically effective amount of a compound of formula (I)

(I)

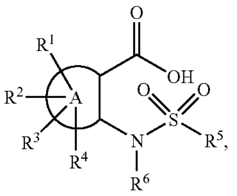

or a therapeutically acceptable salt thereof, wherein A is a five- or six-membered aromatic or non-aromatic ring containing from zero to three atoms selected from the group consisting of nitrogen, oxygen, and sulfur; wherein the five- or six-membered ring is optionally fused to a second five-, six-, or seven-membered aromatic or non-aromatic ring containing from zero to three atoms selected from the group consisting of nitrogen, oxygen, and sulfur; $R^1$, $R^2$ and $R^3$ are independently selected from the group consisting of hydrogen, alkenyl, alkoxy, alkoxyalkyl, alkoxycarbonyl, alkoxycarbonylalkyl, alkyl, alkylcarbonyloxy, alkylidene, alkylsulfanyl, alkylsulfanylalkyl, alkylsulfonyl, alkylsulfonylalkyl, amino, aminoalkyl, aminoalkenyl, aminoalkoxy, aminocarbonylalkenyl, aryl, carboxyalkenyl, carboxyalkyl, cyano, cycloalkyl, (cycloalkyl)alkyl, halo, haloalkoxy, haloalkyl, (heterocycle) alkyl, hydroxy, hydroxyalkyl, nitro; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}$N—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$) Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl ($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl($R_{e4}$)Ncarbonyl($R_{c4}$) N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}$N—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{c5}$) Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e5}R_{f5}$Nalkoxycarbonyl ($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$) N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; $R^6$ is selected from the group consisting of hydrogen, alkyl, alkylsulfanylalkyl, aryl, and arylalkyl.

According to another embodiment of the present invention there is disclosed a method of inhibiting angiogenesis comprising administering to a patient in need of such treatment a therapeutically effective amount of a compound of formula (II)

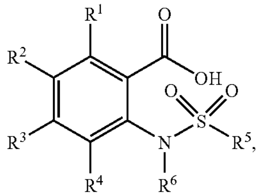

(II)

or a therapeutically acceptable salt thereof, wherein $R^1$, $R^2$ and $R^3$ are independently selected from the group consisting of hydrogen, alkenyl, alkoxy, alkoxyalkyl, alkoxycarbonyl, alkoxycarbonylalkyl, alkyl, alkylcarbonyloxy, alkylidene, alkylsulfanyl, alkylsulfanylalkyl, alkylsulfonyl, alkylsulfonylalkyl, amino, aminoalkyl, aminoalkenyl, aminoalkoxy, aminocarbonylalkenyl, aryl, carboxyalkenyl, carboxyalkyl, cyano, cycloalkyl, (cycloalkyl)alkyl, halo, haloalkoxy, haloalkyl, (heterocycle)alkyl, hydroxy, hydroxyalkyl, nitro; or $R^1$ and $R^2$ together with the carbon atoms to which they are attached, form a five-, six-, or seven-membered saturated or unsaturated carbocyclic ring which can be optionally substituted with 1 or 2 substituents independently selected from the group consisting of alkoxy, alkyl, amino, halo, and haloalkyl; or $R^2$ and $R^3$ together with the carbon atoms to which they are attached, form a five-, six-, or seven-membered saturated or unsaturated carbocyclic ring which can be optionally substituted with 1 or 2 substituents independently selected from the group consisting of alkoxy, alkyl, amino, halo, and haloalkyl; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}$N—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl ($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}N$—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{c5}$)Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; $R^6$ is selected from the group consisting of hydrogen, alkyl, alkylsulfanylalkyl, aryl, and arylalkyl.

According to another embodiment of the present invention there is disclosed a method of inhibiting angiogenesis comprising administering to a patient in need of such treatment a therapeutically effective amount of a compound of formula (III)

(III)

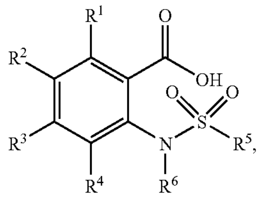

or a therapeutically acceptable salt thereof, wherein $R^1$ is selected from the group consisting of hydrogen, $C_1$-$C_4$ alkyl, $C_2$-$C_4$ alkenyl, $C_2$-$C_4$ alkoxy, halo, haloalkyl, haloakoxy, $R_aR_bN$— and $R_aR_b$Nalkoxy, wherein $R_a$ and $R_b$ are each independently selected from the group consisting of hydrogen and alkyl; $R^2$ is selected from the group consisting of alkoxy, alkoxyalkyl, $C_1$-$C_{10}$ alkyl, alkylsulfanyl, alkylsulfanylalkyl, alkylsulfonyl, alkylsulfonylalkyl, amino, aminoalkyl, cycloalkyl, (cycloalkyl)alkyl, halo, haloalkoxy, and haloalkyl; $R^3$ is selected from the group consisting of hydrogen, alkyl and halogen; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}N$—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are, each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}N$—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{c5}$)Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; and $R^6$ is selected from the group consisting of hydrogen, alkyl, alkylsulfanylalkyl, aryl, and arylalkyl.

According to another embodiment of the present invention there is disclosed a method of inhibiting angiogenesis comprising administering to a patient in need of such treatment a therapeutically effective amount of a compound of formula (IV)

(IV)

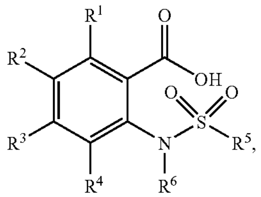

or a therapeutically acceptable salt thereof, wherein $R^1$ and $R^2$, together with the carbon atoms to which they are attached, form a five-, six-, or seven-membered saturated or unsaturated carbocyclic ring which can be optionally substituted with one or two substituents independently selected from the group consisting of alkoxy, alkyl, amino, halo, and haloalkyl;

$R^3$ is selected from the group consisting of hydrogen, alkyl and halogen; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}N$—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}N$—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{c5}$)Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; and $R^6$ is selected from the group consisting of hydrogen, alkyl, alkylsulfanylalkyl, aryl, and arylalkyl.

According to another embodiment of the present invention there is disclosed a method of inhibiting angiogenesis comprising administering to a patient in need of such treatment a therapeutically effective amount of a compound of formula (IV)

(IV)

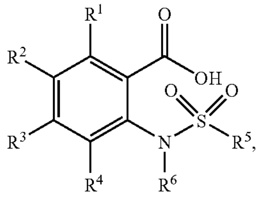

or a therapeutically acceptable salt thereof, wherein $R^1$ and $R^2$, together with the carbon atoms to which they are attached, form a six membered monounsaturated carbocyclic ring which can be optionally substituted with one or two substituents independently selected from the group consisting of alkoxy, alkyl, amino, halo, and haloalkyl; $R^3$ is selected from the group consisting of hydrogen, alkyl and halogen; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}N$—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{e4}R_{f4}$Nalkylsulfonyl, $R_{g4}R_{j4}$Nalkyl($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}N$—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{c5}$)Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; and $R^6$ is selected from the group consisting of hydrogen, alkyl, alkylsulfanylalkyl, aryl, and arylalkyl.

According to another embodiment of the present invention there is disclosed a method of inhibiting angiogenesis comprising administering to a patient in need of such treatment a therapeutically effective amount of a compound of formula (V)

(V)

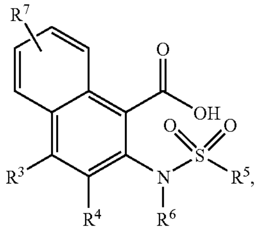

or a therapeutically acceptable salt thereof, wherein $R^3$ is selected from the group consisting of hydrogen, alkyl and halogen; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}$N—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}$N—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{c5}$)Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; $R^6$ is selected from the group consisting of hydrogen, alkyl, alkylsulfanylalkyl, aryl, and arylalkyl; and $R^7$ is selected from the group consisting of hydrogen, $C_1$-$C_3$ alkyl, $C_2$-$C_3$ alkenyl, $C_2$-$C_3$ alkoxy, halo, haloalkyl, haloakoxy, $R_aR_b$N— and $R_aR_b$Nalkoxy, wherein $R_a$ and $R_b$ are each independently selected from the group consisting of hydrogen and alkyl.

According to another embodiment of the present invention there is disclosed a method of inhibiting angiogenesis comprising administering to a patient in need of such treatment a therapeutically effective amount of a compound of formula (VI)

(VI)

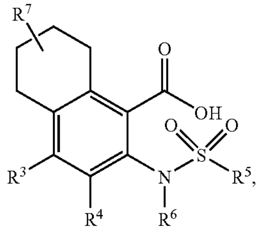

or a therapeutically acceptable salt thereof, wherein $R^3$ is selected from the group consisting of hydrogen, alkyl and halogen; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}$N—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl ($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}$N—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{c5}$)Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; $R^6$ is selected from the group consisting of hydrogen, alkyl, alkylsulfanylalkyl, aryl, and arylalkyl; and $R^7$ is selected from the group consisting of hydrogen, $C_1$-$C_3$ alkyl, $C_2$-$C_3$ alkenyl, $C_2$-$C_3$ alkoxy, halo, haloalkyl, haloakoxy, $R_aR_b$N— and $R_aR_b$Nalkoxy, wherein $R_a$ and $R_b$ are each independently selected from the group consisting of hydrogen and alkyl.

According to another embodiment of the present invention there is disclosed a method of inhibiting angiogenesis comprising administering to a patient in need of such treatment a therapeutically effective amount of a compound of formula (VII)

(VII)

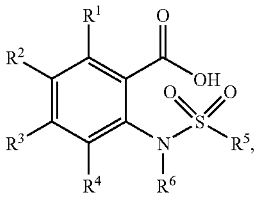

or a therapeutically acceptable salt thereof, wherein $R^1$ is selected from the group consisting of hydrogen, $C_1$-$C_4$ alkyl, $C_2$-$C_4$ alkenyl, $C_1$-$C_4$ alkoxy, halo, haloalkyl, haloakoxy, $R_aR_b$N— and $R_aR_b$Nalkoxy, wherein $R_a$ and $R_b$ are each independently selected from the group consisting of hydrogen and alkyl; $R^2$ and $R^3$, together with the carbon atoms to which they are attached, form a five-, six-, or seven-membered saturated or unsaturated carbocyclic ring which can be optionally substituted with one or two substituents independently selected from the group consisting of alkoxy, alkyl, amino, halo, and haloalkyl; $R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, halo, haloalkoxy, haloalkyl, heteroaryl, heterocycle, heterocyclealkyl, heterocyclealkenyl, hydroxy, hydroxyalkyl, nitro, phenyl, phenylsulfonyl, $R_{c4}R_{d4}$N—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl($R_{e4}$)Ncarbonyl($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle; $R^5$ is selected from the group consisting of alkyl, amino, aminoalkyl, aryl, arylalkenyl, arylalkyl, haloalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_{c5}R_{d5}$N—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{c5}$)Ncarbonyl, $R_{e5}R_{f5}$Nalkyl($R_{c5}$)Ncarbonylalkenyl, $R_{e5}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, halo, haloalkoxy, haloalkyl, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; and $R^6$ is selected from the group consisting of hydrogen, alkyl, alkylsulfanylalkyl, aryl, and arylalkyl.

According to another embodiment of the present invention there is disclosed a method of inhibiting methionine aminopeptidase-2 comprising administering to a patient in need of such treatment a therapeutically effective amount of a compound of formula (I), or a therapeutically acceptable salt thereof.

According to another embodiment of the present invention there is disclosed a method of treating cancer comprising administering to a patient in need of such treatment a therapeutically effective amount of a compound of formula (I), or a therapeutically acceptable salt thereof.

According to another embodiment of the present invention there is disclosed a method of treating cancer comprising administering to a patient in need of such treatment a therapeutically effective amount of a compound of formula (II), or a therapeutically acceptable salt thereof.

According to another embodiment of the present invention there is disclosed a method of treating cancer comprising administering to a patient in need of such treatment a therapeutically effective amount of a compound of formula (III), or a therapeutically acceptable salt thereof.

According to another embodiment of the present invention there is disclosed a method of treating cancer comprising administering to a patient in need of such treatment a therapeutically effective amount of a compound of formula (IV), or a therapeutically acceptable salt thereof.

According to another embodiment of the present invention there is disclosed a method of treating cancer comprising administering to a patient in need of such treatment a therapeutically effective amount of a compound of formula (V), or a therapeutically acceptable salt thereof.

According to another embodiment of the present invention there is disclosed a method of treating cancer comprising administering to a patient in need of such treatment a therapeutically effective amount of a compound of formula (VI), or a therapeutically acceptable salt thereof.

According to another embodiment of the present invention there is disclosed a method of treating cancer comprising administering to a patient in need of such treatment a therapeutically effective amount of a compound of formula (VII), or a therapeutically acceptable salt thereof.

According to another embodiment of the present invention there is disclosed a pharmaceutical composition comprising a compound of claim 1 or a therapeutically acceptable salt thereof in combination with a therapeutically acceptable carrier.

According to another embodiment of the present invention there is disclosed a pharmaceutical composition comprising a compound of formula I or a therapeutically acceptable salt thereof in combination with a therapeutically acceptable carrier.

According to another embodiment of the present invention there is disclosed a pharmaceutical composition comprising a compound of formula II or a therapeutically acceptable salt thereof in combination with a therapeutically acceptable carrier.

According to another embodiment of the present invention there is disclosed a pharmaceutical composition comprising a compound of formula III or a therapeutically acceptable salt thereof in combination with a therapeutically acceptable carrier.

According to another embodiment of the present invention there is disclosed a pharmaceutical composition comprising a compound of formula IV or a therapeutically acceptable salt thereof in combination with a therapeutically acceptable carrier.

According to another embodiment of the present invention there is disclosed a pharmaceutical composition comprising a compound of formula V or a therapeutically acceptable salt thereof in combination with a therapeutically acceptable carrier.

According to another embodiment of the present invention there is disclosed a pharmaceutical composition comprising a compound of formula VI or a therapeutically acceptable salt thereof in combination with a therapeutically acceptable carrier.

According to another embodiment of the present invention there is disclosed a pharmaceutical composition comprising a compound of formula VII or a therapeutically acceptable salt thereof in combination with a therapeutically acceptable carrier.

According to another embodiment of the present invention there is disclosed a method of treating abnormal neovascularization conditions of the eye comprising administering to a patient in need of such treatment a therapeutically effective amount of a compound of formula (I), or a therapeutically acceptable salt thereof.

According to still another embodiment, the present invention is directed to a pharmaceutical composition comprising a therapeutically effective amount of a compound of formula (I-VII) in combination with a pharmaceutically suitable carrier.

As used in the present specification the following terms have the meanings indicated:

As used herein, the singular forms “a”, “an”, and “the” include plural reference unless the context clearly dictates otherwise.

The term “alkenyl,” as used herein, refers to a straight or branched chain group of two to ten carbon atoms containing at least one carbon-carbon double bond.

The term “alkoxy,” as used herein, refers to an alkyl group attached to the parent molecular moiety through an oxygen atom.

The term “alkoxyalkyl,” as used herein, refers to an alkyl group substituted with at least one alkoxy group.

The term “alkoxycarbonyl,” as used herein, refers to an alkoxy group attached to the parent molecular moiety through a carbonyl group.

The term “alkoxycarbonylalkyl,” as used herein, refers to an alkyl group substituted with at least one alkoxycarbonyl group.

The term “alkyl,” as used herein, refers to a group of one to ten atoms derived from a straight or branched chain saturated hydrocarbon.

The term “$C_1$alkyl,” as used herein, refers to an alkyl group with one carbon atom, i.e., a methyl group.

The term “$C_1$-$C_3$ alkyl,” as used-herein, refers to an alkyl group one to three carbon atoms in length.

The term “$C_1$-$C_3$ alkyl,” as used herein, refers to an alkyl group one to three carbon atoms in length.

The term “$C_2$-$C_3$ alkoxy,” as used herein, refers to an alkoxy group two to three carbon atoms in length.

The term “alkylcarbonyl,” as used herein, refers to an alkyl group attached to the parent molecular moiety through a carbonyl group.

The term “alkylcarbonyloxy,” as used herein, refers to an alkylcarbonyl group attached to the parent molecular moiety through an oxygen atom.

The term "alkylsulfanyl," as used herein, refers to an alkyl group attached to the parent molecular moiety through a sulfur atom.

The term "alkylsulfinyl," as used herein, refers to an alkyl group attached to the parent molecular moiety through a sulfoxide group.

The term "alkylsulfanylalkyl," as used herein, refers to an alkyl group substituted with at least one alkylsulfanyl group.

The term "alkylsulfonyl," as used herein, refers to an alkyl group attached to the parent molecular moiety through a sulfonyl group.

The term "amino," as used herein, refers to $R_pR_qN$—, wherein $R_p$ and $R_q$ are independently selected from the group consisting of hydrogen, alkoxyalkyl, alkyl, alkylcarbonyl, alkylsulfanylalkyl, aryl, arylalkyl, arylcarbonyl, cycloalkyl, (cycloalkyl)alkyl, heteroaryl, heteroarylalkyl, heterocycle, (heterocycle)alkyl, (heterocycle)alkylcarbonyl, heterocyclecarbonylalkyl, hydroxyalkyl, ($R_rR_sN$)alkoxyalkoxyalkyl, ($R_rR_sN$)alkoxycarbonyl, ($R_rR_sN$)alkyl, ($R_rR_sN$)alkylcarbonyl, ($R_rR_sN$)carbonyl; wherein $R_r$ and $R_s$ are each independently selected from the group consisting of hydrogen, alkoxyalkyl, alkyl, alkylcarbonyl, $R_tR_vN$alkyl, cycloalkyl, (cycloalkyl)alkyl, heterocycle and phenyl, or $R_r$ and $R_s$ taken together with the nitrogen atom they are each attached form a heterocycle; and wherein the aryl; the aryl part of the arylalkyl, the aryl part of arylcarbonyl; the cycloalkyl; the cycloalkyl part of the (cycloalkyl)alkyl; the heteroaryl; the heteroaryl part of the heteroarylalkyl; the heterocycle; and the heterocycle part of the (heterocycle)alkyl, the heterocycle of (heterocycle)alkylcarbonyl, and the heterocycle part of heterocyclecarbonylalkyl can be further substituted as defined within the scope of the present invention; and wherein $R_t$ and $R_v$ are each independently selected from the group consisting of hydrogen, alkoxyalkyl, alkyl, alkylcarbonyl, cycloalkyl, (cycloalkyl)alkyl, heterocycle and phenyl.

The term "aminoalkenyl," as used herein, refers to an alkenyl group substituted with at least one amino group.

The term "aminoalkoxy," as used herein, refers to an aminoalkyl group attached to the parent molecular moiety through an oxygen atom.

The term "aminoalkoxyalkyl," as used herein, refers to an alkyl group substituted with at least one aminoalkoxy group.

The term "aminoalkoxyalkoxy," as used herein, refers to an aminoalkoxyalkyl group attached to the parent molecular moiety through an oxygen atom.

The term "aminoalkyl," as used herein, refers to an alkyl group substituted with at least one amino group.

The term "aminoalkylsulfanyl," as used herein, refers to an aminoalkyl group attached to the parent molecular moiety through a sulfur atom.

The term "aminoalkylsulfinyl," as used herein, refers to an aminoalkyl group attached to the parent molecular moiety through a sulfinyl group.

The term "aminoalkylsulfonyl," as used herein, refers to an aminoalkyl group attached to the parent molecular moiety through a sulfonyl group.

The term "aminocarbonyl," as used herein, refers to an amino group attached to the parent molecular moiety through a carbonyl group.

The term "aminocarbonylalkenyl," as used herein, refers to an alkenyl group substituted with at least one aminocarbonyl group.

The term "aryl," as used herein, refers to a phenyl group, or a bicyclic or tricyclic fused ring system wherein one or more of the rings is a phenyl group. Bicyclic fused ring systems consist of a phenyl group fused to a monocyclic cycloalkenyl group, a monocyclic cycloalkyl group, or another phenyl group. Tricyclic fused ring systems consist of a bicyclic fused ring system fused to a monocyclic cycloalkenyl group, a monocyclic cycloalkyl group, or another phenyl group. The aryl groups of the present invention can be attached to the parent molecular moiety through any substitutable carbon atom in the group. Representative examples of aryl groups include, but are not limited to, anthracenyl, azulenyl, fluorenyl, indanyl, indenyl, naphthyl, phenyl, and tetrahydronaphthyl. The aryl groups of the present invention can be optionally substituted with one, two, three, four, or five substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_cR_dN$—, $R_cR_d$Nalkyl, $R_cR_d$Nalkenyl, $R_cR_d$Nalkynyl, $R_cR_d$-Nalkoxy, $R_cR_d$Nalkoxycarbonyl, $R_cR_d$Ncarbonyl, $R_cR_d$Ncycloalkyl, $R_cR_d$Nalkylcycloalkyl, $R_cR_d$Ncycloalkylalkyl, $R_cR_d$Nsulfinyl, $R_eR_f$Nalkyl$R_cR_d$N—, $R_eR_f$Nalkyl$R_cR_d$Ncarbonyl, $R_eR_f$Nalkyl$R_cR_d$Ncarbonylalkenyl, $R_eR_f$Nalkylcarbonyl$R_cR_d$N—, $R_eR_f$Nalkoxycarbonyl$R_cR_d$N—, $R_cR_d$-Nalkylsulfanyl, $R_cR_d$Nalkylsulfinyl, $R_cR_d$Nalkylsulfonyl and $R_gR_j$Nalkyl$R_eR_f$Ncarbonyl$R_cR_d$N—. The phenyl, the phenyl of phenylsulfonyl, the heteroaryl, the heterocycle, the heterocycle of heterocyclealkyl, and the heterocycle of heterocyclealkenyl may be further substituted as defined within the scope of this document.

The term "arylalkenyl," as used herein, refers to an alkenyl group substituted with at least one aryl group.

The term "arylalkyl," as used herein, refers to an alkyl group substituted with at least one aryl group.

The term "arylcarbonyl," as used herein, refers to an aryl group attached to the parent molecular moiety through a carbonyl group.

The term "arylsulfonyl," as used herein, refers to an aryl group attached to the parent molecular moiety through a sulfonyl group.

The term "carbonyl," as used herein, refers to —C(O)—.

The term "carboxy," as used herein, refers to —$CO_2H$.

The term "carboxyalkenyl," as used herein, refers to an alkenyl group substituted with at least one carboxy group.

The term "cyano," as used herein, refers to —CN.

The term "cyanoalkyl," as used herein, refers to an alkyl group substituted with at least one cyano group.

The term "cycloalkenyl," as used herein, refers to a non-aromatic, partially unsaturated monocyclic, bicyclic, or tricyclic ring system having three to fourteen carbon atoms and zero heteroatoms. Representative examples of cycloalkenyl groups include, but are not limited to, cyclohexenyl, octahydronaphthalenyl, and norbornylenyl. The cycloalkenyl groups of the present invention can be optionally substituted with one, two, three, four, or five substituents independently selected from the group consisting of alkoxy, alkyl, cyano, halo, haloalkoxy, haloalkyl, and nitro.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to cyclobutyl, cyclohexyl, cyclopropyl, cyclopentyl, bicyclo[3.1.1]heptyl, and adamantyl. The cycloalkyl groups of the present invention can be optionally substituted with one, two, three, four, or five substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, heterocycle, heterocyclealkyl, heterocyclealkenyl, hydroxy, nitro, $R_cR_dN$—, $R_cR_d$-

Nalkyl, $R_cR_d$Nalkenyl, $R_cR_d$Nalkynyl, $R_cR_d$Nalkoxy, $R_cR_d$Nalkoxycarbonyl, $R_cR_d$Ncarbonyl, $R_cR_d$Ncycloalkyl, $R_cR_d$Nalkylcycloalkyl, $R_cR_d$Ncycloalkylalkyl, $R_cR_d$Nsulfinyl, $R_eR_f$Nalkyl$R_cR_d$N—, $R_eR_f$Nalkyl$R_cR_d$Ncarbonyl, $R_eR_f$Nalkyl$R_cR_d$Ncarbonylalkenyl, $R_eR_f$Nalkylcarbonyl$R_cR_d$N—, $R_eR_f$Nalkoxycarbonyl$R_cR_d$N—, $R_cR_d$Nalkylsulfanyl, $R_cR_d$Nalkylsulfinyl, $R_cR_d$Nalkylsulfonyl and $R_gR_j$Nalkyl$R_eR_f$Ncarbonyl$R_cR_d$N—. The phenyl, the phenyl of phenylsulfonyl, the heteroaryl, the heterocycle, the heterocycle of heterocyclealkyl, and the heterocycle of heterocyclealkenyl may be further substituted as defined within the scope of this document.

The term "(cycloalkyl)alkyl," as used herein, refers to an alkyl group substituted with at least one cycloalkyl group.

The terms "halo" and "halogen," as used herein, refer to F, Cl, Br, or I.

The term "haloalkoxy," as used herein, refers to a haloalkyl group attached to the parent molecular moiety through an oxygen atom. A preferred haloalkoxy group of the present invention is trifluoromethoxy.

The term "haloalkyl," as used herein, refers to an alkyl group substituted by one, two, three, or four halogen atoms. A preferred haloalkyl group of the present invention is trifluoromethyl.

The term "heteroaryl," as used herein, refers to an aromatic five- or six-membered ring where at least one atom is selected from the group consisting of N, O, and S, and the remaining atoms are carbon. The term "heteroaryl" also includes bicyclic systems where a heteroaryl ring is fused to a phenyl group, a monocyclic cycloalkenyl group, as defined herein, a monocyclic cycloalkyl group, as defined herein, a monocyclic heterocycle group, as defined herein, or an additional monocyclic heteroaryl group; and tricyclic systems where a bicyclic system is fused to a phenyl group, a monocyclic cycloalkenyl group, as defined herein, a monocyclic cycloalkyl group, as defined herein, a heterocycle group, as defined herein, or an additional monocyclic heteroaryl group. The heteroaryl groups are attached to the parent molecular moiety through any substitutable carbon or nitrogen atom in the group. Representative examples of heteroaryl groups include, but are not limited to, benzoxadiazolyl, benzoxazolyl, benzofuranyl, benzothiadiazolyl, benzothiazolyl, benzothienyl, cinnolinyl, dibenzofuranyl, furanyl, imidazolyl, indazolyl, indolyl, isoxazolyl, isoquinolinyl, isothiazolyl, naphthyridinyl, oxadiazolyl, oxadiazolyl, oxazolyl, pyridinyl, pyridazinyl, pyrimidinyl, pyrazinyl, pyrazolyl, pyrrolyl, quinolinyl, tetrahydrothiopyranyl, thiazolyl, thienopyridinyl, thienyl, triazolyl, thiadiazolyl, and triazinyl. The heteroaryl groups of the present invention can be optionally substituted with one, two, three, four, or five substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, a second heteroaryl, heterocycle, heterocyclealkyl, heterocyclealkenyl, hydroxy, nitro, $R_cR_d$N—, $R_cR_d$Nalkyl, $R_cR_d$Nalkenyl, $R_cR_d$Nalkynyl, $R_cR_d$Nalkoxy, $R_cR_d$Nalkoxycarbonyl, $R_cR_d$Ncarbonyl, $R_cR_d$Ncycloalkyl, $R_cR_d$Nalkylcycloalkyl, $R_cR_d$Ncycloalkylalkyl, $R_cR_d$Nsulfinyl, $R_eR_f$Nalkyl$R_cR_d$N—, $R_eR_f$Nalkyl$R_cR_d$Ncarbonyl, $R_eR_f$Nalkyl$R_cR_d$Ncarbonylalkenyl, $R_eR_f$Nalkylcarbonyl$R_cR_d$N—, $R_eR_f$Nalkoxycarbonyl$R_cR_d$N—, $R_cR_d$Nalkylsulfanyl, $R_cR_d$Nalkylsulfinyl, $R_cR_d$Nalkylsulfonyl and $R_gR_j$Nalkyl$R_eR_f$Ncarbonyl$R_cR_d$N—. The phenyl, the phenyl of phenylsulfonyl, the heterocycle, the heterocycle of heterocyclealkyl, and the heterocycle of heterocyclealkenyl may be further substituted as defined within the scope of this document. The second heteroaryl may be optionally substituted with one two or three groups selected from the group consisting of alkenyl, alkoxy, alkoxycarbonyl, alkyl, alkylcarbonyl, alkylsulfonyl, aminoalkyl, carboxy, cyano, cyanoalkyl, halo, haloalkoxy, haloalkyl, hydroxy, nitro, $R_cR_d$N—, $R_cR_d$Nalkyl, $R_cR_d$Nalkenyl, $R_cR_d$Nalkynyl, $R_cR_d$Nalkoxy, $R_cR_d$Nalkoxycarbonyl, $R_cR_d$Ncarbonyl, $R_cR_d$Ncycloalkyl, $R_cR_d$Nalkylcycloalkyl, $R_cR_d$Ncycloalkylalkyl, $R_cR_d$Nsulfinyl, $R_eR_f$Nalkyl$R_cR_d$N—, $R_eR_f$Nalkyl$R_cR_d$Ncarbonyl, $R_eR_f$Nalkyl$R_cR_d$Ncarbonylalkenyl, $R_eR_f$Nalkylcarbonyl$R_cR_d$N—, $R_eR_f$Nalkoxycarbonyl$R_cR_d$N—, $R_cR_d$Nalkylsulfanyl, $R_cR_d$Nalkylsulfinyl, $R_cR_d$Nalkylsulfonyl and $R_gR_j$Nalkyl$R_eR_f$Ncarbonyl$R_cR_d$N—.

The term "heteroarylalkenyl," as used herein, refers to an alkenyl group substituted with at least one heteroaryl group.

The term "heteroarylalkyl," as used herein, refers to an alkyl group substituted with at least one heteroaryl group.

The term "heteroarylcarbonyl," as used herein, refers to a heteroaryl group attached to the parent molecular moiety through a carbonyl group.

The term "heterocycle," as used herein, refers to a cyclic, non-aromatic, saturated or partially unsaturated three-, four-, five-, six-, or seven-membered ring where at least one atom is selected from the group consisting of oxygen, nitrogen, and sulfur. The term "heterocycle" also includes bicyclic systems where a heterocycle ring is fused to a phenyl group, a monocyclic cycloalkenyl group, a monocyclic cycloalkyl group, or an additional monocyclic heterocycle group; and tricyclic systems where a bicyclic system is fused to a phenyl group, a monocyclic cycloalkenyl group, a monocyclic cycloalkyl group, or an additional monocyclic heterocycle group. The heterocycle groups of the invention are attached to the parent molecular group through any substitutable carbon or nitrogen atom in the group. Representative examples of heterocycle groups include, but are not limited to, benzodioxolyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, and thiomorpholinyl. The heterocycle groups of the present invention can be optionally substituted with one, two, three, four, or five substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, halo, haloalkoxy, haloalkyl, heteroaryl, a second heterocycle, heterocyclealkyl, heterocyclealkenyl, hydroxy, nitro, $R_cR_d$N—, $R_cR_d$Nalkyl, $R_cR_d$Nalkenyl, $R_cR_d$Nalkynyl, $R_cR_d$Nalkoxy, $R_cR_d$Nalkoxycarbonyl, $R_cR_d$Ncarbonyl, $R_cR_d$Ncycloalkyl, $R_cR_d$Nalkylcycloalkyl, $R_cR_d$Ncycloalkylalkyl, $R_cR_d$Nsulfinyl, $R_eR_f$Nalkyl$R_cR_d$N—, $R_eR_f$Nalkyl$R_cR_d$Ncarbonyl, $R_eR_f$Nalkyl$R_cR_d$Ncarbonylalkenyl, $R_eR_f$Nalkylcarbonyl$R_cR_d$N—, $R_eR_f$Nalkoxycarbonyl$R_cR_d$N—, $R_cR_d$Nalkylsulfanyl, $R_cR_d$Nalkylsulfinyl, $R_cR_d$Nalkylsulfonyl and $R_gR_j$Nalkyl$R_eR_f$Ncarbonyl$R_cR_d$N—. The phenyl, the phenyl of phenylsulfonyl, the heteroaryl may be further substituted as defined within the scope of this document. The second heterocycle, the heterocycle of heterocyclealkyl, and the heterocycle of heterocyclealkenyl may be optionally substituted with alkenyl, alkoxy, alkoxycarbonyl, alkyl, alkylcarbonyl, alkylsulfonyl, aminoalkyl, carboxy, cyano, cyanoalkyl, halo, haloalkoxy, haloalkyl, hydroxy, nitro, $R_cR_d$N—, $R_cR_d$Nalkyl, $R_cR_d$Nalkenyl, $R_cR_d$Nalkynyl, $R_cR_d$Nalkoxy, $R_cR_d$Nalkoxycarbonyl, $R_cR_d$Ncarbonyl, $R_cR_d$Ncycloalkyl, $R_cR_d$Nalkylcycloalkyl, $R_cR_d$Ncycloalkylalkyl, $R_cR_d$Nsulfinyl, $R_eR_f$Nalkyl$R_cR_d$N—, $R_eR_f$Nalkyl$R_cR_d$Ncarbonyl, $R_eR_f$Nalkyl$R_cR_d$Ncarbonylalkenyl, $R_eR_f$Nalkylcarbonyl$R_cR_d$N—, $R_eR_f$Nalkoxycarbonyl$R_cR_d$N—, $R_cR_d$Nalkylsulfanyl, $R_cR_d$Nalkylsulfinyl, $R_cR_d$Nalkylsulfonyl and $R_gR_j$NalkylR$_e$R$_f$NcarbonylR$_c$R$_d$N—.

The term "(heterocycle)alkyl," as used herein, refers to an alkyl group substituted with at least one heterocycle group.

The term "(heterocycle)alkylcarbonyl," as used herein, refers to an a (heterocycle)alkyl group attached to the parent molecular moiety through a carbonyl group.

The term "heterocyclecarbonyl," as used herein, refers to a heterocycle group attached to the parent molecular moiety through a carbonyl group.

The term "heterocyclecarbonylalkyl," as used herein, refers to an alkyl group substituted with at least one heterocyclecarbonyl group.

The term "hydroxy," as used herein, refers to —OH.

The term "hydroxyalkenyl," as used herein, refers to an alkenyl group substituted with at least one hydroxy group.

The term "hydroxyalkyl," as used herein, refers to an alkyl group substituted with at least one hydroxy group.

The term "nitro," as used herein, refers to —$NO_2$.

The term "$R_cR_d$N—," as used herein, refers to two groups, $R_c$ and $R_d$, which are attached to the parent molecular moiety through a nitrogen atom. $R_c$ and $R_d$ are independently selected from the group consisting of hydrogen, alkoxyalkyl, alkoxycarbonyl, alkyl, alkylcarbonyl, alkylsulfonyl, aryl, arylalkyl, cycloalkyl, (cycloalkyl)alkyl, haloalkyl, heteroaryl, heteroarylalkyl, heterocycle, (heterocycle)alkyl, hydroxyalkyl, ($R_eR_f$N)alkyl, ($R_eR_f$N)carbonyl, wherein the aryl, the aryl part of the arylalkyl, the cycloalkyl; the cycloalkyl part of the (cycloalkyl)alkyl; the heteroaryl, the heteroaryl part of the heteroarylalkyl; the heterocycle; and the heterocycle part of the (heterocycle)alkyl can be further optionally substituted with one, two, three, four, or five substituents independently selected from the group consisting of alkenyl, alkoxy, alkoxyalkyl, alkoxycarbonyl, alkyl, alkylcarbonyl, carboxy, cyano, halo, haloalkoxy, haloalkyl, hydroxy, hydroxyalkyl, nitro and $R_eR_f$N—.

The term "$R_eR_f$N—," as used herein, refers to two groups, $R_e$ and $R_f$, which are attached to the parent molecular moiety through a nitrogen atom. $R_e$ and $R_f$ are independently selected from the group consisting of hydrogen, alkoxyalkyl, alkyl, alkylcarbonyl, aminoalkyl, cycloalkyl, (cycloalkyl)alkyl, heterocycle and phenyl.

The term "$R_gR_j$N—," as used herein, refers to two groups, $R_g$ and $R_j$, which are attached to the parent molecular moiety through a nitrogen atom. $R_g$ and $R_j$ are independently selected from the group consisting of hydrogen, alkoxyalkyl, alkyl, alkylcarbonyl, aminoalkyl, cycloalkyl, (cycloalkyl)alkyl, heterocycle and phenyl.

The following definitions refer to all amino groups and their substitutents $R_p$, $R_q$, $R_r$, $R_s$, $R_c$, $R_d$, $R_e$, $R_f$, $R_g$ and $R_j$, as they are appended to the molecular moiety. Although the following definitions are represented by $R_r$ and $R_s$, the use of $R_r$ and $R_s$ is meant to be a representation of all possible substituents $R_p$, $R_q$, $R_r$, $R_s$, $R_c$, $R_d$, $R_e$, $R_f$, $R_g$ and $R_j$.

The term "($R_rR_s$N)alkoxy," as used herein, refers to an $R_rR_s$N— group attached to the parent molecular moiety through an alkoxy group.

The term "($R_rR_s$N)alkoxyalkoxyalkyl," as used herein, refers to an ($R_rR_s$N)alkoxy group attached to the parent molecular moiety through an alkoxyalkyl group.

The term "($R_rR_s$N)alkoxycarbonyl," as used herein, refers to an ($R_rR_s$N)alkoxy group attached to the parent molecular moiety through a carbonyl group.

The term "($R_rR_s$N)alkyl," as used herein, refers to an $R_rR_s$N— group attached to the parent molecular moiety through an alkyl group.

The term "($R_rR_s$N)alkylcarbonyl," as used herein, refers to an ($R_rR_s$N)alkyl group attached to the parent molecular moiety through a carbonyl group.

The term "($R_rR_s$N)carbonyl," as used herein, refers to an $R_rR_s$N— group attached to the parent molecular moiety through a carbonyl group.

The term "($R_rR_s$N)alkenyl," as used herein, refers to an $R_rR_s$N— group attached to the parent molecular moiety through an alkenyl group.

The term "($R_rR_s$N)alkynyl," as used herein, refers to an $R_rR_s$N— group attached to the parent molecular moiety through an alkynyl group.

The term "($R_rR_s$N)cycloalkyl," as used herein, refers to an $R_rR_s$N— group attached to the parent molecular moiety through a cycloalkyl group.

The term "($R_rR_s$N)alkylcycloalkyl," as used herein, refers to an $R_rR_s$Nalkyl group attached to the parent molecular moiety through a cycloalkyl group.

The term "($R_rR_s$N)cycloalkylalkyl," as used herein, refers to an $R_rR_s$Ncycloalkyl group attached to the parent molecular moiety through an alkyl group.

The term "$R_rR_s$Nsulfanyl," as used herein, refers to an $R_rR_s$N— group attached to the parent molecular moiety through a sulfanyl group.

The term "$R_rR_s$Nsulfinyl," as used herein, refers to an $R_rR_s$N— group attached to the parent molecular moiety through a sulfinyl group.

The term "$R_rR_s$Nsulfonyl," as used herein, refers to an $R_rR_s$N— group attached to the parent molecular moiety through a sulfonyl group.

The term "$R_eR_f$NalkylR$_c$R$_d$N—," as used herein, refers to an $R_eR_f$Nalkyl group attached to the parent molecular moiety through an $R_cR_d$N— group.

The term "$R_eR_f$NalkylR$_c$R$_d$Ncarbonyl," as used herein, refers to an $R_eR_f$Nalkyl group attached to the parent molecular moiety through an $R_cR_d$Ncarbonyl group.

The term "$R_eR_f$NalkylR$_c$R$_d$Ncarbonylalkenyl," as used herein, refers to an $R_eR_f$Nalkyl group attached to the parent molecular moiety through an $R_cR_d$Ncarbonylalkenyl group.

The term "$R_eR_f$NalkylcarbonylR$_c$R$_d$N—," as used herein, refers to an $R_eR_f$Nalkylcarbonyl group attached to the parent molecular moiety through an $R_cR_d$N— group.

The term "$R_eR_f$NalkoxycarbonylR$_c$R$_d$N—," as used herein, refers to an $R_eR_f$Nalkoxycarbonyl group attached to the parent molecular moiety through an $R_cR_d$N— group.

The term "$R_cR_d$Nalkylsulfanyl," as used herein, refers to an $R_cR_d$Nalkyl group attached to the parent molecular moiety through a sulfanyl group.

The term "$R_cR_d$Nalkylsulfinyl," as used herein, refers to an $R_cR_d$Nalkyl group attached to the parent molecular moiety through a sulfinyl group.

The term "$R_cR_d$Nalkylsulfonyl," as used herein, refers to an $R_cR_d$Nalkyl group attached to the parent molecular moiety through a sulfonyl group.

The term "$R_gR_j$NalkylR$_e$R$_f$NcarbonylR$_c$R$_d$N—" as used herein, refers to an $R_gR_j$NalkylR$_e$R$_f$Ncarbonyl group attached to the parent molecular moiety through an $R_cR_d$N— group.

The term "phenyl," as used herein, refers to 6 membered aryl ring that is appended to the parent molecular moiety. The phenyl groups of the present invention may be optionally substituted with one, two or three groups independently selected from the group consisting of alkenyl, alkoxy, alkoxycarbonyl, alkyl, alkylcarbonyl, alkylsulfonyl, aminoalkyl, carboxy, cyano, cyanoalkyl, halo, haloalkoxy, haloalkyl, hydroxy, nitro, $R_cR_d$N—, $R_cR_d$Nalkyl, $R_cR_d$Nalkenyl, $R_cR_d$Nalkynyl, $R_cR_d$Nalkoxy, $R_cR_d$Nalkoxycarbonyl, $R_cR_d$Ncarbonyl, $R_cR_d$Ncycloalkyl, $R_cR_d$Nalkylcycloalkyl, $R_cR_d$Ncycloalkylalkyl, $R_cR_d$Nsulfinyl, $R_eR_f$NalkylR$_c$R$_d$N—, $R_eR_f$NalkylR$_c$R$_d$Ncarbonyl, $R_eR_f$NalkylR$_c$R$_d$Ncarbonylalkenyl, $R_eR_f$NalkylcarbonylR$_c$R$_d$N—, $R_eR_f$Nalkoxycarbonyl-$R_cR_d$N—, $R_cR_d$Nalkylsulfanyl, $R_cR_d$Nalkylsulfinyl, $R_cR_d$-Nalkylsulfonyl and $R_gR_j$NalkylR$_e$R$_f$NcarbonylR$_c$R$_d$N—.

The term "oxo," as used herein, refers to =O.

The term "sulfinyl," as used herein, refers to S(O)—.

The term "sulfonyl," as used herein, refers to —$SO_2$—.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio; and are effective for their intended use. The term "prodrug," refers to compounds which are rapidly transformed in vivo to parent compounds of formula (I) for example, by hydrolysis in blood.

Because carbon-carbon double bonds exist in the present compounds, the invention contemplates various geometric isomers and mixtures thereof resulting from the arrangement of substituents around these carbon-carbon double bonds. It should be understood that the invention encompasses both isomeric forms, or mixtures thereof, which possess the ability to inhibit angiogenesis. These substituents are designated as being in the E or Z configuration wherein the term "E" represents higher order substituents on opposite sides of the carbon-carbon double bond, and the term "Z" represents higher order substituents on the same side of the carbon-carbon double bond.

In accordance with methods of treatment and pharmaceutical compositions of the invention, the compounds can be administered alone or in combination with other anticancer agents. When using the compounds, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The antiangiogenic effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefore.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Determination of Biological Activity

*Proc. Natl. Acad. Sci. USA* 94: 6099-6103 (1997) and *Chemistry and Biology,* 4(6): 461-471 (1997) report that both AGM-1470 and ovalicin, a sequiterpene isolated from the fungus *Pseudorotium ocalis* have been found to bind to a common bifunctional protein, type 2-methionine aminopeptidase (MetAP-2) and conclude that MetAP2 plays a critical role in the proliferation of endothelial cells and may serve as a promising target for the development of new anti-angiogenic drugs.

Assays for the inhibition of catalytic activity of MetAP2 were performed in 96-well microtiter plates. Compounds to be tested (compounds of formula (I) where $R^2$ is hydrogen) were dissolved in dimethyl sulfoxide at 10 mM and diluted ten-fold in assay buffer (50 mM HEPES, pH 7.4, 125 mM NaCl). Ten microliters of solution of each compound to be tested for inhibition were introduced into each cell of the plate. Zero inhibition of enzyme activity was taken to be the result obtained in cells in which 10 μL of assay buffer was placed. A mixture totaling 90 μL per well and made up of 84 mL of assay buffer, 1 μL of L-amino acid oxidase (Sigma Catalog No. A-9378, ~11 mg/mL), 1 μL of horseradish peroxidase (Sigma Catalog No. P-8451, dissolved in assay buffer at a concentration of 10 mg/mL), 1 μL of the tripeptide Met-Ala-Ser (Bachem) dissolved in assay buffer at concentration of 50 mM, 1 μL of ortho-dianisidine (Sigma Catalog No. D-1954, freshly made solution in water at a concentration of 10 mg/mL), and MetAP2 at a final concentration of 8 nM was rapidly mixed and added to each cell containing test or control compound. The absorbance at 450 nanometers was measured every 20 seconds over a period of twenty minutes using an automatic plate reader. (Molecular Devices, CA, USA). The Vmax in mOD/min, calculated for each well, was used to represent MetAP2 activity. The $I_{C50}$ for each inhibitor was obtained by plotting the remaining activity versus inhibitor concentrations. Representative compounds of the present invention had $I_{C50}$'s between about 0.005 μM and >100 μM. Preferred compounds of the present invention had $I_{C50}$'s between about 0.005 μM and about 10 μM. Most preferred compounds had $I_{C50}$'s of between about 0.005 μM and about 0.1 μM.

As the literature has established a causal link between inhibition of MetAP2 and the resultant inhibition of endothelial cell proliferation and angiogenesis (see *Proc. Natl. Acad. Sci. USA* 94: 6099-6103 (1997) and *Chemistry and Biology,* 4(6): 461-471 (1997)), it can be inferred that the compounds of the invention, including, but not limited to those specified in the examples, possess antiangiogenic activity. As angiogenesis inhibitors, such compounds are useful in the treatment of both primary and metastatic solid tumors, including carcinomas; of breast, colon, rectum, lung, oropharynx, hypopharynx, esophagus, stomach, pancreas, liver, gallbladder and bile ducts, small intestine, urinary tract (including kidney, bladder, and urothelium), female genital tract (including cervix, uterus, and ovaries as well as choriocarcinoma and gestational trophoblastic disease), male genital tract (including prostate, seminal vesicles, testes, and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e., chloromas, plasmacytomas and the plaques and tumors of mycosis fungicides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents. Additionally, the compounds of the invention can be used in the prevention of cancer (chemo prevention). The compounds of the invention can also be useful in the treatment of the aforementioned conditions by mechanisms other than the inhibition of angiogenesis.

Further uses include the treatment and prophylaxis of autoimmune diseases such as rheumatoid, immune and degenerative arthritis; psoriatic arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemagiomas, and capillary proliferation within atherosclerotic plaques; endometriosis; obesity; systemic sclerosis; juvenile angiofibroma; septic shock; cerebral edema (from head trauma); Osler-Webber Syndrome; myocardial angiogenesis; plaque neovascularization; telangiectasia; hemophiliac joints; angiofibroma; and wound granulation. Other uses include the treatment of diseases characterized by excessive or abnormal stimulation of endothelial cells, including not limited to intestinal adhesions, Crohn's disease, atherosclerosis, scleroderma, and hypertrophic scars, i.e., keloids. Another use is as a birth control agent, by inhibiting ovulation and establishment of the placenta. The compounds of the invention are also useful in the treatment of diseases that have angiogenesis as a pathologic consequence such as cat scratch disease (*Rochele minutesalia quintosa*) and ulcers (*Helicobacter pylori*). The compounds of the invention are also useful to reduce bleeding by administration prior to surgery, especially for the treatment of resectable tumors.

As MetAP2 inhibitors, the compounds of the invention also have use as antibacterial, antimalarial, and antileishmaniasis agents.

Synthetic Methods

Abbreviations which have been used in the descriptions of the scheme and the examples that follow are: DIAD for diisopropyl azodicarboxylate; DEAD for diethyl azodicarboxylate; TFA for trifluoracetic acid; dppf for 1,1'-bis(diphenylphosphino)ferrocene; DMSO for dimethylsulfoxide; THF for tetrahydrofuran; and DMF for N,N-dimethylformamide.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups A, $R^1$, $R^2$, $R^3$, $R^4$, and $R^5$ are as defined above unless otherwise noted below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

Scheme 1

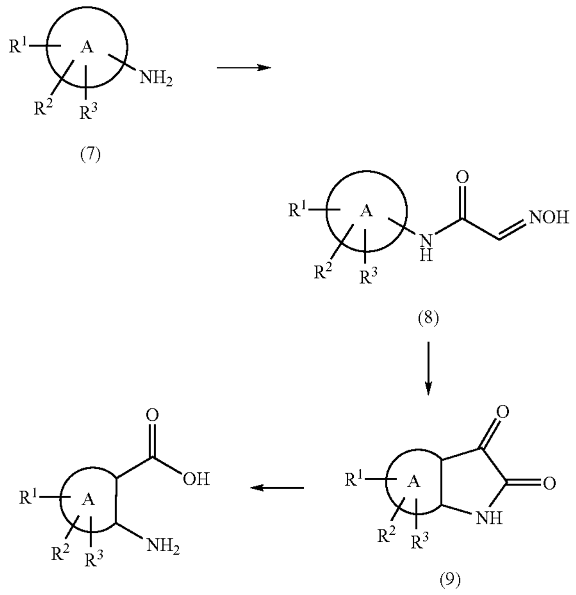

(7) (8) (9) (10)

Scheme 1 shows the synthesis of compounds of formula (10). Compounds of formula (7) can be treated with chloral hydrate in the presence of a dehydrating agent, such as sodium sulfate, then treated with concentrated HCl and hydroxylamine hydrochloride to provide compounds of formula (8). Compounds of formula (8) can be treated with concentrated sulfuric acid to provide compounds of formula (9). Conversion of compounds of formula (9) to compounds of formula (10) can be accomplished by treatment with sodium hydroxide and hydrogen peroxide.

Scheme 2

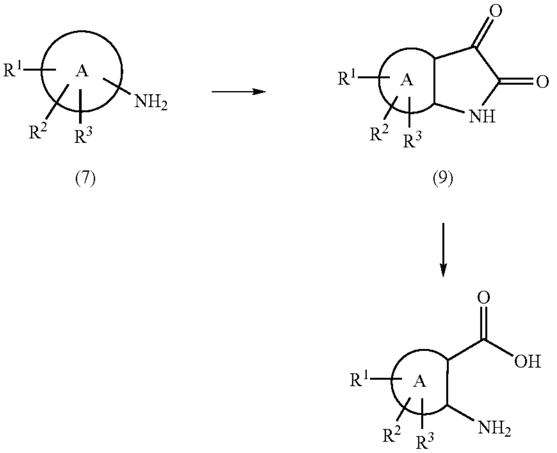

(7) (9) (10)

Scheme 2 shows an alternative preparation of compounds of formula (10). Compounds of formula (7) can be converted to compounds of formula (9) by treatment with glacial acetic acid and diethyl ketomalonate followed by treatment with potassium hydroxide. Conversion of compounds of formula (9) to compounds of formula (10) can be accomplished by the methods described in Scheme 1.

Scheme 3

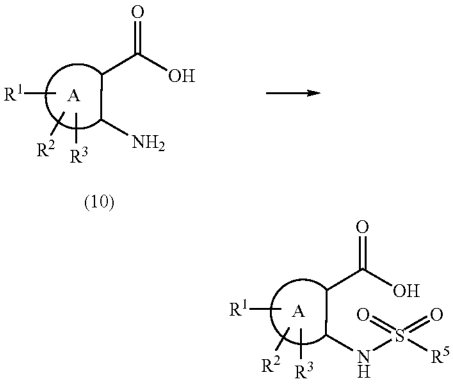

(10) (Ia)

As shown in Scheme 3, compounds of formula (10) can be converted to compounds of formula (Ia) by treatment with chlorotrimethylsilane in the presence of a base such as triethylamine or pyridine, followed by sequential treatment with an appropriately substituted sulfonyl chloride ($R^5$—$SO_2Cl$) and a strong acid such as HCl.

Scheme 4

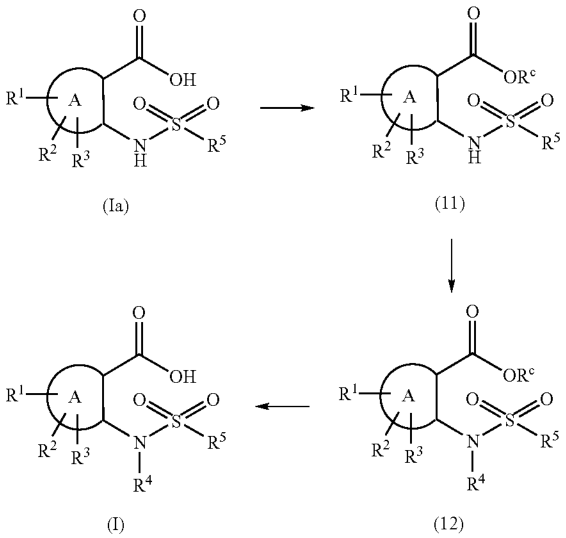

(Ia) (11) (I) (12)

Scheme 4 shows the formation of compounds of formula (I) where $R^4$ is other than hydrogen. Compounds of formula (Ia) (compounds of formula (I) where $R^4$ is hydrogen) can be protected as an alkyl ester using conditions known to those of ordinary skill in the art to provide compounds of formula (11) (where $R_c$ is alkyl). Compounds of formula (11) can be reacted with an appropriately substituted alcohol ($R^4$—OH, where $R^4$ is other than hydrogen) in the presence of a trialkyl- or triarylphosphine (such as tributylphosphine or triphenylphosphine) and either DIAD or DEAD to provide compounds of formula (12) where $R^4$ is other than hydrogen. Hydrolysis of the ester using conditions known to those of ordinary skill in the art provides compounds of formula (I).

Scheme 5

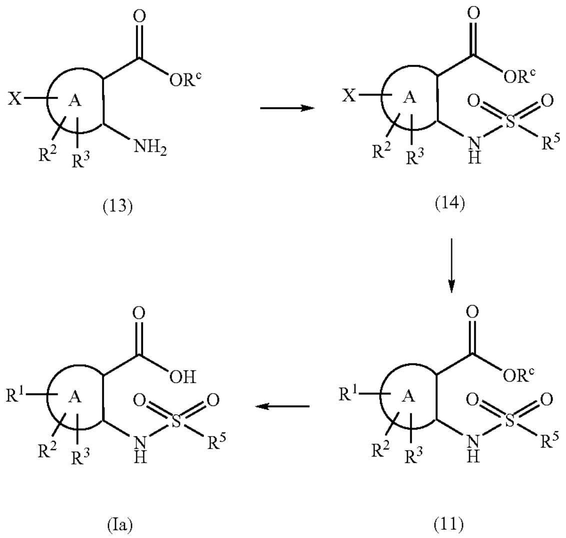

(13) (14) (Ia) (11)

As shown in Scheme 5, compounds of formula (13) where X is Br, Cl, or I and $R^c$ is an alkyl group (prepared by esterifying the corresponding carboxylic acid using methods known to those of ordinary skill in the art) can be converted to compounds of formula (Ia). Compounds of formula (13) can be converted to compounds of formula (14) by the methods described in Scheme 3. Compounds of formula (14) can be reacted with an appropriately substituted organometallic coupling partner ($R^1$-M, where M is a metal such as ZnCl or ZnBr) in the presence of a palladium catalyst (such as Pd(dppf)$Cl_2$) and copper iodide to provide compounds of formula (11). Hydrolysis of the ester with a hydroxide base such as sodium hydroxide or lithium hydroxide provides compounds of formula (Ia) (compounds of formula (I) where $R^4$ is hydrogen).

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.0 (developed by Advanced Chemistry Development, Inc., Toronto, ON, Canada) or were given names which appeared to be consistent with ACD nomenclature.

EXAMPLE 1

5-ethyl-2-[(phenylsulfonyl)amino]benzoic acid

EXAMPLE 1A

N-(4-ethylphenyl)-2-(hydroxyimino)acetamide

A mixture of chloral hydrate (26.48 g, 160 mmol), anhydrous sodium sulfate (381 g, 2.68 mol), and 4-ethylaniline (18.6 mL, 150 mmol) in water (910 mL) at 80° C. was treated sequentially with concentrated HCl (20 mL) and a solution of hydroxylamine hydrochloride (31.8 g, 458 mmol) in water (150 mL). The mixture was heated to 80° C. for 1 hour, cooled to room temperature, and filtered. The filter cake was dried under vacuum to provide the desired product. MS (DCI) m/e 193 $(M+H)^+$, 211 $(M+NH_4)^+$.

EXAMPLE 1B

5-ethyl-1H-indole-2,3-dione

Concentrated sulfuric acid (300 mL) at 50° C. was treated portionwise with Example 1A (28.8 g, 150 mmol), stirred at 50° C. for 30 minutes, poured over ice, stirred for 30 minutes, and filtered. The filter cake was dried under vacuum to provide the desired product. MS (DCI) m/e 176 $(M+H)^+$, 193 $(M+NH_4)^+$.

EXAMPLE 1C

2-amino-5-ethylbenzoic acid

A mixture of Example 1B (11.7 g, 66.9 mmol) in 1M NaOH (300 mL) was treated dropwise with 30% aqueous hydrogen peroxide (300 mL), heated to 50° C. for 30 minutes, cooled to room temperature, and filtered. The filtrate was adjusted to pH 4 with concentrated HCl, cooled to 4° C., and filtered. The filter cake was dried under vacuum to provide the desired product (4.46 g). MS (ESI(−)) m/e 164 $(M-H)^-$.

EXAMPLE 1D 5-ethyl-2-[(phenylsulfonyl)amino]benzoic acid

A solution of Example 1C (0.033 g, 0.200 mmol) in dichloromethane (1 mL) was treated with 1M chlorotrimethylsilane in dichloromethane (440 μL, 0.044 mmol) and pyridine (56.6 μL, 0.70 mmol), shaken for 4 hours at ambient temperature, treated with a solution of benzenesulfonyl chloride (0.042 g, 0.24 mmol) in dichloromethane (1 mL), and shaken for 16 hours at ambient temperature. The mixture was concentrated, the residue was acidified to pH 1.0 with 5% aqueous HCl, and the solution was extracted with dichloromethane. The extracts were washed sequentially with water and brine, dried ($MgSO_4$), filtered, and concentrated. The concentrate was purified by $C_{18}$ reverse-phase HPLC with acetonitrile/water/0.5 mM ammonium acetate to provide the desired product. MS (ESI(+)) m/e 306 $(M+H)^+$, 323 $(M+NH_4)^+$, 328 $(M+Na)^+$; (ESI(−)) m/e 304 $(M-H)^-$; $^1$H NMR (300 MHz, DMSO-$d_6$) δ 10.96 (br s, 1H), 7.78 (d, 2H), 7.73 (d, 1H), 7.64 (m, 1H), 7.55 (m, 2H), 7.42 (m, 2H), 2.54 (q, 2H), 1.10 (t, 3H).

EXAMPLE 2

5-isopropyl-2-[(phenylsulfonyl)amino]benzoic acid

EXAMPLE 2A

N-(2-bromo-4-isopropylphenyl)acetamide

A mixture of 2-bromo-4-isopropylaniline (5.05 g, 23.6 mmol), acetic anhydride (2.4 mL, 25 mmol), and triethylamine (3.5 mL, 25 mmol) in dichloromethane (25 mL) was stirred at ambient temperature for 4 days. The mixture was diluted with dichloromethane, washed sequentially with saturated aqueous $Na_2CO_3$ and 1M HCl, dried ($MgSO_4$), filtered, and concentrated to provide the desired product (5.85 g). MS (DCI) m/e 256, 258 $(M+H)^+$; 273, 275 $(M+NH_4)^+$.

EXAMPLE 2B 2-(acetylamino)-5-isopropylbenzoic acid

A mixture of Example 2A (3.33 g, 13.0 mmol), and [1,1'-bis(diphenylphosphino)ferrocene]dichloropalladium(II) dichloromethane complex (1.00 g, 1.2 mmol) in triethylamine (5.5 mL), dimethylformamide (25 mL), and water (5 mL) was shaken at 120° C. in a reactor pressurized with 850 psi of CO for 18 hours. The mixture was filtered, the filter cake was washed with ethyl acetate, and the combined filtrates were partitioned between diethyl ether and 1M NaOH. The aqueous phase was acidified with 12M HCl and extracted twice with ethyl acetate. The combined extracts were washed with brine, dried ($MgSO_4$), filtered, and concentrated to provide the desired product (2.38 g). MS (ESI(+)) m/e 222 $(M+H)^+$, 244 $(M+Na)^+$; (ESI(−)) m/e 220 $(M-H)^-$.

EXAMPLE 2C 2-amino-5-isopropylbenzoic acid

A mixture of Example 2B (0.621 g, 2.81 mmol) and lithium hydroxide monohydrate (0.38 g, 9.0 mmol) in THF (6 mL) and water (6 mL) was stirred at 60° C. for 72 hours, acidified to pH 3.5 with 1M HCl, and extracted twice with ethyl acetate. The combined extracts were dried ($MgSO_4$), filtered, and concentrated. The concentrate was purified by $C_{18}$ reverse-phase HPLC with acetonitrile/water/0.1% TFA to provide the desired product. MS (ESI(+)) m/e 180 $(M+H)^+$; (ESI(−)) m/e 178 $(M-H)^-$.

EXAMPLE 2D 5-isopropyl-2-[(phenylsulfonyl)amino]benzoic acid

The desired product was prepared by substituting Example 2C for Example 1C in Example 1D. MS (ESI(+)) m/e 320 $(M+H)^+$, 337 $(M+NH_4)^+$, 342 $(M+Na)^+$; (ESI(−)) m/e 318 $(M-H)^-$; $^1$H NMR (300 MHz, DMSO-$d_6$) δ 10.98 (s, 1H), 7.80 (d, 2H), 7.73 (d, 1H), 7.64 (m, 1H), 7.58 (m, 2H), 7.43 (m, 2H), 2.84 (s, 1H), 1.14 (d, 6H).

EXAMPLE 3

6-[(phenylsulfonyl)amino]-5-indanecarboxylic acid

The desired product was prepared by substituting 5-indanamine for 4-ethylaniline in Examples 1A-D. MS (ESI(+)) m/e 318 $(M+H)^+$, 335 $(M+NH_4)^+$, 340 $(M+Na)^+$; (ESI(−)) m/e 316 $(M-H)^-$; $^1$H NMR (300 MHz, DMSO-$d_6$) δ 11.18 (s, 1H), 7.79 (d, 2H), 7.72 (s, 1H), 7.62 (m, 1H), 7.55 (m, 2H), 7.41 (s, 1H), 2.85 (t, 2H), 2.78 (t, 2H), 1.97 (p, 2H).

EXAMPLE 4

5-isobutyl-2-[(phenylsulfonyl)amino]benzoic acid

EXAMPLE 4A methyl 5-bromo-2-[(phenylsulfonyl)amino]benzoate

A mixture of methyl 2-amino-5-bromobenzoate (23.34 g, 101 mmol) in pyridine (100 mL) was treated with a solution of benzenesulfonyl chloride (14 mL, 110 mmol), stirred for 16 hours at ambient temperature, and concentrated. The concentrate was dissolved in dichloromethane, washed twice with 1N $NaHSO_4$, dried ($MgSO_4$), filtered, and concentrated. The concentrate was recrystallized from 3:1 ethanol/water (200 mL) to provide the desired product (33.4 g). MS (DCI) m/e 387, 389 $(M+NH_4)^+$; $^1$H NMR (300 MHz, DMSO-$d_6$) δ 10.32 (s, 1H), 7.91 (d, 1H), 7.80 (d, 1H), 7.77 (s, 1H), 7.75 (dd, 1H), 7.66 (d, 1H), 7.61-7.53 (m, 2H), 7.39 (d, 1H), 3.79 (s, 3H).

EXAMPLE 4B 5-isobutyl-2-[(phenylsulfonyl)amino]benzoic acid

A mixture of Example 4A (0.09 g, 0.24 mmol), Pd(dppf)$Cl_2$ (5 mol %), and CuI (6 mol %) was sealed using a crimper and treated with a solution of isobutylzinc bromide (0.5M in THF, 0.96 mL, 0.48 mmol). The reaction was heated in a single-mode microwave cavity in the Smith synthesizer at 160° C. for 600 seconds and filtered through a 1 micron PTFE syringe filter. The filtrate was concentrated, dissolved in 1:1 $CH_3OH$:DMSO (1.5 mL), and purified using a $C_{18}$ reverse-phase HPLC with acetonitrile/water/1% TFA. The purified ester was saponified by treatment with 10 equivalents of 2N NaOH in 1:1 $CH_3OH$:THF at 70° C. for 48 hours. The mixture was extracted with ethyl acetate and the extract was concentrated to provide the desired product. MS (ESI(+)) m/e 334 $(M+H)^+$, 351 $(M+NH_4)^+$, 356 $(M+Na)^+$; $^1H$ NMR (300 MHz, DMSO-$d_6$) δ 10.90 (s, 1H), 7.80 (m, 2H), 7.40 (m, 3H), 7.10 (s, 1H), 6.80 (m, 1H), 6.50 (m, 1H), 2.20 (d, 2H), 1.70 (m, 1H), 0.80 (d, 6H).

EXAMPLE 5

2-[(phenylsulfonyl)amino]-5-propylbenzoic acid

The desired product was prepared by substituting propylzinc bromide for isobutylzinc bromide in Example 4B. MS (ESI(+)) m/e 320 $(M+H)^+$, 337 $(M+NH_4)^+$, 342 $(M+Na)^+$; (ESI(−)) m/e 318 $(M-H)^-$; $^1H$ NMR (300 MHz, DMSO-$d_6$) δ 10.90 (s, 1H), 7.78 (m, 2H), 7.38 (m, 3H), 7.20 (s, 1H), 6.80 (m, 1H), 6.60 (m, 1H), 2.20 (t, 2H), 1.50 (t, 2H), 0.90 (t, 3H).

EXAMPLE 6

5-cyclopentyl-2-[(phenylsulfonyl)amino]benzoic acid

The desired product was prepared by substituting cyclopentylzinc bromide for isobutylzinc bromide in Example 4B. MS (ESI(+)) m/e 346 $(M+H)^+$, 363 $(M+NH_4)^+$, 368 $(M+Na)^+$; (ESI(−)) m/e 344 $(M-H)^-$; $^1H$ NMR (300 MHz, DMSO-$d_6$) δ 10.92 (s, 1H), 7.80 (m, 2H), 7.40 (m, 3H), 7.20 (s, 1H), 6.80 (m, 1H), 6.60 (m, 1H), 2.60 (m, 1H), 1.82 (m, 2H), 1.62 (m, 2H), 1.50 (m, 2H), 1.40 (m, 2H).

EXAMPLE 7

5-cyclohexyl-2-[(phenylsulfonyl)amino]benzoic acid

The desired product was prepared by substituting cyclohexylzinc bromide for isobutylzinc bromide in Example 4B. MS (ESI(+)) m/e 360 $(M+H)^+$, 377 $(M+NH_4)^+$, 382 $(M+Na)^+$; (ESI(−)) m/e 358 $(M-H)^-$; $^1H$ NMR (300 MHz, DMSO-$d_6$) δ 10.94 (s, 1H), 7.80 (m, 2H), 7.40 (m, 3H), 7.20 (s, 1H), 6.80 (m, 1H), 6.60 (m, 1H), 2.25 (m, 1H), 1.6-1.75 (m, 5H), 1.20-1.35 (m, 5H).

EXAMPLE 8

5-butyl-2-[(phenylsulfonyl)amino]benzoic acid

The desired product was prepared by substituting butylzinc bromide for isobutylzinc bromide in Example 4B. MS (ESI (+)) m/e 334 $(M+H)^+$, 351 $(M+NH_4)^+$, 356 $(M+Na)^+$; (ESI (−)) m/e 332 $(M-H)^-$; $^1H$ NMR (300 MHz, DMSO-$d_6$) δ 10.94 (s, 1H), 7.80 (m, 2H), 7.40 (m, 3H), 7.20 (s, 1H), 6.80 (m, 1H), 6.60 (m, 1H), 2.24 (t, 2H), 1.40 (m, 2H), 1.20 (m, 2H), 0.91 (t, 3H).

EXAMPLE 9

5-(3-methylbutyl)-2-[(phenylsulfonyl)amino]benzoic acid

The desired product was prepared by substituting 3-methylbutylzinc bromide for isobutylzinc bromide in Example 4B. MS (ESI(+)) m/e 348 $(M+H)^+$, 365 $(M+NH_4)^+$, 370 $(M+Na)^+$; (ESI(−)) m/e 346 $(M-H)^-$; $^1H$ NMR (300 MHz, DMSO-$d_6$) δ 10.94 (s, 1H), 7.80 (m, 2H), 7.40 (m, 3H), 7.20 (s, 1H), 6.80 (m, 1H), 6.60 (m, 1H), 2.30 (t, 2H), 1.50 (m, 1H), 1.30 (m, 2H), 0.88 (d, 6H).

EXAMPLE 10

5-(2-methylbutyl)-2-[(phenylsulfonyl)amino]benzoic acid

The desired product was prepared by substituting 2-methylbutylzinc bromide for isobutylzinc bromide in Example 4B. MS (ESI(+)) m/e 348 $(M+H)^+$, 365 $(M+NH_4)^+$, 370 $(M+Na)^+$; (ESI(−)) m/e 346 $(M-H)^-$; $^1H$ NMR (300 MHz, DMSO-$d_6$) δ 10.92 (s, 1H), 7.80 (m, 2H), 7.40 (m, 3H), 7.20 (s, 1H), 6.80 (m, 1H), 6.50 (m, 1H), 2.30 (m, 1H), 2.10 (m, 1H), 1.45 (m, 1H), 1.30 (m, 1H), 1.05 (m, 1H), 0.85 (m, 3H), 0.75 (m, 3H).

EXAMPLE 11

5-pentyl-2-[(phenylsulfonyl)amino]benzoic acid

The desired product was prepared by substituting pentylzinc bromide for isobutylzinc bromide in Example 4B. MS (ESI(+)) m/e 348 $(M+H)^+$, 365 $(M+NH_4)^+$, 370 $(M+Na)^+$; (ESI(−)) m/e 346 $(M-H)^-$; $^1H$ NMR (300 MHz, DMSO-$d_6$) δ (s, 1H), 7.80 (m, 2H), 7.40 (m, 3H), 7.20 (s, 1H), 6.80 (m, 1H), 6.50 (m, 1H), 2.30 (t, 2H), 1.42 (m, 2H), 1.22 (m, 4H), 0.89 (t, 3H).

EXAMPLE 12

5-(2-ethylbutyl)-2-[(phenylsulfonyl)amino]benzoic acid

The desired product was prepared by substituting 2-ethylbutylzinc bromide for isobutylzinc bromide in Example 4B. MS (ESI(+)) m/e 362 $(M+H)^+$, 379 $(M+NH_4)^+$, 384 $(M+Na)^+$; (ESI(−)) m/e 360 $(M-H)^-$; $^1H$ NMR (300 MHz, DMSO-$d_6$) δ 10.92 (s, 1H), 7.80 (m, 2H), 7.38 (m, 3H), 7.20 (s, 1H), 6.80 (m, 1H), 6.50 (m, 1H), 2.20 (d, 2H), 1.30 (m, 1H), 1.08 (m, 4H), 0.80 (t, 6H).

EXAMPLE 13

5-hexyl-2-[(phenylsulfonyl)amino]benzoic acid

The desired product was prepared by substituting hexylzinc bromide for isobutylzinc bromide in Example 4B. MS (ESI(+)) m/e 362 $(M+H)^+$, 379 $(M+NH_4)^+$, 384 $(M+Na)^+$; (ESI(−)) m/e 360 $(M-H)^-$; $^1H$ NMR (300 MHz, DMSO-$d_6$) δ 10.92 (s, 1H), 7.80 (m, 2H), 7.40 (m, 3H), 7.20 (s, 1H), 6.80 (m, 1H), 6.50 (m, 1H), 2.30 (t, 2H), 1.40 (m, 2H), 1.24 (m, 6H), 0.84 (t, 3H).

EXAMPLE 14

2-{[(2-chloro-4-fluorophenyl)sulfonyl]amino}-5-ethylbenzoic acid

The desired product was prepared by substituting 2-chloro-4-fluorobenzenesulfonyl chloride for benzenesulfonyl chloride in Example 1D. MS (ESI(+)) m/e 358 $(M+H)^+$, 375 $(M+NH_4)^+$, 380 $(M+Na)^+$; (ESI(−)) m/e 356 $(M-H)^-$; $^1H$ NMR (300 MHz, DMSO-$d_6$) δ 8.09 (dd, 1H), 7.66 (d, 1H), 7.47 (dd, 1H), 7.30 (td, 1H), 7.08 (d, 1H), 6.98 (dd, 1H), 2.44 (q, 2H), 1.08 (t, 3H).

EXAMPLE 15

5-ethyl-2-{[(3-methylphenyl)sulfonyl]amino}benzoic acid

The desired product was prepared by substituting 3-methylbenzenesulfonyl chloride for benzenesulfonyl chloride in Example 1D. MS (ESI(+)) m/e 320 $(M+H)^+$, 337 $(M+NH_4)^+$, 342 $(M+Na)^+$; (ESI(−)) m/e 318 $(M-H)^-$; $^1$H NMR (300 MHz, DMSO-$d_6$) δ 7.65 (d, 1H), 7.55 (s, 1H), 7.51 (d, 1H), 7.33 (t, 1H), 7.29 (m, 1H), 7.23 (d, 1H), 7.00 (dd, 1H), 2.45 (q, 2H), 2.30 (s, 3H), 1.08 (t, 3H).

EXAMPLE 16

5-ethyl-2-{[(2-fluorophenyl)sulfonyl]amino}benzoic acid

The desired product was prepared by substituting 2-fluorobenzenesulfonyl chloride for benzenesulfonyl chloride in Example 1D. MS (ESI(+)) m/e 324 $(M+H)^+$, 341 $(M+NH_4)^+$, 346 $(M+Na)^+$; (ESI(−)) m/e 322 $(M-H)^-$; $^1$H NMR (300 MHz, DMSO-$d_6$) δ 7.81 (td, 1H), 7.66 (d, 1H), 7.51 (m, 1H), 7.27-7.18 (m, 3H), 7.00 (dd, 1H), 2.45 (q, 2H), 1.08 (t, 3H).

EXAMPLE 17

5-ethyl-2-{[(3-fluorophenyl)sulfonyl]amino}benzoic acid

The desired product was prepared by substituting 3-fluorobenzenesulfonyl chloride for benzenesulfonyl chloride in Example 1D. MS (ESI(+)) m/e 324 $(M+H)^+$, 341 $(M+NH_4)^+$, 346 $(M+Na)^+$; (ESI(−)) m/e 322 $(M-H)^-$; $^1$H NMR (300 MHz, DMSO-$d_6$) δ 7.65 (d, 1H), 7.55 (m, 1H), 7.50 (td, 1H), 7.44 (m, 1H), 7.32 (m, 1H), 7.24 (d, 1H), 7.04 (dd, 1H), 2.45 (q, 2H), 1.09 (t, 3H).

EXAMPLE 18

5-ethyl-2-{[(4-fluorophenyl)sulfonyl]amino}benzoic acid

The desired product was prepared by substituting 4-fluorobenzenesulfonyl chloride for benzenesulfonyl chloride in Example 1D. MS (ESI(+)) m/e 324 $(M+H)^+$, 341 $(M+NH_4)^+$, 346 $(M+Na)^+$; (ESI(−)) m/e 322 $(M-H)^-$; $^1$H NMR (300 MHz, DMSO-$d_6$) δ 7.76 (dd, 2H), 7.65 (d, 1H), 7.28 (t, 2H), 7.24 (d, 1H), 7.05 (dd, 1H), 2.46 (q, 2H), 1.09 (t, 3H).

EXAMPLE 19

2-{[(2-chlorophenyl)sulfonyl]amino}-5-ethylbenzoic acid

The desired product was prepared by substituting 2-chlorobenzenesulfonyl chloride for benzenesulfonyl chloride in Example 1D. MS (ESI(+)) m/e 340, 342 $(M+H)^+$, 357, 359 $(M+NH_4)^+$, 362, 364 $(M+Na)^+$; (ESI(−)) m/e 338, 340 $(M-H)^-$; $^1$H NMR (300 MHz, DMSO-$d_6$) δ 8.06 (d, 1H), 7.67 (d, 1H), 7.47 (m, 2H), 7.43 (m, 1H), 7.09 (d, 1H), 6.97 (dd, 1H), 2.44 (q, 2H), 1.08 (t, 3H).

EXAMPLE 20

2-{[(3-chlorophenyl)sulfonyl]amino}-5-ethylbenzoic acid

The desired product was prepared by substituting 3-chlorobenzenesulfonyl chloride for benzenesulfonyl chloride in Example 1D. MS (ESI(+)) m/e 340, 342 $(M+H)^+$, 357, 359 $(M+NH_4)^+$, 362, 364 $(M+Na)^+$; (ESI(−)) m/e 338, 340 $(M-H)^-$; $^1$H NMR (300 MHz, DMSO-$d_6$) δ 7.65 (m, 3H), 7.53 (m, 1H), 7.48 (t, 1H), 7.22 (d, 1H), 7.04 (dd, 1H), 2.45 (q, 2H), 1.09 (t, 3H).

EXAMPLE 21

2-{[(3,4-difluorophenyl)sulfonyl]amino}-5-ethylbenzoic acid

The desired product was prepared by substituting 3,4-difluorobenzenesulfonyl chloride for benzenesulfonyl chloride in Example 1D. MS (ESI(+)) m/e 342 $(M+H)^+$, 359 $(M+NH_4)^+$, 364 $(M+Na)^+$; (ESI(−)) m/e 340 $(M-H)^-$, $^1$H NMR (300 MHz, DMSO-$d_6$) δ 7.69 (m, 1H), 7.67 (d, 1H), 7.56 (m, 1H), 7.53 (m, 1H), 7.24 (d, 1H), 7.07 (dd, 1H), 2.47 (q, 2H), 1.10 (t, 3H).

EXAMPLE 22

5-ethyl-2-[(1-naphthylsulfonyl)amino]benzoic acid

The desired product was prepared by substituting 1-naphthalenesulfonyl chloride for benzenesulfonyl chloride in Example 1D. MS (ESI(+)) m/e 356 $(M+H)^+$, 373 $(M+NH_4)^+$, 378 $(M+Na)^+$; (ESI(−)) m/e 354 $(M-H)^-$; $^1$H NMR (300 MHz, DMSO-$d_6$) δ 8.70 (d, 1H), 8.20 (d, 1H), 8.09 (d, 1H), 7.98 (d, 1H), 7.62 (t, 1H), 7.60-7.56 (m, 3H), 7.18 (d, 1H), 7.01 (d, 1H), 2.39 (q, 2H), 1.03 (t, 3H).

EXAMPLE 23

5-ethyl-2-({[3-(trifluoromethyl)phenyl]sulfonyl}amino)benzoic acid

The desired product was-prepared by substituting 3-(trifluoromethyl)benzenesulfonyl chloride for benzenesulfonyl chloride in Example 1D. MS (ESI(+)) m/e 374 $(M+H)^+$, 391 $(M+NH_4)^+$, 396 $(M+Na)^+$; (ESI(−)) m/e 372 $(M-H)^-$; $^1$H NMR (300 MHz, DMSO-$d_6$) δ 8.04 (d, 1H), 7.98 (s, 1H), 7.89 (d, 1H), 7.75 (t, 1H), 7.69 (d, 1H), 7.28 (d, 1H), 7.10 (dd, 1H), 2.49 (q, 2H), 1.13 (t, 3H).

EXAMPLE 24

2-{[(2,3-dichlorophenyl)sulfonyl]amino}-5-ethylbenzoic acid

The desired product was prepared by substituting 2,3-dichlorobenzenesulfonyl chloride for benzenesulfonyl chloride in Example 1D. MS (ESI(+)) m/e 374, 376 $(M+H)^+$, 391, 393 $(M+NH_4)^+$, 396, 398 $(M+Na)^+$; (ESI(−)) m/e 372, 374 $(M-H)^-$; $^1$H NMR (300 MHz, DMSO-$d_6$) δ 8.12 (dd, 1H), 7.85 (dd, 1H), 7.73 (d, 1H), 7.53 (t, 1H), 7.22 (d, 1H), 7.18 (dd, 1H), 2.49 (q, 2H), 1.09 (t, 3H).

EXAMPLE 25

2-{[(2,5-dichlorophenyl)sulfonyl]amino}-5-ethylbenzoic acid

The desired product was prepared by substituting 2,5-dichlorobenzenesulfonyl chloride for benzenesulfonyl chloride in Example 1D. MS (ESI(+)) m/e 374, 376 $(M+H)^+$, 391, 393 $(M+NH_4)^+$, 396, 398 $(M+Na)^+$; (ESI(−)) m/e 372, 374 $(M-H)^-$; $^1$H NMR (300 MHz, DMSO-$d_6$) δ 7.99 (d, 1H), 7.67

(d, 1H), 7.54 (dd, 1H), 7.50 (d, 1H), 7.11 (d, 1H), 7.04 (dd, 1H), 2.45 (q, 2H), 1.09 (t, 3H).

EXAMPLE 26

2-{[(3,5-dichlorophenyl)sulfonyl]amino}-5-ethyl-benzoic acid

The desired product was prepared by substituting 3,5-dichlorobenzenesulfonyl chloride for benzenesulfonyl chloride in Example 1D. MS (ESI(+)) m/e 374, 376 $(M+H)^+$, 391, 393 $(M+NH_4)^+$, 396, 398 $(M+Na)^+$; (ESI(−)) m/e 372, 374 $(M-H)^-$; $^1$H NMR (300 MHz, DMSO-$d_6$) δ 7.84 (t, 1H), 7.70 (d, 1H), 7.67 (d, 2H), 7.30 (d, 1H), 7.26 (dd, 1H), 2.52 (q, 2H), 1.12 (t, 3H).

EXAMPLE 27

2-{[(2-bromophenyl)sulfonyl]amino}-5-ethylbenzoic acid

The desired product was prepared by substituting 2-bromobenzenesulfonyl chloride for benzenesulfonyl chloride in Example 1D. MS (ESI(+)) m/e 384, 386 $(M+H)^+$, 401, 403 $(M+NH_4)^+$, 406, 408 $(M+Na)^+$; (ESI(−)) m/e 382, 384 $(M-H)^-$; $^1$H NMR (300 MHz, DMSO-$d_6$) δ 8.09 (dd, 1H), 7.69-7.66 (m, 2H), 7.49 (t, 1H), 7.37 (td, 1H), 7.06 (d, 1H), 6.96 (dd, 1H), 2.44 (q, 2H), 1.08 (t, 3H).

EXAMPLE 28

2-{[(3-bromophenyl)sulfonyl]amino}-5-ethylbenzoic acid

The desired product was prepared by substituting 3-bromobenzenesulfonyl chloride for benzenesulfonyl chloride in Example 1D. MS (ESI(+)) m/e 384, 386 $(M+H)^+$, 401, 403 $(M+NH_4)^+$, 406, 408 $(M+Na)^+$; (ESI(−)) m/e 382, 384 $(M-H)^-$; $^1$H NMR (300 MHz, DMSO-$d_6$) δ 7.82 (t, 1H), 7.74-7.70 (m, 2H), 7.68 (d, 1H), 7.44 (t, 1H), 7.27 (d, 1H), 7.12 (dd, 1H), 2.48 (q, 2H), 1.10 (t, 3H).

EXAMPLE 29

5-ethyl-2-{[(4-methylphenyl)sulfonyl]amino}benzoic acid

The desired product was prepared by substituting 4-methylbenzenesulfonyl chloride for benzenesulfonyl chloride in Example 1D. MS (ESI(+)) m/e 320 $(M+H)^+$, 337 $(M+NH_4)^+$, 342 $(M+Na)^+$; (ESI(−)) m/e 318 $(M-H)^-$; $^1$H NMR (300 MHz, DMSO-$d_6$) δ 7.65 (d, 1H), 7.60 (d, 2H), 7.26-7.22 (m, 3H), 7.00 (dd, 1H), 2.44 (q, 2H), 2.29 (s, 3H), 1.08 (t, 3H).

EXAMPLE 30

2-{[(3-cyanophenyl)sulfonyl]amino}-5-ethylbenzoic acid

The desired product was prepared by substituting 3-cyanobenzenesulfonyl chloride for benzenesulfonyl chloride in Example 1D. MS (ESI(+)) m/e 348 $(M+NH_4)^+$, 353 $(M+Na)^+$; (ESI(−)) m/e 329 $(M-H)^-$; $^1$H NMR (300 MHz, DMSO-$d_6$) δ 8.06 (s, 1H), 8.00 (d, 1H), 7.94 (d, 1H), 7.68 (d, 1H), 7.66 (m, 1H), 7.23 (d, 1H), 7.06 (dd, 1H), 2.44 (q, 2H), 1.09 (t, 3H).

EXAMPLE 31

2-{[(4-cyanophenyl)sulfonyl]amino}-5-ethylbenzoic acid

The desired product was prepared by substituting 4-cyanobenzenesulfonyl chloride for benzenesulfonyl chloride in Example 1D. MS (ESI(+)) m/e 348 $(M+NH_4)^+$, 353 $(M+Na)^+$; (ESI(−)) m/e 329 $(M-H)^-$; $^1$H NMR (300 MHz, DMSO-$d_6$) δ 7.92 (d, 2H), 7.86 (d, 2H), 7.65 (d, 1H), 7.22 (d, 1H), 7.05 (dd, 1H), 2.46 (q, 2H), 1.09 (t, 3H).

EXAMPLE 32

2-{[(2,5-dimethylphenyl)sulfonyl]amino}-5-ethyl-benzoic acid

The desired product was prepared by substituting 2,5-dimethylbenzenesulfonyl chloride for benzenesulfonyl chloride in Example 1D. MS (ESI(+)) m/e 334 $(M+H)^+$, 351 $(M+NH_4)^+$, 356 $(M+Na)^+$; (ESI(−)) m/e 332 $(M-H)^-$; $^1$H NMR (300 MHz, DMSO-$d_6$) δ 7.74 (s, 1H), 7.65 (d, 1H), 7.18 (d, 1H), 7.13 (d, 1H), 7.10 (d, 1H), 6.96 (dd, 1H), 2.49 (s, 3H), 2.43 (q, 2H), 2.29 (s, 3H), 1.08 (t, 3H).

EXAMPLE 33

5-ethyl-2-{[(3-methoxyphenyl)sulfonyl]amino}benzoic acid

The desired product was prepared by substituting 3-methoxybenzenesulfonyl chloride for benzenesulfonyl chloride in Example 1D. MS (ESI(+)) m/e 336 $(M+H)^+$, 353 $(M+NH_4)^+$, 358 $(M+Na)^+$; (ESI(−)) m/e 334 $(M-H)^-$; $^1$H NMR (300 MHz, DMSO-$d_6$) δ 7.66 (d, 1H), 7.36 (t, 1H), 7.30-7.26 (m, 2H), 7.22 (m, 1H), 7.06-7.02 (m, 2H), 3.73 (s, 3H), 2.45 (q, 2H), 1.09 (t, 3H).

EXAMPLE 34

2-{[(3-chloro-4-fluorophenyl)sulfonyl]amino}-5-ethylbenzoic acid

The desired product was prepared by substituting 3-chloro-4-fluorobenzenesulfonyl chloride for benzenesulfonyl chloride in Example 1D. MS (ESI(+)) m/e 358, 360 $(M+H)^+$, 375, 377 $(M+NH_4)^+$, 380, 382 $(M+Na)^+$; (ESI(−)) m/e 356, 358 $(M-H)^-$; $^1$H NMR (300 MHz, DMSO-$d_6$) δ 7.81 (dd, 1H), 7.70 (m, 1H), 7.66 (d, 1H), 7.49 (t, 1H), 7.22 (d, 1H), 7.07 (dd, 1H), 2.46 (q, 2H), 1.10 (t, 3H).

EXAMPLE 35

2-{[(2,5-dimethoxyphenyl)sulfonyl]amino}-5-ethyl-benzoic acid

The desired product was prepared by substituting 2,5-dimethoxybenzenesulfonyl chloride for benzenesulfonyl chloride in Example 1D. MS (ESI(+)) m/e 366 $(M+H)^+$, 383 $(M+NH_4)^+$, 388 $(M+Na)^+$; (ESI(−)) m/e 364 $(M-H)^-$; $^1$H NMR (300 MHz, DMSO-$d_6$) δ 7.67 (d, 1H), 7.31 (d, 1H), 7.21 (d, 1H), 7.02 (dd, 1H), 6.98 (d, 1H), 6.95 (dd, 1H), 3.70 (s, 3H), 3.65 (s, 3H), 2.44 (q, 2H), 1.08 (t, 3H).

EXAMPLE 36

5-ethyl-2-{[(5-fluoro-2-methylphenyl)sulfonyl]amino}benzoic acid

The desired product was prepared by substituting 2-methyl-5-fluorobenzenesulfonyl chloride for benzenesulfonyl chloride in Example 1D. MS (ESI(+)) m/e 338 $(M+H)^+$, 355

$(M+NH_4)^+$, 360 $(M+Na)^+$; (ESI(−)) m/e 336 $(M−H)^-$; $^1H$ NMR (300 MHz, DMSO-$d_6$) δ 7.66 (d, 1H), 7.64 (dd, 1H), 7.29 (dd, 1H), 7.23 (td, 1H), 7.11 (d, 1H), 7.01 (dd, 1H), 2.50 (s, 3H), 2.44 (q, 2H), 1.08 (t, 3H).

EXAMPLE 37

5-ethyl-2-[(8-quinolinylsulfonyl)amino]benzoic acid

The desired product was prepared by substituting 8-chlorosulfonylquinoline for benzenesulfonyl chloride in Example 1D. MS (ESI(+)) m/e 357 $(M+H)^+$, 379 $(M+NH_4)^+$; (ESI(−)) m/e 356 $(M−H)^-$; $^1H$ NMR (300 MHz, DMSO-$d_6$) δ 8.97 (dd, 1H), 8.46-8.42 (m, 2H), 8.22 (d, 1H), 7.71 (t, 1H), 7.64 (dd, 1H), 7.58 (d, 1H), 7.43 (d, 1H), 7.09 (dd, 1H), 2.41 (q, 2H), 1.03 (t, 3H).

EXAMPLE 38

5-ethyl-2-({[2-(methylsulfonyl)phenyl]sulfonyl}amino)benzoic acid

The desired product was prepared by substituting 2-(methylsulfonyl)benzenesulfonyl chloride for benzenesulfonyl chloride in Example 1D. MS (ESI(+)) m/e 384 $(M+H)^+$, 401 $(M+NH_4)^+$, 406 $(M+Na)^+$; (ESI(−)) m/e 382 $(M−H)^-$; $^1H$ NMR (300 MHz, DMSO-$d_6$) δ 8.17 (dd, 1H), 8.04 (dd, 1H), 7.78-7.70 (m, 3H), 7.10 (d, 1H), 7.01 (dd, 1H), 2.50 (s, 3H), 2.46 (q, 2H), 1.09 (t, 3H).

EXAMPLE 39

5-ethyl-2-({[2-(trifluoromethoxy)phenyl]sulfonyl}amino)benzoic acid

The desired product was prepared by substituting 2-(trifluoromethoxy)benzenesulfonyl chloride for benzenesulfonyl chloride in Example 1D. MS (ESI(+)) m/e 390 $(M+H)^+$, 407 $(M+NH_4)^+$, 412 $(M+Na)^+$; (ESI(−)) m/e 388 $(M−H)^-$; $^1H$ NMR (300 MHz, DMSO-$d_6$) δ 7.96 (dd, 1H), 7.66 (d, 1H), 7.58 (td, 1H), 7.43 (t, 1H), 7.39 (d, 1H), 7.15 (d, 1H), 7.01 (dd, 1H), 2.44 (q, 2H), 1.08 (t, 3H).

EXAMPLE 40

2-({[5-(dimethylamino)-1-naphthyl]sulfonyl}amino)-5-ethylbenzoic acid

The desired product was prepared by substituting 5-(dimethylamino)-1-naphthalenesulfonyl chloride for benzenesulfonyl chloride in Example 1D. MS (ESI(+)) m/e 399 $(M+H)^+$, 421 $(M+Na)^+$; (ESI(−)) m/e 398 $(M−H)^-$; $^1H$ NMR (300 MHz, DMSO-$d_6$) δ 8.42 (d, 1H), 8.34 (d, 1H), 8.19 (d, 1H), 7.60 (d, 1H), 7.55 (t, 1H), 7.50 (t, 1H), 7.17 (d, 1H), 7.15 (d, 1H), 6.97 (dd, 1H), 2.78 (s, 6H), 2.40 (q, 2H), 1.04 (t, 3H).

EXAMPLE 41

2-({[3,5-bis(trifluoromethyl)phenyl]sulfonyl}amino)-5-ethylbenzoic acid

The desired product was prepared by substituting 3,5-di(trifluoromethyl)benzenesulfonyl chloride for benzenesulfonyl chloride in Example 1D. MS (ESI(+)) m/e 442 $(M+H)^+$, 459 $(M+NH_4)^+$, 464 $(M+Na)^+$; (ESI(−)) m/e 440 $(M−H)^-$; $^1H$ NMR (300 MHz, DMSO-$d_6$) δ 8.36 (s, 1H), 8.20 (s, 2H), 7.67 (d, 1H), 7.33 (d, 1H), 7.27 (d, 1H), 2.53 (q, 2H), 1.10 (t, 3H).

EXAMPLE 42

2-[(phenylsulfonyl)amino]-1-naphthoic acid

EXAMPLE 42A 1H-benzo[e]indole-1,2(3H)-dione

A mixture of 2-naphthylamine (8.0 g, 56 mmol) in glacial acetic acid (500 mL) was treated with diethyl ketomalonate (9.2 mL, 62 mmol), heated to 120° C. for 4 hours, and concentrated. The concentrate was suspended in a solution of KOH (36.8 g, 690 mmol) in water (736 mL) and stirred overnight with a stream of air blowing into the solution. The resulting mixture was filtered and the filtrate was adjusted to approximately pH 3 with concentrated HCl. The resulting suspension was cooled to 0° C. and filtered. The filter cake was dried under vacuum to provide the desired product (8.76 g, 79%). MS (DCI) m/e 198 $(M+H)^+$, 215 $(M+NH_4)^+$.

EXAMPLE 42B 2-amino-1-naphthoic acid

The desired product was prepared by substituting Example 42A for Example 1B in Example 1C. MS (ESI) m/e 200 $(M−H)^-$.

EXAMPLE 42C

2-[(phenylsulfonyl)amino]-1-naphthoic acid

A mixture of Example 42B (0.033 g, 0.200 mmol) in dichloromethane (1 mL) was treated with 1M chlorotrimethylsilane in dichloromethane (440 μL, 0.044 mmol) and pyridine (56.6 μL, 0.70 mmol), shaken for 4 hours at ambient temperature, treated with a solution of benzenesulfonyl chloride (0.042 g, 0.24 mmol) in dimethylacetamide (1 mL), shaken for 16 hours at ambient temperature, and concentrated. The concentrate was acidified to pH 1.0 with 5% aqueous HCl and extracted with dichloromethane. The extracts were washed sequentially with water and brine, dried ($MgSO_4$), filtered, and concentrated. The concentrate was purified by $C_{18}$ reverse-phase HPLC using acetonitrile/water/0.1% TFA to provide the desired product. MS (ESI(+)) m/e 328 $(M+H)^+$, 345 $(M+NH_4)^+$, 350 $(M+Na)^+$; (ESI(−)) m/e 326 $(M−H)^-$; $^1H$ NMR (300 MHz, DMSO-$d_6$) δ 10.30 (br s, 1H), 8.10 (d, 1H), 7.95 (d, 1H), 7.89 (d, 1H), 7.78 (dd, 2H), 7.63-7.50 (m, 5H), 7.31 (d, 1H).

EXAMPLE 43

2-{[(4-chlorophenyl)sulfonyl]amino}-1-naphthoic acid

The desired product was prepared by substituting 4-chlorobenzenesulfonyl chloride for benzenesulfonyl chloride in Example 42C. MS (ESI(+)) m/e 379, 381 $(M+NH_4)^+$, 384, 386 $(M+Na)^+$; (ESI(−)) m/e 360, 362 $(M−H)^-$; $^1H$ NMR (300 MHz, DMSO-$d_6$) δ 10.36 (br s, 1H), 8.05 (d, 1H), 7.96 (d, 1H), 7.75 (d, 2H), 7.63 (d, 2H), 7.59-7.50 (m, 2H), 7.28 (d, 1H).

EXAMPLE 44

2-{[(4-iodophenyl)sulfonyl]amino}-1-naphthoic acid

The desired product was prepared by substituting 4-iodobenzenesulfonyl chloride for benzenesulfonyl chloride in Example 42C. MS (ESI(+)) m/e 471 $(M+NH_4)^+$, 475.9

$(M+Na)^+$; (ESI(−)) m/e 451.9 $(M-H)^-$; $^1$H NMR (300 MHz, DMSO-$d_6$) δ 8.12 (br d, 1H), 7.98-7.89 (m, 4H), 7.6-7.52 (m, 2H), 7.5 (d, 2H), 7.3 (d, 2H).

EXAMPLE 45

2-[(1-naphthylsulfonyl)amino]-1-naphthoic acid

The desired product was prepared by substituting 1-naphthalenesulfonyl chloride for benzenesulfonyl chloride in Example 42C. MS (ESI(+)) m/e 395 $(M+NH_4)^+$, 400 $(M+Na)^+$; (ESI(−)) m/e 376 $(M-H)^-$; $^1$H NMR (300 MHz, DMSO-$d_6$) δ 8.7 (d, 1H), 8.2 (m, 2H), 8.08 (d, 1H), 7.82 (d, 2H), 7.75-7.4 (m, 6H), 7.24 (d, 1H).

EXAMPLE 46

2-{[(3-fluorophenyl)sulfonyl]amino}-1-naphthoic acid

The desired product was prepared by substituting 3-fluorobenzenesulfonyl chloride for benzenesulfonyl chloride in Example, 42C. MS (ESI(+)) m/e 363 $(M+NH_4)^+$, 368 $(M+Na)^+$; (ESI(−)) m/e 344 $(M-H)^-$; $^1$H NMR (300 MHz, DMSO-$d_6$) δ 8.13 (br d, 1H), 7.98-7.89 (m, 2H), 7.65-7.46 (m, 6H), 7.3 (d, 1H).

EXAMPLE 47

2-{[(4-fluorophenyl)sulfonyl]amino}-1-naphthoic acid

The desired product was prepared by substituting 4-fluorobenzenesulfonyl chloride for benzenesulfonyl chloride in Example 42C. MS (ESI(+)) m/e 363 $(M+NH_4)^+$, 368 $(M+Na)^+$; (ESI(−)) m/e 344 $(M-H)^-$; $^1$H NMR (300 MHz, DMSO-$d_6$) δ 8.1 (br d, 1H), 7.98-7.89 (m, 2H), 7.85-7.75 (m, 2H), 7.62-7.49 (m, 2H), 7.43-7.31 (m, 3H).

EXAMPLE 48

2-{[(3,4-difluorophenyl)sulfonyl]amino}-1-naphthoic acid

The desired product was prepared by substituting 3,4-difluorobenzenesulfonyl chloride for benzenesulfonyl chloride in Example 42C. MS (ESI(+)) m/e 381 $(M+NH_4)^+$, 386 $(M+Na)^+$; (ESI(−)) m/e 362 $(M-H)^-$; $^1$H NMR (300 MHz, DMSO-$d_6$) δ 7.89-7.7 (m, 4H), 7.63-7.5 (m, 3H), 7.47 (m, 1H), 7.35 (m, 1H).

EXAMPLE 49

2-{[(2-chloro-4-fluorophenyl)sulfonyl]amino}-1-naphthoic acid

The desired product was prepared by substituting 2-chloro-4-fluorobenzenesulfonyl chloride for benzenesulfonyl chloride in Example 42C. MS (ESI(+)) m/e 397, 399 $(M+NH_4)^+$, 402, 404 $(M+Na)^+$; (ESI(−)) m/e 378, 380 $(M-H)^-$; $^1$H NMR (300 MHz, DMSO-$d_6$) δ 8.24 (s, 1H), 8.04 (dd, 1H), 7.95 (d, 1H), 7.89 (d, 1H), 7.68 (dd, 1H), 7.58 (t, 1H), 7.50 (t, 1H), 7.42 (d, 1H), 7.365 (td, 1H).

EXAMPLE 50

2-{[(2-methylphenyl)sulfonyl]amino}-1-naphthoic acid

The desired product was prepared by substituting 2-methylbenzenesulfonyl chloride for benzenesulfonyl chloride in Example 42C. MS (ESI(+)) m/e 342 $(M+H)^+$, 359 $(M+NH_4)^+$, 364 $(M+Na)^+$; (ESI(−)) m/e 340 $(M-H)^-$; $^1$H NMR (300 MHz, DMSO-$d_6$) δ 7.93 (t, 1H), 7.87 (d, 1H), 7.83 (d, 1H), 7.65 (d, 1H), 7.56 (m, 1H), 7.51-7.47 (m, 2H), 7.42-7.37 (m, 2H), 7.32 (m, 1H), 2.59 (s, 3H).

EXAMPLE 51

2-{[(3-methylphenyl)sulfonyl]amino}-1-naphthoic acid

The desired product was prepared by substituting 3-methylbenzenesulfonyl chloride for benzenesulfonyl chloride in Example 42C. MS (ESI(+)) m/e 342 $(M+H)^+$, 359 $(M+NH_4)^+$, 364 $(M+Na)^+$; (ESI(−)) m/e 340 $(M-H)^-$; $^1$H NMR (300 MHz, DMSO-$d_6$) δ 8.13 (d, 1H), 7.95 (d, 1H), 7.89 (d, 1H), 7.62 (s, 1H), 7.59-7.55 (m, 2H), 7.51 (td, 1H), 7.44-7.40 (m, 2H), 7.35 (d, 1H), 2.34 (s, 3H).

EXAMPLE 52

2-{[(4-methylphenyl)sulfonyl]amino}-1-naphthoic acid

The desired product was prepared by substituting 4-methylbenzenesulfonyl chloride for benzenesulfonyl chloride in Example 42C. MS (ESI(+)) m/e 342 $(M+H)^+$, 359 $(M+NH_4)^+$, 364 $(M+Na)^+$; (ESI(−)) m/e 340 $(M-H)^-$; $^1$H NMR (300 MHz, DMSO-$d_6$) δ 8.17 (d, 1H), 7.94 (d, 1H), 7.88 (d, 1H), 7.66 (d, 2H), 7.57 (m, 1H), 7.49 (m, 1H), 7.37 (d, 1H), 7.33 (d, 2H), 2.33 (s, 3H).

EXAMPLE 53

2-{[(2-fluorophenyl)sulfonyl]amino}-1-naphthoic acid

The desired product was prepared by substituting 2-fluorobenzenesulfonyl chloride for benzenesulfonyl chloride in Example 42C. MS (ESI(+)) m/e 346 $(M+H)^+$, 363 $(M+NH_4)^+$, 368 $(M+Na)^+$; (ESI(−)) m/e 344 $(M-H)^-$; $^1$H NMR (300 MHz, DMSO-$d_6$) δ 8.20 (m, 1H), 7.96 (d, 1H), 7.89 (d, 1H), 7.77 (td, 1H), 7.67 (m, 1H), 7.57 (t, 1H), 7.50 (t, 1H), 7.45 (d, 1H), 7.38 (t, 1H), 7.31 (t, 1H).

EXAMPLE 54

2-{[(5-fluoro-2-methylphenyl)sulfonyl]amino}-1-naphthoic acid

The desired product was prepared by substituting 5-fluoro-2-methylbenzenesulfonyl chloride for benzenesulfonyl chloride in Example 42C. MS (ESI(+)) m/e 360 $(M+H)^+$, 377 $(M+NH_4)^+$, 382 $(M+Na)^+$; (ESI(−)) m/e 375 $(M-H)^-$; $^1$H NMR (300 MHz, DMSO-$d_6$) δ 8.12 (d, 1H), 7.96 (d, 1H), 7.91 (d, 1H), 7.60-7.50 (m, 3H), 7.44 (dd, 1H), 7.40 (dd, 1H), 7.36 (d, 1H), 2.53 (s, 3H).

EXAMPLE 55

2-{[(2-methoxy-5-methylphenyl)sulfonyl]amino}-1-naphthoic acid

The desired product was prepared by substituting 2-methoxy-5-methylbenzenesulfonyl chloride for benzenesulfonyl chloride in Example 42C. MS (ESI(+)) m/e 372 $(M+H)^+$, 389 $(M+NH_4)^+$, 394 $(M+Na)^+$; (ESI(−)) m/e 370 $(M-H)^-$; $^1$H NMR (300 MHz, DMSO-$d_6$) δ 8.30 (d, 1H), 7.97 (d, 1H), 7.85 (d, 1H), 7.69 (d, 1H), 7.61 (d, 1H), 7.57 (td, 1H), 7.46 (t, 1H), 7.36 (dd, 1H), 7.05 (d, 1H), 3.83 (s, 3H), 2.23 (s, 3H).

EXAMPLE 56

2-{[(2-chloro-6-methylphenyl)sulfonyl]amino}-1-naphthoic acid

The desired product was prepared by substituting 2-chloro-6-methylbenzenesulfonyl chloride for benzenesulfonyl chloride in Example 42C. MS (ESI(+)) m/e 376, 378 $(M+H)^+$, 393, 395 $(M+NH_4)^+$, 398, 400 $(M+Na)^+$; (ESI(−)) m/e 374, 376 $(M-H)^-$; $^1$H NMR (300 MHz, DMSO-$d_6$) δ 8.25 (d, 1H), 7.98 (d, 1H), 7.88 (d, 1H), 7.58 (td, 1H), 7.50 (m, 1H), 7.48-7.42 (m, 3H), 7.35 (dd, 1H), 2.60 (s, 3H).

EXAMPLE 57

2-[(8-quinolinylsulfonyl)amino]-1-naphthoic acid

The desired product was prepared by substituting 8-(chlorosulfonyl)quinoline for benzenesulfonyl chloride in Example 42C. MS (ESI(+)) m/e 379 $(M+H)^+$, 401 $(M+Na)^+$; (ESI(−)) m/e 377 $(M-H)^-$; $^1$H NMR (300 MHz, DMSO-$d_6$) δ 9.11 (dd, 1H), 8.50 (dd, 1H), 8.43 (dd, 1H), 8.27 (dd, 1H), 8.06 (d, 1H), 7.93 (d, 1H), 7.82-7.78 (m, 2H), 7.74-7.70 (m, 2H), 7.49 (td, 1H), 7.40 (t, 1H).

EXAMPLE 58

2-({[2-(trifluoromethoxy)phenyl]sulfonyl}amino)-1-naphthoic acid

The desired product was prepared by substituting 2-(trifluoromethoxy)benzenesulfonyl chloride for benzenesulfonyl chloride in Example 42C. MS (ESI(+)) m/e 412 $(M+H)^+$, 429 $(M+NH_4)^+$, 435 $(M+Na)^+$; (ESI(−)) m/e 410 $(M-H)^-$; $^1$H NMR (300 MHz, DMSO-$d_6$) δ 8.28 (m, 1H), 7.97 (m, 2H), 7.88 (d, 1H), 7.75 (t, 1H), 7.57 (t, 1H), 7.53-7.46 (m, 4H).

EXAMPLE 59

2-{[(3,5-dichloro-2-hydroxyphenyl)sulfonyl]amino}-1-naphthoic acid

The desired product was prepared by substituting 3,5-dichloro-2-hydroxybenzenesulfonyl chloride for benzenesulfonyl chloride in Example 42C. MS (ESI(+)) m/e 429, 431 $(M+NH_4)^+$, 434, 436 $(M+Na)^+$; (ESI(−)) m/e 427, 429 $(M-H)^-$; $^1$H NMR (300 MHz, DMSO-$d_6$) δ 8.23 (d, 1H), 7.99 (d, 1H), 7.89 (d, 1H), 7.83 (d, 1H), 7.66 (d, 1H), 7.59 (td, 1H), 7.51 (d, 1H), 7.48 (d, 1H).

EXAMPLE 60

2-({[4-chloro-3-(trifluoromethyl)phenyl]sulfonyl}amino)-1-naphthoic acid

The desired product was prepared by substituting 4-chloro-3-(trifluoromethyl)benzenesulfonyl chloride for benzenesulfonyl chloride in Example 42C. MS (ESI(+)) m/e 452, 454 $(M+H)^+$, 469, 471 $(M+NH_4)^+$, 474, 476 $(M+Na)^+$; (ESI(−)) m/e 450, 452 $(M-H)^-$; $^1$H NMR (300 MHz, DMSO-$d_6$) δ 8.07 (s, 1H), 8.01-7.89 (m, 5H), 7.59 (t, 1H), 7.53 (t, 1H), 7.33 (t, 1H).

EXAMPLE 61

2-[({2-[(3-aminopropyl)amino]phenyl}sulfonyl)amino]-1-naphthoic acid

EXAMPLE 61A

2-{[(2-bromophenyl)sulfonyl]amino}-1-naphthoic acid

The desired product was prepared by substituting 2-bromobenzenesulfonyl chloride for benzenesulfonyl chloride in Example 42C. MS m/e 405 $(M-H)^-$.

EXAMPLE 61B

2-[({2-[(3-aminopropyl)amino]phenyl}sulfonyl)amino]-1-naphthoic acid

A mixture of Example 61A (90 mg, 0.22 mmol) in N,N-dimethylformamide (1 mL) was treated with ethylene diamine (1 mL), heated to reflux for 2 days, and dried under vacuum. The concentrate was purified by $C_{18}$ reverse-phase HPLC with acetonitrile/water/0.1% TFA to provide the desired product. MS (ESI(−)) m/e 398 $(M-H)^-$; $^1$H NMR (300 MHz, DMSO-$d_6$) δ 10.53 (s, 1H), 8.05 (m, 1H), 7.96 (dd, 1H), 7.70-7.82 (m, 3H), 7.65 (d, 1H), 7.21-7.51 (m, 4H), 6.73 (d, 1H), 6.57 (t, 1H), 3.01-3.26 (m, 4H).

EXAMPLE 62

2-{[(2,4-dimethoxyphenyl)sulfonyl]amino}-1-naphthoic acid

The desired product was prepared by substituting 2,4-dimethoxybenzenesulfonyl chloride for benzenesulfonyl chloride in Example 42C. MS (ESI(+)) m/e 388 $(M+H)^+$, 405 $(M+NH_4)^+$, 410 $(M+Na)^+$; (ESI(−)) m/e 386 $(M-H)^-$; $^1$H NMR (300 MHz, DMSO-$d_6$) δ 9.20 (d, 1H), 7.73 (d, 1H), 7.65-7.58 (m, 3H), 7.35 (m, 2H), 7.22 (td, 1H), 6.52 (dd, 1H), 6.50 (s, 1H), 3.76 (s, 6H).

EXAMPLE 63

2-{[(4-methoxyphenyl)sulfonyl]amino}-1-naphthoic acid

The desired product was prepared by substituting 4-methoxybenzenesulfonyl chloride for benzenesulfonyl chloride in Example 42C. MS (ESI(+)) m/e 358 $(M+H)^+$, 380 $(M+Na)^+$; (ESI(−)) m/e 356 $(M-H)^-$; $^1$H NMR (300 MHz, DMSO-$d_6$) δ 10.25 (br s, 1H), 8.14 (d, 1H), 7.95 (d, 1H), 7.90 (d, 1H), 7.70 (dt, 2H), 7.54 (m, 2H), 7.39 (d, 1H), 7.05 (dt, 1H), 3.79 (s, 3H).

EXAMPLE 64

2-[(butylsulfonyl)amino]-5-ethylbenzoic acid

The desired product was prepared by substituting 1-butanesulfonyl chloride for benzenesulfonyl chloride in Example 1D. MS (ESI(+)) m/e 286 $(M+H)^+$, 303 $(M+NH_4)^+$, 308 $(M+Na)^+$; (ESI(−)) m/e 284 $(M-H)^-$; $^1$H NMR (300

MHz, DMSO-$d_6$) δ 7.77 (d, 1H), 7.32 (d, 1H), 7.11 (dd, 1H), 2.92 (t, 2H), 2.52 (q, 2H), 1.56 (m, 2H), 1.28 (m, 2H), 1.15 (t, 3H), 0.99 (t, 3H).

EXAMPLE 65

5-ethyl-2-[(2-thienylsulfonyl)amino]benzoic acid

The desired product was prepared by substituting 2-thiophenesulfonyl chloride for benzenesulfonyl chloride in Example 1D. MS (ESI(+)) m/e 312 $(M+H)^+$, 329 $(M+NH_4)^+$, 334 $(M+Na)^+$; (ESI(−)) m/e 310 $(M-H)^-$; $^1$H NMR (300 MHz, DMSO-$d_6$) δ 7.67-7.65 (m, 2H), 7.38 (dd, 1H), 7.31 (d, 1H), 7.07 (m, 1H), 6.99 (dd, 1H), 2.47 (q, 2H), 1.10 (t, 3H).

EXAMPLE 66

2-{[(5-chloro-1,3-dimethyl-1H-pyrazol-4-yl)sulfonyl]amino}-5-ethylbenzoic acid The desired product was prepared by substituting 5-chloro-1,3-dimethyl-1H-pyrazole-4-sulfonyl chloride for benzenesulfonyl chloride in Example 1D. MS (ESI(+)) m/e 358, 360 $(M+H)^+$, 375, 377 $(M+NH_4)^+$, 380, 382 $(M+Na)^+$; (ESI(−)) m/e 356, 358 $(M-H)^-$; $^1$H NMR (300 MHz, DMSO-$d_6$) δ 7.67 (d, 1H), 7.17 (d, 1H), 7.02 (dd, 1H), 3.67 (s, 3H), 2.46 (q, 2H), 2.24 (s, 3H), 1.10 (t, 3H).

EXAMPLE 67

5-ethyl-2-({[2-(methoxycarbonyl)-3-thienyl]sulfonyl}amino)benzoic acid

The desired product was prepared by substituting methyl 3-(chlorosulfonyl)-2-thiophenecarboxylate for benzenesulfonyl chloride in Example 1D. MS (ESI(+)) m/e 370 $(M+H)^+$, 387 $(M+NH_4)^+$, 392 $(M+Na)^+$; (ESI(−)) m/e 368 $(M-H)^-$; $^1$H NMR (300 MHz, DMSO-$d_6$) δ 7.81 (d, 1H), 7.69 (d, 1H), 7.39 (d, 1H), 7.19 (d, 1H), 7.01 (dd, 1H), 3.81 (s, 3H), 2.46 (q, 2H), 1.10 (t, 3H).

EXAMPLE 68

2-[(2,1,3-benzothiadiazol-4-ylsulfonyl)amino]-1-naphthoic acid

The desired product was prepared by substituting 2,1,3-benzothiadiazole-4-sulfonyl chloride for benzenesulfonyl chloride in Example 42C. MS (ESI(+)) m/e 403 $(M+NH_4)^+$, 408 $(M+Na)^+$; (ESI(−)) m/e 384 $(M-H)^-$; $^1$H NMR (300 MHz, DMSO-$d_6$) δ 8.36 (d, 1H), 8.22 (d, 1H), 7.99 (d, 1H), 7.96 (d, 1H), 7.87 (dd, 1H), 7.78 (dd, 1H), 7.60 (d, 1H), 7.55-7.44 (m, 2H).

EXAMPLE 69

2-[(butylsulfonyl)amino]-1-naphthoic acid

The desired product was prepared by substituting 1-butanesulfonyl chloride for benzenesulfonyl chloride in Example 42C. MS (ESI(+)) m/e 325 $(M+NH_4)^+$, 330 $(M+Na)^+$; (ESI(−)) m/e 306 $(M-H)^-$; $^1$H NMR (300 MHz, DMSO-$d_6$) δ 8.17 (d, 1H), 8.04 (d, 1H), 7.95 (d, 1H), 7.66 (d, 1H), 7.61 (td, 1H), 7.53 (t, 1H), 3.19 (m, 2H), 1.68 (m, 2H), 1.36 (m, 2H), 0.84 (t, 3H).

EXAMPLE 70

2-[(2-thienylsulfonyl)amino]-1-naphthoic acid

The desired product was prepared by substituting 2-thiophenesulfonyl chloride for benzenesulfonyl chloride in Example 42C. MS (ESI(+)) m/e 351 $(M+NH_4)^+$, 356 $(M+Na)^+$; (ESI(−)) m/e 332 $(M-H)^-$; $^1$H NMR (300 MHz, DMSO-$d_6$) δ 8.36 (d, 1H), 7.96 (d, 1H), 7.89-7.84 (m, 2H), 7.56 (t, 1H), 7.51 (d, 1H), 7.50-7.42 (m, 2H), 7.10 (t, 1H).

EXAMPLE 71

2-[(benzylsulfonyl)amino]-1-naphthoic acid

The desired product was prepared by substituting phenylmethanesulfonyl chloride for benzenesulfonyl chloride in Example 42C. MS (ESI(+)) m/e 359 $(M+NH_4)^+$, 364 $(M+Na)^+$; (ESI(−)) m/e 340 $(M-H)^-$; $^1$H NMR (300 MHz, DMSO-$d_6$) δ 8.28 (d, 1H), 7.98 (d, 1H), 7.93 (d, 1H), 7.60 (t, 1H), 7.57-7.49 (m, 2H), 7.34 (m, 5H), 4.59 (s, 2H).

EXAMPLE 72

2-{[(3,5-dimethyl-4-isoxazolyl)sulfonyl]amino}-1-naphthoic acid

The desired product was prepared by substituting 3,5-dimethyl-4-isoxazolesulfonyl chloride for benzenesulfonyl chloride in Example 42C. MS (ESI(+)) m/e 364 $(M+NH_4)^+$, 369 $(M+Na)^+$; (ESI(−)) m/e 346 $(M-H)^-$; $^1$H NMR (300 MHz, DMSO-$d_6$) δ 8.06 (d, 1H), 8.04 (d, 1H), 7.96 (d, 1H), 7.61 (m, 1H), 7.57 (td, 1H), 7.47 (d, 1H), 2.31 (s, 3H), 2.14 (s, 3H).

EXAMPLE 73

2-({[(E)-2-phenylvinyl]sulfonyl}amino)-1-naphthoic acid

The desired product was prepared by substituting (E)-2-phenylethylenesulfonyl chloride for benzenesulfonyl chloride in Example 42C. MS (ESI(+)) m/e 354 $(M+H)^+$, 371 $(M+NH_4)^+$, 376 $(M+Na)^+$; (ESI(−)) m/e 352 $(M-H)^-$; $^1$H NMR (300 MHz, DMSO-$d_6$) δ 8.18 (d, 1H), 8.02 (d, 1H), 7.93 (d, 1H), 7.66 (m, 2H), 7.64 (d, 1H), 7.59 (td, 1H), 7.51 (t, 1H), 7.45 (d, 1H), 7.42-7.39 (m, 3H), 7.32 (d, 1H).

EXAMPLE 74

2-{[(5-chloro-2-thienyl)sulfonyl]amino}-1-naphthoic acid

The desired product was prepared by substituting 5-chloro-2-thiophenesulfonyl chloride for benzenesulfonyl-chloride in Example 42C. MS (ESI(+)) m/e 385, 387 $(M+NH_4)^+$, 390, 392 $(M+Na)^+$; (ESI(−)) m/e 366, 368 $(M-H)^-$; $^1$H NMR (300 MHz, DMSO-$d_6$) δ 8.11 (d, 1H), 8.02 (d, 1H), 7.95 (d, 1H), 7.61 (t, 1H), 7.55 (t, 1H), 7.39 (d, 1H), 7.37 (d, 1H), 7.18 (d, 1H).

EXAMPLE 75

2-{[(5-chloro-1,3-dimethyl-1H-pyrazol-4-yl)sulfonyl]amino}-1-naphthoic acid The desired product was prepared by substituting 5-chloro-1,3-dimethyl-1H-pyrazole-4-sulfonyl chloride for benzenesulfonyl chloride in Example 42C. MS (ESI(+)) m/e 380, 382 $(M+H)^+$, 397, 399 $(M+NH_4)^+$, 402, 404 $(M+Na)^+$; (ESI(−)) m/e 378, 380 $(M-H)^-$; $^1$H NMR (300 MHz, DMSO-$d_6$) δ 8.16 (d, 1H), 8.04 (d, 1H), 7.94 (d, 1H), 7.59 (td, 1H), 7.55 (d, 1H), 7.53 (t, 1H), 3.69 (s, 3H), 2.11 (s, 3H).

EXAMPLE 76

2-({[2-(methoxycarbonyl)-3-thienyl]sulfonyl}amino)-1-naphthoic acid

The desired product was prepared by substituting methyl 3-(chlorosulfonyl)-2-thiophenecarboxylate for benzenesulfonyl chloride in Example 42C. MS (ESI(+)) m/e 392 $(M+H)^+$, 409 $(M+NH_4)^+$, 414 $(M+Na)^+$; (ESI(−)) m/e 390 $(M-H)^-$; $^1$H NMR (300 MHz, DMSO-$d_6$) δ 8.14 (d, 1H), 7.99 (d, 1H), 7.97 (d, 1H), 7.90 (d, 1H), 7.63 (d, 1H), 7.58 (td, 1H), 7.51-7.48 (m, 2H), 3.90 (s, 3H).

EXAMPLE 77

2-({[5-(3-isoxazolyl)-2-thienyl]sulfonyl}amino)-1-naphthoic acid

The desired product was prepared by substituting 5-(3-isoxazolyl)-2-thiophenesulfonyl chloride for benzenesulfonyl chloride in Example 42C. MS (ESI(+)) m/e 418 $(M+NH_4)^+$, 423 $(M+Na)^+$; (ESI(−)) m/e 399 $(M-H)^-$; $^1$H NMR (300 MHz, DMSO-$d_6$) δ 8.70 (d, 1H), 8.11 (d, 1H), 8.01 (d, 1H), 7.94 (d, 1H), 7.67 (d, 1H), 7.60 (td, 1H), 7.56-7.53 (m, 2H), 7.41 (d, 1H), 7.06 (d, 1H).

EXAMPLE 78

2-{[(2,5-dichloro-3-thienyl)sulfonyl]amino}-1-naphthoic acid

The desired product was prepared by substituting 2,5-dichloro-3-thiophenesulfonyl chloride for benzenesulfonyl chloride in Example 42C. MS (ESI(+)) m/e 419, 421 $(M+NH_4)^+$, 424, 426 $(M+Na)^+$; (ESI(−)) m/e 400, 402 $(M-H)^-$; $^1$H NMR (300 MHz, DMSO-$d_6$) δ 8.11 (d, 1H), 8.02 (d, 1H), 7.95 (d, 1H), 7.61 (td, 1H), 7.55 (t, 1H), 7.42 (d, 1H), 7.24 (s, 1H).

EXAMPLE 79

2-{[(4,5-dichloro-2-thienyl)sulfonyl]amino}-1-naphthoic acid

The desired product was prepared by substituting 4,5-dichloro-2-thiophenesulfonyl chloride for benzenesulfonyl chloride in Example 42C. MS (ESI(+)) m/e 424, 426 $(M+Na)^+$; (ESI(−)) m/e 400, 402 $(M-H)^-$; $^1$H NMR (300 MHz, DMSO-$d_6$) δ 8.08 (d, 1H), 8.03 (d, 1H), 7.97 (d, 1H), 7.61 (td, 1H), 7.57 (t, 1H), 7.55 (s, 1H), 7.41 (d, 1H).

EXAMPLE 80

2-{[(5-bromo-6-chloro-3-pyridinyl)sulfonyl]amino}-1-naphthoic acid

The desired product was prepared by substituting 5-bromo-6-chloro-3-pyridinesulfonyl chloride for benzenesulfonyl chloride in Example 42C. MS (ESI(+)) m/e 463, 465 $(M+Na)^+$; (ESI(−)) m/e 439, 441 $(M-H)^-$; $^1$H NMR (300 MHz, DMSO-$d_6$) δ 8.61 (d, 1H), 8.38 (d, 1H), 8.01-7.96 (m, 3H), 7.60 (td, 1H), 7.56 (t, 1H), 7.40 (d, 1H).

EXAMPLE 81

2-{[(3-chloropropyl)sulfonyl]amino}-1-naphthoic acid

The desired product was prepared by substituting 3-chloro-1-propanesulfonyl chloride for benzenesulfonyl chloride in Example 42C. MS (ESI(+)) m/e 345, 347 $(M+NH_4)^+$, 350, 352 $(M+Na)^+$; (ESI(−)) m/e 326, 328 $(M-H)^-$; $^1$H NMR (300 MHz, DMSO-$d_6$) δ 8.18 (br s, 1H), 8.03 (d, 1H), 7.96 (d, 1H), 7.63 (d, 1H), 7.61 (td, 1H), 7.53 (t, 1H), 3.73 (t, 2H), 3.33 (m, 2H), 2.17 (m, 2H).

EXAMPLE 82

2-[(methylsulfonyl)amino]-1-naphthoic acid

The desired product was prepared by substituting methanesulfonyl chloride for benzenesulfonyl chloride in Example 42C. MS (ESI(−)) m/e 264 $(M-H)^-$; $^1$H NMR (300 MHz, DMSO-$d_6$) δ 9.34 (d, 1H), 7.67-7.83 (m, 3H), 7.41 (dt, 1H), 7.29 (dt, 1H), 7.07 (m, 2H), 2.86 (s, 3H).

EXAMPLE 83

2-[(ethylsulfonyl)amino]-1-naphthoic acid

The desired product was prepared by substituting ethanesulfonyl chloride for benzenesulfonyl chloride in Example 42C. MS (ESI(−)) m/e 278 $(M-H)^-$; $^1$H NMR (300 MHz, DMSO-$d_6$) δ 9.31 (d, 1H), 7.72-7.82 (m, 3H), 7.41 (dt, 1H), 7.29 (dt, 1H), 2.98 (q, 4H), 1.15 (t, 3H).

EXAMPLE 84

2-[(propylsulfonyl)amino]-1-naphthoic acid

The desired product was prepared by substituting 1-propanesulfonyl chloride for benzenesulfonyl chloride in Example 42C. MS (ESI(−)) m/e 292 $(M-H)^-$; $^1$H NMR (300 MHz, DMSO-$d_6$) δ 9.32 (d, 1H), 7.72-7.81 (m, 3H), 7.41 (dt, 1H), 7.29 (dt, 1H), 2.94-2.98 (m, 2H), 1.59-1.71 (m, 2H), 0.87 (t, 3H).

EXAMPLE 85

7-fluoro-2-[(phenylsulfonyl)amino]-1-naphthoic acid

EXAMPLE 85A 7-fluoro-2-naphthylamine

A suspension of 7-nitro-2-naphthylamine (2.06 g, 11.0 mmol, prepared as described in *J. Chem. Soc.* 1949, 1187) in dichloromethane (90 mL) and THF (10 mL) at −20° C. was treated with boron trifluoride diethyletherate (2.1 mL, 16.6 mmol), treated dropwise with tert-butyl nitrite (1.6 mL, 13.5 mmol), warmed to ambient temperature over 2 hours, diluted with diethyl ether (100 mL), and filtered. The filter cake was washed with diethyl ether and dried under vacuum to provide the diazonium tetrafluoroborate salt (3.10 g). The salt was suspended in 1,2-dimethylbenzene, heated to 120° C. until gas evolution ceased, and concentrated. The concentrate was dissolved in dichloromethane (95 mL) and methanol (5 mL), treated with stannous chloride (50 g, 270 mmol, added in three portions), stirred for 4 days, diluted with dichloromethane, treated with 1M NaOH (500 mL), and shaken for 30 seconds. The emulsion was filtered through diatomaceous earth (Celite®) and the filtrate was extracted twice with dichloromethane. The combined extracts were dried ($MgSO_4$), filtered, and concentrated to provide the desired product (1.68 g). MS (DCI) m/e 162 $(M+H)^+$; $^1$H NMR (300 MHz, DMSO-$d_6$) δ 7.67 (dd, 1H), 7.59 (d, 1H), 7.22 (dd, 1H), 6.94 (dd, 1H), 6.88 (dd, 1H), 6.76 (d, 1H).

EXAMPLE 85B 2-amino-7-fluoro-1-naphthoic acid

The desired product was prepared by substituting Example 85A for 2-naphthylamine in Examples 42A and 42B. MS (ESI(−)) m/e 204 $(M-H)^-$; $^1H$ NMR (300 MHz, DMSO-$d_6$) δ 8.32 (dd, 1H), 7.76-7.69 (m, 2H), 7.08-6.98 (m, 2H).

EXAMPLE 85C 7-fluoro-2-[(phenylsulfonyl)amino]-1-naphthoic acid

The desired product was prepared by substituting Example 85B for Example 42B in Example 42C. MS (ESI(+)) m/e 363 $(M+NH_4)^+$, 368 $(M+Na)^+$; (ESI(−)) m/e 344 $(M-H)^-$; $^1H$ NMR (300 MHz, DMSO-$d_6$) δ 7.79-7.71 (m, 4H), 7.65 (d, 1H), 7.46 (dd, 2H), 7.13 (td, 1H).

EXAMPLE 86

7-fluoro-2-{[(4-fluorophenyl)sulfonyl]amino}-1-naphthoic acid

The desired product was prepared by substituting Example 85B and 4-fluorobenzenesulfonyl chloride for Example 42B and benzenesulfonyl chloride respectively, in Example 42C. MS (ESI(+)) m/e 381 $(M+NH_4)^+$, 386 $(M+Na)^+$; (ESI(−)) m/e 362 $(M-H)^-$; $^1H$ NMR (300 MHz, DMSO-$d_6$) δ 7.85-7.72 (m, 5H), 7.64 (d, 1H), 7.28 (t, 2H), 7.13 (td, 1H).

EXAMPLE 87

7-fluoro-2-{[(3-fluorophenyl)sulfonyl]amino}-1-naphthoic acid

The desired product was prepared by substituting Example 85B and 3-fluorobenzenesulfonyl chloride for Example 42B and benzenesulfonyl chloride, respectively, in Example 42C. MS (ESI(+)) m/e 381 $(M+NH_4)^+$, 386 $(M+Na)^+$; (ESI(−)) m/e 362 $(M-H)^-$; $^1H$ NMR (300 MHz, DMSO-$d_6$) δ 7.81 (d, 1H), 7.79 (s, 1H), 7.77 (d, 1H), 7.63 (d, 1H), 7.59 (m, 1H), 7.54-7.49 (m, 2H), 7.34 (td, 1H), 7.17 (td, 1H).

EXAMPLE 88

2-{[(3,4-difluorophenyl)sulfonyl]amino}-7-fluoro-1-naphthoic acid

The desired product was prepared by substituting Example 85B and 3,4-difluorobenzenesulfonyl chloride for Example 42B and benzenesulfonyl chloride, respectively, in Example 42C. MS (ESI(+)) m/e 399 $(M+NH_4)^+$, 404 $(M+Na)^+$; (ESI (−)) m/e 380 $(M-H)^-$; $^1H$ NMR (300 MHz, DMSO-$d_6$) δ 7.81 (d, 1H), 7.79 (s, 1H), 7.77 (d, 1H), 7.63 (d, 1H), 7.59 (m, 1H), 7.54-7.49 (m, 2H), 7.32 (td, 1H), 7.16 (td, 1H).

EXAMPLE 89

2-{[(2,4-difluorophenyl)sulfonyl]amino}-7-fluoro-1-naphthoic acid

The desired product was prepared by substituting Example 85B and 2,4-difluorobenzenesulfonyl chloride for Example 42B and benzenesulfonyl chloride, respectively, in Example 42C. MS (ESI(+)) m/e 399 $(M+NH_4)^+$, 404 $(M+Na)^+$; (ESI (−)) m/e 380 $(M-H)^-$; $^1H$ NMR (300 MHz, DMSO-$d_6$) δ 7.82-7.72 (m, 3H), 7.64 (d, 1H), 7.62-7.57 (m, 1H), 7.54 (dd, 1H), 7.33 (td, 1H), 7.16 (td, 1H).

EXAMPLE 90

2-[(phenylsulfonyl)amino]-5,6,7,8-tetrahydro-1-naphthalenecarboxylic acid

A mixture of Example 42C (0.087 g, 0.27 mmol), and platinum oxide (0.056 g, 0.25 mmol) in acetic acid (7.5 mL) was shaken in a reactor pressurized with 60 psi of $H_2$ at 25° C. for 80 hours and filtered. The filtrate was concentrated and the concentrate was purified by $C_{18}$ reverse-phase HPLC with acetonitrile/water/0.1% trifluoroacetic acid to provide the desired-product. MS (ESI(+)) m/e 332 $(M+H)^+$, 349 $(M+NH_4)^+$, 354 $(M+Na)^+$; (ESI(−) m/e 330 $(M-H)^-$; $^1H$ NMR (300 MHz, DMSO-$d_6$) δ 7.74 (m, 2H), 7.63 (m, 1H), 7.56 (m, 2H), 6.98 (d, 1H), 6.63 (d, 1H), 2.65 (m, 4H), 1.66 (m, 4H).

EXAMPLE 91

6-bromo-2-{[(4-fluorophenyl)sulfonyl]amino}-1-naphthoic acid

EXAMPLE 91A 7-bromo-1H-benzo[e]indole-1,2(3H)-dione

A mixture Example 42A (0.50 g, 2.5 mmol) and bromine (154 μL, 3.0 mmol) in of chloroform (20 mL) and DMF (2 mL) was stirred at ambient temperature for 16 hours and filtered. The filter cake was washed with chloroform and dried under vacuum to provide the desired product (0.50 g, 72%). MS (DCI/$NH_3$) m/e 294 $(M+NH_4)^+$; $^1H$ NMR (300 MHz, DMSO-$d_6$) δ 11.12 (s, 1H), 8.32 (d, 1H), 8.25 (s, 1H), 8.22 (d, 1H), 7.80 (dd, 1H), 7.24 (d, 1H).

EXAMPLE 91B 2-amino-6-bromo-1-naphthoic acid

The desired product was prepared by substituting Example 91A for Example 1B in Example 1C. MS (ESI(−)) m/e 265 $(M-H)^-$; $^1H$ NMR (300 MHz, DMSO-$d_6$) δ 8.48 (d, 1H), 7.90 (d, 1H), 7.71 (d, 1H), 7.50 (dd, 1H), 7.07 (d, 1H).

EXAMPLE 91C 6-bromo-2-{[(4-fluorophenyl)sulfonyl]amino}-1-naphthoic acid

The desired compound was prepared by substituting Example 91B and 4-fluorobenzenesulfonyl chloride for Example 42B and benzenesulfonyl chloride, respectively, in Example 42C. MS (ESI(−)) m/e 424 $(M-H)^-$; $^1H$ NMR (300 MHz, DMSO-$d_6$) δ 9.15 (br s, 1H), 7.98 (d, 1H), 7.83-7.75 (m, 3H), 7.63 (d, 1H), 7.53 (dd, 1H), 7.30 (t, 3H).

EXAMPLE 92

5-bromo-2-[(1-naphthylsulfonyl)amino]benzoic acid

The desired product was prepared by substituting 1-naphthalenesulfonyl chloride for benzenesulfonyl chloride and 4-bromoanthrinilic acid for 4-(trifluoromethyl)anthrinilic acid in Example 93. MS (ESI) m/e 405 $(M-H)^-$; $^1H$ NMR (300 MHz, DMSO-$d_6$) δ 11.92 (br s, 1H), 8.52 (d, 1H), 8.32 (d, 1H), 8.27 (d, 1H), 8.10 (d, 1H), 7.89 (d, 1H), 7.78-7.62 (m, 4H), 7.4 (d, 1H).

EXAMPLE 93

2-[(phenylsulfonyl)amino]-4-(trifluoromethyl)benzoic acid

A mixture of 3-(trifluoromethyl)anthranilic acid (25 mg, 0.122 mmol) in dichloromethane (0.3 mL) was treated with chlorotrimethylsilane (0.27 mL of 1M solution in $CH_2Cl_2$, 0.268 mmol) and pyridine (0.035 mL), stirred at room temperature for four hours, treated with benzenesulfonyl chloride (20.2 μL, 0.159 mmol), stirred overnight at room temperature, and treated with 1N HCl (2.0 mL). The aqueous phase was extracted with ethyl acetate (2×). The combined organic extracts were dried ($MgSO_4$), filtered, and concentrated. The concentrate was purified by preparative HPLC to provide the desired product. MS (ESI(−)) m/e 344 $(M-H)^-$; $^1H$ NMR (300 MHz, $CD_3OD$) δ 8.06 (d, 1H), 7.85 (s, 1H), 7.80 (dt, 2H), 7.56-7.41 (br m, 3H), 7.22 (dt, 1H).

EXAMPLE 94

2-[(phenylsulfonyl)amino]-4-(trifluoromethoxy)benzoic acid

The desired product was prepared by substituting 2-bromo-4-(trifluoromethoxy)aniline for 2-bromo-4-isopropylaniline in Examples 2A-D. MS (ESI(+)) m/e 362 $(M+H)^+$, 379 $(M+NH_4)^+$, 384 $(M+Na)^+$; (ESI(−)) m/e 360 $(M-H)^-$; $^1H$ NMR (300 MHz, DMSO-$d_6$) δ 7.76 (m, 1H), 7.73 (m, 1H), 7.68 (m, 1H), 7.51 (m, 3H), 7.39 (d, 1H), 7.20 (m, 1H).

EXAMPLE 95

5-nitro-2-[(phenylsulfonyl)amino]benzoic acid

EXAMPLE 95A methyl 5-nitro-2-[(phenylsulfonyl)amino]benzoate

A mixture of 2-amino-5-nitrobenzoic acid (151 mg, 0.77 mmol) in dichloromethane (2.0 mL) was treated with chlorotrimethylsilane (1.70 mL of 1M solution in $CH_2Cl_2$, 1.70 mmol) and pyridine (2.0 mL), stirred at room temperature for 30 minutes, treated with benzenesulfonyl chloride (150 μL, 1.16 mmol), stirred overnight at room temperature, warmed to 40° C., stirred overnight, treated with 1N HCl (2.0 mL), and extracted with dichloromethane (2×). The combined extracts were washed with distilled water and brine, dried ($MgSO_4$), filtered, and concentrated. The resulting residue was purified by preparative HPLC to provide the desired product. MS (ESI(−)) m/e 335 $(M-H)^-$; $^1H$ NMR (300 MHz, DMSO-$d_6$) δ 10.96 (s, 1H), 8.58 (d, 1H), 8.39 (dd, 1H), 7.96 (m, 2H), 7.74-7.60 (m, 4H), 3.91 (s, 3H).

EXAMPLE 95B 5-nitro-2-[(phenylsulfonyl)amino]benzoic acid

A solution of Example 95A (10.9 mg, 0.032 mmol) in methanol (0.9 mL) and distilled water (0.01 mL) was treated with lithium hydroxide monohydrate (4.0 mg, 0.096 mmol), heated to 50° C. for 4 hours, cooled to room temperature, treated with 2N HCl (1 mL), and concentrated. The resulting residue was purified by chromatography to provide the desired product as a white solid. MS (ESI(−)) m/e 321 $(M-H)^-$; $^1H$ NMR (300 MHz, DMSO-$d_6$) δ 8.62 (d, 1H), 8.06 (dd, 1H), 7.80 (m, 2H), 7.51 (m, 3H), 7.42 (d, 1H).

EXAMPLE 96

6-[(phenylsulfonyl)amino]-5-quinolinecarboxylic acid

EXAMPLE 96A 6-amino-5-quinolinecarboxylic acid

A mixture of 6-amino-5-quinolinecarbonitrile (0.99 g, 5.9 mmol, prepared as described in *Chem. Pharm. Bull.,* 1985, 33, 13260-1366) in 1-propanol (50 mL) was treated with 10 mL concentrated NaOH and heated to 100° C. for 18 hours. The mixture was concentrated, diluted with water, and washed twice with diethyl ether. The aqueous phase was acidified to pH 5 with 1M HCl and extracted with ethyl acetate in a continuous extractor. The organic extracts were dried ($MgSO_4$), filtered, and concentrated to provide the desired product (0.55 g). MS (DCI) m/e 206 $(M+NH_4)^+$.

EXAMPLE 96B methyl 6-amino-5-quinolinecarboxylate

A solution of Example 96A (0.43 g, 2.3 mmol), benzene (10 mL), and methanol (4 mL) was treated with $TMSCHN_2$ (2.0 mL, 4.0 mmol, 2.0M solution in hexanes), stirred at room temperature for 90 minutes, quenched with glacial acetic acid, and concentrated. The residue was diluted with ethyl acetate, washed with saturated $Na_2CO_3$, dried ($MgSO_4$), filtered, and concentrated to provide the desired product (0.401 g). MS (DCI) m/e 220 $(M+NH_4)^+$.

EXAMPLE 96C methyl 6-[(phenylsulfonyl)amino]-5-quinolinecarboxylate

A solution of Example 96B (0.233 g, 1.20 mmol) in pyridine (4 mL) was treated with benzenesulfonyl chloride (0.20 mL, 1.6 mmol), and stirred for 7 hours at ambient temperature. The mixture was concentrated and the residue was purified by $C_{18}$ reverse-phase HPLC with acetonitrile/water/0.5 mM ammonium acetate to provide the desired product. MS (ESI(+)) m/e 343 $(M+H)^+$.

EXAMPLE 96D

6-[(phenylsulfonyl)amino]-5-quinolinecarboxylic acid

A solution of Example 96C (0.073 g, 0.21 mmol) in methanol (4 mL) was treated with 2 mL conc. NaOH and heated to 70° C. for 18 hours. The mixture was concentrated, diluted with water, acidified to pH 5 with 1M HCl, and extracted with dichloromethane. The extract was dried ($MgSO_4$), filtered, and concentrated to provide the desired product (0.010 g). MS (ESI(+)) m/e 329 $(M+H)^+$; (ESI(−)) m/e 327 $(M-H)^-$; $^1H$ NMR (300 MHz, DMSO-$d_6$) δ 10.01 (dd, 1H), 8.97 (m, 1H), 8.30 (d, 1H), 7.92 (d, 1H), 7.74 (m, 5H), 7.54 (m, 1H).

EXAMPLE 97

6-{[(4-methoxyphenyl)sulfonyl]amino}-5-quinolinecarboxylic acid

The desired product was prepared by substituting 4-methoxybenzenesulfonyl chloride for benzenesulfonyl chloride in Examples 96C-D. MS (ESI(+)) m/e 359 $(M+H)^+$; (ESI(−)) m/e 357 $(M-H)^-$; $^1H$ NMR (300 MHz, DMSO-$d_6$) δ 10.11 (dd, 1H), 8.96 (m, 1H), 8.31 (d, 1H), 7.91 (d, 1H), 7.73 (dd, 1H), 7.70 (d, 2H), 7.03 (d, 2H), 3.78 (s, 3H).

EXAMPLE 98

2-{ethyl[(4-fluorophenyl)sulfonyl]amino}-1-naphthoic acid

EXAMPLE 98A methyl 2-{[(4-fluorophenyl)sulfonyl}amino]-1-naphthoate

The desired product was prepared by substituting 4-fluorobenzenesulfonyl chloride for 2-fluorobenzenesulfonyl chloride in Example 133B. MS (ESI(+)) m/e 360 $(M+H)^+$.

EXAMPLE 98B

2-{ethyl[(4-fluorophenyl)sulfonyl]amino}-1-naphthoic acid

Macroporous polystyrene-bound triphenylphosphine resin (56 mg, 0.17 mmol) was treated with di-tert-butyl azodicarboxylate (29 mg, 0.13 mmol) in THF (0.5 mL), shaken at ambient temperature for 15 minutes, treated with a solution of Example 98A (30 mg, 0.08 mmol) in THF (1 mL), shaken at ambient temperature for 15 minutes, treated with ethanol (0.006 mL, 0.11 mmol), shaken for 16 hours at 60° C., filtered, and concentrated. The residue was dissolved in 2:1 dioxane/water (1 mL), treated with LiOH (25 mg, 0.6 mmol), and heated to 160° C. for 30 minutes in a microwave reactor. The reaction mixture was concentrated and purified by $C_{18}$ reverse-phase HPLC using acetonitrile/water/0.1% TFA to provide the desired product. MS (DCI) m/e 391 $(M+NH_4)^+$; $^1H$ NMR (500 MHz, DMSO-$d_6$) δ 7.99 (m, 2H), 7.92 (m, 1H), 7.81 (br s, 2H), 7.64 (br s, 2H), 7.46 (t, 2H), 7.02 (d, 1H), 3.60 (br s, 2H), 0.99 (t, 3H).

EXAMPLE 99

2-[[(4-fluorophenyl)sulfonyl](propyl)amino]-1-naphthoic acid

The desired product was prepared by substituting 1-propanol for ethanol in Example 98B. MS (DCI) m/e 388 $(M+H)^+$, 405 $(M+NH_4)^+$; $^1H$ NMR (500 MHz, DMSO-$d_6$) δ 8.00 (m, 2H), 7.90 (d, 1H), 7.79 (m, 2H), 7.65 (m, 2H), 7.46 (t, 2H), 7.03 (d, 1H), 3.50 (m, 2H), 1.39 (m, 2H), 0.76 (t, 3H).

EXAMPLE 100

2-{[(4-fluorophenyl)sulfonyl][2-(methylsulfanyl)ethyl]amino}-1-naphthoic acid

The desired product was prepared by substituting 2-(methylsulfanyl)ethanol for ethanol in Example 98B. MS (DCI) m/e 437 $(M+NH_4)^+$; $^1H$ NMR (500 MHz, DMSO-$d_6$) δ 13.62 (br s, 1H), 8.00 (m, 2H), 7.92 (m, 1H), 7.81 (br s, 2H), 7.66 (m, 2H), 7.45 (t, 2H), 7.11 (d, 1H), 3.75 (br s, 2H), 2.57 (br s, 2H), 1.96 (s, 3H).

EXAMPLE 101

2-{[(4-chlorophenyl)sulfonyl]amino}-4,5-dimethoxybenzoic acid

The desired product was prepared by substituting 4-chlorobenzenesulfonyl chloride for 2-fluorobenzenesulfonyl chloride and 2-amino-4,5-dimethoxybenzoic acid for 2-amino-5,6,7,8-tetrahydro-1-naphthoic acid in Example 128D. MS (ESI(+)) m/e 389 $(M+NH_4)^+$, 394 $(M+Na)^+$; MS (ESI(−)) m/e 370 $(M-H)^-$, $^1H$ NMR (300 MHz, DMSO-$d_6$) δ 7.72 (s, 2H), 7.55 (d, 2H), 7.29 (s, 1H), 7.04 (s, 1H), 3.73 (s, 3H), 3.67 (s, 3H).

EXAMPLE 102

5-chloro-2-{[(3,4-dichlorophenyl)sulfonyl]amino}benzoic acid

The desired product was prepared by substituting 3,4-dichlorobenzenesulfonyl chloride for 2-fluorobenzenesulfonyl chloride and 2-amino-5-chlorobenzoic acid for 2-amino-5,6,7,8-tetrahydro-1-naphthoic acid in Example 128D. MS (ESI(+)) m/e 388 $(M+NH_4)^+$; MS (ESI(−)) m/e 378, 380, 382 $(M-H)^-$; $^1H$ NMR (300 MHz, DMSO-$d_6$) δ 7.97 (d, 1H), 7.81 (d, 1H), 7.80 (d, 1H), 7.70 (m, 1H), 7.07 (s, 1H), 6.90 (s, 1H).

EXAMPLE 103

2-{[(4-fluorophenyl)sulfonyl]amino}-8-oxo-5,6,7,8-tetrahydro-1-naphthalenecarboxylic acid

EXAMPLE 103A

N-(1-bromo-8-oxo-5,6,7,8-tetrahydro-2-naphthalenyl)-4-fluorobenzenesulfonamide

The desired product was prepared by substituting 4-fluorobenzenesulfonyl chloride for 2-fluorobenzenesulfonyl chloride in Example 275C. MS (ESI) m/e 397 $(M-H)^-$; $^1H$ NMR (300 MHz, DMSO-$d_6$) δ 9.97 (s, 1H), 7.75 (m, 2H), 7.4 (m, 2H), 7.31 (s, 2H), 2.9 (t, 2H), 2.6 (t, 2H), 1.95 (m, 2H).

EXAMPLE 103B

2-{[(4-fluorophenyl)sulfonyl]amino}-8-oxo-5,6,7,8-tetrahydro-1-naphthalenecarboxylic acid A solution of Example 103A (200 mg, 0.5 mmol) in THF (8 mL), water (2 mL), and treithylamine (153 μL) was treated with $PdCl_2(dppf).CH_2Cl_2$ (43.8 mg) and heated to 120° C. for 16 hours under CO pressure (700 psi). The mixture was filtered and the filtrate was concentrated. The concentrate was purified by reverse-phase HPLC to provide the desired product (120 g, 67% yield). MS (ESI) m/e 362 $(M-H)^-$; $^1H$ NMR (300 MHz, DMSO-$d_6$) δ 12.75 (br s, 1H), 9.76 (br s, 1H), 7.82 (m, 2H), 7.4 (m, 2H), 7.31 (d, 1H), 7.08 (d, 1H), 2.9 (m, 2H), 2.57 (m, 2H), 1.98 (m, 2H).

EXAMPLE 104

3-bromo-2-methyl-6-[(phenylsulfonyl)amino]benzoic acid

EXAMPLE 104A

2-[(tert-butoxycarbonyl)amino]-6-methylbenzoic acid

A mixture of 2-amino-6-methylbenzoic acid (15 g, 99 mmol), di-tert-butyl dicarbonate (22.7 g 104 mmol) and anhydrous acetonitrile (150 mL) was treated with triethylamine (15.2 mL, 109 mmol) and stirred for 18 hours. The reaction was concentrated and the residue was partitioned between water (800 mL) and dichloromethane (750 mL) and acidified to pH 1 with 1M HCl. The organic layer was separated, washed sequentially with 1M HCl, water, and brine, dried ($Na_2SO_4$), filtered and concentrated. The residue was purified by passage through a plug of silica gel (500 g) with 5% methanol in dichloromethane. Concentration afforded the desired product (23.3 g). MS (ESI(+)) m/e 252 $(M+H)^+$, 269 $(M+NH_4)^+$, 274 $(M+Na)^+$; (ESI(−)) m/e 250 $(M-H)^-$; $^1H$ NMR (300 MHz, DMSO-$d_6$) δ 13.36 (br s, 1H), 8.94 (s, 1H), 7.58 (d, 1H), 7.29 (t, 1H), 6.99 (d, 1H), 2.37 (s, 3H), 1.45 (s, 9H).

EXAMPLE 104B 3-bromo-6-[(tert-butoxycarbonyl)amino]-2-methylbenzoic acid

A solution of Example 104A (10 g, 40 mmol) and tetrabutylammonium tribromide (19.2 g, 40 mmol) in DMF (250 mL) was treated slowly with water (250 mL). The resulting suspension was stirred for 18 hours and partitioned between water (1.2 L) and ethyl acetate (500 mL). The organic layer was washed with water (2×1 L), dried ($Na_2SO_4$), filtered, and concentrated. The residue was dissolved in dichloromethane (900 mL), washed with water (5×1 L) and brine, dried ($Na_2SO_4$), filtered, and concentrated to provide the desired product (11.7 g). MS (ESI(−)) m/e 328, 330 $(M-H)^-$; $^1H$ NMR (300 MHz, DMSO-$d_6$) δ 13.60 (br s, 1H), 9.68 (s, 1H), 7.63 (d, 1H), 7.39 (d, 1H), 2.37 (s, 3H), 1.44 (s, 9H).

EXAMPLE 104C 6-amino-3-bromo-2-methylbenzoic acid

A solution of Example 104B (300 mg, 0.9 mmol) in anhydrous 4N HCl/dioxane solution (10 mL) was stirred for 2 hours and concentrated to provide the desired product as the hydrochloride salt. MS (ESI(−)) m/e 228, 230 $(M-H)^-$; $^1H$ NMR (300 MHz, DMSO-$d_6$) δ 7.34 (d, 1H), 6.66 (d, 1H), 4.44 (br s, 3H), 2.34 (s, 3H).

EXAMPLE 104D 3-bromo-2-methyl-6-[(phenylsulfonyl)amino]benzoic acid

A mixture of Example 104C (225 mg, 0.8 mmol), dichloromethane (5 mL), 1M trimethylsilyl chloride in dichloromethane (1.8 mL, 1.8 mmol) was treated with anhydrous pyridine (0.3 mL, 3.8 mmol), stirred for 3 hours, treated with benzenesulfonyl chloride (0.13 mL, 1.0 mmol), and stirred for 18 hours. The mixture was partitioned between dichloromethane (125 mL) and water (100 mL), acidified to pH 1 with 1M HCl, and stirred for 30 minutes. The layers were separated and the organic layer was dried ($Na_2SO_4$), filtered, and concentrated. The concentrate was purified by preparative HPLC on a Waters Symmetry C8 column (25 mm×100 mm, 7 μm particle size) using a gradient of 10% to 100% acetonitrile/0.1% aqueous TFA over 8 min (10 min run time) at a flow rate of 40 mL/min to provide the desired product. MS (ESI(−)) m/e 368, 370 $(M-H)^-$; $^1H$ NMR (300 MHz, DMSO-$d_6$) δ 13.40 (br s, 1H), 9.89 (br s, 1H), 7.76 (m, 2H), 7.64 (m, 1H), 7.57 (m, 3H), 6.72 (d, 1H), 2.30 (s, 3H).

EXAMPLE 105

2-{[(4-fluorophenyl)sulfonyl]amino}-8-hydroxy-5,6,7,8-tetrahydro-1-naphthalenecarboxylic acid A mixture of Example 103B (25 mg, 0.068 mmol) in methanol (3 mL) was treated with $NaBH_4$ (5.2 mg, 0.137 mmol), stirred at room temperature for 3 hours, and concentrated. The concentrate was purified by reverse phase HPLC to provide the desired product. MS (ESI) m/e 364 $(M-H)^-$; $^1H$ NMR (300 MHz, DMSO-$d_6$) δ 7.74 (m, 2H), 7.32 (m, 2H), 7.23 (d, 1H), 7.18 (br s, 1H), 6.9 (d, 1H), 4.59 (br s, 1H), 2.6 (m, 2H), 1.85 (m, 2H), 1.5 (m, 2H).

EXAMPLE 106

8-amino-2-{[(4-fluorophenyl)sulfonyl]amino}-5,6,7,8-tetrahydro-1-naphthalenecarboxylic acid A mixture of Example 103B (20 mg, 0.055 mmol), $NaCNBH_3$ (17.2 mg, 0.275 mmol), and ammonium acetate (42 mg, 0.55 mmol) in methanol (5 mL) was heated to reflux overnight and concentrated. The concentrate was purified by reverse-phase HPLC to provide the desired product. MS (ESI) m/e 363 $(M-H)^-$; $^1H$ NMR (300 MHz, DMSO-$d_6$) δ 8.4 (br s, 2H), 7.66 (m, 2H), 7.36 (m, 2H), 7.25 (d, 1H), 7.14 (d, 1H), 4.42 (br s, 1H), 2.65 (m, 2H), 2.06 (m, 2H), 1.68 (m, 2H).

EXAMPLE 107

2-{[(4-fluorophenyl)sulfonyl]amino}-8-hydroxy-8-methyl-5,6,7,8-tetrahydro-1-naphthalenecarboxylic acid A mixture of Example 103B (40 mg, 0.11 mmol) in diethyl ether (3 mL) and THF (2 mL) was treated with methylmagnesium bromide (3M solution in diethyl ether, 0.11 mL), stirred at 45° C. for 2 hours, quenched with saturated $NH_4Cl$, and partitioned between diethyl ether and brine. The organic phase was dried ($Na_2SO_4$), filtered, concentrated, and purified by reverse-phase HPLC to provide the desired product. MS (ESI) m/e 378 $(M-H)^-$; $^1H$ NMR (300 MHz, DMSO-$d_6$) δ 12.18 (br s, 1H), 8.5 (s, 1H), 7.75 (m, 2H), 7.52 (m, 2H), 7.32 (d, 1H), 6.85 (d, 1H), 2.56 (m, 2H), 1.82-1.73 (m, 1H), 1.72-1.61 (m, 1H), 1.53-1.37 (m, 2H), 1.33 (s, 3H).

EXAMPLE 108

3-cyano-2-methyl-6-[(phenylsulfonyl)amino]benzoic acid

EXAMPLE 108A benzyl 3-bromo-6-[(tert-butoxycarbonyl)amino]-2-methylbenzoate

A mixture of Example 104B (5 g, 15.1 mmol), potassium carbonate (3.1 g, 22.7 mmol), and DMF (150 mL) was treated with benzyl bromide (1.8 mL, 15.1 mmol), stirred for 5 hours, and concentrated. The residue was partitioned between water (1 L) and dichloromethane (750 mL). The organic layer was washed with water and brine, dried ($Na_2SO_4$), filtered, concentrated, and purified by passing through a plug of silica gel (150 g) with 25% dichloromethane in hexane to provide the desired product. MS (ESI(−)) m/e 418, 420 $(M-H)^-$; $^1H$ NMR (300 MHz, DMSO-$d_6$) δ 9.05 (br s, 1H), 7.65 (d, 1H), 7.45 (m, 2H), 7.39 (m, 3H), 7.21 (d, 1H), 5.28 (s, 2H), 2.30 (s, 3H), 1.42 (s, 9H).

EXAMPLE 108B benzyl 6-amino-3-cyano-2-methylbenzoate

A mixture of Example 108A (2 g, 4.8 mmol), zinc cyanide (335 mg, 2.9 mmol), and DMF (48 mL) was degassed with argon for 30 minutes, treated with $Pd(PPh_3)_4$ (330 mg, 0.28 mmol), heated to reflux for 1.5 hours, cooled, and filtered. The filtrate was concentrated and purified using a Biotage 40 gram silica gel cartridge to provide the desired product. MS (ESI (−)) m/e 265 $(M-H)^-$; (DCI) m/e 267 $(M+H)^+$, 284 $(M+NH_4)^+$; $^1H$ NMR (300 MHz, DMSO-$d_6$) δ 7.45 (m, 6H), 6.66 (d, 1H), 6.57 (s, 2H), 5.34 (s, 2H), 3.27 (s, 3H).

EXAMPLE 108C benzyl 3-cyano-2-methyl-6-[(phenylsulfonyl)amino]benzoate

A mixture of Example 108B (576 mg, 2.2 mmol), anhydrous dichloromethane (22 mL), pyridine (0.4 mL) and benzenesulfonyl chloride (0.33 mL) was stirred 18 hours under nitrogen atmosphere. The mixture was concentrated, dissolved in ethyl acetate (100 mL), washed with 0.5M HCl (3×50 mL) and brine, dried ($Na_2SO_4$), filtered, concentrated, and purified on silica gel (20 g) with 50% dichloromethane in hexanes to provide the desired product. MS (ESI(+)) m/e 407 $(M+H)^+$, 424 $(M+NH_4)^+$, 429 $(M+Na)^+$; (ESI(−)) m/e 405 $(M-H)^-$; $^1$H NMR (300 MHz, DMSO-$d_6$) δ 10.59 (br s, 1H), 7.77 (m, 3H), 7.64 (m, 1H), 7.56-7.37 (m, 7H), 7.24 (d, 1H), 5.31 (s, 2H), 2.32 (s, 3H).

EXAMPLE 108D 3-cyano-2-methyl-6-[(phenylsulfonyl)amino]benzoic acid

A mixture of Example 108C (140 mg, 0.34 mmol), 10% Pd/C (73 mg, 0.03 mmol), methanol (4 mL), and THF (8 mL) was stirred under a hydrogen atmosphere for 45 minutes and filtered. The filtrate was concentrated to an oil which was triturated with diethyl ether to provide the desired product. MS (ESI(−)) m/e 315 $(M-H)^-$; $^1$H NMR (300 MHz, DMSO-$d_6$) δ 7.80 (m, 2H), 7.56 (m, 4H), 7.22 (d, 1H), 3.32 (br s, 2H), 2.56 (s, 3H).

EXAMPLE 109

3-cyano-2-methyl-6-[(2-pyridinylsulfonyl)amino]benzoic acid

A solution of Example 110A (115 mg, 0.25 mmol) and $Zn(CN)_2$ (30 mg, 0.25 mmol) in anhydrous DMF (3 mL) was purged with $N_2$, treated with $Pd(PPh_3)_4$ (15 mg), stirred at 90° C. overnight, diluted with ethyl acetate (50 mL), washed with brine, dried ($MgSO_4$), filtered and concentrated. The residue was purified by reverse-phase HPLC to provide the desired product (30.5 mg, 36.0%). $^1$H NMR (DMSO-$d_6$) δ 2.48 (s, 3H), 7.42 (d, 1H), 7.68-7.71 (m, 1H), 7.78 (d, 1H), 8.00 (d, 1H), 8.08-8.12 (dt, 1H), 8.71 (s, 1H); MS (ESI(−)) m/e 316.

EXAMPLE 110

3-bromo-2-methyl-6-[(2-pyridinylsulfonyl)amino]benzoic acid

EXAMPLE 110A benzyl 3-bromo-2-methyl-6-[(2-pyridinylsulfonyl)amino]benzoate

A solution of Example 126B (0.43 g, 1.2 mmol) and 2-pyridinesulfonyl chloride (0.64 g, 3.6 mmol) in dichloromethane (4 mL) at 0° C. was treated dropwise with pyridine (0.29 mL, 3.6 mmol), stirred for 3 hours, treated with dichloromethane (30 mL), washed with 1N aqueous HCl (2×30 mL), and concentrated. The concentrate was chromatographed on a silica gel column eluting with 30% ethyl acetate/hexanes to provide the desired product (0.483 g, 88.3%). $^1$H NMR ($CDCl_3$) δ 2.35 (s, 3H), 5.39 (s, 2H), 7.40-7.46 (m, 6H), 7.55 (d, 1H), 7.75-7.87 (m, 2H), 8.49-8.52 (m, 2H); MS (ESI(+)) m/e 461, 463 $(M+H)^+$.

EXAMPLE 110B 3-bromo-2-methyl-6-[(2-pyridinylsulfonyl)amino]benzoic acid

A solution of Example 110A (150 mg, 0.32 mmol) in methanol (8 mL) was treated with 5% Pd/C (100 mg), stirred under a hydrogen atmosphere for 1 hour, and filtered through diatomaceous earth (Celite®). The filtrate was concentrated and purified by reverse-phase HPLC to provide the desired product (6.5 mg, 6.4%). $^1$H NMR (DMSO-$d_6$) δ 2.31 (s, 3H), 6.99 (d, 1H), 7.58 (d, 1H), 7.69 (d, 1H), 7.88 (dd, 1H), 8.06 (dd, 1H), 8.72 (d, 1H), 10.08 (br s, 1H), 13.58 (br s, 1H); MS (ESI(−)) m/e 371 $(M-H)^-$.

EXAMPLE 111

2-[(2-pyridinylsulfonyl)amino]-1-naphthoic acid

EXAMPLE 111A methyl 2-[(2-pyridinylsulfonyl)amino]-1-naphthoate

A solution of methyl 2-amino-1-naphthoate (85 mg, 0.42 mmol) and 2-pyridinesulfonyl chloride (244 mg, 1.3 mmol) in dichloromethane (1.0 mL) was treated with pyridine (0.15 mL, 1.3 mmol), stirred for 15 minutes, treated with dichloromethane (30 mL), washed with 1N HCl (2×20 mL), and concentrated. The crude product was chromatographed on a silica gel column eluting with 30% ethyl acetate/hexanes to provide the desired product (120 mg, 83.5%). $^1$H NMR ($CDCl_3$) δ 4.09 (s, 3H), 7.35-7.55 (m, 3H), 7.75-7.96 (m, 5H), 8.16 (d, 1H), 8.59 (d, 1H), 9.46 (s, 1H); MS ($DCI/NH_3$) m/e 343 $(M+H)^+$.

EXAMPLE 111B

2-[(2-pyridinylsulfonyl)amino]-1-naphthoic acid

A solution of Example 111A (120 mg, 0.35 mmol) in methanol (4 mL), THF (4 mL), and water (2 mL) was treated with NaOH (150 mg, 3.75 mmol), heated to reflux for 8 days, adjusted to pH 2.0 with 1N HCl, and concentrated. The resulting solid was triturated with methanol. The solution was concentrated and the residue was purifed by reverse-phase HPLC to provide the desired product (23 mg, 20.0%). $^1$H NMR (DMSO-$d_6$) δ 7.49-7.53 (m, 2H), 7.56-7.59 (m, 1H), 7.63-7.66 (m, 1H), 7.88-7.97 (m, 3H), 8.04 (dt, 1H), 8.15 (d, 1H), 8.70 (m, 1H), 10.49 (br s, 1H), 13.96 (br s, 1H); MS (ESI(−)) m/e 327 $(M-H)^-$.

EXAMPLE 112

3-bromo-2-methyl-6-[(3-pyridinylsulfonyl)amino]benzoic acid

EXAMPLE 112A benzyl 3-bromo-2-methyl-6-[(3-pyridinylsulfonyl)amino]benzoate

The desired product was prepared by substituting 3-pyridinesulfonyl chloride for 2-pyridinesulfonyl chloride in Example 110A (0.98 g, 100%). $^1$H NMR ($CDCl_3$) δ 2.30 (s, 3H), 5.15 (s, 2H), 7.27 (dd, 1H), 7.34-7.44 (m, 6H), 7.62 (d, 1H), 7.80 (dt, 1H), 8.23 (s, 1H), 8.66 (m, 1H), 8.85 (s, 1H); MS (ESI(+) m/e 463, 461 $(M+H)^+$.

EXAMPLE 112B 3-bromo-2-methyl-6-[(3-pyridinylsulfonyl)amino]benzoic acid

The desired product was prepared by substituting Example 112A for Example 110A in Example 110B (17 mg, 9.4%). $^1$H NMR (DMSO-$d_6$) δ 2.30 (s, 3H), 6.86 (d, 1H), 7.59-7.62 (m, 2H), 8.08 (d, 1H), 8.80-8.85 (m, 2H), 10.50 (br s, 1H); MS (ESI(−)) m/e 371, 370 $(M-H)^-$.

EXAMPLE 113

3-cyano-2-methyl-6-[(3-pyridinylsulfonyl)amino]benzoic acid

The desired product was prepared by substituting Example 112A for Example 110A in Example 109 (22 mg, 27.8%). $^1$H NMR (DMSO-$d_6$) δ 2.45 (s, 3H), 7.24 (d, 1H), 7.60-7.64 (m, 1H), 7.76 (d, 1H), 8.15-8.18 (m, 1H), 8.15 (d, 1H), 8.82 (d, 1H), 8.95 (s, 1H), 10.5-11.5 (br s, 1H), 13.96 (br s, 1H); MS (ESI(−)) m/e 316 $(M-H)^-$.

EXAMPLE 114

3-butyl-2-methyl-6-[(3-pyridinylsulfonyl)amino]benzoic acid

EXAMPLE 114A benzyl 3-butyl-2-methyl-6-[(3-pyridinylsulfonyl)amino]benzoate

A mixture of Example 112A (115 mg, 0.25 mmol), $K_3PO_4$ (185 mg, 0.875 mmol), n-butylboronic acid (34 mg, 0.325 mmol), and bis(tricyclohexylphosphine)palladium dichloride (18 mg, 0.025 mmol) in toluene (4 mL) and water (0.2 mL) was purged with nitrogen and stirred at 100° C. for 24 hours. The mixture was then directly chromatographed on a silica gel column, eluting with 30% ethyl acetate/hexanes to provide the desired product (87 mg, 39.7%).

EXAMPLE 114B 3-butyl-2-methyl-6-[(3-pyridinylsulfonyl)amino]benzoic acid

A solution of Example 114A (87 mg) in methanol (4 mL), THF (4 mL), and water (1 mL) was treated with 5% Pd/C (100 mg), stirred under a hydrogen atmosphere for 1 hour, and filtered through diatomaceous earth (Celite®), and concentrated to provide the desired product (47 mg). $^1$H NMR (DMSO-$d_6$) δ 0.89 (t, 3H), 1.29-1.34 (m, 2H), 1.40-1.45 (m, 2H), 2.21 (s, 3H), 2.52 (t, 2H), 6.81 (d, 1H), 7.07 (t, 1H), 7.58 (t, 1H), 8.07 (d, 1H), 8.77 (d, 1H), 8.83 (s, 1H); MS (ESI(−)) m/e 347 $(M-H)^-$.

EXAMPLE 115

6-[(1-naphthylsulfonyl)amino]-1H-indole-7-carboxylic acid

A solution of ethyl 6-amino-1H-indole-7-carboxylate (prepared as described in Showalter, H. D. et al., *J. Org. Chem.,* 1996, 61, 1155-1158, 0.05 g, 0.25 mmol) in $CH_2Cl_2$ (5 mL) was treated with 1-naphthalenesulfonyl chloride (0.066 g, 0.29 mmol) and pyridine (0.040 mL, 0.50 mmol), shaken for 16 hours at ambient temperature, filtered, and concentrated. The concentrate was dissolved in 9:1 methanol/water (1 mL), treated with LiOH (25 mg, 0.6 mmol), and heated to 60° C. for 16 hours. The mixture was concentrated and the concentrate was purified by $C_{18}$ reverse-phase HPLC using acetonitrile/water/0.1% TFA to provide the desired product. MS (DCI) m/e 384 $(M+NH_4)^+$; $^1$H NMR (500 MHz, DMSO-$d_6$) δ 12.43 (br s, 1H), 10.77 (s, 1H), 8.62 (d, 1H), 8.30 (dd, 1H), 8.18 (d, 1H), 8.03 (d, 1H), 7.69 (m, 1H), 7.64-7.60 (m, 3H), 7.20 (d, 1H), 7.17 (t, 1H), 6.35 (dd, 1H).

EXAMPLE 116

6-{[(3-fluorophenyl)sulfonyl]amino}-1H-indole-7-carboxylic acid

The desired product was prepared by substituting 3-fluorobenzenesulfonyl chloride for 1-naphthalenesulfonyl chloride in Example 115. MS (DCI) m/e 352 $(M+NH_4)^+$; $^1$H NMR (500 MHz, DMSO-$d_6$) δ 12.01 (br s, 1H), 10.89 (s, 1H), 7.72 (d, 1H), 7.56-7.52 (m, 3H), 7.46-7.43 (m, 1H), 7.27-7.25 (m, 2H), 6.44 (dd, 1H).

EXAMPLE 117

6-{[(4-fluorophenyl)sulfonyl]amino}-1H-indole-7-carboxylic acid

The desired product was prepared by substituting 4-fluorobenzenesulfonyl chloride for 1-naphthalenesulfonyl chloride in Example 115. MS (DCI) m/e 352 $(M+NH_4)^+$; $^1$H NMR (500 MHz, DMSO-$d_6$) δ 11.85 (br s, 1H), 10.88 (s, 1H), 7.80-7.77 (m, 2H), 7.72 (d, 1H), 7.33 (t, 2H), 7.27-7.24 (m, 2H), 6.44 (dd, 1H).

EXAMPLE 118

6-{[(2-chloro-4-methoxyphenyl)sulfonyl]amino}-1H-indole-7-carboxylic acid

The desired product was prepared by substituting 2-chloro-4-methoxybenzenesulfonyl chloride for 1-naphthalenesulfonyl chloride in Example 115. MS (DCI) m/e 398 $(M+NH_4)^+$; $^1$H NMR (500 MHz, DMSO-$d_6$) δ 12.33 (br s, 1H), 10.89 (s, 1H), 8.08 (d, 1H), 7.62 (d, 1H), 7.23 (m, 1H), 7.14 (d, 1H), 7.12 (d, 1H), 7.05 (dd, 1H), 6.40 (dd, 1H).

EXAMPLE 119

6-{[(4-methylphenyl)sulfonyl]amino}-1H-indole-7-carboxylic acid

The desired product was prepared by substituting 4-methylbenzenesulfonyl chloride for 1-naphthalenesulfonyl chloride in Example 115. MS (DCI) m/e 331 $(M+H)^+$, 348 $(M+NH_4)^+$; $^1$H NMR (500 MHz, DMSO-$d_6$) δ 11.70 (br s, 1H), 10.86 (s, 1H), 7.70 (d, 1H), 7.62 (d, 2H), 7.28 (d, 3H), 7.23 (t, 1H), 6.42 (dd, 1H), 2.28 (s, 3H).

EXAMPLE 120

6-{[(2-fluorophenyl)sulfonyl]amino}-1H-indole-7-carboxylic acid

The desired product was prepared by substituting 2-fluorobenzenesulfonyl chloride for 1-naphthalenesulfonyl chloride in Example 115. MS (DCI) m/e 335 $(M+H)^+$, 352 $(M+NH_4)^+$; $^1$H NMR (500 MHz, DMSO-$d_6$) δ 12.20 (br s, 1H), 10.89 (s, 1H), 7.89 (td, 1H), 7.67-7.62 (m, 2H), 7.36-7.32 (m, 2H), 7.24-7.21 (m, 2H), 6.41 (dd, 1H).

EXAMPLE 121

6-{[(4-chlorophenyl)sulfonyl]amino}-1H-indole-7-carboxylic acid

The desired product was prepared by substituting 4-chlorobenzenesulfonyl chloride for 1-naphthalenesulfonyl chloride in Example 115. MS (DCI) m/e $(M+NH_4)^+$; $^1H$ NMR (500 MHz, DMSO-$d_6$) δ 11.81 (br s, 1H), 10.89 (s, 1H), 7.73 (m, 3H), 7.57 (m, 2H), 7.26-7.24 (m, 2H), 6.44 (dd, 1H).

EXAMPLE 122

6-[(phenylsulfonyl)amino]-1H-indole-7-carboxylic acid

The desired product was prepared by substituting benzenesulfonyl chloride for 1-naphthalenesulfonyl chloride in Example 115. MS (DCI) m/e 317 $(M+H)^+$, 334 $(M+NH_4)^+$; $^1H$ NMR (500 MHz, DMSO-$d_6$) δ 11.90 (br s, 1H), 10.86 (s, 1H), 7.74 (m, 2H), 7.70 (d, 1H), 7.56 (m, 1H), 7.50-7.47 (m, 2H), 7.28 (d, 1H), 7.23 (t, 1H), 6.42 (dd, 1H).

EXAMPLE 123

6-{[(3-methylphenyl)sulfonyl]amino}-1H-indole-7-carboxylic acid

The desired product was prepared by substituting 3-methylbenzenesulfonyl chloride for 1-naphthalenesulfonyl chloride in Example 115. MS (DCI) m/e 331 $(M+H)^+$, 348 $(M+NH_4)^+$; $^1H$ NMR (500 MHz, DMSO-$d_6$) δ 11.70 (br s, 1H), 10.86 (s, 1H), 7.70 (d, 1H), 7.58 (s, 1H), 7.53-7.50 (m, 1H), 7.38-7.35 (m, 2H), 7.27 (d, 1H), 7.24 (t, 1H), 6.43 (dd, 1H), 2.29 (s, 3H).

EXAMPLE 124

6-{[(4-methoxyphenyl)sulfonyl]amino}-1H-indole-7-carboxylic acid

The desired product was prepared by substituting 4-methoxybenzenesulfonyl chloride for 1-naphthalenesulfonyl chloride in Example 115. MS (DCI) m/e 347 $(M+H)^+$, 364 $(M+NH_4)^+$; $^1H$ NMR (500 MHz, DMSO-$d_6$) δ 11.76 (br s, 1H), 10.86 (s, 1H), 7.70 (d, 1H), 7.66 (m, 2H), 7.28 (d, 1H), 7.23 (t, 1H), 7.00 (m, 2H), 6.42 (dd, 1H), 3.75 (s, 3H).

EXAMPLE 125

4-bromo-2-[(phenylsulfonyl)amino]benzoic acid

EXAMPLE 125A 4-bromo-2-nitrobenzoic acid

A mixture of 4-bromo-2-nitrotoluene (10 g, 46.2 mmol), pyridine (85 mL) and water (65 mL) was heated to reflux and treated portionwise with potassium permanganate (21.9 g, 138.9 mmol) over 8 hours. Ethanol (7.8 mL) was added and the mixture was filtered while hot through diatomaceous earth (Celite®). The filtrate was concentrated and partitioned between water (200 mL), 10% NaOH (25 mL), and diethyl ether (250 mL). The aqueous phase was acidified to pH 1 with concentrated HCl and the resulting solid was collected by filtration and dried to provide the desired product. MS (ESI (−)) m/e 244, 246 $(M-H)^-$; $^1H$ NMR (300 MHz, DMSO-$d_6$) δ 14.06 (br s, 1H), 8.28 (d, 1H), 7.99 (dd, 1H), 7.81 (d, 1H).

EXAMPLE 125B 2-amino-4-bromobenzoic acid

A mixture of Example 125A (5.1 g, 20.7 mmol) in concentrated ammonium hydroxide (102 mL) was treated with a solution of ammonium iron (II) sulfate (49 g, 125.1 mmol) in water (102 mL) over 5 minutes, heated to reflux for 2 minutes, cooled to room temperature, filtered through diatomaceous earth (Celite®), acidified to pH 1 with concentrated HCl, and extracted with ethyl acetate. The organic layer was dried ($Na_2SO_4$), filtered, and concentrated to provide the desired product. MS (ESI(−)) m/e 214, 216 $(M-H)^-$, $^1H$ NMR (300 MHz, DMSO-$d_6$) δ 7.59 (d, 1H), 6.97 (d, 1H), 6.63 (dd, 1H), 3.32 (br s, 3H).

EXAMPLE 125C 4-bromo-2-[(phenylsulfonyl)amino]benzoic acid

A mixture of Example 125B (2 g, 9.2 mmol) and dichloromethane (56 mL) was treated sequentially with 1M trimethylsilyl chloride (20.4 mL, 20.4 mmol) and pyridine (3.4 mL, 41.7 mmol), stirred for 3 hours, treated with benzenesulfonyl chloride (1.4 mL, 11.1 mmol), stirred for 48 hours, diluted with dichloromethane (100 mL), acidified to pH 1 with 1M HCl and stirred for 15 minutes. The organic layer was dried ($Na_2SO_4$), filtered, and concentrated. Purification by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min provided the desired product as an off-white solid. MS (ESI(−)) m/e 354, 356 $(M-H)^-$; $^1H$ NMR (300 MHz, DMSO-$d_6$) δ 11.36 (br s, 1H), 7.84 (m, 3H), 7.66 (m, 4H), 7.33 (dd, 1H), 3.38 (br s, 1H).

EXAMPLE 126

3-bromo-6-{[(3-fluorophenyl)sulfonyl]amino}-2-methylbenzoic acid

EXAMPLE 126A benzyl 3-bromo-6-[(tert-butoxycarbonyl)amino]-2-methylbenzoate

A mixture of Example 104B (10 g, 30.3 mmol), potassium carbonate (6.3 g, 45.4 mmol), and DMF (300 mL) was treated with benzyl bromide (3.6 mL, 30.3 mmol), stirred for 5 hours, concentrated, and partitioned between water (1 L) and ethyl acetate (1 L). The organic layer was washed with water (2×1 L) and brine, dried ($Na_2SO_4$), filtered, and concentrated to provide the desired product. MS (ESI(+)) m/e 420, 422 $(M+H)^+$, 437, 439 $(M+NH_4)^+$, 442, 444 $(M+Na)^+$; (ESI(−)) m/e 418, 420 $(M-H)^-$; $^1H$ NMR (300 MHz, DMSO-$d_6$) δ 9.04 (s, 1H), 7.65 (d, 1H), 7.45 (m, 2H), 7.37 (m, 3H), 7.22 (d, 1H), 5.28 (s, 2H), 2.30 (s, 3H), 1.42 (s, 9H).

EXAMPLE 126B benzyl 6-amino-3-bromo-2-methylbenzoate

A mixture of Example 126A, dichlormethane (20 mL), and 4N HCl in dioxane (30 mL) was stirred for 18 hours, concentrated, and triturated with a 1:1 mixture of hexanes and diethyl ether (150 mL) to provide the desired product. MS (ESI(+)) m/e 320, 322 $(M+H)^+$; (ESI(−)) m/e 318, 320 $(M-H)^-$; $^1H$ NMR (300 MHz, DMSO-$d_6$) δ 7.40 (m, 5H), 7.31 (d, 1H), 6.56 (d, 1H), 5.33 (s, 2H), 4.92 (br s, 2H), 2.23 (s, 3H).

EXAMPLE 126C benzyl 3-bromo-6-{[(3-fluorophenyl)sulfonyl]amino}-2-methylbenzoate A mixture of Example 126B (760 mg, 2.1 mmol), 3-fluorobenzenesulfonyl chloride (600 mg, 3.1 mmol) in dichloromethane (10 mL) was treated with pyridine (0.690 mL, 8.5 mmol), stirred for 18 hours, diluted with dichloromethane (90 mL), washed with 0.5M HCl (2×100 mL) and brine, dried ($Na_2SO_4$), filtered, concentrated and purified on a Biotage silica gel cartridge (40 g) with 50-75% dichloromethane in hexanes to provide the desired product. MS (ESI(+)) m/e 478, 480 $(M+H)^+$, 495, 497 $(M+NH_4)^+$, 500, 502 $(M+Na)^+$; (ESI (−)) m/e 476, 478 $(M-H)^-$; $^1$H NMR (300 MHz, DMSO-$d_6$) δ 10.23 (s, 1H), 7.64-7.35 (m, 10H), 6.83 (d, 1H), 5.25 (s, 2H), 2.19 (s, 3H).

EXAMPLE 126D 3-bromo-6-{[(3-fluorophenyl)sulfonyl]amino}-2-methylbenzoic acid

The desired compound was prepared by substituting Example 126C for Example 108C in Example 108D and was purified by preparative HPLC on a Waters Symmetry C8 column (25 mm×100 mm, 7 μm particle size) using a gradient of 10% to 100% acetonitrile:0.1% aqueous TFA over 8 minutes (10 minute run time) at a flow rate of 40 mL/min to provide the desired product. MS (ESI(−)) m/e 386, 388 $(M-H)^-$; $^1$H NMR (300 MHz, DMSO-$d_6$) δ 13.65 (br s, 1H), 10.11 (br s, 1H), 7.56 (m, 5H), 6.77 (d, 1H), 2.30 (s, 3H).

EXAMPLE 127

3-bromo-6-{[(4-fluorophenyl)sulfonyl]amino}-2-methylbenzoic acid

The desired product was prepared by substituting 4-fluorobenzenesulfonyl chloride for benzenesulfonyl chloride in Example 104D and purifying on a Biotage silica gel cartridge (90 g) with 7.5% methanol in dichloromethane followed by trituration with 1:2 diethyl ether in hexanes. MS (ESI(−)) m/e 386, 388 $(M-H)^-$; $^1$H NMR (300 MHz, DMSO-$d_6$) δ 13.38 (br s, 1H), 10.37 (br s, 1H), 7.81 (m, 2H), 7.58 (d, 1H), 7.40 (m, 2H), 6.71 (d, 1H), 2.31 (s, 3H).

EXAMPLE 128

2-{[(4-fluorophenyl)sulfonyl]amino}-5,6,7,8-tetrahydro-1-naphthalenecarboxylic acid

EXAMPLE 128A tert-butyl 1,2-dioxo-1,2-dihydro-3H-benzo[e]indole-3-carboxylate

A mixture of Example 42A (19.72 g, 100 mmol), di-tert-butyl dicarbonate (26.2 g, 120 mmol, 1.2 eq.), acetonitrile (180 mL), and DMAP (0.92 g, 0.075 eq.) was stirred at room temperature for 2 hours, treated with MTBE (100 mL), stirred for 30 minutes, cooled in an ice/water bath for 1 hour, and filtered. The filter cake was washed with MTBE and dried in a vacuum oven to provide 15.83 g of the desired product. The filtrate was concentrated to provide 12.3 g of additional product. $^1$H NMR ($CDCl_3$) δ 8.70 (dq, 1H), 8.19 (d, 1H), 8.11 (d, 1H), 7.80 (d, 1H), 7.65 (q, 1H), 7.48 (q, 1H) 1.68 (s, 9H); $^{13}$C NMR ($CDCl_3$) δ 178.4, 155.4, 151.1, 147.7, 139.9, 130.9, 130.0, 128.4, 128.1, 126.4, 123.6, 115.1, 111.2, 85.4, 28.3.

EXAMPLE 128B

2-[(tert-butoxycarbonyl)amino]-1-naphthoic acid

A mixture of Example 128A (12 g, 40 mmol) in THF (100 mL) at 5° C. was treated slowly with 1N NaOH (200 mL, 5 eq.) then treated with 30% $H_2O_2$ (17.5 mL, 5 eq.). The solution was stirred at 5-10° C. for 20 minutes, warmed to room temperature, and stirred for 1 hour. The mixture was treated with ethyl acetate (500 mL), cooled to 5-10° C., and acidified to pH 3 with 2N HCl. The organic phase was washed with water (100 mL) and brine (100 mL), checked for residual hydrogen peroxide with a test strip, dried ($Na_2SO_4$), filtered, and concentrated to provide the desired product (10.68, 92%). $^1$H NMR ($CDCl_3$) δ 9.30 (s, 1H), 8.46 (d, 1H), 8.33 (d, 1H), 7.84 (d, 1H), 7.68 (d, 1H), 7.44 (C, 1H), 7.32 (ABq, 1H), 1.47 (s, 9H); $^{13}$C NMR ($CDCl_3$) δ 173.0, 152.6, 139.9, 139.8, 133.8, 131.1, 129.5, 128.1, 127.7, 125.4, 124.6, 119.3, 81.4, 28.5.

EXAMPLE 128C 2-amino-5,6,7,8-tetrahydro-1-naphthoic acid

A mixture of Example 128B (14.21 g, 49.46 mmol) and $Pt_2O$ (7.00 g, 30.8 mmol) in acetic acid (200 mL) was shaken in a reactor pressurized with 60 psi of $H_2$ at 25° C. for 80 hours, filtered, and concentrated. The concentrate was treated with dichloromethane (142 mL) and TFA (24 mL) and stirred for 3 hours. The organic layer was washed with NaOH (2×250 mL) and brine (200 mL), dried ($MgSO_4$), filtered, and concentrated to provide the desired product (8.17 g, 86%). MS (ESI(+)) m/e 192 $(M+H)^+$; MS (ESI(−)) m/e 190 $(M-H)^-$; $^1$H NMR (300 MHz, DMSO-$d_6$) δ 6.83 (d, 1H), 6.53 (d, 1H), 2.72 (m, 2H), 2.57 (m, 2H), 1.64 (m, 4H).

EXAMPLE 128D

2-{[(4-fluorophenyl)sulfonyl]amino}-5,6,7,8-tetrahydro-1-naphthalenecarboxylic acid A mixture of Example 128C (0.033 g, 0.200 mmol) in dichloromethane (1 mL) was treated with 1M trimethylsilyl chloride in dichloromethane (440 μL, 0.044 mmol) and pyridine (56.6 μL, 0.70 mmol), shaken for 4 hours at ambient temperature, treated with a solution of 4-fluorobenzenesulfonyl chloride (0.042 g, 0.24 mmol) in dimethylacetamide (1 mL), shaken for 16 hours at ambient temperature, and concentrated. The concentrate was acidified to pH 1.0 with 5% aqueous HCl and extracted with dichloromethane. The extracts were washed sequentially with water and brine, dried ($MgSO_4$); filtered, and concentrated. The concentrate was purified by $C_{18}$ reverse-phase HPLC using acetonitrile/water/0.1% TFA to provide the desired product. MS (ESI(+)) m/e 367 $(M+NH_4)^+$, 372 $(M+Na)^+$; MS (ESI(−)) m/e 348

(M−H)$^-$; $^1$H NMR (300 MHz, DMSO-$d_6$) δ 9.62 (s, 1H), 7.77 (dd, 2H), 7.40 (t, 2H), 7.00 (d, 1H), 6.65 (d, 1H), 2.65 (m, 4H), 1.67 (m, 4H).

EXAMPLE 129

3-oxo-5-[(phenylsulfonyl)amino]-4-indanecarboxylic acid

EXAMPLE 129A 6-nitro-1-indanone

A solution of concentrated $H_2SO_4$ at 0° C. was treated with 1-indanone (6.00 g, 45.4 mmol) then treated dropwise with $KNO_3$ (5.00 g, 49.94 mmol) in concentrated $H_2SO_4$ while maintaining the internal temperature at no more than 15° C. The reaction was stirred for 1 hour after the addition was complete, then poured onto ice. The resulting solids were collected by filtration, washed with water, and dried under vacuum to give a 4:1 mixture of 6-nitro- and 4-nitro-1-indanone (5.04 g, 63%). MS (ESI(+) m/e 178 (M+H)$^+$, 195 (M+$NH_4$)$^+$; MS (ESI(−)) m/e 176 (M−H)$^-$; $^1$H NMR (300 MHz, DMSO-$d_6$, 6-nitro-1-indanone) δ 8.49 (dd, 1H), 8.29 (d, 1H), 7.87 (d, 1H), 3.25 (m, 2H), 2.78 (m, 2H); $^1$H NMR (300 MHz, DMSO-$d_6$), 4-nitro-1-indanone) δ 8.51 (dd, 1H), 8.07 (dd, 1H), 7.74 (t, 1H), 3.53 (m, 2H), 2.76 (m, 2H).

EXAMPLE 129B 6-amino-1-indanone

A solution of Example 129A (19.68 g, 111 mmol) in ethanol (111 mL) was treated sequentially with iron powder (43.0 g, 770 mmol) and solid ammonium chloride (3.70 g, 69.2 mmol). The resulting suspension was stirred at 90° C. for 1 hour, cooled to room temperature, diluted with brine, and extracted with diethyl ether (4×100 mL). The combined organic layers were dried ($MgSO_4$), filtered, and concentrated to provide the desired product as a 6:1 mixture of 6-amino- and 4-amino-1-indanone (14.20 g, 87%). $^1$H NMR (300 MHz, DMSO-$d_6$, 6-amino-1-indanone) δ 7.21 (d, 1H), 6.92 (dd, 1H), 6.75 (d, 1H), 5.27 (br s, 2H), 2.90 (t, 2H), 2.54 (m, 2H); $^1$H NMR (300 MHz, DMSO-$d_6$), 4-amino-1-indanone) δ 7.10 (t, 1H), 6.81 (m, 2H), 2.80 (m, 2H), 2.59 (m, 2H).

EXAMPLE 129C 6-amino-7-bromo-1-indanone

A solution of Example 129B (2.0516 g, 13.94 mmol) in 9:1 $CHCl_3$.DMF (52 mL) was slowly treated with $Br_2$ (0.71 mL, 13.94 mmol), stirred for 1 hour, and filtered. The filter cake was dried under vacuum to provide the desired product (2.7127 g, 63%). MS (ESI(+)) m/e 226, 228 (M+H)$^+$; MS (ESI(−)) m/e 225, 227 (M−H)$^-$; $^1$H NMR (300 MHz, DMSO-$d_6$) δ 7.28 (dt, 1H), 7.17 (d, 1H), 5.87 (br s, 3H), 2.89 (m, 2H), 2.62 (m, 2H).

EXAMPLE 129D

N-(4-bromo-3-oxo-2,3-dihydro-1H-inden-5-yl)benzenesulfonamide

A solution of Example 129C (1.0808 g, 3.52 mmol) in pyridine (17.5 mL) was treated with phenylsulfonyl chloride (0.58 mL, 4.58 mmol), stirred for 2 hours, diluted with $CH_2Cl_2$, washed with 1N HCl (3×50 mL) and brine (50 mL), dried ($MgSO_4$), filtered, and concentrated. The residue was purified by flash column chromatography on silica gel with 9:1 hexanes/ethyl acetate to provide the desired product (450 mg, 35%); MS (ESI(+)) m/e 368 (M+H)$^+$; MS (ESI(−)) m/e 364, 366 (M−H)$^-$; $^1$H NMR (300 MHz, DMSO-$d_6$) δ 7.70 (m, 2H), 7.63 (m, 1H), 7.56 (m, 2H), 7.51 (m, 1H), 7.42 (m, 1H), 3.00 (m, 2H), 2.66 (m, 2H).

EXAMPLE 129E 3-oxo-5-[(phenylsulfonyl)amino]-4-indanecarboxylic acid

A solution of Example 129D (0.1112 g, 0.303 mmol) in 4:1 THF/$H_2O$ in a Parr bomb was treated with triethylamine (92 μL) and $PdCl_2$(dppf) (24.8 mg). The bomb was charged to 700 psi with CO, stirred for 24 hours at 120° C., and concentrated. The concentrate was purified by $C_{18}$ reverse-phase HPLC using acetonitrile/water/0.1% TFA to provide the desired product. MS (ESI(+)) m/e 332 (M+H)$^+$, 349 (M+$NH_4$)$^+$, 354 (M+Na)$^+$; MS (ESI(−)) m/e 330 (M−H)$^-$; $^1$H NMR (300 MHz, DMSO-$d_6$) δ 7.72 (m, 1H), 7.52 (m, 4H), 7.33 (d, 1H), 7.22 (d, 1H), 2.99 (m, 1H), 2.88 (m, 1H), 2.73 (m, 1H), 2.27 (m, 1H).

EXAMPLE 130

3-ethyl-2-methyl-6-[(2-pyridinylsulfonyl)amino]benzoic acid

EXAMPLE 130A benzyl 2-methyl-6-[(2-pyridinylsulfonyl)amino]-3-vinylbenzoate

The title compound was prepared from Example 110A according to the procedure of Example 230B with a yield of 50%. $^1$H NMR (DMSO-$d_6$) δ 2.12 (s, 3H), 5.26 (s, 2H), 3.68 (t, 2H), 5.34 (d, 1H), 5.65 (d, 1H), 6.89 (dd, 1H), 6.98 (d, 1H), 7.35-7.40 (m, 5H), 7.47 (d, 1H), 7.65 (t, 1H), 7.87 (d, 1H), 8.05 (t, 1H), 8.73 (d, 1H), 10.04 (s, 1H); MS (ESI(+)) m/e 409 (M+H)$^+$.

EXAMPLE 130B 3-ethyl-2-methyl-6-[(2-pyridinylsulfonyl)amino]benzoic acid

Example 130A (0.46 g, 1.12 mmole) was hydrogenated in methanol (4 mL), THF (4 mL), and water (2 mL) over 10% Pd/C (150 mg) under one hydrogen at ambient temperature for 16 hours. Filtration and evaporation of the solvents provided the desired product (0.36 g, 100%). $^1$H NMR (DMSO-$d_6$) δ 1.02 (t, 3H), 2.08 (s, 3H), 2.58 (q, 2H), 6.82 (d, 1H), 7.02 (d, 1H), 7.58 (t, 1H), 7.58 (d, 1H), 7.98 (t, 1H), 8.65 (d, 1H), 9.80 (br s, 1H), 13 (br s, 1H); MS (ESI(−)) m/e 319 (M−H)$^-$.

EXAMPLE 131

2-{[(4-fluorophenyl)sulfonyl]amino}-5,6-dihydro-1-naphthalenecarboxylic acid

EXAMPLE 131A

N-(1-bromo-5,6-dihydro-2-naphthalenyl)-4-fluorobenzenesulfonamide

A mixture of Example 103A (150 mg, 0.38 mmol) and $NaBH_4$ (14.3 mg, 0.38 mmol) in isopropanol (3 mL) was heated to reflux overnight and partitioned between diethyl ether and brine. The organic phase was dried ($Na_2SO_4$), filtered, concentrated, dissolved in toluene (5 mL), and treated with p-toluenesulfonic acid. The mixture was heated to reflux for 1 hour, cooled to room temperature, and passed through a silica gel plug with dichloromethane to provide the desired product (95 mg, 68% yield). MS ($DCI/NH_3$) m/e 400 $(M+NH_4)^+$; $^1H$ NMR (300 MHz, DMSO-$d_6$) δ 9.84 (s, 1H), 7.75 (m, 2H), 7.39 (m, 2H), 7.08 (d, 1H), 6.9 (d, 1H), 6.69 (m, 1H), 6.22 (m, 1H), 2.71 (t, 2H), 2.21 (m, 2H).

EXAMPLE 131B

2-{[(4-fluorophenyl)sulfonyl]amino}-5,6-dihydro-1-naphthalenecarboxylic acid

The desired product was prepared by substituting Example 131A for Example 103A in Example 103B. MS (ESI) m/e 346 $(M-H)^-$; $^1H$ NMR (300 MHz, DMSO-$d_6$) δ 7.79 (m, 2H), 7.38 (m, 2H), 7.05 (d, 1H), 6.84 (m, 2H), 6.1 (m, 1H), 2.63 (m, 2H), 2.15 (m, 2H).

EXAMPLE 132

2-{[(4-fluorophenyl)sulfonyl]amino}-8-methyl-5,6-dihydro-1-naphthalenecarboxylic acid

EXAMPLE 132A

N-(1-bromo-8-methyl-5,6-dihydro-2-naphthalenyl)-4-fluorobenzenesulfonamide

The desired product was prepared by substituting Example 103A for Example 275C in Example 275D. MS (ESI) m/e 394 $(M-H)^-$; $^1H$ NMR (300 MHz, DMSO-$d_6$) δ 9.8 (s, 1H), 7.74 (m, 2H), 7.4 (m, 2H), 7.16 (d, 1H), 6.92 (d, 1H), 6.15 (dt, 1H), 2.57 (m, 2H), 2.18 (s, 3H), 1.98 (m, 2H).

EXAMPLE 132B

2-{[(4-fluorophenyl)sulfonyl]amino}-8-methyl-5,6-dihydro-1-naphthalenecarboxylic acid The desired product was prepared by substituting Example 132A for Example 103A in Example 103B. MS (ESI) m/e 360 $(M-H)^-$; $^1H$ NMR (300 MHz, DMSO-$d_6$) δ 7.82 (m, 2H), 7.41 (m, 2H), 7.11 (d, 1H), 6.68 (d, 1H), 6.02 (t, 1H), 2.56 (m, 2H), 2.05 (m, 2H), 1.98 (s, 3H).

EXAMPLE 133

2-({[2-(butylamino)phenyl]sulfonyl}amino)-1-naphthoic acid

EXAMPLE 133A methyl 2-amino-1-naphthoic acid

2-Amino-1-naphthoic acid (3.21 g, 17.2 mmol) in 4:1 benzene/$CH_3OH$ (125 mL) was treated with trimethylsilyldiazomethane (9.0 mL, 18.0 mmol, 2.0M solution in hexanes), stirred for 2.5 hours, quenched with acetic acid (0.5 mL), and concentrated. The concentrate was purified by flash column chromatography (4:1 hexanes/ethyl acetate) to provide the desired compound (3.25 g). MS (ESI(+)) m/e 202 $(M+H)^+$; (ESI(−)) m/e 200 $(M-H)^-$.

EXAMPLE 133B methyl 2-{[(2-fluorophenyl)sulfonyl]amino}-1-naphthoate

A solution of Example 133A (6.97 g, 34.7 mmol) in pyridine (70 mL) was treated with 2-fluorobenzenesulfonyl chloride (7.86 g, 40.4 mmol), stirred for 16 hours at ambient temperature, concentrated, diluted with 1M $NaHSO_4$, and extracted with dichloromethane. The extract was dried ($MgSO_4$), filtered, and concentrated. The concentrate was purified by flash column chromatography on silica gel with 30% ethyl acetate/hexanes to provide the desired product (6.04 g). MS (ESI(+)) m/e 360 $(M+H)^+$.

EXAMPLE 133C 2-({[2-(butylamino)phenyl]sulfonyl}amino)-1-naphthoic acid

A solution of Example 133B (0.060 g, 0.17 mmol), triethylamine (0.070 mL, 0.50 mmol), and butylamine (0.088 mL, 0.85 mmol) in anhydrous acetonitrile (0.6 mL) was heated to 200° C. for 20 minutes in a microwave reactor and concentrated. The concentrate was dissolved in 9:1 methanol/water (1 mL), treated with LiOH (25 mg, 0.6 mmol), and heated to 65° C. for 16 hours. The reaction mixture was concentrated and the concentrate was purified by $C_{18}$ reverse-phase HPLC using acetonitrile/water/0.1% TFA to provide the desired product. MS (DCI) m/e 399 $(M+H)^+$; $^1H$ NMR (500 MHz, DMSO-$d_6$) δ 13.73 (br s, 1H), 10.30 (br s, 1H), 8.16 (br s, 1H), 7.88 (m, 2H), 7.57 (m, 2H), 7.49 (t, 1H), 7.34 (m, 1H), 7.26 (d, 1H), 6.72 (d, 1H), 6.59 (t, 1H), 5.87 (br s, 1H), 3.04 (t, 2H), 1.41 (quint, 2H), 1.26 (sext, 2H), 0.82 (t, 3H).

EXAMPLE 134

2-({[2-(sec-butylamino)phenyl]sulfonyl}amino)-1-naphthoic acid

The desired product was prepared by substituting 2-aminobutane for butylamine in Example 133C. MS (DCI) m/e 399 $(M+H)^+$; $^1H$ NMR (500 MHz, DMSO-$d_6$) δ 13.80 (br s, 1H), 10.63 (br s, 1H), 8.26 (br s, 1H), 7.89 (d, 1H), 7.86 (d, 1H), 7.60 (dd, 1H), 7.56 (t, 1H), 7.47 (t, 1H), 7.32 (m, 1H), 7.28 (d, 1H), 6.72 (d, 1H), 6.58 (t, 1H), 5.75 (d, 1H), 3.42 (quint, 1H), 1.43 (m, 1H), 1.34 (m, 1H), 0.97 (d, 3H), 0.80 (t, 3H).

EXAMPLE 135

2-({[2-(isobutylamino)phenyl]sulfonyl}amino)-1-naphthoic acid

The desired product was prepared by substituting isobutylamine for butylamine in Example 133C. MS (DCI) m/e 399 $(M+H)^+$; $^1H$ NMR (500 MHz, DMSO-$d_6$) δ 13.76 (br s, 1H), 10.31 (br s, 1H), 8.19 (br s, 1H), 7.90 (d, 1H), 7.86 (d, 1H), 7.57 (m, 2H), 7.48 (t, 1H), 7.34 (m, 1H), 7.28 (d, 1H), 6.74 (d, 1H), 6.59 (t, 1H), 6.03 (br s, 1H), 2.90 (d, 2H), 1.79 (septet, 1H), 0.86 (d, 6H).

EXAMPLE 136

2-({[2-(pentylamino)phenyl]sulfonyl}amino)-1-naphthoic acid

The desired product was prepared by substituting 1-aminopentane for butylamine in Example 133C. MS (DCI) m/e 413 $(M+H)^+$; $^1H$ NMR (500 MHz, DMSO-$d_6$) δ 13.73 (br s, 1H), 10.26 (br s, 1H), 8.17 (br s, 1H), 7.88 (t, 2H), 7.56 (m, 2H), 7.48 (t, 1H), 7.34 (m, 1H), 7.25 (d, 1H), 6.72 (d, 1H), 6.60 (t, 1H), 5.88 (br s, 1H), 3.03 (t, 2H), 1.43 (quint, 2H), 1.22 (m, 4H), 0.82 (t, 3H).

EXAMPLE 137

2-[({2-[(1-methylbutyl)amino]phenyl}sulfonyl)amino]-1-naphthoic acid

The desired product was prepared by substituting 2-aminopentane for butylamine in Example 133C. MS (DCI) m/e 413 $(M+H)^+$; $^1H$ NMR (500 MHz, DMSO-$d_6$) δ 13.73 (br s, 1H), 10.36 (br s, 1H), 8.25 (br s, 1H), 7.88 (m, 2H), 7.60 (dd, 1H), 7.56 (t, 1H), 7.48 (t, 1H), 7.32 (m, 1H), 7.25 (d, 1H), 6.71 (d, 1H), 6.59 (t, 1H), 5.73 (d, 1H), 3.47 (m, 1H), 1.34 (m, 1H), 1.21 (m, 3H), 0.96 (d, 3H), 0.77 (t, 3H).

EXAMPLE 138

2-[({2-[(2-methylbutyl)amino]phenyl}sulfonyl)amino]-1-naphthoic acid

The desired product was prepared by substituting 2-methylbutylamine for butylamine in Example 133C. MS (DCI) m/e 413 $(M+H)^+$; $^1H$ NMR (500 MHz, DMSO-$d_6$) δ 13.75 (br, s, 1H), 10.34 (br s, 1H), 8.20 (br s, 1H), 7.88 (m, 2H), 7.57 (m, 2H), 7.48 (t, 1H), 7.34 (m, 1H), 7.26 (d, 1H), 6.73 (d, 1H), 6.60 (t, 1H), 5.99 (br s, 1H), 2.97 (m, 1H), 2.86 (m, 1H), 1.54 (m, 1H), 1.34 (m, 1H), 1.08 (m, 1H), 0.81 (m, 6H).

EXAMPLE 139

2-[({2-[(3-methylbutyl)amino]phenyl}sulfonyl)amino]-1-naphthoic acid

The desired product was prepared by substituting 3-methylbutylamine for butylamine in Example 133C. MS (DCI) m/e 413 $(M+H)^+$; $^1H$ NMR (500 MHz, DMSO-$d_6$) δ 13.72 (br s, 1H), 10.27 (br s, 1H), 8.18 (br s, 1H), 7.88 (t, 2H), 7.57 (m, 2H), 7.49 (t, 1H), 7.35 (m, 1H), 7.24 (d, 1H), 6.71 (d, 1H), 6.60 (t, 1H), 5.82 (br s, 1H), 3.01 (t, 2H), 1.52 (m, 1H), 1.28 (q, 2H), 0.80 (d, 6H).

EXAMPLE 140

2-[({2-[(1,2-dimethylpropyl)amino]phenyl}sulfonyl)amino]-1-naphthoic acid

The desired product was prepared by substituting 2-amino-3-methylbutane for butylamine in Example 133C. MS (DCI) m/e 413 $(M+H)^+$; $^1H$ NMR (500 MHz, DMSO-$d_6$) δ 13.77 (br s, 1H), 10.43 (br s, 1H), 8.29 (br s, 1H), 7.90 (d, 1H), 7.86 (d, 1H), 7.61 (dd, 1H), 7.56 (t, 1H), 7.47 (t, 1H), 7.31 (m, 2H), 6.74 (d, 1H), 6.58 (t, 1H), 5.88 (d, 1H), 3.38 (m, 1H), 1.70 (m, 1H), 0.90 (d, 3H), 0.84 (d, 3H), 0.79 (d, 3H).

EXAMPLE 141

2-({[2-(neopentylamino)phenyl]sulfonyl}amino)-1-naphthoic acid

The desired product was prepared by substituting 1-amino-2,2-dimethylpropane for butylamine in Example 133C. MS (DCI) m/e 413 $(M+H)^+$; $^1H$ NMR (500 MHz, DMSO-$d_6$) δ 13.78 (br s, 1H), 10.42 (br s, 1H), 8.23 (br s, 1H), 7.91 (d, 1H), 7.87 (d, 1H), 7.57 (m, 2H), 7.48 (t, 1H), 7.32 (m, 2H), 6.80 (d, 1H), 6.59 (t, 1H), 6.05 (br s, 1H), 2.88 (d, 2H), 0.88 (s, 9H).

EXAMPLE 142

2-[({2-[(1-ethylpropyl)amino]phenyl}sulfonyl)amino]-1-naphthoic acid

The desired product was prepared by substituting 1-amino-2-ethylpropane for butylamine in Example 133C. MS (DCI) m/e 413 $(M+H)^+$; $^1H$ NMR (500 MHz, DMSO-$d_6$) δ 13.73 (br s, 1H), 10.47 (br s, 1H), 8.28 (br s, 1H), 7.86 (m, 2H), 7.61 (dd, 1H), 7.56 (t, 1H), 7.47 (t, 1H), 7.31 (t, 1H), 7.26 (d, 1H), 6.74 (d, 1H), 6.58 (t, 1H), 5.77 (d, 1H), 1.37 (m, 4H), 0.75 (t, 6H).

EXAMPLE 143

2-({[2-(hexylamino)phenyl]sulfonyl}amino)-1-naphthoic acid

The desired product was prepared by substituting 1-aminohexane for butylamine in Example 133C. MS (DCI) m/e 427 $(M+H)^+$; $^1H$ NMR (500 MHz, DMSO-$d_6$) δ 13.73 (br s, 1H), 10.28 (br s, 1H), 8.17 (br s, 1H), 7.88 (2H), 7.56 (m, 2H), 7.48 (t, 1H), 7.34 (m, 1H), 7.25 (d, 1H), 6.72 (d, 1H), 6.60 (t, 1H), 5.88 (br s, 1H), 3.03 (t, 2H), 1.41 (quint, 2H), 1.20 (m, 6H), 0.83 (t, 3H).

EXAMPLE 144

2-[({2-[(3,3-dimethylbutyl)amino]phenyl}sulfonyl)amino]-1-naphthoic acid

The desired product was prepared by substituting 1-amino-3,3-dimethylbutane for butylamine in Example 133C. MS (DCI) m/e 427 $(M+H)^+$; $^1H$ NMR (500 MHz, DMSO-$d_6$) δ 13.71 (br s, 1H), 10.21 (br s, 1H), 8.18 (br s, 1H), 7.88 (t, 2H), 7.57 (m, 2H), 7.49 (t, 1H), 7.35 (m, 1H), 7.23 (d, 1H), 6.70 (d, 1H), 6.61 (t, 1H), 5.74 (br s, 1H), 2.98 (m, 2H), 1.24 (m, 2H), 0.84 (s, 9H).

EXAMPLE 145

3-ethyl-6-{[(4-fluorophenyl)sulfonyl]amino}-2-methylbenzoic acid

EXAMPLE 145A benzyl 6-[(tert-butoxycarbonyl)amino]-2-methyl-3-vinylbenzoate

A mixture of Example 126A (1.4 g, 3.3 mmol), DMF (33 mL) and tributyl(vinyl)tin (1.1 mL, 3.8 mmol) was degassed with argon 30 minutes, treated with $Pd(PPh_3)_4$ (577 mg, 0.5 mmol), heated to 90° C. for 18 hours, and concentrated. The concentrate was purified by flash column chromatography on silica gel (200 g) with 50% dichloromethane/hexanes to provide the desired product. MS (ESI(+)) m/e 368 $(M+H)^+$; (ESI(−)) m/e 366 $(M-H)^-$; $^1$H NMR (300 MHz, DMSO-$d_6$) δ 8.87 (s, 1H), 7.54 (d, 1H), 7.45 (m, 2H), 7.37 (m, 3H), 7.27 (d, 1H), 6.94 (dd, 1H), 5.64 (dd, 1H), 5.31 (dd, 1H), 5.27 (s, 2H), 2.21 (s, 3H), 1.42 (s, 9H).

EXAMPLE 145B

6-[(tert-butoxycarbonyl)amino]-3-ethyl-2-methylbenzoic acid

A mixture of Example 145A (450 mg, 1.2 mmol), palladium hydroxide (540 mg), and methanol (150 mL) was heated to 50° C. in a Paar shaker under 65 psi hydrogen pressure for 72 hours. The mixture was filtered, concentrated, and purified by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min to provide the desired product. MS (ESI(+)) m/e 280 $(M+H)^+$, 297 $(M+NH_4)^+$, 302 $(M+Na)^+$; (ESI(−)) m/e 278 $(M-H)^-$; $^1$H NMR (300 MHz, DMSO-$d_6$) δ 13.28 (br s, 1H), 8.35 (s, 1H), 7.32 (d, 1H), 7.17 (d, 1H), 2.58 (q, 2H), 2.24 (s, 3H), 1.43 (s, 9H), 1.12 (t, 3H).

EXAMPLE 145C 3-ethyl-6-{[(4-fluorophenyl)sulfonyl]amino}-2-methylbenzoic acid

The desired product was prepared by substituting Example 145B for Example 104B in Examples 104C-D. MS (ESI(+)) m/e 355 $(M+NH_4)^+$; (ESI(−)) m/e 336 $(M-H)^-$; $^1$H NMR (300 MHz, DMSO-$d_6$) δ 13.15 (br s, 1H), 9.64 (br s, 1H), 7.81 (m, 2H), 7.40 (m, 2H), 7.11 (d, 1H), 6.70 (d, 1H), 2.57 (q, 2H), 2.18 (s, 3H), 1.10 (t, 3H).

EXAMPLE 146

3-chloro-2-{[(4-fluorophenyl)sulfonyl]amino}-1-naphthoic acid

EXAMPLE 146A methyl 2-amino-3-chloro-1-naphthoate

A mixture of methyl 2-amino-1-naphthoate (0.7 g, 3.48 mmol) in acetonitrile (15 mL) was treated with N-chlorosuccinimide (490 mg, 3.65 mmol), stirred at 60° C. for 7 hours, cooled to room temperature, stirred overnight, concentrated, and purified by flash column chromatography on silica gel with 10% ethyl acetate/n-hexane to provide the desired product (270 mg). MS (ESI(−)) m/e 234 $(M-H)^-$; $^1$H NMR (300 MHz, DMSO-$d_6$) δ 8.13 (s, 1H), 8.10 (d, 1H), 7.75 (d, 1H), 7.46 (dt, 1H), 7.26 (dt, 1H), 6.62 (s, 2H), 3.95 (s, 3H).

EXAMPLE 146B methyl 3-chloro-2-{[(4-fluorophenyl)sulfonyl]amino}-1-naphthoate

A mixture of Example 146A (270 mg, 1.15 mmol) in 1:1 pyridine/dichloromethane (10 mL) was treated with 4-chlorobenzenesulfonyl chloride (340 mg, 1.725 mmol) and DMAP (14 mg, 0.115 mmol), stirred at room temperature overnight, and concentrated. The residue was dissolved in ethyl acetate, washed sequentially with brine (2×), 10% potassium hydrogen sulfate (3×), and brine, dried ($MgSO_4$), filtered, and concentrated. The residue was purified by silica gel column chromatography with 10% ethyl acetate/hexanes to provide 30 mg of the desired product. MS (ESI(−)) m/e 392 $(M-H)^-$; $^1$H NMR (300 MHz, DMSO-$d_6$) δ 10.35 (s, 1H), 8.28 (s, 1H), 7.99 (m, 1H), 7.5 (m, 1H), 7.62-7.77 (m, 4H), 7.38-7.44 (m, 2H), 3.76 (s, 3H).

EXAMPLE 146C 3-chloro-2-{[(4-fluorophenyl)sulfonyl]amino}-1-naphthoic acid

A solution of Example 146B in dioxane (3 mL) and water (0.3 mL) was treated with 3N LiOH (0.6 mL); stirred at 50° C. for 4 days, acidified with 1N HCl, treated with ethyl acetate, washed with brine (3×), dried ($MgSO_4$), filtered, and concentrated and ethyl acetate was added. The ethyl acetate layer was washed with brine (3×), dried over magnesium sulfate anhydrous. The concentrate was purified by reverse phase chromatography to provide 1.5 mg of the desired product. MS (ESI(−)) m/e 346 $(M-H)^-$.

EXAMPLE 147

2-[(phenylsulfonyl)amino]-4-vinylbenzoic acid

The desired product was prepared by substituting Example 125C (356 mg, 1.0 mmol) for Example 126A in Example 145A and raising the temperature to 105° C. The cured product was purified by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min to provide the desired product. MS (ESI(+)) m/e 304 $(M+H)^+$; (ESI(−)) m/e 302 $(M-H)^-$; $^1$H NMR (300 MHz, DMSO-$d_6$) δ 13.93 (br s, 1H), 11.20 (br s, 1H), 7.82 (m, 3H), 7.56 (m, 4H), 7.24 (dd, 1H), 6.75 (dd, 1H), 5.87 (d, 1H), 5.44 (d, 1H).

EXAMPLE 148

2-methyl-3-propyl-6-[(2-pyridinylsulfonyl)amino]benzoic acid

EXAMPLE 148A benzyl 6-[(tert-butoxycarbonyl)amino]-2-methyl-3-propylbenzoate

A mixture of Example 126A (0.52 g, 1.25 mmol), 2-propyl-1,3,2-benzodioxaborole (0.50 g, 3.0 mmol), Pd(dppf)$Cl_2$ (24 mg, 0.03 mmol) and $Tl_2CO_3$ (0.75 g, 1.6 mmol) in THF (15 mL) in a scintillation vial was purged with argon, sealed, and shaken at 90° C. for 72 hours. The mixture was treated with brine (25 mL) and extracted with ethyl acetate. The extract was dried ($Mg_2SO_4$), filtered, and concentrated. The residue was purified by flash column chromatography on silica gel eluting with 5% ethyl acetate/hexanes to provide the desired product (0.38 g, 80.0%). $^1$H NMR ($CDCl_3$) δ 0.94 (t, 3H), 1.48 (s, 9H), 1.55 (m, 2H), 2.24 (s, 3H), 2.54 (t, 2H), 5.38 (s, 2H), 7.15 (d, 1H), 7.36-7.46 (m, 5H), 7.77 (d, 1H).

EXAMPLE 148B benzyl 6-amino-2-methyl-3-propylbenzoate

A solution of Example 148A (0.38 g, 1.0 mmol) in 4N HCl/dioxane was stirred at ambient temperature overnight and concentrated to provide the desired product (0.32 g, 100%). $^1$H NMR (DMSO-$d_6$) δ 0.86 (t, 3H), 1.40-1.52 (m, 2H), 2.16 (s, 3H), 2.22 (t, 2H), 5.34 (s, 2H), 7.11 (d, 1H), 7.30-7.50 (m, 5H); MS (ESI(+) m/e 284 (M+H)$^+$.

EXAMPLE 148C benzyl 2-methyl-3-propyl-6-[(2-pyridinylsulfonyl)amino]benzoate

The desired product was prepared by substituting Example 148B (100 mg, 0.22 mmol) for Example 104D in Example 110A. The crude product was used directly in the next step.

EXAMPLE 148D 2-methyl-3-propyl-6-[(2-pyridinylsulfonyl)amino]benzoic acid

The desired product was prepared by substituting Example 148C (~80 mg, 0.2 mmol) for Example 110A in Example 110B. The crude product was purified by preparative HPLC, to provide the desired product (4.5 mg). $^1$H NMR (DMSO-$d_6$) δ 0.89 (t, 3H), 1.45-1.48 (m, 2H), 2.18 (s, 3H), 2.52 (t, 2H), 6.89 (d, 1H), 7.08 (d, 1H), 7.64-7.67 (m, 1H), 7.86 (d, 1H), 8.01-8.05 (m, 1H), 8.72 (d, 1H), 9.72 (br s, 1H), 13.20 (br s, 1H); MS (ESI(−)) m/e 333 (M−H)$^-$.

EXAMPLE 149

2-{[(2-{[(3-methoxypropyl)amino]carbonyl}phenyl)sulfonyl]amino}-1-naphthoic acid

EXAMPLE 149A methyl 2-({[2-(methoxycarbonyl)phenyl]sulfonyl}amino)-1-naphthoate

A solution of 133A (0.50 g, 2.48 mmol) in dichloromethane (8.0 mL) was treated with chlorotrimethylsilane (3.0 mL of 1M solution in $CH_2Cl_2$, 2.98 mmol) and pyridine (8.0 mL), stirred at room temperature for 1 hour, treated with methyl 2-(chlorosulfonyl)benzoate (0.873 g, 3.72 mmol), stirred overnight at room temperature treated with 1N HCl (20 mL), and extracted with dichloromethane (2×). The combined organic phases were dried ($MgSO_4$), filtered, and concentrated. The resulting residue was purified by preparative HPLC to provide the desired product. MS (ESI(+)) m/e 400 (M+H)$^+$; (ESI(−)) m/e 398 (M−H)$^-$; $^1$H NMR (300 MHz, DMSO-$d_6$) δ 9.67 (s, 1H), 8.04 (d, 1H), 7.95 (d, 1H), 7.85 (d, 7.90, 1H), 7.80 (d, 1H), 7.72 (m, 2H), 7.65 (ddd, 1H), 7.56 (m, 2H), 7.50 (d, 1H), 3.80 (s, 3H), 3.78 (s, 3H).

EXAMPLE 149B 2-({[1-(methoxycarbonyl)-2-naphthyl]amino}sulfonyl)benzoic acid

A solution of Example 149A (0.60 g, 1.50 mmol) in methanol (16 mL) and distilled water (1.8 mL) was treated with lithium hydroxide monohydrate (0.19 g, 4.50 mmol), heated to 60° C. for four days, cooled to room temperature treated with 1N HCl, and extracted with ethyl acetate (2×). The combined extracts were washed with brine, dried ($MgSO_4$), filtered, and concentrated to provide the desired product. MS (ESI(−)) m/e 384 (M−H)$^-$; $^1$H NMR (300 MHz, DMSO-$d_6$) δ 14.25 (br s, 1H), 9.38 (br s, 1H), 8.06 (d, 1H), 7.94 (dd, 1H), 7.80 (m, 3H), 7.72 (dt, 1H), 7.66 (d, 1H), 7.62 (dd, 1H), 7.54 (dt, 2H), 3.81 (s, 3H).

EXAMPLE 149C methyl 2-{[(2-{[(3-methoxypropyl)amino]carbonyl}phenyl)sulfonyl]amino}-1-naphthoate A solution of Example 149B (93.0 mg, 0.241 mmol) in dichloromethane (3.0 mL) was treated with 1-hydroxybenzotriazole hydrate (34 mg, 0.253 mmol) and 4-methylmorpholine (32 μL, 0.297 mmol), stirred at room temperature for 10 minutes, treated with 1-(3-dimethylaminopropyl)-3-ethylcarbodiimide hydrochloride (51 mg, 0.266 mmol), 4-dimethylaminopyridine (3 mg, 0.025 mmol), and 1-methoxy-3-aminopropane (37 μL, 0.363 mmol), stirred for 1 hour, heated to 40° C., stirred overnight, treated with 4-dimethylaminopyridine (3 mg, 0.025 mmol) and 4-methylmorpholine (53 μL, 0.482 mmol), heated to 40° C. for 3 days, cooled to room temperature, and treated with distilled water. The aqueous layer was extracted with dichloromethane (2×) and the combined organic phases were washed with brine, dried ($MgSO_4$), filtered, and concentrated. The resulting residue was purified by preparative HPLC to provide the desired product. MS (ESI(+)) m/e 457 (M+H)$^+$, 479, (M+Na)$^+$; (ESI (−)) m/e 455 (M−H)$^-$.

EXAMPLE 149D

2-{[(2-{[(3-methoxypropyl)amino]carbonyl}phenyl)sulfonyl]amino}-1-naphthoic acid A solution of Example 149D (54.1 mg, 0.118 mmol) in methanol (1.0 mL) was treated with KOH (0.3 mL of 45% w/w solution), heated to reflux, stirred overnight, cooled to room temperature, and treated with 1N HCl. The aqueous phase was extracted with dichloromethane (2×). The combined organic phases were washed with brine, dried ($MgSO_4$), filtered, and concentrated. The resulting residue was purified by preparative HPLC to provide the desired product. MS (ESI(+)) m/e 443 (M+H)$^+$, 465 (M+Na)$^+$; (ESI (−)) m/e 441 (M−H)$^-$; $^1$H NMR (300 MHz, DMSO-$d_6$) δ 9.66 (br s, 1H), 8.79 (t, 1H), 8.01 (br s, 1H), 7.96 (d, 7.90 (dd, 1H), 7.80 (d, 1H), 7.71 (dt, 1H), 7.54 (m, 5H), 3.42 (t, 2H), 3.34 (t, 2H), 3.26 (s, 3H), 1.79 (quint, 2H).

EXAMPLE 150

6-{[(4-fluorophenyl)sulfonyl]amino}-2-methyl-3-propylbenzoic acid

EXAMPLE 150A benzyl 6-{[(4-fluorophenyl)sulfonyl]amino}-2-methyl-3-propylbenzoate The desired product was prepared by substituting Example 148B (120 mg, 0.37 mmol) and 4-fluorobenzenesulfonyl chloride (88 mg, 0.45 mmol) for Example 104D and 2-pyridinesulfonyl chloride, respectively, in Example 110A. The crude product was used directly in the next step.

EXAMPLE 150B

6-{[(4-fluorophenyl)sulfonyl]amino}-2-methyl-3-propylbenzoic acid

The product was prepared by substituting Example 150A (149 mg) for Example 110A in Example 110B. The crude product was purified by preparative HPLC to provide the desired product (27.5 mg, 22.0%). $^1$H NMR (DMSO-$d_6$) δ 0.90 (t, 3H), 1.46-1.51 (m, 2H), 2.18 (s, 3H), 2.53 (t, 2H), 6.69 (d, 1H), 7.08 (d, 1H), 7.40 (t, 2H), 7.78 (m, 2H), 9.60 (br s, 1H), 13.09 (br s, 1H); MS (ESI(−)) m/e 350 $(M-H)^-$.

EXAMPLE 151

3-bromo-6-{[(4-fluorophenyl)sulfonyl]amino}-2-methoxybenzoic acid

EXAMPLE 151A

2-[(tert-butoxycarbonyl)amino]-6-methoxybenzoic acid

A mixture of 2-amino-6-methoxybenzoic acid (1.64 g, 9.8 mmol), di-tert-butyldicarbonate (2.25 g 10.3 mmol), acetonitrile (16 mL), and triethylamine (1.5 mL, 10.8 mmol) was stirred for 18 hours and concentrated. The concentrate was purified on a Biotage silica gel cartridge (40 g) with 1% methanol/dichloromethane to provide the desired product. MS (ESI(+)) m/e 268 $(M+H)^+$, 285 $(M+NH_4)^+$, 290 $(M+Na)^+$; (ESI(−)) m/e 266 $(M-H)^-$; $^1$H NMR (300 MHz, DMSO-$d_6$) δ 13.01 (br s, 1H), 8.77 (s, 1H), 7.34 (m, 2H), 6.82 (m, 1H), 3.78 (s, 3H), 1.44 (s, 9H).

EXAMPLE 151B 3-bromo-6-[(tert-butoxycarbonyl)amino]-2-methoxybenzoic acid

A mixture of Example 151A (730 mg, 2.7 mmol) and tetrabutylammonium tribromide (1.3 g, 2.7 mmol) in DMF (15 mL) was treated dropwise with water (15 mL), stirred for 18 hours, and partitioned between water (250 mL) and ethyl acetate (250 mL). The organic phase was concentrated, diluted with dichloromethane (250 mL), washed with water (7×250 mL) and brine, dried ($Na_2SO_4$), filtered, concentrated and purified on silica gel with dichloromethane to provide the desired product. MS (ESI(+)) m/e 363, 365 $(M+NH_4)^+$, 368, 370 $(M+Na)^+$; (ESI(−)) m/e 344, 346 $(M-H)^-$; $^1$H NMR (300 MHz, DMSO-$d_6$) δ 13.50 (br s, 1H), 8.92 (s, 1H), 7.65 (d, 1H), 7.36 (d, 1H), 3.79 (s, 3H), 1.44 (s, 9H).

EXAMPLE 151C 3-bromo-6-{[(4-fluorophenyl)sulfonyl]amino}-2-methoxybenzoic acid

The desired product was prepared by substituting Example 151B for Example 104B in Examples 104C-D. MS (ESI(+)) m/e 426, 428 $(M+NH_4)^+$; (ESI(−)) m/e 402, 404 $(M-H)^-$; $^1$H NMR (300 MHz, DMSO-$d_6$) δ 13.26 (br s, 1H), 10.19 (br s, 1H), 7.80 (m, 2H), 7.60 (d, 1H), 7.42 (m, 2H), 6.80 (d, 1H), 3.75 (s, 3H).

EXAMPLE 152

2-[({2-[(2-ethoxyethyl)amino]phenyl}sulfonyl)amino]-1-naphthoic acid

The desired product was prepared by substituting 2-ethoxyethylamine for butylamine in Example 133C. MS (DCI) m/e 415 $(M+H)^+$; $^1$H NMR (500 MHz, DMSO-$d_6$) δ 13.70 (br s, 1H), 10.42 (br s, 1H), 8.23 (br s, 1H), 7.90 (d, 1H), 7.86 (d, 1H), 7.56 (m, 2H), 7.47 (t, 1H), 7.37-7.33 (m, 2H), 6.78 (d, 1H), 6.61 (t, 1H), 6.14 (br s, 1H), 3.51 (t, 2H), 3.44 (q, 2H), 3.24 (m, 2H), 1.10 (t, 3H).

EXAMPLE 153

2-[({2-[(2-isopropoxyethyl)amino]phenyl}sulfonyl)amino]-1-naphthoic acid

The desired product was prepared by substituting 2-isopropoxyethylamine for butylamine in Example 133C. MS (DCI) m/e 429 $(M+H)^+$; $^1$H NMR (500 MHz, DMSO-$d_6$) δ 13.84 (br s, 1H), 10.37 (br s, 1H), 8.23 (br s, 1H), 7.91 (d, 1H), 7.86 (d, 1H), 7.56 (m, 2H), 7.47 (t, 1H), 7.38 (d, 1H), 7.34 (m, 1H), 6.76 (d, 1H), 6.61 (t, 1H), 6.15 (br s, 1H), 3.59-3.50 (m, 3H), 3.20 (m, 2H), 1.08 (d, 6H).

EXAMPLE 154

2-[({2-[(3-propoxypropyl)amino]phenyl}sulfonyl)amino]-1-naphthoic acid

The desired product was prepared by substituting 3-propoxypropylamine for butylamine in Example 133C. MS (DCI) m/e 443 $(M+H)^+$; $^1$H NMR (500 MHz, DMSO-$d_6$) δ 13.74 (br s, 1H), 10.31 (br s, 1H), 8.21 (br s, 1H), 7.88 (d, 1H), 7.86 (d, 1H), 7.56 (m, 2H), 7.47 (t, 1H), 7.34 (m, 1H), 7.30 (d, 1H), 6.75 (d, 1H), 6.60 (t, 1H), 6.00 (br s, 1H), 3.35 (t, 2H), 3.24 (t, 2H), 3.16 (m, 2H), 1.72 (quint, 2H), 1.48 (sext, 2H), 0.83 (t, 3H).

EXAMPLE 155

2-[({2-[(3-methoxypropyl)amino]phenyl}sulfonyl)amino]-1-naphthoic acid

The desired product was prepared by substituting 3-methoxypropylamine for butylamine in Example 133C. MS (DCI) m/e 415 $(M+H)^+$; $^1$H NMR (500 MHz, DMSO-$d_6$) δ 13.69 (br s, 1H), 10.27 (br s, 1H), 8.22 (br s, 1H), 7.89 (d, 1H), 7.86 (d, 1H), 7.56 (m, 2H), 7.47 (t, 1H), 7.36-7.30 (m, 2H), 6.74 (d, 1H), 6.59 (t, 1H), 6.04 (br s, 1H), 3.34 (t, 2H), 3.20 (s, 3H), 3.15 (t, 2H), 1.74 (quint, 2H).

EXAMPLE 156

2-[({2-[(cyclopropylmethyl)amino]phenyl}sulfonyl)amino]-1-naphthoic acid

The desired product was prepared by substituting cyclopropylmethylamine for butylamine in Example 133C. MS (DCI) m/e 397 $(M+H)^+$; $^1$H NMR (500 MHz, DMSO-$d_6$) δ 13.75 (br s, 1H), 10.36 (br s, 1H), 8.19 (br s, 1H), 7.91 (d, 1H), 7.87 (d, 1H), 7.57 (m, 2H), 7.48 (t, 1H), 7.33 (m, 2H), 6.74 (d, 1H), 6.59 (t, 1H), 6.03 (br s, 1H), 2.96 (d, 1H), 1.07-0.99 (m, 1H), 0.43 (ddd, 2H), 0.21-0.18 (m, 2H).

EXAMPLE 157

2-({[2-(cyclopentylamino)phenyl]sulfonyl}amino)-1-naphthoic acid

The desired product was prepared by substituting cyclopentylamine for butylamine in Example 133C. MS (DCI) m/e 411 $(M+H)^+$; $^1H$ NMR (500 MHz, DMSO-$d_6$) δ 13.72 (br s, 1H), 10.35 (br s, 1H), 8.24 (br s, 1H), 7.88 (m, 2H), 7.60-7.55 (m, 2H), 7.48 (t, 1H), 7.33 (m, 1H), 7.25 (d, 1H), 6.71 (d, 1H), 6.60 (t, 1H), 5.83 (br s, 1H), 3.70 (br s, 1H), 1.88-1.82 (m, 2H), 1.49-1.45 (m, 4H), 1.26-1.20 (m, 2H).

EXAMPLE 158

2-[({2-[(cyclopentylmethyl)amino]phenyl}sulfonyl)amino]-1-naphthoic acid

The desired product was prepared by substituting cyclopentylmethylamine for butylamine in Example 133C. MS (DCI) m/e 425 $(M+H)^+$; $^1H$ NMR (500 MHz, DMSO-$d_6$) δ 13.71 (br s, 1H), 10.31 (br s, 1H), 8.17 (br s, 1H), 7.90 (d, 1H), 7.88 (d, 1H), 7.57 (m, 2H), 7.49 (t, 1H), 7.34 (m, 1H), 7.27 (d, 1H), 6.74 (d, 1H), 6.60 (t, 1H), 5.95 (br s, 1H), 2.96 (d, 2H), 1.99 (septet, 1H), 1.67-1.61 (m, 2H), 1.56-1.50 (m, 2H), 1.47-1.40 (m, 2H), 1.16-1.09 (m, 2H).

EXAMPLE 159

2-({[2-(cyclohexylamino)phenyl]sulfonyl}amino)-1-naphthoic acid

The desired product was prepared by substituting cyclohexylamine for butylamine in Example 133C. MS (DCI) m/e 425 $(M+H)^+$; $^1H$ NMR (500 MHz, DMSO-$d_6$) δ 13.71 (br s, 1H), 10.38 (br s, 1H), 8.21 (d, 1H), 7.91 (d, 1H), 7.88 (d, 1H), 7.59-7.56 (m, 2H), 7.49 (t, 1H), 7.32 (m, 1H), 7.28 (d, 1H), 6.74 (d, 1H), 6.58 (m, 1H), 5.78 (d, 1H), 1.76-1.73 (m, 2H), 1.57-1.48 (m, 3H), 1.31-1.22 (m, 2H), 1.12-0.97 (m, 3H).

EXAMPLE 160

2-[({2-[(2-ethylhexyl)amino]phenyl}sulfonyl)amino]-1-naphthoic acid

The desired product was prepared by substituting 2-ethylhexylamine for butylamine in Example 133C. MS (DCI) m/e 455 $(M+H)^+$; $^1H$ NMR (500 MHz, DMSO-$d_6$) δ 13.77 (br s, 1H), 10.32 (br s, 1H), 8.22 (br s, 1H), 7.87 (t, 2H), 7.60-7.55 (m, 2H), 7.48 (t, 1H), 7.35 (m, 1H), 7.24 (d, 1H), 6.72 (d, 1H), 6.60 (t, 1H), 5.97 (br s, 1H), 2.94 (m, 2H), 1.45-1.41 (m, 1H), 1.27-1.18 (m, 8H), 0.81 (t, 3H), 0.77 (t, 3H).

EXAMPLE 161

2-[({2-[(3-hydroxypropyl)amino]phenyl}sulfonyl)amino]-1-naphthoic acid

The desired product was prepared by substituting 3-amino-1-propanol for butylamine in Example 133C. MS (DCI) m/e 401 $(M+H)^+$; $^1H$ NMR (500 MHz, DMSO-$d_6$) δ 8.22 (br s, 1H), 8.11 (d, 1H), 7.88 (d, 1H), 7.83 (d, 1H), 7.52-7.47 (m, 2H), 7.49 (t, 1H), 7.30 (m, 1H), 7.24 (d, 1H), 6.70 (d, 1H), 6.52 (t, 1H), 5.95 (br s, 1H), 3.11 (t, 2H), 1.61 (quint, 2H).

EXAMPLE 162

2-[({2-[(4-hydroxybutyl)amino]phenyl}sulfonyl)amino]-1-naphthoic acid

The desired product was prepared by substituting 4-amino-1-propanol for butylamine in Example 133C. MS (DCI) m/e 415 $(M+H)^+$; $^1H$ NMR (500 MHz, DMSO-$d_6$) δ 7.88 (d, 1H), 7.86 (d, 1H), 7.58-7.54 (m, 2H), 7.50-7.46 (m, 2H), 7.34 (m, 1H), 7.29 (d, 1H), 6.74 (d, 1H), 6.58 (t, 1H), 5.92 (br s, 1H), 3.38 (t, 2H), 3.06 (t, 2H), 1.52 (m, 2H), 1.44 (m, 2H).

776455 EXAMPLE 163

2-[({2-[(2-propoxyethyl)amino]phenyl}sulfonyl)amino]-1-naphthoic acid

The desired product was prepared by substituting 2-propoxyethylamine for butylamine in Example 133C. MS (DCI) m/e 429 $(M+H)^+$; $^1H$ NMR (500 MHz, DMSO-$d_6$) δ 13.81 (br s, 1H), 10.30 (br s, 1H), 8.21 (br s, 1H), 7.91 (d, 1H), 7.87 (d, 1H), 7.56 (m, 2H), 7.55 (m, 1H), 7.38-7.33 (m, 2H), 6.78 (d, 1H), 6.61 (t, 1H), 6.15 (br s, 1H), 3.51 (t, 2H), 3.34 (t, 2H), 3.24 (m, 2H), 1.49 (m, 2H), 0.85 (t, 3H).

EXAMPLE 164

2-[({2-[(3-ethoxypropyl)amino]phenyl}sulfonyl)amino]-1-naphthoic acid

The desired product was prepared by substituting 3-ethoxypropylamine for butylamine in Example 133C. MS (DCI) m/e 429 $(M+H)^+$; $^1H$ NMR (500 MHz, DMSO-$d_6$) δ 13.81 (br s, 1H), 10.29 (br s, 1H), 8.19 (br s, 1H), 7.90-7.85 (m, 2H), 7.56 (m, 2H), 7.48 (m, 1H), 7.35 (m, 1H), 7.30 (d, 1H), 6.75 (d, 1H), 6.60 (t, 1H), 6.02 (br s, 1H), 3.37-3.33 (m, 4H), 3.16 (t, 2H), 1.72 (m, 2H), 1.09 (t, 3H).

EXAMPLE 165

2-[({2-[(3-butoxypropyl)amino]phenyl}sulfonyl)amino]-1-naphthoic acid

The desired product was prepared by substituting 3-butoxypropylamine for butylamine in Example 133C. MS (DCI) m/e 457 $(M+H)^+$; $^1H$ NMR (500 MHz, DMSO-$d_6$) δ 13.74 (br s, 1H), 10.27 (br s, 1H), 8.19 (br s, 1H), 7.89-7.85 (m, 2H), 7.56 (m, 2H), 7.47 (m, 1H), 7.34 (m, 1H), 7.29 (d, 1H), 6.75 (d, 1H), 6.60 (t, 1H), 6.00 (br s, 1H), 3.35 (t, 2H), 3.28 (m, 2H), 3.15 (t, 2H), 1.72 (m, 2H), 1.47-1.42 (m, 2H), 1.28 (m, 2H), 0.85 (t, 3H).

EXAMPLE 166

2-[({2-[(3-isopropoxypropyl)amino]phenyl}sulfonyl)amino]-1-naphthoic acid

The desired product was prepared by substituting 3-isopropoxypropylamine for butylamine in Example 133C. MS (DCI) m/e 443 $(M+H)^+$; $^1H$ NMR (500 MHz, DMSO-$d_6$) δ 8.13 (br s, 1H), 7.83-7.79 (m, 2H), 7.49 (m, 2H), 7.41 (m, 1H), 7.28 (m, 1H), 7.22 (d, 1H), 6.69 (d, 1H), 6.53 (t, 1H), 5.93 (br s, 1H), 3.35 (m, 1H), 3.09 (t, 2H), 1.62 (m, 2H), 0.98 (d, 6H).

EXAMPLE 167

2-[({2-[(3-isobutoxypropyl)amino]phenyl}sulfonyl)amino]-1-naphthoic acid

The desired product was prepared by substituting 3-isobutoxypropylamine for butylamine in Example 133C. MS (DCI) m/e 457 $(M+H)^+$; $^1H$ NMR (500 MHz, DMSO-$d_6$) δ 13.77 (br s, 1H), 10.25 (br s, 1H), 8.14 (m, 1H), 7.90-7.86 (m, 2H), 7.57 (m, 2H), 7.49 (m, 1H), 7.35 (m, 1H), 7.27 (d, 1H), 6.76 (d, 1H), 6.60 (t, 1H), 5.99 (br s, 1H), 3.34 (t, 2H), 3.16 (t, 2H), 3.05 (d, 2H), 1.80-1.69 (m, 2H), 0.82 (d, 6H).

EXAMPLE 168

2-{[(2-{[3-(methylsulfanyl)propyl]amino}phenyl) sulfonyl]amino}-1-naphthoic acid The desired product was prepared by substituting 3-(methylsulfanyl)propylamine for butylamine in Example 133C. MS (DCI) m/e 431 $(M+H)^+$; $^1$H NMR (500 MHz, DMSO-$d_6$) δ 13.77 (br s, 1H), 10.18 (br s, 1H), 8.14 (br s, 1H), 7.88 (t, 2H), 7.57 (m, 2H), 7.49 (m, 1H), 7.36 (m, 1H), 7.24 (d, 1H), 6.78 (d, 1H), 6.61 (t, 1H), 5.97 (br s, 1H), 3.19 (t, 2H), 2.46 (t, 2H), 2.00 (s, 3H), 1.74 (m, 2H).

EXAMPLE 169

2-{[(2-{[3-(diethylamino)propyl]amino}phenyl) sulfonyl]amino}-1-naphthoic acid

The desired product was prepared by substituting 3-(diethylamino)propylamine for butylamine in Example 133C. MS (DCI) m/e 456 $(M+H)^+$; $^1$H NMR (500 MHz, DMSO-$d_6$) δ 8.24 (br s, 1H, 7.80-7.76 (m, 2H), 7.51 (d, 1H), 7.46 (m, 1H) 7.38 (m, 2H), 7.28 (m, 1H), 6.73 (d, 1H), 6.53 (t, 1H), 6.06 (br s, 1H), 3.38 (m, 2H), 3.02 (m, 6H), 1.74 (m, 2H), 1.08 (t, 6H).

EXAMPLE 170

2-[({2-[(2-methoxyethyl)amino]phenyl}sulfonyl) amino]-1-naphthoic acid

The desired product was prepared by substituting 2-methoxyethylamine for butylamine in Example 133C. MS (DCI) m/e 401 $(M+H)^+$; $^1$H NMR (500 MHz, DMSO-$d_6$) δ 13.76 (br s, 1H), 10.33 (br s, 1H), 8.23 (br s, 1H), 7.91-7.85 (m, 2H), 7.56 (m, 2H), 7.47 (m, 1H), 7.44 (m, 1H), 7.35 (m, 1H), 6.78 (d, 1H), 6.61 (m, 1H), 6.10 (br s, 1H), 3.47 (t, 2H), 3.26 (s, 3H).

EXAMPLE 171

2-({[2-(1-pyrrolidinylcarbonyl)phenyl] sulfonyl}amino)-1-naphthoic acid

EXAMPLE 171A methyl 2-({[2-(1-pyrrolidinylcarbonyl)phenyl] sulfonyl}amino)-1-naphthoate The desired product was prepared by substituting pyrrolidine for 1-methoxy-3-aminopropane in Examples 149A-C. MS (ESI(+)) m/e 443 $(M+H)^+$, 465 $(M+Na)^+$; (ESI(−)) m/e 441 $(M-H)^-$; $^1$H NMR (300 MHz, DMSO-$d_6$) δ 9.29 (s, 1H), 8.00 (d, 1H), 7.94 (dd, 1H), 7.82 (d, 1H), 7.70 (m, 2H), 7.60-7.50 (m, 5H), 3.84 (s, 3H), 3.50 (t, 2H), 3.05 (br t, 2H), 1.87 (quint, 2H), 1.72 (quint, 2H).

EXAMPLE 171B 2-({[2-(1-pyrrolidinylcarbonyl)phenyl] sulfonyl}amino)-1-naphthoic acid A solution of Example 171A (30.7 mg, 0.070 mmol) in dioxane (1.0 mL) and distilled water (0.5 mL) was treated with lithium hydroxide monohydrate (9.0 mg, 0.21 mmol), stirred overnight at 60° C., treated with additional lithium hydroxide monohydrate (15.0 mg, 0.357 mmol), heated to 60° C. for an additional three days, and concentrated. The resulting residue was purified by preparative HPLC to provide the desired product. MS (ESI(+)) m/e 425 $(M+H)^+$, 447 $(M+Na)^+$; (ESI(−)) m/e 423 $(M-H)^-$; $^1$H NMR (300 MHz, DMSO-$d_6$) δ 9.73 (br s, 1H), 8.10 (d, 1H), 7.96 (d, 1H), 7.89 (d, 2H), 7.70 (dt, 1H), 7.54 (m, 5H), 3.49 (t, 2H), 3.04 (t, 2H), 1.86 (q, 2H), 1.70 (t, 2H).

EXAMPLE 172

2-methyl-6-[(2-pyridinylsulfonyl)amino]-3-vinylbenzoic acid

EXAMPLE 172A benzyl 2-methyl-6-[(2-pyridinylsulfonyl)amino]-3-vinylbenzoate

A solution of Example 110A (1.38 g, 3.0 mmol), dibutyl vinylboronate (0.83 g, 4.5 mmol), CsF (1.36 g, 9.0 mmol), and $Pd(PPh_3)_4$ (0.17 g, 0.15 mmol) in DME (12 mL) and methanol (6 mL) was purged with argon and stirred at 80° C. for 36 hours. The mixture was treated with brine (30 mL) and extracted with ethyl acetate. The ethyl acetate solution was dried ($MgSO_4$), filtered and concentrated. The residue was purified by flash column chromatography on a silica gel with 30% ethyl acetate/hexanes to provide the desired product (0.57 g, 46.6%). $^1$H NMR (DMSO-$d_6$) δ 2.12 (s, 3H), 5.26 (s, 2H), 5.34 (d, 1H), 5.65 (d, 1H), 6.86-6.91 (dd, 1H), 6.98 (d, 1H), 7.31-7.47 (m, 6H), 7.65 (m, 1H), 9.87 (d, 1H), 8.04 (dt, 1H), 8.74 (d, 1H), 10.04 (s, 1H); MS (ESI(+)) m/e 409 $(M+H)^+$. Further elution of the column with 5% methanol in ethyl acetate with 0.1% acetic acid provided another white solid (0.125 g) which was identified as Example 172B.

EXAMPLE 172B 2-methyl-6-[(2-pyridinylsulfonyl)amino]-3-vinylbenzoic acid

The desired product was isolated as described in Example 172A. $^1$H NMR (DMSO-$d_6$) δ 2.26 (s, 3H), 5.30 (d, 1H), 5.60 (d, 1H), 6.88-6.94 (dd, 1H), 7.05 (d, 1H), 7.41 (d, 1H), 7.65 (t, 1H), 7.89 (d, 1H), 8.05 (d, 1H), 8.71 (d, 1H); MS (ESI(−)) m/e 317 $(M-H)^-$.

EXAMPLE 173

6-{[(4-fluorophenyl)sulfonyl]amino}-2-methyl-3-vinylbenzoic acid

EXAMPLE 173A benzyl 3-bromo-6-{[(4-fluorophenyl)sulfonyl] amino}-2-methylbenzoate A solution of Example 126B (2.57 g, 7.13 mmol), 4-fluorobenzenesulfonyl chloride (1.92 g, 7.8 mmol) in dichloromethane (40 mL) was treated with pyridine (1.44 mL, 17.8 mmol), stirred for 48 hours at ambient temperature, washed with 1N HCl (2×30 mL). The organic solution was dried ($MgSO_4$), filtered, and concentrated. The resulting solid was triturated twice with hexanes to provide the desired product (3.10 g, 91.2%). $^1$H NMR (DMSO-$d_6$) δ 2.19 (s, 3H), 5.25 (s, 2H), 6.86 (d, 2H), 7.35-7.46 (m, 7H), 7.63 (d, 1H), 7.75 (m, 2H), 10.07 (s, 1H). MS (ESI(−)) m/e 476, 478 $(M-H)^-$.

EXAMPLE 173B benzyl 6-{[(4-fluorophenyl)sulfonyl]amino}-2-methyl-3-vinylbenzoate The desired product was prepared by substituting Example 173A (1.43 g, 3.0 mmol) for Example 110A in Example 172A. The crude product was purified by flash column chromatography on silica gel, eluted first with 30% ethyl acetate/hexanes (0.40 g). MS (ESI(−)) m/e 424 $(M-H)^-$. Further elution with 5% methanol in hexanes containing 0.5% acetic acid provided Example 173C.

EXAMPLE 173C

6-{[(4-fluorophenyl)sulfonyl]amino}-2-methyl-3-vinylbenzoic acid

The desired product was prepared as described in Example 173B. $^1H$ NMR (DMSO-$d_6$) δ 2.22 (s, 3H), 5.34 (dd, 1H), 5.63, 5.67 (dd, 1H), 6.82 (d, 1H), 6.88-6.95 (q, 1H), 7.38-7.45 (m, 3H), 7.78-7.82 (m, 2H), 9.74 (s, 1H), 13.27 (br s, 1H); MS (ESI(−)) m/e 334 $(M-H)^-$.

EXAMPLE 174

2-[({2-[(4-methyl-1-piperazinyl)carbonyl]phenyl}sulfonyl)amino]-1-naphthoic acid

EXAMPLE 174A methyl 2-[({2-[(4-methyl-1-piperazinyl)carbonyl]phenyl}sulfonyl)amino]-1-naphthoate The desired product was prepared by substituting 1-methylpiperazine for pyrrolidine in Examples 149A-C. MS (ESI(+)) m/e 454 $(M+H)^+$, 476 $(M+Na)^+$; (ESI(−)) m/e 452 $(M-H)^-$; $^1H$ NMR (300 MHz, DMSO-$d_6$) δ 9.85 (br s, 1H), 8.12 (d, 1H), 7.96 (d, 2H), 7.91 (d, 1H), 7.75 (t, 1H), 7.68-7.55 (m, 2H), 7.52 (br m, 1H), 7.44 (d, 1H), 3.39 (m, 4H), 3.40 (br s, 3H), 2.82 (m, 4H).

EXAMPLE 174B

2-[({2-[(4-methyl-1-piperazinyl)carbonyl]phenyl}sulfonyl)amino]-1-naphthoic acid To a stirring solution of 174A (48 mg, 0.103 mmol) in dioxane (1.5 mL) and distilled water (0.75 mL) was added lithium hydroxide monohydrate (13 mg, 0.308 mmol). The solution was stirred at 60° C. for three days. The solution was cooled, 1N HCl was added, solvent was evaporated, and the resulting residue was purified by preparative HPLC to provide the desired product as a tar. MS (ESI(+)) m/e 454 $(M+H)^+$, 476: $(M+Na)^+$; (ESI(−)) m/e 452 $(M-H)^-$; $^1H$ NMR (300 MHz, DMSO-$d_6$) δ 9.84 (br s, 1H), 9.49 (br d, 1H), 8.02 (d, 2H), 7.94 (dd, 1H), 7.84 (dd, 1H), 7.78 (d, 1H), 7.74 (d, 1H), 7.63-7.48 (m, 5H), 3.85 (s, 3H), 3.17 (s, 3H), 3.13 (m, 4H), 2.81 (m, 4H).

EXAMPLE 175

2-{[(2-chloro-4-fluorophenyl)sulfonyl]amino}-5,6,7,8-tetrahydro-1-naphthalenecarboxylic acid The desired product was prepared by substituting 2-chloro-4-fluorobenzenesulfonyl chloride for 4-fluorobenzenesulfonyl chloride in Example 128D. MS (ESI(+)) m/e 401 $(M+NH_4)^+$; MS (ESI(−)) m/e 382 $(M-H)^-$; $^1H$ NMR (300 MHz, DMSO-$d_6$) δ 8.06 (dd, 1H), 7.50 (dd, 1H), 7.30 (td, 1H), 6.96 (d, 1H), 6.78 (d, 1H), 3.00 (m, 2H), 2.57 (m, 2H), 1.59 (m, 4H).

EXAMPLE 176

2-[(2-thienylsulfonyl)amino]-5,6,7,8-tetrahydro-1-naphthalenecarboxylic acid

The desired product was prepared by substituting 2-thiophenesulfonyl chloride for 4-fluorobenzenesulfonyl chloride in Example 128D. MS (ESI(+)) m/e 355 $(M+NH_4)^+$; MS (ESI(−)) m/e 336 $(M-H)^-$; $^1H$ NMR (300 MHz, DMSO-$d_6$) δ 7.69 (dd, 1H), 7.37 (dd, 1H), 7.22 (d, 1H), 7.00 (dd, 1H), 6.86 (d, 1H), 3.00 (m, 2H), 2.60 (m, 2H), 1.59 (m, 4H).

EXAMPLE 177

2-[(benzylsulfonyl)amino]-5,6,7,8-tetrahydro-1-naphthalenecarboxylic acid

The desired product was prepared by substituting phenylmethanesulfonyl chloride for 4-fluorobenzenesulfonyl chloride in Example 128D. MS (ESI(+)) m/e 363 $(M+NH_4)^+$; MS (ESI(−)) m/e 344 $(M-H)^-$; $^1H$ NMR (300 MHz, DMSO-$d_6$) δ 7.31 (m, 3H), 7.27 (m, 2H), 7.11 (d, 1H), 6.94 (d, 1H), 4.25 (s, 2H), 2.94 (m, 2H), 2.68 (m, 2H), 1.66 (m, 4H).

EXAMPLE 178

2-{[(2-methylphenyl)sulfonyl]amino}-5,6,7,8-tetrahydro-1-naphthalenecarboxylic acid The desired product was prepared by substituting 2-methylbenzenesulfonyl chloride for 4-fluorobenzenesulfonyl chloride in Example 128D. MS (ESI(+)) m/e 363 $(M+NH_4)^+$; MS (ESI(−)) m/e 344 $(M-H)^-$; $^1H$ NMR (300 MHz, DMSO-$d_6$) δ 7.87 (d, 1H), 7.40 (t, 1H), 7.28 (t, 1H), 7.01 (d, 1H), 6.74 (d, 1H), 2.96 (m, 2H), 2.56 (m, 5H), 1.57 (m, 4H).

EXAMPLE 179

2-{[(3-methylphenyl)sulfonyl]amino}-5,6,7,8-tetrahydro-1-naphthalenecarboxylic acid The desired product was prepared by substituting 3-methylbenzenesulfonyl chloride for 4-fluorobenzenesulfonyl chloride in Example 128D. MS (ESI(+)) m/e 363 $(M+NH_4)^+$; MS (ESI(−)) m/e 344 $(M-H)^-$; $^1H$ NMR (300 MHz, DMSO-$d_6$) δ 7.55 (s, 1H), 7.50 (d, 1H), 7.33 (m, 2H), 7.09 (d, 1H), 6.79 (d, 1H), 2.94 (m, 2H), 2.58 (m, 2H), 2.31 (s, 3H), 1.58 (m, 4H).

EXAMPLE 180

2-{[(4-methylphenyl)sulfonyl]amino}-5,6,7,8-tetrahydro-1-naphthalenecarboxylic acid The desired product was prepared by substituting 4-methylbenzenesulfonyl chloride for 4-fluorobenzenesulfonyl chloride in Example 128D. MS (ESI(+)) m/e 363 $(M+NH_4)^+$; MS (ESI(−)) m/e 344 $(M-H)^{31}$; $^1H$ NMR (300 MHz, DMSO-$d_6$) δ 7.59 (d, 2H), 7.26 (d, 2H), 7.09 (d, 1H), 6.79 (d, 1H), 2.93 (m, 2H), 2.57 (m, 2H), 2.30 (s, 3H), 1.58 (m, 4H).

EXAMPLE 181

2-{[(2-fluorophenyl)sulfonyl]amino}-5,6,7,8-tetrahydro-1-naphthalenecarboxylic acid The desired product was prepared by substituting 2-fluorobenzenesulfonyl chloride for 4-fluorobenzenesulfonyl chloride in Example 128D. MS (ESI(+)) m/e 367 $(M+NH_4)^+$; MS (ESI(−)) m/e 348 $(M-H)^-$; $^1H$ NMR (300 MHz, DMSO- $d_6$) δ 7.78 (td, 1H), 7.53 (m, 1H), 7.25 (m, 2H), 7.08 (d, 1H), 6.78 (d, 1H), 3.00 (m, 2H), 2.57 (m, 2H), 1.58 (m, 4H).

EXAMPLE 182

2-{[(3-fluorophenyl)sulfonyl]amino}-5,6,7,8-tetrahydro-1-naphthalenecarboxylic acid The desired product was prepared by substituting 3-fluorobenzenesulfonyl chloride for 4-fluorobenzenesulfonyl chloride in Example 128D. MS (ESI(+)) m/e 367 $(M+NH_4)^+$; MS (ESI(−)) m/e 348 $(M-H)^-$; $^1H$ NMR (300 MHz, DMSO-$d_6$) δ 7.52 (m, 2H), 7.44 (m, 1H), 7.37 (m, 1H), 7.13 (d, 1H), 6.83 (d, 1H), 2.98 (m, 2H), 2.58 (m, 2H), 1.58 (m, 4H).

EXAMPLE 183

2-{[(3-cyanophenyl)sulfonyl]amino}-5,6,7,8-tetrahydro-1-naphthalenecarboxylic acid The desired product was prepared by substituting 3-cyanobenzenesulfonyl chloride for 4-fluorobenzenesulfonyl chloride in Example 128D. MS (ESI(+)) m/e 374 $(M+NH_4)^+$; MS (ESI(−)) m/e 355 $(M-H)^-$; $^1H$ NMR (300 MHz, DMSO-$d_6$) δ 8.04 (s, 1H), 7.97 (d, 2H), 7.68 (t, 1H), 7.05 (d, 1H), 6.87 (d, 1H), 2.93 (m, 2H), 2.60 (m, 2H), 1.60 (m, 4H).

EXAMPLE 184

2-{[(4-cyanophenyl)sulfonyl]amino}-5,6,7,8-tetrahydro-1-naphthalenecarboxylic acid The desired product was prepared by substituting 4-cyanobenzenesulfonyl chloride for 4-fluorobenzenesulfonyl chloride in Example 128D. MS (ESI(+)) m/e 374 $(M+NH_4)^+$; MS (ESI(−)) m/e 355 $(M-H)^-$; $^1H$ NMR (300 MHz, DMSO-$d_6$) δ 7.91 (d, 2H), 7.83 (d, 2H), 7.12 (d, 1H), 6.83 (d, 1H), 2.99 (m, 2H), 2.58 (m, 2H), 1.58 (m, 4H).

EXAMPLE 185

2-{[(2,5-dimethylphenyl)sulfonyl]amino}-5,6,7,8-tetrahydro-1-naphthalenecarboxylic acid The desired product was prepared by substituting 2,5-dimethylbenzenesulfonyl chloride for 4-fluorobenzenesulfonyl chloride in Example 128D. MS (ESI(+)) m/e 377 $(M+NH_4)^+$; MS (ESI(−)) m/e 358 $(M-H)^-$; $^1H$ NMR (300 MHz, DMSO-$d_6$) δ 7.70 (s, 1H), 7.21 (d, 1H), 7.15 (d, 1H), 6.99 (d, 1H), 6.75 (d, 1H), 2.94 (m, 2H), 2.56 (m, 2H), 2.50 (s, 3H), 2.29 (s, 3H), 1.58 (m, 4H).

EXAMPLE 186

2-{[(3-methoxyphenyl)sulfonyl]amino}-5,6,7,8-tetrahydro-1-naphthalenecarboxylic acid The desired product was prepared by substituting 3-methoxybenzenesulfonyl chloride for 4-fluorobenzenesulfonyl chloride in Example 128D. MS (ESI(+)) m/e 379 $(M+NH_4)^+$; MS (ESI(−)) m/e 360 $(M-H)^-$; $^1H$ NMR (300 MHz, DMSO-$d_6$) δ 7.36 (t, 1H), 7.27 (m, 1H), 7.22 (m, 1H), 7.12 (d, 1H), 7.05 (dd, 1H), 6.80 (d, 1H), 3.76 (s, 3H), 2.95 (m, 2H), 2.58 (m, 2H), 1.58 (m, 4H).

EXAMPLE 187

2-{[(4-methoxyphenyl)sulfonyl]amino}-5,6,7,8-tetrahydro-1-naphthalenecarboxylic acid The desired product was prepared by substituting 4-methoxybenzenesulfonyl chloride for 4-fluorobenzenesulfonyl chloride in Example 128D. MS (ESI(+)) m/e 379 $(M+NH_4)^+$; MS (ESI(−)) m/e 360 $(M-H)^-$; $^1H$ NMR (300 MHz, DMSO-$d_6$) δ 7.64 (d, 2H), 7.07 (d, 1H), 6.98 (d, 2H), 6.81 (d, 1H), 3.77 (s, 3H), 2.90 (m, 2H), 2.59 (m, 2H), 1.59 (m, 4H).

EXAMPLE 188

2-{[(2-chlorophenyl)sulfonyl]amino}-5,6,7,8-tetrahydro-1-naphthalenecarboxylic acid The desired product was prepared by substituting 2-chlorobenzenesulfonyl chloride for 4-fluorobenzenesulfonyl chloride in Example 128D. MS (ESI(+)) m/e 383 $(M+NH_4)^+$; MS (ESI(−)) m/e 364 $(M-H)^-$; $^1H$ NMR (300 MHz, DMSO-$d_6$) δ 8.02 (d, 1H), 7.50 (m, 2H), 7.44 (m, 1H), 6.97 (d, 1H), 6.76 (d, 1H), 3.00 (m, 2H), 2.56 (m, 2H), 1.58 (m, 4H).

EXAMPLE 189

2-{[(3-chlorophenyl)sulfonyl]amino}-5,6,7,8-tetrahydro-1-naphthalenecarboxylic acid The desired product was prepared by substituting 3-chlorobenzenesulfonyl chloride for 4-fluorobenzenesulfonyl chloride in Example 128D. MS (ESI(+)) m/e 383 $(M+NH_4)^+$; MS (ESI(−)) m/e 364 $(M-H)^-$; $^1H$ NMR (300 MHz, DMSO-$d_6$) δ 7.65 (m, 2H), 7.56 (m, 1H), 7.49 (t, 1H), 7.12 (d, 1H), 6.84 (d, 1H), 2.98 (m, 2H), 2.58 (m, 2H), 1.58 (m, 4H).

EXAMPLE 190

2-{[(4-chlorophenyl)sulfonyl]amino}-5,6,7,8-tetrahydro-1-naphthalenecarboxylic acid The desired product was prepared by substituting 4-chlorobenzenesulfonyl chloride for 4-fluorobenzenesulfonyl chloride in Example 128D. MS (ESI(+)) m/e 383 $(M+NH_4)^+$; MS (ESI(−)) m/e 364 $(M-H)^-$; $^1H$ NMR (300 MHz, DMSO-$d_6$) δ 7.68 (d, 2H), 7.54 (d, 2H), 7.01 (d, 1H), 6.85 (d, 1H), 2.90 (m, 2H), 2.60 (m, 2H), 1.60 (m, 4H).

EXAMPLE 191

2-{[(2,4-difluorophenyl)sulfonyl]amino}-5,6,7,8-tetrahydro-1-naphthalenecarboxylic acid The desired product was prepared by substituting 2,4-difluorobenzenesulfonyl chloride for 4-fluorobenzenesulfonyl chloride in Example 128D. MS (ESI(+)) m/e 385 $(M+NH_4)^+$; MS (ESI(−)) m/e 366 $(M-H)^-$; $^1H$ NMR (300 MHz, DMSO-$d_6$) δ 7.82 (m, 1H), 7.31 (td, 1H), 7.14 (td, 1H), 7.07 (d, 1H), 6.80 (d, 1H), 3.01 (m, 2H), 2.58 (m, 2H), 1.59 (m, 4H).

EXAMPLE 192

2-{[(3,4-difluorophenyl)sulfonyl]amino}-5,6,7,8-tetrahydro-1-naphthalenecarboxylic acid The desired product was prepared by substituting 3,4-difluorobenzenesulfonyl chloride for 4-fluorobenzenesulfonyl chloride in Example 128D. MS (ESI(+)) m/e 385 $(M+NH_4)^+$; MS (ESI(−)) m/e 366 $(M-H)^-$; $^1H$ NMR (300 MHz, DMSO-$d_6$) δ 7.67 (m, 1H), 7.53 (m, 2H), 7.07 (d, 1H), 6.87 (d, 1H), 2.93 (m, 2H), 2.60 (m, 2H), 1.60 (m, 4H).

EXAMPLE 193

2-{[(4-propylphenyl)sulfonyl]amino}-5,6,7,8-tetrahydro-1-naphthalenecarboxylic acid The desired product was prepared by substituting 4-propylbenzenesulfonyl chloride for 4-fluorobenzenesulfonyl chloride in Example 128D. MS (ESI(+)) m/e 391 $(M+NH_4)^+$; MS (ESI(−)) m/e 372 $(M-H)^-$; $^1H$ NMR (300 MHz, DMSO-$d_6$) δ 7.62 (d, 2H), 7.29 (d, 2H), 7.02 (d, 1H), 6.83 (d, 1H), 2.88 (m, 2H), 2.59 (m, 2H), 2.56 (m, 2H), 1.59 (m, 4H), 1.55 (m, 2H), 0.86 (t, 3H).

EXAMPLE 194

2-{[(4-isopropylphenyl)sulfonyl]amino}-5,6,7,8-tetrahydro-1-naphthalenecarboxylic acid The desired product was prepared by substituting 4-(2-methylethyl)benzenesulfonyl chloride for 4-fluorobenzenesulfonyl chloride in Example 128D. MS (ESI(+)) m/e 391 $(M+NH_4)^+$; MS (ESI(−)) m/e 372 $(M-H)^-$; $^1H$ NMR (300 MHz, DMSO-$d_6$) δ 7.66 (d, 2H), 7.39 (d, 2H), 6.93 (d, 1H), 6.84 (d, 1H), 2.94 (sept, 1H), 2.75 (m, 2H), 2.63 (m, 2H), 1.64 (m, 4H), 1.19 (d, 6H).

EXAMPLE 195

2-[(2-naphthylsulfonyl)amino]-5,6,7,8-tetrahydro-1-naphthalenecarboxylic acid

The desired product was prepared by substituting 2-naphthalenesulfonyl chloride for 4-fluorobenzenesulfonyl chloride in Example 128D. MS (ESI(+)) m/e 399 $(M+NH_4)^+$; MS (ESI(−)) m/e 380 $(M-H)^-$; $^1H$ NMR (300 MHz, DMSO-$d_6$) δ 8.38 (s, 1H), 8.07 (d, 1H), 7.97 (d, 1H), 7.94 (d, 1H), 7.71 (dd, 1H), 7.62 (m, 2H), 7.20 (d, 2H), 6.77 (d, 2H), 2.93 (m, 2H), 2.54 (m, 2H), 1.54 (m, 4H).

EXAMPLE 196

2-[(1-naphthylsulfonyl)amino]-5,6,7,8-tetrahydro-1-naphthalenecarboxylic acid

The desired product was prepared by substituting 1-naphthalenesulfonyl chloride for 4-fluorobenzenesulfonyl chloride in Example 128D. MS (ESI(+)) m/e 399 $(M+NH_4)^+$; MS (ESI(−)) m/e 380 $(M-H)^-$; $^1H$ NMR (300 MHz, DMSO-$d_6$) δ 8.70 (d, 1H), 8.16 (d, 1H), 8.10 (d, 1H), 8.04 (d, 1H), 7.64 (m, 2H), 7.58 (t, 1H), 6.81 (d, 1H), 6.69 (m, 1H), 2.76 (m, 2H), 2.57 (m, 2H), 1.60 (m, 4H).

EXAMPLE 197

2-{[(4-tert-butylphenyl)sulfonyl]amino}-5,6,7,8-tetrahydro-1-naphthalenecarboxylic acid The desired product was prepared by substituting 4-tert-butylbenzenesulfonyl chloride for 4-fluorobenzenesulfonyl chloride in Example 128D. MS (ESI(+)) m/e 388 $(M+H)^+$, 405 $(M+NH_4)^+$; MS (ESI(−)) m/e 386 $(M-H)^-$; $^1H$ NMR (300 MHz, DMSO-$d_6$) δ 7.67 (d, 2H), 7.54 (d, 2H), 6.92 (d, 1H), 6.88 (d, 1H), 2.77 (m, 2H), 2.63 (m, 2H), 1.63 (m, 4H), 1.28 (s, 9H).

EXAMPLE 198

2-{[(3-chloro-4-fluorophenyl)sulfonyl]amino}-5,6,7,8-tetrahydro-1-naphthalenecarboxylic acid The desired product was prepared by substituting 3-chloro-4-fluorobenzenesulfonyl chloride for 4-fluorobenzenesulfonyl chloride in Example 128D. MS (ESI(+)) m/e 401 $(M+NH_4)^+$; MS (ESI(−)) m/e 382 $(M-H)^-$; $^1H$ NMR (300 MHz, DMSO-$d_6$) δ 7.83 (dd, 1H), 7.68 (ddd, 1H), 7.55 (t, 1H), 6.95 (d, 1H), 6.90 (d, 1H), 2.80 (m, 2H), 2.64 (m, 2H), 1.63 (m, 4H).

EXAMPLE 199

2-({[4-(acetylamino)phenyl]sulfonyl}amino)-5,6,7,8-tetrahydro-1-naphthalenecarboxylic acid The desired product was prepared by substituting 4-(N-acetylamino)benzenesulfonyl chloride for 4-fluorobenzenesulfonyl chloride in Example 128D. MS (ESI(+)) m/e 389 $(M+H)^+$; MS (ESI(−)) m/e 387 $(M-H)^-$; $^1H$ NMR (300 MHz, DMSO-$d_6$) δ 10.19 (s, 1H), 7.61 (s, 4H), 7.09 (d, 1H), 6.77 (d, 1H), 2.94 (m, 2H), 2.57 (m, 2H), 2.03 (s, 3H), 1.57 (m, 4H).

EXAMPLE 200

2-{[(2,5-dimethoxyphenyl)sulfonyl]amino}-5,6,7,8-tetrahydro-1-naphthalenecarboxylic acid The desired product was prepared by substituting 2,5-dimethoxybenzenesulfonyl chloride for 4-fluorobenzenesulfonyl chloride in Example 128D. MS (ESI(+)) m/e 409 $(M+NH_4)^+$; MS (ESI(−)) m/e 390 $(M-H)^-$; $^1H$ NMR (300 MHz, DMSO-$d_6$) δ 7.21 (d, 1H), 7.11 (m, 3H), 6.93 (d, 1H), 3.80 (s, 3H), 3.70 (s, 3H), 2.77 (m, 2H), 2.61 (m, 2H), 1.62 (m, 4H).

EXAMPLE 201

2-{[(3,4-dimethoxyphenyl)sulfonyl]amino}-5,6,7,8-tetrahydro-1-naphthalenecarboxylic acid The desired product was prepared by substituting 3,4-dimethoxybenzenesulfonyl chloride for 4-fluorobenzenesulfonyl chloride in Example 128D. MS (ESI(+)) m/e 409 $(M+NH_4)^+$; MS (ESI(−)) m/e 390 $(M-H)^-$; $^1H$ NMR (300 MHz, DMSO-$d_6$) δ 7.28 (dd, 1H), 7.23 (d, 1H), 7.01 (d, 1H), 6.93 (2, 1H), 6.90 (d, 1H), 3.79 (s, 3H), 3.76 (s, 3H), 2.78 (m, 2H), 2.62 (m, 2H), 1.62 (m, 4H).

EXAMPLE 202

2-({[3-(trifluoromethyl)phenyl]sulfonyl}amino)-5,6,7,8-tetrahydro-1-naphthalenecarboxylic acid The desired product was prepared by substituting 3-(trifluoromethyl)benzenesulfonyl chloride for 4-fluorobenzenesulfonyl chloride in Example 128D. MS (ESI(+)) m/e 417 $(M+NH_4)^+$; MS (ESI(−)) m/e 398 $(M-H)^-$; $^1H$ NMR (300 MHz, DMSO-$d_6$) δ 7.98 (m, 3H), 7.77 (t, 1H), 6.94 (d, 1H), 6.83 (d, 1H), 2.77 (m, 2H), 2.63 (m, 2H), 1.63 (m, 4H).

EXAMPLE 203

2-({[4-(trifluoromethyl)phenyl]sulfonyl}amino)-5,6,7,8-tetrahydro-1-naphthalenecarboxylic acid The desired product was prepared by substituting 4-(trifluoromethyl)benzenesulfonyl chloride for 4-fluorobenzenesulfonyl chloride in Example 128D. MS (ESI(+)) m/e 417 $(M+NH_4)^+$; MS (ESI(−)) m/e 398 $(M-H)^-$; $^1H$ NMR (300

MHz, DMSO-$d_6$) δ 7.91 (s, 4H), 6.94 (d, 1H), 6.84 (d, 1H), 2.77 (m, 2H), 2.64 (m, 2H), 1.64 (m, 4H).

EXAMPLE 204

2-{[(2,3-dichlorophenyl)sulfonyl]amino}-5,6,7,8-tetrahydro-1-naphthalenecarboxylic acid The desired product was prepared by substituting 2,3-dichlorobenzenesulfonyl chloride for 4-fluorobenzenesulfonyl chloride in Example 128D. MS (ESI(+)) m/e 417 $(M+NH_4)^+$; MS (ESI(−)) m/e 398 $(M-H)^-$; $^1H$ NMR (300 MHz, DMSO-$d_6$) δ 7.92 (dd, 1H), 7.83 (dd, 1H), 7.47 (t, 1H), 6.91 (d, 1H), 6.88 (d, 1H), 2.81 (m, 2H), 2.62 (m, 2H), 1.63 (m, 4H).

EXAMPLE 205

2-{[(2,4-dichlorophenyl)sulfonyl]amino}-5,6,7,8-tetrahydro-1-naphthalenecarboxylic acid The desired product was prepared by substituting 2,4-dichlorobenzenesulfonyl chloride for 4-fluorobenzenesulfonyl chloride in Example 128D. MS (ESI(+)) m/e 417 $(M+NH_4)^+$; MS (ESI(−)) m/e 398 $(M-H)^-$; $^1H$ NMR (300 MHz, DMSO-$d_6$) δ 7.91 (d, 1H), 7.76 (d, 1H), 7.53 (dd, 1H), 6.92 (d, 1H), 6.89 (d, 1H), 2.82 (m, 2H), 2.62 (m, 2H), 1.63 (m, 4H).

EXAMPLE 206

2-{[(2,5-dichlorophenyl)sulfonyl]amino}-5,6,7,8-tetrahydro-1-naphthalenecarboxylic acid The desired product was prepared by substituting 2,5-dichlorobenzenesulfonyl chloride for 4-fluorobenzenesulfonyl chloride in Example 128D. MS (ESI(+)) m/e 417 $(M+NH_4)^+$; MS (ESI(−)) m/e 398 $(M-H)^-$; $^1H$ NMR (300 MHz, DMSO-$d_6$) δ 7.84 (d, 1H), 7.67 (m, 2H), 6.99 (d, 1H), 6.87 (d, 1H), 2.75 (m, 2H), 2.65 (m, 2H), 1.65 (m, 4H).

EXAMPLE 207

2-{[(3,4-dichlorophenyl)sulfonyl]amino}-5,6,7,8-tetrahydro-1-naphthalenecarboxylic acid The desired product was prepared by substituting 3,4-dichlorobenzenesulfonyl chloride for 4-fluorobenzenesulfonyl chloride in Example 128D. MS (ESI(+)) m/e 417 $(M+NH_4)^+$; MS (ESI(−)) m/e 398 $(M-H)^-$; $^1H$ NMR (300 MHz, DMSO-$d_6$) δ 7.85 (d, 1H), 7.78 (d, 1H), 7.63 (dd, 1H), 6.95 (d, 1H), 6.90 (d, 1H), 2.80 (m, 2H), 2.64 (m, 2H), 1.63 (m, 4H).

EXAMPLE 208

2-{[(3,5-dichlorophenyl)sulfonyl]amino}-5,6,7,8-tetrahydro-1-naphthalenecarboxylic acid The desired product was prepared by substituting 3,5-dichlorobenzenesulfonyl chloride for 4-fluorobenzenesulfonyl chloride in Example 128D. MS (ESI(+)) m/e 417 $(M+NH_4)^+$; MS (ESI(−)) m/e 398 $(M-H)^-$; $^1H$ NMR (300 MHz, DMSO-$d_6$) δ 7.77 (t, 1H), 7.61 (d, 2H), 7.08 (d, 1H), 6.89 (d, 1H), 2.96 (m, 2H), 2.60 (m, 2H), 1.60 (m, 4H).

EXAMPLE 209

2-[(1,1'-biphenyl-4-ylsulfonyl)amino]-5,6,7,8-tetrahydro-1-naphthalenecarboxylic acid The desired product was prepared by substituting 4-phenylbenzenesulfonyl chloride for 4-fluorobenzenesulfonyl chloride in Example 128D. MS (ESI(+)) m/e 425 $(M+NH_4)^+$; MS (ESI(−)) m/e 406 $(M-H)^-$; $^1H$ NMR (300 MHz, DMSO-$d_6$) δ 7.77 (m, 4H), 7.67 (d, 2H), 7.47 (t, 2H), 7.39 (t, 1H), 7.18 (d, 1H), 6.82 (d, 1H), 2.96 (m, 2H), 2.58 (m, 2H), 1.57 (m, 4H).

EXAMPLE 210

2-{[(2-bromophenyl)sulfonyl]amino}-5,6,7,8-tetrahydro-1-naphthalenecarboxylic acid The desired product was prepared by substituting 2-bromobenzenesulfonyl chloride for 4-fluorobenzenesulfonyl chloride in Example 128D. MS (ESI(+)) m/e 429 $(M+NH_4)^+$; MS (ESI(−)) m/e 410 $(M-H)^-$; $^1H$ NMR (300 MHz, DMSO-$d_6$) δ 8.01 (dd, 1H), 7.75 (dd, 1H), 7.51 (td, 1H), 7.45 (td, 1H), 6.90 (d, 1H), 6.86 (d, 1H), 2.88 (m, 2H), 2.59 (m, 2H), 1.61 (m, 4H).

EXAMPLE 211

2-{[(3-bromophenyl)sulfonyl]amino}-5,6,7,8-tetrahydro-1-naphthalenecarboxylic acid The desired product was prepared by substituting 3-bromobenzenesulfonyl chloride for 4-fluorobenzenesulfonyl chloride in Example 128D. MS (ESI(+)) m/e 429 $(M+NH_4)^+$; MS (ESI(−)) m/e 410 $(M-H)^-$; $^1H$ NMR (300 MHz, DMSO-$d_6$) δ 7.83 (t, 1H), 7.77 (m, 1H), 7.70 (m, 1H), 7.47 (t, 1H), 6.92 (d, 2H), 6.89 (d, 2H), 2.82 (m, 2H), 2.63 (m, 2H), 1.63 (m, 4H).

EXAMPLE 212

2-{[(4-bromophenyl)sulfonyl]amino}-5,6,7,8-tetrahydro-1-naphthalenecarboxylic acid The desired product was prepared by substituting 4-bromobenzenesulfonyl chloride for 4-fluorobenzenesulfonyl chloride in Example 128D. MS (ESI(+)) m/e 429 $(M+NH_4)^+$; MS (ESI(−)) m/e 310 $(M-H)^-$; $^1H$ NMR (300 MHz, DMSO-$d_6$) δ 7.72 (d, 2H), 7.63 (d, 2H), 6.92 (d, 1H), 6.88 (d, 1H), 2.80 (m, 2H), 2.63 (m, 2H), 1.63 (m, 4H).

EXAMPLE 213

2-({[4-(trifluoromethoxy)phenyl]sulfonyl}amino)-5,6,7,8-tetrahydro-1-naphthalenecarboxylic acid The desired product was prepared by substituting 4-(trifluoromethoxy)benzenesulfonyl chloride for 4-fluorobenzenesulfonyl chloride in Example 128D. MS (ESI(+)) m/e 433 $(M+NH_4)^+$; MS (ESI(−)) m/e 414 $(M-H)^-$; $^1H$ NMR (300

MHz, DMSO-$d_6$) δ 7.84 (d, 2H), 7.51 (d, 2H), 6.94 (d, 1H), 6.85 (d, 1H), 2.77 (m, 2H), 2.64 (m, 2H), 1.64 (m, 4H).

EXAMPLE 214

3-(3-methoxy-3-oxopropyl)-2-methyl-6-[(2-pyridinylsulfonyl)amino]benzoic acid

EXAMPLE 214A benzyl 3-[(1E)-3-methoxy-3-oxo-1-propenyl]-2-methyl-6-[(2-pyridinylsulfonyl)amino]benzoate A mixture of grounded 4 Å molecular sieves (0.4 g), $NaHCO_3$ (94 mg), and tetrabutylammonium chloride (125 mg), in anhydrous DMF (4 mL) was stirred for 15 minutes at room temperature. To the mixture was added 2-dicyclohexylphosphino-2'-(N,N-dimethylamino)biphenyl (35 mg), Example 110A (210 mg, 0.45 mmol), and methyl acrylate (0.3 mL), and the mixture was stirred for another 15 minutes at room temperature, purged with argon and treated with $Pd(OAc)_2$ (10 mg). The mixture was stirred at 100° C. for 48 hours, treated with brine (10 mL), and extracted with ethyl acetate. The solution was dried ($MgSO_4$), filtered and concentrated. The residue was purified by flash column chromatography on silica gel with 30% ethyl acetate/hexanes to provide the desired product (131 mg, 62.5%). MS (ESI+) m/e 467 $(M+H)^+$.

EXAMPLE 214B 3-(3-methoxy-3-oxopropyl)-2-methyl-6-[(2-pyridinylsulfonyl)amino]benzoic acid A solution of Example 214A (131 mg) in methanol (10 mL) was treated with Pd/C (10%, 150 mg) under one atmosphere of hydrogen for 16 hours. Filtration and evaporation of the solvents to provide the desired product. $^1H$ NMR (DMSO-$d_6$) δ 2.20 (s, 3H), 2.54 (t, 2H), 2.80 (t, 2H), 3.57 (s, 3H), 6.90 (d, 1H), 7.10 (d, 1H), 7.66 (m, 1H), 7.87 (d, 1H), 8.04 (q, 1H), 8.73 (d, 1H), 9.70 (s, 1H), 13.20 (br s, 1H); MS (ESI(−)) m/e 377 $(M-H)^-$.

EXAMPLE 215

2-{[(4-fluorophenyl)sulfonyl]amino}-5-(methylfulfanyl)benzoic acid

The desired product was prepared by substituting 4-fluorobenzenesulfonyl chloride for benzenesulfonyl chloride and 2-amino-5-methylsulfanylbenzioic acid (prepared as described in *Org. Prep. Proc. Int.* 1981, 13, 189-196) for Example 1C in Example 1D. MS (ESI(+)) m/e 324 $(M+H)^+$, 341 $(M+NH_4)^+$, 346 $(M+Na)^+$; (ESI(−)) m/e 322 $(M-H)^-$; $^1H$ NMR (300 MHz, DMSO-$d_6$) δ 7.84 (dd, 2H), 7.68 (m, 1H), 7.46 (m, 2H), 7.40 (t, 2H), 2.44 (s, 3H).

778728 EXAMPLE 216

2-{[(4-fluorophenyl)sulfonyl]amino}-8-methyl-5,6,7,8-tetrahydro-1-naphthalenecarboxylic acid

EXAMPLE 216A

N-(1-bromo-8-methyl-5,6,7,8-tetrahydro-2-naphthalenyl)-4-fluorobenzenesulfonamide A mixture of Example 132A (90 mg) in methanol (18 mL) was hydrogenated in the presence of $PtO_2$ (18 mg) for 16 hours. The reaction mixture was filtered and concentrated to provide the desired product in quantitative yield. MS (ESI) m/e 397 $(M-H)^-$; $^1H$ NMR (300 MHz, DMSO-$d_6$) δ 9.77 (s, 1H), 7.71 (m, 2H), 7.39 (m, 2H), 7.03 (d, 1H), 6.92 (d, 1H), 3.05 (m, 1H), 2.69 (m, 2H), 1.7 (m, 4H), 1.07 (d, 3H).

EXAMPLE 216B

2-{[(4-fluorophenyl)sulfonyl]amino}-8-methyl-5,6,7,8-tetrahydro-1-naphthalenecarboxylic acid The desired product was prepared by substituting Example 216A for Example 103A in Example 103B. MS (ESI) m/e 362 $(M-H)^-$; $^1H$ NMR (300 MHz, DMSO-$d_6$) δ 13.15 (br s, 1H), 9.62 (br s, 1H), 7.76 (m, 2H), 7.4 (m, 2H), 6.98 (d, 1H), 6.62 (d, 1H), 2.7 (m, 2H), 1.85-1.54 (m, 4H), 1.08 (br s, 3H).

EXAMPLE 217

3-(2-carboxyethyl)-2-methyl-6-[(2-pyridinylsulfonyl)amino]benzoic acid

A solution of Example 214 (45 mg, 0.12 mmol) and NaOH (40 mg, 1.0 mmol) in THF (10 mL) and water (1 mL) was stirred for 3 hours, adjusted to pH 3, then concentrated. The resulting solid was triturated with ethyl acetate to provide the desired product (40 mg, 91.5%). $^1H$ NMR (DMSO-$d_6$) δ 2.20 (s, 3H), 2.43 (t, 2H), 2.77 (t, 2H), 6.90 (d, 1H), 7.09 (d, 1H), 7.66 (d, 1H), 7.88 (d, 1H), 8.04 (q, 1H), 8.72 (d, 1H), 9.83 (s, 1H), 12.16 (br s, 1H), 13.19 (br s, 1H); MS (ESI(−)) m/e 363 $(M-H)^-$.

EXAMPLE 218

5-(methylsulfanyl)-2-[(phenylsulfonyl)amino]benzoic acid

The desired product was prepared by substituting 2-amino-5-(methylsulfanyl)benzoic acid (prepared as described in *Org. Prep. Proc. Int.* 1981, 13, 189-196) for Example 1C in Example 1D. MS (ESI(+)) m/e 324 $(M+H)^+$, 359 $(M+NH_4)$+, 364 $(M+Na)^+$; (ESI(−)) m/e 340 $(M-H)^-$; $^1H$ NMR (300 MHz, DMSO-$d_6$) 7.79 (m, 1H), 7.76 (m, 1H), 7.68 (m, 1H), 7.64 (d, 1H), 7.56 (t, 2H), 7.47 (d, 2H), 2.43 (s, 3H).

EXAMPLE 219

2-{[(2-{[2-(dimethylamino)ethyl]amino}phenyl)sulfonyl]amino}-5,6,7,8-tetrahydro-1-naphthalenecarboxylic acid The desired product was prepared by substituting N,N-dimethyl-1,2-ethanediamine for N,N-diethyl-1,3-propanediamine in Example 229B. MS (DCI) m/e 418 $(M+H)^+$; $^1H$ NMR (500 MHz, DMSO-$d_6$) δ 13.12 (br s, 1H), 9.52 (br s, 1H), 7.40 (m, 2H), 6.95 (d, 1H), 6.90 (d, 1H), 6.88 (br s, 1H), 6.65 (t, 1H), 6.07 (t, 1H), 3.60 (q, 2H), 3.27 (t, 2H), 2.86 (s, 6H), 2.64 (m, 4H), 1.63 (br s, 4H).

EXAMPLE 220

2-{[(2-{[2-(diethylamino)ethyl]amino}phenyl)sulfonyl]amino}-5,6,7,8-tetrahydro-1-naphthalenecarboxylic acid The desired product was prepared by substituting N,N-diethyl-1,2-ethanediamine for N,N-diethyl-1,3-propanediamine in Example 229B. MS (DCI) m/e 446 $(M+H)^+$; $^1H$ NMR (500 MHz, DMSO-$d_6$) δ 13.18 (br s, 1H), 9.52 (br s, 1H), 7.42 (m, 2H), 6.94 (d, 1H), 6.89 (d, 1H), 6.79 (br s, 1H), 6.67 (m, 1H), 6.05 (br s, 1H), 3.59 (q, 2H), 3.23 (m, 6H), 2.64 (m, 4H), 1.64 (br s, 4H), 1.20 (t, 6H).

EXAMPLE 221

2-{[(2-{[2-(1-pyrrolidinyl)ethyl]amino}phenyl)sulfonyl]amino}-5,6,7,8-tetrahydro-1-naphthalenecarboxylic acid The desired product was prepared by substituting 2-(1-pyrrolidinyl)ethanamine for N,N-diethyl-1,3-propanediamine in Example 229B. MS (DCI) m/e 444 $(M+H)^+$; $^1$H NMR (500 MHz, DMSO-$d_6$) δ 9.85 (br s, 1H), 7.40 (m, 2H), 6.96 (d, 1H), 6.89 (m, 2H), 6.65 (t, 1H), 6.10 (t, 1H), 3.58 (m, 4H), 3.30 (m, 4H), 2.64 (br s, 4H), 1.94 (br s, 4H), 1.63 (br s, 4H).

EXAMPLE 222

2-{[(2-{[3-(dimethylamino)propyl]amino}phenyl)sulfonyl]amino}-5,6,7,8-tetrahydro-1-naphthalenecarboxylic acid The desired product was prepared by substituting N,N-dimethyl-1,3-propanediamine for N,N-diethyl-1,3-propanediamine in Example 229B. MS (DCI) m/e 432 $(M+H)^+$; $^1$H NMR (500 MHz, DMSO-$d_6$) δ 13.18 (br s, 1H), 9.53 (br s, 1H), 7.50 (d, 1H), 7.39 (t, 1H), 6.94 (d, 1H), 6.82 (d, 1H), 6.76 (br s, 1H), 6.62 (t, 1H), 6.04 (br s, 1H), 3.26 (m, 2H), 3.14 (m, 2H), 2.76 (s, 6H), 2.68 (m, 2H), 2.64 (br s, 2H), 1.89 (m, 2H), 1.65 (br s, 4H).

EXAMPLE 223

2-{[(2-{[3-(4-methyl-1-piperazinyl)propyl]amino}phenyl)sulfonyl]amino}-5,6,7,8-tetrahydro-1-naphthalenecarboxylic acid The desired product was prepared by substituting 3-(4-methyl-1-piperazinyl)-1-propanamine for N,N-diethyl-1,3-propanediamine in Example 229B. MS (DCI) m/e 487 $(M+H)^+$; $^1$H NMR (500 MHz, DMSO-$d_6$) δ 9.56 (br s, 1H), 7.50 (dd, 1H), 7.39 (m, 1H), 6.96 (d, 1H), 6.80 (d, 1H), 6.66 (d, 1H), 6.62 (t, 1H), 6.02 (br s, 1H), 3.30 (t, 4H), 3.20 (m, 4H), 2.73 (br s, 3H), 2.65 (m, 4H), 1.66 (m, 4H).

EXAMPLE 224

2-{[(2-{[3-(1-piperidinyl)propyl]amino}phenyl)sulfonyl]amino}-5,6,7,8-tetrahydro-1-naphthalenecarboxylic acid The desired product was prepared by substituting 3-(1-piperidinyl)-1-propanamine for 3-(N,N-diethylamino)propylamine in Example 229B. MS (DCI) m/e 472 $(M+H)^+$; $^1$H NMR (500 MHz, DMSO-$d_6$) δ 13.22 (br s, 1H), 9.54 (br s, 1H), 7.51 (d, 1H), 7.40 (t, 1H), 6.94 (d, 1H), 6.82 (d, 1H), 6.63 (m, 1H), 6.05 (br s, 1H), 3.27 (m, 4H), 3.10 (m, 2H), 2.67-2.64 (m, 4H), 1.89 (m, 2H), 1.78 (br s, 2H), 1.58 (br s, 2H), 1.65 (br s, 6H).

EXAMPLE 225

3-butyl-6-{[(4-fluorophenyl)sulfonyl]amino}-2-methylbenzoic acid

EXAMPLE 225A benzyl 3-bromo-6-{[(4-fluorophenyl)sulfonyl]amino}-2-methylbenzoate A mixture of Example 126B (760 mg, 2.1 mmol), 4-fluorobenzenesulfonyl chloride (600 mg, 3.1 mmol), dichloromethane (10 mL), and pyridine (0.69 mL, 8.5 mmol) was stirred for 18 hours, diluted with dichloromethane (100 mL), washed with 0.5M HCl (2×100 mL) and brine, dried ($Na_2SO_4$), filtered, concentrated and purified on a Biotage silica gel cartridge (40 g) eluted with 50-75% dichloromethane/hexanes to provide the desired product. MS (ESI (+) lm/e 478, 480 $(M+H)^+$, 495, 497 $(M+NH_4)^+$, 500, 502 $(M+Na)^+$; (ESI(−)) m/e 476, 478 $(M-H)^-$; $^1$H NMR (300 MHz, DMSO-$d_6$) δ 10.09 (s, 1H), 7.73 (m, 2H), 7.62 (d, 1H), 7.40 (m, 7H), 6.85 (d, 1H), 5.25 (s, 2H), 2.19 (s, 3H).

EXAMPLE 225B 3-butyl-6-{[(4-fluorophenyl)sulfonyl]amino}-2-methylbenzoic acid

A mixture of Example 225A (123 mg, 0.26 mmol), potassium phosphate (192 mg, 0.9 mmol), butylboronic acid (34 mg, 0.33 mmol), bis(tricyclohexylphosphino)palladium dichloride (19 mg, 0.03 mmol), toluene (4 mL), and water (0.2 mL) was purged with argon and shaken at 100° C. for 36 hours in a sealed container. The mixture was diluted with ethyl acetate (10 mL), washed with water (2×10 mL) and brine, dried ($Na_2SO_4$), filtered, concentrated and passed through a silica gel cartridge (20 g) with 15% ethyl acetate/hexanes. The isolated solid was substituted for Example 108C in Example 108D and purified by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min to provide the desired-product. MS (ESI(+)) m/e 383 $(M+NH_4)^+$; (ESI(−)) m/e 364 $(M-H)^-$; $^1$H NMR (300 MHz, DMSO-$d_6$) δ 13.09 (br s, 1H), 9.74 (br s, 1H), 7.78 (m, 2H), 7.39 (m, 2H), 7.08 (d, 1H), 6.71 (d, 1H), 2.55 (q, 2H), 2.18 (s, 3H), 1.44 (m, 2H), 1.32 (m, 2H), 0.91 (t, 3H).

EXAMPLE 226

2-chloro-3-ethyl-6-{[(4-fluorophenyl)sulfonyl]amino}benzoic acid

EXAMPLE 226A

2-[(tert-butoxycarbonyl)amino]-6-chlorobenzoic acid

The desired product was prepared by substituting 2-amino-6-chlorobenzoic acid for 2-amino-6-methylbenzoic acid in Example 104A. MS (ESI(+)) m/e 272 $(M+H)^+$, 289 $(M+NH_4)^+$, 294 $(M+Na)^+$; (ESI(−)) m/e 270 $(M-H)^-$; $^1$H NMR (300 MHz, DMSO-$d_6$) δ 13.58 (br s, 1H), 8.83 (s, 1H), 7.49 (dd, 1H), 7.39 (t, 1H), 7.26 (dd, 1H), 1.44 (s, 9H).

EXAMPLE 226B 3-bromo-6-[(tert-butoxycarbonyl)amino]-2-chlorobenzoic acid

The desired product was prepared by substituting Example 226A for Example 104A in Example 104B. MS (ESI(+)) m/e 350, 352 $(M+H)^+$, 367, 369 $(M+NH_4)^+$, 372, 374 $(M+Na)^+$; (ESI(−)) m/e 348, 350 $(M-H)^-$; $^1H$ NMR (300 MHz, DMSO-$d_6$) δ 13.79 (br s, 1H), 8.86 (s, 1H), 7.78 (d, 1H), 7.43 (d, 1H), 1.44 (s, 9H).

EXAMPLE 226C benzyl 3-bromo-6-[(tert-butoxycarbonyl)amino]-2-chlorobenzoate

The desired product was prepared by substituting Example 226B for Example 104B in Example 108A. MS (ESI(+)) m/e 440, 442 $(M+H)^+$, 457, 459 $(M+NH_4)^+$, 462, 464 $(M+Na)^+$; (ESI(−)) m/e 438, 440 $(M-H)^-$; $^1H$ NMR (300 MHz, DMSO-$d_6$) δ 9.34 (s, 1H), 7.82 (d, 1H), 7.48-7.33 (m, 6H), 5.29 (s, 2H), 1.43 (s, 9H).

EXAMPLE 226D benzyl 6-amino-3-bromo-2-chlorobenzoate

The desired product was prepared by substituting Example 226C for Example 126A in Example 126B. MS (ESI(−)) m/e 338, 340 $(M-H)^-$; $^1H$ NMR (300 MHz, DMSO-$d_6$) δ 7.42 (m, 6H), 6.63 (d, 1H), 5.33 (s, 2H), 4.37 (br s, 2H).

EXAMPLE 226E benzyl 3-bromo-2-chloro-6-{[(4-fluorophenyl)sulfonyl]amino}benzoate The desired product was prepared by substituting Example 226D and 4-fluorobenzenesulfonyl chloride for Example 126B and 3-fluorobenzenesulfonyl chloride, respectively, in Example 126C. MS (ESI(+)) m/e 498, 500 $(M+H)^+$, 515, 517 $(M+NH_4)^+$, 520, 522 $(M+Na)^+$; (ESI(−)) m/e 496, 498 $(M-H)^-$; $^1H$ NMR (300 MHz, DMSO-$d_6$) δ 10.46 (s, 1H), 7.80 (d, 1H), 7.75 (m, 2H), 7.40 (m, 7H), 7.05 (d, 1H), 5.27 (s, 2H).

EXAMPLE 226F benzyl 2-chloro-6-{[(4-fluorophenyl)sulfonyl]amino}-3-vinylbenzoate A mixture of Example 226E (160 mg, 0.32 mmol), dibutyl vinylborate (88 mg, 0.48 mmol), CsF (146 mg, 0.96 mmol), $Pd(PPh_3)_4$ (37 mg, 0.03 mmol), DME (3.2 mL) and methanol (1.6 mL) was purged with argon, sealed in a vial and microwaved at 150° C. for 240 seconds. The mixture was diluted with ethyl acetate (50 mL), washed with brine, dried ($Na_2SO_4$), filtered, concentrated and purified on a Biotage silica gel cartridge (40 g) with 10% ethyl acetate/hexanes to provide the desired product. MS (ESI(+)) m/e 446 $(M+H)^+$, 463 $(M+NH)^+$, 468 $(M+Na)^+$; (ESI(−)) m/e 444 $(M-H)^-$; $^1H$ NMR (300 MHz, DMSO-$d_6$) δ 10.36 (s, 1H), 7.76 (m, 3H), 7.38 (m, 7H), 7.10 (d, 1H), 6.93 (dd, 1H), 5.86 (d, 1H), 5.51 (d, 1H), 5.26 (s, 2H).

EXAMPLE 226G 2-chloro-3-ethyl-6-{[(4-fluorophenyl)sulfonyl]amino}benzoic acid

The desired product was prepared by substituting Example 226F for Example 108C in Example 108D and extending the reaction time to 18 hours. MS (ESI(+)) m/e 375 $(M+NH_4)^+$; (ESI(−)) m/e 356 $(M-H)^-$; $^1H$ NMR (300 MHz, DMSO-$d_6$) δ 7.80 (m, 2H), 7.38 (m, 2H), 7.22 (d, 1H), 6.97 (d, 1H), 3.34 (br s, 2H), 2.64 (q, 2H), 1.11 (t, 3H).

EXAMPLE 227

2-chloro-6-{[(4-fluorophenyl)sulfonyl]amino}benzoic acid

The crude product, which was one of two products isolated from this reaction, was prepared by substituting Example 226E for Example 108C in Example 108D and using 1M aqueous NaOH (0.6 mL, 0.6 mmol) to the reaction mixture. The crude product purified by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min. MS ESI(−) m/e 328 $(M-H)^-$; $^1H$ NMR (300 MHz, DMSO-$d_6$) δ 13.58 (br s, 1H), 10.18 (br s, 1H), 7.80 (m, 2H), 7.41 (m, 2H), 7.35 (m, 2H), 6.97 (dd, 1H).

EXAMPLE 228

3-bromo-2-chloro-6-{[(4-fluorophenyl)sulfonyl]amino}benzoic acid

The crude product was prepared by substituting Example 226E for Example 108C in Example 108D and adding 1M aqueous NaOH (0.6 mL, 0.6 mmol) to the reaction mixture. Purification was accomplished by preparative HPLC on a Waters Symmetry C8 column (25 mm×100 mm, 7 μm particle size) using a gradient of 10% to 100% acetonitrile:0.1% aqueous TFA over 8 minutes (10 minute run time) at a flow rate of 40 mL/min. MS (ESI(−)) m/e 406, 408 $(M-H)^-$; $^1H$ NMR (300 MHz, DMSO-$d_6$) δ 13.67 (br s, 1H), 10.30 (br s, 1H), 7.81 (m, 2H), 7.74 (d, 1H), 7.42 (m, 2H), 6.93 (d, 1H).

EXAMPLE 229

2-{[(2-{[3-(diethylamino)propyl]amino}phenyl)sulfonyl]amino}-5,6,7,8-tetrahydro-1-naphthalenecarboxylic acid

EXAMPLE 229A methyl 2-{[(2-fluorophenyl)sulfonyl]amino}-5,6,7,8-tetrahydro-1-naphthalenecarboxylate The desired product was prepared by substituting 2-fluorobenzenesulfonyl chloride for methyl 2-(chlorosulfonyl)benzoate in Example 379A. MS (ESI(+)) m/e 364 $(M+H)^+$; (ESI(−)) m/e 362 $(M-H)^-$; $^1H$ NMR (300 MHz, DMSO-$d_6$) δ 7.64 (m, 2H), 7.38 (dt, 1H), 7.28 (dt, 1H), 7.02 (d, 1H), 6.90 (d, 1H), 3.64 (s, 3H), 2.65 (br s, 2H), 2.51 (br s, 2H), 1.67 (br s, 4H).

EXAMPLE 229B

2-{[(2-{[3-(diethylamino)propyl]amino}phenyl)sulfonyl]amino}-5,6,7,8-tetrahydro-1-naphthalenecarboxylic acid A mixture of Example 229A (143 mg, 0.393 mmol), triethylamine (0.165 mL), acetonitrile (1.2 mL), and N,N-diethyl-1,3-propanediamine (0.37 mL, 2.36 mmol) was sealed and heated in microwave for fifteen hundred seconds at 200° C. The solution was cooled and adjusted to pH 5 with 1N HCl.

The aqueous layer was extracted with ethyl acetate (3×) and the combined organic fractions were washed with brine, dried ($MgSO_4$), filtered, and concentrated. The concentrate was purified by preparative HPLC to provide the desired product. MS (ESI(+)) m/e 460 $(M+H)^+$; (ESI(−)) m/e 458 $(M-H)^-$; $^1H$ NMR (300 MHz, DMSO-$d_6$) δ 13.15 (br s, 1H), 9.54 (s, 1H), 9.02 (br s, 1H), 7.51 (dd, 1H), 7.41 (dt, 1H), 6.96 (2, 1H), 6.86 (d, 1H), 6.64 (m, 2H), 6.00 (t, 1H), 3.29 (q, 2H), 3.09 (m, 7H), 2.65 (br s, 4H), 1.89 (m, 2H), 1.67 (br s, 4H), 1.14 (t, 6H).

EXAMPLE 230

3-ethyl-6-{[(2-fluorophenyl)sulfonyl]amino}-2-methylbenzoic acid

EXAMPLE 230A benzyl 3-bromo-6-{[(2-fluorophenyl)sulfonyl]amino}-2-methylbenzoate The desired product was prepared by substituting 2-fluorobenzenesulfonyl chloride for 4-fluorobenzenesulfonyl chloride in Example 173A (1.1 g, 100%). $^1H$ NMR (DMSO-$d_6$) δ 2.18 (s, 3H), 5.20 (s, 2H), 6.95 (d, 1H), 7.11 (d, 1H), 7.30-7.45 (m, 6H), 7.64-7.71 (m, 3H), 10.36 (s, 1H); MS (ESI(−)) m/e 476, 478 $(M-H)^-$.

EXAMPLE 230B benzyl 6-{[(2-fluorophenyl)sulfonyl]amino}-2-methyl-3-vinylbenzoate Five identical reactions were run on a microwave instrument. For each reaction, Example 230A (0.21 g, 0.44 mmol), di-n-butyl vinylboronate (0.18 g, 1.0 mmol), CsF (0.23 g, 1.5 mmol), and $Pd(PPh_3)_4$ (30 mg, 0.025 mmol) was mixed with DME (3.0 mL) and methanol (1.5 mL) in a thick-wall tube. Each mixture was purged with argon and the tube was sealed and heated to 150° C. for 4 minutes. The combined reaction mixture was washed with brine, filtered, and concentrated. The crude product was purified by flash column chromatography on silica gel eluting with 30% ethyl acetate/hexanes to provide a mixture of the desired product and the corresponding carboxylic acid (0.7 g).

EXAMPLE 230C 3-ethyl-6-{[(2-fluorophenyl)sulfonyl]amino}-2-methylbenzoic acid

A mixture of Example 230B (0.7 g) in methanol (8 mL) and water (1 mL) was hydrogenated over 10% Pd/C (0.15 g) for 6 hours at room temperature to provide the desired product. $^1H$ NMR (DMSO-$d_6$) δ 1.09 (t, 3H), 2.18 (s, 3H), 2.54 (q, 2H), 6.86 (d, 1H), 7.12 (d, 1H), 7.30-7.43 (m, 2H), 7.66-7.71 (m, 2H), 9.75 (s, 1H), 13.18 (br s, 1H); MS (ESI(−)) m/e 336 $(M-H)^-$.

EXAMPLE 231

6-{[(2-{[3-(diethylamino)propyl]amino}phenyl)sulfonyl]amino}-3-ethyl-2-methylbenzoic acid A solution of Example 230C (40 mg, 0.12 mmol), triethylamine (0.1 mL), and N,N-diethyl-1,3-propanediamine (0.1 mL) in acetonitrile (1.0 mL) was heated to 200° C. for 1 hour on a Personal Chemistry microwave instrument. The mixture was then purified by reverse phase HPLC to provide the desired product (5.8 mg, 10.8%). $^1H$ NMR (DMSO-$d_6$) δ 1.07 (t, 3H), 1.12 (t, 6H), 2.19 (s, 3H), 2.53 (q, 2H), 3.05-3.12 (m, 8H), 6.02 (br s, 1H), 6.62-6.66 (m, 2H), 6.84 (d, 1H), 7.03 (d, 1H), 7.40 (t, 1H), 7.52 (d, 1H), 8.98 (br s, 1H), 9.50 (br s, 1H); MS (ESI(+)) m/e 448 $(M+H)^+$.

EXAMPLE 232

6-{[(2-{[4-(N,N-dimethylamino)butyl]amino}phenyl)sulfonyl]amino}-3-ethyl-2-methylbenzoic acid The desired product was prepared by substituting N,N-dimethyl-1,4-butanediamine for N,N-diethyl-1,3-propanediamine in Example 231 (45.2%). $^1H$ NMR (DMSO-$d_6$) δ 1.07 (t, 3H), 1.52-1.58 (m, 2H), 1.64-1.69 (m, 2H), 2.19 (s, 3H), 2.53 (q, 2H), 2.70 (s, 6H), 2.98-3.05 (m, 2H), 3.17 (t, 2H), 5.92 (br s, 1H), 6.60-6.64 (m, 2H), 6.79 (d, 1H), 7.03 (d, 1H), 7.38 (t, 1H), 7.52 (d, 1H), 9.47 (br s, 1H), 9.80 (br s, 1H); MS (ESI(+)) m/e 434 $(M+H)^+$.

EXAMPLE 233

3-[1,2-dihydroxyethyl]-6-{[(4-fluorophenyl)sulfonyl]amino}-2-methylbenzoic acid

A solution of Example 173C (0.21 g, 0.62 mmol) in THF (8 mL) and water (1 mL) was treated with N-methylmorpholine oxide (0.11 g, 0.95 mmol) in one portion and dropwise with OsO4 (2.5% wt solution in tert-butanol, 0.5 mL). The mixture was stirred at room temperature for 4 hours, treated with water (20 mL), followed by 5% aqueous $NaHCO_3$ (10 mL), and extracted with diethyl ether (2×10 mL). The aqueous solution was adjusted to pH 2.0 with 1N HCl and extracted with ethyl acetate (3×10 mL). The combined extracts were dried ($MgSO_4$) filtered, and concentrated to provide the desired product (101 mg, 43.5%). $^1H$ NMR (DMSO-$d_6$) δ 2.22 (s, 3H), 4.73 (m, 2H), 5.18 (m, 1H), 6.79 (d, 1H), 7.34 (d, 1H), 7.40 (m, 2H), 7.80 (m, 2H), 9.80 (br s, 1H), 12.90 (br s, 1H); MS (ESI(−)) m/e 368 $(M-H)^-$.

EXAMPLE 234

6-{[(4-fluorophenyl)sulfonyl]amino}-3-(hydroxymethyl)-2-methylbenzoic acid

EXAMPLE 234A benzyl 6-{[(4-fluorophenyl)sulfonyl]amino}-3-(hydroxymethyl)-2-methylbenzoate A solution of Example 173B (127 mg, 0.3 mmol) in dioxane (6 mL) and water (2 mL) was treated with $OSO_4$ (2.5% wt in t-butanol, 0.5 mL), stirred for 8 minutes at ambient temperature, treated with $NaIO_4$ (128 mg, 0.6 mmol), stirred for 30 minutes, diluted with brine, and extracted with ethyl acetate. The ethyl acetate solution was dried ($MgSO_4$), filtered, and concentrated. This concentrate was dissolved in absolute ethanol (5 mL) and THF (5 mL), treated with $NaBH_4$ (7 mg), stirred for 30 minutes, treated with brine (10 mL), and extracted with ethyl acetate. The ethyl acetate solution was dried ($MgSO_4$), filtered and concentrated. The residue was purified by flash column chromatography with 45% ethyl acetate/hexanes to provide the desired product (71 mg, 56.7%). $^1H$ NMR (DMSO-$d_6$) δ 2.05 (s, 3H), 4.42 (d, 2H), 5.12 (t, 1H), 5.24 (s, 2H), 6.84 (d, 1H), 7.35-7.46 (m, 8H), 7.70-7.75 (m, 2H), 9.81 (s, 1H); MS (ESI(−)) m/e 428 $(M-H)^-$.

EXAMPLE 234B

6-{[(4-fluorophenyl)sulfonyl]amino}-3-(hydroxymethyl)-2-methylbenzoic acid

A mixture of Example 234A (71 mg, 0.17 mmol) in methanol (8 mL) was treated with 10% Pd/C (0.15 g) for 1 hour under a hydrogen atmosphere. Filtration and solvent evaporation gave the desired compound. $^1H$ NMR (DMSO-$d_6$) δ 2.15 (s, 3H), 4.43 (s, 2H), 5.15 (br s, 1H), 6.77 (d, 1H), 7.28 (d, 1H), 7.30-7.41 (m, 2H), 7.75-7.79 (m, 2H), 9.62 (s, 1H), 13.05 (br s, 1H); MS (ESI(−)) m/e 338 $(M-H)^-$.

EXAMPLE 235

6-{[(2-{[2-(diethylamino)ethyl]amino}phenyl)sulfonyl]amino}-3-ethyl-2-methylbenzoic acid The desired product was prepared by substituting N',N'-diethyl-1,2-ethanediamine for N,N-diethyl-1,3-propanediamine in Example 231 (37.7%). $^1H$ NMR (DMSO-$d_6$) δ 1.07 (t, 3H), 1.18 (t, 6H), 2.17 (s, 3H), 2.53 (q, 2H), 3.16-3.25 (m, 8H), 6.02 (br t, 1H), 6.68 (dd, 1H), 6.77 (m, 1H), 6.89 (d, 1H), 7.03 (d, 1H), 7.41 (t, 1H), 7.49 (d, 1H), 9.60 (br s, 1H); MS (ESI(+)) m/e 434 $(M+H)^+$.

EXAMPLE 236

3-ethyl-6-{[(2-{[3-(1H-imidazol-1-yl)propyl]amino}phenyl)sulfonyl]amino}-2-methylbenzoic acid The desired product was prepared by substituting 3-(1H-imidazol-1-yl)-1-propanamine for N,N-diethyl-1,3-propanediamine in Example 231 (33.3% yield). $^1H$ NMR (DMSO-$d_6$) δ 1.06 (t, 3H), 2.07-2.12 (m, 2H), 2.17 (s, 3H), 2.53 (q, 2H), 3.17 (m, 2H), 4.25 (t, 2H), 5.93 (br s, 1H), 6.63-6.67 (m, 2H), 6.78 (d, 1H), 7.03 (d, 1H), 7.40 (dd, 1H), 7.52 (d, 1H), 7.69 (s, 1H), 7.75 (s, 1H), 9.10 (s, 1H), 9.47 (br s, 1H), 14.2 (br s, 1H); MS (ESI(+)) m/e 443 $(M+H)^+$.

EXAMPLE 237

6-[({2-[[3-(dimethylamino)propyl](methyl)amino]phenyl}sulfonyl)amino]-3-ethyl-2-methylbenzoic acid The desired product was prepared by substituting N,N,N'-trimethyl-1,3-propanediamine for N,N-diethyl-1,3-propanediamine in Example 231 (9.8% yield). MS (ESI(+)) m/e 434 $(M+H)^+$.

EXAMPLE 238

3-ethyl-2-methyl-6-({[2-(4-methyl-1-piperazinyl)phenyl]sulfonyl}amino)benzoic acid The desired product was prepared by substituting 1-methylpiperazine for N,N-diethyl-1,3-propanediamine in Example 231 (35.0%). $^1H$ NMR (DMSO-$d_6$) δ 1.08 (t, 3H), 2.17 (s, 3H), 2.53 (q, 2H), 2.83 (s, 3H), 3.01 (m, 4H), 3.47 (m, 4H), 6.85 (d, 1H), 7.10 (d, 1H), 7.31 (t, 1H), 7.48 (d, 1H), 7.65 (t, 1H), 7.78 (d, 1H), 9.05 (br s, 1H), 9.60 (br s, 1H); MS (ESI(+)) m/e 418 $(M+H)^+$.

EXAMPLE 239

2-{[(3,5-dimethyl-4-isoxazolyl)sulfonyl]amino}-5,6,7,8-tetrahydro-1-naphthalenecarboxylic acid The desired product was prepared by substituting 3,5-dimethyl-4-isoxazolylsulfonyl chloride for 4-fluorobenzenesulfonyl chloride in Example 128D. MS (ESI(+)) m/e 368 $(M+NH_4)^+$, 373 $(M+Na)^+$; MS (ESI(−)) m/e 349 $(M-H)^-$; $^1H$ NMR (300 MHz, DMSO-$d_6$) δ 7.07 (d, 1H), 6.88 (d, 1H), 3.00 (m, 2H), 2.61 (m, 2H), 2.51 (s, 3H), 2.21 (s, 3H), 1.60 (m, 4H).

EXAMPLE 240

2-{[(5-chloro-2-thienyl)sulfonyl]amino}-5,6,7,8-tetrahydro-1-naphthalenecarboxylic acid The desired product was prepared by substituting 5-chloro-2-thiophenesulfonyl chloride for 4-fluorobenzenesulfonyl chloride in Example 128D. MS (ESI(+)) m/e 389 $(M+NH_4)^+$, 394 $(M+Na)^+$; MS (ESI(−)) m/e 370 $(M-H)^-$; $^1H$ NMR (300 MHz, DMSO-$d_6$) δ 7.21 (d, 1H), 7.19 (d, 1H), 7.03 (d, 1H), 6.89 (d, 1H), 3.03 (m, 2H), 2.61 (m, 2H), 1.60 (m, 4H).

EXAMPLE 241

2-{[(5-fluoro-2-methylphenyl)sulfonyl]amino}-5,6,7,8-tetrahydro-1-naphthalenecarboxylic acid The desired product was prepared by substituting 5-fluoro-2-methylbenzenesulfonyl chloride for 4-fluorobenzenesulfonyl chloride in Example 128D. MS (ESI(+)) m/e 381 $(M+NH_4)^+$, 386 $(M+Na)^+$; MS (ESI(−)) m/e 362 $(M-H)^-$; $^1H$ NMR (300 MHz, DMSO-$d_6$) δ 7.60 (dd, 1H), 7.29 (dd, 1H), 7.23 (td, 1H), 7.02 (d, 1H), 6.78 (d, 1H) 3.00 (m, 2H), 2.56 (m, 2H), 2.50 (s, 3H), 1.58 (m, 4H).

EXAMPLE 242

2-{[(2-methoxy-5-methylphenyl)sulfonyl]amino}-5,6,7,8-tetrahydro-1-naphthalenecarboxylic acid The desired product was prepared by substituting 2-methoxy-5-methylbenzenesulfonyl chloride for 4-fluorobenzenesulfonyl chloride in Example 128D; MS (ESI(+)) m/e 376 $(M+H)$-393 $(M+NH_4)^+$, 398 $(M+Na)^+$; MS (ESI(−)) m/e 414 $(M-H)^-$; $^1H$ NMR (300 MHz, DMSO-$d_6$) δ 7.55 (d, 1H), 7.28 (dd, 1H), 7.10 (d, 1H), 6.96 (d, 1H), 6.71 (d, 2H), 3.76 (s, 3H), 2.88 (m, 2H), 2.56 (m, 2H), 2.23 (s, 3H), 1.64 (m, 4H).

EXAMPLE 243

2-{[(3-nitrophenyl)sulfonyl]amino}-5,6,7,8-tetrahydro-1-naphthalenecarboxylic acid The desired product was prepared by substituting 3-nitrobenzenesulfonyl chloride for 4-fluorobenzenesulfonyl chloride in Example 128D. MS (ESI(+)) m/e 394 $(M+NH_4)^+$, 399 $(M+Na)^+$; MS (ESI(−)) m/e 375 $(M-H)^-$; $^1H$ NMR (300 MHz, DMSO-$d_6$) δ 8.41 (s, 1H), 8.34 (d, 1H), 8.07 (s, 1H), 7.77 (t, 1H), 7.04 (m, 1H), 6.89 (d, 1H), 2.90 (m, 2H), 2.60 (m, 2H), 1.64 (m, 4H).

EXAMPLE 244

2-{[(2-chloro-6-methylphenyl)sulfonyl]amino}-5,6,7,8-tetrahydro-1-naphthalenecarboxylic acid The desired product was prepared by substituting 2-chloro-6-methylbenzenesulfonyl chloride for 4-fluorobenzenesulfonyl chloride in Example 128D. MS (ESI(+)) m/e 397 $(M+NH_4)^+$, 402 $(M+Na)^+$; MS (ESI(−)) m/e 378 $(M-H)^-$; $^1H$ NMR (300 MHz, DMSO-$d_6$) δ 7.34 (dd, 1H), 7.32 (t, 1H), 7.26 (dd, 1H), 6.89 (d, 1H), 6.75 (d, 1H), 2.99 (m, 2H), 2.68 (s, 3H), 2.55 (m, 2H), 1.58 (m, 4H).

EXAMPLE 245

2-{[(5-chloro-1,3-dimethyl-1H-pyrazol-4-yl)sulfonyl]amino}-5,6,7,8-tetrahydro-1-naphthalenecarboxylic acid The desired product was prepared by substituting 5-chloro-1,3-dimethyl-(4-pyrazolyl)sulfonyl chloride for 4-fluorobenzenesulfonyl chloride in Example 128D. MS (ESI(+)) m/e 401 $(M+H)^+$, 401 $(M+NH_4)^+$, 406 $(M+Na)^+$; MS (ESI(−)) m/e 382 $(M-H)^-$; $^1H$ NMR (300 MHz, DMSO-$d_6$) δ 7.08 (d, 1H), 6.82 (d, 1H), 3.67 (s, 3H), 2.97 (m, 2H), 2.60 (m, 2H), 2.22 (s, 3H), 1.64 (m, 4H).

EXAMPLE 246

2-[(mesitylsulfonyl)amino]-5,6,7,8-tetrahydro-1-naphthalenecarboxylic acid

The desired product was prepared by substituting 2,4,6-trimethylbenzenesulfonyl chloride for 4-fluorobenzenesulfonyl chloride in Example 128D. MS (ESI(+)) m/e 374 $(M+H)^+$, 391 $(M+NH_4)^+$, 396 $(M+Na)^+$; MS (ESI(−)) m/e 372 $(M-H)^-$; $^1H$ NMR (300 MHz, DMSO-$d_6$) δ 6.94 (s, 2H), 6.83 (d, 1H), 6.77 (d, 1H), 2.89 (m, 2H), 2.57 (m, 2H), 2.55 (s, 6H), 2.20 (s, 3H), 1.59 (m, 4H).

EXAMPLE 247

2-{[(4-nitrophenyl)sulfonyl]amino}-5,6,7,8-tetrahydro-1-naphthalenecarboxylic acid The desired product was prepared by substituting 4-nitrobenzenesulfonyl chloride for 4-fluorobenzenesulfonyl chloride in Example 128D. MS (ESI(+)) m/e 394 $(M+NH_4)^+$, 399 $(M+Na)^+$; MS (ESI(−)) m/e 375 $(M-H)^-$; $^1H$ NMR (300 MHz, DMSO-$d_6$) δ 8.27 (d, 2H), 7.92 (d, 2H), 7.11 (d, 1H), 6.84 (d, 1H), 2.97 (m, 2H), 2.58 (m, 2H), 1.58 (m, 4H).

EXAMPLE 248

2-{[(3-chloro-4-methylphenyl)sulfonyl]amino}-5,6,7,8-tetrahydro-1-naphthalenecarboxylic acid The desired product was prepared by substituting 3-chloro-4-methylbenzenesulfonyl chloride for 4-fluorobenzenesulfonyl chloride in Example 128D. MS (ESI(+)) m/e 397 $(M+NH_4)^+$, 402 $(M+Na)^+$; MS (ESI(−)) m/e 378 $(M-H)^-$; $^1H$ NMR (300 MHz, DMSO-$d_6$) δ 7.64 (d, 1H), 7.54 (dd, 1H), 7.44 (d, 1H), 7.09 (d, 1H), 6.84 (d, 1H), 2.95 (m, 2H), 2.59 (m, 2H), 2.32 (s, 3H), 1.59 (m, 4H).

EXAMPLE 249

2-[(2,1,3-benzothiadiazol-4-ylsulfonyl)amino]-5,6,7,8-tetrahydro-1-naphthalenecarboxylic acid The desired product was prepared by substituting 2,1,3-benzothiadiazole-4-sulfonyl chloride for 4-fluorobenzenesulfonyl chloride in Example 128D. MS (ESI(+)) m/e 407 $(M+NH_4)^+$, 412 $(M+Na)^+$; MS (ESI(−)) m/e 388 $(M-H)^-$; $^1H$ NMR (300 MHz, DMSO-$d_6$) δ 8.23 (d, 1H), 8.13 (d, 1H), 7.76 (dd, 1H), 7.12 (d, 1H), 6.76 (d, 1H), 2.91 (m, 2H), 2.54 (m, 2H), 1.55 (m, 4H).

EXAMPLE 250

2-{[(2-methyl-5-nitrophenyl)sulfonyl]amino}-5,6,7,8-tetrahydro-1-naphthalenecarboxylic acid The desired product was prepared by substituting 2-methyl-5-nitrobenzenesulfonyl chloride for 4-fluorobenzenesulfonyl chloride in Example 128D. MS (ESI(+)) m/e 408 $(M+NH_4)^+$, 413 $(M+Na)^+$; MS (ESI(−)) m/e 389 $(M-H)^-$; $^1H$ NMR (300 MHz, DMSO-$d_6$) δ 8.62 (d, 1H), 8.20 (dd, 1H), 7.55 (d, 1H), 7.00 (d, 1H), 6.79 (d, 1H), 3.01 (m, 2H), 2.66 (s, 3H), 2.54 (m, 2H), 1.57 (m, 4H).

EXAMPLE 251

2-({[5-(3-isoxazolyl)-2-thieinyl]sulfonyl}amino)-5,6,7,8-tetrahydro-1-naphthalenecarboxylic acid The desired product was prepared by substituting 5-(3-isoxazolyl)-2-thiophenesulfonyl chloride for 4-fluorobenzenesulfonyl chloride in Example 128D. MS (ESI(+)) m/e 422 $(M+NH_4)^+$, 427 $(M+Na)^+$; MS (ESI(−)) m/e 403 $(M-H)^-$; $^1H$ NMR (300 MHz, DMSO-$d_6$) δ 8.64 (d, 1H), 7.55 (d, 1H), 7.39 (d, 1H), 7.22 (d, 1H), 6.95 (d, 1H), 6.91 (d, 1H), 3.00 (m, 2H), 2.61 (m, 2H), 1.60 (m, 4H).

EXAMPLE 252

2-{[(2,5-dichloro-3-thienyl)sulfonyl]amino}-5,6,7,8-tetrahydro-1-naphthalenecarboxylic acid The desired product was prepared by substituting 2,5-dichloro-3-thiophenesulfonyl chloride for 4-fluorobenzenesulfonyl chloride in Example 128D. MS (ESI(+)) m/e 423 $(M+NH_4)^+$, 428 $(M+Na)^+$; MS (ESI(−)) m/e 403 $(M-H)^-$; $^1H$ NMR (300 MHz, DMSO-$d_6$) δ 7.16 (s, 1H), 7.10 (d, 1H), 6.88 (d, 1H), 3.03 (m, 2H), 2.61 (m, 2H), 1.61 (m, 4H).

EXAMPLE 253

2-{[(4,5-dichloro-2-thienyl)sulfonyl]amino}-5,6,7,8-tetrahydro-1-naphthalenecarboxylic acid The desired product was prepared by substituting 4,5-dichloro-2-thienylsulfonyl chloride for 4-fluorobenzenesulfonyl chloride in Example 128D. MS (ESI(+)) m/e 423 $(M+NH_4)^+$, 428 $(M+Na)^+$; MS (ESI(−)) m/e 403 $(M-H)^-$; $^1H$ NMR (300 MHz, DMSO-$d_6$) δ 7.39 (s, 1H), 7.09 (d, 1H), 6.99 (d, 1H), 2.89 (m, 2H), 2.65 (m, 2H), 1.64 (m, 4H).

EXAMPLE 254

2-{[(7-chloro-2,1,3-benzoxadiazol-4-yl)sulfonyl]amino}-5,6,7,8-tetrahydro-1-naphthalenecarboxylic acid The desired product was prepared by substituting 7-chloro-2,1,3-benzoxadiazole-4-sulfonyl chloride for 4-fluorobenzenesulfonyl chloride in Example 128D. MS (ESI(+)) m/e 425 $(M+NH_4)^+$, 430 $(M+Na)^+$; MS (ESI(−)) m/e 406 $(M-H)^-$; $^1H$ NMR (300 MHz, DMSO-$d_6$) δ 7.88 (d, 1H), 7.79 (d, 1H), 7.14 (d, 1H), 6.83 (d, 1H), 2.98 (m, 2H), 2.56 (m, 2H), 1.57 (m, 4H).

EXAMPLE 255

2-{[(4-chloro-3-nitrophenyl)sulfonyl]amino}-5,6,7,8-tetrahydro-1-naphthalenecarboxylic acid The desired product was prepared by substituting 4-chloro-3-nitrobenzenesulfonyl chloride for 4-fluorobenzenesulfonyl chloride in Example 128D. MS (ESI(+)) m/e 433 $(M+Na)^+$; MS (ESI(−)) m/e 409 $(M-H)^-$; $^1H$ NMR (300 MHz, DMSO- $d_6$) δ 8.28 (d, 1H), 7.91 (dd, 1H), 7.87 (d, 1H), 7.03 (d, 1H), 6.90 (d, 1H), 2.91 (m, 2H), 2.61 (m, 2H), 1.6 (m, 4H).

EXAMPLE 256

2-({[2-(trifluoromethoxy)phenyl]sulfonyl}amino)-5,6,7,8-tetrahydro-1-naphthalenecarboxylic acid The desired product was prepared by substituting 2-(trifluoromethoxy)benzenesulfonyl chloride for 4-fluorobenzenesulfonyl chloride in Example 128D. MS (ESI(+)) m/e 433 $(M+NH_4)^+$, 438 $(M+Na)^+$; MS (ESI(−)) m/e 414 $(M-H)^-$; $^1H$ NMR (300 MHz, DMSO-$d_6$) δ 7.90 (dd, 1H), 7.61 (m, 1H), 7.42 (m, 2H), 7.01 (d, 1H), 6.80 (d, 1H), 2.99 (m, 2H), 2.57 (m, 2H), 1.59 (m, 4H).

EXAMPLE 257

2-{[(5-chloro-4-nitro-2-thienyl)sulfonyl]amino}-5,6,7,8-tetrahydro-1-naphthalenecarboxylic acid The desired product was prepared by substituting 5-chloro-4-nitro-2-thiophenesulfonyl chloride for 4-fluorobenzenesulfonyl chloride in Example 128D. MS (ESI(−)) m/e 415 $(M-H)^-$; $^1H$ NMR (300 MHz, DMSO-$d_6$) δ 7.64 (s, 1H), 7.22 (d, 1H), 6.93 (d, 1H), 2.98 (m, 2H), 2.61 (m, 2H), 1.61 (m, 4H).

EXAMPLE 258

2-{[(2,4-dinitrophenyl)sulfonyl]amino}-5,6,7,8-tetrahydro-1-naphthalenecarboxylic acid The desired product was prepared by substituting 2,4-dinitrobenzenesulfonyl chloride for 4-fluorobenzenesulfonyl chloride in Example 128D. MS (ESI(+)) m/e 439 $(M+NH_4)^+$, 444 $(M+Na)^+$; MS (ESI(−)) m/e 420 $(M-H)^-$; $^1H$ NMR (300 MHz, DMSO-$d_6$) δ 8.75 (d, 1H), 8.50 (dd, 1H), 8.10 (d, 1H), 6.95 (m, 2H), 2.82 (m, 2H), 2.64 (m, 2H), 1.64 (m, 4H).

EXAMPLE 259

2-({[5-(dimethylamino)-1-naphthyl]sulfonyl}amino)-5,6,7,8-tetrahydro-1-naphthalenecarboxylic acid The desired product was prepared by substituting 5-(N,N-dimethylamino)-1-naphthalenesulfonyl chloride for 4-fluorobenzenesulfonyl chloride in Example 128D. MS (ESI(+)) m/e 425 $(M+H)^+$, 447 $(M+Na)^+$; MS (ESI(−)) m/e 423 $(M-H)^-$; $^1H$ NMR (300 MHz, DMSO-$d_6$) δ 8.40 (d, 1H), 8.34 (d, 1H), 8.16 (d, 1H), 7.54 (dd, 1H), 7.49 (dd, 1H), 7.18 (d, 1H), 7.03 (d, 1H), 6.72 (d, 1H), 2.97 (m, 2H), 2.78 (s, 6H), 2.49 (m, 2H), 1.54 (m, 4H).

EXAMPLE 260

2-({[4-chloro-3-(trifluoromethyl)phenyl]sulfonyl}amino)-5,6,7,8-tetrahydro-1-naphthalenecarboxylic acid The desired product was prepared by substituting 4-chloro-3-(trifluoromethyl)benzenesulfonyl chloride for 4-fluorobenzenesulfonyl chloride in Example 128D. MS (ESI(+)) m/e 451 $(M+NH_4)^+$, 456 $(M+Na)^+$; MS (ESI(−)) m/e 432 $(M-H)^-$; $^1H$ NMR (300 MHz, DMSO-$d_6$) δ 8.00 (d, 1H), 7.93 (dd, 1H), 7.85 (d, 1H), 7.04 (d, 1H), 6.90 (d, 1H), 2.91 (m, 2H), 2.61 (m, 2H), 1.61 (m, 4H).

EXAMPLE 261

2-{[(2,4,5-trichlorophenyl)sulfonyl]amino}-5,6,7,8-tetrahydro-1-naphthalenecarboxylic acid The desired product was prepared by substituting 2,4,5-trichlorobenzenesulfonyl chloride for 4-fluorobenzenesulfonyl chloride in Example 128D. MS (ESI(+)) m/e 433 $(M+H)^+$, 451 $(M+NH_4)^+$, 456 $(M+Na)^+$; MS (ESI(−)) m/e 432 $(M-H)^-$; $^1H$ NMR (300 MHz, DMSO-$d_6$) δ 8.12 (s, 1H), 7.87 (s, 1H), 7.00 (d, 1H), 6.83 (d, 1H), 3.03 (m, 2H), 2.57 (m, 2H), 1.59 (m, 4H).

EXAMPLE 262

2-{[(2,3,4-trichlorophenyl)sulfonyl]amino}-5,6,7,8-tetrahydro-1-naphthalenecarboxylic acid The desired product was prepared by substituting 2,3,4-trichlorobenzenesulfonyl chloride for 4-fluorobenzenesulfonyl chloride in Example 128D. MS (ESI(+)) m/e 451 $(M+NH_4)^+$, 456 $(M+Na)^+$; MS (ESI(−)) m/e 432 $(M-H)^-$; $^1H$ NMR (300 MHz, DMSO-$d_6$) δ 8.01 (d, 1H), 7.74 (d, 1H), 6.99 (d, 1H), 6.79 (d, 1H), 3.03 (m, 2H), 2.56 (m, 2H), 1.59 (m, 4H).

EXAMPLE 263

2-{[(5-chloro-3-methyl-1-benzothien-2-yl)sulfonyl]amino}-5,6,7,8-tetrahydro-1-naphthalenecarboxylic acid The desired product was prepared by substituting 5-chloro-5-methyl-1-benzothiophene-2-sulfonyl chloride for 4-fluorobenzenesulfonyl chloride in Example 128D. MS (ESI(+)) m/e 453 $(M+NH_4)^+$, 458 $(M+Na)^+$; MS (ESI(−)) m/e 434 $(M-H)^-$; $^1H$ NMR (300 MHz, DMSO-$d_6$) δ 7.96 (d, 1H), 7.88 (d, 1H), 7.45 (dd, 1H), 7.22 (d, 1H), 6.81 (d, 1H), 3.00 (m, 2H), 2.55 (m, 2H), 2.49 (s, 3H), 1.57 (m, 4H).

EXAMPLE 264

2-{[(5-bromo-2-methoxyphenyl)sulfonyl]amino}-5,6,7,8-tetrahydro-1-naphthalenecarboxylic acid The desired product was prepared by substituting 5-bromo-2-methoxybenzenesulfonyl chloride for 4-fluorobenzenesulfonyl chloride in Example 128D. MS (ESI(+)) m/e 457 $(M+NH_4)^+$, 462 $(M+Na)^+$; MS (ESI(−)) m/e 438 $(M-H)^-$; $^1H$ NMR (300 MHz, DMSO-$d_6$) δ 7.78 (d, 1H), 7.64 (dd, 1H), 7.10 (d, 1H), 7.05 (d, 1H), 6.77 (d, 1H), 3.17 (s, 3H), 2.92 (m, 2H), 2.57 (m, 2H), 1.58 (m, 4H).

EXAMPLE 265

2-({[3,5-bis(trifluoromethyl)phenyl]sulfonyl}amino)-5,6,7,8-tetrahydro-1-naphthalenecarboxylic acid The desired product was prepared by substituting 3,5-bis(trifluoromethyl)benzenesulfonyl chloride for 4-fluorobenzenesulfonyl chloride in Example 128D MS (ESI(+)) m/e 485 $(M+NH_4)^+$, 490 $(M+Na)^+$; MS (ESI(−)) m/e 466 $(M-H)^-$; $^1H$ NMR (300 MHz, DMSO-$d_6$) δ 8.31 (s, 1H), 8.16 (s, 2H), 7.03 (d, 1H), 6.93 (d, 1H), 2.86 (m, 2H), 2.61 (m, 2H), 1.61 (m, 4H).

EXAMPLE 266

2-({[2-butoxy-5-(1,1-dimethylpropyl)phenyl]sulfonyl}amino)-5,6,7,8-tetrahydro-1-naphthalenecarboxylic acid The desired product was prepared by substituting 2-butoxy-5-(1,1-dimethylpropyl)benzenesulfonyl chloride for 4-fluorobenzenesulfonyl chloride in Example 128D. MS (ESI(+)) m/e 474 $(M+H)^+$, 491 $(M+NH_4)^+$, 496 $(M+Na)^+$; MS (ESI(−)) m/e 472 $(M-H)^-$; $^1H$ NMR (300 MHz, DMSO-$d_6$) δ 7.67 (d, 1H), 7.43 (dd, 1H), 7.02 (d, 1H), 6.99 (d, 1H), 6.74 (d, 1H), 4.01 (t, 2H), 2.84 (m, 2H), 2.55 (m, 2H), 1.76 (m, 2H), 1.59 (m, 4H), 1.53 (m, 2H), 1.43 (m, 2H), 1.19 (s, 6H), 0.91 (t, 3H), 0.53 (t, 3H).

EXAMPLE 267

2-({[5-(phenylsulfonyl)-2-thienyl]sulfonyl}amino)-5,6,7,8-tetrahydro-1-naphthalenecarboxylic acid The desired product was prepared by substituting 5-phenylsulfonyl)-2-thiophenesulfonyl chloride for 4-fluorobenzenesulfonyl chloride in Example 128D. MS (ESI(+)) m/e 495 $(M+NH_4)^+$, 500 $(M+Na)^+$; MS (ESI(−)) m/e 476 $(M-H)^-$; $^1H$ NMR (300 MHz, DMSO-$d_6$) δ 7.96 (d, 2H), 7.73 (t, 1H), 7.68 (d, 1H), 7.64 (m, 2H), 7.32 (d, 1H), 7.19 (d, 1H), 6.88 (d, 1H), 2.99 (m, 2H), 2.60 (m, 2H), 1.60 (m, 4H).

EXAMPLE 268

2-{[(5-{[(4-chlorobenzoyl)amino]methyl}-2-thienyl)sulfonyl]amino}-5,6,7,8-tetrahydro-1-naphthalenecarboxylic acid The desired product was prepared by substituting 5-{[(4-chlorobenzoyl)amino]methyl}-2-thiophenesulfonyl chloride for 4-fluorobenzenesulfonyl chloride in Example 128D. MS (ESI(+)) m/e 505 $(M+H)^+$, 522 $(M+NH_4)^+$, 527 $(M+Na)^+$, MS (ESI(−)) m/e 503 $(M-H)^-$; $^1H$ NMR (300 MHz, DMSO-$d_6$) δ 9.26 (t, 1H), 7.87 (d, 2H), 7.54 (d, 2H), 7.26 (d, 1H), 7.11 (d, 1H), 6.93 (d, 1H), 6.88 (d, 1H), 4.57 (d, 2H), 2.94 (m, 2H), 2.61 (m, 2H), 1.60 (m, 4H).

EXAMPLE 269

2-{[(5-bromo-6-chloro-3-pyridinyl)sulfonyl]amino}-5,6,7,8-tetrahydro-1-naphthalenecarboxylic acid The desired product was prepared by substituting 5-bromo-6-chloro-3-pyridinesulfonyl chloride for 4-fluorobenzenesulfonyl chloride in Example 128D. MS (ESI(+)) m/e 467 $(M+NH_4)^+$; MS (ESI(−)) m/e 443 $(M-H)^-$; $^1H$ NMR (300 MHz, DMSO-$d_6$) δ 8.59 (s, 1H), 8.28 (s, 1H), 7.44 (d, 1H), 6.89 (d, 1H), 2.98 (m, 2H), 2.60 (m, 2H), 1.60 (m, 4H).

EXAMPLE 270

2-{[(2-nitrophenyl)sulfonyl]amino}-5,6,7,8-tetrahydro-1-naphthalenecarboxylic acid The desired product was prepared by substituting 2-nitrobenzenesulfonyl chloride for 4-fluorobenzenesulfonyl chloride in Example 128D. MS (ESI(+)) m/e 467 $(M+NH_4)^+$; MS (ESI(−)) m/e 443 $(M-H)^-$; $^1H$ NMR (300 MHz, DMSO-$d_6$) δ 8.59 (s, 1H), 8.28 (s, 1H), 7.44 (d, 1H), 6.89 (d, 1H), 2.98 (m, 2H), 2.60 (m, 2H), 1.60 (m, 4H).

EXAMPLE 271

2-[({5-[(benzoylamino)methyl]-2-thienyl}sulfonyl)amino]-5,6,7,8-tetrahydro-1-naphthalenecarboxylic acid The desired product was prepared by substituting 5-[(benzoylamino)methyl]-2-thiophenesulfonyl chloride for 4-fluorobenzenesulfonyl chloride in Example 128D. MS (ESI(+)) m/e 471 $(M+H)^+$, 488 $(M+NH_4)^+$, 493 $(M+Na)^+$; MS (ESI (−)) m/e 469 $(M-H)^-$; $^1H$ NMR (300 MHz, DMSO-$d_6$) δ 9.16 (t, 1H), 7.85 (d, 2H), 7.54 (t, 1H), 7.46 (t, 2H), 7.25 (d, 1H), 7.15 (d, 1H), 6.91 (d, 1H), 6.86 (d, 1H), 4.56 (d, 2H), 2.97 (m, 2H), 2.60 (m, 2H), 1.60 (m, 4H).

EXAMPLE 272

6-{[(4-fluorophenyl)sulfonyl]amino}-3-[1-hydroxyethyl]-2-methylbenzoic acid

EXAMPLE 272A benzyl 6-{[(4-fluorophenyl)sulfonyl]amino}-3-(1-hydroxyethyl)-2-methylbenzoate A solution of Example 173B (150 mg, 0.35 mmol) in dioxane (6 mL) and water (2 mL) was added $OSO_4$ (2.5% wt in t-butanol, 0.5 mL) was stirred for 8 minutes at ambient temperature, treated with $NaIO_4$ (128 mg, 0.6 mmol), stirred for 30 minutes, treated with brine, and extracted with ethyl acetate. The extract was dried ($MgSO_4$), filtered, and concentrated. The concentrate was dissolved in anhydrous THF (6 mL), cooled to 0° C., treated dropwise with methyl magnesium bromide (3.0M in diethyl ether, 0.37 mL), treated with water (20 mL) and 1N HCl (1.0 mL), and extracted with ethyl acetate (2×20 mL). The ethyl acetate solution was dried ($MgSO_4$), filtered and concentrated. The residue was purified by flash column chromatography on silica gel with 40% ethyl acetate/hexanes to provide the desired product.

EXAMPLE 272

6-{[(4-fluorophenyl)sulfonyl]amino}-3-[1-hydroxyethyl]-2-methylbenzoic acid

A mixture of Example 272A (79 mg, 0.22 mmol) in methanol (8 mL) and water (1.0 mL) was treated with 10% Pd/C (160 mg) and stirred under hydrogen for 16 hours. Filtration and solvent evaporation gave the desired compound (51 mg). $^1H$ NMR (DMSO-$d_6$) δ 1.23 (s, 3H), 2.21 (s, 3H), 4.87 (m, 1H), 5.06 (br s, 1H), 6.82 (d, 1H), 7.36-7.41 (m, 3H), 7.78-7.82 (m, 2H), 10.4 (s, 1H), 13.2 (br s, 1H); MS (ESI(−)) m/e 352 $(M-H)^-$.

EXAMPLE 275

2-{[(2-{[2-(dimethylamino)ethyl]amino}phenyl)sulfonyl]amino}-8-methyl-5,6-dihydro-1-naphthalenecarboxylic acid

EXAMPLE 275A 7-amino-3,4-dihydro-1(2H)-naphthalenone

A solution of 7-nitro-3,4-dihydro-1(2H)-naphthalenone (10.0 g, 52.3 mmol) in ethanol/water (4:1 mixture, 200 mL) was treated with iron (10.3 g), and ammonium chloride (1.1 g), stirred at 85° C. for 4 hours, and filtered. The filtrate was concentrated and the concentrate was dissolved in 400 mL of ethyl acetate, washed with brine (5×), dried ($Na_2SO_4$), filtered, and concentrated. The concentrate was treated with diethyl ether and filtered. The filter cake was washed with diethyl ether and dried under vacuum to provide 7.56 g of the desired product. The filtrate was concentrated to provide 0.39 g of additional product. MS (DCI) m/e 162 $(M+H)^+$, 179 $(M+NH_4)^+$.

EXAMPLE 275B 7-amino-8-bromo-3,4-dihydro-1(2H)-naphthalenone

A solution of Example 275A (7.95 g, 49.32 mmol) in 90 mL of chloroform and 9 mL of N,N-dimethylformamide at 0° C. was treated with bromine (2.52 mL, 49.32 mmol) over 5 minutes, stirred at 0° C. for an additional 30 minutes, and filtered. The filter cake was washed well with chloroform and dried to provide 8.61 g of the desired product as the hydrobromide salt. An additional 0.88 g of the desired hydrobromide salt was isolated after the chloroform layer was basified with 10% sodium hydrogen carbonate, followed by silica gel chromatography purification. MS (DCI) m/e 241 $(M+H)^+$.

EXAMPLE 275C

N-(1-bromo-8-oxo-5,6,7,8-tetrahydro-2-naphthalenyl)-2-fluorobenzenesulfonamide

A suspension of Example 275B (8.59 g, 26.76 mmol) in 60 mL of dichloromethane was treated with pyridine (21.64 mL, 0.2676 mol) and 2-fluorobenzenesulfonyl chloride (90 mL, 29.44 mmol), stirred at room temperature for 1 day, and concentrated. The residue was dissolved in 250 mL of ethyl acetate, washed with 10% potassium hydrogen sulfate (5×) and brine (3×), dried ($MgSO_4$), filtered, and concentrated. The residue was treated with diethyl ether and the resulting precipitate was collected by filtration, washed with diethyl ether, and dried to provide 8.36 g of the desired product. An additional 720 mg of the compound was isolated from the above ethereal solution. MS (ESI(+)) m/e 416 $(M+NH_4)^+$; MS (ESI(−)) m/e 387 $(M-H)^-$; $^1$H NMR (300 MHz, DMSO-$d_6$) δ 10.23 (s, 1H), (dd, 1H), 7.64-7.74 (m, 2H), 7.30-7.46 (m, 4H), 2.92 (t, 2H), 2.60 (t, 2H), 1.96 (m, 2H).

EXAMPLE 275D

N-(1-bromo-8-methyl-5,6-dihydro-2-naphthalenyl)-2-fluorobenzenesulfonamide

A solution of Example 275C (3.40 g, 8.56 mmol) in 100 mL THF/diethyl ether (1:1) was treated dropwise with 3M methylmagnesium bromide in diethyl ether (8.56 mL, 25.68 mmol), heated to 70° C. for 4 hours, treated with saturated ammonium chloride, and partitioned between. 150 mL of ethyl acetate and 50 mL of brine. The ethyl acetate layer was washed with brine (4×), dried ($MgSO_4$), filtered, and concentrated. The concentrate (3.31 g, 8 mmol) was gently refluxed in 50 mL of toluene in the presence of p-toluenesulfonic acid monohydrate (1.52 g, 8 mmol) for 1 hour at 110° C., treated with 100 mL of ethyl acetate, washed with brine (4×), dried ($MgSO_4$), filtered, and concentrated. The concentrate was purified by silica gel column chromatography eluting with 10% ethyl acetate in n-hexane to provide the desired product (1.84 g). MS (ESI(+)) m/e 415 $(M+NH_4)^+$; MS (ESI(−)) m/e 394 $(M-H)^-$; $^1$H NMR (300 MHz, DMSO-$d_6$) δ 10.08 (s, 1H), 7.63-7.74 (m, 2H), 7.40-7.42 (m, 1H), 7.29-7.35 (dt, 1H), 7.15 (d, 1H), 6.97 (d, 1H), 3.29 (m, 1H), 2.55-2.61 (m, 2H), 2.19 (s, 3H), 1.97-2.00 (m, 2H).

EXAMPLE 275E methyl 2-{[(2-fluorophenyl)sulfonyl]amino}-8-methyl-5,6-dihydro-1-naphthalenecarboxylate A solution of Example 275D (2.85 g) in 100 mL of methanol was treated with lithium carbonate (1.6 g) and $PdCl_2$(dppf).$CH_2Cl_2$ (588 mg), heated to 120° C. under 500 psi carbon monoxide pressure for 16 hours, and concentrated. The residue was purified by silica gel column chromatography eluting with 10% ethyl acetate in n-hexane to yield 2.50 g of the desired product. MS (ESI(+)) m/e 393 $(M+NH_4)^+$; MS (ESI(−)) m/e 374 $(M-H)^-$; $^1$H NMR (300 MHz, DMSO-$d_6$) δ 9.89 (s, 1H), 7.65-7.73 (m, 2H), 7.45 (t, 1H), 7.33 (t, 1H), 7.22 (d, 1H), 6.92 (d, 1H), 6.04 (br s, 1H), 3.62 (s, 3H), 2.58-2.61 (m, 2H), 2.06 (br. 2H), 1.81 (s, 3H).

EXAMPLE 275F methyl 2-{[(2-fluorophenyl)sulfonyl]amino}-8-methyl-5,6,7,8-tetrahydro-1-naphthalenecarboxylate A solution of Example 275E (1.58 g) in 100 mL of ethyl acetate was hydrogenated under 60 psi pressure for 16 hours in the presence of 475 mg of 10% palladium on charcoal. The mixture was filtered, concentrated, treated with diethyl ether, and filtered. The filter cake was washed with diethyl ether to provide 1.5 g of the desired product as a mixture of R and S isomers. MS (ESI(+)) m/e 395 $(M+NH_4)^+$; MS (ESI(−)) m/e 376 $(M-H)^-$; $^1$H NMR (300 MHz, DMSO-$d_6$) δ 9.91 (s, 1H), 7.61-7.71 (m, 2H), 7.40-7.46 (m, 1H), 7.31 (dt, 1H), 7.08 (d, 1H), 6.87 (d, 1H), 3.65 (s, 3H), 3.05-3.08 (m, 1H), 2.64-2.78 (m, 2H), 1.58-1.79 (m, 4H), 1.02 (d, 3H).

EXAMPLE 275G

2-{[(2-{[2-(dimethylamino)ethyl]amino}phenyl)sulfonyl]amino}-8-methyl-5,6-dihydro-1-naphthalenecarboxylic acid A mixture of Example 275E (50 mg, 0.133 mmol), N,N-dimethylethylenediamine (117 μl, 1.06 mmol), and triethylamine (56 mL, 0.4 μmol) in 0.5 mL of acetonitrile was heated to 200° C. for 1200 seconds in a microwave oven. The obtained reaction mixture containing a crude product was purified by reverse phase column chromatography to provide 59 mg of the desired product. MS (ESI(+)) m/e 430 $(M+H)^+$; MS (ESI(−)) m/e 428 $(M-H)^-$; $^1$H NMR (300 MHz, DMSO-$d_6$) δ 7.48 (dd, 1H), 7.42 (d, 1H), 7.06 (d, 1H), 6.93 (d, 1H), 6.66-6.76 (m, 2H), 6.10 (t, 1H), 5.99 (t, 1H), 5.75 (s, 3H), 3.59-3.64 (m, 2H), 3.25-3.30 (m, 2H), 2.85 (m, 6H), 2.54-2.56 (m, 2H), 1.96-2.09 (m, 5H).

EXAMPLE 276

8-methyl-2-{[(2-{[2-(1-pyrrolidinyl)ethyl]amino}phenyl)sulfonyl]amino}-5,6-dihydro-1-naphthalenecarboxylic acid The desired product was prepared by substituting 1-(2-aminoethyl)pyrrolidine (135 μL, 1.06 mmol) for N,N-dimethlethylenediamine in Example 275G. MS (ESI(+)) m/e 456 $(M+H)^+$; MS (ESI(−)) m/e 454 $(M-H)^-$; $^1$H NMR (300 MHz, DMSO-$d_6$) δ 9.64 (s, 1H), 6.59-7.62 (br m, 6H), 6.10 (br s, 1H), 5.77-5.87 (m, 1H), 3.61 (br. 4H), 2.93-3.14 (m, 2H), 1.74-2.16 (br m., 8H).

EXAMPLE 277

8-methyl-2-{[(2-{[3-(4-methyl-1-piperazinyl)propyl]amino}phenyl)sulfonyl]amino}-5,6-dihydro-1-naphthalenecarboxylic acid The desired product was prepared by substituting 3-(4-methyl-1-piperazinyl)propylamine (125 μL, 0.8 mmol) for N,N-dimethylethylenediamine in Example 275G. MS (ESI(+)) m/e 499 $(M+H)^+$; MS (ESI(−)) m/e 497 $(M-H)^-$.

EXAMPLE 278

2-{[(2-{[3-(dimethylamino)propyl]amino}phenyl)sulfonyl]amino}-8-methyl-5,6-dihydro-1-naphthalenecarboxylic acid The desired product was prepared by substituting 3-N,N-dimethylaminopropylamine (134 μL, 1.06 mmol) for N,N-dimethylethylenediamine in Example 275G. MS (ESI(+)) m/e 444 $(M+H)^+$; MS (ESI(−)) m/e 442 $(M-H)^-$; $^1H$ NMR (300 MHz, DMSO-$d_6$) δ 9.47 (br s, 2H), 7.56 (dd, 1H), 7.43 (t, 1H), 7.06 (d, 1H), 6.85 (d, 1H), 6.58-6.72 (m, 2H), 6.03 (br., 1H), 5.75 (s, 1H), 3.20-3.29 (m, 3H), 3.07-3.16 (m, 2H), 2.68-2.82 (m, 8H), 2.54-2.60 (m, 2H), 1.97-2.11 (m, 4H), 1.83-1.95 (m, 2H).

EXAMPLE 279

2-{[(2-{[3-(diethylamino)propyl]amino}phenyl)sulfonyl]amino}-8-methyl-5,6-dihydro-1-naphthalenecarboxylic acid The desired product was prepared by substituting 3-N,N-diethylaminopropylamine (168 μL, 1.06 mmol) for N,N-dimethylethylenediamine in Example 275G. MS (ESI(+)) m/e 472 $(M+H)^+$, 494 $(M+Na)^+$; MS (ESI(−)) m/e 470 $(M-H)^-$; $^1H$ NMR (300 MHz, DMSO-$d_6$) δ 9.46 (br s, 1H), 9.10 (br s, 1H), 7.56 (dd, 1H), 7.42 (t, 1H), 7.05 (d, 1H), 6.87 (d, 1H), 6.58-6.72 (m, 2H), 5.98-6.12 (br m, 2H), 5.75 (s, 1H), 3.38-3.56 (m, 2H), 3.30 (m, 3H), 3.00-3.16 (m, 6H), 2.56 (m, 1H), 1.95-2.10 (m, 5H), 1.85-1.93 (m, 2H), 1.13 (t, 6H).

EXAMPLE 280

2-{[(2-{[2-(diethylamino)ethyl]amino}phenyl)sulfonyl]amino}-8-methyl-5,6-dihydro-1-naphthalenecarboxylic acid The desired product was prepared by substituting N,N-diethylaminoethyleneamine (150 μL, 1.06 mmol) for N,N-dimethylethylenediamine in Example 275G. MS (ESI(+)) m/e 458 $(M+H)^+$, 472 $(M+Na)^+$; MS (ESI(−)) m/e 456 $(M-H)^-$; $^1H$ NMR (300 MHz, DMSO-$d_6$) δ 9.73 (br s, 1H), 9.50 (br. 1H), 7.39-7.49 (m, 2H), 7.04 (d, 1H), 6.83-6.91 (m, 2H), 6.67 (t, 1H), 6.08 (t, 1H), 5.98 (s, 1H), 5.75 (s, 1H), 3.52-3.71 (m, 3H), 3.09-3.33 (m, 6H), 1.87-2.09 (m, 5H), 1.09-1.30 (m, 6H).

EXAMPLE 281

8-methyl-2-{[(2-{[2-(4-morpholinyl)ethyl]amino}phenyl)sulfonyl]amino}-5,6-dihydro-1-naphthalenecarboxylic acid The desired product was prepared by substituting N-2-aminoethylmorpholine (105 μL, 0.8 mmol) for N,N-dimethylethylenediamine in Example 275G. MS (ESI(+)) m/e 472 $(M+H)^+$; MS (ESI(−)) m/e 470 $(M-H)^-$; $^1H$ NMR (300 MHz, DMSO-$d_6$) δ 10.14 (br s, 1H), 9.44 (br. 1H), 7.29-7.36 (m, 2H), 7.02 (d, 1H), 6.82-6.87 (m, 2H), 6.56 (t, 1H), 6.15 (t, 1H), 5.86 (s, 1H), 5.75 (s, 1H), 3.82-3.97 (m, 4H), 3.59-3.68 (m, 4H), 2.73-2.56 (m, 2H), 2.18-2.04 (m, 2H), 1.81-2.02 (m, 5H).

EXAMPLE 282

8-methyl-2-({[2-({3-[3-(methylamino)phenyl]propyl}amino)phenyl]sulfonyl}amino)-5,6-dihydro-1-naphthalenecarboxylic acid The desired product was prepared by substituting N-(3-aminopropyl)-N-methylaniline (131 μL, 0.8 mmol) for N,N-dimethylethylenediamine in Example 275G. MS (ESI(+)) m/e 506 $(M+H)^+$; MS (ESI(−)) m/e 504 $(M-H)^-$; $^1H$ NMR (300 MHz, DMSO-$d_6$) δ 9.41 (s, 1H), 7.53 (d, 1H), 7.39 (t, 1H), 7.15 (t, 1H), 7.02 (d, 1H), 6.74-6.80 (m, 3H), 6.61-6.66 (m, 2H), 6.54 (d, 1H), 6.02 (br s. 1H), 5.75 (s, 2H), 3.39 (t, 2H), 3.20 (t, 2H), 2.87 (s, 3H), 2.55-2.65 (m, 2H), 1.96-2.06 (m, 4H), 1.77 (m, 2H).

EXAMPLE 283

2-({[2-(4-benzyl-1-piperazinyl)phenyl]sulfonyl}amino)-8-methyl-5,6-dihydro-1-naphthalenecarboxylic acid The desired product was prepared by substituting 1-benzylpiperazine (139 μL, 0.8 mmol) for N,N-dimethylethylenediamine in Example 275G. MS (ESI(+)) m/e 518 $(M+H)^+$, 540 $(M+NH_4)^+$; MS (ESI(−)) m/e 516 $(M-H)^-$; $^1H$ NMR (300 MHz, DMSO-$d_6$) δ 8.94 (s, 1H), 7.83 (d, 1H), 7.67 (d, 1H), 7.24-7.58 (m, 6H), 7.34 (t, 1H), 7.13 (d, 1H), 6.86 (d, 1H), 6.04 (br t, 1H), 5.75 (s, 2H), 4.32 (br. 2H), 3.00-3.45 (m, 6H), 2.55-2.57 (m, 2H), 1.92-2.08 (m, 5H).

EXAMPLE 285

2-{[(2-{[4-(N,N-dimethylamino)butyl]amino}phenyl)sulfonyl]amino}-8-methyl-5,6-dihydro-1-naphthalenecarboxylic acid The desired product was prepared by substituting N,N-dimethyl-1,4-butanediamine (123 μL, 1.06 mmol) for N,N-dimethylethylenediamine in Example 275G. MS (ESI(+)) m/e 458 $(M+H)^+$, 408 $(M+Na)^+$; MS (ESI(−)) m/e 456 $(M-H)^-$; $^1H$ NMR (300 MHz, DMSO-$d_6$) δ 9.43 (s, 1H), 7.54 (dd, 1H), 7.39-7.44 (m, 1H), 7.06 (d, 1H), 6.83 (d, 1H), 6.57-6.67 (m, 2H), 6.03 (br, 1H), 5.97 (br t, 1H), 5.75 (s, 1H), 3.20 (m, 2H), 3.03-3.08 (m, 2H), 2.72-2.79 (m, 8H, includes 2.73 S, 2.72 S, 6H), 2.53-2.58 (m, 2H), 2.02-2.09 (m, 4H), 1.58-1.72 (m, 4H).

EXAMPLE 286

2-{[(2-{[3-(dibutylamino)propyl]amino}phenyl)sulfonyl]amino}-8-methyl-5,6-dihydro-1-naphthalenecarboxylic acid The desired product was prepared by substituting N,N-dibutyl-1,3-propanediamine (123 μL, 0.8 mmol) for N,N-dimethylethylenediamine in Example 275G. MS (ESI(+)) m/e 528 $(M+H)^+$; MS (ESI(−)) m/e 526 $(M-H)^-$; $^1H$ NMR (300 MHz, DMSO-$d_6$) δ 9.46 (s, 1H), 7.58 (dd, 1H), 7.39-

7.45 (m, 1H), 7.04 (d, 1H), 6.87 (d, 1H), 6.64-6.69 (m, 2H), 5.95-6.16 (br. m, 2H), 5.75 (s, 1H), 3.07-3.20 (m, 2H), 2.95-3.01 (m, 3H), 2.54-2.56 (m, 2H), 1.85-2.11 (m, 6H), 1.46-1.59 (m, 3H), 1.19-1.33 (m, 3H), 0.82-0.95 (m, 4H).

EXAMPLE 287

2-{[(4-fluorophenyl)sulfonyl]amino}-8-methyl-7-oxo-5,6,7,8-tetrahydro-1-naphthalenecarboxylic acid

EXAMPLE 287A

N-(1-bromo-8-methyl-7-oxo-5,6,7,8-tetrahydro-2-naphthalenyl)-4-fluorobenzenesulfonamide A mixture of Example 132A (170 mg, 0.43 mmol) in $CH_2Cl_2$ (5 mL) at 0° C. was treated with mCPBA (136 mg, 0.47 mmol), warmed to room temperature, stirred for 2 hours, diluted with ethyl acetate, washed with $NaHCO_3$ and brine, dried ($Na_2SO_4$), filtered, and concentrated. The concentrate was dissolved in toluene (5 mL), treated with activated-zinc iodide (37 mg, 0.12 mmol), heated to reflux for 1 hour, diluted with diethyl ether, washed with brine, dried ($Na_2SO_4$), filtered, and concentrated to provide the desired product (140 mg, 79% yield). MS (ESI) m/e 410 $(M-H)^-$; $^1H$ NMR (300 MHz, DMSO-$d_6$) δ 9.92 (s, 1H), 7.73 (m, 2H), 7.4 (m, 2H), 7.24 (d, 1H), 7.0 (d, 1H), 3.6 (q, 1H), 3.15 (m, 1H), 2.93 (m, 1H), 2.59 (m, 1H), 2.41 (m, 1H), 1.2 (d, 3H).

EXAMPLE 287B

2-{[(4-fluorophenyl)sulfonyl]amino}-8-methyl-7-oxo-5,6,7,8-tetrahydro-1-naphthalenecarboxylic acid The desired product was prepared according to the procedure of Example 103B substituting Example 287A for Example 103A. MS (ESI) m/e 376 $(M-H)^-$; $^1H$ NMR (300 MHz, DMSO-$d_6$) δ 9.78 (br s, 1H), 7.78 (m, 2H), 7.4 (m, 2H), 7.25 (d, 1H), 6.8 (d, 1H), 3.56 (q, 1H), 3.65 (m, 1H), 2.9 (m, 1H), 2.62 (m, 1H), 2.4 (m, 1H), 1.25 (d, 3H).

EXAMPLE 288

2-{[(2-{[3-(1H-imidazol-1-yl)propyl]amino}phenyl)sulfonyl]amino}-8-methyl-5,6-dihydro-1-naphthalenecarboxylic acid The desired product was prepared according to the procedure of Example 275G substituting 3-(1H-imidazol-1-yl)propylamine for N,N-dimethylethylenediamine. MS (ESI) m/e 466 $(M-H)^-$; $^1H$ NMR (300 MHz, DMSO-$d_6$) δ 9.4 (br s, 1H), 9.07 (s, 1H), 7.75 (t, 1H), 7.69 (t, 1H), 7.59 (dd, 1H), 7.42 (dt, 1H), 7.05 (d, 1H), 6.81 (d, 1H), 6.67 (t, 1H), 6.58 (d, 1H), 6.01 (t, 1H), 5.96 (t, 1H), 4.24 (t, 2H), 3.2 (q, 2H), 2.54 (m, 2H), 2.1 (m, 4H), 2.0 (s, 3H).

EXAMPLE 289

8-methyl-2-{[(2-{[3-(1-pyrrolidinyl)propyl]amino}phenyl)sulfonyl]amino}-5,6-dihydro-1-naphthalenecarboxylic acid The desired product was prepared according to the procedure of Example 275G substituting 3-(1-pyrrolidinyl)propylamine for N,N-dimethylethylenediamine. MS (ESI) m/e 468 $(M-H)^-$; $^1H$ NMR (300 MHz, DMSO-$d_6$) δ 9.4 (br s, 1H), 7.56 (dd, 1H), 7.43 (dt, 1H), 7.07 (d, 1H), 6.86 (d, 1H), 6.68 (t, 1H), 6.6 (m, 1H), 6.05 (br s, 2H), 3.28 (m, 4H), 3.17 (m, 2H), 2.94 (m, 2H), 2.55 (m, 4H), 2.05 (m, 2H), 2.01 (s, 3H), 1.88 (m, 4H).

EXAMPLE 290

8-methyl-2-{[(2-{[3-(1-piperidinyl)propyl]amino}phenyl)sulfonyl]amino}-5,6-dihydro-1-naphthalenecarboxylic acid The desired product was prepared according to the procedure of Example 275G substituting 3-(1-piperidinyl)propylamine for N,N-dimethylethylenediamine. MS (ESI) m/e 482 $(M-H)^-$; $^1H$ NMR (300 MHz, DMSO-$d_6$) δ 7.56 (dd, 1H), 7.42 (t, 1H), 7.05 (d, 1H), 6.85 (d, 1H), 6.67 (t, 2H), 6.05 (m, 2H), 3.28 (q, 4H), 3.08 (m, 2H), 2.8 (m, 2H), 2.53 (m, 2H), 2.05 (m, 2H), 2.02 (s, 3H), 1.9 (m, 2H), 1.76 (m, 2H), 1.6 (m, 3H), 1.33 (m, 1H).

EXAMPLE 291

8-methyl-2-({[2-({2-[(1-methyl-2-pyrrolidinyl]ethyl}amino)phenyl]sulfonyl}amino)-5,6-dihydro-1-naphthalenecarboxylic acid The desired product was prepared according to the procedure of Example 275G substituting 2-[(1-methyl-2-pyrrolidinyl]ethylamine for N,N-dimethylethylenediamine. MS (ESI) m/e 469 $(M-H)^-$; $^1H$ NMR (300 MHz, DMSO-d) δ 13.32 (br s, 1H), 9.2 (br s, 1H), 7.56 (dd, 1H), 7.43 (t, 1H), 7.05 (d, 1H), 6.87 (d, 1H), 6.68 (t, 1H), 6.51 (m, 1H), 6.02 (m, 2H), 3.53 (m, 1H), 3.24 (m, 4H), 3.02 (m, 1H), 2.75 (s, 3H), 2.72 (m, 1H), 2.54 (m, 2H), 2.34-2.11 (m, 2H), 2.07 (m, 1H), 2.01 (s, 3H), 1.98-1.85 (m, 1H), 1.82-1.58 (m, 2H).

EXAMPLE 292

8-methyl-2-({[2-({3-[(2-methyl-1-piperidinyl]propyl}amino)phenyl]sulfonyl}amino)-5,6-dihydro-1-naphthalenecarboxylic acid The desired product was prepared according to the procedure of Example 275G substituting 3-(2-methyl-1-piperidinyl)propylamine for N,N-dimethylethylenediamine. MS (ESI) m/e 497 $(M-H)^-$; $^1H$ NMR (300 MHz, DMSO-$d_6$) δ 13.32 (br s, 1H), 9.2 (br s, 1H), 7.56 (dd, 1H), 7.43 (t, 1H), 7.05 (d, 1H), 6.87 (d, 1H), 6.67 (t, 1H), 6.56 (m, 1H), 6.04 (m, 2H), 3.31 (m, 3H), 3.07 (m, 3H), 2.87 (m, 1H), 2.53 (m, 2H), 2.05 (m, 2H), 2.02 (s, 3H), 1.95-1.75 (m, 3H), 1.75-1.48 (m, 4H), 1.42 (m, 1H), 1.18 (d, 3H).

EXAMPLE 293

2-{[(2-{[3-(dimethylamino)-2,2-dimethylpropyl]amino}phenyl)sulfonyl]amino}-8-methyl-5,6-dihydro-1-naphthalenecarboxylic acid The desired product was prepared by substituting N,N,2,2-tetramethyl-1,3-propanediamine (169 μL, 1.06 mmol) for N,N-dimethylethylenediamine in Example 275G. MS (ESI (+)) m/e 472 $(M+H)^+$, 494 $(M+Na)^+$; MS (ESI(−)) m/e 470 $(M-H)^-$; $^1H$ NMR (300 MHz, DMSO-$d_6$) δ 9.48 (s, 1H), 8.88 (s, 1H), 7.76 (dd, 1H), 7.39-7.45 (m, 1H), 7.08 (d, 1H), 6.92-6.95 (m, 1H), 6.69 (t, 1H), 6.58 (d, 1H), 5.97-6.07 (m, 2H), 3.48 (br m, 6H), 3.09-3.12 (m, 4H), 2.82 (s, 6H), 2.54-2.59 (m, 2H), 2.02-2.07 (m, 5H), 1.02 (br s, 6H).

EXAMPLE 294

2-{[(2-aminophenyl)sulfonyl]amino}-5,6,7,8-tetrahydro-1-naphthalenecarboxylic acid A solution of Example 270 (1.4192 g, 3.77 mmol) in methanol (20 mL) was added to Raney-nickel (14.1 g). The vessel was pressurized to 60 psi with $H_2$ and shaken for 5 hours. The reaction was then filtered and concentrated to yield the desired product (1.18 g, 90%). MS (ESI(+)) m/e 332 $(M+H)^+$, 364 $(M+NH_4)^+$, 369 $(M+Na)^+$; MS (ESI(−)) m/e 345 $(M-H)^-$; $^1$H NMR (300 MHz, DMSO-$d_6$) δ 7.48 (d, 1H), 7.17 (t, 1H), 6.92 (d, 1H), 6.80 (d, 1H), 6.71 (d, 3H), 6.52 (t, 1H), 2.92 (m, 2H), 2.58 (m, 2H), 1.60 (m, 4H).

EXAMPLE 295

8-methyl-2-{[(2-{[2-(1-piperidinyl)ethyl]amino}phenyl)sulfonyl]amino}-5,6-dihydro-1-naphthalenecarboxylic acid The desired product was prepared according to the procedure of Example 275G substituting 2-(1-piperidinyl)ethylamine for N,N-dimethylethylenediamine. MS (ESI) m/e 468 $(M-H)^-$; $^1$H NMR (300 MHz, DMSO-$d_6$) δ 7.28 (m, 3H), 6.92 (d, 1H), 6.8 (d, 1H), 6.52 (t, 1H), 6.13 (m, 1H), 5.81 (m, 1H), 3.62 (m, 2H), 3.29 (m, 4H), 3.15 (m, 2H), 2.48 (m, 4H), 1.98 (m, 2H), 1.92 (s, 3H), 1.79 (m, 4H).

EXAMPLE 297

2-[({2-[(N,N-diethylglycyl)amino]phenyl}sulfonyl)amino]-5,6,7,8-tetrahydro-1-naphthalenecarboxylic acid A solution of Example 294 (0.0590 g, 0.17 mmol) in $CH_2Cl_2$ (3.0 mL) was treated with chloroacetyl chloride (16 μL, 0.20 mmol) and pyridine (69 μL, 0.85 mmol), stirred 4 hours at room temperature, then quenched with 1N HCl (10 mL). The layers were separated and the organic layer was washed with brine, dried ($MgSO_4$), filtered, and concentrated to a residue (45.0 mg). The residue was dissolved in acetone (0.4 mL), treated with diethylamine (50 μL, 0.48 mmol), heated to 60° C. for 2 hours, cooled to room temperature, diluted with ethyl acetate (10 mL), and washed with 1N HCl (10 mL). The organic layer was dried ($MgSO_4$), filtered and concentrated. The concentrate was purified by $C_{18}$ reverse-phase HPLC using acetonitrile/water/0.1% TFA to provide the desired product (8.7 mg, 18%). MS (ESI(+)) m/e 460 $(M+H)^+$; MS (ESI(−)) m/e 458 $(M-H)^-$; $^1$H NMR (300 MHz, DMSO-$d_6$) δ 7.79 (m, 2H), 7.56 (m, 1H), 7.23 (m, 2H), 6.90 (m, 1H), 3.30 (m, 4H), 2.80 (m, 2H), 2.73 (s, 2H), 2.59 (m, 2H), 1.61 (m, 4H), 1.06 (m, 6H).

EXAMPLE 298

2-[({2-[(N,N-diethyl-β-alanyl)amino]phenyl}sulfonyl)amino]-5,6,7,8-tetrahydro-1-naphthalenecarboxylic acid The desired product was prepared by substituting 3-chloropropanoyl chloride for chloroacetyl chloride in Example 297. MS (ESI(+)) m/e 474 $(M+H)^+$; MS (ESI(−)) m/e 472 $(M-H)^-$; $^1$H NMR (300 MHz, DMSO-$d_6$) δ 7.65 (m, 2H), 7.55 (m, 1H), 7.22 (m, 2H), 6.89 (m, 1H), 3.38 (m, 2H), 3.17 (q, 4H), 3.08 (m, 2H), 2.80 (m, 2H), 2.57 (m, 2H), 2.55 (m, 4H), 2.43 (m, 2H), 1.75 (m, 2H), 1.57 (m, 4H), 1.27 (t, 6H).

EXAMPLE 299

2-({[2-({[2-(diethylamino)ethyl]amino}carbonyl)phenyl]sulfonyl}amino)-1-naphthoic acid

EXAMPLE 299A methyl 2-({[2-({[2-(diethylamino)ethyl]amino}carbonyl)phenyl]sulfonyl}amino)-1-naphthoate A solution of Example 149B (228 mg, 0.592 mmol) in dimethylformamide (3.0 mL) was treated with 4-methylmorpholine (230 μL, 2.07 mmol), cooled to 0° C., treated with O-(7-azabenzotriazol-1-yl)-N,N,N',N'-tetramethyluronium hexafluorophosphate (450 mg, 1.18 mmol), stirred for 1 hour, treated with 3-(N,N-diethylamino)propylamine (166 μL, 1.18 mmol), warmed to room temperature, stirred overnight, treated with distilled water, and extracted with ethyl acetate three times. The combined extracts were washed with brine, dried ($MgSO_4$), filtered, and concentrated. The resulting residue was purified by preparative HPLC to provide the desired product. MS (ESI(+)) m/e 484 $(M+H)^+$; (ESI(−)) m/e 482 $(M-H)^-$; $^1$H NMR (300 MHz, DMSO-$d_6$) δ 9.36 (s, 1H), 9.21 (br s, 1H), 9.11 (t, 1H), 8.04 (d, 1H), 7.94 (dd, 1H), 7.79-7.68 (m, 4H), 7.62 (d, 1H), 7.60-7.53 (m, 3H), 3.81 (s, 3H), 3.67 (m, 2H), 3.26 (m, 6H), 1.26 (t, 6H).

EXAMPLE 299B 2-({[2-({[2-(diethylamino)ethyl]amino}carbonyl)phenyl]sulfonyl}amino)-1-naphthoic acid A solution of Example 299A (244 mg, 0.505 mmol) in dioxane (8 mL) and distilled water (4 mL) was treated with lithium hydroxide monohydrate (212 mg, 5.05 mmol), stirred at 60° C. overnight, cooled to room temperature, treated with 1N HCl, and extracted with ethyl acetate two times. The combined organic fractions were washed with brine, dried ($MgSO_4$), filtered, and concentrated. The resulting residue was purified by preparative HPLC to provide the desired product. MS (ESI(+)) m/e 470 $(M+H)^+$; (ESI(−)) m/e 468 $(M-H)^-$; $^1$H NMR (300 MHz, DMSO-$d_6$) δ 9.73 (br s, 1H), 9.10 (br s, 1H), 9.01 (t, 1H), 7.99 (t, 2H), 7.92 (dd, 1H), 7.84 (dd, 1H), 7.76 (dt, 1H), 7.70-7.45 (m, 5H), 3.65 (m, 4H), 3.25 (m, 4H), 1.24 (t, 6H).

EXAMPLE 300

2-{[(2-{[2-(1-piperazinyl)ethyl]amino}phenyl)sulfonyl]amino}-5,6,7,8-tetrahydro-1-naphthalenecarboxylic acid The desired product was prepared by substituting 1-(2-aminoethyl)piperizine for for N,N-diethyl-1,3-propanediamine in Example 229B. MS (DCI) m/e 460 $(M+H)^+$; $^1$H NMR (500 MHz, DMSO-$d_6$) δ 9.96 (br s, 1H), 7.38 (m, 2H), 6.95 (br s, 2H), 6.87 (d, 1H), 6.63 (t, 1H), 6.11 (br s, 1H), 3.86 (br s, 4H), 3.62 (m, 4H), 3.27 (m, 4H), 2.64 (br s, 4H), 1.63 (br s, 4H).

EXAMPLE 301

2-{[(2-{[3-(2-oxo-1-pyrrolidinyl)propyl]amino}phenyl)sulfonyl]amino}-5,6,7,8-tetrahydro-1-naphthalenecarboxylic acid The desired product was prepared by substituting 1-(3-aminopropyl)-2-pyrrolidinone for N,N-diethyl-1,3-propanediamine in Example 229B. MS (DCI) m/e 472 $(M+H)^+$;

$^1H$ NMR (500 MHz, DMSO-$d_6$) δ 13.11 (br s, 1H), 9.50 (br s, 1H), 7.48 (dd, 1H), 7.37 (m, 1H), 6.94 (d, 1H), 6.76 (d, 1H), 6.60 (m, 2H), 5.91 (m, 1H), 3.32 (t, 2H), 3.22 (t, 2H), 3.11 (m, 2H), 2.65 (m, 4H), 2.23 (t, 2H), 1.92 (m, 2H), 1.71 (m, 2H), 1.66 (br s, 4H).

EXAMPLE 302

2-{[(2-{[3-(4-morpholinyl)propyl]amino}phenyl) sulfonyl]amino}-5,6,7,8-tetrahydro-1-naphthalenecarboxylic acid The desired product was prepared by substituting 1-(3-aminopropyl)morpholine for N,N-diethyl-1,3-propanediamine in Example 229B. MS (DCI) m/e 474 (M+H)$^+$; $^1H$ NMR (500 MHz, DMSO-$d_6$) δ 7.44 (d, 1H), 7.33 (t, 1H), 7.08 (br s, 1H), 6.92 (d, 1H), 6.76 (d, 1H), 6.54 (t, 1H), 6.18 (br s, 1H), 3.79 (br s, 4H), 3.26-3.17 (m, 8H), 2.73 (br s, 2H), 2.62 (br s, 2H), 1.81 (br s, 2H), 1.62 (br s, 4H).

EXAMPLE 303

2-({[2-({2-[1-methyl-2-pyrrolidinyl]ethyl}amino) phenyl]sulfonyl}amino)-5,6,7,8-tetrahydro-1-naphthalenecarboxylic acid The desired product was prepared by substituting 2-(2-aminoethyl)-1-methylpyrrolidine for N,N-diethyl-1,3-propanediamine in Example 229B. MS (ESI(+)) m/e 458 (M+H)$^+$, 480 (M+Na)$^+$; (ESI(−)) m/e 456 (M−H)$^-$; $^1H$ NMR (300 MHz, DMSO-$d_6$) δ 13.20 (br s, 1H), 10.02 (br s, 1H), 9.54 (s, 1H), 7.52 (dd, 1H), 7.42 (dt, 1H), 6.96 (d, 1H), 6.86 (d, 1H), 6.65 (t, 1H), 6.60 (d, 1H), 5.97 (br s, 1H), 3.26 (m, 4H), 2.98 (quint, 1H), 2.72 (d, 3H), 2.65 (br s, 4H), 2.33-2.13 (m, 2H), 2.00-1.75 (m, 2H), 1.67 (br s, 5H).

EXAMPLE 304

2-({[2-({3-[2-methyl-1-piperidinyl]propyl}amino) phenyl]sulfonyl}amino)-5,6,7,8-tetrahydro-1-naphthalenecarboxylic acid The desired product was prepared by substituting 1-(3-aminopropyl)-2-methylpiperidine for N,N-diethyl-1,3-propanediamine in Example 229B. MS (DCI) m/e 486 (M+H)$^+$; $^1H$ NMR (500 MHz, DMSO-$d_6$) δ 13.18 (br s, 1H), 9.53 (br s, 1H), 7.52 (d, 1H), 7.41 (m, 1H), 6.94 (d, 1H), 6.85 (m, 1H), 6.65 (m, 2H), 6.03 (br s, 1H), 3.05 (m, 3H), 2.65 (m, 4H), 1.91-1.44 (m, 12H), 1.20 (br s, 3H).

EXAMPLE 305

-2-{[(2-{[1-(ethoxycarbonyl)-4-piperidinyl] amino}phenyl)sulfonyl]amino}-5,6,7,8-tetrahydro-1-naphthalenecarboxylic acid The desired product was prepared by substituting ethyl 4-amino-1-piperidinecarboxylate for N,N-diethyl-1,3-propanediamine in Example 229B. MS (DCI) m/e 502 (M+H)$^+$; $^1H$ NMR (500 MHz, DMSO-$d_6$) δ 13.08 (br s, 1H), 9.50 (br s, 1H), 7.50 (dd, 1H), 7.35 (m, 1H), 6.94 (d, 1H), 6.81 (d, 1H), 6.63-6.56 (m, 2H), 5.73 (d, 1H), 4.04 (q, 2H), 3.80 (d, 2H), 3.54 (m, 1H), 2.97 (br s, 2H), 2.66-2.64 (m, 4H), 1.79 (d, 2H), 1.66 (br s, 4H), 1.18 (t, 3H).

EXAMPLE 306

2-{[(2-{[2-(4-morpholinyl)ethyl]amino}phenyl)sulfonyl]amino}-5,6,7,8-tetrahydro-1-naphthalenecarboxylic acid The desired product was prepared by substituting 1-(2-aminoethyl)morpholine for N,N-diethyl-1,3-propanediamine in Example 229B. MS (DCI) m/e 460 (M+H)$^+$; $^1H$ NMR (500 MHz, DMSO-$d_6$) δ 7.38 (m, 2H), 6.95 (br s, 2H), 6.87 (d, 1H), 6.63 (t, 1H), 6.11 (m, 1H), 3.86 (br s, 4H), 3.62 (m, 4H), 3.27 (m, 4H), 2.64 (br s, 4H), 1.63 (br s, 4H).

EXAMPLE 307

2-({[2-({2-[bis(2-hydroxyethyl)amino]ethyl}amino) phenyl]sulfonyl}amino)-5,6,7,8-tetrahydro-1-naphthalenecarboxylic acid The desired product was prepared by substituting 2-(N,N-bis(2-hydroxyethyl)amino)ethylamine for N,N-diethyl-1,3-propanediamine in Example 229B. MS (DCI) m/e 478 (M+H)$^+$; $^1H$ NMR (500 MHz, DMSO-$d_6$) δ 13.00 (br s, 1H), 9.48 (br s, 1H), 7.47 (d, 1H), 7.42 (t, 1H), 6.94 (t, 2H), 6.69 (br s, 1H), 6.67 (t, 1H), 6.07 (m, 1H), 3.78 (m, 4H), 3.64 (m, 2H), 2.65 (br s, 4H), 1.65 (br s, 4H).

EXAMPLE 308

2-{[(2-{[2-(1-piperidinyl)ethyl]amino}phenyl)sulfonyl]amino}-5,6,7,8-tetrahydro-1-naphthalenecarboxylic acid The desired product was prepared by substituting 1-(2-aminoethyl)piperidine for N,N-diethyl-1,3-propanediamine in Example 229B. MS (DCI) m/e 458 (M+H)$^+$; $^1H$ NMR (500 MHz, DMSO-$d_6$) δ 9.61 (br s, 1H), 7.45-7.39 (m, 2H), 6.95 (d, 1H), 6.88 (d, 1H), 6.81 (br s, 1H), 6.66 (t, 1H), 6.07 (m, 1H), 3.61 (m, 3H), 3.23 (m, 3H), 2.64 (br s, 4H), 1.77-1.64 (br m, 10H).

EXAMPLE 309

2-{[(2-{[4-(diethylamino)-1-methylbutyl] amino}phenyl)sulfonyl]amino}-5,6,7,8-tetrahydro-1-naphthalenecarboxylic acid The desired product was prepared by substituting 4-(N,N-diethylamino)-1-methylbutylamine for N,N-diethyl-1,3-propanediamine in Example 229B. MS (DCI) m/e 488 (M+H)$^+$; $^1H$ NMR (500 MHz, DMSO-$d_6$) δ 13.10 (br s, 1H), 9.66 (br s, 1H), 7.54 (d, 1H), 7.35 (t, 1H), 6.93 (d, 1H), 6.80 (d, 1H), 6.59 (t, 1H), 5.65 (d, 1H), 3.63 (m, 1H), 3.07-2.97 (br m, 6H), 2.63 (br s, 4H), 1.76-1.47 (br m, 8H), 1.16 (t, 6H), 1.10 (d, 3H).

EXAMPLE 310

2-{[(2-{[3-(dibutylamino)propyl]amino}phenyl) sulfonyl]amino}-5,6,7,8-tetrahydro-1-naphthalenecarboxylic acid The desired product was prepared by substituting 3-(N,N-dibutylamino)propylamine for N,N-diethyl-1,3-propanediamine in Example 229B. MS (DCI) m/e 516 (M+H)$^+$; $^1H$ NMR (500 MHz, DMSO-$d_6$) δ 13.22 (br s, 1H), 9.59 (br s, 1H), 7.51 (d, 1H), 7.40 (t, 1H), 6.93 (d, 1H), 6.84 (d, 1H), 6.71 (br s, 1H), 6.63 (t, 1H), 6.05 (br s, 1H), 3.16 (br s, 3H), 2.99 (m, 5H), 2.68 (br s, 2H), 2.64 (br s, 2H), 1.88 (m, 2H), 1.65 (br s, 4H), 1.52 (m, 4H), 1.28 (m, 4H), 0.86 (t, 6H).

EXAMPLE 311

2-{[(2-{[3-(1H-imidazol-1-yl)propyl]amino}phenyl) sulfonyl]amino}-5,6,7,8-tetrahydro-1-naphthalenecarboxylic acid The desired product was prepared by substituting 1-(3-aminopropyl)imidazole for N,N-diethyl-1,3-propanediamine in Example 229B. MS (DCI) m/e 455 (M+H)$^+$; $^1H$ NMR (500 MHz, DMSO-$d_6$) δ 13.87 (br s, 1H), 9.56 (br s, 1H), 9.03 (br s, 1H), 7.74 (s, 1H), 7.67 (s, 1H), 7.51 (dd, 1H), 7.39 (m, 1H), 6.95 (d, 1H), 6.78 (d, 1H), 6.67-6.63 (m, 2H), 5.93 (t, 1H), 3.20-3.16 (m, 4H), 2.63 (m, 4H), 2.10 (m, 2H), 1.65 (br s, 4H).

EXAMPLE 312

2-{[(2-{[3-(dimethylamino)-2,2-dimethylpropyl]amino}phenyl)sulfonyl]amino}-5,6,7,8-tetrahydro-1-naphthalenecarboxylic acid The desired product was prepared by substituting 3-N,N-dimethylamino-2,2-dimethylpropylamine for N,N-diethyl-1,3-propanediamine in Example 229B. MS (ESI(+)) m/e 460 $(M+H)^+$; (ESI(−)) m/e 458 $(M-H)^-$; $^1H$ NMR (300 MHz, DMSO-$d_6$) δ 7.53 (dd, 1H), 7.40 (dt, 1H), 6.97 (d, 1H), 6.92 (d, 1H), 6.68 (t, 1H), 6.58 (d, 1H), 3.09 (s, 2H), 3.06 (m, 2H), 2.83 (s, 6H), 2.66 (m, 4H), 1.67 (m, 4H), 1.01 (s, 6H).

EXAMPLE 313

2-{[(2-{[4-(N,N-dimethylamino)butyl]amino}phenyl)sulfonyl]amino}-5,6,7,8-tetrahydro-1-naphthalenecarboxylic acid The desired product was prepared by substituting 4-(N,N-dimethylamino)butylamine for N,N-diethyl-1,3-propanediamine in Example 229B. MS (DCI) m/e 446 $(M+H)^+$; $^1H$ NMR (500 MHz, DMSO-$d_6$) δ 13.09 (br s, 1H), 9.52 (br s, 1H), 7.51 (d, 1H), 7.38 (m, 1H), 6.95 (d, 1H), 6.79 (d, 1H), 6.68 (br s, 1H), 6.62 (t, 1H), 5.90 (br s, 1H), 3.18 (m, 2H), 3.06 (m, 2H), 2.74 (s, 6H), 2.68-2.65 (m, 4H), 1.69-1.66 (m, 6H), 1.57 (m, 2H).

EXAMPLE 314

2-{[(2-{[2-(dipropylamino)ethyl]amino}phenyl)sulfonyl]amino}-5,6,7,8-tetrahydro-1-naphthalenecarboxylic acid The desired product was prepared by substituting 2-(N,N-dipropylamino)ethylamine for N,N-diethyl-1,3-propanediamine in Example 229B. MS (DCI) m/e 474 $(M+H)^+$; $^1H$ NMR (500 MHz, DMSO-$d_6$) δ 13.13 (br s, 1H), 9.49 (br s, 1H), 7.46-7.40 (m, 2H), 6.94 (d, 1H), 6.89 (d, 1H), 6.77 (br s, 1H), 6.67 (m, 1H), 6.05 (m, 1H), 3.59 (m, 2H), 3.27 (m, 2H), 3.12-3.09 (m, 4H), 2.64 (br s, 4H), 1.64 (br s, 8H), 0.90 (t, 6H).

EXAMPLE 315

2-{[(2-{[3-(1-pyrrolidinyl)propyl]amino}phenyl)sulfonyl]amino}-5,6,7,8-tetrahydro-1-naphthalenecarboxylic acid The desired product was prepared by substituting 1-(3-aminopropyl)pyrrolidine for N,N-diethyl-1,3-propanediamine in Example 229B. MS (DCI) m/e 458 $(M+H)^+$; $^1H$ NMR (500 MHz, DMSO-$d_6$) δ 13.14 (br s, 1H), 9.72 (br s, 1H), 7.51 (dd, 1H), 7.40 (m, 1H), 6.95 (d, 1H), 6.83 (d, 1H), 6.72 (br s, 1H), 6.64 (t, 1H), 6.01 (br s, 1H), 3.27 (m, 4H), 3.18 (m, 4H), 2.67-2.64 (m, 4H), 1.89 (m, 6H), 1.65 (br s, 4H).

EXAMPLE 316

2-{[(2-{[2-(diisopropylamino)ethyl]amino}phenyl)sulfonyl]amino}-5,6,7,8-tetrahydro-1-naphthalenecarboxylic acid The desired product was prepared by substituting 2-(N,N-diisopropylamino)ethylamine for N,N-diethyl-1,3-propanediamine in Example 229B. MS (DCI) m/e 474 $(M+H)^+$; $^1H$ NMR (500 MHz, DMSO-$d_6$) δ 13.15 (br s, 1H), 9.45 (br s, 1H), 7.53 (d, 1H), 7.45 (t, 1H), 6.95 (d, 1H), 6.84 (d, 1H), 6.71 (m, 2H), 6.11 (br s, 1H), 1.80 (m, 2H), 3.55 (m, 2H), 3.25 (m, 2H), 2.65 (m, 4H), 1.65 (br s, 4H), 1.28 (d, 12H).

EXAMPLE 317

2-{[(2-{[4-(diethylamino)butanoyl]amino}phenyl)sulfonyl]amino}-5,6,7,8-tetrahydro-1-naphthalenecarboxylic acid The desired product was prepared by substituting 4-chlorobutanoyl chloride for chloroacetyl chloride in Example 297. MS (ESI(+)) m/e 488 $(M+H)^+$; MS (ESI(−)) m/e 486 $(M-H)^-$; $^1H$ NMR (300 MHz, DMSO-$d_6$) δ 9.73 (s, 1H), 8.15 (d, 1H), 7.79 (dd, 1H), 7.41 (td, 1H), 7.11 (td, 1H), 7.04 (d, 1H), 3.30 (m, 4H), 2.92 (m, 2H), 2.55 (m, 4H), 2.43 (m, 2H), 1.75 (m, 2H), 1.57 (m, 4H), 0.98 (t, 6H).

EXAMPLE 318

3-ethyl-6-{[(2-fluorophenyl)sulfonyl]amino}-2-methoxybenzoic acid

EXAMPLE 318A benzyl 3-bromo-6-[(tert-butoxycarbonyl)amino]-2-methoxybenzoate

The desired product was prepared by substituting Example 151B for Example 104B in Example 108A. MS (ESI(+)) m/e 436, 438 $(M+H)^+$, 453, 455 $(M+NH_4)^+$, 458, 460 $(M+Na)^+$; (ESI(−)) m/e 434, 436 $(M-H)^-$; $^1H$ NMR (300 MHz, DMSO-$d_6$) δ 9.27 (s, 1H), 7.66 (d, 1H), 7.40 (m, 5H), 7.17 (d, 1H), 5.27 (s, 2H), 3.70 (s, 3H), 1.43 (s, 9H).

EXAMPLE 318B benzyl 6-amino-3-bromo-2-methoxybenzoate

The desired product was prepared by substituting Example 318A for Example 126A in Example 126B. MS (ESI(+)) m/e 336, 338 $(M+H)^+$; (ESI(−)) m/e 334, 336 $(M-H)^-$; $^1H$ NMR (300 MHz, DMSO-$d_6$) δ 7.41 (m, 5H), 7.34 (d, 1H), 6.49 (d, 1H), 5.33 (s, 2H), 3.93 (br s, 2H), 3.62 (s, 3H).

EXAMPLE 318C benzyl 3-bromo-6-{[(2-fluorophenyl)sulfonyl]amino}-2-methoxybenzoate The desired product was prepared by substituting Example 318B and 2-fluorobenzenesulfonyl chloride for Example 126B and 3-fluorobenzenesulfonyl chloride, respectively, in Example 126C. MS (ESI(+)) m/e 494, 496 $(M+H)^+$, 511, 513 $(M+NH_4)^+$, 516, 518 $(M+Na)^+$; (ESI(−)) m/e 492, 494 $(M-H)^-$; $^1H$ NMR (300 MHz, DMSO-$d_6$) δ 10.50 (s, 1H), 7.70 (m, 3H), 7.42 (m, 7H), 6.81 (d, 1H), 5.22 (s, 2H), 3.62 (s, 3H).

EXAMPLE 318D benzyl 6-{[(2-fluorophenyl)sulfonyl]amino}-2-methoxy-3-vinylbenzoate The desired product was prepared by substituting Example 318C for Example 226E in Example 226F. MS (ESI(+)) m/e 442 $(M+H)^+$, 459 $(M+NH_4)^+$, 464 $(M+Na)^+$; (ESI(−)) m/e 440 $(M-H)^-$; $^1H$ NMR (300 MHz, DMSO-$d_6$) δ 10.34 (s, 1H), 7.71 (m, 2H), 7.62 (d, 1H), 7.40 (m, 7H), 6.95 (d, 1H), 6.78 (dd, 1H), 5.82 (d, 1H), 5.36 (d, 1H), 5.21 (s, 2H), 3.53 (s, 3H)

EXAMPLE 318E 3-ethyl-6-{[(2-fluorophenyl)sulfonyl]amino}-2-methoxybenzoic acid

The desired product was prepared by substituting Example 318D for Example 226F in Example 226G with purification by preparative HPLC on a Waters Symmetry C8 column (25 mm×100 mm, 7 μm particle size) using a gradient of 10% to 100% acetonitrile:0.1% aqueous TFA over 8 minutes (10 minute run time) at a flow rate of 40 mL/min. MS (ESI(+)) m/e 354 $(M+H)^+$, 371 $(M+NH_4)^+$, 376 $(M+Na)^+$; (ESI(−)) m/e 352 $(M-H)^-$; $^1$H NMR (300 MHz, DMSO-$d_6$) δ 13.27 (br s, 1H), 10.12 (br s, 1H), 7.72 (m, 2H), 7.40 (t, 1H), 7.33 (t, 1H), 7.20 (d, 1H), 6.88 (d, 1H), 3.67 (s, 3H), 2.56 (q, 2H), 1.11 (t, 3H).

EXAMPLE 319

3-ethyl-2-methoxy-6-({[2-({3-[(2R)-2-methyl-1-piperidinyl]propyl}amino)phenyl]sulfonyl}amino) benzoic acid A mixture of Example 318E (50 mg, 0.14 mmol), triethylamine (0.1 mL, 0.71 mmol), acetonitrile (1 mL) and 1-(3-aminopropyl)-2-pipecoline (177 mg, 1.1 mmol) was purged with argon, sealed in a vial and microwaved at 150° C. for 55 minutes. Purification by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min provided the desired product. MS (ESI(+)) m/e 490 $(M+H)^+$; (ESI(−)) m/e 488 $(M-H)^-$; $^1$H NMR (300 MHz, DMSO-$d_6$) δ 13.24 (br s, 1H), 9.71 (br s, 1H), 7.58 (dd, 1H), 7.42 (t, 1H), 7.13 (d, 1H), 6.87 (dd, 1H), 6.67 (m, 2H), 6.05 (m, 1H), 3.69 (s, 3H), 3.36 (m, 2H), 3.12 (m, 2H), 3.05 (m, 2H), 2.88 (m, 1H), 2.54 (q, 2H), 1.86 (m, 4H), 1.64 (m, 2H), 1.43 (m, 2H), 1.20 (d, 3H), 1.10 (t, 3H).

EXAMPLE 320

6-{[(2-{[3-(diethylamino)propyl]amino}phenyl) sulfonyl]amino}-3-ethyl-2-hydroxybenzoic acid The desired product was prepared by substituting N,N-diethylaminopropylamine for 1-(3-aminopropyl)-2-pipecoline in Example 319 and changing the heating conditions to 200° C. for 25 minutes. MS (ESI(+)) m/e 450 $(M+H)^+$; (ESI (−)) m/e 448 $(M-H)^-$; $^1$H NMR (300 MHz, DMSO-$d_6$) δ 15.72 (s, 1H), 14.75 (s, 1H), 9.11 (br s, 1H), 7.63 (d, 1H), 7.33 (t, 1H), 6.88 (d, 1H), 6.77 (d, 1H), 6.66 (m, 2H), 5.84 (t, 1H), 3.27 (m, 4H), 3.18 (m, 4H), 2.36 (q, 2H), 1.89 (m, 2H), 1.19 (t, 6H), 1.02 (t, 3H).

EXAMPLE 321

3-ethyl-2-methoxy-6-{[(2-{[3-(1-piperidinyl)propyl] amino}phenyl)sulfonyl]amino}benzoic acid The desired product was prepared by substituting 3-(1-piperidino)propylamine for 1-(3-aminopropyl)-2-pipecoline in Example 319. MS (ESI(+)) m/e 476 $(M+H)^+$; (ESI(−)) m/e 474 $(M-H)^-$; $^1$H NMR (300 MHz, DMSO-$d_6$) δ 13.27 (s, 1H), 9.77 (br s, 1H), 7.51 (dd, 1H), 7.41 (t, 1H), 7.13 (d, 1H), 6.84 (d, 1H), 6.71 (d, 1H), 6.66 (t, 1H), 6.04 (m, 1H), 3.68 (s, 3H), 3.38 (m, 2H), 3.25 (m, 2H), 3.09 (m, 2H), 2.81 (m, 2H), 2.52 (q, 2H), 1.91 (m, 2H), 1.77 (m, 2H), 1.64 (m, 3H), 1.37 (m, 1H), 1.10 (t, 3H).

EXAMPLE 322

3-ethyl-2-hydroxy-6-{[(2-{[3-(1-piperidinyl)propyl] amino}phenyl)sulfonyl]amino}benzoic acid The desired product was prepared by substituting 3-(1-piperidino)propylamine for 1-(3-aminopropyl)-2-pipecoline in Example 319. MS (ESI(+)) m/e 462 $(M+H)^+$; (ESI(−)) m/e 460 $(M-H)^-$; $^1$H NMR (300 MHz, DMSO-$d_6$) δ 15.64 (s, 1H), 14.66 (s, 1H), 9.13 (br s, 1H), 7.62 (d, 1H), 7.33 (m, 1H), 6.89 (d, 1H), 6.75 (d, 1H), 6.70 (d, 1H), 6.63 (m, 1H), 5.85 (t, 1H), 3.27 (m, 6H), 2.92 (m, 2H), 2.37 (q, 2H), 1.91 (m, 2H), 1.80 (m, 2H), 1.69 (m, 3H), 1.42 (m, 1H), 1.02 (t, 3H).

EXAMPLE 323

3-ethyl-2-hydroxy-6-{[(2-{[3-(4-methyl-1-piperazinyl)propyl]amino}phenyl)sulfonyl]amino}benzoic acid The desired product was prepared by substituting 1-(3-aminopropyl)-4-methylpiperazine for 1-(3-aminopropyl)-2-pipecoline in Example 319. MS (ESI(+)) m/e 477 $(M+H)^+$; (ESI(−)) m/e 475 $(M-H)^-$; $^1$H NMR (300 MHz, DMSO-$d_6$) δ 14.39 (s, 1H), 7.63 (dd, 1H), 7.33 (t, 1H), 6.93 (d, 1H), 6.74 (m, 2H), 6.62 (t, 1H), 5.87 (br s, 1H), 3.46 (br s, 10H), 3.23 (m, 4H), 2.86 (s, 3H), 2.38 (q, 2H), 1.90 (m, 2H), 1.02 (t, 3H).

EXAMPLE 324

6-{[(2-{[4-(N,N-dimethylamino)butyl] amino}phenyl)sulfonyl]amino}-3-ethyl-2-methoxybenzoic acid The desired product was prepared by substituting 4-(N,N-dimethylamino)butylamine for 1-(3-aminopropyl)-2-pipecoline in Example 319. MS (ESI(+)) m/e 450 $(M+H)^+$; (ESI (−)) m/e 448 $(M-H)^-$; $^1$H NMR (300 MHz, DMSO-$d_6$) δ 10.18 (br s, 1H), 9.64 (br s, 1H), 7.51 (d, 1H), 7.36 (t, 1H), 7.15 (d, 1H), 6.78 (d, 1H), 6.62 (m, 2H), 5.89 (br s, 1H), 3.67 (s, 3H), 3.15 (m, 2H), 3.04 (m, 2H), 2.69 (s, 3H), 2.67 (s, 3H), 2.51 (q, 2H), 1.69 (m, 2H), 1.56 (m, 2H), 1.09 (t, 3H).

EXAMPLE 325

3-ethyl-2-methoxy-6-{[(2-{[3-(4-methyl-1-piperazinyl)propyl]amino}phenyl)sulfonyl]amino}benzoic acid The desired product was prepared by substituting 1-(3-aminopropyl)-4-methylpiperazine for 1-(3-aminopropyl)-2-pipecoline in Example 319. MS (ESI(+)) m/e 491 $(M+H)^+$; (ESI(−)) m/e 489 $(M-H)^-$; $^1$H NMR (300 MHz, DMSO-$d_6$) δ 9.38 (br s, 1H), 7.28 (dd, 1H), 7.12 (dt, 1H), 6.98 (d, 1H), 6.54 (d, 1H), 6.42 (d, 1H), 6.37 (t, 1H), 5.72 (br s, 1H), 3.40 (s, 3H), 2.93 (m, 2H), 2.78 (br m, 9H), 2.54 (m, 2H), 2.49 (s, 3H), 2.26 (q, 2H), 1.53 (m, 2H), 0.83 (t, 3H).

EXAMPLE 328

2-({[2-({[2-(1-piperidinyl)ethyl]amino}carbonyl) phenyl]sulfonyl}amino)-1-naphthoic acid

EXAMPLE 328A methyl 2-({[2-({[2-(1-piperidinyl)ethyl]amino}carbonyl)phenyl]sulfonyl}amino)-1-naphthoate The desired product was prepared by substituting 1-(2-aminoethyl)piperidine for 3-(N,N-diethylamino)propylamine in Example 299A. MS (ESI(+)) m/e 496 $(M+H)^+$; (ESI(−)) m/e 494 $(M-H)^-$; $^1H$ NMR (300 MHz, DMSO-$d_6$) δ 9.37 (s, 1H), 9.13 (t, 1H), 9.04 (s, 1H), 8.04 (d, 1H), 7.95 (m, 1H), 7.77 (m, 2H), 7.70 (m, 2H), 7.62 (m, 1H), 7.56 (m, 2H), 3.81 (s, 3H), 3.70 (q, 3H), 3.55 (m, 3H), 3.29 (m, 2H), 3.01 (m, 2H), 1.86 (d, 2H), 1.68 (m, 2H).

EXAMPLE 328B 2-({[2-({[2-(1-piperidinyl)ethyl]amino}carbonyl)phenyl]sulfonyl}amino)-1-naphthoic acid In a small microwave reactor vessel was placed Example 328A (64.7 mg, 0.131 mmol), dioxane (1 mL), distilled water (0.5 mL), and lithium hydroxide monohydrate (55.0 mg, 1.31 mmol). The vial was sealed and heated in microwave for nine hundred seconds at 160° C. The solution was cooled to room temperature, treated with 1N HCl, and concentrated. The resulting residue was purified by preparative HPLC to provide the desired product. MS (ESI(+)) m/e 482 $(M+H)^+$; (ESI(−)) m/e 480 $(M-H)^-$; $^1H$ NMR (300 MHz, DMSO-$d_6$) δ 8.91 (d, 1H), 8.45 (br t, 1H), 7.71 (d, 1H), 7.67 (d, 1H), 7.65 (d, 1H), 7.55 (d, 1H), 7.48 (dt, 1H), 7.42-7.34 (m, 3H), 7.24 (t, 1H), 3.44 (q, 3H), 2.71 (t, 2H), 2.60 (br s, 4H), 1.55 (quint, 4H), 1.39 (m, 2H).

EXAMPLE 330

2-{[(2-{[3-(ethylamino)propyl]amino}phenyl)sulfonyl]amino}-5,6,7,8-tetrahydro-1-naphthalenecarboxylic acid The desired product was prepared by substituting 3-ethylaminopropylamine for 3-(N,N-diethylamino)propylamine in Example 229B. MS (ESI(+)) m/e 432 $(M+H)^+$; (ESI(−)) m/e 430 $(M-H)^-$; $^1H$ NMR (300 MHz, DMSO-$d_6$) δ 7.51 (dd, 1H), 7.40 (dt, 1H), 6.94 (d, 1H), 6.84 (d, 1H), 6.63 (m, 2H), 6.01 (m, 1H), 3.31 (m, 2H), 2.95 (m, 4H), 2.65 (m, 4H), 1.85 (m, 2H), 1.66 (m, 4H), 1.15 (t, 3H).

EXAMPLE 331

2-({[2-({3-[bis(2-hydroxyethyl)amino]propyl}amino)phenyl]sulfonyl}amino)-5,6,7,8-tetrahydro-1-naphthalenecarboxylic acid The desired product was prepared by substituting 2-[(3-aminopropyl)(2-hydroxyethyl)amino]ethanol for 3-(N,N-diethylamino)propylamine in Example 229B. MS (ESI(+)) m/e 492 $(M+H)^+$; (ESI(−)) m/e 490 $(M-H)^-$; $^1H$ NMR (300 MHz, DMSO-$d_6$) δ 7.50 (dd, 1H), 7.41 (dt, 1H), 6.96 (d, 1H), 6.85 (d, 1H), 6.64 (m, 2H), 5.99 (m, 1H), 3.73 (t, 4H), 3.24 (m, 8H), 2.65 (m, 4H), 1.96 (m, 2H), 1.67 (m, 4H).

EXAMPLE 332

2-({[2-({3-[(tert-butoxycarbonyl)amino]propyl}amino)phenyl]sulfonyl}amino)-5,6,7,8-tetrahydro-1-naphthalenecarboxylic acid The desired product was prepared by substituting tert-butyl 3-aminopropylcarbamate for 3-(N,N-diethylamino)propylamine in Example 229B. MS (ESI(+)) m/e 504 $(M+H)^+$, 526 $(M+Na)^+$; (ESI(−)) m/e 502 $(M-H)^-$; $^1H$ NMR (300 MHz, DMSO-$d_6$) δ 7.47 (dd, 1H), 7.37 (dt, 1H), 6.95 (d, 1H), 6.76 (d, 1H), 6.60 (m, 2H), 5.90 (m, 1H), 3.14 (m, 2H), 2.97 (q, 2H), 2.65 (m, 4H), 1.66 (m, 4H), 1.64 (m, 2H), 1.38 (s, 9H).

EXAMPLE 333

2-({[2-({3-[(tert-butoxycarbonyl)(methyl)amino]propyl}amino)phenyl]sulfonyl}amino)-5,6,7,8-tetrahydro-1-naphthalenecarboxylic acid The desired product was prepared by substituting tert-butyl 3-aminopropyl(methyl)carbamate for 3-(N,N-diethylamino)propylamine in Example 229B. MS (ESI(+)) m/e 518 $(M+H)^+$, 540 $(M+Na)^+$; (ESI(−)) m/e 516 $(M-H)^-$; $^1H$ NMR (300 MHz, DMSO-$d_6$) δ 7.49 (dd, 1H), 7.38 (dt, 1H), 6.94 (d, 1H), 6.75 (d, 1H), 6.60 (m, 2H), 5.89 (m, 1H), 3.19 (m, 2H), 3.10 (m, 2H), 2.76 (s, 3H), 2.65 (m, 4H), 1.71 (m, 2H), 1.66 (m, 4H), 1.36 (s, 9H).

EXAMPLE 334

2-({[2-({3-[(2-hydroxyethyl)amino]propyl}amino)phenyl]sulfonyl}amino)-5,6,7,8-tetrahydro-1-naphthalenecarboxylic acid The desired product was prepared by substituting 2-[(3-aminopropyl)amino]ethanol for 3-(N,N-diethylamino)propylamine in Example 229B. MS (ESI(+)) m/e 448 $(M+H)^+$; (ESI(−)) m/e 446 $(M-H)^-$; $^1H$ NMR (300 MHz, DMSO-$d_6$) δ 7.51 (dd, 1H), 7.41 (dt, 1H), 6.95 (d, 1H), 6.84 (d, 1H), 6.64 (m, 2H), 6.00 (m, 1H), 3.63 (t, 2H), 3.28 (m, 2H), 2.96 (m, 4H), 2.65 (m, 4H), 1.89 (m, 2H), 1.67 (m, 4H).

EXAMPLE 335

2-[({2-[(3-aminopropyl)amino]phenyl}sulfonyl)amino]-5,6,7,8-tetrahydro-1-naphthalenecarboxylic acid Example 332 (0.035 g, 0.070 mmol) was dissolved in saturated HCl/dioxane (2 mL), stirred for 1 hour, concentrated, treated with diethyl ether, then concentrated to provide the desired product. MS (ESI(+)) m/e 404 $(M+H)^+$, 426 $(M+Na)^+$; (ESI(−)) m/e 402 $(M-H)^-$; $^1H$ NMR (300 MHz, DMSO-$d_6$) δ 7.48 (dd, 1H), 7.41 (dt, 1H), 6.95 (d, 1H), 6.84 (d, 1H), 6.60 (m, 2H), 5.98 (m, 1H), 3.28 (m, 2H), 2.85 (m, 2H), 2.65 (m, 4H), 1.84 (m, 2H), 1.67 (m, 4H).

EXAMPLE 336

2-{[(2-{[3-(methylamino)propyl]amino}phenyl)sulfonyl]amino}-5,6,7,8-tetrahydro-1-naphthalenecarboxylic acid The desired product was prepared by substituting Example 333 for Example 332 in Example 335. MS (ESI(+)) m/e 418 $(M+H)^+$; (ESI(−)) m/e 416 $(M-H)^-$; $^1H$ NMR (300 MHz, DMSO-$d_6$) δ 7.50 (dd, 1H), 7.41 (dt, 1H), 6.96 (d, 1H), 6.83 (d, 1H), 6.63 (m, 2H), 5.99 (m, 1H), 3.57 (s, 3H), 3.27 (m, 2H), 2.94 (m, 2H), 2.65 (m, 4H), 1.87 (m, 2H), 1.67 (m, 4H).

EXAMPLE 337

6-{[(4-fluorophenyl)sulfonyl]amino}-2-methoxy-3-vinylbenzoic acid

EXAMPLE 337A benzyl 3-bromo-6-{[(4-fluorophenyl)sulfonyl]amino}-2-methoxybenzoate The desired product was prepared by substituting Example 318B and 4-fluorobenzenesulfonyl chloride for Example 126B and 3-fluorobenzenesulfonyl chloride, respectively, in Example 126C. MS (ESI(+)) m/e 494, 496 $(M+H)^+$, 511, 513 $(M+NH_4)^+$, 516, 518 $(M+Na)^+$; (ESI(−)) m/e 492, 494 $(M-H)^-$; $^1H$ NMR (300 MHz, DMSO-$d_6$) δ 10.23 (s, 1H), 7.73 (m, 2H), 7.66 (d, 1H), 7.42 (m, 7H), 6.86 (d, 1H), 5.26 (s, 2H), 3.63 (s, 3H).

EXAMPLE 337B

6-{[(4-fluorophenyl)sulfonyl]amino}-2-methoxy-3-vinylbenzoic acid

The desired product was prepared by substituting Example 337A for Example 226E in Example 226F with the heating time increased to 300 seconds. MS (ESI(+)) m/e 352 $(M+H)^+$, 369 $(M+NH_4)^+$; (ESI(−)) m/e 350 $(M-H)^-$; $^1H$ NMR (300 MHz, DMSO-$d_6$) δ 13.23 (br s, 1H), 9.93 (s, 1H), 7.80 (m, 2H), 7.60 (d, 1H), 7.41 (m, 2H), 6.84 (m, 2H), 5.85 (d, 1H), 5.38 (d, 1H), 3.66 (s, 3H).

EXAMPLE 338

2-[({2-[({[2-(diethylamino)ethyl]amino}carbonyl)amino]phenyl}sulfonyl)amino]-5,6,7,8-tetrahydro-1-naphthalenecarboxylic acid A mixture of Example 294 (30.2 mg, 0.09 mmol), triphosgene (8.5 mg, 0.03 mmol), and pyridine (1 mL) was stirred for 3 hours at 70° C., treated with N,N-diethylethylenediamine (61 μL, 0.44 mmol), stirred for 18 hours at 70° C., concentrated, and purified by $C_{18}$ reverse-phase HPLC using acetonitrile/water/0.1% TFA to provide the desired product (2.0 mg, 5%). MS (ESI(+)) m/e 489 $(M+H)^+$; MS (ESI(−)) m/e 487 $(M-H)^-$; $^1H$ NMR (300 MHz, DMSO-$d_6$) δ 8.27 (s, 1H), 8.18 (d, 1H), 7.69 (dd, 1H), 7.53 (td, 1H), 7.47 (m, 1H), 7.10 (t, 1H), 6.95 (d, 1H), 6.65 (s, 1H), 3.19 (m, 6H), 2.66 (m, 4H), 1.66 (m, 4H), 1.20 (t, 6H).

EXAMPLE 339

2-({[2-({[2-(diethylamino)ethoxy]carbonyl}amino)phenyl]sulfonyl}amino)-5,6,7,8-tetrahydro-1-naphthalenecarboxylic acid A mixture of Example 294 (36.7 mg, 0.11 mmol), triphosgene (10.4 mg, 0.033 mmol), and pyridine (1 mL) was stirred for 3 hours at 70° C., treated with 2-(diethylamino)ethanol (70 μL, 0.53 mmol), stirred for 18 hours at 70° C., concentrated, and purified by $Cl_{18}$ reverse-phase HPLC using acetonitrile/water/0.1% TFA to provide the desired product (4.5 mg, 9%). MS (ESI(+)) m/e 490 $(M+H)^+$; MS (ESI(−)) m/e 488 $(M-H)^-$; $^1H$ NMR (300 MHz, DMSO-$d_6$) δ 8.80 (s, 1H), 8.04 (d, 1H), 7.74 (dd, 1H), 7.64 (m, 1H), 7.24 (t, 1H), 6.97 (d, 1H), 6.65 (m, 1H), 4.40 (t, 2H), 3.20 (q, 6H), 2.56 (m, 4H), 1.66 (m, 4H), 1.20 (t, 6H).

EXAMPLE 340

8-methyl-2-{[(2-{[3-(1-pyrrolidinyl)propyl]amino}phenyl)sulfonyl]amino}-5,6,7,8-tetrahydro-1-naphthalenecarboxylic acid The desired product was prepared by substituting Example 275F and 3-(1-pyrrolidinyl)propylamine for Example 275E and N,N-dimethylethylenediamine, respectively, in Example 275G. MS (ESI) m/e 470 $(M-H)^-$; $^1H$ NMR (300 MHz, DMSO-$d_6$) δ 9.45 (br s, 1H), 7.52 (dd, 1H), 7.42 (dt, 1H), 6.93 (d, 1H), 6.84 (d, 1H), 6.66 (t, 1H), 6.59 (d, 1H), 6.0 (t, 1H), 3.27 (q, 4H), 3.18 (m, 2H), 2.97 (m, 2H), 2.73-2.61 (m, 2H), 1.95-1.85 (m, 6H), 1.76-1.61 (m, 4H), 1.1 (d, 3H).

EXAMPLE 341

8-methyl-2-{[(2-{[3-(4-methyl-1-piperazinyl)propyl]amino}phenyl)sulfonyl]amino}-5,6,7,8-tetrahydro-1-naphthalenecarboxylic acid The desired product was prepared by substituting Example 275F (50 mg, 0.133 mmol) and 1-(3-aminopropyl)-4-methylpiperazine (125 μL, 0.8 mmol) for Example 275E and N,N-dimethlethylenediamine, respectively, in Example 275G. MS (ESI(+)) m/e 501 $(M+H)^+$; MS (ESI(−)) m/e 499 $(M-H)^-$; $^1H$ NMR (300 MHz, DMSO-$d_6$) δ 9.41 (s, 1H), 7.50 (d, 1H), 7.40 (t, 1H), 6.95 (d, 1H), 6.81 (d, 1H), 6.60-6.66 (m, 2H), 6.01 (s, 1H), 3.14-3.35 (m, 6H), 2.61-2.86 (m, 10H), 1.62-1.82 (m, 6H), 1.07-1.11 (m, 3H).

EXAMPLE 342

2-{[(2-{[3-(diethylamino)propyl]amino}phenyl)sulfonyl]amino}-8-methyl-5,6,7,8-tetrahydro-1-naphthalenecarboxylic acid The desired product was prepared by substituting Example 275F (50 mg, 0.133 mmol) and 3-N,N-diethylaminopropylamine (168 μL, 1.06 mmol) for Example 275E and N,N-dimethylethylenediamine, respectively, in Example 275G. MS (ESI(+)) m/e 474 $(M+H)^+$, 496 $(M+Na)^+$; MS (ESI(−)) m/e 472 $(M-H)^-$; $^1H$ NMR (300 MHz, DMSO-$d_6$) δ 9.49 (s, 1H), 7.52 (dd, 1H), 7.42 (t, 1H), 6.93 (d, 1H), 6.86 (d, 1H), 6.59-6.68 (m, 2H), 6.03 (t, 1H), 3.27-3.32 (m, 3H), 3.05-3.17 (m, 5H), 2.54-2.73 (m, 2H), 1.83-1.95 (m, 2H), 1.61-1.75 (m, 3H), 1.09-1.16 (m, 6H).

EXAMPLE 343

8-methyl-2-({[2-({3-[2-methyl-1-piperidinyl]propyl}amino)phenyl]sulfonyl}amino)-5,6,7,8-tetrahydro-1-naphthalenecarboxylic acid The desired product was prepared by substituting Example 275F (50 mg, 0.133 mmol) and 1-(3-aminopropyl)-2-pipecoline (140 μL, 0.8 mmol) for Example 275E and N,N-dimethylethylenediamine, respectively, in Example 275G. MS (ESI(+)) m/e 500 $(M+H)^+$; MS (ESI(−)) m/e 498 $(M-H)^-$; $^1H$ NMR (300 MHz, DMSO-$d_6$) δ 9.42 (s, 1H), 8.99 (br s, 1H), 7.53 (d, 1H), 7.43 (t, 1H), 6.94 (d, 1H), 6.88 (d, 1H), 6.66 (t, 1H), 6.56 (d, 1H), 6.03 (br t, 1H), 3.57-3.90 (m, 5H), 3.33-3.42 (m, 2H), 2.98-3.14 (m, 2H), 2.83-2.92 (m, 1H), 2.61-2.75 (m, 2H), 1.37-1.97 (m, 13H), 1.10-1.20 (m, 6H)

EXAMPLE 344

(8R)-8-methyl-2-({[2-({2-[1-methyl-2-pyrrolidinyl]ethyl}amino)phenyl]sulfonyl}amino)-5,6,7,8-tetrahydro-1-naphthalenecarboxylic acid Example 275F was separated into individual enantiomers by preparative column chromatography (Chiralpak AS 5 cm×30 cm; mobile phase: 20:80 ethyl alcohol/hexanes; Flow rate 30 mL/min) to obtain pure enatiomer respectively. The desired product was prepared by substituting the first enantiomer (50 mg, 0.133 mmol) and 2-(2-aminoethyl)-1-methylpyrrolidine (154 μL, 1.06 mmol) for Example 275E and N,N-dimethylethylenediamine, respectively, in Example 275G. MS (ESI(+)) m/e 472 $(M+H)^+$; MS (ESI(−)) m/e 470 $(M-H)^-$; $^1$H NMR (300 MHz, DMSO-$d_6$) δ 9.42 (s, 2H), 7.53 (dd, 1H), 7.43 (t, 1H), 6.94 (d, 1H), 6.86 (d, 1H), 6.67 (t, 1H), 6.54 (d, 1H), 5.99 (t, 1H), 3.18-3.31 (m, 4H), 2.92-3.08 (m, 2H), 2.54-2.83 (m, 4H), 2.04-2.34 (m, 3H), 1.82-1.97 (m, 2H), 1.58-1.80 (m, 6H), 1.11 (d, 3H).

EXAMPLE 345

2-{[(2-{[3-(dimethylamino)-2,2-dimethylpropyl]amino}phenyl)sulfonyl]amino}-8-methyl-5,6,7,8-tetrahydro-1-naphthalenecarboxylic acid The desired product was prepared by substituting Example 275F and 3-N,N-dimethylamino-2,2-dimethylpropylamine for Example 275E and N,N-dimethylethylenediamine, respectively, in Example 275G. MS (ESI) m/e 472 $(M-H)^-$; $^1$H NMR (300 MHz, DMSO-$d_6$) δ 7.53 (dd, 1H), 7.4 (dt, 1H), 6.93 (t, 2H), 6.68 (t, 1H), 6.53 (d, 1H), 5.96 (br s, 1H), 3.3 (m, 1H), 3.08 (s, 4H), 2.83 (s, 6H), 2.76-2.59 (m, 2H), 1.73-1.65 (m, 4H), 1.1 (d, 3H), 0.99 (d, 6H).

EXAMPLE 346

2-{[(2-{[4-(1-pyrrolidinyl)butanoyl]amino}phenyl)sulfonyl]amino}-5,6,7,8-tetrahydro-1-naphthalenecarboxylic acid The desired product was prepared by substituting 4-chlorobutanoyl chloride and pyrroldine for chloroacetyl chloride and diethylamine, respectively, in Example 297. MS (ESI(+)) m/e 486 $(M+H)^+$; MS (ESI(−)) m/e 484 $(M-H)^-$; $^1$H NMR (300 MHz, DMSO-$d_6$) δ 9.18 (s, 1H), 8.15 (d, 1H), 7.71 (dd, 1H), 7.62 (ddd, 1H), 7.25 (td, 1H), 6.96 (d, 1H), 6.54 (d, 1H), 3.17 (m, 3H), 3.01 (m, 1H), 2.67 (m, 4H), 2.46 (m, 2H), 1.92 (m, 6H), 1.67 (m, 4H).

EXAMPLE 347

2-({[2-({4-[2-methyl-1-pyrrolidinyl]butanoyl}amino)phenyl]sulfonyl}amino)-5,6,7,8-tetrahydro-1-naphthalenecarboxylic acid The desired product was prepared by substituting 4-chlorobutanoyl chloride and 2-methylpyrrolidine for chloroacetyl chloride and diethylamine, respectively, in Example 297. MS (ESI(+)) m/e 500 $(M+H)^+$; MS (ESI(−)) m/e 498 $(M-H)^-$; $^1$H NMR (300 MHz, DMSO-$d_6$) δ 9.20 (s, 1H), 8.13 (d, 1H), 7.71 (dd, 1H), 7.63 (ddd, 1H), 7.26 (td, 1H), 6.97 (d, 1H), 6.51 (d, 1H), 3.09 (m, 2H), 2.96 (m, 1H), 2.66 (m, 4H), 2.47 (m, 2H), 2.20 (m, 2H), 1.93 (m, 4H), 1.67 (m, 6H), 1.33 (d, 3H).

EXAMPLE 348

2-({[2-({4-[2,5-dimethyl-1-pyrrolidinyl]butanoyl}amino)phenyl]sulfonyl}amino)-5,6,7,8-tetrahydro-1-naphthalenecarboxylic acid The desired product was prepared by substituting 4-chlorobutanoyl chloride and 2,5-dimethylpyrrolidine for chloroacetyl chloride and diethylamine, respectively, in Example 297. MS (ESI(+)) m/e 514 $(M+H)^+$; MS (ESI(−)) m/e 512 $(M-H)^-$; $^1$H NMR (300 MHz, DMSO-$d_6$) δ 9.23 (s, 1H), 8.12 (d, 1H), 7.71 (dd, 1H), 7.63 (ddd, 1H), 7.26 (td, 1H), 6.96 (d, 1H), 6.51 (d, 1H), 355 (m, 1H), 3.17 (m, 1H), 2.67 (m, 4H), 2.48 (m, 2H), 2.16 (m, 2H), 1.93 (m, 2H), 1.67 (m, 6H), 1.35 (d, 6H).

EXAMPLE 349

2-{[(2-{[4-(1-piperidinyl)butanoyl]amino}phenyl)sulfonyl]amino}-5,6,7,8-tetrahydro-1-naphthalenecarboxylic acid The desired product was prepared by substituting 4-chlorobutanoyl chloride and piperidine for chloroacetyl chloride and diethylamine, respectively, in Example 297. MS (ESI(+)) m/e 500 $(M+H)^+$; MS (ESI(−)) m/e 498 $(M-H)^-$; $^1$H NMR (300 MHz, DMSO-$d_6$) δ 9.19 (s, 1H), 8.15 (d, 1H), 7.71 (dd, 1H), 7.62 (td, 1H), 7.26 (td, 1H), 6.96 (d, 1H), 6.53 (d, 1H), 3.46 (m, 2H), 3.07 (m, 2H), 2.87 (m, 2H), 2.67 (m, 4H), 2.46 (m, 2H), 1.94 (m, 2H), 1.79 (m, 2H), 1.67 (m, 7H), 1.40 M, 1H).

EXAMPLE 350

2-({[2-({4-[(2)-2-methyl-1-piperidinyl]butanoyl}amino)phenyl]sulfonyl}amino)-5,6,7,8-tetrahydro-1-naphthalenecarboxylic acid The desired product was prepared by substituting 4-chlorobutanoyl chloride and 2-methylpiperidine for chloroacetyl chloride and diethylamine, respectively, in Example 297. MS (ESI(+)) m/e 514 $(M+H)^+$; MS (ESI(−)) m/e 512 $(M-H)^-$; $^1$H NMR (300 MHz, DMSO-$d_6$) δ 9.19 (s, 1H), 8.12 (d, 1H), 7.72 (d, 1H), 7.62 (m, 1H), 7.26 (t, 1H), 6.95 (d, 1H), 6.55 (d, 1H), 3.20 (m, 3H), 3.04 (m, 1H), 2.67 (m, 4H), 2.48 (m, 2H), 1.91 (m, 3H), 1.67 (m, 6H), 1.48 (m, 1H), 1.28 (m, 3H).

EXAMPLE 351

2-({[2-({4-[(3)-3-methyl-1-piperidinyl]butanoyl}amino)phenyl]sulfonyl}amino)-5,6,7,8-tetrahydro-1-naphthalenecarboxylic acid The desired product was prepared by substituting 4-chlorobutanoyl chloride and 3-methylpiperidine for chloroacetyl chloride and diethylamine, respectively, in Example 297. MS (ESI(+)) m/e 514 $(M+H)^+$; MS (ESI(−)) m/e 512 $(M-H)^-$; $^1$H NMR (300 MHz, DMSO-$d_6$) δ 9.19 (s, 1H), 8.14 (d, 1H), 7.71 (dd, 1H), 7.62 (ddd, 1H), 7.25 (td, 1H), 6.95 (d, 1H), 6.53 (d, 1H), 3.40 (m, 4H), 3.07 (m, 2H), 2.66 (m, 4H), 2.46 (m, 2H), 1.96 (m, 2H), 1.81 (m, 2H), 1.67 (m, 4H), 1.08 (d, 3H).

EXAMPLE 352

2-{[(2-{[4-(4-methyl-1-piperidinyl)butanoyl]amino}phenyl)sulfonyl]amino}-5,6,7,8-tetrahydro-1-naphthalenecarboxylic acid The desired product was prepared by substituting 4-chlorobutanoyl chloride and 4-methylpiperidine for chloroacetyl chloride and diethylamine, respectively, in Example 297. MS (ESI(+)) m/e 514 $(M+H)^+$; MS (ESI(−)) m/e 512 $(M-H)^-$; $^1$H NMR (300 MHz, DMSO-$d_6$) δ 9.18 (s, 1H), 8.14 (d, 1H), 7.72 (dd, 1H), 7.62 (ddd, 1H), 7.25 (td, 1H), 6.95 (d, 3H), 6.55 (d, 1H), 3.45 (m, 2H), 3.11 (m, 2H), 2.89 (m, 2H), 2.67 (m, 4H), 2.47 (m, 2H), 1.95 (m, 2H), 1.80 (m, 2H), 1.67 (m, 4H), 1.33 (m, 1H), 0.92 (d, 3H).

EXAMPLE 353

2-({[2-({4-[(2R)-2-ethyl-1-piperidinyl] butanoyl}amino)phenyl]sulfonyl}amino)-5,6,7,8-tetrahydro-1-naphthalenecarboxylic acid The desired product was prepared by substituting 4-chlorobutanoyl chloride and (2R)-2-ethylpiperidine for chloroacetyl chloride and diethylamine, respectively, in Example 297. MS (ESI(+)) m/e 528 $(M+H)^+$; MS (ESI(−)) m/e 526 $(M-H)^-$; $^1H$ NMR (300 MHz, DMSO-$d_6$) δ 9.20 (s, 1H), 8.12 (d, 1H), 7.71 (dd, 1H), 7.62 (t, 1H), 7.26 (t, 1H), 6.95 (d, 1H), 6.54 (m, 1H), 3.08 (m, 5H), 2.66 (m, 4H), 2.27 (m, 1H), 1.93 (m, 3H), 1.67 (m, 9H), 1.46 (m, 1H), 0.90 (t, 3H).

EXAMPLE 354

2-{[(2-{[4-(1-azepanyl)butanoyl]amino}phenyl)sulfonyl]amino}-5,6,7,8-tetrahydro-1-naphthalenecarboxylic acid The desired product was prepared by substituting 4-chlorobutanoyl chloride and azepane for chloroacetyl chloride and diethylamine, respectively, in Example 297. MS (ESI(+)) m/e 514 $(M+H)^+$; MS (ESI(−)) m/e 512 $(M-H)^-$; $^1H$ NMR (300 MHz, DMSO-$d_6$) δ 9.20 (s, 1H), 8.13 (d, 1H), 7.71 (dd, 1H), 7.62 (ddd, 1H), 7.26 (td, 1H), 6.95 (d, 1H), 6.53 (d, 1H), 3.86 (m, 2H), 3.12 (m, 4H), 2.66 (m, 4H), 2.45 (t, 2H), 1.95 (m, 2H), 1.79 (m, 4H), 1.67 (m, 4H), 1.61 (m, 4H).

EXAMPLE 356

7,8-dimethyl-2-{[(2-{[3-(1-pyrrolidinyl)propyl] amino}phenyl)sulfonyl]amino}-5,8-dihydro-1-naphthalenecarboxylic acid

EXAMPLE 356A

N-(1-bromo-7,8-dimethyl-5,8-dihydro-2-naphthalenyl)-2-fluorobenzenesulfonamide

The desired product was prepared by substituting Example 287A for Example 275C in Example 275D. MS (ESI) m/e 409 $(M-H)^-$; $^1H$ NMR (300 MHz, DMSO-$d_6$) δ 10.1 (s, 1H), 7.7 (m, 1H), 7.63 (dt, 1H), 7.42 (m, 1H), 7.3 (dt, 1H), 7.12 (d, 1H), 6.98 (d, 1H), 5.58 (m, 1H), 3.35 (m, 2H), 3.21 (m, 1H), 1.8 (s, 3H), 1.07 (d, 3H).

EXAMPLE 356B methyl 2-{[(2-fluorophenyl)sulfonyl]amino}-7,8-dimethyl-5,8-dihydro-1-naphthalenecarboxylate The desired product was prepared according to the procedure of Example 275E substituting Example 356A for 275D. MS (ESI) m/e 388 $(M-H)^-$; $^1H$ NMR (300 MHz, DMSO-$d_6$) δ 10.02 (s, 1H), 7.7 (m, 1H), 7.63 (dt, 1H), 7.43 (m, 1H), 7.31 (dt, 1H), 7.18 (d, 1H), 6.94 (d, 1H), 5.6 (m, 1H), 3.68 (s, 3H), 3.23 (m, 3H), 1.76 (s, 3H), 1.04 (d, 3H).

EXAMPLE 356C 7,8-dimethyl-2-{[(2-{[3-(1-pyrrolidinyl)propyl] amino}phenyl)sulfonyl]amino}-5,8-dihydro-1-naphthalenecarboxylic acid The desired product was prepared according to the procedure of Example 275G substituting Example 356B for 275E and 3-(1-pyrrolidinyl)propylamine for N,N-dimethylethylenediamine. MS (ESI) m/e 482 $(M-H)^-$; $^1H$ NMR (300 MHz, DMSO-$d_6$) δ 9.5 (br d, 1H), 7.72 (dd, 1H), 7.53 (m, 1H), 7.42 (dt, 1H), 7.05 (d, 1H), 6.84 (d, 1H), 6.65 (t, 1H), 6.0 (t, 1H), 5.60 (m, 1H), 3.26 (m, 3H), 3.18 (m, 3H), 2.94 (m, 3H), 2.38 (d, 2H), 1.99-1.86 (m, 6H), 1.1 (d, 3H).

EXAMPLE 357

7,8-dimethyl-2-({[2-({2-[1-methyl-2-pyrrolidinyl] ethyl}amino)phenyl]sulfonyl}amino)-5,8-dihydro-1-naphthalenecarboxylic acid The desired product was prepared according to the procedure of Example 275G substituting Example 356B for 275E and 2-(1-methyl-2-pyrrolidinyl)ethylamine for N,N-dimethylethylenediamine. MS (ESI) m/e 482 $(M-H)^-$; $^1H$ NMR (300 MHz, DMSO-$d_6$) δ 9.46 (br d, 1H), 7.7 (t, 1H), 7.53 (m, 1H), 7.42 (t, 1H), 7.05 (d, 1H), 6.84 (m, 1H), 6.66 (m, 1H), 6.0 (m, 1H), 5.60 (m, 1H), 3.53 (m, 1H), 3.25 (m, 4H), 3.02 (m, 1H), 2.76 (d, 3H), 2.38 (d, 2H), 2.28-2.08 (m, 2H), 1.91 (m, 2H), 1.79 (s, 3H), 1.68 (m, 2H), 1.1 (d, 3H).

EXAMPLE 358

2-[({2-[(1-benzyl-4-piperidinyl)amino] phenyl}sulfonyl)amino]-5,6,7,8-tetrahydro-1-naphthalenecarboxylic acid The desired product was prepared by substituting 4-amino-1-benzylpiperidine for 3-(N,N-diethylamino)propylamine in Example 229B. MS (ESI(+)) m/e 520 $(M+H)^+$; MS (ESI(−)) m/e 518 $(M-H)^-$; $^1H$ NMR (300 MHz, DMSO-$d_6$) δ 9.63 (s, 1H), 7.51 (m, 6H), 7.37 (m, 1H), 6.93 (d, 1H), 6.89 (d, 1H), 6.65 (m, 1H), 6.55 (d, 1H), 5.72 (d, 1H), 4.33 (m, 1H), 3.96 (s, 2H), 3.44 (m, 2H), 3.06 (m, 2H), 2.65 (m, 4H), 211 (m, 2H), 1.96 (m, 2H), 1.65 (m, 4H).

EXAMPLE 359

2-[({2-[(1,2,2,6,6-pentamethyl-4-piperidinyl)amino] phenyl}sulfonyl)amino]-5,6,7,8-tetrahydro-1-naphthalenecarboxylic acid The desired product was prepared by substituting 4-amino-1,2,2,6,6-pentamethylpiperidine for 3-(N,N-diethylamino) propylamine in Example 229B. MS (ESI(+)) m/e 500 $(M+H)^+$; MS (ESI(−)) m/e 498 $(M-H)^-$; $^1H$ NMR (300 MHz, DMSO-$d_6$) δ 9.68 (s, 1H), 8.45 (s, 1H), 7.52 (dd, 1H), 7.42 (ddd, 1H), 6.94 (d, 1H), 6.68 (t, 1H), 6.50 (d, 1H), 5.70 (d, 1H), 3.99 (m, 1H), 2.75 (s, 3H), 2.67 (m, 4H), 2.10 (m, 2H), 1.68 (m, 4H), 1.57 (t, 2H), 1.46 (s, 6H), 1.40 (s, 6H).

EXAMPLE 360

3-ethyl-2-methoxy-6-[(2-pyridinylsulfonyl)amino] benzoic acid

EXAMPLE 360A benzyl 3-bromo-2-methoxy-6-[(2-pyridinylsulfonyl) amino]benzoate

The desired product was prepared by substituting Example 318B for Example 126B and 2-pyridinesulfonyl chloride for 3-fluorobenzenesulfonyl chloride in Example 126C. MS (ESI (+)) m/e 477, 479 $(M+H)^+$, 494, 496 $(M+NH_4)^+$, 499, 501 $(M+Na)^+$; (ESI(−)) m/e 475, 477 $(M-H)^-$; $^1H$ NMR (300 MHz, DMSO-$d_6$) δ 10.37 (s, 1H), 8.07 (m, 1H), 8.07 (m, 1H), 7.91 (d, 1H), 7.67 (m, 2H), 7.40 (m, 5H), 6.97 (d, 1H), 5.27 (s, 2H), 3.64 (s, 3H).

EXAMPLE 360B benzyl 2-methoxy-6-[(2-pyridinylsulfonyl)amino]-3-vinylbenzoate

The desired product was prepared by substituting Example 360A for Example 226E in Example 226F with the heating time increased to 300 seconds. MS (ESI(+)) m/e 425 $(M+H)^+$, 442 $(M+NH_4)^+$, 447 $(M+Na)^+$; (ESI(−)) m/e 423 $(M-H)^-$; $^1H$ NMR (300 MHz, DMSO-$d_6$) δ 10.23 (s, 1H), 8.72 (m, 1H), 8.06 (dt, 1H), 7.91 (d, 1H), 7.66 (m, 1H), 7.60 (d, 1H), 7.40 (m, 5H), 6.98 (d, 1H), 6.78 (dd, 1H), 5.82 (d, 1H), 5.35 (d, 1H), 5.26 (s, 2H), 3.55 (s, 3H)

EXAMPLE 360C 3-ethyl-2-methoxy-6-[(2-pyridinylsulfonyl)amino]benzoic acid

The desired product was prepared by substituting Example 360B for Example 226F in Example 226G with purification by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min. MS (ESI(+)) m/e 337 $(M+H)^+$, 354 $(M+NH_4)^+$, 359 $(M+Na)^+$; (ESI(−)) m/e 335 $(M-H)^-$; $^1H$ NMR (300 MHz, DMSO-$d_6$) δ 13.20 (br s, 1H), 9.84 (br s. 1H), 8.70 (d, 1H), 8.04 (m, 1H), 7.87 (d, 1H), 7.65 (m, 1H), 7.20 (d, 1H), 6.89 (d, 1H), 3.67 (s, 3H), 2.54 (q, 2H), 1.10 (t, 3H).

EXAMPLE 361

3-ethyl-6-{[(4-fluorophenyl)sulfonyl]amino}-2-methoxybenzoic acid

EXAMPLE 361A benzyl 6-{[(4-fluorophenyl)sulfonyl]amino}-2-methoxy-3-vinylbenzoate The desired product was prepared by substituting Example 337A for Example 226E in Example 226F with the heating time increased to 300 seconds. MS (ESI(+)) m/e 442 $(M+H)^+$, 459 $(M+NH_4)^+$, 464 $(M+Na)^+$; (ESI(−)) m/e 440 $(M-H)^-$; $^1H$ NMR (300 MHz, DMSO-$d_6$) δ 10.10 (s, 1H), 7.75 (m, 2H), 7.61 (d, 1H), 7.36 (m, 7H), 6.90 (d, 1H), 6.78 (dd, 1H), 5.82 (d, 1H), 5.36 (d, 1H), 5.25 (s, 2H), 3.54 (s, 3H).

EXAMPLE 361B 3-ethyl-6-{[(4-fluorophenyl)sulfonyl]amino}-2-methoxybenzoic acid

The desired product was prepared by substituting Example 361A for Example 226F in Example 226G with purification by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min. MS (ESI(+)) m/e 354 $(M+H)^+$, 371 $(M+NH_4)^+$, 376 $(M+Na)^+$; (ESI(−)) m/e 352 $(M-H)^-$; $^1H$ NMR (300 MHz, DMSO-$d_6$) δ 13.07 (br s, 1H), 9.68 (s, 1H), 7.74 (m, 2H), 7.34 (m, 2H), 7.14 (d, 1H), 6.68 (d, 1H), 3.62 (s, 3H), 2.50 (q, 2H), 1.07 (t, 3H).

EXAMPLE 362

2-{[(2-{[3-(dimethylamino)-2,2-dimethylpropyl]amino}phenyl)sulfonyl]amino}-7,7-dimethyl-8-oxo-5,6,7,8-tetrahydro-1-naphthalenecarboxylic acid

EXAMPLE 362A 2,2-dimethyl-7-nitro-3,4-dihydro-1(2H)-naphthalenone

A mixture of 7-nitro 1-tetralone (1.91 g, 10 mmol) in 15 mL of THF was cooled to −78° C., treated dropwise with 2M lithium diisopropylamine (15 mL, 30 mmol), stirred at −78° C. for 15 minutes, treated with methyl iodide (3.11 mL, 50 mmol), stirred at −78° C. for 10 minutes, warmed to room temperature, and stirred overnight. The mixture was quenched with 10% ammonium chloride and treated with ethyl acetate. The organic phase was washed with brine, dried ($Na_2SO_4$), filtered, and concentrated under reduced pressure. The crude product was purified by silica gel column chromatography eluting with 10% ethyl acetate in n-hexane to provide the desired product. MS (ESI(−)) m/e 218 $(M-H)^-$; $^1H$ NMR (300 MHz, DMSO-$d_6$) δ 8.56 (d, 1H), 8.34-8.38 (d, 1H), 7.67 (d, 1H), 3.11 (t, 2H), 1.99 (t, 2H), 1.16 (s, 6H).

EXAMPLE 362B 7-amino-8-bromo-2,2-dimethyl-3,4-dihydro-1(2H)-naphthalenone

A mixture of Example 362A (1.05 g, 4.79 mmol) in 4:1 ethanol/water (20 mL) was reduced with iron (1.1 g) in the presence of ammonium chloride (0.12 g) using the procedure described in Example 275A. The crude product (0.91 g, 4.79 mmol) was treated with bromine (0.245 mL, 4.79 mmol) in 9 mL of chloroform and 0.9 mL of N,N-dimethylformamide following the procedure described in Example 275B. The obtained hydrobromide salt was treated with 10% sodium hydrogen carbonate in ethyl acetate. The ethyl acetate layer was washed with brine (4×), dried ($Na_2SO_4$), filtered, and concentrated. The residue was purified by silica gel column chromatography eluting with 10% ethyl acetate in n-hexane to provide 730 mg of the desired product. MS (ESI(−)) m/e 266 $(M-H)^-$; $^1H$ NMR (300 MHz, DMSO-$d_6$) δ 6.97 (m, 2H), 5.39 (m, 2H), 2.80 (t, 2H), 1.84 (t, 2H), 1.10 (s, 6H).

EXAMPLE 362C

N-(1-bromo-7,7-dimethyl-8-oxo-5,6,7,8-tetrahydro-2-naphthalenyl)-2-fluorobenzenesulfonamide A mixture of Example 362B (730 mg, 2.72 mmol) and 2-fluorobenzenesulfonyl chloride (0.396 mL, 2.99 mmol) in pyridine (2.20 mL, 27.2 mmol) and dichloromethane (10 mL) was reacted as described in Example 275C to yield 0.98 g of the desired compound. MS (ESI(−)) m/e 425 $(M-H)^-$; $^1H$ NMR (300 MHz, DMSO-$d_6$) δ 10.21 (s, 1H), 7.63-7.72 (m, 2H), 7.41 (t, 1H), 7.26-7.35 (m, 3H), 2.93 (t, 2H), 1.86 (t, 2H), 1.08 (s, 6H).

EXAMPLE 362D methyl 2-{[(2-fluorophenyl)sulfonyl]amino}-7,7-dimethyl-8-oxo-5,6,7,8-tetrahydro-1-naphthalenecarboxylate The desired product (200 mg) was prepared by substituting Example 362C (300 mg) for Example 275D in Example 275E. MS (ESI(+)) m/e 423 $(M+NH_4)^+$m/e 428 $(M+Na)^+$; MS (ESI(−)) m/e 404 $(M-H)^-$; $^1H$ NMR (300 MHz, DMSO-$d_6$) δ 10.15 (s, 1H), 7.63-7.72 (m, 2H), 7.28-7.47 (m, 4H), 3.53 (s, 3H), 2.93 (t, 2H), 1.89 (t, 2H), 1.07 (s, 6H).

EXAMPLE 362E

2-{[(2-{[3-(dimethylamino)-2,2-dimethylpropyl]amino}phenyl)sulfonyl]amino}-7,7-dimethyl-8-oxo-5,6,7,8-tetrahydro-1-naphthalenecarboxylic acid The desired product was prepared by substituting Example 362D (50 mg, 0.133 mmol) and N,N,2,2-tetramethyl-1,3-propanediamine (168 μL, 1.06 mmol) for Example 275E and N,N-dimethylethylenediamine, respectively, in Example 275G. MS (ESI(+)) m/e 502 $(M+H)^+$; MS (ESI(−)) m/e 500 $(M-H)^-$; $^1$H NMR (300 MHz, DMSO-$d_6$) δ 9.64 (s, 1H), 8.97 (s, 1H), 7.55 (dd, 1H), 7.42 (dt, 1H), 7.26 (d, 1H), 7.05 (d, 1H), 6.96 (d, 1H), 6.88 (t, 1H), 5.97 (br t, 1H), 3.12-3.15 (m, 4H), 2.89-2.97 (m, 2H), 2.84 (s, 6H), 1.87-1.91 (m, 2H), 1.10 (s, 6H), 1.03 (s, 6H).

EXAMPLE 363

7,7-dimethyl-2-({[2-({2-[1-methyl-2-pyrrolidinyl]ethyl}amino)phenyl]sulfonyl}amino)-8-oxo-5,6,7,8-tetrahydro-1-naphthalenecarboxylic acid The desired product was prepared by substituting Example 362D (50 mg, 0.133 mmol) and 2-(2-aminoethyl)1-methylpyrrolidine (154 μL, 1.06 mmol) for Example 275E and N,N-dimethylethylenediamine, respectively, in Example 275G. MS (ESI(+)) m/e 500 $(M+H)^+$m/e 522 $(M+Na)^+$; MS (ESI(−)) m/e 498 $(M-H)^-$; $^1$H NMR (300 MHz, DMSO-$d_6$) δ 9.55 (s, 1H), 9.37 (s, 1H), 7.59 (dd, 1H), 7.45 (dt, 1H), 7.24 (d, 1H), 7.02 (d, 1H), 6.89 (d, 1H), 6.69 (t, 1H), 6.05 (br t, 1H), 2.89-2.97 (m, 2H), 2.74-2.75 (d, 3H), 2.15-2.31 (m, 2H), 1.86-1.98 (m, 5H), 1.10 (s, 6H).

EXAMPLE 364

7,7-dimethyl-2-({[2-({3-[2-methyl-1-piperidinyl]propyl}amino)phenyl]sulfonyl}amino)-8-oxo-5,6,7,8-tetrahydro-1-naphthalenecarboxylic acid The desired product was prepared by substituting Example 362D (50 mg, 0.133 mmol) and 1-(3-aminopropyl)-2-pipecoline (140 μL, 0.8 mmol) for Example 275E and N,N-dimethylethylenediamine, respectively, in Example 275E. MS (ESI(+)) m/e 528 $(M+H)^+$m/e 550 $(M+Na)^+$; MS (ESI(−)) m/e 526 $(M-H)^-$; $^1$H NMR (300 MHz, DMSO-$d_6$) δ 9.54 (s, 1H), 9.00 (s, 1H), 7.59 (dd, 1H), 7.45 (dt, 1H), 7.24 (d, 1H), 7.00 (d, 1H), 6.89 (d, 1H), 6.69 (t, 1H), 6.06 (br t, 1H), 3.27-3.38 (m, 2H), 3.02-3.11 (m, 2H), 2.85-2.92 (m, 2H), 1.51-1.95 (m, 8H), 1.39-1.47 (m, 2H), 1.10-1.18 (m, 9H).

EXAMPLE 365

7,7-dimethyl-8-oxo-2-{[(2-{[3-(1-pyrrolidinyl)propyl]amino}phenyl)sulfonyl]amino}-5,6,7,8-tetrahydro-1-naphthalenecarboxylic acid The desired product was prepared by substituting Example 362D (50 mg, 0.133 mmol) and 1-(3-aminopropyl)pyrrolidine (102 μL, 0.8 mmol) for Example 275E and N,N-dimethylethylenediamine, respectively, in Example 275E. MS (ESI (+)) m/e 500 $(M+H)^+$; MS (ESI(−)) m/e 498 $(M-H)^-$; $^1$H NMR (300 MHz, DMSO-$d_6$) δ 9.53 (s, 1H), 7.59 (dd, 1H), 7.44 (dt, 1H), 7.25 (d, 1H), 7.05 (d, 1H), 6.87 (d, 1H), 6.68 (t, 1H), 6.04 (br t, 1H), 3.43-3.60 (m, 2H), 3.24-3.35 (m, 2H), 3.12-3.23 (m, 2H), 2.83-3.02 (m, 4H), 1.75-1.97 (m, 6H), 1.10 (s, 6H).

EXAMPLE 366

8-methylene-2-({[2-({3-[(2S)-2-methyl-1-piperidinyl]propyl}amino)phenyl]sulfonyl}amino)-5,6,7,8-tetrahydro-1-naphthalenecarboxylic acid

EXAMPLE 366A

N-(1-bromo-8-methylene-5,6,7,8-tetrahydro-2-naphthalenyl)-2-fluorobenzenesulfonamide A solution of Example 275C (2.0 g, 5 mmol) in 25 mL of THF at 0° C. was treated with Tebbe reagent (0.5M in toluene, 11 mL, 5.5 mmol), stirred at 0° C. for 15 minutes, warmed to room temperature, and stirred overnight. The mixture was treated with 30 mL of diethyl ether then treated dropwise with 0.1N sodium hydroxide until gas evolution was not observed. The mixture was treated with ethyl acetate and the organic phase was washed with water (2×) and brine (3×), dried ($MgSO_4$), filtered, concentrated, and purified by silica gel column chromatography eluting with 20% ethyl acetate in n-hexane to provide 290 mg of the desired product. MS (ESI (+)) m/e 414 $(M+NH_4)^+$; MS (ESI(−)) m/e 395 $(M-H)^-$; $^1$H NMR (300 MHz, DMSO-$d_6$) δ 10.09 (s, 1H), 7.64-7.72 (m, 2H), 7.42 (dt, 1H), 7.32 (d, 1H), 7.10 (d, 1H), 7.00 (d, 1H), 5.35 (s, 2H), 2.61 (t, 2H), 2.40 (t, 2H), 1.74 (m, 2H).

EXAMPLE 366B methyl 2-{[(2-fluorophenyl)sulfonyl]amino}-8-methylene-5,6,7,8-tetrahydro-1-naphthalenecarboxylate The desired product was prepared by substituting Example 366A (340 mg) for Example 275E in Example 275G to provide 90 mg. MS (ESI(+)) m/e 393 $(M+NH_4)^+$; MS (ESI(−)) m/e 374 $(M-H)^-$; $^1$H NMR (300 MHz, DMSO-$d_6$) δ 9.91 (s, 1H), 7.63-7.73 (m, 2H), 7.44 (dt, 1H), 7.32 (d, 1H), 7.17 (d, 1H), 7.00 (d, 1H), 5.04 (s, 1H), 4.87 (s, 1H), 3.54 (s, 3H), 2.721 (t, 2H), 2.41 (t, 2H), 1.78 (m, 2H).

EXAMPLE 366C 8-methylene-2-({[2-({3-[(2)-2-methyl-1-piperidinyl]propyl}amino)phenyl]sulfonyl}amino)-5,6,7,8-tetrahydro-1-naphthalenecarboxylic acid The desired product was prepared by substituting Example 366B (40 mg, 0.13 mmol) and 1-(3-aminopropyl)pipecoline (140 μL, 0.8 mmol) for Example 275E and N,N-dimethylethylenediamine, respectively, in Example 275E. MS (ESI(+)) m/e 498 $(M+NH_4)^+$; MS (ESI(−)) m/e 496 $(M-H)^-$; $^1$H NMR (300 MHz, DMSO-$d_6$) δ 9.91 (s, 1H), 7.66-7.74 (dt, 1H), 7.57 (dd, 1H), 7.44 (dt, 1H), 7.31-7.34 (m, 1H), 6.88 (m, 1H), 6.68 (m, 1H), 6.06 (br s, 1H), 5.20 (s, 1H), 5.10 (s, 1H), 4.45 (m, 1H), 4.00 (m, 1H), 3.24-3.55 (m, 2H), 3.02-3.16 (m, 2H), 2.61-2.74 (m, 2H), 2.44 (m, 2H), 1.37-2.01 (m, 5H), 1.08-1.27 (m, 3H).

EXAMPLE 367

8-methylene-2-{[(2-{[3-(4-methyl-1-piperazinyl)propyl]amino}phenyl)sulfonyl]amino}-5,6,7,8-tetrahydro-1-naphthalenecarboxylic acid The desired product was prepared by substituting Example 366B (40 mg, 0.13 mmol) and 1-(3-aminopropyl)-4-methylpiperazine (130 μL, 0.8 mmol) for Example 275E and N,N-dimethylethylenediamine, respectively, in Example 275G. MS (ESI(+)) m/e 499 $(M+H)^+$; MS (ESI(−)) m/e 497 $(M-H)^-$; $^1$H NMR (300 MHz, DMSO-$d_6$) δ 11.0 (s, 1H), 7.53-7.69 (m, 1H), 7.42 (dd, 1H), 7.34 (d, 1H), 6.83 (d, 1H), 5.18 (s, 1H), 5.10 (s, 1H), 3.18-3.26 (m, 2H), 2.65-2.80 (m, 5H), 2.44 (m, 1H), 1.76-1.90 (m, 2H).

EXAMPLE 368

8-methylene-2-{[(2-{[3-(1-pyrrolidinyl)propyl]amino}phenyl)sulfonyl]amino}-5,6,7,8-tetrahydro-1-naphthalenecarboxylic acid The desired product was prepared by substituting Example 366B (50 mg, 0.133 mmol); and 1-(3-aminopropyl)pyrrolidine (120 μL, 0.8 mmol) for Example 275E and N,N-dimethylethylenediamine, respectively, in Example 275G. MS (ESI (+)) m/e 470 $(M+H)^+$; MS (ESI(−)) m/e 468 $(M-H)^-$; $^1$H NMR (300 MHz, DMSO-$d_6$) δ 11.00 (s, 1H), 9.56 (s, 1H), 7.70 (dd, 1H), 7.43 (dt, 1H), 7.35 (d, 1H), 7.02 (d, 1H), 6.86 (d, 1H), 6.68 (t, 1H), 6.03 (br t, 1H), 5.19 (s, 1H), 5.10 (s, 1H), 3.98-4.03 (m, 2H), 2.95-3.30 (m, 8H), 2.42-2.76 (m, 4H), 1.86-2.04 (m, 6H).

EXAMPLE 369

2-{[(2-{[4-(aminocarbonyl)-1-piperidinyl]carbonyl}phenyl)sulfonyl]amino}-1-naphthoic acid The desired product was prepared by substituting isonipecotamide for 1-(2-aminoethyl)piperdine in Examples 328A-B. MS (ESI(−)) m/e 480 $(M-H)^-$; $^1$H NMR (300 MHz, DMSO-$d_6$) δ 9.44 (t, 1H), 7.79 (d, 1H), 7.75 (d, 1H), 7.65 (m, 2H), 7.56 (d, 1H), 7.50 (dd, 1H), 7.41 (m, 2H), 7.24 (m, 2H), 4.39 (d, 1H), 4.12 (m, 1H), 3.75 (m, 2H), 3.15 (m, 1H), 2.90 (m, 1H), 2.42 (br s, 1H), 1.95-1.60 (m, 2H), 1.50 (m, 1H), 1.33 (m, 1H).

EXAMPLE 371

3-bromo-6-{[(2-{[3-(dimethylamino)-2,2-dimethylpropyl]amino}phenyl)sulfonyl]amino}-2-methoxybenzoic acid

EXAMPLE 371A 3-bromo-6-{[(2-fluorophenyl)sulfonyl]amino}-2-methoxybenzoic acid

A mixture of Example 318C (150 mg, 0.3 mmol), lithium hydroxide (127 mg, 3.0 mmol), dioxane (3 mL), and water (1.5 mL) was sealed in a vial and microwaved at 160° C. for 15 minutes. The mixture was acidified to pH 1 with 1M HCl and extracted with ethyl acetate. The ethyl acetate was washed with brine, dried ($Na_2SO_4$), filtered, and concentrated to an oil which was triturated with 1:1 hexanes/diethyl ether to provide the desired product. MS (ESI(+)) m/e 404, 406 $(M+H)^+$, 421, 423 $(M+NH_4)^+$, 426, 428 $(M+Na)^+$; (ESI(−)) m/e 402, 404 $(M-H)^-$; $^1$H NMR (300 MHz, DMSO-$d_6$) δ 13.48 (br s, 1H), 10.34 (br s, 1H), 7.72 (m, 2H), 7.63 (d, 1H), 7.41 (m, 1H), 7.34 (m, 1H), 6.89 (d, 1H), 3.75 (s, 3H).

EXAMPLE 371B 3-bromo-6-{[(2-{[3-(dimethylamino)-2,2-dimethylpropyl]amino}phenyl)sulfonyl]amino}-2-methoxybenzoic acid A mixture of Example 371A (150 mg, 0.37 mmol), acetonitrile (2.5 mL), triethylamine (0.26 mL, 1.86 mmol), and N,N,2,2-tetramethyl-1,3-propanediamine (381 mg, 3.0 mmol) was sealed in a vial and shaken at 65° C. for 144 hours and heated to 80° C. for 18 hours. The mixture was concentrated and the residue was purified by preparative HPLC on a; Waters Symmetry C8 column (25 mm×100 mm, 7 μm particle size) using a gradient of 10% to 100% acetonitrile/10 mmol aqueous ammonium acetate over 8 minutes (10 minute run time) at a flow rate of 40 mL/min to provide the desired product. MS (ESI(+)) m/e 514, 516 $(M+H)^+$; (ESI(−)) m/e 512, 514 $(M-H)^-$; $^1$H NMR (300 MHz, DMSO-$d_6$) δ 12.07 (br s, 1H), 7.61 (d, 1H), 7.38 (d, 1H), 7.31 (t, 1H), 7.01 (d, 1H), 6.85 (t, 1H), 6.63 (t, 1H), 5.75 (s, 1H), 3.68 (s, 3H), 3.26 (br s, 1H), 3.09 (m, 4H), 2.79 (br s, 6H), 1.07 (s, 6H).

EXAMPLE 372

3-bromo-2-methoxy-6-{[(2-{[3-(1-pyrrolidinyl)propyl]amino}phenyl)sulfonyl]amino}benzoic acid The desired product was prepared by substituting 1-(3-aminopropyl)pyrrolidine for N,N,2,2-tetramethyl-1,3-propanediamine in Example 371B. MS (ESI(+)) m/e 512, 514 $(M+H)^+$; (ESI(−)) m/e 510, 512 $(M-H)^-$; $^1$H NMR (300 MHz, DMSO-$d_6$) δ 12.14 (br s, 1H), 7.45 (d, 1H), 7.41 (d, 1H), 7.30 (t, 1H), 7.20 (d, 1H), 6.76 (d, 1H), 6.53 (t, 1H), 6.14 (m, 1H), 3.65 (s, 3H), 3.37 (m, 8H), 3.30 (br m, 1H), 1.94 (m, 4H), 1.84 (m, 2H).

EXAMPLE 375

3-bromo-2-hydroxy-6-({[2-({2-[1-methyl-2-pyrrolidinyl]ethyl}amino)phenyl]sulfonyl}amino)benzoic acid The desired product, which was one of two products isolated from this reaction was prepared by substituting 2-(2-aminoethyl)-1-methylpyrrolidine for N,N,2,2-tetramethyl-1,3-propanediamine in Example 371B. MS (ESI(+)) m/e 498, 500 $(M+H)^+$; (ESI(−)) m/e 496, 498 $(M-H)^-$; $^1$H NMR (300 MHz, DMSO-$d_6$) δ 16.99 (s, 1H), 14.50 (s, 1H), 9.32 (br s, 1H), 7.68 (d, 1H), 7.37 (t, 1H), 7.31 (d, 1H), 6.81 (d, 1H), 6.66 (m, 2H), 5.76 (br s, 1H), 3.55 (m, 1H), 3.44 (m, 1H), 3.24 (m, 2H), 3.15 (m, 1H), 2.62 (br s, 3H), 2.23 (m, 2H), 2.03 (m, 1H), 1.83 (m, 1H), 1.75 (m, 1H), 1.66 (m, 1H).

EXAMPLE 376

3-bromo-2-methoxy-6-{[(2-{[3-(1-piperidinyl)propyl]amino}phenyl)sulfonyl]amino}benzoic acid The desired product was prepared by substituting 3-(1-piperidino)propylamine for N,N,2,2-tetramethyl-1,3-propanediamine in Example 371B. MS (ESI(+)) m/e 526, 528 $(M+H)^+$; (ESI(−)) m/e 524, 526 $(M-H)^-$; $^1$H NMR (300 MHz, DMSO-$d_6$) δ 11.17 (br s, 1H), 7.45 (dd, 1H), 7.41 (d, 1H), 7.24 (dt, 1H), 7.19 (d, 1H), 6.74 (d, 1H), 6.52 (t, 1H), 6.19 (br s, 1H), 3.67 (s, 3H), 3.30 (br s, 1H), 3.14 (m, 2H), 3.11 (m, 4H), 3.03 (m, 2H), 1.77 (m, 2H), 1.69 (m, 4H), 1.54 (m, 2H).

EXAMPLE 379

2-({[2-({[2-(diethylamino)ethyl]amino}carbonyl)phenyl]sulfonyl}amino)-5,6,7,8-tetrahydro-1-naphthalenecarboxylic acid

EXAMPLE 379A methyl 2-({[2-(methoxycarbonyl)phenyl]sulfonyl}amino)-5,6,7,8-tetrahydro-1-naphthalenecarboxylate A solution of Example 418A (1.81 g, 8.35 mmol) in dichloromethane (25.5 mL) was treated with chlorotrimethylsilane (6.7 mL of 1M $CH_2Cl_2$ solution, 16.7 mmol) and pyridine (25.5 mL), stirred at room temperature for 10 minutes, treated with methyl 2-(chlorosulfonyl)benzoate (2.61 g, 11.11 mmol), stirred overnight at room temperature, and treated with 1N HCl (50 mL). The aqueous phase was extracted with dichloromethane two times and the combined organic phases were washed with water and brine, dried ($MgSO_4$), filtered, and concentrated. The resulting residue was purified by preparative HPLC to provide the desired product. MS (ESI(+)) m/e 404 $(M+H)^+$; 480 $(M+Na)^+$; (ESI(−)) m/e 402 $(M-H)^-$; $^1$H NMR (300 MHz, DMSO-$d_6$) δ 9.14 (s, 1H), 7.77-7.65 (m, 4H), 7.12 (d, 1H), 6.98 (d, 1H), 3.01 (s, 3H), 3.63 (s, 3H), 2.68 (br s, 2H), 2.53 (br s, 2H), 1.66 (br m, 4H).

EXAMPLE 379B 2-({[1-(methoxycarbonyl)-5,6,7,8-tetrahydro-2-naphthalenyl]amino}sulfonyl)benzoic acid A solution of Example 379A (3.04 g, 7.54 mmol) in methanol (70 mL) and distilled water (7.8 mL) was treated with lithium hydroxide monohydrate (1.58 g, 37.7 mmol), heated to 60° C. overnight, cooled to room temperature, treated with 1N HCl, and concentrated. The aqueous layer was washed with dichloromethane two times and the combined organic phases were dried ($MgSO_4$), filtered, and concentrated to provide the desired product. MS (ESI(+)) m/e 388 $(M+H)^+$; $^1$H NMR (300 MHz, DMSO-$d_6$) δ 14.00 (br s, 1H), 8.85 (br s, 1H), 7.83 (d, 1H), 7.73 (m, 2H), 7.64 (m, 1H), 7.13 (s, 2H), 3.63 (s, 3H), 2.67 (br s, 2H), 2.51 (br s, 2H), 1.65 (br m, 4H).

EXAMPLE 379C methyl 2-({[2-({[2-(diethylamino)ethyl]amino}carbonyl)phenyl]sulfonyl}amino)-5,6,7,8-tetrahydro-1-naphthalenecarboxylate A solution of Example 327B (100 mg, 0.257 mmol) in dimethylformamide (2.0 mL) was treated with 4-methylmorpholine (109 μL, 0.992 mmol) and O-(7-azabenzotriazol-1-yl)-N,N,N',N'-tetramethyluronium hexafluorophosphate (188.5 mg, 0.496 mmol), stirred for one hour at room temperature, treated with N,N-diethylethylenediamine (72 μL, 0.514 mmol), stirred overnight at room temperature, and treated with 1N HCl. The aqueous layer was washed with dichloromethane two times and the combined organic phases were dried ($MgSO_4$), filtered and concentrated. The resulting residue was purified by preparative HPLC to provide the desired product. MS (ESI(+)) m/e 488 $(M+H)^+$; (ESI(−)) m/e 486 $(M-H)^-$; $^1$H NMR (300 MHz, DMSO-$d_6$) δ 9.10 (br s, 1H), 9.06 (t, 1H), 9.84 (s, 1H), 7.77 (dt, 1H), 7.68 (dd, 2H), 7.62 (m, 1H), 7.12 (d, 1H), 7.08 (d, 1H), 3.64 (m, 2H), 3.63 (s, 3H), 3.29-3.22 (m, 6H), 2.68 (br s, 2H), 2.51 (br s, 2H), 1.65 (br m, 4H), 1.24 (t, 6H).

EXAMPLE 379D 2-({[2-({[2-(diethylamino)ethyl]amino}carbonyl)phenyl]sulfonyl}amino)-5,6,7,8-tetrahydro-1-naphthalenecarboxylic acid In a small microwave reactor vessel (2.0 mL) was placed Example 379C (13.8 mg, 0.028 mmol), dioxane (0.5 mL), distilled water (0.25 mL), and lithium hydroxide monohydrate (12.0 mg, 0.283 mmol). The vial was sealed and heated in microwave for twelve hundred seconds at 160° C. The solution was cooled to room temperature, treated with 1N HCl, and concentrated. The resulting residue was purified by preparative HPLC to provide the desired product. MS (ESI (+)) m/e 474 $(M+H)^+$; (ESI(−)) m/e 472 $(M-H)^-$; $^1$H NMR (300 MHz, DMSO-$d_6$) δ 13.20 (br s, 1H), 9.14 (br s, 1H), 9.02 (t, 2H), 7.77 (m, 2H), 7.65 (m, 2H), 7.04 (d, 1H), 6.93 (d, 1H), 3.63 (q, 1H), 3.25 (m, 6H), 2.67 (br s, 2H), 2.61 (br s, 2H), 1.66 (br s, 4H), 1.23 (t, 6H).

EXAMPLE 379E

2-Amino-5,6,7,8-tetrahydro-naphthalene-1-carboxylic acid methyl ester

The white solid from Example 128B (7.17 g, 24.61 mmol) was dissolved in benzene (250 ml) and methanol (62 ml). To the stirring solution was added 2 M trimethylsilyldiazomethane (12.3 ml) until the yellow color persisted for ten minutes. The reaction was then stirred at room temperature or 1 hour. To the solution was added acetic acid until the yellow color disappeared. The solvent was then removed. The crude material (7.52 g, 24.61 mmol) was dissolved in acetic acid (100 mL) and $Pt_2O$ (3.50 g, 15.4 mmol) was added shaken in a reactor pressurized with 60 psi of $H_2$ at 25° C. for 80 hours, filtered, and concentrated. The concentrate was treated with dichloromethane (70 mL) and TFA (12 mL) and stirred for 3 hours. The organic layer was washed with NaOH (2×250 mL) and brine (200 mL), dried ($MgSO_4$), filtered, and concentrated to provide the desired product. MS (ESI(+)) m/e 206+H)$^+$; $^1$H NMR (300 MHz, DMSO-$d_6$) δ 6.83 (d, 1H), 6.53 (d, 1H), 5.26 (bs, 2H), 3.78 (s, 3H), 2.62 (m, 2H), 2.57 (m, 2H), 1.64 (m, 4H).

EXAMPLE 380

2-{[(2-{[[3-(dimethylamino)propyl](methyl)amino]carbonyl}phenyl)sulfonyl]amino}-1-naphthoic acid

EXAMPLE 380A methyl 2-{[(2-{[[3-(dimethylamino)propyl](methyl)amino]carbonyl}phenyl)sulfonyl]amino}-1-naphthoate A solution of Example 149B (102 mg, 0.264 mmol) in dichloromethane (1.0 mL) was treated with 4-methylmorpholine (87 μL, 0.792 mmol), 4-dimethylaminopyridine (3 mg, 0.025 mmol), N,N,N',-trimethyl-1,3-propanediamine (42.6 μL, 0.290 mmol), and bromotripyrrolidinophosphonium hexafluorophosphate (123.3 mg, 0.265 mmol), stirred at room temperature for 3 days, and treated with 1N HCl. The aqueous layer was extracted with ethyl acetate three times and the combined organic phases were washed with brine, dried ($MgSO_4$), filtered, and concentrated. The resulting residue was purified by preparative HPLC to provide the desired product. MS (ESI(+)) m/e 484 $(M+H)^+$; (ESI(−)) m/e 482 $(M-H)^-$; $^1$H NMR (300 MHz, DMSO-$d_6$) δ 9.49 (s, 1H), 9.26 (s, 1H), 8.02 (d, 1H), 7.94 (dd, 1H), 7.1 (dd, 1H), 7.72 (dt, 1H), 7.61-7.48 (m, 5H), 3.84 (s, 3H), 3.19 (br s, 2H), 3.07 (m, 2H), 2.82 (d, 6H), 2.67 (s, 3H), 1.98 (quint, 2H).

EXAMPLE 380B

2-{[(2-{[[3-(dimethylamino)propyl](methyl)amino]carbonyl}phenyl)sulfonyl]amino}-1-naphthoic acid The desired product was prepared by substituting Example 380A for Example 328A in Example 328B. MS (ESI(+)) m/e 470 $(M+H)^+$; (ESI(−)) m/e 468 $(M-H)^-$; $^1$H NMR (300 MHz, DMSO-$d_6$) δ 9.35 (br s, 1H), 8.16 (br d, 1H), 7.94 (dd, 2H), 7.90 (d, 1H), 7.71 (m, 1H), 7.60 (dt, 1H), 7.56 (m, 1H), 7.50

(m, 2H), 7.43 (d, 1H), 3.73 (br s, 1H), 3.18 (br s, 2H), 3.09 (m, 1H), 2.86 (m, 1H), 2.81 (s, 4H), 2.67 (s, 4H), 1.98 (quint, 1H), 1.75-1.90 (m, 1H).

EXAMPLE 381

2-{[(2-{[3-(isopropylamino)propyl]amino}phenyl) sulfonyl]amino}-8-methyl-5,6,7,8-tetrahydro-1-naphthalenecarboxylic acid The desired product was prepared according to the procedure of Example 275G substituting Example 275F for 275E and 3-(isopropylamino)propylamine for N,N-dimethylethylenediamine. MS (ESI) m/e 458 $(M-H)^-$; $^1$H NMR (300 MHz, DMSO-$d_6$) δ 9.46 (br s, 1H), 8.22 (br s, 1H), 7.51 (dd, 1H), 7.42 (dt, 1H), 6.92 (d, 1H), 6.86 (d, 1H), 6.65 (t, 1H), 6.56 (br s, 1H), 6.03 (t, 1H), 3.24 (m, 3H), 2.97 (m, 2H), 2.64 (m, 2H), 1.85 (m, 2H), 1.73-1.64 (m, 4H), 1.16 (d, 6H), 1.1 (d, 3H).

EXAMPLE 383

3-bromo-2-chloro-6-{[(2-fluorophenyl)sulfonyl] amino}benzoic acid

EXAMPLE 383A benzyl 3-bromo-2-chloro-6-{[(2-fluorophenyl)sulfonyl]amino}benzoate The desired product was prepared by substituting Example 226D for Example 126B in Example 126C and substituting 2-fluorobenzenesulfonyl chloride for 3-fluorobenzenesulfonyl chloride. MS (ESI(+)) m/e 498, 500 $(M+H)^+$, 515, 517 $(M+NH_4)^+$, 520, 522 $(M+Na)^+$; (ESI(−)) m/e 496, 498 $(M-H)^-$; $^1$H NMR (300 MHz, DMSO-$d_6$) δ 10.75 (br s, 1H), 7.83 (d, 1H), 7.70 (m, 2H), 7.39 (m, 7H), 7.14 (d, 1H), 5.20 (s, 2H).

EXAMPLE 383B 3-bromo-2-chloro-6-{[(2-fluorophenyl)sulfonyl] amino}benzoic acid

The desired product was prepared by substituting Example 383A for Example 226F in Example 226G. MS (ESI(+)) m/e 425, 427 $(M+NH_4)^+$, 430, 432 $(M+Na)^+$; (ESI(−)) m/e 406, 408 $(M-H)^-$; $^1$H NMR (300 MHz, DMSO-$d_6$) δ 10.50 (br s, 1H), 7.71 (d, 1H), 7.66 (m, 2H), 7.36 (d, 1H), 7.28 (m, 1H), 7.03 (d, 1H), 3.35 (br s, 1H).

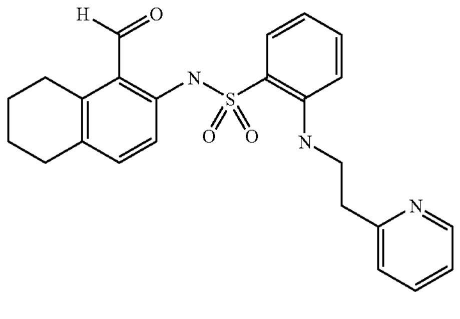

EXAMPLE 384

2-{[(2-{[2-(2-pyridinyl)ethyl]amino}phenyl)sulfonyl]amino}-5,6,7,8-tetrahydro-1-naphthalenecarboxylic acid The desired product was prepared by substituting 2-(2-aminoethyl)pyridine for 3-(N,N-diethylamino)propylamine in Example 229B. MS (DCI) m/e 452 $(M+H)^+$; $^1$H NMR (400 MHz, DMSO-$d_6$) δ 8.51 (ddd, 1H), 7.70 (td, 1H), 7.54 (dd, 1H), 7.33 (d, 1H), 7.29 (ddd, 1H), 7.22 (ddd, 1H), 6.90 (d, 1H), 6.80 (d, 1H), 6.76 (d, 1H), 6.58 (m, 1H), 6.14 (br s, 1H), 3.47 (t, 2H), 3.02 (t, 2H), 2.90 (m, 2H), 2.59 (m, 2H), 1.60 (m, 4H).

EXAMPLE 385

2-ethoxy-3-ethyl-6-{[(2-fluorophenyl)sulfonyl] amino}benzoic acid

EXAMPLE 385A 5-methoxy-2H-3,1-benzoxazine-2,4(1H)-dione

A solution of NaOH (6.6 g, 165 mmol) in water (300 mL) was treated with 2-amino-6-methoxybenzoic acid (10 g, 59.9 mmol); cooled to 0° C., treated dropwise with a 20% wt solution of phosgene in toluene (75 mL), stirred overnight at room temperature and filtered. The filter cake provided 10.5 g of the desired product (yield: 91.0%). $^1$H NMR (DMSO-$d_6$) δ 3.85 (s, 3H), 6.65 (d, 1H), 6.80 (d, 1H), 7.65 (t, 1H), 11.58 (br s, 1H); MS (ESI(−) m/e 192 $(M-H)^-$.

EXAMPLE 385B 6-bromo-5-methoxy-2H-3,1-benzoxazine-2,4(1H)-dione

A solution of Example 385A (10.5 g, 54.4 mmol) in DMF (100 mL) and dichloromethane (200 mL) was cooled to 0° C., treated portionwise with NBS (14.4 g, 80.9 mmol) over 40 minutes, stirred overnight at room temperature and filtered. The filtrate was concentrated to provide the desired product (~20 g) which was used directly in the next step.

EXAMPLE 385C 6-bromo-5-hydroxy-2H-3,1-benzoxazine-2,4(1H)-dione

A mixture of Example 385B (20 g) in dichloromethane (600 mL) at 0° C. was treated with $AlCl_3$ (39 g, 293 mmol) in several portions and stirred vigorously overnight at room temperature. The mixture was treated with brine (300 mL), stirred for 10 minutes, and extracted with ethyl acetate. The extract was dried ($MgSO_4$), filtered, and concentrated to provide the desired product (18 g) which was used directly in the next step.

EXAMPLE 385D methyl 6-amino-3-bromo-2-hydroxybenzoate

A mixture of Example 385C (~18 g) in methanol (400 mL) was heated to reflux for 2 hours and then purified on a silica gel column with 20% ethyl acetate in hexanes to provide the desired product (3.95 g, 29.8% yield for three steps). $^1$H NMR (DMSO-$d_6$) δ 3.90 (s, 3H), 6.22 (d, 1H), 6.60 (s, 2H), 7.30 (d, 1H), 11.70 (s, 1H); MS (DCI/$NH_3$) m/e 246, 248 $(M+H)^+$.

EXAMPLE 385E methyl 6-amino-3-bromo-2-ethoxybenzoate

A solution of Example 385D (1.0 g, 4.08 mmol) in anhydrous DMF (20 mL) was treated with $Cs_2CO_3$ (1.46 g, 4.5 mmol), cooled to 0° C., stirred for 10 minutes, treated with a solution of iodoethane (0.94 g, 6.1 mmol) in DMF (3 mL), warmed to room temperature over 2 hours, treated with brine (80 mL), and extracted with ethyl acetate. The organic solution was dried ($MgSO_4$), filtered and concentrated. The residue was purified on a silica gel column with 20% ethyl acetate in hexanes to provide the desired product (1.1 g, 98.2% yield). $^1H$ NMR (DMSO-$d_6$) δ 1.28 (t, 3H), 3.75 (s, 3H), 3.95 (q, 2H), 5.48 (s, 2H), 6.24 (d, 1H), 7.40 (d, 1H), 11.70 (s, 1H); MS (DCI/$NH_3$) m/e 274, 276 $(M+H)^+$.

EXAMPLE 385F methyl 3-bromo-2-ethoxy-6-{[(2-fluorophenyl)sulfonyl]amino}benzoate A solution of Example 385E (1.1 g, 4.0 mmol), 2-fluorobenzenesulfonyl chloride (0.94 g, 4.8 mmol), and pyridine (0.65 mL, 8.0 mmol) in dichloromethane (20 mL) was stirred for 4 days at room temperature. The solution was then washed with aqueous 1N HCl, dried ($MgSO_4$), filtered, and concentrated to give a solid which was triturated with hexane to provide the desired product, 1.56 g, 90.3%. $^1H$ NMR (DMSO-$d_6$) δ 1.22 (t, 3H), 3.65 (s, 3H), 3.90 (q, 2H), 6.95 (d, 1H), 7.35 (t, 1H), 7.42 (dd, 1H), 7.65-7.80 (m, 3H), 10.40 (s, 1H); MS (ESI(−)) m/e 430, 432 $(M-H)^-$.

EXAMPLE 385G methyl 2-ethoxy-6-{[(2-fluorophenyl)sulfonyl]amino}-3-vinylbenzoate The desired product was prepared by substituting Example 385F (1.5 g, 3.5 mmol) for Example 230A in Example 230B (1.1 g, 80.3% yield). $^1H$ NMR (DMSO-$d_6$) δ 1.22 (t, 3H), 3.65 (s, 3H), 3.78 (q, 2H), 5.25 (d, 1H), 5.82 (d, 1H), 6.80 (dd, 1H), 6.98 (d, 1H), 7.35 (t, 1H), 7.42 (dd, 1H), 7.60-7.72 (m, 3H), 10.22 (s, 1H); MS (ESI(−)) m/e 378 $(M-H)^-$.

EXAMPLE 385H methyl 2-ethoxy-3-ethyl-6-{[(2-fluorophenyl)sulfonyl]amino}benzoate A mixture of Example 385G (1.1 g, 2.90 mmol) in methanol (20 mL) was treated with 10% Pd/C (300 mg) under a hydrogen atomosphere for 6 hours. Filtration and evaporation of the solvent gave 1.06 g of the desired product. $^1H$ NMR (DMSO-$d_6$) δ 1.10 (t, 3H), 1.22 (t, 3H), 2.54 (q, 2H), 3.62 (s, 3H), 3.80 (q, 2H), 6.98 (d, 1H), 7.25 (d, 1H), 7.30 (t, 1H), 7.42 (dd, 1H), 7.60-7.75 (m, 2H), 10.05 (s, 1H); MS (ESI(−)) m/e 380 $(M-H)^-$.

EXAMPLE 385I 2-ethoxy-3-ethyl-6-{[(2-fluorophenyl)sulfonyl]amino}benzoic acid

Two reactions were run simultaneously. For each reaction, a solution of Example 385H (0.26 g, 0.68 mmol) and lithium hydroxide hydrate (0.275 g, 6.5 mmol) in dioxane (3 mL) and water (1.5 mL) was heated to 160° C. for 15 minutes. The combined reaction mixture was acidified to pH 2.0 with 1 N HCl and extracted with ethyl acetate. The extract was dried ($MgSO_4$), filtered, and concentrated to provide the desired product, 0.475 g, 94.8% yield. $^1H$ NMR (DMSO-$d_6$) δ 1.10 (t, 3H) 1.22 (t, 3H), 2.54 (q, 2H), 3.80 (q, 2H), 6.80 (d, 1H), 7.20 (d, 1H), 7.30 (t, 1H), 7.40 (dd, 1H), 7.65-7.75 (m, 2H), 9.90 (s, 1H), 13.25 (br s, 1H); MS (ESI(−)) m/e 366 $(M-H)^-$.

EXAMPLE 386

2-ethoxy-6-{[(4-fluorophenyl)sulfonyl]amino}benzoic acid

EXAMPLE 386A 5-hydroxy-2H-3,1-benzoxazine-2,4(1H)-dione

A suspension of Example 385A (1.93 g, 10 mmol) in dichloromethane (100 mL) was treated with $AlCl_3$ (2.6 g, 20 mmol), stirred at room temperature overnight, treated slowly with brine (100 mL) while vigorously stirring, and extracted with ethyl acetate. The desired product was obtained as a white solid after evaporation of the solvent. Yield: 1.74 g, 97.2%. $^1H$ NMR (DMSO-$d_6$) δ 6.55 (d, 1H), 6.65 (d, 1H), 7.50 (t, 1H), 10.35 (s, 1H), 11.62 (br s, 1H); MS (ESI(−)) m/e 178 $(M-H)^-$.

EXAMPLE 386B methyl 2-amino-6-hydroxybenzoate

A mixture of Example 386A (1.0 g, 5.6 mmol) and methanol (40 mL) was heated to reflux for 6 hours, concentrated, and purified on a silica gel column eluting with 30% ethyl acetate in hexanes to provide the desired product, 0.81 g, 86.6%. $^1H$ NMR (DMSO-$d_6$) δ 3.88 (s, 3H), 5.95 (d, 1H), 6.20 (d, 1H), 6.34 (s, 214), 7.02 (t, 1H), 10.88 (s, 1H); MS (DCI/$NH_3$): m/e 168 $(M+H)^+$.

EXAMPLE 386C methyl 2-amino-6-ethoxybenzoate

The desired product was prepared by substituting Example 386B (0.80 g, 4.790 mmol) for Example 385D in Example 385E, yielding 0.85 g, 91.4%. $^1H$ NMR (DMSO-$d_6$) δ 1.28 (t, 3H), 3.70 (s, 3H), 3.92 (q, 2H), 5.60 (s, 2H), 6.15 (d, 1H), 6.28 (d, 1H), 7.02 (t, 1H); MS (DCI/$NH_3$) m/e 196 $(M+H)^+$.

EXAMPLE 386D methyl 2-ethoxy-6-{[(4-fluorophenyl)sulfonyl]amino}benzoate

The desired product was prepared by substituting Example 386C (60 mg, 0.31 mmol) and 4-fluorobenzenesulfonyl chloride for Example 385E and 2-fluorobenzenesulfonyl chloride, respectively, in Example 385F (90 mg, 82.5%). $^1H$ NMR (DMSO-$d_6$) δ 1.24 (t, 3H), 3.65 (s, 3H), 3.98 (q, 2H), 6.68 (d, 1H), 6.90 (d, 1H), 7.28 (t, 1H), 7.40 (t, 2H), 7.75 (dd, 2H), 9.85 (s, 1H); MS (DCI/$NH_3$) m/e 371 $(M+NH_4)$.

EXAMPLE 386E 2-ethoxy-6-{[(4-fluorophenyl)sulfonyl]amino}benzoic acid

The desired product was prepared by substituting Example 386D (100 mg, 0.28 mmol) for Example 385H in Example 385I (49 mg, 51.6%). $^1H$ NMR (DMSO-$d_6$) δ 1.20 (t, 3H), 3.98 (q, 2H), 6.60 (d, 1H), 6.88 (d, 1H), 7.20 (t, 1H), 7.35 (t, 2H), 7.75 (dd, 2H), 9.82 (br s, 1H), 12.85 (br s, 1H); MS (ESI(−)) m/e 338 $(M-H)^-$.

EXAMPLE 387

3-bromo-2-ethoxy-6-{[(4-fluorophenyl)sulfonyl]amino}benzoic acid

EXAMPLE 387A methyl 3-bromo-2-ethoxy-6-{[(4-fluorophenyl)sulfonyl]amino}benzoate The desired product was prepared by substituting 4-fluorobenzenesulfonyl chloride for 2-fluorobenzenesulfonyl chloride in Example 385F (145 mg, 93.5%). $^1$H NMR (DMSO-$d_6$) δ 1.22 (t, 3H), 3.70 (s, 3H), 3.96 (q, 2H), 6.88 (d, 1H), 7.40 (t, 2H), 7.65 (d, 1H), 7.75 (t, 2H), 10.10 (s, 1H); MS (ESI(−)) m/e 430, 432 $(M-H)^-$.

EXAMPLE 387B 3-bromo-2-ethoxy-6-{[(4-fluorophenyl)sulfonyl]amino}benzoic acid

The desired product was prepared by substituting Example 387A (30 mg, 0.069 mmol) for Example 385H in Example 385I (yield 16.8 mg). $^1$H NMR (DMSO-$d_6$) δ 1.22 (t, 3H), 3.96 (q, 2H), 6.88 (d, 1H), 7.20 (d, 1H), 7.30 (t, 1H), 7.40 (dd, 1H), 7.65-7.75 (m, 2H), 9.90 (s, 1H), 13.25 (br s, 1H); MS (ESI(−)) m/e 416, 418 $(M-H)^-$.

EXAMPLE 388

2-ethoxy-3-ethyl-6-{[(4-fluorophenyl)sulfonyl]amino}benzoic acid

EXAMPLE 388A methyl 2-ethoxy-6-{[(4-fluorophenyl)sulfonyl]amino}-3-vinylbenzoate The desired product was prepared by substituting Example 387A (100 mg, 0.23 mmol) for Example 230A in Example 230B, yielding 65 mg, 74.7%. $^1$H NMR (DMSO-$d_6$) δ 1.20 (t, 3H), 3.68 (s, 3H), 3.80 (q, 2H), 5.35 (d, 1H), 5.80 (d, 1H), 6.80 (dd, 1H), 6.92 (d, 1H), 7.40 (t, 2H), 7.60 (d, 1H), 7.75 (t, 2H), 9.98 (s, 1H); MS (ESI(−)) m/e 378 $(M-H)^-$.

EXAMPLE 388B methyl 2-ethoxy-3-ethyl-6-{[(4-fluorophenyl)sulfonyl]amino}benzoate A mixture of Example 388A (66 mg, 0.15 mmol) in methanol was treated with 10% Pd/C (50 mg) and stirred under a hydrogen atmosphere overnight at room temperature. Filtration and evaporation of the solvent gave the desired product.

EXAMPLE 388C 2-ethoxy-3-ethyl-6-{[(4-fluorophenyl)sulfonyl]amino}benzoic acid

The desired product was prepared by substituting Example 388B (71 mg, 0.18 mmol) for Example 385H in Example 385I, yielding 36.5 mg. $^1$H NMR (DMSO-$d_6$) δ 1.10 (t, 3H), 1.22 (t, 3H), 2.52 (q; 2H), 3.80 (q, 2H), 6.70 (d, 1H), 7.20 (d, 1H), 7.38 (t, 2H), 7.78 (dd, 2H), 9.70 (s, 1H), 13.25 (br s, 1H); MS (ESI(−)) m/e 366 $(M-H)^-$.

EXAMPLE 389

2-chloro-6-{[(2-{[4-(N,N-dimethylamino)butyl]amino}phenyl)sulfonyl]amino}-3-ethylbenzoic acid

EXAMPLE 389A benzyl 2-chloro-6-{[(2-fluorophenyl)sulfonyl]amino}-3-vinylbenzoate The desired product was prepared by substituting Example 383A for Example 226E in Example 226F. MS (ESI(+)) m/e 446 $(M+H)^+$, 463 $(M+NH_4)^+$, 468 $(M+Na)^+$; (ESI(−)) m/e 444 $(M-H)^-$; $^1$H NMR (300 MHz, DMSO-$d_6$) δ 10.63 (br s, 1H), 7.72 (m, 3H), 7.41 (m, 7H), 7.18 (d, 1H), 6.93 (dd, 1H), 5.87 (d, 1H), 5.48 (d, 1H), 5.20 (s, 2H).

EXAMPLE 389B 2-chloro-3-ethyl-6-{[(2-fluorophenyl)sulfonyl]amino}benzoic acid

The desired product was prepared by substituting Example 389A for Example 226F in Example 226G. MS (ESI(+)) m/e 375 $(M+NH_4)^+$; (ESI(−)) m/e 356 $(M-H)^-$; $^1$H NMR (300 MHz, DMSO-$d_6$) δ 13.50 (br s, 1H), 10.70 (br s, 1H), 7.69 (m, 1H), 7.42 (m, 2H), 7.32 (m, 2H), 7.00 (d, 1H), 2.66 (q, 2H), 1.13 (t, 3H).

EXAMPLE 389C 2-chloro-6-{[(2-{[4-(N,N-dimethylamino)butyl]amino}phenyl)sulfonyl]amino}-3-ethylbenzoic acid A mixture of Example 389B (133 mg, 0.4 mmol), 4-(N,N-dimethylamino)butylamine (346 mg, 3.0 mmol), acetonitrile (3 mL), and triethylamine (0.3 mL, 1.9 mmol) was sealed in a vial and shaken at to 80° C. for 72 hours. The mixture was purified by preparative HPLC on a Waters Symmetry C8 column (25 mm×100 mm, 7 μm particle size) using a gradient of 10% to 100% acetonitrile/10 mmol aqueous ammonium acetate over 8 minutes (10 minute run time) at a flow rate of 40 mL/min to provide the desired product. MS (ESI(+)) m/e 454 $(M+H)^+$; (ESI(−)) m/e 452 $(M-H)^-$; $^1$H NMR (300 MHz, DMSO-$d_6$) δ 7.64 (d, 1H), 7.43 (d, 1H), 7.36 (m, 1H), 7.16 (d, 1H), 6.77 (d, 1H), 6.61 (t, 1H), 5.78 (br s, 1H), 3.31 (br s, 2H), 3.23 (m, 2H), 3.04 (m, 2H), 2.76 (s, 6H), 2.59 (q, 2H), 1.86 (m, 2H), 1.66 (m, 2H), 1.09 (t, 3H).

EXAMPLE 390

2-chloro-6-{[(2-{[3-(dimethylamino)-2,2-dimethylpropyl]amino}phenyl)sulfonyl]amino}-3-ethylbenzoic acid The desired product was prepared by substituting N,N,2,2-tetramethyl-1,3-propanediamine for 4-(N,N-dimethylamino)butylamine in Example 389C. MS (ESI(+)) m/e 468 $(M+H)^+$; (ESI(−)) m/e 466 $(M-H)^-$; $^1$H NMR (300 MHz, DMSO-$d_6$) δ 7.51 (d, 1H), 7.25 (m, 1H), 7-13 (d, 1H), 7.04 (d, 1H), 6.83 (d, 1H), 6.53 (t, 1H), 3.47 (br s, 3H), 3.03 (s, 4H), 2.77 (s, 6H), 2.51 (q, 2H), 1.00 (m, 9H).

EXAMPLE 391

2-chloro-3-ethyl-6-({[2-({2-[1-methyl-2-pyrrolidinyl]ethyl}amino)phenyl]sulfonyl}amino)benzoic acid The desired compound was prepared by substituting 2-(2-aminoethyl)-1-methylpyrrolidine for 4-(N,N-dimethylamino)butylamine in Example 389C. MS (ESI(+)) m/e 466 $(M+H)^+$; (ESI(−)) m/e 464 $(M-H)^-$; $^1$H NMR (300 MHz, DMSO-$d_6$) δ 7.52 (d, 1H), 7.35 (m, 2H), 7.11 (d, 1H), 6.79 (d, 1H), 6.58 (t, 1H), 5.95 (br s, 1H), 3.69 (m, 1H), 3.50 (br s, 2H), 3.33 (m, 2H), 3.20 (m, 2H), 2.70 (s, 3H), 2.56 (q, 2H), 2.31 (m, 1H), 2.10 (m, 1H), 2.00 (m, 2H), 1.84 (m, 1H), 1.70 (m, 1H), 1.08 (t, 3H).

EXAMPLE 392

(8S)-8-methyl-2-({[2-({2-[1-methyl-2-pyrrolidinyl]ethyl}amino)phenyl]sulfonyl}amino)-5,6,7,8-tetrahydro-1-naphthalenecarboxylic acid The compound of Example 275F was separated into individual enantiomers by preparative column chromatography (Chiralpak AS 5 cm×30 cm; mobile phase: 20:80 ethyl alcohol/hexanes; flow rate 30 mL/min).

The desired product was prepared by substituting the later fraction (50 mg, 0.133 mmol) and 2-(2-aminoethyl)-1-methylpyrrolidine (154 μL, 1.06 mmol) for Example 275E and N,N-dimethylethylenediamine, respectively, in Example 275F. MS (ESI(+)) m/e 472 $(M+H)^+$; MS (ESI(−)) m/e 470 $(M-H)^-$; $^1$H NMR (300 MHz, DMSO-$d_6$) δ 9.42 (s, 2H), 7.54 (dd, 1H), 7.43 (t, 1H), 6.94 (d, 1H), 6.87 (d, 1H), 6.67 (t, 1H), 6.55 (d, 1H), 5.99 (t, 1H), 3.17-3.31 (m, 4H), 2.92-3.08 (m, 2H), 2.54-2.83 (m, 4H), 2.10-2.34 (m, 3H), 1.82-1.97 (m, 2H), 1.58-1.80 (m, 6H), 1.11 (d, 3H).

EXAMPLE 393

2-{[(2-{[2,2-dimethyl-3-(1-piperidinyl)propyl]amino}phenyl)sulfonyl]amino}-8-methyl-5,6,7,8-tetrahydro-1-naphthalenecarboxylic acid

EXAMPLE 393A 2,2-dimethyl-3-oxo-3-(1-piperidinyl)propanenitrile

A solution of 1-cyanoacetylpiperidine (2.28 g, 15 mmol) in 60 mL THF was cooled to −78° C., treated with 1.6M n-butyllithium in hexanes (20.63 mL, 33 mmol), stirred at −78° C. for 30 minutes, treated with methyl iodide (4.67 mL, 75 mmol), stirred at −78° C. for 1 hour, warmed to room temperature, stirred overnight, and treated with 15 mL of ammonium chloride and 100 mL of ethyl acetate. The organic layer was washed with brine (3×), dried ($MgSO_4$), filtered, and concentrated. The residue was purified by silica gel column chromatography, eluting with 20% acetone in n-hexanes to give 1.01 g of the desired product. MS (DCI) m/e 198 $(M+NH_4)^+$; $^1$H NMR (300 MHz, DMSO-$d_6$) δ 3.34-3.68 (m, 4H), 1.61 (s, 6H), 1.34 (m, 2H), 1.13 (m, 2H), 0.87-0.92 (m, 2H).

EXAMPLE 393B 2,2-dimethyl-3-(1-piperidinyl)-1-propanamine

A solution of Example 393A (0.9 g, 5 mmol) in 10 mL of THF was treated with a 1M solution of LAH in THF (10 mL, 10 mmol), stirred at room temperature for 6 hours, cooled to 0° C., and treated with 10 mL of saturated ammonium chloride and 30 mL of diethyl ether. The organic layer was washed with saturated ammonium chloride solution (3×), dried ($Na_2SO_4$), filtered, and concentrated to provide the desired product. MS (ESI(+)) m/e 171 $(M+H)^+$.

EXAMPLE 393C

2-{[(2-{[2,2-dimethyl-3-(1-piperidinyl)propyl]amino}phenyl)sulfonyl]amino}-8-methyl-5,6,7,8-tetrahydro-1-naphthalenecarboxylic acid The desired product was prepared by substituting Example 275F (50 mg, 0.133 mmol) and 1-(3-aminopropyl)-4-methylpiperazine (125 μL, 0.8 mmol) for Example 275E and N,N-dimethylethylenediamine, respectively, in Example 275G. MS (ESI(+)) m/e 514 $(M+H)^+$; MS (ESI(−)) m/e 512 $(M-H)^-$; $^1$H NMR (300 MHz, DMSO-$d_6$) δ 9.51 (s, 2H), 8.34 (s, 1H), 7.54 (dd, 1H), 7.41 (t, 1H), 6.93 (t, 1H), 6.68 (t, 1H), 6.53 (d, 1H), 5.98 (t, 1H), 3.27-3.39 (m, 4H), 2.59-2.72 (m, 2H), 1.63-1.80 (m, 8H), 1.11 (d, 3H), 1.01 (d, 6H).

EXAMPLE 394

2-({[2-({[1-(tert-butoxycarbonyl)-3-piperidinyl]methyl}amino)phenyl]sulfonyl}amino)-5,6,7,8-tetrahydro-1-naphthalenecarboxylic acid The desired product was prepared by substituting 1-tert-butoxycarbonyl-3-(aminomethyl)piperidine for 3-(N,N-diethylamino)propylamine in Example 229B. MS (ESI(+)) m/e 544 $(M+H)^+$, 561 $(M+NH_4)^+$, 566 $(M+Na)^+$; (ESI(−)) m/e 542 $(M-H)^-$; $^1$H NMR (300 MHz, DMSO-$d_6$) δ 7.59 (dd, 1H), 7.22 (dt, 1H), 6.97 (d, 1H), 6.75 (d, 1H), 6.67 (d, 1H), 6.55 (t, 1H), 6.02 (m, 1H), 3.93 (m, 4H), 3.00 (m, 4H), 2.56 (m, 2H), 1.65 (m, 3H), 1.58 (m, 4H), 1.39 (s, 9H), 1.03 (m, 2H).

EXAMPLE 395

2-({[2-({[1-(tert-butoxycarbonyl)-3-pyrrolidinyl]methyl}amino)phenyl]sulfonyl}amino)-5,6,7,8-tetrahydro-1-naphthalenecarboxylic acid The desired product was prepared by substituting 1-tert-butoxycarbonyl-3-(aminomethyl)pyrrolidine for 3-(N,N-diethylamino)propylamine in Example 229B. MS (ESI(+)) m/e 530 $(M+H)^+$, 547 $(M+NH_4)^+$, 552 $(M+Na)^+$; (ESI(−)) m/e 528 $(M-H)^-$; $^1$H NMR (300 MHz, DMSO-$d_6$) δ 7.56 (dd, 1H), 7.26 (dt, 1H), 6.91 (d, 1H), 6.80 (d, 1H), 6.72 (d, 1H), 6.58 (t, 1H), 6.01 (m, 1H), 3.18-3.07 (m, 4H), 2.92 (m, 4H), 2.58 (m, 2H), 2.25 (m, 1H), 1.95 (m, 2H), 1.59 (m, 4H), 1.40 (s, 9H).

EXAMPLE 396

2-({[2-({[1-(tert-butoxycarbonyl)-4-piperidinyl]methyl}amino)phenyl]sulfonyl}amino)-5,6,7,8-tetrahydro-1-naphthalenecarboxylic acid The desired product was prepared by substituting 1-tertbutoxycarbonyl-4-(aminomethyl)piperidine for 3-(N,N-diethylamino)propylamine in Example 229B. MS (ESI(+)) m/e 544 $(M+H)^+$, 561 $(M+NH_4)^+$, 566 $(M+Na)^+$; (ESI(−)) m/e 542 $(M-H)^-$; $^1$H NMR (300 MHz, DMSO-$d_6$) δ 7.58 (dd, 1H), 7.24 (dt, 1H), 6.93 (d, 1H), 6.78 (d, 1H), 6.68 (d, 1H), 6.56 (t, 1H), 6.02 (m, 1H), 3.92 (d, 2H), 3.00 (m, 4H), 2.63, (m, 2H), 2.57 (m, 2H), 1.66 (m, 3H), 1.59 (m, 4H), 1.39 (s, 9H), 1.00 (m, 2H).

EXAMPLE 397

2-{[(2-{[(3S)-3-piperidinylmethyl]amino}phenyl)sulfonyl]amino}-5,6,7,8-tetrahydro-1-naphthalenecarboxylic acid The desired product was prepared by substituting Example 394 for Example 332 in Example 335. MS (ESI(+)) m/e 444 $(M+H)^+$, 461 $(M+NH_4)^+$, 466 $(M+Na)^+$; (ESI(−)) m/e 442 $(M-H)^-$; $^1$H NMR (300 MHz, DMSO-$d_6$) δ 7.51 (dd, 1H), 7.38 (dt, 1H), 6.96 (d, 1H), 6.82 (d, 1H), 6.63 (m, 2H), 6.04 (m, 1H), 3.69 (m, 1H), 3.49 (m, 1H), 3.08 (m, 2H), 2.83 (m, 2H), 2.65 (m, 4H), 1.83 (m, 3H), 1.67 (m, 4H), 1.29 (m, 2H).

EXAMPLE 398

2-{[(2-{[(3S)-3-pyrrolidinylmethyl]amino}phenyl) sulfonyl]amino}-5,6,7,8-tetrahydro-1-naphthalenecarboxylic acid The desired product was prepared by substituting Example 395 for Example 332 in Example 335. MS (ESI(+)) m/e 430 $(M+H)^+$; (ESI(−)) m/e 428 $(M-H)^-$; $^1H$ NMR (300 MHz, DMSO-$d_6$) δ 7.51 (dd, 1H), 7.40 (dt, 1H), 6.95 (d, 1H), 6.87 (d, 1H), 6.65 (t, 1H), 6.59 (d, 1H), 6.01 (m, 1H), 3.11 (m, 4H), 3.02 (m, 2H), 2.65 (m, 4H), 2.02 (m, 1H), 1.67 (m, 4H) 1.28 (m, 2H).

EXAMPLE 399

2-[({2-[(4-piperidinylmethyl)amino] phenyl}sulfonyl)amino]-5,6,7,8-tetrahydro-1-naphthalenecarboxylic acid The desired product was prepared by substituting Example 396 for Example 332 in Example 335. MS (ESI(+)) m/e 444 $(M+H)^+$, 466 $(M+Na)^+$; (ESI(−)) m/e 442 $(M-H)^-$; $^1H$ NMR (300 MHz, DMSO-$d_6$) δ 7.51 (dd, 1H), 7.38 (dt, 1H), 6.95 (d, 1H), 6.82 (d, 1H), 6.63 (m, 2H), 3.26 (d, 2H), 3.06 (m, 2H), 2.81, (m, 2H), 2.66 (m, 4H), 1.83 (m, 3H), 1.67 (m, 4H), 1.33 (m, 2H).

EXAMPLE 400

2-({[2-({2-[1-cyclobutyl-2-piperidinyl]ethyl}amino) phenyl]sulfonyl}amino)-5,6,7,8-tetrahydro-1-naphthalenecarboxylic acid The desired product was prepared by substituting cyclobutanone for cyclopentanone in Example 401B. MS (DCI) m/e 512 $(M+H)^+$; $^1H$ NMR (500 MHz, DMSO-$d_6$) δ 13.21 (br s, 1H), 7.54 (d, 1H), 7.40 (t, 1H), 6.93 (br s, 1H), 6.84 (d, 1H), 6.65 (t, 2H), 6.03 (br s, 1H), 4.02 (br s, 1H), 3.63 (br s, 1H), 3.35 (br s, 3H), 2.99 (br s, 1H), 2.70 (br s, 2H), 2.63 (br s, 2H), 2.00 (br s, 4H), 1.83 (br s, 3H), 1.65-1.54 (m, 11H).

EXAMPLE 401

2-({[2-({2-[1-cyclopentyl-2-piperidinyl] ethyl}amino)phenyl]sulfonyl}amino)-5,6,7,8-tetrahydro-1-naphthalenecarboxylic acid

EXAMPLE 401A 2-({[2-({2-[(2S)-2-piperidinyl]ethyl}amino)phenyl] sulfonyl}amino)-5,6,7,8-tetrahydro-1-naphthalenecarboxylic acid A mixture of Example 384 (0.16 g, 0.35 mmol), and platinum oxide (0.20 g) in acetic acid (35 mL) was shaken in a reactor pressurized with 60 psi of $H_2$ at 25° C. for 80 hours, filtered, and concentrated to provide the desired product. MS (DCI) m/e 458 $(M+H)^+$.

EXAMPLE 401B 2-({[2-({2-[1-cyclopentyl-2-piperidinyl] ethyl}amino)phenyl]sulfonyl}amino)-5,6,7,8-tetrahydro-1-naphthalenecarboxylic acid A solution of Example 401A (0.022 g, 0.044 mmol) in DMF (1.0 mL) was treated with acetic acid (0.05 mL) and cyclopentanone (0.005 mL, 0.06 mmol). The mixture was shaken at 50° C. for 20 minutes, treated with macroporous polystyrene bound cyanoborohydride resin (47 mg, 0.13 mmol), shaken at 70° C. for 15 hours, concentrated, and purified by $C_{18}$ reverse-phase HPLC using acetonitrile/water/0.1% TFA to provide the desired product. MS (DCI) m/e 526 $(M+H)^+$; $^1H$ NMR (500 MHz, DMSO-$d_6$) δ 13.21 (br s, 1H), 7.54 (d, 1H), 7.40 (t, 1H), 6.93 (br s, 1H), 6.84 (d, 1H), 6.65 (t, 2H), 6.03 (br s, 1H), 4.02 (br s, 1H), 3.63 (br s, 1H), 3.35 (br s, 3H), 2.99 (br s, 1H), 2.70 (br s, 2H), 2.63 (br s, 2H), 2.00 (br s, 4H), 1.83 (br s, 3H), 1.65-1.54 (m, 13H).

EXAMPLE 402

7,7-dimethyl-2-({[2-({2-[1-methyl-2-pyrrolidinyl] ethyl}amino)phenyl]sulfonyl}amino)-5,6,7,8-tetrahydro-1-naphthalenecarboxylic acid

EXAMPLE 402A methyl 2-{[(2-fluorophenyl)sulfonyl]amino}-7,7-dimethyl-5,6,7,8-tetrahydro-1-naphthalenecarboxylate A mixture of Example 362D (600 mg) and $Pd(OH)_2$ on carbon (370 mg) in 50 mL of acetic acid and 0.6 mL of concentrated sulfuric acid was reacted under 60 psi pressure for 5 days. After insoluble was filtered off and the filtrate was concentrated in vacuo, the residue was purified by silica gel column chromatography eluting with 10% ethyl acetate in n-hexane to provide 30 mg of the desired product. MS (ESI (+)) m/e 409 $(M+NH_4)^+$; MS (ESI(−)) m/e 390 $(M-H)^-$.

EXAMPLE 402B 7,7-dimethyl-2-({[2-({2-[1-methyl-2-pyrrolidinyl] ethyl}amino)phenyl]sulfonyl}amino)-5,6,7,8-tetrahydro-1-naphthalenecarboxylic acid The desired product was prepared by substituting Example 402A (30 mg, 0.077 mmol) and 2-(2-aminoethyl)-1-methylpyrrolidine (89 μL, 0.6 mmol) for Example 275E and N,N-dimethylethylenediamine, respectively, in Example 275G. MS (ESI(+)) m/e 486 $(M+H)^+$; 508 $(M+Na)^+$; MS (ESI(−)) m/e 484 $(M-H)^-$; $^1H$ NMR (300 MHz, DMSO-$d_6$) δ 9.50 (s, 1H), 7.53 (dd, 1H), 7.42 (t, 1H), 7.00 (d, 1H), 6.59-6.86 (, 2H), 5.99 (t, 1H), 3.49-3.90 (m, 2H), 3.20-3.30 (m, 2H), 2.97-3.07 (m, 1H), 2.64-2.77 (m, 5H), 2.43 (m, 2H), 2.11-2.23 (m, 2H), 1.60-2.00 (m, 4H), 1.46 (d, 2H), 0.90 (s, 6H).

EXAMPLE 403

2-{[(2-fluorophenyl)sulfonyll]amino}-8-methyl-5,6,7,8-tetrahydro-1-naphthalenecarboxylic acid The desired product was isolated as a by-product of Example 404D (6.6 mg). MS (ESI(+)) m/e 381 $(M+NH_4)^+$; MS (ESI(−)) m/e 362 $(M-H)^-$; $^1H$ NMR (300 MHz, DMSO-$d_6$) δ 9.65 (s, 1H), 7.64-7.73 (m, 2H), 7.29-7.44 (m, 2H), 7.01 (d, 1H), 6.79 (d, 1H), 3.20-3.26 (m, 1H), 2.68-2.76 (m, 2H), 1.60-1.79 (m, 4H), 1.08 (d, 3H).

EXAMPLE 404

2-{[(2-{[2,2-dimethyl-3-(1-pyrrolidinyl)propyl] amino}phenyl)sulfonyl]amino}-8-methyl-5,6,7,8-tetrahydro-1-naphthalenecarboxylic acid

EXAMPLE 404A 3-oxo-3-(1-pyrrolidinyl)propanenitrile

Ethyl cyanoacetate (5.33 mL, 50 mmol) and pyrrolidine (20.87 mL, 250 mmol) were gently refluxed at 90° C. in an oil bath for 8 hours. Excess pyrrolidine was removed by concentration and the residue was triturated with diethyl ether. This was purified by silica gel column chromatography eluting with 50% acetone in n-hexane to provide the desired product (5.0 g). MS (DCI) m/e 139 $(M+H)^+$, 156 $(M+NH_4)^+$; $^1H$ NMR (300 MHz, DMSO-$d_6$) δ 3.90 (s, 2H), 3.27-3.38 (m, 4H), 1.73-1.91 (m, 4H).

EXAMPLE 404B 2,2-dimethyl-3-oxo-3-(1-pyrrolidinyl)propanenitrile

The desired product was prepared by substituting Example 404A (2.76 g, 20 mmol), 1.6M n-butyllithium in hexanes (27.5 mL, 44 mmol) and iodomethane (6.23 mL, 100 mmol) in 50 mL of THF according to the method described in Example 393A to yield 1.32 g of the compound. MS (DCI) m/e 167 $(M+H)^+$, 184 $(M+NH_4)^+$; $^1H$ NMR (300 MHz, $CDCl_3$) δ 3.78 (s, 2H), 3.53 (m, 2H), 2.01 (m, 2H), 1.88 (m, 2H), 1.61 (s, 6H).

EXAMPLE 404C 2,2-dimethyl-3-(1-pyrrolidinyl)-1-propanamine

The desired product was prepared by substituting Example 404B (1.32 g, 7.95 mmol) for Example 393A in Example 393B and using 5 mL THF instead of 10 mL. MS (DCI) m/e 157 $(M+H)^+$.

EXAMPLE 404D

2-{[(2-{[2,2-dimethyl-3-(1-pyrrolidinyl)propyl]amino}phenyl)sulfonyl]amino}-8-methyl-5,6,7,8-tetrahydro-1-naphthalenecarboxylic acid The desired product was prepared by substituting Example 275F (50 mg, 0.133 mmol) and Example 404C (127 μL, 0.8 mmol) for Example 275E and N,N-dimethylethylenediamine, respectively, in Example 275G. MS (ESI(+)) m/e 500 $(M+H)^+$; MS (ESI(−)) m/e 498 $(M-H)^-$; $^1H$ NMR (300 MHz, DMSO-$d_6$) δ 7.88 (dd, 1H), 7.55 (dt, 1H), 7.40 (d, 1H), 7.17 (t, 1H), 6.94 (d, 1H), 6.77 (d, 1H), 5.99 (t, 1H), 3.37-3.45 (m, 1H), 3.18-3.25 (m, 3H), 3.08-3.15 (m, 3H), 2.60-2.66 (m, 2H), 1.86-1.91 (m, 7H), 1.56-1.75 (m, 7H), 1.08 (m, 3H).

EXAMPLE 405

2-{[(2-{[2-ethyl-2-(1-piperidinylmethyl)butyl]amino}phenyl)sulfonyl]amino}-8-methyl-5,6,7,8-tetrahydro-1-naphthalenecarboxylic acid

EXAMPLE 405A 2-ethyl-2-(1-piperidinylcarbonyl)butanenitrile

The compound was synthesized from 1-cyanoacetylpiperidine (1.52 g, 10 mmol), bromoethane (3.73 mL, 50 mmol) and 1.6M n-butyllithium in hexane (13.75 mL, 22 mmol) in 40 mL of THF according to the method described in Example 393A to give 0.92 g. MS (ESI(+)) m/e 209 $(M+H)^+$; 226 $(M+NH_4)^+$; $^1H$ NMR (300 MHz, DMSO-$d_6$) δ 3.44-3.67 (m, 4H), 2.00-2.10 (m, 2H), 1.79-1.86 (m, 2H), 1.43-1.70 (m, 6H), 1.03-1.07 (m, 6H).

EXAMPLE 405B 2-ethyl-2-(1-piperidinylmethyl)-1-butanamine

This was prepared from Example 405A (0.92 g, 4.4 mmol) and 1M LAH (8.8 mL, 8.8 mmol) in 3 mL, of THF according to the method described in Example 393B to yield the desired product. MS (DCI) m/e 199 $(M+H)^+$.

EXAMPLE 405C

2-{[(2-{[2-ethyl-2-(1-piperidinylmethyl)butyl]amino}phenyl)sulfonyl]amino}-8-methyl-5,6,7,8-tetrahydro-1-naphthalenecarboxylic acid The desired product was prepared by substituting Example 275F (50 mg, 0.133 mmol) and Example 405B (159 μL, 0.8 mmol) for Example 275E and N,N-dimethylethylenediamine, respectively, in Example 275G. MS (ESI(+)) m/e 540 $(M+H)^+$; $^1H$ NMR (300 MHz, DMSO-$d_6$) δ 9.65 (s, 1H), 7.64-7.73 (m, 2H), 7.55 (dt, 1H), 7.40 (t, 1H), 7.31 (t, 1H), 7.01 (d, 1H), 6.79 (d, 1H), 5.87 (t, 1H), 3.22-3.31 (m, 3H), 2.96-3.13 (m, 3H), 2.61-2.77 (m, 4H), 1.56-1.80 (m, 14H), 1.34 (m, 1H), 1.08 (d, 3H), 0.75-0.83 (m, 6H).

EXAMPLE 406

2-ethoxy-3-ethyl-6-({[2-({2-[1-methyl-2-pyrrolidinyl]ethyl}amino)phenyl]sulfonyl}amino)benzoic acid A solution of Example 385I (120 mg, 0.33 mmol), triethylamine (0.24 mL) and N-methyl-2-(2'-aminoethyl)pyrrolidine (217 mg, 1.7 mmol) in acetonitrile (3 mL) was heated to 120° C. in a sealed vial for 2 days, concentrated, and purified using a reverse phase HPLC, giving the desired product, 79 mg, 50.3%. $^1H$ NMR (DMSO-$d_6$) δ 1.08 (t, 3H), 1.28 (t, 3H), 1.60-1.70 (m, 1H), 1.80-2.00 (m, 3H), 2.12-2.30 (m, 2H), 2.53 (q, 2H), 2.68 (s, 3H), 2.90-3.04 (m, 1H), 3.20-3.32 (m, 3H), 3.50-3.60 (m, 1H), 3.90 (q, 2H), 5.98 (br s, 1H), 6.60 (d, 1H), 6.68 (t, 1H), 6.85 (d, 1H), 7.15 (d, 1H), 7.40 (t, 1H), 7.58 (d, 1H), 9.68 (s, 1H), 10.48 (br s, 1H); MS (ESI(+)) m/e 476 $(M+H)^+$.

EXAMPLE 407

6-{[(2-{[3-(dimethylamino)-2,2-dimethylpropyl]amino}phenyl)sulfonyl]amino}-2-ethoxy-3-ethylbenzoic acid The desired product was prepared by substituting 2-dimethyl-3-(N,N-dimethylamino)propylamine for N-methyl-2-(2'-aminoethyl)pyrrolidine in Example 406, yielding 64 mg, 40.7%. $^1H$ NMR (DMSO-$d_6$) δ 1.02 (s, 6H), 1.08 (t, 3H), 1.25 (t, 3H), 2.53 (q, 2H), 2.75 (s, 6H), 3.08 (s, 2H), 3.18 (s, 2H), 3.82 (q, 2H), 5.95 (br s, 1H), 6.60 (d, 1H), 6.65 (t, 1H), 6.55 (d, 1H), 7.15 (d, 1H), 7.40 (t, 1H), 7.58 (d, 1H), 9.78 (br s, 1H), 13.20 (br s, 1H); MS (ESI(+)) m/e 476 $(M+H)^+$.

EXAMPLE 408

6-[({2-[(3-aminopropyl)amino]phenyl}sulfonyl)amino]-2-ethoxy-3-ethylbenzoic acid

EXAMPLE 408A 6-({[2-({3-[(tert-butoxycarbonyl)amino]propyl}amino)phenyl]sulfonyl}amino)-2-ethoxy-3-ethylbenzoic acid The desired product was prepared by substituting 3-(N-tert-butoxycarbonylamino)propylamine for N-methyl-2-(2'-aminoethyl)pyrrolidine in Example 406.

EXAMPLE 408B

6-[({2-[(3-aminopropyl)amino]phenyl}sulfonyl)amino]-2-ethoxy-3-ethylbenzoic acid The desired product was prepared as the hydrochloride salt by treating Example 408A (85 mg) with 4N HCl in dioxane (10 mL) at room temperature for 6 hours, evaporation of the solvent gave the desired produce yielding 67 mg, 48.1%. $^1H$ NMR ($DMSO-d_6$) δ 1.10 (t, 3H), 1.25 (t, 3H), 1.84 (m, 2H), 2.53 (q, 2H), 2.86 (m, 2H), 3.26 (m, 2H), 3.82 (q, 2H), 5.95 (br s, 1H), 6.60-6.70 (m, 2H), 6.82 (d, 1H), 7.12 (d, 1H), 7.40 (t, 1H), 7.52 (d, 1H), 7.98 (br s, 3H), 9.60 (s, 1H), 13.00 (br s, 1H); MS (ESI(+)) m/e 422 $(M+H)^+$.

EXAMPLE 409

6-{[(2-{[4-(dimethylamino)butyl]amino}phenyl)sulfonyl]amino}-2-ethoxy-3-ethylbenzoic acid The desired product was prepared by substituting 4-(N,N-dimethylamino)butylamine for N-methyl-2-(2'-aminoethyl)pyrrolidine in Example 406, yielding 78 mg, 50.9%. $^1H$ NMR ($DMSO-d_6$) δ 1.08 (t, 3H), 1.25 (t, 3H), 1.55 (m, 2H), 1.68 (m, 2H), 2.53 (q, 2H), 2.68 (s, 6H), 3.04 (m, 2H), 3.15 (m, 2H), 3.82 (q, 2H), 5.95 (br s, 1H), 6.60-6.70 (m, 2H), 6.78 (d, 1H), 7.15 (d, 1H), 7.40 (t, 1H), 7.52 (d, 1H), 9.60 (s, 1H), 10.06 (br s, 1H); MS (ESI(+)) m/e 464 $(M+H)^+$.

EXAMPLE 410

3-bromo-6-({[2-({2-[1-methyl-2-pyrrolidinyl]ethyl}amino)phenyl]sulfonyl}amino)-2-propoxybenzoic acid

EXAMPLE 410A methyl 6-amino-3-bromo-2-propoxybenzoate

The title compound was prepared from Example 385D (0.5 g, 2.04 mmole) according to the procedure of Example 385E, substituting iodoethane with 1-iodopropane. Yield: 0.55 g, 94.2%. $^1H$ NMR ($DMSO-d_6$) δ 0.95 (t, 3H), 1.68 (m, 2H), 3.80 (s, 3H), 3.82 (t, 2H), 5.82 (s, 2H), 6.44 (d, 1H), 7.28 (d, 1H); MS ($DCI/NH_3$) m/e 288, 290 $(M+H)^+$.

EXAMPLE 410B methyl 3-bromo-6-{[(2-fluorophenyl)sulfonyl]amino}-2-propoxybenzoate The title compound was prepared from Example 410A (0.55 g, 1.9 mmol) and 2-fluorobenzenesulfonyl chloride according to the procedure of Example 385F, yielding 0.70 g, 82.6%. $^1H$ NMR ($DMSO-d_6$) δ 0.92 (t, 3H), 1.62 (m, 2H), 3.62 (s, 3H), 3.82 (s, 3H), 6.98 (d, 1H), 7.30-7.48 (m, 2H), 7.60-7.80 (m, 3H), 10.40 (s, 1H); MS (ESI(−)) m/e 444, 446 $(M+H)^+$.

EXAMPLE 410C 3-bromo-6-{[(2-fluorophenyl)sulfonyl]amino}-2-propoxybenzoic acid

The title compound was prepared from Example 410B (0.3 g, 0.67 mmole) according to the procedure of Example 385I, yielding 0.28 g, 96.7%. $^1H$ NMR ($DMSO-d_6$) δ 0.96 (t, 3H), 1.65 (m, 2H), 3.82 (t, 2H), 6.96 (d, 1H), 7.30-7.48 (m, 2H), 7.60 (d, 1H), 7.64-7.80 (m, 2H), 10.40 (s, 1H); MS (ESI(−)) m/e 430, 432 $(M-H)^-$.

EXAMPLE 411

3-bromo-6-{[(2-{[3-(dimethylamino)-2,2-dimethylpropyl]amino}phenyl)sulfonyl]amino}-2-propoxybenzoic acid The title compound was prepared from Example 410C (50 mg, 0.16 mmol) according to the procedure of Example 406, yielding 12 mg, 14.0%. $^1H$ NMR ($DMSO-d_6$) δ 0.95 (t, 3H), 1.22-1.35 (m, 4H), 1.80-2.02 (m, 2H), 2.10-2.30 (m, 2H), 2.70 (s, 3H), 2.90-3.05 (m, 1H), 3.20-3.38 (m, 4H), 3.85 (t, 2H), 6.68 (d, 1H), 6.84 (d, 1H), 7.40 (t, 1H), 7.54 (m, 2H), 7.68 (dd, 1H), 9.90 (br s, 1H), 10.30 (br s, 1H); MS (ESI(−)) m/e 538, 540 $(M-H)^-$.

EXAMPLE 413

3-bromo-6-{[(2-{[4-(N,N-dimethylamino)butyl]amino}phenyl)sulfonyl]amino}-2-propoxybenzoic acid The title compound was prepared from Example 410 (50 mg, 0.16 mmol) and 4-(N,N-dimethylamino)butylamine according to the procedure of Example 406, yielding 29 mg, 34.1%. $^1H$ NMR ($DMSO-d_6$) δ 0.96 (t, 3H), 1.50-1.60 (m, 2H), 1.62-1.75 (m, 4H), 2.68 (s, 6H), 3.00-3.10 (m, 2H), 3.12-3.20 (m, 2H), 3.85 (t, 2H), 6.60 (t, 1H), 6.68 (d, 1H), 6.80 (d, 1H), 7.40 (t, 1H), 7.50-7.60 (m, 2H), 9.86 (br s, 1H), 10.28 (br s, 1H); MS (ESI(−)) m/e 528, 526 $(M-H)^-$.

EXAMPLE 415

3-bromo-6-{[(2-{[3-(4-morpholinyl)propyl]amino}phenyl)sulfonyl]amino}-2-propoxybenzoic acid The title compound was prepared from Example 410 (50 mg, 0.16 mmol) and 3-(4-morpholinyl)propylamine according to the procedure of Example 406, yielding 41 mg, 46%. $^1H$ NMR ($DMSO-d_6$) δ 0.95 (t, 3H), 1.60-1.65 (m, 2H), 1.90-2.00 (m, 2H), 2.90-3.08 (m, 2H), 3.10-3.18 (t, 2H), 3.20-3.30 (t, 2H), 3.30-3.42 m, 2H), 3.70-3.82 (m, 2H), 3.85 (t, 2H), 3.95 (m, 2H), 6.65 (t, 1H), 6.72 (d, 1H), 6.85 (d, 1H), 7.40 (t, 1H), 7.58 (m, 2H), 9.90 (br s, 1H), 10.70 (br s, 1H); MS (ESI(+)) m/e 554, 556 $(M+H)^+$.

EXAMPLE 416

3-bromo-6-{[(2-fluorophenyl)sulfonyl]amino}-2-propoxybenzoic acid

The title compound was prepared from Example 410B (0.3 g, 0.67 mmole) according to the procedure of Example 385, yielding 0.28 g, 96.7%. $^1H$ NMR ($DMSO-d_6$): δ0.96 (t, 3H), 1.65 (m, 2H), 3.82 (t, 2H), 6.96(d, 1H), 7.30-7.48(m, 2H), 7.60(d, 1H), 7.64-7.80(m, 2H), 10.40(s, 1H). MS (ESI−): m/z 430, 432, base peaks.

EXAMPLE 417

(7S,8S)-7-(acetyloxy)-8-methyl-2-({[2-({2-[(1-methyl-2-pyrrolidinyl]ethyl}amino)phenyl]sulfonyl}amino)-5,6,7,8-tetrahydro-1-naphthalenecarboxylic acid

EXAMPLE 417A

N-[(7S,8S)-1-bromo-7-hydroxy-8-methyl-5,6,7,8-tetrahydro-2-naphthalenyl]-2-fluorobenzenesulfonamide A mixture of R-[N,N'-bis(monoisopinocampheylborane)-N,N,N',N'-tetramethylethylenediamine] (1.25 g, 3.0 mmol) in THF (5 mL) was treated with boron trifluoride etherate, stirred at room temperature for 1.5 hours, and filtered. The filter cake was washed with THF (2.5 mL). Half of the solution containing the free isopinocamphenylborane (1.5 mmol) was cooled to −25° C., treated with a solution of Example 275D (500 mg, 1.25 mmol) in THF (3 mL), stirred at −20° C. for 48 hours, warmed to 0° C., and quenched with methanol (0.5 mL). The solution was treated with 3M NaOH (1.1 mL), followed by 30% $H_2O_2$ (0.9 mL) dropwise, stirred for 1 hour at 50° C., cooled to room temperature, extracted with diethyl ether, dried ($Na_2SO_4$), filtered, and concentrated. The concentrate was purified by flash column chromatography on silica gel with 30% acetone/hexanes to give 300 mg (57% yield). MS (ESI) m/e 412 $(M-H)^-$; $^1H$ NMR (300 MHz, DMSO-$d_6$) δ 10.02 (s, 1H), 7.69 (m, 1H), 7.63 (dt, 1H), 7.42 (m, 1H), 7.30 (dt, 1H), 7.0 (d, 1H), 6.92 (d, 1H), 4.73 (d, 1H), 3.85 (m, 1H), 2.95 (m, 1H), 2.82 (m, 1H), 2.6 (m, 1H), 1.81 (m, 1H), 1.69 (m, 1H), 0.98 (d, 3H).

EXAMPLE 417B (1S,2S)-8-bromo-7-{[(2-fluorophenyl)sulfonyl]amino}-1-methyl-1,2,3,4-tetrahydro-2-naphthalenyl acetate A mixture of Example 417A (300 mg, 0.73 mmol) and acetic anhydride (0.1 mL, 1.1 mmol) in $CH_2Cl_2$ (7 mL) was treated with pyridine (0.6 mL, 7.3 mmol) and DMAP (9.0 mg, 0.07 mmol), stirred at room temperature for 3 hours and partitioned between diethyl ether and 1N HCl. The organic phase was washed with brine, dried ($MgSO_4$), filtered, and concentrated. The crude product was purified by silica gel plug filtration eluting with 20% acetone/hexanes to provide the desired product (330 mg, 92% yield). MS (ESI) m/e 455 $(M-H)^-$; $^1H$ NMR (300 MHz, DMSO-$d_6$) δ 8.06 (m, 1H), 7.84 (m, 1H), 7.52 (m, 2H), 7.43 (m, 1H), 7.34 (m, 1H), 5.07 (m, 1H), 3.23 (m, 1H), 2.9 (m, 2H), 1.99, 1.93 (s, 3H), 1.87, 1.80 (s, 2H), 1.23 (dd, 3H).

EXAMPLE 417C methyl (7S,8S)-7-(acetyloxy)-2-{[(2-fluorophenyl)sulfonyl]amino}-8-methyl-5,6,7,8-tetrahydro-1-naphthalenecarboxylate The desired product was prepared according to the procedure of Example 275E substituting Example 417B for Example 275D. MS (ESI) m/e 434 $(M-H)^-$; $^1H$ NMR (300 MHz, DMSO-$d_6$) δ 10.0 (s, 1H), 7.68 (m, 2H), 7.43 (t, 1H), 7.32 (t, 1H), 7.14 (d, 1H), 6.91 (d, 1H), 4.9 (m, 1H), 3.65 (s, 3H), 3.11 (m, 1H), 2.73 (m, 2H), 1.93 (s, 3H), 1.92 (m, 2H), 1.03 (d, 3H).

EXAMPLE 417D (7S,8S)-7-(acetyloxy)-8-methyl-2-({[2-({2-[(1-methyl-2-pyrrolidinyl]ethyl}amino)phenyl]sulfonyl}amino)-5,6,7,8-tetrahydro-1-naphthalenecarboxylic acid The desired product was prepared according to the procedure of Example 275G substituting Example 417C for Example 275E and substituting 2-(1-methyl-2-pyrrolidinyl)ethylamine for N,N-dimethylethylenediamine. MS (ESI) m/e 528 $(M-H)^-$; $^1H$ NMR (300 MHz, DMSO-$d_6$) δ 9.5 (br d, 1H), 7.56 (d, 1H), 7.43 (t, 1H), 7.0 (d, 1H), 6.87 (d, 1H), 6.69 (t, 1H), 6.6 (d, 1H), 6.0 (m, 1H), 4.91 (m, 1H), 3.53 (m, 1H), 3.23 (m, 3H), 3.02 (m, 1H), 2.73 (m, 5H), 2.27 (d, 1H), 2.17 (m, 2H), 1.93 (d, 3H), 1.91 (m, 2H), 1.68 (m, 2H), 1.12 (d, 3H).

EXAMPLE 418

2-{[(2-{[({2-[1-methyl-2-pyrrolidinyl]ethyl}amino)carbonyl]amino}phenyl)sulfonyl]amino}-5,6,7,8-tetrahydro-1-naphthalenecarboxylic acid

EXAMPLE 418A methyl 2-amino-5,6,7,8-tetrahydro-1-naphthoate

A 500 mL RB flask was charged with Example 128B (13.66 g, 47.54 mmol), benzene (190 mL), and MeOH (48 mL). To this stirred solution under $N_2$ was added $TMSCHN_2$ (30.9 mL, 61.81 mmol, 2.0M solution in hexanes). The reaction was stirred at room temperature for 1 hour, then quenched with 3 mL glacial AcOH. The solvent was evaporated to dryness to give a residue. The residue was dissolved in 150 mL AcOH. $PtO_2$ (7.00 g) was added to a 500 mL reaction vessel for a Parr shaker, then purged with Ar. The solution of the residue in AcOH was then added. The vessel was fitted to the Parr shaker and charged with $H_2$ to 60 psi (fill and vent 3×). The shaker was run for 3 hours, then filtered and evaporated to dryness to yield a solid residue. A 500 mL RB flask was charged with the residue and $CH_2Cl_2$ (154 mL). To this flask was added TFA (26 mL). The reaction was stirred for 3 hours, then transferred to a separatory funnel. The organic layer was washed with NaOH (2×250 mL) and brine (200 mL), dried over $MgSO_4$, filtered, and evaporated to dryness to give the desired product (8.72 g, 91%). MS (ESI+Q1MS) m/e 206 $(M+H)^+$; $^1H$-NMR (DMSO) δ 6.83 (d, 1H), 6.52 (d, 2H), 5.26 (s, 2H), 3.78 (s, 3H), 2.62 (m, 2H), 2.56 (m, 2H), 1.63 (quint., 4H).

EXAMPLE 418B methyl 2-{[(2-nitrophenyl)sulfonyl]amino}-5,6,7,8-tetrahydro-1-naphthalenecarboxylate A solution of Example 418A (4.74 g, 23.09 mmol) in pyridine (46 mL) was treated with 2-nitrobenzenesulfonyl chloride (5.37 g, 24.25 mmol), stirred 24 hours, concentrated, diluted with ethyl acetate (150 mL), washed with 1N HCl (2×100 mL) and brine (100 mL), dried ($MgSO_4$), filtered, and concentrated. The residue was purified by column chromatography (3:1 hexanes/ethyl acetate) to provide the desired product (5.93 g, 66%). MS (ESI(+)) m/e 408 $(M+NH_4)^+$; MS (ESI(−)) m/e 389 $(M-H)^-$; $^1H$ NMR (300 MHz, DMSO-$d_6$) δ 10.01 (s, 1H), 7.98 (d, 1H), 7.87 (m, 1H), 7.81 (m, 2H), 7.12 (d, 1H), 6.92 (d, 1H), 3.60 (s, 3H), 2.70 (m, 2H), 2.53 (m, 2H), 1.67 (m, 4H).

EXAMPLE 418C methyl 2-{[(2-aminophenyl)sulfonyl]amino}-5,6,7,8-tetrahydro-1-naphthalenecarboxylate A solution of Example 418B (2.0873 g, 5.35 mmol) in 4:1 methanol:ethyl acetate (120 mL) was treated with Raney nickel (4.00 g), pressurized to 60 psi with $H_2$ and shaken for 2 hours. The reaction was then filtered and the filtrate was concentrated to yield the desired product (1.8750 g, 97%). MS (ESI(+)) m/e 361 $(M+H)^+$, 383 $(M+Na)^+$; MS (ESI(−)) m/e 359 $(M-H)^-$; $^1H$ NMR (300 MHz, DMSO-$d_6$) δ 7.32 (dd, 1H), 7.23 (td, 1H), 7.02 (d, 1H), 6.80 (m, 2H), 6.52 (td, 1H), 3.74 (s, 3H), 2.65 (m, 2H), 2.53 (m, 2H), 1.65 (m, 4H).

EXAMPLE 418D

2-{[(2-{[({2-[1-methyl-2-pyrrolidinyl]ethyl}amino) carbonyl]amino}phenyl)sulfonyl]amino}-5,6,7,8-tetrahydro-1-naphthalenecarboxylic acid A solution of Example 418C (145.6 mg, 0.404 mmol) in THF (0.25 mL) was treated with carbonyldiimidazole (65.5 mg, 0.404 mmol), heated to 50° C. for 1.5 hours, cooled to room temperature, treated with 2-(2-aminoethyl)-1-methylpyrrolidine. (58 µL, 0.404 mmol), stirred for 24 hours, and concentrated. The residue was dissolved in pyridine (0.5 mL), treated with LiI (162.2 mg, 1.212 mmol), heated in a microwave reactor at 150° C. for 25 minutes, concentrated, and purified by $C_{18}$ reverse-phase HPLC using acetonitrile/water/0.1% TFA to provide the desired product. (58.7 mg, 29%). MS (ESI(−)) m/e 499 (M−H)-; $^{1}$H NMR (300 MHz, DMSO-$d_6$) δ 9.74 (s, 1H), 8.21 (m, 1H), 7.66 (dd, 1H), 7.53 (ddd, 1H), 7.32 (t, 1H), 7.07 (td, 1H), 6.96 (d, 1H), 6.53 (d, 1H), 3.18 (m, 3H), 3.01 (m, 2H), 2.78 (s, 3H), 2.66 (m, 4H), 2.30 (m, 2H), 1.92 (m, 2H), 1.67 (m, 4H), 1.28 (m, 1H), 0.87 (m, 1H).

EXAMPLE 419

2-({[2-({4-[2,5-dimethyl-1-pyrrolidinyl] butanoyl}amino)phenyl]sulfonyl}amino)-5,6,7,8-tetrahydro-1-naphthalenecarboxylic acid The desired product was prepared by substituting 4-chlorobutanoyl chloride and 2,5-dimethylpyrrolidine for chloroacetyl chloride and diethylamine, respectively, in Example 297. MS (ESI(+)) m/e 514 $(M+H)^+$; MS (ESI(−)) m/e 512 $(M-H)^-$; $^{1}$H NMR (300 MHz, DMSO-$d_6$) δ 9.23 (s, 1H), 8.12 (d, 1H), 7.71 (dd, 1H), 7.63 (ddd, 1H), 7.26 (td, 1H), 6.96 (d, 1H), 6.51 (d, 1H), 355 (m, 1H), 3.17 (m, 1H), 2.67 (m, 4H), 2.48 (m, 2H), 2.16 (m, 2H), 1.93 (m, 2H), 1.67 (m, 6H), 1.35 (d, 6H).

EXAMPLE 420

2-[({2-[({2-[1-methyl-2-pyrrolidinyl]ethyl}amino) carbonyl]phenyl}sulfonyl)amino]-1-naphthoic acid The desired product was prepared by substituting 2-(2-aminoethyl)-1-methylpyrrolidine for 1-(2-aminoethyl)piperdine in Examples 328A-B. MS (ESI(+)) m/e 482 $(M+H)^+$; (ESI(−)) m/e 480 $(M-H)^-$; $^{1}$H NMR (300 MHz, DMSO-$d_6$) δ 8.85 (s, 1H), 8.15 (br s, 1H), 7.94 (d, 1H), 7.91 (d, 1H), 7.84 (d, 1H), 7.72 (t, 1H), 7.61-7.53 (m, 5H), 7.47 (t, 1H), 3.60 (br s, 1H), 3.44 (m, 3H), 3.08 (br s, 1H), 2.83 (s, 3H), 2.38 (br s, 1H), 2.19 (br s, 1H), 2.12-1.83 (m, 2H), 1.80-1.65 (m, 2H).

EXAMPLE 421

2-({[2-({[3-(1-pyrrolidinyl)propyl]amino}carbonyl) phenyl]sulfonyl}amino)-1-naphthoic acid The desired product was prepared by substituting 1-(3-aminopropyl)pyrrolidine for 1-(2-aminoethyl)piperdine in Examples 328A-B. MS (ESI(+)) m/e 482 $(M+H)^+$; (ESI(−)) m/e 480 $(M-H)^-$; $^{1}$H NMR (300 MHz, DMSO-$d_6$) δ 8.88 (br s, 1H), 8.08 (br s, 1H), 7.95 (d, 1H), 7.90 (d, 1H), 7.85 (t, 1H), 7.73 (t, 1H), 7.62 (m, 2H), 7.56 (m, 2H), 7.48 (m, 1H), 3.82 (m, 3H), 3.67 (m, 2H), 3.43 (m, 4H), 2.16 (m, 4H), 1.91 (br s, 1H).

EXAMPLE 422

2-({[2-({[3-(isopropylamino)propyl] amino}carbonyl)phenyl]sulfonyl}amino)-1-naphthoic acid The desired product was prepared by substituting N-isopropyl-1,3-propanediamine for 1-(2-aminoethyl)piperdine in Examples 328A-B. Following the procedure 328A-B, except substituting for 1-(2-aminoethyl)piperdine, the desired product was obtained as an oil. MS (ESI(+)) m/e 470 $(M+H)^+$; (ESI(−)) n/e 468 $(M-H)^-$; $^{1}$H NMR (300 MHz, DMSO-$d_6$) □ 8.88 (br s, 1H), 8.29 (br s, 1H), 8.09 (br s, 1H), 7.94 (d, 1H), 7.89 (d, 1H), 7.82 (d, 1H), 7.72 (t, 1H), 7.60 (t, 2H), 7.55 (m, 2H), 7.48 (t, 1H), 3.40 (m, 3H), 3.04 (br s, 2H), 1.89 (quint, 2H), 1.24 (d, 6H).

EXAMPLE 423

2-[({2-[({[2-(1-piperidinyl)ethyl]amino}carbonyl) amino]phenyl}sulfonyl)amino]-5,6,7,8-tetrahydro-1-naphthalenecarboxylic acid The desired product was prepared by substituting 2-(1-piperidinyl)ethylamine for 2-(2-aminoethyl)-1-methylpyrrolidine in Example 418D. MS (ESI(+)) m/e 501 $(M+H)^+$; MS (ESI(−)) m/e 499 $(M-H)^-$; $^{1}$H NMR (300 MHz, DMSO-$d_6$) δ 9.89 (s, 1H), 8.27 (s, 1H), 8.21 (dd, 1H), 7.68 (dd, 1H), 7.55 (ddd, 1H), 7.47 (t, 1H), 7.09 (ddd, 1H), 6.95 (d, 1H), 6.60 (d, 1H), 3.50 (m, 2H), 3.45 (g, 2H), 3.16 (m, 2H), 2.91 (m, 2H), 2.66 (m, 4H), 1.82 (m, 2H), 1.67 (m, 7H), 1.39 (m, 1H).

EXAMPLE 424

2-[({2-[({[2-(1-piperazinyl)ethyl]amino}carbonyl) amino]phenyl}sulfonyl)amino]-5,6,7,8-tetrahydro-1-naphthalenecarboxylic acid The desired product was prepared by substituting 2-(1-piperazinyl)ethylamine for 2-(2-aminoethyl)-1-methylpyrrolidine in Example 418D. MS (ESI(+)) m/e 502 $(M+H)^+$; MS (ESI(−)) m/e 500 $(M-H)^-$; $^{1}$H NMR (300 MHz, DMSO-$d_6$) δ 8.92 (s, 1H), 8.19 (m, 1H), 7.68 (dd, 1H), 7.52 (ddd, 1H), 7.47 (t, 1H), 7.07 (ddd, 1H), 6.95 (d, 1H), 6.76 (d, 1H), 3.40 (q, 2H), 3.34 (m, 4H), 3.24 (m, 4H), 3.07 (m, 2H), 2.66 (m, 4H), 1.65 (m, 4H).

EXAMPLE 425

2-{[(2-{[({3-[2-methyl-1-piperidinyl]propyl}amino) carbonyl]amino}phenyl)sulfonyl]amino}-5,6,7,8-tetrahydro-1-naphthalenecarboxylic acid The desired product was prepared by substituting 3-[2-methyl-1-piperidinyl]propylamine for 2-(2-aminoethyl)-1-methylpyrrolidine in Example 418D. MS (ESI(+)) m/e 529 $(M+H)^+$; MS (ESI(−)) m/e 527 $(M-H)^-$; $^{1}$H NMR (300 MHz, DMSO-$d_6$) δ 8.19 (m, 2H), 7.68 (d, 1H), 7.53 (t, 1H), 7.32 (m, 1H), 7.08 (ddd, 1H), 6.95 (d, 1H), 6.55 (m, 1H), 3.59 (m, 1H), 3.15 (m, 4H), 3.00 (m, 1H), 2.87 (m, 1H), 2.65 (m, 4H), 1.80 (m, 4H), 1.67 (m, 7H), 1.45 (m, 1H), 1.25 (d, 3H).

EXAMPLE 426

2-[({2-[({[2-(4-morpholinyl)ethyl]amino}carbonyl)amino]phenyl}sulfonyl)amino]-5,6,7,8-tetrahydro-1-naphthalenecarboxylic acid The desired product was prepared by substituting 2-(4-morpholinyl)ethylamine for 2-(2-aminoethyl)-1-methylpyrrolidine in Example 418D. MS (ESI(−)) m/e 501 $(M-H)^-$; $^1H$ NMR (300 MHz, DMSO-$d_6$) δ 8.21 (m, 2H), 7.68 (dd, 1H), 7.54 (m, 2H), 7.07 (ddd, 1H), 6.94 (d, 1H), 6.77 (d, 1H), 3.84 (m, 4H), 3.46 (m, 4H), 3.24 (t, 4H), 2.67 (m, 4H), 1.65 (m, 4H).

EXAMPLE 427

2-[({2-[({[3-(4-morpholinyl)propyl]amino}carbonyl)amino]phenyl}sulfonyl)amino]-5,6,7,8-tetrahydro-1-naphthalenecarboxylic acid The desired product was prepared by substituting 3-(4-morpholinyl)-1-propylamine for 2-(2-aminoethyl)-1-methylpyrrolidine in Example 418D. MS (ESI(+)) m/e 517 $(M+H)^+$; MS (ESI(−)) m/e 515 $(M-H)^-$; $^1H$ NMR (300 MHz, DMSO-$d_6$) δ 8.18 (m, 2H), 7.70 (d, 1H), 7.53 (ddd, 1H), 7.37 (m, 1H), 7.08 (ddd, 1H), 6.95 (d, 1H), 6.63 (m, 1H), 3.93 (m, 2H), 3.39 (m, 2H), 3.12 (m, 6H), 2.67 (m, 4H), 1.82 (m, 4H).

EXAMPLE 428

2-[({2-[({[4-(diethylamino)-1-methylbutyl]amino}carbonyl)amino]phenyl}sulfonyl)amino]-5,6,7,8-tetrahydro-1-naphthalenecarboxylic acid The desired product was prepared by substituting N-[4-aminopentyl]-N,N-diethylamine for 2-(2-aminoethyl)-1-methylpyrrolidine in Example 418D. MS (ESI(+)) m/e 531 $(M+H)^+$; MS (ESI(−)) m/e 529 $(M-H)^-$; $^1H$ NMR (300 MHz, DMSO-$d_6$) δ 8.25 (dd, 1H), 8.15 (s, 1H), 7.67 (dd, 1H), 7.52 (ddd, 1H), 7.11 (d, 1H), 7.06 (ddd, 1H), 6.95 (d, 1H), 6.53 (d, 1H), 3.72 (m, 1H), 3.07 (m, 6H), 2.66 (m, 4H), 1.67 (m, 4H), 1.62 (m, 2H), 1.45 (m, 2H), 1.15 (t, 6H), 1.12 (t, 3H).

EXAMPLE 429

2-[({2-[({[3-(dimethylamino)-2,2-dimethylpropyl]amino}carbonyl)amino]phenyl}sulfonyl)amino]-5,6,7,8-tetrahydro-1-naphthalenecarboxylic acid The desired product was prepared by substituting N-(3-amino-2,2-dimethylpropyl)-N,N-dimethylamine for 2-(2-aminoethyl)-1-methylpyrrolidine in Example 418D. MS (ESI(+)) m/e 503 $(M+H)^+$; MS (ESI(−)) m/e 501 $(M-H)^-$; $^1H$ NMR (300 MHz, DMSO-$d_6$) δ 8.25 (s, 1H), 8.11 (dd, 1H), 7.69 (dd, 1H), 7.55 (ddd, 1H), 7.47 (t, 1H), 7.11 (ddd, 1H), 6.95 (d, 1H), 6.56 (d, 1H), 3.10 (d, 2H), 2.98 (s, 2H), 2.84 (s, 6H), 2.66 (m, 4H), 1.67 (m, 4H), 1.01 (s, 6H).

EXAMPLE 430

2-[({2-[({[3-(1-piperidinyl)propyl]amino}carbonyl)amino]phenyl}sulfonyl)amino]-5,6,7,8-tetrahydro-1-naphthalenecarboxylic acid The desired product was prepared by substituting 3-(1-piperidinyl)propylamine for 2-(2-aminoethyl)-1-methylpyrrolidine in Example 418D. MS (ESI(+)) m/e 515 $(M+H)^+$; MS (ESI(−)) m/e 513 $(M-H)^-$; $^1H$ NMR (300 MHz, DMSO-$d_6$) δ 8.18 (m, 2H), 7.69 (dd, 1H), 7.53 (ddd, 1H), 7.34 (s, 1H), 7.08 (ddd, 1H), 6.95 (d, 1H), 6.59 (m, 1H), 3.42 (d, 2H), 3.14 (q, 2H), 3.06 (m, 2H), 2.83 (m, 2H), 2.67 (m, 4H), 1.82 (m, 5H), 1.66 (m, 6H), 1.38 (m, 1H).

EXAMPLE 431

2-[({2-[({[3-(1-piperazinyl)propyl]amino}carbonyl)amino]phenyl}sulfonyl)amino]-5,6,7,8-tetrahydro-1-naphthalenecarboxylic acid The desired product was prepared by substituting 3-(1-piperazinyl)propylamine for 2-(2-aminoethyl)-1-methylpyrrolidine in Example 418D. MS (ESI(+)) m/e 538 $(M+Na)^+$; MS (ESI(−)) m/e 514 $(M-H)^-$; $^1H$ NMR (300 MHz, DMSO-$d_6$) δ 8.18 (m, 2H), 7.69 (dd, 1H), 7.53 (ddd, 1H), 7.28 (s, 1H), 6.95 (d, 1H), 6.59 (d, 1H), 3.16 (m, 7H), 2.87 (m, 2H), 2.76 (m, 2H), 2.68 (m, 4H), 1.73 (m, 2H), 1.67 (m, 4H).

EXAMPLE 432

3-ethyl-6-{[(2-fluorophenyl)sulfonyl]amino}-2-propoxybenzoic acid

EXAMPLE 432A methyl 6-{[(2-fluorophenyl)sulfonyl]amino}-2-propoxy-3-vinylbenzoate The title compound was prepared from Example 410B according to the procedure of Example 230B with an average yield of 89%. $^1H$ NMR (DMSO-$d_6$) δ 0.90 (t, 3H), 1.55-1.68 (m, 2H), 3.65 (s, 3H), 3.68 (t, 2H), 5.34 (d, 1H), 5.80 (d, 1H), 6.80 (dd, 1H), 7.00 (d, 1H), 7.34 (t, 1H), 7.42 (t, 1H), 7.60-7.78 (m, 3H), 10.24 (s, 1H); MS (ESI(−)) m/e 392 $(M-H)^-$.

EXAMPLE 432B methyl 3-ethyl-6-{[(2-fluorophenyl)sulfonyl]amino}-2-propoxybenzoate Example 432A (0.316 g, 0.8 mmole) was hydrogenated in methanol (10 mL) over 10% Pd/C (0.3 g) for 16 hours under one atmosphere of hydrogen. Filtration and evaporation of the solvent provided the desired product (0.28 g, 87.3%).

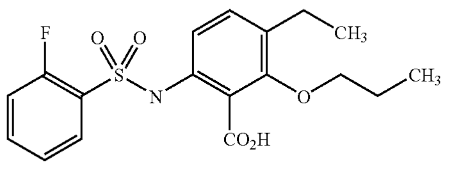

EXAMPLE 432C 3-ethyl-6-{[(2-fluorophenyl)sulfonyl]amino}-2-propoxybenzoic acid

The title compound was prepared from Example 432B (0.27 g, 0.7 mmole) according to the procedure of Example 385I, yielding 0.24 g, 88.1%. $^1H$ NMR (DMSO-$d_6$) δ 0.90 (t, 3H), 1.08 (t, 3H), 1.60-1.70 (m, 2H), 2.55 (q, 2H), 3.72 (t, 3H), 6.82 (d, 1H), 7.20 (d, 1H), 7.30 (t, 1H), 7.40 (t, 1H), 7.60-7.78 (m, 2H), 9.92 (s, 1H), 13.22 (br s, 1H); MS (ESI(−)) m/e 380 $(M-H)^-$.

EXAMPLE 433

3-ethyl-6-({[2-({2-[(2S)-1-methyl-2-pyrrolidinyl]ethyl}amino)phenyl]sulfonyl}amino)-2-propoxybenzoic acid The title compound was prepared from Example 432C (44 mg, 0.115 mmol) according to the procedure of Example 406, yielding 35 mg, 62.2%. $^1$H NMR (DMSO-$d_6$) δ 0.90 (t, 3H), 1.05 (t, 3H), 1.55-1.62 (m, 2H), 1.65-1.80 (m, 1H), 1.82-1.90 (m, 1H), 1.95-2.05 (m, 2H), 2.10-2.30 (m, 2H), 2.45 (q, 2H), 2.70 (s, 3H), 3.05-3.40 (m, 5H), 3.85 (t, 2H), 6.55 (t, 1H), 6.72 (d, 1H), 6.96 (d, 1H), 7.05 (m, 1H), 7.30 (t, 1H), 7.50 (d, 1H), 10.5-12.8(bs, 2H); MS (ESI(−)) m/e 488 $(M-H)^-$.

EXAMPLE 434

3-ethyl-6-({[2-({3-[2-methyl-1-piperidinyl]propyl}amino)phenyl]sulfonyl}amino)-2-propoxybenzoic acid The title compound was prepared from Example 432C (44 mg, 0.115 mmole) and 2,2-dimethyl-3-(N,N-dimethylamino)propylamine according to the procedure of Example 406, yielding 23 mg, 40.7%. $^1$H NMR (DMSO-$d_6$) δ 0.90 (t, 3H), 1.03 (s, 9H), 1.55-1.68 (m, 2H), 2.46 (q, 2H), 2.68 (s, 6H), 2.82 (s, 2H), 3.05 (s, 2H), 3.72 (t, 2H), 6.68 (d, 1H), 6.60 (t, 1H), 6.83 (d, 1H), 6.90 (d, 1H), 7.00 (d, 1H), 7.28 (t, 1H), 7.58 (d, 1H); MS (ESI(−)) m/e 490 $(M-H)^-$.

EXAMPLE 435

3-ethyl-6-{[(2-{[3-(4-morpholinyl)propyl]amino}phenyl)sulfonyl]amino}-2-propoxybenzoic acid The title compound was prepared from Example 432C (44 mg, 0.115 mmole) and N-(3-aminopropyl)morpholine according to the procedure of Example 406, yielding 50 mg, 86.1%. $^1$H NMR (DMSO-$d_6$) δ 0.90 (t, 3H), 1.05 (t, 3H), 1.60-1.68 (m, 2H), 1.70-1.78 (m, 2H), 2.30-2.50 (m, 6H), 3.10-3.20 (m, 4H), 3.50-3.62 (m, 4H), 3.75 (t, 2H), 6.55 (t, 1H), 6.68 (d, 1H), 6.84-6.92 (m, 2H), 7.25 (t, 1H), 7.68 (d, 1H); MS (ESI(−)) m/e 504 $(M-H)^-$.

EXAMPLE 436

3-bromo-6-{[(2-{[4-(N,N-dimethylamino)butyl]amino}phenyl)sulfonyl]amino}-2-methoxybenzoic acid The desired product was prepared by substituting N,N-dimethylaminobutylamine for N,N,2,2-tetramethyl-1,3-propanediamine in Example 371B. MS (ESI(+)) m/e 500, 502 $(M+H)^+$; (ESI(−)) m/e 498, 500 $(M-H)^-$; $^1$H NMR (300 MHz, DMSO-$d_6$) δ 12.27 (br s, 1H), 7.65 (d, 1H), 7.44 (d, 1H), 7.37 (m, 1H), 7.24 (d, 1H), 6.78 (d, 1H), 6.63 (t, 1H), 5.76 (br s, 1H), 3.73 (s, 3H), 3.31 (br s, 1H), 3.24 (m, 2H), 3.05 (m, 2H), 2.79 (s, 6H), 1.84 (m, 2H), 1.64 (m, 2H).

EXAMPLE 437

3-bromo-6-{[(2-{[4-(N,N-dimethylamino)butyl]amino}phenyl)sulfonyl]amino}-2-hydroxybenzoic acid The desired product, which was one of two isolated from the reaction, was prepared by substituting N,N-dimethylaminobutylamine for N,N,2,2-tetramethyl-1,3-propanediamine in Example 371B. MS (ESI(+)) m/e 486, 488 $(M+H)^+$; (ESI(−)) m/e 484, 486 $(M-H)^-$; $^1$H NMR (300 MHz, DMSO-$d_6$) δ 16.41 (s, 1H), 14.08 (s, 1H), 9.57 (br s, 1H), 7.65 (d, 1H), 7.34 (m, 2H), 6.77 (m, 2H), 6.64 (t, 1H), 5.77 (br s, 1H), 3.21 (m, 2H), 3.09 (m, 2H), 2.83 (s, 6H), 1.78 (m, 2H), 1.62 (m, 2H).

EXAMPLE 438

3-bromo-2-hydroxy-6-{[(2-{[3-(1-piperidinyl)propyl]amino}phenyl)sulfonyl]amino}benzoic acid The desired product, which was one of two isolated from this reaction, was prepared by substituting 3-(1-piperidinyl)propylamine for N,N,2,2-tetramethyl-1,3-propanediamine in Example 371B. MS (ESI(+)) m/e 512, 514 $(M+H)^+$; (ESI(−)) m/e 510, 512 $(M-H)^-$; $^1$H NMR (300 MHz, DMSO-$d_6$) δ 16.89 (s, 1H), 14.46 (s, 1H), 8.89 (br s, 1H), 7.66 (d, 1H), 7.35 (m, 1H), 7.29 (d, 1H), 6.76 (d, 1H), 6.68 (d, 1H), 6.65 (t, 1H), 5.62 (t, 1H), 3.75 (m, 4H), 3.15 (m, 2H), 2.61 (m, 2H), 1.90 (m, 2H), 1.70 (m, 4H), 1.48 (m, 2H).

EXAMPLE 439

3-bromo-2-hydroxy-6-{[(2-{[3-(4-methyl-1-piperazinyl)propyl]amino}phenyl)sulfonyl]amino}benzoic acid The desired product, which was one of two isolated from this reaction, was prepared by substituting 1-(3-aminopropyl)-4-methylpiperazine for N,N,2,2-tetramethyl-1,3-propanediamine in Example 371B. MS (ESI(+)) m/e 512, 514 $(M+H)^+$; (ESI(−)) m/e 510, 512 $(M-H)^-$; $^1$H NMR (300 MHz, DMSO-$d_6$) δ 17.15 (s, 1H), 14.57 (s, 1H), 9.24 (br s, 1H), 7.64 (d, 1H), 7.34 (t, 1H), 7.27 (d, 1H), 6.74 (d, 1H), 6.62 (m, 2H), 5.88 (s, 1H), 3.19 (br m, 10H), 2.78 (m, 2H), 2.28 (m, 3H), 1.76 (m, 2H).

EXAMPLE 440

3-bromo-2-hydroxy-6-{[(2-{[3-(1-pyrrolidinyl)propyl]amino}phenyl)sulfonyl]amino}benzoic acid The desired product, which was one of two isolated from this reaction, was prepared by substituting 1-(3-aminopropyl)pyrrolidine for N,N,2,2-tetramethyl-1,3-propanediamine in Example 371B. MS (ESI(+)) m/e 498, 500 $(M+H)^+$; (ESI(−)) m/e 496, 498 $(M-H)^-$; $^1$H NMR (300 MHz, DMSO-$d_6$) δ 16.92 (s, 1H), 14.50 (s, 1H), 9.41 (br s, 1H), 7.68 (d, 1H), 7.37 (t, 1H), 7.30 (d, 1H), 6.78 (d, 1H), 6.70 (d, 1H), 6.68 (t, 1H), 5.80 (t, 1H), 3.62 (m, 2H), 3.23 (m, 4H), 3.07 (m, 2H), 1.91 (m, 6H).

EXAMPLE 441

3-bromo-6-{[(2-{[3-(diethylamino)propyl]amino}phenyl)sulfonyl]amino}-2-methoxybenzoic acid The desired product was prepared by substituting 1-(N,N-diethylamino)propylamine for N,N,2,2-tetramethyl-1,3-propanediamine in Example 371B. MS (ESI(+)) m/e 514, 516 $(M+H)^+$; (ESI(−)) m/e 512, 514 $(M-H)^-$; $^1$H NMR (300 MHz, DMSO-$D_6$) δ 11.92 (br s, 1H), 7.46 (d, 1H), 7.41 (d, 1H), 7.29 (t, 1H), 7.19 (d, 1H), 6.75 (d, 1H), 6.52 (t, 1H), 6.16 (br s, 1H), 3.64 (s, 3H), 3.30 (br s, 1H), 3.26 (m, 2H), 3.12 (m, 6H), 1.80 (m, 2H), 1.18 (t, 6H).

EXAMPLE 442

3-bromo-6-{[(2-{[3-(diethylamino)propyl]amino}phenyl)sulfonyl]amino}-2-hydroxybenzoic acid The desired product, which was one of two isolated from this reaction, was prepared by substituting 1-(N,N-diethylamino)propylamine for N,N,2,2-tetramethyl-1,3-propanediamine in Example 371B. MS (ESI(+)) m/e 500, 502 $(M+H)^+$; (ESI(−)) m/e 498, 500 $(M-H)^-$; $^1H$ NMR (300 MHz, DMSO-$d_6$) δ 16.94 (s, 1H), 14.50 (s, 1H), 8.98 (br s, 1H), 7.63 (d, 1H), 7.36 (t, 1H), 7.28 (d, 1H), 6.77 (d, 1H), 6.65 (m, 2H), 5.80 (t, 1H), 3.27 (m, 2H), 3.17 (m, 6H), 1.90 (m, 2H), 1.18 (t, 6H).

EXAMPLE 443

6-{[(2-{[4-(N,N-dimethylamino)butyl]amino}phenyl)sulfonyl]amino}-3-ethyl-2-hydroxybenzoic acid The desired product, which was one of two isolated from this reaction, was prepared by substituting Example 318E for Example 389B in Example 389C. MS (ESI(+)) m/e 436 $(M+H)^+$; (ESI(−)) m/e 434 $(M-H)^-$; $^1H$ NMR (300 MHz, DMSO-$d_6$) δ 15.05 (s, 1H), 13.94 (s, 1H), 10.10 (br s, 1H), 7.64 (d, 1H), 7.34 (t, 1H), 6.95 (d, 1H), 6.79 (d, 1H), 6.74 (d, 1H), 6.61 (t, 1H), 5.77 (t, 1H), 3.19 (m, 2H), 3.09 (m, 2H), 2.83 (s, 6H), 2.37 (q, 2H), 1.80 (m, 2H), 1.62 (m, 2H), 1.03 (t, 3H).

EXAMPLE 444

6-{[(2-{[3-(dimethylamino)-2,2-dimethylpropyl]amino}phenyl)sulfonyl]amino}-3-ethyl-2-methoxybenzoic acid The desired compound was prepared by substituting N,N,2,2-tetramethyl-1,3-propanediamine and Example 318E for 4-(N,N-dimethylamino)butylamine and Example 389B, respectively, in Example 389C. MS (ESI(+)) m/e 464 $(M+H)^+$; (ESI(−)) m/e 462 $(M-H)^-$; $^1H$ NMR (300 MHz, DMSO-$d_6$) δ 7.60 (d, 1H), 7.31 (m, 1H), 7.00 (m, 2H), 6.86 (d, 1H), 6.62 (t, 1H), 3.64 (s, 3H), 3.59 (br s, 3H), 3.08 (s, 2H), 2.96 (br s, 2H), 2.73 (s, 6H), 2.46 (q, 2H), 1.06 (m, 9H).

EXAMPLE 445

3-ethyl-2-hydroxy-6-({[2-({2-[(1-methyl-2-pyrrolidinyl]ethyl}amino)phenyl]sulfonyl}amino)benzoic acid The desired product, which was one of two isolated from this reaction, was prepared by substituting Example 318E and 2-(2-aminoethyl)-1-methylpyrrolidine for Example 389B and 4-(N,N-dimethylamino)butylamine, respectively, in Example 389C. MS (ESI(+)) m/e 448 $(M+H)^+$; (ESI(−)) m/e 446 $(M-H)^-$; $^1H$ NMR (300 MHz, DMSO-$d_6$) δ 15.83 (br s, 1H), 14.81 (br s, 1H), 9.34 (br s, 1H), 7.67 (d, 1H), 7.33 (t, 1H), 6.86 (d, 1H), 6.77 (d, 1H), 6.63 (m, 2H), 5.74 (br s, 1H), 3.51 (m, 3H), 3.22 (m, 2H), 2.81 (s, 3H), 2.36 (q, 2H), 2.22 (m, 2H), 2.01 (m, 1H), 1.88 (m, 1H), 1.75 (m, 1H), 1.64 (m, 1H), 1.01 (t, 3H).

EXAMPLE 446

6-{[(2-{[3-(diethylamino)propyl]amino}phenyl)sulfonyl]amino}-3-ethyl-2-methoxybenzoic acid The desired compound was prepared by substituting 1-(N,N-diethylamino)propylamine and Example 318E for 4-(N,N-dimethylamino)butylamine and Example 389B, respectively, in Example 389C. MS (ESI(+)) m/e 464 $(M+H)^+$; (ESI(−)) m/e 462 $(M-H)^-$; $^1H$ NMR (300 MHz, DMSO-$d_6$) δ 7.45 (d, 1H), 7.26 (t, 1H), 7.13 (d, 1H), 6.99 (d, 1H), 6.72 (d, 1H), 6.50 (t, 1H), 6.16 (br s, 1H), 3.59 (s, 3H), 3.30 (br s, 2H), 3.24 (m, 4H), 3.04 (m, 4H), 2.41 (q, 2H), 1.75 (m, 2H), 1.15 (t, 6H), 1.03 (t, 3H).

EXAMPLE 447

3-ethyl-2-methoxy-6-{[(2-{[3-(1-pyrrolidinyl)propyl]amino}phenyl)sulfonyl]amino}benzoic acid The desired compound was prepared by substituting Example 318E and 1-(3-aminopropyl)pyrrolidine for Example 389B and 4-(N,N-dimethylamino)butylamine, respectively, in Example 389C. MS (ESI(+)) m/e 462 $(M+H)^+$; (ESI(−)) m/e 460 $(M-H)^-$; $^1H$ NMR (300 MHz, DMSO-$d_6$) δ 12.05 (br s, 1H), 7.42 (d, 1H), 7.26 (t, 1H), 7.17 (d, 1H), 6.99 (d, 1H), 6.73 (d, 1H), 6.48 (t, 1H), 6.16 (br s, 1H), 3.58 (s, 3H), 3.36 (m, 4H), 3.30 (br s, 1H), 3.27 (m, 4H), 2.40 (q, 2H), 1.92 (m, 4H), 1.81 (m, 2H), 1.02 (t, 3H).

EXAMPLE 448

3-ethyl-2-hydroxy-6-{[(2-{[3-(1-pyrrolidinyl)propyl]amino}phenyl)sulfonyl]amino}benzoic acid The desired product, which was one of two isolated from this reaction, was prepared by substituting 1-(3-aminopropyl)pyrrolidine and Example 318E for 4-(N,N-dimethylamino)butylamine and Example 389B, respectively, in Example 389C. MS (ESI(+)) m/e 448 $(M+H)^+$; (ESI(−)) m/e 446 $(M-H)^-$; $^1H$ NMR (300 MHz, DMSO-$d_6$) δ 15.71 (s, 1H), 14.73 (s, 1H), 9.44 (br s, 1H), 7.64 (dd, 1H), 7.33 (dt, 1H), 6.88 (d, 1H), 6.75 (d, 1H), 6.66 (d, 1H), 6.63 (t, 1H), 5.80 (t, 1H), 3.26 (m, 8H), 2.36 (q, 2H), 1.92 (m, 6H), 1.01 (t, 3H).

EXAMPLE 449

3-ethyl-2-methoxy-6-{[(2-{[3-(4-morpholinyl)propyl]amino}phenyl)sulfonyl]amino}benzoic acid The desired compound was prepared by substituting 4-(3-aminopropyl)morpholine and Example 318E for 4-(N,N-dimethylamino)butylamine and Example 389B, respectively, in Example 389C. MS (ESI(+)) m/e 478 $(M+H)^+$; (ESI(−)) m/e 476 $(M-H)^-$; $^1H$ NMR (300 MHz, DMSO-$d_6$) δ 7.41 (dd, 1H), 7.27 (dt, 1H), 7.16 (d, 1H), 7.02 (d, 1H), 6.73 (d, 1H), 6.48 (t, 1H), 6.24 (br s, 1H), 3.79 (m, 4H), 3.62 (s, 3H), 3.57 (br s, 2H), 3.25 (m, 6H), 3.16 (m, 2H), 2.42 (q, 2H), 1.76 (m, 2H), 1.04 (t, 3H).

EXAMPLE 450

3-ethyl-2-methoxy-6-{[(2-{[4-(1-pyrrolidinyl)butyl]amino}phenyl)sulfonyl]amino}benzoic acid The desired compound was prepared by substituting 4-(1-pyrrolidinyl)butylamine and Example 318E for 4-(N,N-dimethylamino)butylamine and Example 389B, respectively, in Example 389C. MS (ESI(+)) m/e 476 $(M+H)^+$; (ESI(−)) m/e 474 $(M-H)^-$; $^1H$ NMR (300 MHz, DMSO-$d_6$) δ 12.73 (br s, 1H), 11.54 (br s, 1H), 7.60 (dd, 1H), 7.32 (dt, 1H), 7.17 (d, 1H), 7.02 (d, 1H), 6.75 (d, 1H), 6.58 (t, 1H), 5.75 (m, 1H), 3.63 (s, 3H), 3.20 (m, 4H), 3.08 (m, 4H), 2.44 (q, 2H), 1.93 (m, 4H), 1.85 (m, 2H), 1.65 (m, 2H), 1.04 (t, 3H).

EXAMPLE 451

3-bromo-2-methoxy-6-{[(2-{[3-(4-methyl-1-piperazinyl)propyl]amino}phenyl)sulfonyl]amino}benzoic acid The desired product was prepared by substituting 1-(3-aminopropyl)-4-methylpiperazine for N,N,2,2-tetramethyl-1,3-propanediamine in Example 371B. MS (ESI(+)) m/e 541, 543 $(M+H)^+$; (ESI(−)) m/e 539, 541 $(M-H)^-$; $^1H$ NMR (300 MHz, DMSO-$d_6$) δ 7.45 (br d, 1H), 7.41 (d, 1H), 7.29 (dt, 1H), 7.18 (br d, 1H), 6.71 (d, 1H), 6.52 (t, 1H), 6.21 (br s, 1H), 3.68 (s, 3H), 3.30 (br s, 4H), 3.27 (br s, 6H), 3.16 (m, 4H), 2.31 (br s, 3H), 1.76 (m, 2H).

EXAMPLE 452

3-bromo-2-methoxy-6-({[2-({3-[2-methyl-1-piperidinyl]propyl}amino)phenyl]sulfonyl}amino)benzoic acid The desired product was prepared by substituting 3-[2-methyl-1-piperidinyl]-1-propanamine for N,N,2,2-tetramethyl-1,3-propanediamine in Example 371B. MS (ESI(+)) m/e 540, 542 $(M+H)^+$; (ESI(−)) m/e 538, 540 $(M-H)^-$; $^1H$ NMR (300 MHz, DMSO-$d_6$) δ 11.96 (br s, 1H), 7.46 (br d, 1H), 7.42 (d, 1H), 7.30 (dt, 1H), 7.18 (br d, 1H), 6.74 (d, 1H), 6.53 (t, 1H), 6.14 (br s, 1H), 3.67 (s, 3H), 3.41 (m, 2H), 3.30 (br s, 1H), 3.20 (m, 4H), 3.04 (m, 1H), 1.86 (m, 2H), 1.72 (m, 2H), 1.64 (m, 2H), 1.50 (m, 2H), 1.31 (br s. 3H).

EXAMPLE 453

3-ethyl-2-methoxy-6-({[2-({2-[1-methyl-2-pyrrolidinyl]ethyl}amino)phenyl]sulfonyl}amino)benzoic acid The desired compound was prepared by substituting Example 318E and 2-(2-aminoethyl)-1-methylpyrrolidine for Example 389B and 4-(N,N-dimethylamino)butylamine, respectively, in Example 389C. MS (ESI(+)) m/e 462 $(M+H)^+$; (ESI(−)) m/e 460 $(M-H)^-$; $^1H$ NMR (300 MHz, DMSO-$d_6$) δ 7.57 (d, 1H), 7.24 (dt, 1H), 7.09 (br m, 1H), 6.98 (d, 1H), 6.75 (d, 1H), 6.55 (t, 1H), 5.77 (br m, 1H), 3.67 (s, 3H), 3.33 (br s, 2H), 3.32 (m, 5H), 2.71 (br s, 3H), 2.43 (q, 2H), 2.31 (m, 1H), 2.12 (m, 1H), 2.01 (m, 2H), 1.81 (m, 1H), 1.71 (m, 1H), 1.04 (t, 3H).

EXAMPLE 454

3-ethyl-6-{[(2-{[3-(1H-imidazol-1-yl)propyl]amino}phenyl)sulfonyl]amino}-2-methoxybenzoic acid The desired compound was prepared by substituting Example 318E and 1-(3-aminopropyl)imidazole for Example 389B and 4-(N,N-dimethylamino)butylamine, respectively, in Example 389C. MS (ESI(+)) m/e 459 $(M+H)^+$; (ESI(−)) m/e 457 $(M-H)^-$; $^1H$ NMR (300 MHz, DMSO-$d_6$) δ 8.04 (s, 1H), 7.60 (d, 1H), 7.32 (m, 2H), 7.09 (m, 2H), 6.79 (d, 1H), 6.70 (d, 1H), 6.63 (t, 1H), 5.89 (br s, 1H), 4.12 (t, 2H), 3.95 (br s, 2H), 3.64 (s, 3H), 3.08 (m, 2H), 2.46 (q, 2H), 2.02 (m, 2H), 1.06 (t, 3H).

EXAMPLE 455

3-ethyl-2-hydroxy-6-{[(2-{[3-(1H-imidazol-1-yl)propyl]amino}phenyl)sulfonyl]amino}benzoic acid The desired product, which was one of two isolated from this reaction, was prepared by substituting 1-(3-aminopropyl)imidazole and Example 318E for 4-(N,N-dimethylamino)butylamine and Example 389B, respectively, in Example 389C. MS (ESI(+)) m/e 445 $(M+H)^+$; (ESI(−)) m/e 443 $(M-H)^-$; $^1H$ NMR (300 MHz, DMSO-$d_6$) δ 15.84 (s, 1H), 14.92 (s, 1H), 11.95 (br s, 1H), 8.64 (s, 1H), 7.65 (m, 1H), 7.32 (m, 2H), 7.13 (br m, 2H), 6.86 (dd, 1H), 6.65 (m, 2H), 5.89 (t, 1H), 4.27 (t, 2H), 3.13 (m, 2H), 2.38 (q, 2H), 2.10 (m, 2H), 1.02 (t, 3H).

EXAMPLE 456

3-ethyl-2-hydroxy-6-{[(2-{[3-(4-morpholinyl)propyl]amino}phenyl)sulfonyl]amino}benzoic acid The desired product, which was one of two isolated from this reaction, was prepared by substituting Example 318E and 4-(3-aminopropyl)morpholine for Example 389B and 4-(N,N-dimethylamino)butylamine, respectively, in Example 389C. MS (ESI(+)) m/e 464 $(M+H)^+$; (ESI(−)) m/e 462 $(M-H)^-$; $^1H$ NMR (300 MHz, DMSO-$d_6$) δ 15.55 (s, 1H), 14.57 (s, 1H), 9.71 (br s, 1H), 7.73 (dd, 1H), 7.33 (dt, 1H), 6.92 (d, 1H), 6.76 (d, 1H), 6.72 (d, 1H), 6.63 (t, 1H), 5.86 (t, 1H), 3.98 (br m, 2H), 3.72 (br m, 4H), 3.26 (m 4H), 3.14 (br m, 2H), 2.38 (q, 2H), 1.98 (m, 2H), 1.02 (t, 3H).

EXAMPLE 457

3-bromo-5-ethyl-6-methyl-2-[(2-pyridinylsulfonyl)amino]benzoic acid

To a solution of Example 130B (50 mg, 0.16 mmole) in DMF (5 mL) was added tetra-n-butylammonium tribromide (85 mg, 0.176 mmole), then water (5 mL). After stirring overnight at ambient temperature, the solvents were evaporated and the residue was partitioned between water and ethyl acetate (20 mL each). The two phases were separated and the aqueous phase was extracted with ethyl acetate. The combined organic extracts were dried ($MgSO_4$), filtered and concentrated. The residue was purified on a silica gel column eluting with 5% methanol in dichloromethane with 1% acetic acid to provide the desired product, 70 mg (95%). $^1H$ NMR (DMSO-$d_6$) δ 1.2 (t, 3H), 2.04 (s, 3H), 2.55 (q, 2H), 7.15 (s, 1H), 7.25 (t, 1H), 7.68 (d, 1H0, 7.86 (t, 1H), 8.58 (d, 1H), 10.05-13.00 (br s, 2H). MS (ESI(−)) m/e 397, 399 $(M-H)^-$.

EXAMPLE 458

2-{[(2-{[1-methyl-2-pyrrolidinyl]ethyl}amino}phenyl)sulfonyl]amino)-8-methoxy-5,6,7,8-tetrahydro-1-naphthalenecarboxylic acid

EXAMPLE 458A methyl 2-{[(2-fluorophenyl)sulfonyl]amino}-8-oxo-5,6,7,8-tetrahydro-1-naphthalenecarboxylate The desired product was prepared according to the procedure of Example 275E substituting Example 275C for 275D. MS (ESI) m/e 376 $(M-H)^-$; $^1H$ NMR (300 MHz, DMSO-$d_6$) δ 10.16 (s, 1H), 7.72-7.62 (m, 2H), 7.46-7.40 (m, 3H), 7.31 (t, 1H), 3.53 (s, 3H), 2.93 (t, 2H), 2.57 (t, 2H), 1.99 (m, 2H).

EXAMPLE 458B methyl 2-{[(2-fluorophenyl)sulfonyl]amino}-8-methoxy-5,6-dihydro-1-naphthalenecarboxylate A mixture of Example 458A (240 mg, 0.64 mmol), trimethylorthoformate (0.7 mL, 6.4 mmol) and pyridinium p-toluenesulfonate (80 mg, 0.32 mmol) in methanol (7 mL) was refluxed overnight, cooled to room temperature, and partitioned between diethyl ether and brine. The organic phase was dried ($MgSO_4$), filtered, concentrated, and passed through a silica gel plug eluting with 30% acetone/hexanes to provide the desired product (210 mg, 83% yield). MS (ESI) m/e 390 $(M-H)^-$, $^1H$ NMR (300 MHz, DMSO-$d_6$) δ 9.82 (s, 1H), 7.73-7.62 (m, 2H), 7.44 (m, 1H), 7.31 (t, 1H), 7.22 (d, 1H), 7.02 (d, 1H), 5.19 (t, 1H), 3.54 (s, 3H), 3.50 (s, 3H), 2.64 (t, 2H), 2.19 (m, 2H).

EXAMPLE 458C methyl 2-{[(2-fluorophenyl)sulfonyl]amino}-8-methoxy-5,6,7,8-tetrahydro-1-naphthalenecarboxylate A mixture of Example 458B (352 mg, 0.9 mmol) and 10% Pd/C (99.8 mg) in ethyl acetate (18 mL) was hydrogenated under 50 psi of hydrogen for 2.5 days. After filtration and concentration, the desired product was isolated in quantitative yield. MS ($DCI/NH_3$) m/e 411 $(M+NH_4)^+$; $^1H$ NMR (300 MHz, DMSO-$d_6$) δ 9.84 (s, 1H), 7.7-7.61 (m, 2H), 7.43 (m, 1H), 7.31 (t, 1H), 7.12 (d, 1H), 7.01 (d, 1H), 4.42 (t, 1H), 3.63 (s, 3H), 3.15 (s, 3H), 2.70-2.61 (m, 2H), 1.86 (m, 1H), 1.77-1.55 (m, 3H).

EXAMPLE 458D

2-{[(2-{[1-methyl-2-pyrrolidinyl]ethyl}amino}phenyl)sulfonyl]amino)-8-methoxy-5,6,7,8-tetrahydro-1-naphthalenecarboxylic acid The desired product was prepared according to the procedure of Example 275G substituting Example 458C for Example 275E and 2-(1-methyl-2-pyrrolidinyl)ethylamine for N,N-dimethylethylenediamine. MS (ESI) m/e 486 $(M-H)^-$; $^1H$ NMR (300 MHz, DMSO-$d_6$) δ 13.05 (br s, 1H), 9.34 (br d, 1H), 7.53 (dd, 1H), 7.42 (t, 1H), 6.98 (d, 1H), 6.86 (d, 1H), 6.69 (m, 2H), 6.0 (m, 1H), 4.57 (t, 1H), 3.25 (m, 3H), 3.23 (s, 3H), 3.02 (m, 1H), 2.75-2.64 (m, 6H), 2.3-2.1 (m, 2H), 1.92 (m, 2H), 1.83 (m, 2H), 1.67 (m, 4H).

EXAMPLE 459

2-{[(2-{[3-(isopropylamino)propyl]amino}phenyl)sulfonyl]amino}-8-methoxy-5,6,7,8-tetrahydro-1-naphthalenecarboxylic acid The desired product was prepared according to the procedure of Example 275G substituting Example 458C for Example 275E and 3-(isopropylamino)propylamine for N,N-dimethylethylenediamine. MS (ESI) m/e 474 $(M-H)^-$; $^1H$ NMR (300 MHz, DMSO-$d_6$) δ 13.02 (br s, 1H), 9.35 (br d, 1H), 8.2 (br s, 1H), 7.5 (dd, 1H), 7.41 (t, 1H), 6.98 (d, 1H), 6.85 (d, 1H), 6.72 (m, 1H), 6.64 (t, 1H), 6.06 (t, 1H), 4.60 (m, 1H), 3.33 (m, 3H), 3.22 (s, 3H), 2.96 (m, 2H), 2.64 (m, 2H), 1.83 (m, 4H), 1.7-1.55 (m, 2H), 1.17 (d, 6H).

EXAMPLE 460

2-[({2-[({2-[1-methyl-2-pyrrolidinyl]ethyl}amino)carbonyl]phenyl}sulfonyl)amino]-5,6,7,8-tetrahydro-1-naphthalenecarboxylic acid The desired product was prepared by substituting 2-(2-aminoethyl)-1-methylpyrrolidine for N,N-diethylethylenediamine in Examples 379A-D. MS (ESI(+)) m/e 486 $(M+H)^+$; (ESI(−)) m/e 484 $(M-H)^-$; $^1H$ NMR (300 MHz, DMSO-$d_6$) δ 13.15 (br s, 1H), 9.46 (br s, 1H), 9.00 (s, 1H), 8.89 (t, 1H), 7.75 (dd, 2H), 7.62 (m, 2H), 7.02 (d, 1H), 6.92 (d, 1H), 3.57 (m, 2H), 3.32 (m, 3H), 3.06 (quint, 1H), 2.81 (d, 3H), 2.65 (s, 2H), 2.60 (s, 2H), 2.37 (m, 1H), 2.16 (m, 1H), 1.99 (m, 1H), 1.90 (m, 1H), 1.70 (m, 1H) 1.65 (s, 4H).

EXAMPLE 461

2-[({4-[({2-[1-methyl-2-pyrrolidinyl]ethyl}amino)carbonyl]-3-thienyl}sulfonyl)amino]-5,6,7,8-tetrahydro-1-naphthalenecarboxylic acid The desired product was prepared by substituting 2-(2-aminoethyl)-1-methylpyrrolidine for N,N-diethylethylenediamine in Examples 463C-D. MS (ESI(+)) m/e 492 $(M+H)^+$; (ESI(−)) m/e 490 $(M-H)^-$; $^1H$ NMR (300 MHz, DMSO-$d_6$) δ 9.46 (br s, 1H), 8.71 (s, 1H), 7.88 (d, 0.26H) minor, 7.79 (d, 0.72H) major, 7.40 (d, 0.28H) minor, 7.32 (d, 0.78H) major, 7.05 (d, 0.33H) minor, 7.03 (d, 0.77H) major, 6.98 (d, 0.30H) minor, 6.85 (d, 0.72H) major, 3.70 (br s, 2H), 3.20 (br s, 1H), 2.78 (s, 3H), 2.66 (d, 5H), 2.35-1.83 (m, 3H), 1.67 (m, 6H).

EXAMPLE 462

2-({[2-({[2-(1-piperidinyl)ethyl]amino}carbonyl)phenyl]sulfonyl}amino)-5,6,7,8-tetrahydro-1-naphthalenecarboxylic acid The desired product was prepared by substituting 1-(2-aminoethyl)piperidine for N,N-diethylethylenediamine in Examples 379A-D. MS (ESI(+)) m/e 486 $(M+H)^+$; (ESI(−)) m/e 484 $(M-H)^-$; $^1H$ NMR (300 MHz, DMSO-$d_6$) δ 9.02 (br m, 2H), 7.78 (m, 2H), 7.64 (m, 2H), 7.04 (d, 1H), 6.93 (d, 1H), 3.66 (q, 3H), 3.26 (t, 3H), 2.98 (br s, 2H), 2.67 (br s, 2H), 2.61 (br s, 2H), 1.83 (br m, 2H), 1.66 (t, 7H), 1.40 (br s, 1H).

EXAMPLE 463

2-({[4-({[2-(diethylamino)ethyl]amino}carbonyl)-3-thienyl]sulfonyl}amino)-5,6,7,8-tetrahydro-1-naphthalenecarboxylic acid

EXAMPLE 463A methyl 3-({[1-(methoxycarbonyl)-5,6,7,8-tetrahydro-2-naphthalenyl]amino}sulfonyl)-2-thiophenecarboxylate The desired product was prepared by substituting methyl 3-(chlorosulfonyl)-2-thiophenecarboxylate for methyl 2-(chlorosulfonyl)benzoate in Example 379A. MS (ESI(+)) m/e 410 $(M+H)^+$, 432 $(M+Na)^+$; (ESI(−)) m/e 408 $(M-H)^-$; $^1H$ NMR (300 MHz, DMSO-$d_6$) δ 9.02 (br s, 1H), 7.96 (d, 1H), 7.36 (d, 1H), 7.10 (dd, 2H), 3.88 (s, 3H), 3.75 (s, 3H), 2.67 (br s, 2H), 2.54 (br s, 2H), 1.65 (quint, 4H).

EXAMPLE 463B 3-({[1-(methoxycarbonyl)-5,6,7,8-tetrahydro-2-naphthalenyl]amino}sulfonyl)-2-thiophenecarboxylic acid A solution of Example 463A (1.37 g, 3.36 mmol) in methanol (31 mL) and distilled water (3.5 mL) was treated with lithium hydroxide monohydrate (0.704 g, 16.78 mmol), heated to 60° C. for 30 minutes, cooled to room temperature, treated with 1N HCl, and concentrated. The aqueous layer was extracted with dichloromethane twice and the combined organic fractions were dried ($MgSO_4$), filtered, and concentrated to provide the desired product. MS (ESI(+)) m/e 396 $(M+H)^+$; (ESI(−)) m/e 394 $(M-H)^-$; $^1H$ NMR (300 MHz, DMSO-$d_6$) δ 8.98 (br s, 1H), 7.89 (d, 1H), 7.33 (d, 1H), 7.12 (s, 2H), 3.77 (s, 3H), 2.67 (br s, 2H), 2.53 (br s, 2H), 1.65 (quint, 4H).

EXAMPLE 463C methyl 2-({[2-({[2-(diethylamino)ethyl]amino}carbonyl)-3-thienyl]sulfonyl}amino)-5,6,7,8-tetrahydro-1-naphthalenecarboxylate A solution of Example 463B (100 mg, 0.253 mmol) in DMF (2.0 mL) was treated with 4-methylmorpholine (111 μL, 1.012 mmol) and O-(7-azabenzotriazol-1-yl)-N,N,N',N'-tetramethyluronium hexafluorophosphate (192 mg, 0.506 mmol), stirred for one hour at room temperature, treated with N,N-diethylethylenediamine (71 μL, 0.506 mmol), stirred for 3 days at room temperature, treated with 1N HCl, and extracted twice with dichloromethane. The combined extracts were dried ($MgSO_4$), filtered, concentrated, and purified by preparative HPLC to provide the desired product. MS (ESI(+)) m/e 494 $(M+H)^+$; (ESI(−)) m/e 492 $(M-H)^-$; $^1$H NMR (300 MHz, DMSO-$d_6$) δ 9.41 (s, 1H), 9.06 (br s, 1H), 8.82 (t, 1H), 7.82 (d, 1H), 7.26 (d, 1H), 7.10 (d, 1H), 6.92 (d, 1H), 3.77 (s, 3H), 3.24-3.14 (m, 8H), 2.68 (br s, 2H), 2.55 (br s, 2H), 1.66 (quint, 4H), 1.21 (t, 6H).

EXAMPLE 463D 2-({[4-({[2-(diethylamino)ethyl]amino}carbonyl)-3-thienyl]sulfonyl}amino)-5,6,7,8-tetrahydro-1-naphthalenecarboxylic acid In a small microwave reactor vessel (2.0 mL) was placed Example 463C (23.1 mg, 0.046 mmol), pyridine (0.5 mL), and lithium iodide (18.4 mg, 0.137 mmol). The vial was sealed and heated in microwave for fifteen hundred seconds at 160° C. The solution was cooled to room temperature, treated with 1N HCl, and concentrated. The resulting residue was purified by preparative HPLC to provide the desired product. MS (ESI(+)) m/e 480 $(M+H)^+$; (ESI(−)) m/e 478 $(M-H)^-$; $^1$H NMR (300 MHz, DMSO-$d_6$) δ 9.50 (br s, 1H), 8.81 (t, 1H), 7.82 (d, 1H), 7.33 (d, 1H), 7.04 (d, 1H), 6.87 (d, 1H), 3.55 (m, 2H), 3.25-3.17 (m, 6H), 2.66 (m, 4H), 1.67 (quint, 4H), 1.21 (t, 6H).

EXAMPLE 464

2-({[4-({[2-(1-piperidinyl)ethyl]amino}carbonyl)-3-thienyl]sulfonyl}amino)-5,6,7,8-tetrahydro-1-naphthalenecarboxylic acid The desired product was prepared by substituting 1-(2-aminoethyl)piperidine for N,N-diethylethylenediamine in Examples 463C-D. MS (ESI(+)) m/e 492 $(M+H)^+$; (ESI(−)) m/e 490 $(M-H)^-$; $^1$H NMR (300 MHz, DMSO-$d_6$) δ 8.83 (t, 1H), 7.82 (d, 1H), 7.32 (d, 1H), 7.03 (d, 1H), 6.88 (d, 1H), 3.58 (q, 3H), 3.22 (t, 3H), 3.12-2.85 (br s, 2H), 2.66 (br d, 4H), 1.85-1.70 (br s, 3H), 1.67 (br t, 6H), 1.61-1:37 (br s, 1H).

EXAMPLE 465

6-[({2-[(3-aminopropyl)amino]phenyl}sulfonyl)amino]-3-ethyl-2-methoxybenzoic acid The desired compound was prepared by substituting Example 318E and 1,3-diaminopropane for Example 389B and 4-(N,N-dimethylamino)butylamine, respectively, in Example 389C. MS (ESI(+)) m/e 408 $(M+H)^+$; (ESI(−)) m/e 406 $(M-H)^-$; $^1$H NMR (300 MHz, DMSO-$d_6$) δ 8.58 (br s, 1H), 7.47 (dd, 1H), 7.28 (dt, 2H), 7.14 (d, 1H), 6.98 (d, 1H), 6.75 (d, 1H), 6.52 (t, 1H), 5.94 (m, 1H), 3.60 (s, 3H), 3.30 (br s, 2H), 3.27 (m, 2H), 3.11 (m, 2H), 2.43 (q, 2H), 1.84 (m, 2H), 1.04 (t, 3H).

EXAMPLE 466

6-[({2-[(3-aminopropyl)amino]phenyl}sulfonyl)amino]-3-ethyl-2-hydroxybenzoic acid The desired product, which was one of two isolated from this reaction, was prepared by substituting 1,3-diaminopropane and Example 318E for 4-(N,N-dimethylamino)butylamine and Example 389B, respectively, in Example 389C. MS (ESI(+)) m/e 394 $(M+H)^+$; (ESI(−)) m/e 392 $(M-H)^-$; $^1$H NMR (300 MHz, DMSO-$d_6$) δ 15.68 (s, 1H), 14.65 (s, 1H), 7.65 (br s, 1H), 7.59 (dd, 1H), 7.31 (dt, 2H), 6.89 (d, 1H), 6.76 (d, 1H), 6.67 (d, 1H), 6.61 (t, 1H), 5.89 (m, 1H), 3.31 (br s, 1H), 3.27 (m, 2H), 2.95 (m, 2H), 2.31 (q, 2H), 1.85 (m, 2H), 1.03 (t, 3H).

EXAMPLE 467

2-(carboxymethoxy)-3-ethyl-6-{[(4-fluorophenyl)sulfonyl]amino}benzoic acid

EXAMPLE 467A methyl 6-amino-3-bromo-2-(2-methoxy-2-oxoethoxy)benzoate

The title compound was prepared from Example 385D (0.5 g, 2.0 mmole) and methyl bromoacetate according to the procedure of Example 385E, yielding 0.67 g, 100%. $^1$H NMR (DMSO-$d_6$) δ 3.68 (s, 3H), 3.72 (s, 3H), 4.55 (s, 2H), 6.03 (s, 2H), 6.55 (d, 1H), 7.32 (d, 1H); MS (DCI/$NH_3$) m/e 318, 320 $(M+H)^+$.

EXAMPLE 467B methyl 3-bromo-6-{[(4-fluorophenyl)sulfonyl]amino}-2-(2-methoxy-2-oxoethoxy)benzoate The title compound was prepared from Example 467A (0.33 g, 1.04 mmol) and 4-fluorobenzenesulfonyl chloride according to the procedure of Example 385F, yielding 0.45 g, 91.8%. $^1$H NMR (DMSO-$d_6$) δ 3.68 (s, 3H), 3.72 (s, 3H), 4.58 (s, 2H), 6.94 (d, 1H), 7.42 (t, 2H), 7.68-7.80 (m, 3H); MS (ESI(−)) m/e 474, 476 $(M-H)^-$.

EXAMPLE 467C methyl 6-{[(4-fluorophenyl)sulfonyl]amino}-2-(2-methoxy-2-oxoethoxy)-3-vinylbenzoate The title compound was prepared from Example 467B (0.40 g, 0.84 mmol) according to the procedure of Example 230B, yielding 0.31 g, 88.2%. $^1$H NMR (DMSO-$d_6$) δ 3.68 (s, 3H), 3.70 (s, 3H), 4.46 (s, 2H), 5.38 (d, 1H), 5.80 (d, 1H), 6.82 (dd, 1H), 7.00 (d, 1H), 7.40 (t, 2H), 7.65 (d, 1H), 7.75 (d, 2H), 10.02 (s, 1H); MS (ESI(−)) m/e 422 $(M-H)^-$.

EXAMPLE 467D methyl 3-ethyl-6-{[(4-fluorophenyl)sulfonyl]amino}-2-(2-methoxy-2-oxoethoxy)benzoate A mixture of Example 467C (0.31 g, 0.7 mmole) in methanol (10 mL) was treated with 10% Pd/C (100 mg) at ambient temperature under one atmosphere of hydrogen for 16 hours. Filtration and evaporation of the solvent provided the desired product. 0.29 g, 97.5%. $^1$H NMR (DMSO-$d_6$) δ 1.10 (t, 3H), 2.54 (q, 2H), 3.64 (s, 3H), 3.70 (s, 3H), 4.48 (s, 2H), 6.85 (d, 1H), 7.28 (d, 1H), 7.40 (t, 2H), 7.70 (t, 2H), 9.86 (s, 1H); MS (ESI(−)) m/e 424 $(M-H)^-$.

EXAMPLE 467E 2-(carboxymethoxy)-3-ethyl-6-{[(4-fluorophenyl)sulfonyl]amino}benzoic acid The title compound was prepared from Example 467D (50 mg, 0.12 mmol) according to the procedure of Example 385I, yielding 24 mg, 50.4%. $^1$H NMR (DMSO-$d_6$) δ 1.10 (t, 3H), 2.58 (q, 2H), 4.40 (s, 2H), 6.80 (d, 1H), 7.20 (d, 1H), 7.40 (t, 2H), 7.80 (t, 2H), 9.78 (s, 1H), 11.00-13.00 (br s, 1H); MS (ESI(−)) m/e 396, $(M-H)^-$.

EXAMPLE 468

6-({[2-(dimethylamino)phenyl]sulfonyl}amino)-3-ethyl-2-methoxybenzoic acid

The desired product was prepared by substituting N,N,2,2-tetramethyl-1,3-propanediamine and Example 318E for 4-(N,N-dimethylamino)butylamine and Example 389B, respectively, in Example 389C. MS (ESI(+)) m/e 379 $(M+H)^+$; (ESI(−)) m/e 377 $(M-H)^-$; $^1$H NMR (300 MHz, DMSO-$d_6$) δ 7.90 (d, 1H), 7.57 (t, 1H), 7.37 (d, 1H), 7.21 (t, 1H), 6.83 (s, 2H), 3.66 (s, 3H), 3.34 (br s, 2H), 2.59 (2, 6H), 2.42 (q, 2H), 1.04 (t, 3H).

EXAMPLE 469

6-{[(2-{[3-(dimethylamino)-2,2-dimethylpropyl]amino}phenyl)sulfonyl]amino}-3-ethyl-2-hydroxybenzoic acid The indicated compound, which was one of two isolated from this reaction, was prepared by substituting N,N,2,2-tetramethyl-1,3-propanediamine and Example 318E for 4-(N,N-dimethylamino)butylamine and Example 389B, respectively, in Example 389C. MS (ESI(+)) m/e 450 $(M+H)^+$; (ESI(−)) m/e 448 $(M-H)^-$; $^1$H NMR (300 MHz, DMSO-$d_6$) δ 16.08 (br s, 1H), 15.03 (s, 1H), 10.24 (br s, 1H), 9.02 (br s, 1H), 7.62 (m, 1H), 7.32 (m, 1H), 6.88 (m, 1H), 6.80 (m, 1H), 6.62 (m, 2H), 3.02 (m, 2H), 2.36 (q, 2H), 2.25 (m, 8H), 1.04 (t, 3H), 0.93 (s, 3H), 0.92 (s, 3H).

EXAMPLE 470

3-bromo-5-ethyl-2-{[(2-fluorophenyl)sulfonyl]amino}-6-methoxybenzoic acid

EXAMPLE 470A 5-methoxy-2H-3,1-benzoxazine-2,4(1H)-dione

A solution of 2-amino-6-methoxybenzoic acid (10 g, 60 mmol), water (330 mL), and sodium hydroxide (7.2 g, 176 mmol) was treated with phosgene (20% solution in toluene, 82 mL, 164 mmol) over 1 hour and filtered. The filter cake was dried to provide the desired product. MS (ESI(+)) m/e 194 $(M+H)^+$, 211 $(M+NH_4)^+$, 216 $(M+Na)^+$; (ESI(−)) m/e 192 $(M-H)^+$; $^1$H NMR (300 MHz, DMSO-$d_6$) δ 11.57 (s, 1H), 7.64 (t, 1H), 6.84 (d, 1H), 6.68 (d, 1H), 3.88 (s, 3H).

EXAMPLE 470B methyl 6-amino-3-bromo-2-methoxybenzoate

A mixture of Example 470A (9.8 g, 50.7 mmol), DMF (50 mL), and dichloromethane (150 mL) was cooled to 0° C., treated portionwise with N-bromosuccinimide (12.6 g, 76 mmol), stirred until all the starting material was consumed, and filtered. The filter cake was washed with dichloromethane combined filtrates were concentrated, treated with anhydrous methanol (450 mL), and heated to reflux for 54 hours. Purification by flash column chromatography on silica gel with 15% ethyl acetate/hexanes provided the desired product. MS (ESI(+)) m/e 260, 262 $(M+H)^+$, 277, 279 $(M+NH_4)^+$, 282, 284 $(M+Na)^+$; (ESI(−)) m/e 258, 260 $(M-H)^-$; $^1$H NMR (300 MHz, DMSO-$d_6$) δ 7.34 (d, 1H), 6.50 (d, 1H), 5.63 (s, 2H), 3.82 (s, 3H), 3.71 (s, 3H).

EXAMPLE 470C methyl 3-bromo-6-{[(2-fluorophenyl)sulfonyl]amino}-2-methoxybenzoate The desired product was prepared by substituting Example 470B and 2-fluorobenzenesulfonyl chloride for Example 126B and 3-fluorobenzenesulfonyl chloride, respectively, in Example 126C. MS (ESI(+)) m/e 418, 420 $(M+H)^+$, 435, 437 $(M+NH_4)^+$, 440, 442 $(M+Na)^+$; (ESI(−)) m/e 416, 418 $(M-H)^-$; $^1$H NMR (300 MHz, DMSO-$d_6$) δ 10.43 (s, 1H), 7.71 (m, 3H), 7.41 (m, 1H), 7.35 (m, 1H), 7.50 (d, 1H), 3.73 (s, 3H), 3.67 (s, 3H).

EXAMPLE 470D methyl 6-{[(2-fluorophenyl)sulfonyl]amino}-2-methoxy-3-vinylbenzoate The desired product was prepared by substituting Example 470C for Example 226E in Example 226F. MS (ESI(+)) m/e 366 $(M+H)^+$, 383 $(M+NH_4)^+$, 388 $(M+Na)^+$; (ESI(−)) m/e 364 $(M-H)^-$; $^1$H NMR (300 MHz, DMSO-$d_6$) δ 10.28 (s, 1H), 7.71 (m, 2H), 7.64 (d, 1H), 7.43 (m, 1H), 7.34 (m, 1H), 7.00 (d, 1H), 6.80 (dd, 1H), 5.82 (d, 1H), 5.36 (d, 1H), 3.67 (s, 3H), 3.53 (s, 3H).

EXAMPLE 470E methyl 3-ethyl-6-{[(2-fluorophenyl)sulfonyl]amino}-2-methoxybenzoate The desired product was prepared by substituting Example 470D for Example 226F in Example 226G MS (ESI(+)) m/e 368 $(M+H)^+$, 385 $(M+NH_4)^+$, 390 $(M+Na)^+$; (ESI(−)) m/e 366 $(M-H)^-$; $^1$H NMR (300 MHz, DMSO-$d_6$) δ 10.09 (s, 1H), 7.68 (m, 2H), 7.42 (m, 1H), 7.32 (m, 1H), 7.25 (d, 1H), 6.89 (d, 1H), 3.66 (s, 3H), 3.63 (s, 3H), 2.55 (q, 2H), 1.12 (t, 3H).

EXAMPLE 470F methyl 3-bromo-5-ethyl-2-{[(2-fluorophenyl)sulfonyl]amino}-6-methoxybenzoate The desired product was prepared by substituting Example 470E for Example 104A in Example 104B. The crude product was purified by flash column chromatography on silica gel with 20% ethyl acetate in hexanes. MS (ESI(+)) m/e 446, 448 $(M+H)^+$, 463, 465 $(M+NH_4)^+$, 468, 470 $(M+Na)^+$; (ESI(−)) m/e 444, 446 $(M-H)^-$; $^1$H NMR (300 MHz, DMSO-$d_6$) δ 10.31 (s, 1H), 7.68 (m, 2H), 7.63 (s, 1H), 7.42 (m, 1H), 7.33 (m, 1H), 3.67 (s, 3H), 3.50 (s, 3H), 2.59 (q, 2H), 1.15 (t, 3H).

EXAMPLE 470G 3-bromo-5-ethyl-2-{[(2-fluorophenyl)sulfonyl]amino}-6-methoxybenzoic acid A mixture of Example 470F (75 mg, 0.2 mmol), lithium hydroxide (70 mg, 2.0 mmol), dioxane (1.5 mL), and water (0.75 mL) was sealed in a vial and microwaved at 160° C. for 15 minutes. Purification by preparative HPLC on a Waters Symmetry C8 column (25 mm×100 mm, 7 μm particle size) using a gradient of 10% to 100% acetonitrile/10 mmol aqueous ammonium acetate over 8 minutes (10 minute run time) at a flow rate of 40 mL/min provided the desired compound. MS (ESI(+)) m/e 432, 434 $(M+H)^+$; (ESI(−)) m/e 430, 432 $(M-H)^-$; $^1H$ NMR (300 MHz, DMSO-$d_6$) δ 7.68 (m, 1H), 7.57 (m, 1H), 7.28 (m, 3H), 3.65 (s, 3H), 2.49 (m, 4H), 1.09 (t, 3H).

EXAMPLE 471

5-ethyl-2-{[(2-fluorophenyl)sulfonyl]amino}-4-methoxy-1,1'-biphenyl-3-carboxylic acid

EXAMPLE 471A methyl 5-ethyl-2-{[(2-fluorophenyl)sulfonyl]amino}-4-methoxy-1,1'-biphenyl-3-carboxylate The desired product was prepared by substituting Example 470F and phenylboronic acid for Example 226E and dibutyl vinylborate, respectively, in Example 226F. MS (ESI(+)) m/e 444 $(M+H)^+$, 461 $(M+NH_4)^+$, 466 $(M+Na)^+$; (ESI(−)) m/e 442 $(M-H)^-$; $^1H$ NMR (300 MHz, DMSO-$d_6$) δ 9.85 (s, 1H), 7.27 (m, 1H), 7.24 (m, 3H), 7.20 (s, 1H), 7.14 (m, 3H), 7.08 (m, 1H), 7.03 (m, 1H), 3.73 (s, 3H), 3.65 (s, 3H), 2.64 (q, 2H), 1.17 (t, 3H).

EXAMPLE 471B 5-ethyl-2-{[(2-fluorophenyl)sulfonyl]amino}-4-methoxy-1,1'-biphenyl-3-carboxylic acid The desired product was prepared by substituting Example 471A for Example 470F in Example 470G. MS (ESI(+)) m/e 430 $(M+H)^+$, 447 $(M+NH_4)^+$, 452 $(M+Na)^+$; (ESI(−)) m/e 428 $(M-H)^-$; $^1H$ NMR (300 MHz, DMSO-$d_6$) δ 7.45 (m, 1H), 7.19 (d, 1H), 7.14 (m, 2H), 6.98 (m, 5H), 6.89 (s, 1H), 3.72 (s, 3H), 3.33 (br s, 2H), 2.55 (q, 2H), 1.14 (t, 3H).

EXAMPLE 472

(8R)-2-({[2-({2-[(2S)-1-(tert-butoxycarbonyl)-2-pyrrolidinyl]ethyl}amino)phenyl]sulfonyl}amino)-8-methyl-5,6,7,8-tetrahydro-1-naphthalenecarboxylic acid The desired product was prepared by substituting Example 275F (50 mg, 0.133 mmol) and the compound of example 535B (170 μL, 0.8 mmol) for Example 275E and N,N-dimethlethylenediamine, respectively, in Example 275G. High performance liquid chromatography (column: phenomenex $C_{18}$ 10μ, gradient 50% through 100% acetonitrile in water) gave a separation of the diastereomer. The title compound was an earlier eluting fraction 28 mg MS (ESI(−)) m/e 556 (M−H) 456 $(M-H-Boc)^-$; $^1H$ NMR (300 MHz, DMSO-$d_6$) δ 9.33 (s, 1H), 7.48 (d, 1H), 7.40 (t, 1H), 6.92 (d, 1H), 6.75 (d, 1H), 6.60 (dt, 1H), 6.54 (d, 1H), 5.93 (s, 1H), 3.75 (m, 1H), 3.14-3.35 (m, 6H), 2.61-2.86 (m, 10H), 1.62-1.82 (m, 6H), 1.45 (s, 9H), 1.10 (d, 3H).

EXAMPLE 473

(8S)-2-({[2-({2-[(2S)-1-(tert-butoxycarbonyl)-2-pyrrolidinyl]ethyl}amino)phenyl]sulfonyl}amino)-8-methyl-5,6,7,8-tetrahydro-1-naphthalenecarboxylic acid This was isolated as a single isomer during the high performance liquid chromatography as described in example 472.22 mg of the title compound was isolated. MS (ESI(−)) m/e 556 (M−H)-456 $(M-H-Boc)^-$; $^1H$ NMR (300 MHz, DMSO-$d_6$) δ 9.34 (s, 1H), 7.49 (d, 1H), 7.37 (t, 1H), 6.92 (d, 1H), 6.75 (d, 1H), 6.56 (dt, 1H), 6.54 (d, 1H), 5.92 (s, 1H), 3.75 (m, 1H), 3.09-3.31 (m, 6H), 2.59-2.74 (m, 10H), 1.64-1.98 (m, 6H), 1.40 (s, 9H), 1.10 (d, 3H).

EXAMPLE 474

(8S)-8-methyl-2-({[2-({2-[(2S)-2-pyrrolidinyl]ethyl}amino)phenyl]sulfonyl}amino)-5,6,7,8-tetrahydro-1-naphthalenecarboxylic acid The product of example 473 (215 mg) was treated with 2 ml of 4N-hydrochloric acid in dioxane at room temperature for 1 hour. Solvent was removed and the residue was treated with ether, the obtained solid was dried under high vacuum to yield 5.7 mg MS (ESI(−)) m/e 456 $(M-H)^-$.

EXAMPLE 475

(8R)-8-methyl-2-({[2-({2-[(2S)-2-pyrrolidinyl]ethyl}amino)phenyl]sulfonyl}amino)-5,6,7,8-tetrahydro-1-naphthalenecarboxylic acid The product of example 472 (20 mg) was treated in the same fashion as has described in example 474 to yield 5.5 mg of the title compound. MS (ESI(−)) m/e 456 $(M-H)^-$.

EXAMPLE 476

3-[(1E)-3-({2-[1-methyl-2-pyrrolidinyl]ethyl}amino)-3-oxo-1-propenyl]-2-[(phenylsulfonyl)amino]-5,6,7,8-tetrahydro-1-naphthalenecarboxylic acid

EXAMPLE 476A methyl 2-amino-3-bromo-5,6,7,8-tetrahydro-1-naphthalenecarboxylate

Methyl 2-amino-1-naphthoate (0.5 g, 2.4 mmol) in chloroform (5 mL) and DMF (1 mL) was treated with bromine (0.125 mL, 2.4 mmol) for 30 minutes, concentrated, and dissolved in ethyl acetate. The organic layer was washed with $NaHCO_3$ (3×), brine (3×) and water (3×), dried ($Na_2SO_4$), filtered, and concentrated to provide the desired product (0.69 g). MS (DCI) m/e 284, 286 $(M+H)^+$.

EXAMPLE 476B methyl 2-amino-3-[(1E)-3-tert-butoxy-3-oxo-1-propenyl]-5,6,7,8-tetrahydro-1-naphthalenecarboxylate A mixture of Example 476A (0.327 g, 1.2 mmol), tert-butyl acrylate (0.203 mL, 1.40 mmol), acetonitrile (1.5 mL), tri(ortho-tolyl)phosphine (0.035 g, 0.12 mmol), palladium diacetate (0.013 g, 0.06 mmol), and triethylamine (0.32 mL, 2.3 mmol) was sealed and heated in a microwave reactor for 10 minutes at 200° C. The reaction mixture was concentrated and purified by flash chromatography (15% ethyl acetate/hexanes) to provide the desired product (0.12 g, 32%); MS (DCI) m/e 332 $(M+H)^+$.

EXAMPLE 476C methyl 3-[(1E)-3-tert-butoxy-3-oxo-1-propenyl]-2-[(phenylsulfonyl)amino]-5,6,7,8-tetrahydro-1-naphthalenecarboxylate A solution of Example 476B (0.12 g, 0.36 mmol) in pyridine (1 mL) was treated with benzenesulfonyl chloride (0.071 g, 0.40 mmol), and stirred for 16 hours at ambient temperature. The mixture was concentrated, diluted with 1M $NaHSO_4$ and extracted with dichloromethane. The extract was dried ($MgSO_4$), filtered, and concentrated. The concentrate was purified by flash chromatography eluting with 30% ethyl acetate/hexanes gave the desired product (0.12 g). MS (DCI) m/e 472 $(M+H)^+$.

EXAMPLE 476D (2E)-3-{4-(methoxycarbonyl)-3-[(phenylsulfonyl)amino]-5,6,7,8-tetrahydro-2-naphthalenyl}acrylic acid A mixture of Example 476C (0.12 g, 0.25 mmol) in $CH_2Cl_2$ (3 mL) was treated with TFA (6 mL), stirred for 2 hours, and diluted with $CH_2Cl_2$. The organic layer was washed with 1M NaOH and brine (200 mL), dried ($MgSO_4$), filtered, and concentrated to provide the desired product (0.11 g). MS (DCI) m/e 416 $(M+H)^+$.

EXAMPLE 476E

3-[(1E)-3-({2-[1-methyl-2-pyrrolidinyl]ethyl}amino)-3-oxo-1-propenyl]-2-[(phenylsulfonyl)amino]-5,6,7,8-tetrahydro-1-naphthalenecarboxylic acid A mixture of Example 476D (20 mg, 0.05 mmol) in DMF (1.0 mL) was treated with macroporous polystyrene bound DCC resin (105 mg, 0.14 mmol), 1-hydroxybenzotriazole hydrate (7 mg, 0.05 mmol), diisopropylethylamine (0.026 mL, 0.15 mmol) and 2-(aminoethyl)-1-methylpyrrolidine (0.010 mL, 0.07 mmol), heated to 55° C. for 16 hours, and concentrated. The concentrate was dissolved in 0.5 mL 2:1 dioxane/water, treated with LiOH (13 mg, 0.3 mmol), and heated to 160° C. for 27.5 minutes in a microwave reactor. The reaction mixture was concentrated and the residue was purified by $C_{18}$ reverse-phase HPLC using acetonitrile/water/0.1% TFA to provide the desired product. MS (DCI) m/e 512 $(M+H)^+$; $^1H$ NMR (500 MHz, DMSO-$d_6$) δ 12.89 (br s, 1H), 9.37 (br s, 1H), 7.99 (t, 1H), 7.61 (d, 2H), 7.54 (t, 1H), 7.46-7.43 (m, 3H), 7.31 (s, 1H), 6.28 (d, 1H), 3.23 (m, 4H), 3.08 (m, 1H), 2.84 (d, 3H), 2.75 (m, 2H), 2.65 (m, 2H), 2.30 (m, 1H), 2.04 (m, 2H), 1.90 (m, 1H), 1.71-1.63 (m, 6H).

EXAMPLE 477

3-((1E)-3-oxo-3-{[2-(1-piperidinyl)ethyl]amino}-1-propenyl)-2-[(phenylsulfonyl)amino]-5,6,7,8-tetrahydro-1-naphthalenecarboxylic acid The desired product was prepared by substituting 1-(2-aminoethyl)piperidine for 2-aminoethyl-1-methylpyrrolidine in Example 476E. MS (DCI) m/e 512 $(M+H)^+$; $^1H$ NMR (500 MHz, DMSO-$d_6$) δ 12.90 (br s, 1H), 9.07 (br s, 1H), 8.16 (t, 1H), 7.62 (d, 2H), 7.55 (m, 1H), 7.49-7.44 (m, 3H), 7.32 (s, 1H), 6.30 (d, 1H), 3.51 (m, 4H), 3.16 (q, 2H), 2.94 (m, 2H), 2.76 (m, 2H), 2.65 (m, 2H), 1.84 (m, 2H), 1.71-1.63 (m, 7H), 1.41 (m, 1H).

EXAMPLE 478

3-((1E)-3-oxo-3-{[3-(1-piperidinyl)propyl]amino}-1-propenyl)-2-[(phenylsulfonyl)amino]-5,6,7,8-tetrahydro-1-naphthalenecarboxylic acid The desired product was prepared by substituting 1-(3-aminopropyl)piperidine for 2-aminoethyl-1-methylpyrrolidine in Example 476E. MS (DCI) m/e 526 $(M+H)^+$; $^1H$ NMR (500 MHz, DMSO-$d_6$) δ 12.88 (br s, 1H), 8.96 (br s, 1H), 8.03 (t, 1H), 7.62 (m, 2H), 7.54 (m, 1H), 7.48-7.44 (m, 3H), 7.31 (s, 1H), 6.29 (d, 1H), 3.45 (m, 2H), 3.21 (q, 2H), 3.05 (m, 2H), 2.88 (m, 2H), 2.75 (m, 2H), 2.64 (m, 2H), 1.83 (m, 4H), 1.71-1.60 (m, 7H), 1.39 (m, 1H).

EXAMPLE 479

3-[(1E)-3-({[1-ethyl-2-pyrrolidinyl]methyl}amino)-3-oxo-1-propenyl]-2-[(phenylsulfonyl)amino]-5,6,7,8-tetrahydro-1-naphthalenecarboxylic acid The desired product was prepared by substituting 2-(aminomethyl)-1-ethylpyrrolidine for 2-aminoethyl-1-methylpyrrolidine in Example 476E. MS (DCI) m/e 512 $(M+H)^+$; $^1H$ NMR (500 MHz, DMSO-$d_6$) δ 12.90 (br s, 1H), 9.20 (br s, 1H), 8.30 (t, 1H), 7.62 (m, 2H), 7.54 (m, 1H), 7.51-7.44 (m, 3H), 7.35 (s, 1H), 6.34 (d, 1H), 3.52 (m, 5H), 3.12 (m, 2H), 2.76 (m, 2H), 2.65 (m, 2H), 2.14 (m, 1H), 2.00 (m, 1H), 1.87 (m, 1H), 1.71 (m, 5H), 1.27 (t, 3H).

EXAMPLE 480

3-((1E)-3-{[2-(dimethylamino)ethyl]amino}-3-oxo-1-propenyl)-2-[(phenylsulfonyl)amino]-5,6,7,8-tetrahydro-1-naphthalenecarboxylic acid The desired product was prepared by substituting 2-(N,N-dimethylamino)ethylamine for 2-aminoethyl-1-methylpyrrolidine in Example 476E. MS (DCI) m/e 472 $(M+H)^+$; $^1H$ NMR (500 MHz, DMSO-$d_6$) δ 12.84 (br s, 1H), 9.47 (br s, 1H), 8.17 (t, 1H), 7.62 (m, 2H), 7.55 (m, 1H), 7.50-7.44 (m, 3H), 7.32 (s, 1H), 6.30 (d, 1H), 3.49 (q, 2H), 3.19 (m, 2H), 2.85 (s, 3H), 2.84 (s, 3H), 2.76 (m, 2H), 2.65 (m, 2H), 1.71 (m, 4H).

EXAMPLE 481

3-[(E)-2-carboxyvinyl]-2-[(phenylsulfonyl)amino]-5,6,7,8-tetrahydro-1-naphthalenecarboxylic acid A solution of Example 476D (20 mg, 0.05 mmol) in 0.5 mL of 2:1 dioxane water was treated with LiOH (13 mg, 0.3 mmol) and heated to 160° C. for 27.5 minutes in a microwave reactor. The reaction mixture was concentrated and the residue was purified by $C_{18}$ reverse-phase HPLC using acetonitrile/water/0.1% TFA to provide the desired product. MS (DCI) m/e 419 $(M+NH_4)^+$; $^1H$ NMR (500 MHz, DMSO-$d_6$) δ 12.92 (br s, 1H), 12.11 (br s, 1H), 9.69 (br s, 1H), 7.60 (m, 2H), 7.54 (m, 1H), 7.49-7.42 (m, 4H), 6.13 (d, 1H), 2.75 (m, 2H), 2.67 (m, 2H), 1.70 (m, 4H).

EXAMPLE 482

2-({[2-({2-[(2S)-1-(2-ethylbutyl)-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B in Example 557C. MS (DCI) m/e 528 $(M+H)^+$; $^1H$ NMR (500 MHz, DMSO-$d_6$) δ 13.19 (br s, 1H), 7.54 (m, 1H), 7.40 (m, 1H), 6.92 (d, 1H), 6.84 (d, 1H), 6.65 (m, 2H), 5.97 (br s, 1H) 3.59 (br s, 1H), 2.94 (br s, 2H), 2.78 (m, 2H), 2.63 (br s, 4H), 2.30 (br s, 2H), 1.97 (br s, 2H), 1.81-1.56 (m, 9H), 1.26 (m, 4H).

EXAMPLE 483

2-({[2-({2-[(2S)-1-(cyclopropylmethyl)-2-pyrrolidinyl]ethyl}amino)phenyl]sulfonyl}amino)-5,6,7,8-tetrahydro-1-naphthalenecarboxylic acid The desired product was prepared by substituting Example 552D for of Example 557B and substituting cyclopropanecarboxaldehyde for 2-ethylbutanal in Example 557C. MS (DCI) m/e 498 $(M+H)^+$; $^1H$ NMR (500 MHz, DMSO-$d_6$) δ 13.24 (br s, 1H), 9.53 (br s, 1H), 7.55 (m, 1H), 7.39 (m, 1H), 6.92 (d, 1H), 6.83 (d, 1H), 6.65 (m, 2H), 5.93 (br s, 1H), 3.59 (br s, 1H), 3.02 (br s, 2H), 2.77 (m, 2H), 2.63 (br s, 4H), 2.28 (m, 2H), 1.97 (m, 2H), 1.78-1.65 (m, 8H), 0.98 (br s, 1H), 0.54 (m, 2H), 0.31-0.27 (m, 2H).

EXAMPLE 484

2-({[2-({2-[(2S)-1-(cyclopentylmethyl)-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and substituting cyclopentanecarboxaldehyde for 2-ethylbutanal in Example 557C. MS (DCI) m/e 526 $(M+H)^+$; $^1H$ NMR (500 MHz, DMSO-$d_6$) δ 13.21 (br s, 1H), 9.61 (br s, 1H), 7.56 (m, 1H), 7.39 (m, 1H), 6.92 (d, 1H), 6.84 (d, 1H), 6.65 (m, 2H), 5.94 (br s, 1H), 3.58 (br s, 1H), 3.08 (br m, 2H), 2.84 (m, 2H), 2.62 (br s, 4H), 2.28 (m, 2H), 2.08 (m, 2H), 1.96 (m, 2H), 1.74-1.46 (m, 16H).

EXAMPLE 485

2-({[2-({2-[(2S)-1-(cyclohexylmethyl)-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and substituting cyclohexanecarboxaldehyde for 2-ethylbutanal in Example 557C. MS (DCI) m/e 540 $(M+H)^+$; $^1H$ NMR (500 MHz, DMSO-$d_6$) δ 13.24 (br s, 1H), 9.58 (br s, 1H), 7.55 (m, 1H), 7.41 (m, 1H), 6.92 (d, 1H), 6.84 (d, 1H), 6.66 (br s, 2H), 6.00 (br s, 1H), 3.59 (br s, 1H), 3.05 (m, 2H), 2.93 (br s, 2H), 2.71 (br m, 2H), 2.63 (br s, 4H), 2.28 (br s, 2H), 1.96 (m, 2H), 1.79-1.60 (m, 15H), 1.13 (m, 2H).

EXAMPLE 486

2-({[2-({2-[(2S)-1-isobutyl-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and substituting 2-methylpropanal for 2-ethylbutanal in Example 557C. MS (DCI) m/e 500 $(M+H)^+$; $^1H$ NMR (500 MHz, DMSO-$d_6$) δ 13.21 (br s, 1H), 9.59 (br s, 1H), 7.55 (d, 1H), 7.41 (m, 1H), 6.93 (d, 1H), 6.84 (d, 1H), 6.65 (br s, 2H), 6.00 (br s, 1H), 3.58 (br s, 1H), 3.08 (br s, 2H), 2.94 (br s, 2H), 2.63 (br s, 4H), 2.28 (br s, 2H), 1.95 (br s, 2H), 1.80 (br s, 2H), 1.65 (br s, 7H), 0.92 (d, 3H), 0.90 (d, 3H).

EXAMPLE 487

2-[methyl({2-[(4-piperidinylmethyl)amino]phenyl}sulfonyl)amino]-5,6,7,8-tetrahydro-1-naphthalenecarboxylic acid

EXAMPLE 487A methyl 2-[methyl({2-[(4-piperidinylmethyl)amino]phenyl}sulfonyl)amino]-5,6,7,8-tetrahydro-1-naphthalenecarboxylate A mixture of the trifluoroacetate salt of Example 399 (0.86 g, 1.5 mmol) in benzene (20 mL) and methanol (5 mL) was treated with $TMSCHN_2$ (1.5 mL, 3.0 mmol, 2.0M solution in hexanes). The reaction was stirred at room temperature for 1 hour, quenched with acetic acid, and diluted with dichloromethane. The organic phase was washed with aqueous $NaHCO_3$, dried ($MgSO_4$), filtered, and concentrated. The concentrate was dissolved in benzene (20 mL) and methanol (5 mL), treated with $TMSCHN_2$ (1.5 mL, 3.0 mmol, 2.0M solution in hexanes), stirred at room temperature for 1 hour, quenched with acetic acid, and diluted with dichloromethane. The organic layer was washed with aqueous $NaHCO_3$, dried ($MgSO_4$), filtered, and concentrated. The crude material was purified by $C_{18}$ reverse-phase HPLC with acetonitrile/water/0.1% trifluoroacetic acid to provide the desired product (0.064 g). MS (ESI(+)) m/e 472 $(M+H)^+$.

EXAMPLE 487B

2-[methyl({2-[(4-piperidinylmethyl)amino]phenyl}sulfonyl)amino]-5,6,7,8-tetrahydro-1-naphthalenecarboxylic acid A mixture of Example 487A (0.064 g, 0.14 mmol) in 1.4 mL pyridine was treated with LiI (0.068 g, 0.5 mmol), heated to 150° C. for 25 minutes in a microwave reactor, and concentrated. The concentrate was purified by $C_{18}$ reverse-phase HPLC using acetonitrile/water/0.1% TFA to provide the desired product (14.3 mg). MS (ESI(+)) m/e 458 $(M+H)^+$; (ESI(−)) m/e 456 $(M-H)^-$; $^1H$ NMR (300 MHz, DMSO-$d_6$) δ 7.58 (dd, 1H), 7.37 (dt, 1H), 7.19 (d, 1H), 6.85 (d, 1H), 6.82 (d, 1H), 6.57 (t, 1H), 6.43 (m, 1H), 3.19 (m, 4H), 2.90 (s, 3H), 2.72, (m, 2H), 2.68 (m, 4H), 1.83 (m, 3H), 1.68 (m, 6H).

EXAMPLE 488

2-({[2-({2-[(2S)-1-(2-methylbutyl)-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and substituting 2-methylbutanal for 2-ethylbutanal in Example 557C. MS (DCI) m/e 514 $(M+H)^+$; $^1H$ NMR (500 MHz, DMSO-$d_6$) δ 13.24 (br s, 1H), 9.59 (br s, 1H), 7.54 (m, 1H), 7.41 (br s, 1H), 6.92 (d, 1H), 6.84 (d, 1H), 6.66 (br s, 2H), 5.99 (br s, 1H), 3.59 (br s, 1H), 3.11-2.91 (br m, 4H), 2.63 (br s, 4H), 2.28 (m, 2H), 1.97 (m, 2H), 1.81 (br s, 2H), 1.65 (br s, 9H), 0.91 (d, 3H), 0.82 (t, 3H).

EXAMPLE 489

2-({[2-({2-[(2S)-1-(1-cyclopropylethyl)-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and acetylcyclopropane for 2-ethylbutanal in Example 557C. MS (DCI) m/e 512 $(M+H)^+$; $^1H$ NMR (500 MHz, DMSO-$d_6$) δ 13.17 (br s, 1H), 9.59 (br s, 1H), 7.55 (m, 1H), 7.40 (m, 1H), 6.93 (d, 1H), 6.84 (m, 1H), 6.65 (m, 2H), 5.95 (br s, 1H), 3.72 (br s, 0.5H), 3.59 (br s, 0.5H), 3.43 (br s, 1H), 2.76 (m, 2H), 2.68 (br s, 2H), 2.64 (br s, 2H), 2.25 (m, 2H), 1.94 (m, 2H), 1.77 (m, 2H), 1.66 (br s, 6H), 1.19 (m, 3H), 0.97 (br s, 0.5H), 0.89 (br s, 0.5H), 0.55 (d, 1H), 0-50-0.43 (m, 2H), 0.26 (m, 0.5H), 0.16 (m, 0.5H).

EXAMPLE 490

2-({[2-({2-[(2S)-1-tetrahydro-2H-pyran-4-yl-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and substituting tetrahydro-4H-pyran-4-one for 2-ethylbutanal in Example 557C. MS (DCI) m/e 528 $(M+H)^+$; $^1H$ NMR (500 MHz, DMSO-$d_6$) δ 9.51 (br s, 1H), 7.55 (d, 1H), 7.43 (t, 1H), 6.96 (d, 1H), 6.86 (d, 1H), 6.67 (t, 1H), 6.63 (d, 1H), 6.01 (br s, 1H), 3.86 (m, 1H), 3.78 (m, 1H), 3.63 (m, 1H), 2.66 (m, 4H), 2.20 (m, 2H), 2.09 (br s, 1H), 1.93 (m, 4H), 1.78 (m, 4H), 1.67 (m, 4H), 1.56 (m, 2H).

EXAMPLE 491

2-({[2-({2-[(2S)-1-(1,3,3-trimethylbutyl)-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and substituting 4,4-dimethyl-2-pentanone for 2-ethylbutanal in Example 557C. MS (DCI) m/e 542 $(M+H)^+$; $^1H$ NMR (500 MHz, DMSO-$d_6$) δ 9.51 (br s, 1H), 7.54 (d, 1H), 7.40 (m, 1H), 6.94 (d, 1H), 6.82 (d, 1H), 6.66 (m, 2H), 6.02 (br s, 1H), 3.10 (m, 2H), 2.67-2.64 (m, 4H), 2.29 (m, 1H), 2.21 (m, 1H), 1.92 (m, 2H), 1.79 (br s, 1H), 1.67 (m, 6H), 1.53 (d, 1H), 1.26 (d, 3H), 0.84 (s, 9H).

EXAMPLE 492

2-({[2-({2-[(2S)-1-tetrahydro-3-thienyl-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and dihydro-3(2H)-thiophenone for 2-ethylbutanal in Example 557C. MS (DCI) m/e 530 $(M+H)^+$; $^1H$ NMR (500 MHz, DMSO-$d_6$) δ13.22 (br s, 1H), 9.55 (br s, 1H), 7.55 (m, 1H), 7.42 (m, 1H), 6.94 (d, 1H), 6.86 (d, 1H), 6.67 (m, 2H), 5.97 (br s, 1H), 3.79 (m, 1H), 3.64 (m, 1H), 3.46 (br s, 1H), 3.01 (m, 1H), 2.80 (m, 3H), 2.67-2.64 (m, 4H), 2.32-2.23 (br m, 2H), 2.13 (br s, 2H), 1.97 (m, 2H), 1.79 (br s, 2H), 1.66 (br s, 4H).

EXAMPLE 493

2-({[2-({2-[(2S)-1-cyclopentyl-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and cyclopentanone for 2-ethylbutanal in Example 557C. MS (DCI) m/e 512 $(M+H)^+$; $^1H$ NMR (500 MHz, DMSO-$d_6$) δ 13.24 (br s, 1H), 9.59 (br s, 1H), 7.57 (d, 1H), 7.42 (t, 1H), 6.94 (d, 1H), 6.85 (d, 1H), 6.67 (t, 2H), 5.98 (br s, 1H), 3.49 (m, 5H), 3.10 (m, 1H), 2.68-2.63 (m, 4H), 2.25 (m, 1H), 1.95 (m, 2H), 1.77 (br s, 3H), 1.65-1.37 (m, 12H).

EXAMPLE 494

2-({[2-({2-[(2S)-1-(1-methyl-4-piperidinyl)-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and 1-methyl-4-piperidone for 2-ethylbutanal in Example 557C. MS (DCI) m/e 541 $(M+H)^+$;

$^1H$ NMR (500 MHz, DMSO-$d_6$) δ 13.24 (br s, 1H), 9.61 (br s, 1H), 7.54 (dd, 1H), 7.42 (m, 1H), 6.97 (d, 1H), 6.86 (d, 1H), 6.67 (m, 2H), 5.93 (br s, 1H), 3.67 (br s, 2H), 3.12-3.07 (m, 4H), 2.88 (br s, 2H), 2.76 (s, 3H), 2.67 (m, 4H), 2.18 (br s, 2H), 2.07 (m, 2H), 1.95 (m, 2H), 1.82 (br s, 4H), 1.67 (m, 4H).

EXAMPLE 495

2-({[2-({2-[(2S)-1-tetrahydro-2H-thiopyran-4-yl-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and tetrahydro-4H-thiopyran-4-one for 2-ethylbutanal in Example 557C. MS (DCI) m/e 544 $(M+H)^+$; $^1H$ NMR (500 MHz, DMSO-$d_6$) δ 13.24 (br s, 1H), 9.56 (br s, 1H), 7.56 (dd, 1H), 7.42 (m, 1H), 6.96 (d, 1H), 6.86 (d, 1H), 6.67 (t, 2H), 5.99 (br s, 1H), 3.62 (br s, 1H), 3.18 (m, 2H), 2.68-2.54 (m, 8H), 2.20 (br s, 2H), 2.13 (m, 2H), 1.90 (br s, 1H), 1.79 (br s, 1H), 1.67 (m, 7H), 1.58 (m, 1H).

EXAMPLE 496

2-({[2-({2-[(2S)-1-cyclohexyl-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and cyclohexanone for 2-ethylbutanal in Example 557C. MS (DCI) m/e 526 $(M+H)^+$; $^1H$ NMR (500 MHz, DMSO-$d_6$) δ 13.20 (br s, 1H), 9.57 (br s, 1H), 7.56 (d, 1H), 7.41 (t, 1H), 6.94 (d, 1H), 6.85 (d, 1H), 6.66 (m, 2H), 5.96 (br s, 1H), 3.61 (br s, 1H), 3.18-3.08 (m, 3H), 2.68-2.64 (m, 4H), 2.17 (br s, 2H), 1.92 (br s, 2H), 1.85-1.72 (m, 4H), 1.66 (m, 6H), 1.53 (m, 1H), 1.32-1.01 (m, 5H).

EXAMPLE 497

-({[2-({2-[(2)-1-isopropyl-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and acetone for 2-ethylbutanal in Example 557C. MS (DCI) m/e 526 $(M+H)^+$; $^1H$ NMR (500 MHz, DMSO-$d_6$) δ 13.20 (br s, 1H), 9.57 (br s, 1H), 7.56 (d, 1H), 7.41 (t, 1H), 6.94 (d, 1H), 6.85 (d, 1H), 6.66 (m, 2H), 5.96 (br s, 1H), 3.61 (br s, 1H), 3.18-3.08 (m, 3H), 2.68-2.64 (m, 4H), 2.17 (br s, 2H), 1.92 (br s, 2H), 1.85-1.72 (m, 4H), 1.66 (m, 6H), 1.53 (m, 1H), 1.32-1.01 (m, 5H).

EXAMPLE 498

2-[({2-[(2-{(2S)-1-[1-(3-pyridinyl)ethyl]-2-pyrrolidinyl}ethyl)amino]phenyl}sulfonyl)amino]-5,6,7,8-tetrahydro-1-naphthalenecarboxylic acid The desired product was prepared by substituting Example 552D for Example 557B and 3-acetylpyridine for 2-ethylbutanal in Example 557C. MS (DCI) m/e 549 $(M+H)^+$; $^1H$ NMR (500 MHz, DMSO-$d_6$) δ 9.51 (br s, 1H), 8.70 (d, 1H), 8.62 (d, 1H), 7.92 (d, 1H), 7.56 (d, 1H), 7.43 (m, 2H), 6.94 (d, 1H), 6.82 (d, 1H), 6.68 (t, 1H), 6.64 (d, 1H), 6.07 (br s, 1H), 4.62 (q, 1H), 3.24 (m, 4H), 2.96 (m, 1H), 2.68-2.63 (m, 4H), 1.90 (br s, 1H), 1.81 (m, 4H), 1.65 (m, 5H), 1.54 (d, 3H).

796313 EXAMPLE 500

(8R)-8-methyl-2-({[2-({2-[(2R)-2-pyrrolidinyl]ethyl}amino)phenyl]sulfonyl}amino)-5,6,7,8-tetrahydro-1-naphthalenecarboxylic acid.

EXAMPLE 500A tert-butyl(2R)-2-(2-aminoethyl)-1-pyrrolidinecarboxylate

The desired product was prepared by substituting N-tert-butoxycarbonyl-D-proline for N-tert-butoxycarbonyl-L-proline in Examples 535A-B. MS (DCI/$NH_3$) m/e 215 $(M+H)^+$; $^1H$ NMR (300 MHz, DMSO-$d_6$) δ 3.74 (m, 1H), 3.26-3.19 (m, 4H), 1.81-1.7 (m, 5H), 1.6 (m, 1H), 1.39 (s, 3H).

EXAMPLE 500B 8-methyl-2-({[2-({2-[(2R)-2-pyrrolidinyl]ethyl}amino)phenyl]sulfonyl}amino)-5,6,7,8-tetrahydro-1-naphthalenecarboxylic acid The desired product was prepared according to the procedure of Example 275G substituting Example 275F for 275E and Example 500A for N,N-dimethylethylenediamine, then treating the crude product with 4M HCl in dioxane for 2 hours and then concentrated under reduced pressure to provide the titled compound. MS (ESI) m/e 456 $(M-H)^-$; $^1H$ NMR (300 MHz, DMSO-$d_6$) δ 9.4 (br s, 1H), 8.43 (br s, 1H), 7.51 (m, 1H), 7.41 (t, 1H), 6.93 (dd, 1H), 6.84 (d, 1H), 6.65 (t, 1H), 6.6 (m, 1H), 5.96 (m, 1H), 3.46 (m, 1H), 3.18 (m, 3H), 2.65 (m, 3H), 2.11 (m, 2H), 1.91 (m, 4H), 1.63 (m, 4H), 1.1 (d, 3H).

EXAMPLE 501

3-bromo-2-methoxy-6-({[2-({2-[1-methyl-2-pyrrolidinyl]ethyl}amino)phenyl]sulfonyl}amino)benzoic acid The desired product was prepared by substituting 2-(2-aminoethyl)-1-methylpyrrolidine for N,N,2,2-tetramethyl-1,3-propanediamine in Example 371B. MS (ESI(+)) m/e 512, 514 $(M+H)^+$; (ESI(−)) m/e 510, 512 $(M-H)^-$; $^1H$ NMR (300 MHz, DMSO-$d_6$) δ 7.55 (d, 1H), 7.38 (d, 1H), 7.31 (t, 1H), 7.10 (m, 1H), 6.75 (d, 1H), 6.59 (t, 1H), 5.86 (br s, 1H), 3.97 (s, 3H), 3.30 (br s, 2H), 3.16 (m, 5H), 2.72 (br s, 3H), 2.26 (m, 1H) 2.12 (m, 1H), 1.98 (m, 2H), 1.82 (m, 1H), 1.72 (m, 1H).

EXAMPLE 502

3-bromo-2-hydroxy-6-({[2-({3-[(2-methyl-1-piperidinyl]propyl}amino)phenyl]sulfonyl}amino)benzoic acid The desired product, which was one of two isolated from this reaction, was prepared by substituting 3-[2-methyl-1-piperidinyl]propylamine for N,N,2,2-tetramethyl-1,3-propanediamine in Example 371B. MS (ESI(+)) m/e 426, 428 $(M+H)^+$; (ESI(−)) m/e 424, 426 $(M-H)^-$; $^1H$ NMR (300 MHz, DMSO-$d_6$) δ 16.96 (br m, 1H), 14.48 (s, 1H), 8.97 (br m, 1H), 7.64 (dd, 1H), 7.36 (dt, 1H), 7.30 (d, 1H), 6.80 (d, 1H), 6.66 (m, 2H), 5.84 (t, 1H), 3.46 (m, 2H), 3.31 (m, 2H), 3.14 (m, 2H), 2.95 (m, 1H), 1.86 (m, 4H), 1.66 (m, 2H), 1.48 (m, 2H), 1.25 (br s, 3H).

EXAMPLE 503

2-{[(2-{[2-(diethylamino)ethyl]sulfanyl}phenyl)sulfonyl]amino}-5,6,7,8-tetrahydro-1-naphthalenecarboxylic acid A suspension of 2-(diethylamino)ethanethiol hydrochloride (560 mg, 3.30 mmol) and 60% sodium hydride dispersion (224 mg, 10.18 mmol) was stirred in 3 mL of dry DMF until hydrogen evolution ceased. The mixture was treated with a solution of 2-([(2-fluorophenyl)sulfonyl]amino)-5,6,7,8-tetrahydro-1-napthalenecarboxylic acid methyl ester (200 mg, 0.55 mmol) in 1 mL of DMF, stirred at 70 to 75° C. overnight, and concentrated. The concentrate was purified by $C_{18}$ reverse-phase HPLC using acetonitrile/water/0.1% TFA to provide the desired product (200 mg, 78.7%). MS (APCI) m/e 462.8 $(M+H)^+$; $^1H$ NMR (400 MHz, $CD_3OD$) δ 7.89 (dd, 1H), 7.65 (dd, 1H), 7.57 (dt, 1H) 7.34 (dt, 1H), 7.18 (d, 1H), 7.00 (d, 1H), 3.34-3.51 (m, 4H), 3.29 (m, 2H), 3.25 (q, 4H), 2.65-2.77 (m, 4H), 1.70 (m, 4H), 1.28 (t, 6H).

EXAMPLE 504

2-({[2-({[3-(diethylamino)propyl]amino}carbonyl)phenyl]sulfonyl}amino)-5,6,7,8-tetrahydro-1-naphthalenecarboxylic acid The desired product was prepared by substituting 3-(N,N-diethylamino)propylamine for N,N-diethylethylenediamine in Example 379. MS (ESI(+)) m/e 488 $(M+H)^+$, 510 $(M+Na)^+$; (ESI(−)) m/e 486 $(M-H)^-$; $^1H$ NMR (300 MHz, DMSO-$d_6$) δ 13.14 (br s, 1H), 9.01 (s, 2H), 8.92 (t, 1H), 7.75 (dt, 2H), 7.63 (dd, 2H), 7.03 (d, 1H), 6.92 (d, 1H), 3.39 (q, 2H), 3.14 (m, 6H), 2.66 (br s, 2H), 2.61 (br s, 2H), 1.89 (m, 2H), 1.20 (t, 6H).

EXAMPLE 505

2-({[2-({[3-(dimethylamino)-2,2-dimethylpropyl]amino}carbonyl)phenyl]sulfonyl}amino)-5,6,7,8-tetrahydro-1-naphthalenecarboxylic acid The desired product was prepared by substituting N,N,2,2-tetramethyl-1,3-propanediamine for N,N-diethylethylenediamine in Example 379. MS (ESI(+)) m/e 488 $(M+H)^+$, 510 $(M+Na)^+$; (ESI(−)) m/e 486 $(M-H)^-$; $^1H$ NMR (300 MHz, DMSO-$d_6$) δ 13.14 (br s, 1H), 9.05 (s, 1H), 9.00 (t, 1H), 8.89 (br s, 1H), 7.80 (d, 1H), 7.75 (dd, 2H), 7.67 (d, 2H), 7.04 (d, 1H), 6.90 (d, 1H), 3.28 (d, 2H), 3.10 (br s, 2H), 2.90 (s, 6H), 2.67 (br s, 2H), 2.61 (br s, 2H), 1.66 (br s, 4H), 1.06 (s, 6H).

EXAMPLE 506

2-({[2-({[3-(diethylamino)propyl]amino}carbonyl)-3-thienyl]sulfonyl}amino)-5,6,7,8-tetrahydro-1-naphthalenecarboxylic acid The desired product was prepared by substituting 3-(N,N-diethylamino)propylamine for N,N-diethylethylenediamine in Example 463. MS (ESI(+)) m/e 494 $(M+H)^+$, 516 $(M+Na)^+$; (ESI(−)) m/e 492 $(M-H)^-$; $^1H$ NMR (300 MHz, DMSO-$d_6$) δ 13.22 (br s, 1H), 9.45 (br s, 1H), 8.98 (br s, 1H), 8.72 (t, 1H), 7.79 (d, 1H), 7.31 (d, 1H), 7.04 (d, 1H), 6.86 (d, 1H), 3.30 (m, 2H), 3.10 (m, 6H), 2.66 (m, 4H), 1.85 (m, 2H), 1.67 (br s, 4H), 1.17 (t, 6H).

EXAMPLE 507

2-({[2-({[3-(dimethylamino)-2,2-dimethylpropyl]amino}carbonyl)-3-thienyl]sulfonyl}amino)-5,6,7,8-tetrahydro-1-naphthalenecarboxylic acid The desired product was prepared by substituting N,N,2,2-tetramethyl-1,3-propanediamine for N,N-diethylethylenediamine in Example 463. MS (ESI(+)) m/e 494 $(M+H)^+$; (ESI(−)) m/e 492 $(M-H)^-$; $^1H$ NMR (300 MHz, DMSO-$d_6$) δ 13.20 (br s, 1H), 9.57 (br s, 1H), 8.81 (br s, 2H), 7.85 (d, 1H), 7.35 (d, 1H), 7.02 (d, 1H), 6.77 (d, 1H), 3.19 (d, 2H), 2.98 (s, 2H), 2.82 (s, 6H), 2.67 (m, 4H), 1.68 (br s, 4H), 0.98 (s, 6H).

EXAMPLE 508

2-({[2-({[(4-(diethylamino)-1-methylbutyl]amino}carbonyl)-3-thienyl]sulfonyl}amino)-5,6,7,8-tetrahydro-1-naphthalenecarboxylic acid The desired product was prepared by substituting N-[4-aminopentyl]-N,N-diethylamine for N,N-diethylethylenediamine in Example 463. MS (ESI(−)) m/e 520 $(M-H)^-$; $^1H$ NMR (300 MHz, DMSO-$d_6$) δ 13.20 (br s, 1H), 9.45 (br s, 1H), 8.91 (br s, 1H), 8.44 (d, 1H), 7.79 (d, 1H), 7.32 (d, 1H), 7.04 (d, 1H), 6.82 (d, 1H), 3.94 (m, 1H), 3.09 (m, 6H), 2.66 (br d, 4H), 1.67 (br s, 4H), 1.62 (br m, 2H), 1.48 (m, 2H), 1.17 (t, 6H), 1.10 (d, 3H).

EXAMPLE 509

2-{[(2-{[[3-(dimethylamino)propyl](methyl)amino]carbonyl}-3-thienyl)sulfonyl]amino}-5,6,7,8-tetrahydro-1-naphthalenecarboxylic acid The desired product was prepared by substituting N,N,N',-trimethyl-1,3-propanediamine for N,N-diethylethylenediamine in Example 463. MS (ESI(+)) m/e 480 $(M+H)^+$, 502 $(M+Na)^+$; (ESI(−)) m/e 478 $(M-H)^-$; $^1H$ NMR (300 MHz, DMSO-$d_6$) δ 13.20 (br s, 1H), 9.82 (s, 1H), 9.11 (br s, 1H), 7.84 (d, 1H), 7.36 (d, 1H), 7.02 (d, 1H), 6.75 (d, 1H), 3.44 (t, 2H), 3.07 (m, 2H), 2.2.74 (d, 6H), 2.66 (br d, 4H), 2.55 (s, 3H), 1.87 (quint, 2H),), 1.68 (br s, 4H).

EXAMPLE 510

2-{[(2-{[3-(dimethylamino)-2,2-dimethylpropyl]amino}phenyl)sulfonyl]amino}-6,7,8,9-tetrahydro-5H-benzo[7]annulene-1-carboxylic acid

EXAMPLE 510A methyl 2-chloro-6-{[(2-fluorophenyl)sulfonyl]amino}benzoate

A solution of 6-chloroanthranilic acid (1.9549 g, 11.57 mmol) in 4:1 benzene/methanol (58 mL) was treated with trimethylsilyldiazomethane (7.0 mL, 14.0 mmol, 2.0M solution in hexanes), stirred for 18 hours, quenched with acetic acid (1 mL), and concentrated. The concentrate (2.04 g, 10.99 mmol) was dissolved in pyridine (22 mL), treated with 2-fluorobenzenesulfonyl chloride (1.75 mL, 13.19 mmol), stirred for 18 hours, quenched with 1N HCl (200 mL), and treated with ethyl acetate (100 mL). The organic layer was washed with brine (100 mL), dried ($MgSO_4$), filtered, and concentrated. The concentrate was purified by flash column chromatography (3:1 hexanes/ethyl acetate) to provide the desired product (2.50 g, 66%). MS (ESI(+)) m/e 361 $(M+H)^+$, 366 $(M+NH_4)^+$; MS (ESI(−)) m/e 342 $(M-H)^-$; $^1H$ NMR (300 MHz, DMSO-$d_6$) δ 10.52 (br s, 1H), 7.72 (m, 2H), 7.43 (m, 3H), 7.37 (td, 1H), 7.22 (dd, 1H), 3.68 (s, 3H).

EXAMPLE 510B benzyl 4-pentynoate

A solution of 4-pentynoic acid (5.25 g, 53.5 mmol) in DMF (107 mL) was treated with $K_2CO_3$ (11.09 g, 80.3 mmol) and benzyl bromide (6.37 mL, 53.5 mmol), stirred for 24 hours, diluted with water (200 mL), and extracted with diethyl ether (3×150 mL). The combined organic extracts were dried ($MgSO_4$), filtered, and concentrated. The residue was purified by flash chromatography to provide the desired product (10.07 g, 100%). MS (ESI(+)) m/e 206 $(M+NH_4)^+$; $^1H$ NMR (300 MHz, DMSO-$d_6$) δ 7.37 (m, 5H), 5.12 (s, 2H), 2.61 (t, 1H), 2.57 (m, 2H), 2.42 (m, 2H).

EXAMPLE 510C benzyl(4E)-5-(tributylstannyl)-4-pentenoate

A mixture of Example 510B (8.7017 g, 46.23 mmol), tributyltin hydride (14.5 mL, 54.09 mmol), and AIBN (228 mg, 1.39 mmol) was stirred at 80° C. for 24 hours, cooled to room temperature, and purified by flash column chromatography to provide the desired product (16.4529 g, 74%). $^1H$ NMR (300 MHz, DMSO-$d_6$) δ 7.35 (m, 5H), 5.93 (m, 1H), 5.09 (m, 1H), 5.07 (s, 2H), 2.44 (m, 2H), 2.38 (m, 2H), 1.45 (m, 6H), 1.25 (m, 6H), 0.85 (m, 15H).

EXAMPLE 510D methyl 2-[(1E)-5-(benzyloxy)-5-oxo-1-pentenyl]-6-{[(2-fluorophenyl)sulfonyl]amino}benzoate A mixture of Example 510C (0.860 g, 1.79 mmol), Example 510A (0.514 g, 1.50 mmol), dioxane (5.0 mL), bis(tri-tert-butylphosphine)palladium(0) (38.2 mg, 0.075 mmol), and cesium fluoride (0.500 g, 3.29 mmol) was sealed and heated in a microwave reactor for 25 minutes at 170° C. This procedure was repeated a total of 17 times. The products were then combined and diluted with ethyl acetate (100 mL). The resulting suspension was then washed with 1N HCl (100 mL) and brine (100 mL), dried ($MgSO_4$), filtered, and concentrated. The concentrate was purified by flash chromatography (3:1 hexanes/ethyl acetate) to provide the desired product (9.84 g, 78%). MS (ESI(+)) m/e 515 $(M+NH_4)^+$; MS (ESI(−)) m/e 496 $(M-H)^-$; $^1H$ NMR (300 MHz, DMSO-$d_6$) δ 8.98 (br s, 1H), 7.83 (td, 1H), 7.51 (m, 2H), 7.31 (m, 5H), 7.26 (m, 2H), 7.19 (m, 1H), 7.12 (m, 1H), 6.56 (m, 1H), 5.98 (m, 1H), 5.11 (s, 2H), 3.88 (s, 3H), 2.52 (m, 4H).

EXAMPLE 510E

5-[3-{[(2-fluorophenyl)sulfonyl]amino}-2-(methoxycarbonyl)phenyl]pentanoic acid

A solution of Example 510D (9.84 g, 19.77 mmol) in methanol (150 mL) was added to $Pd(OH)_2$ (1.97 g). The suspension was shaken in a reactor pressurized with 60 psi of $H_2$ at 25° C. for 24 hours, filtered, and concentrated. The concentrate was dissolved in 4:1 methanol/$H_2O$ (200 mL), treated with LiOH (1.38 g, 57.66 mmol), stirred for 18 hours, quenched with 1N HCl (100 mL), and concentrated. The remaining solution was extracted with ethyl acetate (2×100 mL). The combined extracts were washed with brine (100 mL), dried ($MgSO_4$), filtered, and concentrated to provide desired product (7.80 g, 96%). MS (ESI(+)) m/e 427 $(M+NH_4)^+$, 432 $(M+Na)^+$; MS (ESI(−)) m/e 408 $(M-H)^-$; $^1H$ NMR (300 MHz, DMSO-$d_6$) δ 11.97 (br s, 1H), 10.05 (br s, 1H), 7.68 (m, 2H), 7.41 (dd, 1H), 7.31 (t, 2H), 7.15 (d, 1H), 7.02 (d, 1H), 3.66 (s, 3H), 2.53 (m, 2H), 2.17 (m, 2H), 1.44 (m, 4H).

EXAMPLE 510F methyl 2-{[(2-fluorophenyl)sulfonyl]amino}-5-oxo-6,7,8,9-tetrahydro-5H-benzo[7]annulene-1-carboxylate A solution of Example 510E (3.74 g, 9.13 mmol) in dichloroethane (183 mL) was treated with trifluoroacetic anhydride (2.58 mL, 18.3 mmol) and gallium (III) triflate (0.944 g, 1.83 mmol), stirred at 90° C. for 1.5 hours, and cooled to room temperature. The reaction was quenched with saturated aqueous sodium bicarbonate (200 mL), and the aqueous layer was extracted with $CH_2Cl_2$ (4×50 mL). The combined organic layers were dried ($MgSO_4$), filtered, and concentrated. The concentrate was purified by flash chromatography (7:3 hexanes/ethyl acetate) to provide the desired product (2.73 g, 76%). MS (ESI(+)) m/e 392 $(M+H)^+$, 409 $(M+NH_4)^+$, 414 $(M+Na)^+$; MS (ESI(−)) m/e 390 $(M-H)^-$; $^1H$ NMR (300 MHz, DMSO-$d_6$) δ 10.46 (br s, 1H), 7.74 (m, 2H), 7.52 (d, 1H), 7.43 (dd, 1H), 7.35 (td, 1H), 7.25 (d, 1H), 3.70 (s, 3H), 2.67 (t, 2H), 2.61 (m, 2H), 1.72 (m, 2H), 1.60 (m, 2H).

EXAMPLE 510G methyl 2-{[(2-fluorophenyl)sulfonyl]amino}-5-methoxy-6,7,8,9-tetrahydro-5H-benzo[7]annulene-1-carboxylate and methyl 2-{[(2-fluorophenyl)sulfonyl]amino}-6,7,8,9-tetrahydro-5H-benzo[7]annulene-1-carboxylate A solution of Example 510F (3.47 g, 8.87 mmol) in 100:1 methanol/concentrated HCl (152 mL) was added to 10% Pd/C (700 mg). The resulting suspension was reacted under 60 psi $H_2$ at 50° C. for 16 hours and filtered. The filtrate was concentrated and purified by flash chromatography to provide Example 510G (methyl 2-{[(2-fluorophenyl)sulfonyl]amino}-5-methoxy-6,7,8,9-tetrahydro-5H-benzo[7]annulene-1-carboxylate) (1.16 g, 32%) and Example 510H (methyl 2-{[(2-fluorophenyl)sulfonyl]amino}-6,7,8,9-tetrahydro-5H-benzo[7]annulene-1-carboxylate) (1.05 g, 31%). Example 510G: MS (ESI(+)) m/e 408 $(M+H)^+$, 425 $(M+NH_4)^+$; MS (ESI(−)) m/e 406 $(M-H)^-$; $^1H$ NMR (300 MHz, DMSO-$d_6$) δ 10.00 (br s, 1H), 7.69 (m, 2H), 7.42 (t, 1H), 7.31 (t, 1H), 7.28 (d, 1H), 7.00 (d, 1H), 4.37 (d, 1H), 3.65 (s, 3H), 3.21 (s, 3H), 2.70 (m, 1H), 2.49 (m, 1H), 1.61 (m, 2H), 1.59 (m, 3H), 1.37 (m, 1H). Example 510H: MS (ESI(+)) m/e 378 $(M+H)^+$, 395 $(M+NH_4)^+$, 400 $(M+Na)^+$; MS (ESI(−)) m/e 376 $(M-H)^-$; $^1H$ NMR (300 MHz, DMSO-$d_6$) δ 9.86 (br s, 1H), 7.61 (m, 2H), 7.35 (dd, 1H), 7.24 (td, 1H), 7.06 (d, 1H), 6.81 (d, 1H), 3.58 (s, 3H), 2.67 (t, 2H), 2.50 (m, 2H), 1.65 (m, 2H), 1.42 (m, 2H).

EXAMPLE 510I

2-{[(2-{[3-(dimethylamino)-2,2-dimethylpropyl]amino}phenyl)sulfonyl]amino}-6,7,8,9-tetrahydro-5H-benzo[7]annulene-1-carboxylic acid The desired product was prepared by substituting Example 510H and N,N,2,2-tetramethyl-1,3-propanediamine for Example 229A and 3-(N,N-diethylamino)propylamine, respectively, in Example 229B. MS (ESI(+)) m/e 474 $(M+H)^+$; MS (ESI(−)) m/e 472 $(M-H)^-$; $^1H$ NMR (300 MHz, DMSO-$d_6$) δ 7.55 (dd, 1H), 7.41 (td, 1H), 7.00 (d, 1H), 6.93 (d, 1H), 6.68 (t, 1H), 6.52 (d, 1H), 5.98 (br s, 1H), 3.09 (m, 4H), 2.73 (s, 6H), 2.73 (m, 4H), 1.75 (m, 2H), 1.52 (m, 4H), 1.01 (s, 6H).

EXAMPLE 511

2-{[(2-{[3-(4-cyclopentyl-1-piperazinyl)propyl]amino}phenyl)sulfonyl]amino}-8-methyl-5,6,7,8-tetrahydro-1-naphthalenecarboxylic acid

EXAMPLE 511A

3-(4-cyclopentyl-1-piperazinyl)-1-propanamine

A mixture of N-(3-bromopropyl)phthalimide (0.8 g, 3.0 mmol), 1-cyclopentylpiperazine (0.46 g, 3.0 mmol), and $K_2CO_3$ (1.66 g, 12.0 mmol) in $CH_3CN$ (30 mL) was heated to reflux for 3 hours, cooled to room temperature, and filtered through diatomaceous earth (Celite®). The filtrate was concentrated, treated with 6N HCl (9.0 mL) and acetic acid (18.0 mL), heated to reflux overnight, and concentrated. The residue was treated with potassium carbonate (1.66 g) in $CH_3CN$ (30 mL) for 1 hour. After filtration of the solid, the solvent was evaporated to provide the desired product. MS (DCI/$NH_3$) m/e 212 $(M+H)^+$; $^1H$ NMR (300 MHz, DMSO-$d_6$) δ 8.04 (br s, 2H), 3.68 (m, 4H), 3.41 (m, 4H), 3.21 (m, 2H), 2.91 (m, 2H), 2.0 (m, 4H), 1.84-1.73 (m, 4H), 1.55 (m, 2H).

EXAMPLE 511B

2-{[(2-{[3-(4-cyclopentyl-1-piperazinyl)propyl]amino}phenyl)sulfonyl]amino}-8-methyl-5,6,7,8-tetrahydro-1-naphthalenecarboxylic acid The desired product was prepared according to the procedure of Example 275G substituting Example 275F for 275E and Example 511A for N,N-dimethylethylenediamine. MS (ESI) m/e 553 $(M-H)^-$; $^1H$ NMR (300 MHz, DMSO-$d_6$) δ 7.51 (dd, 1H), 7.39 (dt, 1H), 6.95 (d, 1H), 6.8 (d, 1H), 6.62 (m, 2H), 3.3 (m, 4H), 3.21 (m, 4H), 2.87 (m, 2H), 2.65 (m, 5H), 1.95 (m, 4H), 1.8-1.5 (m, 10H), 1.1 (d, 3H).

EXAMPLE 512

2-{[(2-{[3-(4-isopropyl-1-piperazinyl)propyl]amino}phenyl)sulfonyl]amino}-8-methyl-5,6,7,8-tetrahydro-1-naphthalenecarboxylic acid

EXAMPLE 512A

3-(4-isopropyl-1-piperazinyl)-1-propanamine

The desired product was prepared according to the procedure of Example 511A substituting 1-isopropylpiperazine for 1-cyclopentylpiperazine. MS (DCI/$NH_3$) m/e 186 $(M+H)^+$; $^1H$ NMR (300 MHz, DMSO-$d_6$) δ 2.57 (m, 1H), 2.40 (m, 6H), 2.32 (m, 4H), 2.25 (t, 2H), 1.47 (m, 2H), 0.94 (d, 6H).

EXAMPLE 512B

2-{[(2-{[3-(4-isopropyl-1-piperazinyl)propyl]amino}phenyl)sulfonyl]amino}-8-methyl-5,6,7,8-tetrahydro-1-naphthalenecarboxylic acid The desired product was prepared according to the procedure of Example 275G substituting Example 275F for 275E and Example 512A for N,N-dimethylethylenediamine. MS (ESI) m/e 527 $(M-H)^-$; $^1H$ NMR (300 MHz, DMSO-$d_6$) δ

7.49 (dd, 1H), 7.38 (dt, 1H), 6.95 (d, 1H), 6.8 (d, 1H), 6.63 (m, 2H), 3.3 (m, 4H), 3.21 (m, 4H), 2.96 (m, 2H), 2.66 (m, 5H), 1.8-1.6 (m, 6H), 1.21 (d, 6H), 1.09 (d, 3H).

EXAMPLE 513

2-({[2-({2-[(2S)-1-(2-pyridinylmethyl)-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and 2-pyridinecarbaldehyde for 2-ethylbutanal in Example 557C. MS (DCI) m/e 535 $(M+H)^+$; $^1H$ NMR (500 MHz, DMSO-$d_6$) 13.36 (br s, 1H), 9.51 (br s, 1H), 8.63 (m, 1H), 7.86 (m, 1H), 7.54 (dd, 1H), 7.46-7.38 (m, 3H), 6.95 (d, 1H), 6.78 (d, 1H), 6.67 (t, 1H), 6.60 (d, 1H), 5.99 (br s, 1H), 4.58 (d, 1H), 4.30 (d, 1H), 2.64 (m, 4H), 2.31 (m, 1H), 2.13 (m, 1H), 1.98-1.70 (m, 4H), 1.65 (m, 4H).

EXAMPLE 514

2-({[2-({2-[(2S)-1-cyclobutyl-2-pyrrolidinyl]ethyl}amino)phenyl]sulfonyl}amino)-5,6,7,8-tetrahydro-1-naphthalenecarboxylic acid The desired product was prepared by substituting Example 552D for Example 557B and cyclobutanone for 2-ethylbutanal in Example 557C. MS (DCI) m/e 498 $(M+NH_4)^+$; $^1H$ NMR (500 MHz, DMSO-$d_6$) 13.31 (br s, 1H), 9.66 (br s, 1H), 7.58 (d, 1H), 7.40 (m, 1H), 6.94 (m, 1H), 6.83 (d, 1H), 6.67 (m, 1H), 6.51 (m, 1H), 6.02 (br s, 1H), 2.96 (br m, 2H), 2.70-2.63 (m, 4H), 2.27 (br s, 2H), 2.07-1.94 (m, 8H), 1.65 (br s, 6H).

EXAMPLE 515

2-({[2-({[4-(diethylamino)butyl]amino}carbonyl)phenyl]sulfonyl}amino)-5,6,7,8-tetrahydro-1-naphthalenecarboxylic acid The desired product was prepared by substituting 4-(N,N-diethylamino)butylamine for N,N-diethylethylenediamine in Example 379. MS (ESI(+)) m/e 502 $(M+H)^+$; (ESI(−)) m/e 500 $(M-H)^-$; $^1H$ NMR (300 MHz, DMSO-$d_6$) δ 13.11 (br s, 1H), 9.03 (s, 1H), 8.93 (br s, 1H), 8.86 (t, 1H), 7.74 (dt, 2H), 7.62 (dd, 2H), 7.03 (d, 1H), 6.90 (d, 1H), 3.58 (m, 2H), 3.33 (q, 2H), 3.12 (m, 4H), 2.66 (br s, 2H), 2.60 (br s, 2H), 1.74-1.56 (m, 8H), 1.20 (t, 6H).

EXAMPLE 516

2-({[2-({[4-(diethylamino)butyl]amino}carbonyl)-3-thienyl]sulfonyl}amino)-5,6,7,8-tetrahydro-1-naphthalenecarboxylic acid The desired product was prepared by substituting 4-(N,N-diethylamino)butylamine for N,N-diethylethylenediamine in Example 463. MS (ESI(+)) m/e 508 $(M+H)^+$; (ESI(−)) m/e 506 $(M-H)^-$; $^1H$ NMR (300 MHz, DMSO-$d_6$) δ 13.19 (br s, 1H), 9.44 (br s, 1H), 8.92 (br s, 1H), 8.64 (t, 1H), 7.79 (d, 1H), 7.31 (d, 1H), 7.04 (d, 1H), 6.84 (d, 1H), 3.24 (q, 2H), 3.16-3.02 (m, 6H), 2.66 (m, 4H), 1.73-1.48 (m, 8H), 1.18 (t, 6H).

EXAMPLE 517

2-({[2-({[4-(diethylamino)butyl]amino}carbonyl)-4-fluorophenyl]sulfonyl}amino)-5,6,7,8-tetrahydro-1-naphthalenecarboxylic acid The desired product was prepared by substituting 4-(N,N-diethylamino)butylamine for N-(4-aminopentyl)-N,N-diethylamine in Examples 518B-C. MS (ESI(+)) m/e 520 $(M+H)^+$; (ESI(−)) m/e 518 $(M-H)^-$; $^1H$ NMR (300 MHz, DMSO-$d_6$) δ 13.14 (br s, 1H), 8.98 (s, 1H), 8.90 (t, 1H), 7.78 (dd, 1H), 7.52-7.42 (m, 2H), 7.04 (d, 1H), 6.92 (d, 1H), 3.33 (m, 4H), 3.17-3.04 (m, 6H), 2.67 (br s, 2H), 2.60 (br s, 2H), 1.75-1.56 (m, 8H), 1.20 (t, 6H).

EXAMPLE 518

2-({[2-({[(4-(diethylamino)-1-methylbutyl]amino}carbonyl)-4-fluorophenyl]sulfonyl}amino)-5,6,7,8-tetrahydro-1-naphthalenecarboxylic acid

EXAMPLE 518A methyl 2-{[(2-bromo-4-fluorophenyl)sulfonyl]amino}-5,6,7,8-tetrahydro-1-naphthalenecarboxylate The desired product was prepared by substituting 2-bromo-4-fluorobenzenesulfonyl chloride for methyl 2-(chlorosulfonyl)benzoate in Example 379A. MS (ESI(+)) m/e 442, 444 $(M+H)^+$; (ESI(−)) m/e 440, 442 $(M-H)^-$; $^1H$ NMR (300 MHz, DMSO-$d_6$) δ 9.93 (s, 1H), 7.88 (dd, 2H), 7.39 (dt, 1H), 7.08 (d, 1H), 6.86 (d, 1H), 3.70 (s, 3H), 2.67 (br s, 2H), 2.54 (br s, 2H), 1.66 (br m, 4H).

EXAMPLE 518B methyl 2-({[2-({[4-(diethylamino)-1-methylbutyl]amino}carbonyl)-4-fluorophenyl]sulfonyl}amino)-5,6,7,8-tetrahydro-1-naphthalenecarboxylate In a high pressure vessel was placed Example 518A (1.26 g, 2.85 mmol), THF (12 mL), triethylamine (6 mL), N-(4-aminopentyl)-N,N-diethylamine (4.5 g, 28.4 mmol), and $PdCl_2(dppf).CH_2Cl_2$ (233 mg). The solution was stirred at 120° C. under 450 psi carbon monoxide for 16 hours, cooled to room temperature, and filtered. The filtrate was treated with 1N HCl and the aqueous layer was extracted with ethyl acetate two times. The combined organic fractions were dried ($MgSO_4$), filtered, and concentrated. The resulting residue was purified by preparative HPLC to provide the desired product. MS (ESI(+)) m/e 548 $(M+H)^+$; (ESI(−)) m/e 546 $(M-H)^-$; $^1H$ NMR (300 MHz, DMSO-$d_6$) δ 8.93 (br s, 1H), 8.87 (s, 1H), 8.82 (d, 1H), 7.70 (dd, 1H), 7.53 (dt, 1H), 7.12 (d, 1H), 7.06 (d, 1H), 4.02 (m, 2H), 3.18-3.02 (m, 6H), 2.68 (br s, 2H), 2.51 (br s, 2H), 1.75-163 (br m, 5H), 1.55 (m, 2H), 1.20 (m, 9H).

EXAMPLE 518C 2-({[2-({[(4-(diethylamino)-1-methylbutyl]amino}carbonyl)-4-fluorophenyl]sulfonyl}amino)-5,6,7,8-tetrahydro-1-naphthalenecarboxylic acid The desired product was prepared by substituting Example 518B for Example 463C in Example 463D. MS (ESI(+)) m/e 534 $(M+H)^+$; (ESI(−)) m/e 532 $(M-H)^-$; $^1H$ NMR (300 MHz, DMSO-$d_6$) δ 13.13 (br s, 1H), 9.45 (br s, 1H), 8.96 (br s, 2H), 8.74 (d, 1H), 7.78 (dd, 1H), 7.50-7.42 (m, 2H), 7.04 (d, 1H), 6.92 (d, 1H), 4.02 (m, 1H), 3.18-3.02 (m, 6H), 2.67 (br s, 2H), 2.60 (br s, 2H), 1.74-163 (br m, 6H), 1.52 (m, 2H), 1.19 (m, 9H).

EXAMPLE 519

2-({[2-({[(4-(diethylamino)-1-methylbutyl]amino}carbonyl)phenyl]sulfonyll}amino)-5,6,7,8-tetrahydro-1-naphthalenecarboxylic acid The desired product was prepared by substituting N-(4-aminopentyl)-N,N-diethylamine for N,N-diethylethylenediamine in Example 379. MS (ESI(+)) m/e 516 $(M+H)^+$, 538

$(M+Na)^+$; (ESI(−)) m/e 514 $(M-H)^-$; $^1H$ NMR (300 MHz, DMSO-$d_6$) δ 9.18 (br s, 1H), 9.02 (br s, 1H), 8.70 (d, 1H), 7.74 (dt, 2H), 7.61 (m, 2H), 7.02 (d, 1H), 6.89 (d, 1H), 4.04 (quint, 1H), 3.17-3.00 (m, 6H), 2.66 (br s, 2H), 2.61 (br s, 2H), 1.72 (m, 2H), 1.66 (s, 4H), 1.54 (q, 2H), 1.20 (m, 9H).

EXAMPLE 520

8-methyl-2-{[(2-{[3-(4-morpholinyl)propyl]amino}phenyl)sulfonyl]amino}-5,6,7,8-tetrahydro-1-naphthalenecarboxylic acid

EXAMPLE 520A 3-(4-morpholinyl)-3-oxopropanenitrile

Ethyl cyanoacetate (5.33 mL, 50 mmol) and morpholine (17.49 mL, 0.2 mol) were gently refluxed at 90° C. in an oil bath for 2 days. The mixture was concentrated and the residue was purified by silica gel column chromatography eluting with 50% acetone in n-hexane. 5.93 g of the compound was obtained. MS (DCI) m/e 155 $(M+H)^+$, 172 $(M+NH_4)^+$; $^1H$ NMR (300 MHz, DMSO-$d_6$) δ 4.03 (s, 2H), 3.53-3.59 (m, 4H), 3.42-3.45 (m, 2H), 3.32-3.35 (m, 2H).

EXAMPLE 520B 3-(4-morpholinyl)-1-propanamine

The desired product was prepared from Example 520A (0.77 g, 5 mmol) and 1M LAH (10 mL, 10 mmol) in 3 mL of THF following the procedure described in Example 393B to yield the desired product. MS (DCI) m/e 145 $(M+H)^+$.

EXAMPLE 520C 8-methyl-2-{[(2-{[3-(4-morpholinyl)propyl]amino}phenyl)sulfonyl]amino}-5,6,7,8-tetrahydro-1-naphthalenecarboxylic acid The desired product was prepared by substituting Example 275F (50 mg, 0.133 mmol) and Example 520B (123 μL, 0.8 mmol) for Example 275E and N,N-dimethylethylenediamine. MS (ESI(+)) m/e 488 $(M+H)^+$; MS (ESI(−)) m/e 486 $(M-H)^-$; $^1H$ NMR (300 MHz, DMSO-$d_6$) δ 9.50 (s, 1H), 7.50 (d, 1H), 7.40 (t, 1H), 6.93 (d, 1H), 6.82 (d, 1H), 6.63 (t, 1H), 6.08 (t, 1H), 3.80-4.00 (m, 2H), 3.50-3.75 (m, 3H), 3.03-3.19 (m, 3H), 2.57-2.73 (m, 2H), 1.54-2.00 (m, 5H), 1.08 (d, 3H).

EXAMPLE 521

(8R)-2-{[(2-{[3-(diethylamino)propyl]amino}phenyl)sulfonyl]amino}-8-methyl-5,6,7,8-tetrahydro-1-naphthalenecarboxylic acid The compound of Example 275F was separated into individual enantiomers by preparative column chromatography (Chiralpak AS 5 cm×30 cm; mobile phase: ethyl alcohol/hexane=20:80; Flow rate 30 mL/min) to obtain pure enatiomers respectively.

The desired product was prepared by substituting the product which eluted first (50 mg, 0.133 mmol) and 3-(N,N-diethylamino)propylamine (168 μL, 1.06 mmol) for Example 275E and N,N-dimethylethylenediamine, respectively, in Example 275G. MS (ESI(+)) m/e 474 $(M+H)^+$; MS (ESI(−)) m/e 472 $(M-H)^-$; $^1H$ NMR (300 MHz, DMSO-$d_6$) δ 9.44 (s, 1H), 9.07 (s, 1H), 7.53 (dd, 1H), 7.42 (t, 1H), 6.93 (d, 1H), 6.87 (d, 1H), 6.66 (t, 1H), 6.56 (d, 1H), 6.02 (t, 1H), 3.24-3.32 (m, 3H), 3.07-3.07 (m, 6H), 2.54-2.74 (m, 2H), 1.85-1.93 (m, 2H), 1.61-1.72 (m, 4H), 1.09-1.15 (m, 9H).

EXAMPLE 522

(8S)-2-{[(2-{[3-(diethylamino)propyl]amino}phenyl)sulfonyl]amino}-8-methyl-5,6,7,8-tetrahydro-1-naphthalenecarboxylic acid The compound of Example 275F was separated into individual enantiomers by preparative column chromatography (Chiralpak AS 5 cm×30 cm; mobile phase: ethyl alcohol: hexane=20:80; Flow rate 30 mL/min) to obtain pure enatiomers respectively.

The desired product was prepared by substituting the product which eluted last (50 mg, 0.133 mmol) and 3-(N,N-diethylamino)propylamine (168 μL, 1.06 mmol) for Example 275E and N,N-dimethylethylenediamine, respectively, in Example 275G. MS (ESI(+)) m/e 474 $(M+H)^+$; 496 $(M+Na)^+$; MS (ESI(−)) m/e 472 $(M-H)^-$; $^1H$ NMR (300 MHz, DMSO-$d_6$) δ 9.44 (s, 1H), 9.00 (s, 1H), 7.53 (dd, 1H), 7.42 (t, 1H), 6.93 (d, 1H), 6.88 (d, 1H), 6.66 (t, 1H), 6.57 (d, 1H), 6.02 (t, 1H), 3.26-3.32 (m, 4H), 3.02-3.14 (m, 6H), 2.54-2.73 (m, 2H), 1.83-1.93 (m, 2H), 1.61-1.72 (m, 4H), 1.09-1.15 (m, 9H).

EXAMPLE 523

2-(2-aminoethoxy)-3-ethyl-6-{[(4-fluorophenyl)sulfonyl]amino}benzoic acid

EXAMPLE 523A methyl 6-amino-3-bromo-2-[2-(1-oxo-1,3-dihydro-2H-isoindol-2-yl)ethoxy]benzoate The title compound was prepared from Example 385D (0.735 g, 3 mmol) and N-(2-bromoethyl)phthalimide according to the procedure of Example 385E, yielding 0.75 g, 77.7%. $^1H$ NMR (DMSO-$d_6$) δ 3.62 (s, 3H), 3.92 (t, 2H), 4.05 (t, 2H), 5.90 (s, 2H), 6.45 (d, 1H), 7.25 (d, 1H), 7.80-7.92 (m, 4H); MS (ESI(+)) m/e 418, 420 $(M+H)^+$.

EXAMPLE 523B methyl 6-amino-2-[2-(1-oxo-1,3-dihydro-2H-isoindol-2-yl)ethoxy]-3-vinylbenzoate The title compound was prepared from Example 523A (0.75 g, 1.79 mmol) according to the procedure of Example 230B, yielding 0.52 g, 79.3%. $^1H$ NMR (DMSO-$d_6$) δ 3.60 (s, 3H), 3.92 (s, 4H), 4.88 (d, 1H), 5.45 (d, 1H), 5.88 (s, 2H), 6.50 (d, 1H), 6.65 (dd, 1H), 7.38 (d, 1H), 7.80-7.92 (m, 4H); MS (ESI(+)) m/e 367 $(M+H)^+$.

EXAMPLE 523C methyl 6-amino-3-ethyl-2-[2-(1-oxo-1,3-dihydro-2H-isoindol-2-yl)ethoxy]benzoate Example 523B (0.52 g) was hydrogenated in methanol (10 mL) over Pd/C (300 mg) at ambient temperature under one atmosphere of hydrogen for 16 hours. Filtration and evaporation of the solvent to give the title compound.

EXAMPLE 523D methyl 2-[2-(1,3-dioxo-1,3-dihydro-2H-isoindol-2-yl)ethoxy]-3-ethyl-6-{[(4-fluorophenyl)sulfonyl]amino}benzoate The title compound was prepared from Example 523C (0.23 g, 0.61 mmol) and 4-fluorobenzenesulfonyl chloride according to the procedure of Example 385F, yielding 0.278 g, 86.6%. $^1$H NMR (DMSO-$d_6$) δ 0.98 (t, 3H), 2.42 (q, 2H), 3.50 (s, 3H), 3.92 (t, 2H), 3.98 (t, 2H), 6.80 (d, 1H), 7.20 (d, 1H), 7.38 (t, 2H), 6.68 (dd, 2H), 7.80-7.92 (m, 4H); MS (ESI(−)) m/e 525 (M−H)$^-$.

EXAMPLE 523E 2-(2-aminoethoxy)-3-ethyl-6-{[(4-fluorophenyl)sulfonyl]amino}benzoic acid The title compound was prepared from Example 523D (50 mg, 0.095 mmol) according to the procedure of Example 385, yielding 8.6 mg, 23.8%. $^1$H NMR (DMSO-$d_6$) δ 1.08 (t, 3H), 2.42 (q, 2H), 3.05 (t, 2H), 3.90 (t, 2H), 7.06 (d, 1H), 7.12 (d, 1H), 7.30 (t, 2H), 7.75 (dd, 2H), 8.20 (br s, 2H); MS (ESI(−)) m/e 381 (M−H)$^-$.

EXAMPLE 524

2-(2-aminoethoxy)-6-{[(2-bromophenyl)sulfonyl]amino}-3-ethylbenzoic acid

EXAMPLE 524A methyl 6-{[(2-bromophenyl)sulfonyl]amino}-2-[2-(1,3-dioxo-1,3-dihydro-2H-isoindol-2-yl)ethoxy]-3-ethylbenzoate The title compound was prepared from Example 523C (0.23 g, 0.61 mmol) and 2-bromobenzenesulfonyl chloride according to the procedure of Example 385F, yielding 0.358 g, 100%. $^1$H NMR (DMSO-$d_6$) δ 0.98 (t, 3H), 2.42 (q, 2H), 3.50 (s, 3H), 3.90 (t, 2H), 3.98 (t, 2H), 6.82 (d, 1H), 7.22 (d, 1H), 7.50-7.55 (m, 2H), 7.80-7.92 (m, 6H), 9.95 (s, 1H); MS (ESI(−)) m/e 585 and 587 (M−H)$^-$.

EXAMPLE 524B 2-(2-aminoethoxy)-6-{[(2-bromophenyl)sulfonyl]amino}-3-ethylbenzoic acid The title compound was prepared from Example 524A (50 mg, 0.085 mmol) according to the procedure of Example 385I, yielding 11.5 mg, 27.3%. $^1$H NMR (DMSO-$d_6$) δ 1.06 (t, 3H), 2.45 (q, 2H), 3.10 (t, 2H), 3.92 (t, 2H), 6.88 (d, 1H), 7.10 (d, 1H), 7.48 (t, 1H), 7.54 (t, 1H), 7.75 (d, 1H), 8.10 (d, 1H), 8.00-8.40 (br s, 3H), 15.45 (br s, 1H); MS (ESI(−)) m/e 381 (M−H)$^-$.

EXAMPLE 525

2-(2-aminoethoxy)-6-[({2-[(1E)-3,3-dimethyl-1-butenyl]phenyl}sulfonyl)amino]-3-ethylbenzoic acid

EXAMPLE 525A methyl 6-[({2-[(1E)-3,3-dimethyl-1-butenyl]phenyl}sulfonyl)amino]-2-[2-(1,3-dioxo-1,3-dihydro-2H-isoindol-2-yl)ethoxy]-3-ethylbenzoate The title compound was prepared from 524A (150 mg, 0.256 mmol) and trans-2-tert-butylvinylboronic acid (50 mg, 0.38 mmol) according to the procedure of Example 230B, yielding 102 mg, 74.8%.

EXAMPLE 525B 2-(2-aminoethoxy)-6-[({2-[(1E)-3,3-dimethyl-1-butenyl]phenyl}sulfonyl)amino]-3-ethylbenzoic acid The title compound was prepared from Example 525A (48 mg, 0.104 mmol) according to the procedure of Example 385I, yielding 3.8 mg, 9.0%. $^1$H NMR (DMSO-$d_6$) δ 1.06 (t, 3H), 1.08 (s, 9H), 2.45 (q, 2H), 3.08 (t, 2H), 3.92 (t, 2H), 6.22 (d, 1H), 6.88 (d, 1H), 7.00 (d, 1H), 7.14 (d, 1H), 7.35 (t, 1H), 7.50 (t, 1H), 7.62 (d, 1H), 7.90 (d, 1H), 8.25 (br s, 3H), 15.08 (br s, 1H); MS (ESI(−)) m/e 445 (M−H)$^-$.

EXAMPLE 526

2-(2-aminoethoxy)-6-({[2-(3,3-dimethylbutyl)phenyl]sulfonyl}amino)-3-ethylbenzoic acid

EXAMPLE 526A methyl 6-({[2-(3,3-dimethylbutyl)phenyl]sulfonyl}amino)-2-[2-(1,3-dioxo-1,3-dihydro-2H-isoindol-2-yl)ethoxy]-3-ethylbenzoate Example 525A (50 mg) was hydrogenated in methanol (10 mL) over 10% Pd/C (50 mg) at ambient temperature under one atmosphere of hydrogen for 16 h. Filtration and evaporation of the solvent gave the title compound 55 mg, 100%.

EXAMPLE 526B 2-(2-aminoethoxy)-6-({[2-(3,3-dimethylbutyl)phenyl]sulfonyl}amino)-3-ethylbenzoic acid The title compound was prepared from Example 526A (55 mg, 0.093 mmol) according to the procedure of Example 385I, yielding 1.8 mg, 4.3%. $^1$H NMR (DMSO-$d_6$) δ 0.92 (s, 9H), 1.08 (t, 3H), 1.44 (t, 2H), 2.45 (q, 2H), 2.90 (t, 2H), 3.08 (t, 2H), 3.92 (t, 2H), 6.95 (d, 1H), 7.00 (d, 1H), 7.147.35 (m, 2H), 7.47 (t, 1H), 7.84 (d, 1H), 8.25 (br s, 3H), 14.46 (br s, 1H); MS (ESI(−)) m/e 447 (M−H)$^-$.

EXAMPLE 527

2-(2-aminoethoxy)-3-ethyl-6-{[(2-propylphenyl)sulfonyl]amino}benzoic acid

EXAMPLE 527A methyl 2-[2-(1,3-dioxo-1,3-dihydro-2H-isoindol-2-yl)ethoxy]-3-ethyl-6-[({2-[(1E)-1-propenyl]phenyl}sulfonyl)amino]benzoate The title compound was prepared from 524A (150 mg, 0.256 mmol) and trans-propenylboronic acid (35 mg, 0.38 mmol) according to the procedure of Example 230B, yielding 128 mg, 91.2%. $^1$H NMR (DMSO-$d_6$) δ 0.98 (t, 3H), 1.76 (d, 3H), 2.42 (q, 2H), 3.48 (s, 3H), 3.90 (t, 2H), 3.98 (t, 2H), 6.16-6.26 (m, 1H), 6.78 (d, 1H), 6.87 (d, 1H), 7.18 (d, 1H), 7.32 (t, 1H), 7.54 (t, 1H), 7.65 (d, 1H), 7.72 (d, 1H), 7.80-7.94 (m, 4H), 9.75 (s, 1H); MS (DCI/$NH_3$) m/e 566 (M+$NH_4$)$^+$.

EXAMPLE 527B methyl 2-[2-(1,3-dioxo-1,3-dihydro-2H-isoindol-2-yl)ethoxy]-3-ethyl-6-{[(2-propylphenyl)sulfonyl]amino}benzoate Example 527A (0.128 g, 0.23 mmol) was hydrogenated in methanol (10 mL) over 10% Pd/C (0.1 g) at ambient temperature under one atmosphere of hydrogen. Filtration and evaporation of the solvent gave the title compound, 125 mg, 98%. $^1$H NMR (DMSO-$d_6$) δ 0.88 (t, 3H), 0.98 (t, 3H), 1.50-1.60 (m, 2H), 2.42 (q, 2H), 2.82 (t, 2H), 3.48 (s, 3H), 3.88 (m, 2H), 3.98 (m, 2H), 6.78 (d, 1H), 7.18 (d, 1H), 7.29 (t, 1H), 7.38 (d, 1H), 7.45-7.55 (m, 1H), 7.69 (d, 1H), 7.80-7.94 (m, 4H), 9.75 (s, 1H); MS (ESI(−)) m/e 549 $(M-H)^-$.

EXAMPLE 527C 2-(2-aminoethoxy)-3-ethyl-6-{[(2-propylphenyl) sulfonyl]amino}benzoic acid The title compound was prepared from Example 527B (55 mg, 0.093 mmol) according to the procedure of Example 385I, yielding 8.6 mg, 9.4%. $^1$H NMR (DMSO-$d_6$) δ 0.88 (t, 3H), 1.05 (t, 3H), 1.50-1.60 (m, 2H), 2.42 (q, 2H), 2.82 (t, 2H), 3.06 (m, 2H), 3.95 (m, 2H), 6.92 (d, 1H), 7.00 (d, 1H), 7.29 (t, 1H), 7.35 (d, 1H), 7.45 (t, 1H), 7.90 (d, 1H), 8.00-8.40 (br s, 3H), 14.70 (br s, 1H). MS (ESI(−)) m/e 405 $(M-H)^-$.

EXAMPLE 528

2-[({2-[(4-pyridinylmethyl)amino]phenyl}sulfonyl) amino]-5,6,7,8-tetrahydro-1-naphthalenecarboxylic acid The desired product was prepared by substituting 4-aminomethylpyridine for N,N-diethyl-1,3-propanediamine in Example 229B. MS (ESI(+)) m/e 438 $(M+H)^+$; (ESI(−)) m/e 436 $(M-H)^-$; $^1$H NMR (300 MHz, DMSO-$d_6$) δ 8.64 (d, 2H), 7.62 (d, 2H), 7.56 (dd, 1H), 7.30 (dt, 1H), 6.97 (d, 1H), 6.65 (m, 2H), 6.57 (d, 1H), 4.66 (d, 2H), 2.67 (m, 4H), 1.68 (m, 4H).

EXAMPLE 529

2-[({2-[(1E)-4-(diethylamino)-1-butenyl] phenyl}sulfonyl)amino]-5,6,7,8-tetrahydro-1-naphthalenecarboxylic acid

EXAMPLE 529A

N,N-diethyl-3-butyn-1-amine

A mixture of 3-butynyl 4-methylbenzenesulfonate (10 mL, 57 mmol), $K_2CO_3$ (7.9 g, 57 mmol), and diethylamine (23.5 mL, 228 mmol) in 100 mL of THF was heated to reflux for 31 hours, cooled to room temperature, and filtered. The filtrate was concentrated under vacuum at a distillation temperature of 60° C. to provide 11.2 g of a 53 wt % solution of the desired product in THF (5.9 g assay, 83% yield). $^1$H NMR (400 MHz, DMSO-$d_6$) δ 0.93 (t, J=7.07 Hz, 6H) 2.21 (m, 2H) 2.44 (q, J=7.04 Hz, 4H) 2.55 (m, 2H) 2.72 (t, J=2.68 Hz, 1H).

EXAMPLE 529B AND EXAMPLE 529C

N,N-diethyl-N-[(3Z)-4-(tributylstannyl)-3-butenyl] amine compound and

N,N-diethyl-N-[(3E)-4-(tributylstannyl)-3-butenyl] amine

A solution of Example 529A (1.76 g, 7.5 mmol), tributyltin hydride (3.2 mL, 12 mmol), and azobisisobutyronitrile (0.12 g, 0.1 equiv.) in 35 mL of benzene was heated to 80° C. for 3 hours, at which point more azobisisobutyronitrile (0.25 g, 0.2 equiv.) was added. After heating an additional 5 hours, the reaction was cooled to room temperature, and the solution was concentrated and purified by silica gel chromatography to provide 1.85 g (59%) of Example 529B. $^1$H NMR (400 MHz, $CDCl_3$) δ 0.87 (m, 15H) 1.03 (t, J=7.14 Hz, 6H) 1.30 (m, 6H) 1.49 (m, 6H) 2.28 (m, 2H) 2.53 (m, 6H) 5.92 (m, 2H)

The chromatography also yielded 0.45 g (14%) of Example 529C. $^1$H NMR (400 MHz, $CDCl_3$) δ 0.90 (m, 15H) 1.04 (t, J=7.14 Hz, 6H) 1.32 (m, 6H) 1.49 (m, 6H) 2.19 (m, 2H) 2.53 (m, 6H) 5.84 (dt, J=12.45, 1.18 Hz, 1H) 6.46 (dt, J=12.42, 6.90 Hz, 1H)

EXAMPLE 529D methyl 2-[({2-[(1E)-4-(diethylamino)-1-butenyl] phenyl}sulfonyl)amino]-5,6,7,8-tetrahydro-1-naphthalenecarboxylate A mixture of Example 529B (1.10 g, 2.6 mmol), methyl 2-[({2-bromophenyl}sulfonyl)amino]-5,6,7,8-tetrahydro-1-naphthalenecarboxylate (848 mg, 2.0 mmol) and bis(tri-tert-butylphosphine)palladium (212 mg, 0.4 mmol) in 4 mL of toluene was stirred at ambient temperature for 20.5 hours. The resulting solution was purified by silical gel chromatography to yield 0.95 g (100%) of the desired product. $^1$H NMR (400 MHz, $CDCl_3$) δ 1.00 (t, J=7.14 Hz, 6H) 1.70 (m, 4H) 2.38 (m, 2H) 2.59 (m, 6H) 2.69 (m, 4H) 3.74 (s, 3H) 5.29 (s, 1H) 6.06 (m, 1H) 6.84 (d, J=8.23 Hz, 1H) 6.93 (d, J=8.20 Hz, 1H) 7.16 (d, J=15.78 Hz, 1H) 7.25 (m, 1H) 7.46 (m, 2H) 7.85 (d, J=7.96 Hz, 1H).

EXAMPLE 529E

2-[({2-[(1E)-4-(diethylamino)-1-butenyl] phenyl}sulfonyl)amino]-5,6,7,8-tetrahydro-1-naphthalenecarboxylic acid A mixture of Example 529D (373 mg, 0.8 mmol) and LiI (428 mg, 4 equiv.) in 8 mL of pyridine was heated at 150° C. for 35 minutes in a microwave. The product was purified in two fractions by preparative HPLC on a Waters Symmetry C8 column (40 mm×100 mm, 7 μm particle size) using a gradient of 0% to 95% acetonitrile/0.1% aqueous TFA over 12 minutes (15 minute run time) at a flow rate of 70 mL/min to yield 257 mg (70%) of the desired product. MS (ESI(+)) m/e 457 $(M+H)^+$; MS (ESI(−)) m/e 455 $(M-H)^-$; $^1$H NMR (400 MHz, DMSO-$d_6$) δ 1.20 (t, J=7.27 Hz, 6H) 1.64 (m, 4H) 2.61 (m, 6H) 3.18 (m, 6H) 6.21 (ddd, J=15.40, 6.90, 6.79 Hz, 1H) 6.65 (m, 1H) 6.92 (d, J=8.23 Hz, 1H) 7.25 (d, J=15.64 Hz, 1H) 7.37 (t, J=8.23 Hz, 1H) 7.58 (t, J=7.96 Hz, 1H) 7.67 (m, 1H) 7.75 (dd, J=7.96, 1.37 Hz, 1H).

EXAMPLE 530

2-{[(2-{[3-(diethylamino)propyl]sulfanyl}phenyl) sulfonyl]amino}-5,6,7,8-tetrahydro-1-naphthalenecarboxylic acid The desired product was prepared by substituting 3-(diethylamino)propanethiol hydrochloride for 2-(diethylamino) ethanethiol hydrochloride in Example 503 (46 mg, 17.6%); MS (APCI) m/e 477.3 $(M+H)^+$; $^1$H NMR (400 MHz, $CD_3OD$) δ 7.92 (dd, 1H), 7.59 (dd, 1H), 7.53 (dt, 1H) 7.29 (dt, 1H), 7.17 (d, 1H), 6.99 (d, 1H), 3.27-3.35 (m, 4H), 3.19 (m, 6H), 2.65-2.80 (m, 4H), 2.08 (m, 2H), 1.70 (m, 4H), 1.26 (t, 6H).

EXAMPLE 533

2-{[(2-{[2-(diethylamino)ethyl]sulfinyl}phenyl)sulfonyl]amino}-5,6,7,8-tetrahydro-1-naphthalenecarboxylic acid A 91 mg sample of Example 503 was dissolved in 2.5 mL of glacial acetic acid. To this was added 650 mg of 30% hydrogen peroxide solution. After stirring at room temperature for 8.3 hours the reaction mixture was concentrated and purified by $C_{18}$ reverse-phase HPLC using acetonitrile/water/

0.1% TFA to provide the desired product (45 mg, 47.8%). MS (APCI): m/e 479.1 $(M+H)^+$; $^1H$ NMR (400 MHz, $CD_3OD$) δ 8.13 (dd, 1H), 7.90 (dt, 1H), 7.84 (dd, 1H) 7.70 (dt, 1H), 7.09 (d, 1H), 6.98 (d, 1H), 3.60-3.73 (m, 2H), 3.42-3.50 (m, 1H), 3.23-3.32 (m, 4H), 3.01-3.10 (m, 1H), 2.66-2.78 (m, 4H), 1.65-1.80 (m, 4H), 1.31 (t, 6H).

EXAMPLE 534

2-[({2-[3-(diethylamino)propoxy]phenyl}sulfonyl) amino]-5,6,7,8-tetrahydro-1-naphthalenecarboxylic acid A solution of 3-diethylamino-1-propanol (217 mg, 1.65 mmol) in 1 mL dry DMF was added dropwise to 60% sodium hydride dispersion (55 mg, 1.38 mmol). The mixture was stirred until hydrogen evolution ceased. To this mixture was added a solution of 2-([(2-fluorophenyl)sulfonyl]amino)-5,6,7,8-tetrahydro-1-napthalenecarboxylic acid methyl ester (100 mg, 0.28 mmol) in 1 mL of DMF. The mixture was stirred at 70 to 75° C. for three days, concentrated, and dissolved in 2 mL of pyridine. The mixture was treated with 3 equivalents of sodium iodide, heated in a microwave reactor at 150° C. for 25 minutes, and concentrated. The concentrate was purified by $C_{18}$ reverse-phase HPLC using acetonitrile/water/0.1% TFA to provide the desired product (36 mg, 57.1%). MS (APCI): m/e 461.3 $(M+H)^+$; $^1H$ NMR (400 MHz, $CD_3OD$) δ 7.74 (dd, 1H), 7.54 (dt, 1H), 7.27 (d, 1H) 7.12 (d, 1H), 6.98-7.04 (m, 2H), 4.27 (t, 2H), 3.43-3.51 (m, 2H), 3.25-3.36 (m, 6H), 3.65-3.81 (m, 4H), 3.35 (m, 2H), 1.70 (m, 4H), 1.37 (t, 6H).

EXAMPLE 535

2-({[2-({2-[(2S)-1-isopropyl-2-pyrrolidinyl] ethyl}amino)phenyl]sulfonyl}amino)-8-methyl-5,6,7,8-tetrahydro-1-naphthalenecarboxylic acid

EXAMPLE 535A tert-butyl(2S)-2-({[(4-methylphenyl)sulfonyl] oxy}methyl)-1-pyrrolidinecarboxylate A mixture of tert-butoxycarbonyl-L-proline (10.76 g, 50 mmol), N,O-dimethylhydroxylamine hydrochloride (5.364 g, 55 mmol), triethylamine (7.67 mL, 55 mmol), and ethyl diisopropylcarbodiimide hydrochloride (11.50 g, 55 mmol in 120 mL of dichloromethane was stirred for at 0° C. for 2 hours and at room temperature for over night. Solvent was removed and the residue was dissolved in 300 ml of ethyl acetate. The ethyl acetate layer was washed with water (2×), 10%-sodium bicarbonate (3×), 10%-sodium hydrogen sulfate (3×), brine (3×), dried over magnesium sulfate. After filtered, the filtrate was concentrated in vacuo to provide 11.95 g of tert-butoxicarbonyl-L-proline N,O-dimethylhydroxylamide.

Sodium borohydride (3.50 g, 92.52 mmol) was suspended in 150 mL of a mixture of THF/ethyl alcohol (2:3) and stirred at 0° C. for 10 minutes. Lithium chloride (3.92 g, 92.52 mmol) was added and stirred for an additional 15 minutes at 0° C. A solution of the above concentrate (11.95 g, 46.26 mmol) in 50 mL of THF/ethyl alcohol (2:3) was added and the mixture was stirred at 0° C. for 10 minutes and at room temperature for 18 hours. The mixture was treated with 50 mL of 20% acetic acid and extracted with ethyl acetate. The extract was washed with brine (2×), 10% sodium bicarbonate (2×), and brine (2×), dried ($MgSO_4$), filtered, and concentrated to provide 11.63 g of tert-butoxycarbonyl-L-prolinol. The concentrate (1.79 g, 8.91 mmol) was reacted with p-toluenesulfonyl chloride (2.04 g, 10.69 mmol) in pyridine (3.60 mL, 44.55 mmol) and 20 mL of dichloromethane at 0° C. for 3 hours and at room temperature over night. Solvents were removed and the residue was dissolved in 50 ml of ethyl acetate. The ethyl acetate layer was washed with 10%-sodium hydrogen sulfate (3×), brine (3×), dried over magnesium sulfate anhydrous. After filtered, the filtrate was evaporated to dryness. The crude product was purified by silica gel column chromatography eluting with 10% ethyl acetate in n-hexane to provide the desired product. MS (ESI(+)) m/e 373 $(M+NH_4)^+$; 256 (M+H-Boc)$^+$; 300 (M+H-tBu)$^+$; $^1H$ NMR (300 MHz, DMSO-$d_6$) δ 7.84 (d, 2H), 7.55 (d, 2H), 4.10 (m, 2H), 3.90 (m, 1H), 3.20-3.28 (m, 2H), 1.85-2.06 (m, 1H), 1.74-1.83 (m, 3H), 1.36-1.42 (m, 9H).

EXAMPLE 535B tert-butyl(2S)-2-(2-aminoethyl)-1-pyrrolidinecarboxylate

A mixture of Example 535A (2.37 g, 6.67 mmol) and sodium cyanide (980 mg, 20 mmol) in 5 mL of DMSO and 0.5 mL of water was stirred at 50° C. overnight, treated with 50 mL of ethyl acetate, washed with brine (4×), dried ($MgSO_4$), filtered, and concentrated. The concentrate (520 mg) was treated with Raney® nickel (2.6 g) in 60 mL of 20% $NH_3$ in methanol for 16 hours at room temperature under 60 psi pressure, filtered, and concentrated to provide the desired product. MS (ESI(+)) m/e 215 $(M+H)^+$; $^1H$ NMR (300 MHz, $CDCl_3$) δ 3.78-3.97 (m, 1H), 3.24-3.50 (m, 2H), 2.63-2.76 (m, 2H), 1.79-2.00 (m, 5H), 1.54-1.69 (m, 1H), 1.47 (s, 9H).

EXAMPLE 535C tert-butyl(2S)-2-(2-{[(benzyloxy)carbonyl] amino}ethyl)-1-pyrrolidinecarboxylate A mixture of Example 535B (560 mg, 2.62 mmol), benzyloxycarbonylsuccinimide ester (0.783 g, 3.93 mmol, and triethylamine (0.55 mL, 3.93 mmol) in 10 mL of dichloromethane was stirred overnight, concentrated, treated with ethyl acetate, washed with brine, 10% potassium hydrogen sulfate (3×), and brine (3×), dried ($MgSO_4$), filtered, concentrated, and purified by silica gel column chromatography, eluting with 20% ethyl acetate in n-hexane to provide 0.81 g of the desired product. MS (ESI(+)) m/e 347 $(M+H)^+$; $^1H$ NMR (300 MHz, $CDCl_3$) δ 7.28-7.39 (m, 5H), 7.23 (br, 1H), 5.00 (s, 2H), 3.62-3.74 (m, 1H), 3.19-3.29 (m, 2H), 2.92-3.05 (m, 2H), 1.73-1.91 (m, 5H), 1.54-1.62 (m, 1H), 1.38 (s, 9H).

EXAMPLE 535D benzyl 2-[(2S)-1-isopropyl-2-pyrrolidinyl]ethylcarbamate

Example 535C (0.81 g) was treated with 8 mL of 4N-hydrochloric acid in dioxane for 45 minutes at room temperature. The solvent was removed and the residue was extracted with diethyl ether (3×). The combined extracts concentrated then dried under high vacuum to provide 700 mg of the hydrochloride salt MS (ESI(+)) m/e 249 $(M+H)^+$.

The hydrochloride salt (310 mg, 1.09 mmol) was treated with 2-bromopropane (0.31 mL, 3.27 mmol) in 3 mL of acetonitrile in the presence of potassium carbonate (600 mg, 4.36 mmol) at 60° C. for 2 days and filtered. The filtrate was concentrated to provide the desired product. MS (ESI(+)) m/e 291 $(M+H)^+$; $^1H$ NMR (300 MHz, $CDCl_3$) δ 7.30-7.38 (m, 5H), 7.22 (t, 1H), 5.00 (s, 2H), 2.97-3.05 (m, 2H), 2.84-2.91

(m, 1H), 2.59-2.75 (m, 2H), 2.34-2.43 (m, 1H), 1.72-1.81 (m, 1H), 1.53-1.65 (m, 3H), 1.28-1.42 (m, 2H), 1.01 (d, 3H), 0.86 (d, 3H).

EXAMPLE 535E

2-[(2S)-1-isopropyl-2-pyrrolidinyl]ethanamine

Example 535D (0.3 g) was hydrogenated in 30 mL of methanol in the presence of 30 mg 10% Pd/C under 60 psi pressure of hydrogen for 32 hours at room temperature and filtered. The filtrate was concentrated to provide 150 mg of the desired product. MS (ESI(+)) m/e 157 $(M+H)^+$; $^1$H NMR (300 MHz, $CDCl_3$) δ 2.94-3.03 (m, 1H), 2.87-2.92 (m, 1H), 2.63-2.82 (m, 2H), 2.44-2.52 (m, 1H), 1.69-1.90 (m, 3H), 1.37-1.65 (m, 4H), 1.13 (d, 3H), 0.97 (d, 3H).

EXAMPLE 535F 2-({[2-({2-[(2S)-1-isopropyl-2-pyrrolidinyl]ethyl}amino)phenyl]sulfonyl}amino)-8-methyl-5,6,7,8-tetrahydro-1-naphthalenecarboxylic acid The desired product was prepared by substituting Example 275F (50 mg, 0.133 mmol) and Example 535E (150 mg, 0.96 mmol) for Example 275E and N,N-dimethylethylenediamine, respectively, in Example 275G. MS (ESI(+)) m/e 500 $(M+H)^+$; MS (ESI(−)) m/e 498 $(M-H)^-$; $^1$H NMR (300 MHz, DMSO-$d_6$) δ 9.44 (s, 1H), 9.08 (s, 1H), 7.55 (dd, 1H), 7.43 (t, 1H), 6.93 (d, 1H), 6.87 (d, 1H), 6.67 (t, 1H), 6.57 (d, 1H), 6.01 (t, 1H), 3.21-3.62 (m, 1H), 3.07-3.19 (m, 1H), 2.54-2.74 (m, 2H), 2.18-2.28 (m, 1H), 2.01-2.15 (m, 1H), 1.85-1.93 (m, 2H), 1.57-1.81 (m, 7H), 1.08-1.12 (m, 9H).

EXAMPLE 536

2-{[(2-{[4-(N,N-dimethylamino)butyl]amino}phenyl)sulfonyl]amino}-6,7,8,9-tetrahydro-5H-benzo[7]annulene-1-carboxylic acid The desired product was prepared by substituting N,N-dimethyl-1,4-butanediamine for N,N,2,2-tetramethyl-1,3-propanediamine in Example 510. MS (ESI(+)) m/e 460 $(M+H)^+$; MS (ESI(−)) m/e 458 $(M-H)^-$; $^1$H NMR (300 MHz, DMSO-$d_6$) δ 9.48 (br s, 1H), 7.53 (dd, 1H), 7.40 (td, 1H), 7.0 (d, 1H), 6.80 (d, 1H), 6.64 (t, 1H), 6.53 (d, 1H), 5.94 (br s, 1H), 3.18 (m, 2H), 3.05 (m, 2H), 2.73 (s, 6H), 2.70 (m, 4H), 1.74 (m, 2H), 1.65 (m, 2H), 1.52 (m, 6H).

EXAMPLE 537

2-{[(2-{[3-(1-pyrrolidinyl)propyl]amino}phenyl)sulfonyl]amino}-6,7,8,9-tetrahydro-5H-benzo[7]annulene-1-carboxylic acid The desired product was prepared by substituting 3-(1-pyrrolidinyl)-1-propanamine for N,N,2,2-tetramethyl-1,3-propanediamine in Example 510. MS (ESI(+)) m/e 486 $(M+H)^+$; MS (ESI(−)) m/e 484 $(M-H)^-$; $^1$H NMR (300 MHz, DMSO-$d_6$) δ 9.45 (br s, 2H), 7.53 (dd, 1H), 7.43 (ddd, 1H), 6.99 (d, 1H), 6.85 (d, 1H), 6.67 (t, 1H), 6.54 (d, 1H), 6.01 (br s, 1H), 3.50 (m, 2H), 3.27 (m, 2H), 3.17 (m, 2H), 2.94 (m, 2H), 2.71 (m, 4H), 1.74 (m, 2H), 1.65 (m, 2H), 1.52 (m, 6H).

EXAMPLE 538

2-{[(2-{[2-(1-piperidinyl)ethyl]amino}phenyl)sulfonyl]amino}-6,7,8,9-tetrahydro-5H-benzo[7]annulene-1-carboxylic acid The desired product was prepared by substituting 2-(1-piperidinyl)ethanamine for N,N,2,2-tetramethyl-1,3-propanediamine in Example 510. MS (ESI(+)) m/e 472 $(M+H)^+$; MS (ESI(−)) m/e 470 $(M-H)^-$; $^1$H NMR (300 MHz, DMSO-$d_6$) δ 9.45 (br s, 1H), 7.56 (dd, 1H), 7.43 (ddd, 1H), 6.99 (d, 1H), 6.85 (d, 1H), 6.67 (t, 1H), 6.54 (d, 1H), 6.03 (br s, 1H), 3.36 (m, 2H), 3.27 (m, 2H), 3.07 (m, 2H), 2.81 (m, 2H), 2.71 (m, 4H), 1.92 (m, 2H), 1.76 (m, 5H), 1.60 (m, 2H), 1.52 (m, 4H), 1.36 (m, 1H).

EXAMPLE 539

2-{[(2-{[3-(4-morpholinyl)propyl]amino}phenyl)sulfonyl]amino}-6,7,8,9-tetrahydro-5H-benzo[7]annulene-1-carboxylic acid The desired product was prepared by substituting 3-(4-morpholinyl)propanamine for N,N,2,2-tetramethyl-1,3-propanediamine in Example 510. MS (ESI(+)) m/e 487 $(M+H)^+$; MS (ESI(−)) m/e 486 $(M-H)^-$; $^1$H NMR (300 MHz, DMSO-$d_6$) δ 9.44 (br s, 2H), 7.55 (dd, 1H), 7.42 (ddd, 1H), 6.99 (d, 1H), 6.85 (d, 1H), 6.67 (t, 1H), 6.57 (d, 1H), 6.04 (br s, 1H), 3.63 (m, 2H), 3.37 (m, 2H), 3.27 (m, 3H), 3.16 (m, 3H), 3.02 (m, 2H), 2.71 (m, 4H), 1.93 (m, 2H), 1.74 (m, 2H), 1.52 (m, 4H).

EXAMPLE 540

2-{[(2-{[3-(4-methyl-1-piperazinyl)propyl]amino}phenyl)sulfonyl]amino}-6,7,8,9-tetrahydro-5H-benzo[7]annulene-1-carboxylic acid The desired product was prepared by substituting 3-(4-methyl-1-piperazinyl)-1-propanamine for N,N,2,2-tetramethyl-1,3-propanediamine in Example 510. MS (ESI(+)) m/e 501 $(M+H)^+$; MS (ESI(−)) m/e 499 $(M-H)^-$; $^1$H NMR (300 MHz, DMSO-$d_6$) δ 9.43 (br s, 2H), 7.54 (dd, 1H), 7.40 (ddd, 1H), 7.00 (d, 1H), 6.82 (d, 1H), 6.65 (t, 1H), 6.56 (d, 1H), 6.02 (br s, 1H), 3.37 (m, 2H), 3.22 (m, 4H), 3.16 (m, 2H), 2.88 (m, 2H), 2.79 (s, 3H), 2.71 (m, 6H), 1.82 (m, 2H), 1.74 (m, 2H), 1.52 (m, 4H).

EXAMPLE 541

2-({[2-({3-[2-methyl-1-piperidinyl]propyl}amino)phenyl]sulfonyl}amino)-6,7,8,9-tetrahydro-5H-benzo[7]annulene-1-carboxylic acid The desired product was prepared by substituting 3-[2-methyl-1-piperidinyl]-1-propanamine for N,N,2,2-tetramethyl-1,3-propanediamine in Example 510. MS (ESI(+)) m/e 500 $(M+H)^+$; MS (ESI(−)) m/e 498 $(M-H)^-$; $^1$H NMR (300 MHz, DMSO-$d_6$) δ 9.44 (br s, 2H), 7.56 (dd, 1H), 7.43 (ddd, 1H), 6.99 (d, 1H), 6.87 (d, 1H), 6.68 (t, 1H), 6.51 (d, 1H), 6.05 (br s, 1H), 3.30 (m, 4H), 3.17 (m, 3H), 2.70 (m, 4H), 1.88 (m, 3H), 1.69 (m, 4H), 1.52 (m, 6H) 1.41 (m, 1H), 1.17 (d, 3H).

EXAMPLE 542

2-{[(2-{[3-(dimethylamino)propyl]amino}phenyl)sulfonyl]amino}-6,7,8,9-tetrahydro-5H-benzo[7]annulene-1-carboxylic acid The desired product was prepared by substituting N,N-dimethyl-1,3-propanediamine for N,N,2,2-tetramethyl-1,3-propanediamine in Example 510. MS (ESI(+)) m/e 446 $(M+H)^+$; MS (ESI(−)) m/e 444 $(M-H)^-$; $^1$H NMR (300 MHz, DMSO-$d_6$) δ 9.44 (br s, 2H), 7.55 (dd, 1H), 7.42 (ddd, 1H), 6.99 (d, 1H), 6.84 (d, 1H), 6.67 (t, 1H), 6.55 (d, 1H), 6.01 (br s, 1H), 3.25 (m, 2H), 3.10 (m, 2H), 2.75 (s, 6H), 2.71 (m, 4H), 1.90 (m, 2H), 1.76 (m, 2H) 1.52 (m, 4H).

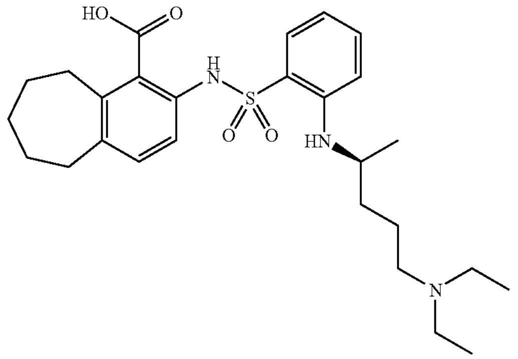

EXAMPLE 543

2-{[(2-{[4-(diethylamino)-1-methylbutyl] amino}phenyl)sulfonyl]amino}-6,7,8,9-tetrahydro-5H-benzo [7]annulene-1-carboxylic acid The desired product was prepared by substituting N-[4-aminopentyl]-N,N-diethylamine for N,N,2,2-tetramethyl-1,3-propanediamine in Example 510. MS (ESI(+)) m/e 502 $(M+H)^+$; MS (ESI(−)) m/e 500 $(M-H)^-$; $^1H$ NMR (300 MHz, DMSO-$d_6$) δ 9.62 (br s, 1H), 7.54 (dd, 1H), 7.39 (ddd, 1H), 6.98 (d, 1H), 6.81 (d, 1H), 6.62 (t, 1H), 6.52 (d, 1H), 5.68 (d, 1H), 3.64 (m, 1H), 3.01 (m, 6H), 2.71 (m, 4H), 1.75 (m, 2H), 1.63 (m, 2H) 1.52 (m, 6H), 1.12 (t, 6H), 1.08 (d, 3H).

EXAMPLE 544

2-{[(2-{[3-(diethylamino)propyl]amino}phenyl) sulfonyl]amino}-6,7,8,9-tetrahydro-5H-benzo[7] annulene-1-carboxylic acid The desired product was prepared by substituting N,N-diethyl-1,3-propanediamine for N,N,2,2-tetramethyl-1,3-propanediamine in Example 510. MS (ESI(+)) m/e 474 $(M+H)^+$; MS (ESI(−)) m/e 472 $(M-H)^-$; $^1H$ NMR (300 MHz, DMSO-$d_6$) δ 9.46 (br s, 1H), 9.21 (br s, 1H), 7.56 (dd, 1H), 7.43 (ddd, 1H), 6.99 (d, 1H), 6.87 (d, 1H), 6.67 (t, 1H), 6.52 (d, 1H), 6.04 (br s, 1H), 3.30 (m, 2H), 3.06 (m, 6H), 2.71 (m, 4H), 1.89 (m, 2H), 1.75 (m, 2H) 1.52 (m, 6H), 1.12 (t, 3H).

EXAMPLE 545

2-{[(2-{[4-(diethylamino)butyl]amino}phenyl)sulfonyl]amino}-6,7,8,9-tetrahydro-5H-benzo[7]annulene-1-carboxylic acid The desired product was prepared by substituting N,N-diethyl-1,4-butanediamine for N,N,2,2-tetramethyl-1,3-propanediamine in Example 510. MS (ESI(+)) m/e 488 $(M+H)^+$; MS (ESI(−)) m/e 486 $(M-H)^-$; $^1H$ NMR (300 MHz, DMSO-$d_6$) δ 9.46 (br s, 1H), 9.04 (br s, 1H), 7.54 (dd, 1H), 7.41 (ddd, 1H), 7.00 (d, 1H), 6.82 (d, 1H), 6.64 (t, 1H), 6.51 (d, 1H), 5.95 (br s, 1H), 3.20 (m, 2H), 3.06 (m, 6H), 2.71 (m, 4H), 1.76 (m, 2H), 1.60 (m, 4H) 1.52 (m, 4H), 1.15 (t, 3H).

EXAMPLE 546

2-({[2-({3-[2,6-dimethyl-1-piperidinyl] propyl}amino)phenyl]sulfonyl}amino)-6,7,8,9-tetrahydro-5H-benzo[7]annulene-1-carboxylic acid The desired product was prepared by substituting 3-[2,6-dimethyl-1-piperidinyl]-1-propanamine for N,N,2,2-tetramethyl-1,3-propanediamine in Example 510. MS (ESI(+)) m/e 514 $(M+H)^+$; MS (ESI(−)) m/e 512 $(M-H)^-$; $^1H$ NMR (300 MHz, DMSO-$d_6$) δ 9.44 (br s, 1H), 8.78 (br s, 1H), 7.57 (dd, 1H), 7.43 (ddd, 1H), 6.99 (d, 1H), 6.89 (d, 1H), 6.67 (t, 1H), 6.51 (d, 1H), 6.07 (br s, 1H), 3.35 (m, 3H), 3.20 (m, 3H), 2.71 (m, 4H), 1.80 (m, 6H), 1.63 (m, 1H), 1.52 (m, 7H), 1.18 (d, 6H).

EXAMPLE 547

2-[({2-[(4-pyridinylmethyl)amino]phenyl}sulfonyl) amino]-6,7,8,9-tetrahydro-5H-benzo[7]annulene-1-carboxylic acid The desired product was prepared by substituting 1-(4-pyridinyl)methanamine for N,N,2,2-tetramethyl-1,3-propanediamine in Example 510. MS (ESI(+)) m/e 452 $(M+H)^+$; MS (ESI(−)) m/e 450 $(M-H)^-$; $^1H$ NMR (300 MHz, DMSO-$d_6$) δ 9.55 (br s, 1H), 8.63 (d, 2H), 7.60 (m, 2H), 7.31 (t, 1H), 7.01 (d, 1H), 6.79 (m, 1H), 6.68 (t, 1H), 6.55 (m, 2H), 4.65 (d, 1H), 2.71 (m, 4H), 1.75 (m, 2H), 1.52 (m, 4H).

EXAMPLE 548

2-{[(2-{4-[(1-methyl-4-piperidinyl)methyl]-1-piperazinyl}phenyl)sulfonyl]amino}-6,7,8,9-tetrahydro-5H-benzo[7]annulene-1-carboxylic acid The desired product was prepared by substituting 1-[(1-methyl-4-piperidinyl)methyl]-4-piperazine for N,N,2,2-tetramethyl-1,3-propanediamine in Example 510. MS (ESI(+)) m/e 541 $(M+H)^+$; MS (ESI(−)) m/e 539 $(M-H)^-$; $^1H$ NMR (300 MHz, DMSO-$d_6$) δ 9.67 (br s, 1H), 9.51 (br s, 1H), 8.94 (s, 1H), 7.81 (dd, 1H), 7.69 (ddd, 1H), 7.49 (d, 1H), 7.34 (t, 1H), 7.06 (d, 1H), 6.76 (d, 1H), 3.61 (m, 2H), 3.49 (m, 2H), 3.31 (m, 4H), 3.10 (m, 4H), 2.90 (m, 2H), 2.78 (d, 3H), 2.71 (m, 4H), 1.99 (m, 2H), 1.74 (m, 2H), 1.50 (m, 4H), 1.40 (m, 1H).

EXAMPLE 549

2-{[(2-{[3-(dibutylamino)propyl]amino}phenyl) sulfonyl]amino}-6,7,8,9-tetrahydro-5H-benzo[7] annulene-1-carboxylic acid The desired product was prepared by substituting N,N-dibutyl-1,3-propanediamine for N,N,2,2-tetramethyl-1,3-propanediamine in Example 510. MS (ESI(+)) m/e 530 $(M+H)^+$; MS (ESI(−)) m/e 528 $(M-H)^-$; $^1H$ NMR (300 MHz, DMSO-$d_6$) δ 9.45 (br s, 1H), 8.98 (br s, 1H), 7.56 (dd, 1H), 7.44 (ddd, 1H), 6.98 (d, 1H), 6.87 (d, 1H), 6.68 (t, 1H), 6.50 (d, 1H), 3.32 (m, 2H), 3.11 (m, 2H), 2.97 (m, 4H), 2.71 (m, 4H), 1.89 (m, 2H), 1.74 (m, 2H), 1.50 (m, 8H), 1.22 (m, 4H), 0.84 (t, 6H).

EXAMPLE 550

2-{[(2-fluorophenyl)sulfonyl]amino}-6,7,8,9-tetrahydro-5H-benzo [7]annulene-1-carboxylic acid The desired product was prepared by substituting Example 510H for Example 463C in Example 463D. MS (ESI(+)) m/e 381 $(M+NH_4)^+$; MS (ESI(−)) m/e 362 $(M-H)^-$; $^1H$ NMR (300 MHz, DMSO-$d_6$) δ 9.48 (br s, 1H), 7.47 (m, 2H), 7.18 (t, 1H), 7.09 (t, 1H), 6.84 (d, 1H), 6.56 (d, 1H), 2.71 (m, 4H) 1.50 (m, 2H), 1.28 (m, 4H).

EXAMPLE 551

2-{[(2-{3-piperidinylmethyl]amino}phenyl)sulfonyl] amino}-6,7,8,9-tetrahydro-5H-benzo[7]annulene-1-carboxylic acid The desired product was prepared by substituting 3-piperidinylmethylamine for N,N,2,2-tetramethyl-1,3-propanediamine in Example 510. MS (ESI(+)) m/e 458 $(M+H)^+$; MS (ESI(−)) m/e 456 $(M-H)^-$; $^1$H NMR (300 MHz, DMSO-$d_6$) δ 7.53 (m, 1H), 7.38 (m, 1H), 6.97 (m, 1H), 6.86 (m, 1H), 6.62 (m, 1H), 6.45 (m, 1H), 3.15 (m, 6H), 2.71 (m, 4H), 1.76 (m, 6H), 1.52 (m, 4H), 1.38 (m, 1H).

EXAMPLE 552

2-({[2-({2-[(2S)-2-pyrrolidinyl]ethyl}amino)phenyl] sulfonyl}amino)-5,6,7,8-tetrahydro-1-naphthalenecarboxylic acid

EXAMPLE 552A tert-butyl(2R)-1-(2-hydroxyethyl)-1-pyrrolidinecarboxylate

A mixture of [(2R)-1-(tert-butoxycarbonyl)-2-pyrrolidinyl]acetic acid (1.004 g, 4.4 mmol) in THF (10 mL) at −10° C. was treated with NMM (0.484 mL, 4.4 mmol) and isopropyl chloroformate (0.572 mL, 4.4 mmol), stirred for 30 minutes, filtered, then added dropwise to a stirred solution of sodium borohydride (0.37 g, 9.8 mmol) in water (4 mL) and stirred for 1 hour. The solution was acidified to pH 4 with 0.1M HCl, then transferred to a separatory funnel and extracted with ethyl acetate. The organic layer was dried ($MgSO_4$), filtered, and concentrated to provide the desired product (0.546 g). MS (DCI) m/e 216 $(M+H)^+$.

EXAMPLE 552B methyl 2-{[(2-nitrophenyl)sulfonyl]amino}-5,6,7,8-tetrahydro-1-naphthalenecarboxylate The desired product was prepared by substituting 2-nitrobenzenesulfonyl chloride for 2-fluorobenzenesulfonyl chloride in Example 229A. MS (ESI(+)) m/e 391 $(M+H)^+$.

EXAMPLE 552C methyl 2-{[(2-aminophenyl)sulfonyl]amino}-5,6,7,8-tetrahydro-1-naphthalenecarboxylate The desired product was prepared by substituting Example 552B for Example 270 in Example 294. MS (ESI(+)) m/e 361 $(M+H)^+$.

EXAMPLE 552D methyl 2-({[2-({2-[(2S)-2-pyrrolidinyl]ethyl}amino) phenyl]sulfonyl}amino)-5,6,7,8-tetrahydro-1-naphthalenecarboxylate A mixture of Example 552A (0.546 g, 2.5 mmol) in dimethylacetamide (14 mL) was treated with Dess-Martin periodinane (8.25 mL of 15 wt % solution in $CH_2Cl_2$, 2.1 mmol) stirred for 15 minutes, and filtered. The filtrate was added to a solution of Example 552C (1.005 g, 2.79 mmol) in $CH_2Cl_2$/methanol (11 mL) and the resulting mixture was treated with acetic acid (1.65 mL) and macroporous polystyrene bound cyanoborohydride resin (3.3 g, 7.5 mmol), shaken at 70° C. for 15 hours, filtered, concentrated, and purified by flash chromatography eluting with 30% ethyl acetate/hexanes. The purified product was dissolved in $CH_2Cl_2$ (100 mL), treated with TFA (20 mL), stirred for 1.5 hours, and concentrated to provide the desired product. MS (DCI) m/e 444 $(M+H)^+$.

EXAMPLE 552E 2-({[2-({2-[(2S)-2-pyrrolidinyl]ethyl}amino)phenyl] sulfonyl}amino)-5,6,7,8-tetrahydro-1-naphthalenecarboxylic acid The desired product was prepared by substituting Example 552D for Example 318C in Example 371A. MS (DCI) m/e 444 $(M+H)^+$; $^1$H NMR (500 MHz, $CD_3OD$) 7.54 (dd, 1H), 7.38 (m, 1H), 7.13 (d, 1H), 7.02 (d, 1H), 6.80 (d, 1H), 6.65 (m, 1H), 3.71 (m, 1H), 3.44 (t, 1H), 2.72 (br m, 4H), 2.38-2.27 (m, 2H), 2.14-2.00 (m, 4H), 1.72 (m, 4H).

EXAMPLE 553

2-{[(2-{[2,2-dimethyl-3-(4-morpholinyl)propyl] amino}phenyl)sulfonyl]amino}-8-methyl-5,6,7,8-tetrahydro-1-naphthalenecarboxylic acid

EXAMPLE 553A 2,2-dimethyl-3-(4-morpholinyl)-3-oxopropanenitrile

A mixture of Example 520A (1.54 g, 10 mmol), sodium hydride (60% in oil, 0.98 g, 22 mmol) and methyl iodide (1.56 mL, 25 mmol) in 20 mL of DMSO was stirred at room temperature overnight and treated with 10 mL of saturated ammonium chloride and 50 mL of ethyl acetate. The ethyl acetate layer was washed with saturated ammonium chloride solution, (2×), brine (4×), and dried ($MgSO_4$), filtered, concentrated, and purified by silica gel column chromatography eluting with 40% ethyl acetate in n-hexane to provide 1.28 g of the desired product. MS (ESI(+)) m/e 183 $(M+H)^+$, m/e 200 $(M+NH_4)^+$; $^1$H NMR (300 MHz, DMSO-$d_6$) □ 3.62 (br s, 8H), 1.53 (s, 6H).

EXAMPLE 553B 2,2-dimethyl-3-(4-morpholinyl)-1-propanamine

The desired product was prepared by reacting Example 553A (0.91 g, 5 mmol) and 1M LAH (10 mL, 10 mmol) in 3 mL of THF according to the method described in Example 393B. MS (DCI) m/e 173 $(M+H)^+$.

EXAMPLE 553C

2-{[(2-{[2,2-dimethyl-3-(4-morpholinyl)propyl] amino}phenyl)sulfonyl]amino}-8-methyl-5,6,7,8-tetrahydro-1-naphthalenecarboxylic acid The desired product was prepared by substituting Example 275F (50 mg, 0.133 mmol) and Example 553B (160 mg, 0.93 mmol) for Example 275E and N,N-dimethylethylenediamine, respectively, in Example 275G. MS (ESI(+)) m/e 516 $(M+H)^+$; MS (ESI(−)) m/e 514 $(M-H)^-$; $^1$H NMR (300 MHz, DMSO-$d_6$) δ 9.49 (s, 1H), 7.53 (dd, 1H), 7.39 (t, 1H), 6.94 (d, 1H), 6.87 (d, 1H), 6.67 (t, 1H), 6.56 (d, 1H), 5.99 (t, 1H), 3.72-3.88 (m; 4H), 3.01-3.31 (m, 4H), 2.56-2.8 (m, 2H), 2.15-2.33 (m, 2H), 1.57-1.83 (m, 4H), 1.10 (d, 3H), 0.96-1.05 (m, 6H).

EXAMPLE 554

2-[({2-[(3-hydroxy-2,2-dimethylpropyl)amino]phenyl}sulfonyl)amino]-8-methyl-5,6,7,8-tetrahydro-1-naphthalenecarboxylic acid The desired product was isolated from Example 553 as a by-product. MS (ESI(+)) m/e 447 $(M+H)^+$, 469 $(M+Na)^+$; MS (ESI(−)) m/e 445 $(M-H)^-$; $^1H$ NMR (300 MHz, DMSO-$d_6$) δ 9.42 (s, 1H), 9.26 (s, 1H), 7.48 (dd, 1H), 7.34 (t, 1H), 6.95 (d, 1H), 6.82 (d, 1H), 6.61 (t, 1H), 6.58 (d, 1H), 6.01 (t, 1H), 3.17 (m, 2H), 2.92-2.97 (m, 2H), 2.57-2.75 (m, 2H), 2.09-2.27 (m, 1H), 1.58-1.78 (m, 6H), 1.09 (d, 3H), 0.81 (s, 6H).

EXAMPLE 555

2-[({2-[(3-{4-[4-(trifluoromethyl)-2-pyrimidinyl]-1-piperazinyl}propyl)amino]phenyl}sulfonyl)amino]-5,6,7,8-tetrahydro-1-naphthalenecarboxylic acid A mixture of Example 275F (100 mg, 0.275 mmol) in 1.0 mL of N-methylpyrrolidinone was treated with 151 mg of 3-[4-(4-trifluoromethylpyrimidin-2-yl)-piperazin-1-yl]-propylamine and 58 mg of potassium phosphate, warmed to 160° C., stirred for 16 hours, concentrated, and purified by $C_{18}$ reverse-phase HPLC using acetonitrile/water/0.1% TFA to provide the desired product (63 mg, 36%). MS (ESI) m/e 619 $(M+H)^+$; $^1H$ NMR (400 MHz, $CD_3OD$) δ 8.66 (d, J=4.80 Hz, 1H), 7.52 (dd, J=7.96, 1.51 Hz, 1H), 7.34 (m, 1H), 7.24 (d, J=8.37 Hz, 1H), 7.03 (d, J=4.94 Hz, 1H), 6.97 (d, J=8.37 Hz, 1H), 6.80 (d, J=7.68 Hz, 1H), 6.57-6.61 (m, 1H), 3.75-4.25 (m, 4H), 3.25-3.40 (m, 8H), 2.65-2.76 (m, 4H), 2.03-2.10 (m, 2H), 1.65-1.69 (m, 4H).

EXAMPLE 556

2-{[(2-{[3-(1-azepanyl)propyl]amino}phenyl)sulfonyl]amino}-5,6,7,8-tetrahydro-1-naphthalenecarboxylic acid The desired product was prepared by substituting 3-(1-azepanyl)-1-propanamine for 3-(N,N-diethylamino)propylamine in Example 229B. MS (ESI) m/e 486 $(M+H)^+$; $^1H$ NMR (400 MHz, $CD_3OD$) δ 7.53 (dd, J=8.03, 1.58 Hz, 1H), 7.37 (m, 1H), 7.10 (m, 1H), 7.01 (d, J=8.37 Hz, 1H), 6.80 (d, J=7.96 Hz, 1H), 6.63 (m, 1H), 3.1-3.7 (m 8H), 2.70-2.80 (m, 4H) 1.65-1.75 (m, 8H) 1.80-2.0 (m, 4H) 2.0-2.1 (m, 2H).

EXAMPLE 557

2-({[2-({[1-(2-ethylbutyl)-4-piperidinyl]methyl}amino)phenyl]sulfonyl}amino)-5,6,7,8-tetrahydro-1-naphthalenecarboxylic acid

EXAMPLE 557A tert-butyl 4-({[2-({[1-(methoxycarbonyl)-5,6,7,8-tetrahydro-2-naphthalenyl]amino}sulfonyl)phenyl]amino}methyl)-1-piperidinecarboxylate A mixture of Example 396 (2.69 g, 5.0 mmol) in benzene (40 mL) and methanol (10 mL) was treated with $TMSCHN_2$ (3.0 mL, 6.0 mmol, 2.0M solution in hexanes). The reaction was stirred at room temperature for 1 hour, then quenched with acetic acid, and diluted with ethyl acetate. The organic layer was washed with aqueous $NaHCO_3$, dried ($MgSO_4$), filtered, concentrated, and purified by column chromatography (25% ethyl acetate/hexanes) to provide the desired product. MS (ESI(+)) m/e 528 $(M+H)^+$.

EXAMPLE 557B methyl 2-[({2-[(4-piperidinylmethyl)amino]phenyl}sulfonyl)amino]-5,6,7,8-tetrahydro-1-naphthalenecarboxylate A solution of Example 557A (0.587 g, 1.1 mmol) in $CH_2Cl_2$ (10 mL) was treated with TFA (2 mL). The reaction was stirred for 3 hours, concentrated, and diluted with $CH_2Cl_2$. The organic layer was washed with pH 7 buffer solution, dried ($MgSO_4$), filtered, and concentrated to provide the desired product. (MS (ESI(+)) m/e 458 $(M+H)^+$.

EXAMPLE 557C 2-({[2-({[1-(2-ethylbutyl)-4-piperidinyl]methyl}amino)phenyl]sulfonyl}amino)-5,6,7,8-tetrahydro-1-naphthalenecarboxylic acid A mixture of Example 557B (0.026 g, 0.06 mmol) in DMF (2.5 mL) was treated with acetic acid (0.01 mL) and 2-ethylbutanal (0.025 g, 0.06 mmol). The mixture was shaken at 50° C. for 20 minutes, treated with macroporous polystyrene bound cyanoborohydride resin (85 mg, 0.2 mmol), shaken at 70° C. for 5 hours, and filtered. The filtrate was concentrated, dissolved in 1 mL 2:1 dioxane water, treated with LiOH (25 mg, 0.6 mmol) and heated to 160° C. for 30 minutes in a microwave reactor. The reaction mixture was concentrated and the residues purified by $C_{18}$ reverse-phase HPLC using acetonitrile/water/0.1% TFA to provide the desired product (6.5 mg). MS (ESI(+)) m/e 528 $(M+H)^+$; (ESI(−)) m/e 526 $(M-H)^-$; $^1H$ NMR (300 MHz, DMSO-$d_6$) δ 7.51 (dd, 1H), 7.38 (dt, 1H), 6.94 (d, 1H), 6.84 (d, 1H), 6.62 (m, 2H), 6.07 (m, 1H), 3.13 (m, 2H), 2.95-2.80, (m, 4H), 2.66 (m, 4H), 1.83 (m, 3H), 1.66 (m, 5H), 1.34 (m, 6H), 0.85 (t, 6H).

EXAMPLE 558

2-{[(2-{[(1-cyclopentyl-4-piperidinyl)methyl]amino}phenyl)sulfonyl]amino}-5,6,7,8-tetrahydro-1-naphthalenecarboxylic acid The desired product was prepared by substituting cyclopentanone for 2-ethylbutanal in Example 557C. MS (ESI(+)) m/e 512 $(M+H)^+$; (ESI(−)) m/e 510 $(M-H)^-$; $^1H$ NMR (300 MHz, DMSO-$d_6$) δ 7.51 (dd, 1H), 7.38 (dt, 1H), 6.95 (d, 1H), 6.84 (d, 1H), 6.62 (m, 2H), 6.07 (t, 1H), 3.26 (d, 2H), 3.12 (m, 2H), 2.88, (m, 2H), 2.65 (m, 4H), 2.05-1.85 (m, 5H), 1.75-1.50 (m, 1H), 1.39 (m, 2H).

EXAMPLE 559

2-[({2-[({1-[1-methylpropyl]-4-piperidinyl}methyl)amino]phenyl}sulfonyl)amino]-5,6,7,8-tetrahydro-1-naphthalenecarboxylic acid The desired product was prepared by substituting 2-butanone for 2-ethylbutanal in Example 557C. MS (ESI(+)) m/e 514 $(M+H)^+$; (ESI(−)) m/e 512 $(M-H)^-$; $^1H$ NMR (300 MHz, DMSO-$d_6$) δ 7.51 (dd, 1H), 7.39 (dt, 1H), 6.95 (d, 1H), 6.83 (d, 1H), 6.63 (m, 2H), 6.06 (br t, 1H), 3.15 (m, 1H), 3.10 (m, 2H), 2.95-2.80, (m, 4H), 2.65 (m, 4H), 1.85 (m, 3H), 1.67 (m, 4H), 1.50-1.35 (m, 3H), 1.16 (m, 1H), 0.94 (d, 3H), 0.88 (t, 3H).

EXAMPLE 560

2-{[(2-{[(1-isobutyl-4-piperidinyl)methyl]amino}phenyl)sulfonyl]amino}-5,6,7,8-tetrahydro-1-naphthalenecarboxylic acid The desired product was prepared by substituting 2-methylpropanal for 2-ethylbutanal in Example 557C. MS (ESI(+)) m/e 500 $(M+H)^+$; (ESI(−)) m/e 498 $(M-H)^-$; $^1$H NMR (300 MHz, DMSO-$d_6$) δ 7.51 (dd, 1H), 7.37 (dt, 1H), 6.94 (d, 1H), 6.84 (d, 1H), 6.61 (m, 2H), 6.07 (br t, 1H), 3.13 (m, 2H), 3.01 (m, 2H), 2.90-2.80, (m, 4H), 2.66 (m, 4H), 2.08 (m, 1H), 1.84 (m, 3H), 1.66 (m, 4H), 1.48 (m, 1H), 1.16 (m, 1H), 0.95 (d, 6H).

EXAMPLE 561

2-{[(2-{[(1-methyl-4-piperidinyl)methyl]amino}phenyl)sulfonyl]amino}-5,6,7,8-tetrahydro-1-naphthalenecarboxylic acid The desired product was prepared by substituting 37% aqueous formaldehyde for 2-ethylbutanal in Example 557C. MS (ESI(+)) m/e 458 $(M+H)^+$; (ESI(−)) m/e 456 $(M-H)^-$; $^1$H NMR (300 MHz, DMSO-$d_6$) δ 7.51 (dd, 1H), 7.38 (dt, 1H), 6.94 (d, 1H), 6.83 (d, 1H), 6.62 (m, 2H), 6.05 (br t, 1H), 3.17 (s, 3H), 3.10 (m, 2H), 2.86 (m, 2H), 2.74 (m, 2H), 2.65 (m, 4H), 1.86 (m, 3H), 1.67 (m, 4H), 1.36 (m, 2H).

EXAMPLE 562

2-{[(2-{[(1'-methyl-1,4'-bipiperidin-4-yl)methyl]amino}phenyl)sulfonyl]amino}-5,6,7,8-tetrahydro-1-naphthalenecarboxylic acid The desired product was prepared by substituting 1-methyl-4-piperidone for 2-ethylbutanal in Example 557C. MS (ESI(+)) m/e 541 $(M+H)^+$; (ESI(−)) m/e 539 $(M-H)^-$; $^1$H NMR (300 MHz, DMSO-$d_6$) δ 7.51 (dd, 1H), 7.39 (dt, 1H), 6.96 (d, 1H), 6.84 (d, 1H), 6.62, (m, 2H), 6.09 (br t, 1H), 3.58 (m, 2H), 3.51 (m, 2H), 3.34 (m, 1H), 3.12 (m, 2H), 2.97, (m, 4H), 2.78 (s, 3H), 2.66 (m, 4H), 2.25 (m, 2H), 2.00-1.82 (m, 5H), 1.67 (m, 4H), 1.42 (m, 2H).

EXAMPLE 563

2-{[(2-{[(1-isopropyl-4-piperidinyl)methyl]amino}phenyl)sulfonyl]amino}-5,6,7,8-tetrahydro-1-naphthalenecarboxylic acid The desired product was prepared by substituting acetone for 2-ethylbutanal in Example 557C. MS (ESI(+)) m/e 486 $(M+H)^+$; (ESI(−)) m/e 484 $(M-H)^-$; $^1$H NMR (300 MHz, DMSO-$d_6$) δ 7.51 (dd, 1H), 7.38 (dt, 1H), 6.95 (d, 1H), 6.84 (d, 1H), 6.62 (m, 2H), 6.09 (br t, 1H), 3.52 (m, 2H), 3.12 (m, 3H), 2.89, (m, 2H), 2.66 (m, 4H), 1.90 (m, 3H), 1.67 (m, 4H), 1.42 (m, 2H), 1.22 (d, 6H).

EXAMPLE 564

2-[({2-[(1E)-3-(diethylamino)-1-propenyl]phenyl}sulfonyl)amino]-5,6,7,8-tetrahydro-1-naphthalenecarboxylic acid

EXAMPLE 564A AND EXAMPLE 564B

N,N-diethyl-N-[(2E)-3-(tributylstannyl)-2-propenyl]amine and

N,N-diethyl-N-[(2E)-3-(tributylstannyl)-2-propenyl]amine

A solution of N,N-diethyl-N-2-propynylamine (4.23 g, 38 mmol), tributyltin hydride (16.3 mL, 60.8 mmol), and azobisisobutyronitrile (0.62 g, 0.1 equiv.) in 150 mL of benzene was heated to 80° C. for 3.5 hours. After cooling to room temperature, the solution was concentrated and purified by silica gel chromatography to provide 9.9 g (65%) of Example 564A. $^1$H NMR (400 MHz, DMSO-$d_6$) δ 0.93 (t, J=7.07 Hz, 6H) 2.21 (m, 2H) 2.44 (q, J=7.04 Hz, 4H) 2.55 (m, 2H) 2.72 (t, J=2.68 Hz, 1H); $^1$H NMR (400 MHz, $CDCl_3$) δ 0.87 (m, 15H) 1.03 (t, J=7.14 Hz, 6H) 1.29 (m, 8H) 1.48 (m, 6H) 2.53 (q, J=7.04 Hz, 4H) 3.14 (m, 2H) 6.03 (m, 2H).

The chromatography also yielded 0.40 g (2.5%) of Example 564B. $^1$H NMR (400 MHz, $CDCl_3$) δ 0.90 (m, 15H) 1.04 (t, J=7.20 Hz, 6H) 1.29 (m, 8H) 1.49 (m, 6H) 2.52 (q, J=7.18 Hz, 4H) 3.08 (dd, J=6.17, 1.51 Hz, 2H) 5.97 (dt, J=12.62, 1.51 Hz, 1H) 6.58 (ddd, J=12.66, 6.28, 6.17 Hz, 1H).

EXAMPLE 564C methyl 2-[({2-[(1E)-3-(diethylamino)-1-propenyl]phenyl}sulfonyl)amino]-5,6,7,8-tetrahydro-1-naphthalenecarboxylate The desired product was prepared from Example 564A (730 mg, 1.8 mmol), methyl 2-[({2-bromophenyl}sulfonyl)amino]-5,6,7,8-tetrahydro-1-naphthalenecarboxylate (636 mg, 1.5 mmol) and bis(tri-tert-butylphosphine)palladium (153 mg, 0.3 mmol) in 6 mL of toluene for 2 days according to the procedure described in Example 529D (490 mg, 72%). $^1$H NMR (400 MHz, $CDCl_3$) δ 1.06 (t, J=7.14 Hz, 6H) 1.69 (dd, J=7.96, 4.25 Hz, 4H) 2.57 (q, J=7.14 Hz, 4H) 2.69 (m, 4H) 3.21 (dd, J=6.72, 1.51 Hz, 2H) 3.69 (s, 3H) 6.14 (dt, J=15.64, 6.72 Hz, 1H) 7.03 (d, J=8-0.37 Hz, 1H) 7.20 (m, 2H) 7.28 (td, J=7.62, 1.37 Hz, 1H) 7.46 (m, 1H)7.55 (m, 1H) 7.88 (dd, J=7.96, 1.10 Hz, 1H).

EXAMPLE 564D

2-[({2-[(1E)-3-(diethylamino)-1-propenyl]phenyl}sulfonyl)amino]-5,6,7,8-tetrahydro-1-naphthalenecarboxylic acid The desired product was prepared from Example 564C (456 mg, 1.0 mmol) and LiI (535 mg, 4 equiv.) in 10 mL of pyridine according to the procedure described in Example 529E (239 mg, 54%). MS (ESI(+)) m/e 443 $(M+H)^+$; MS (ESI(−)) m/e 441 $(M-H)^-$; $^1$H NMR (400 MHz, DMSO-$d_6$) δ 1.22 (t, J=7.27 Hz, 6H) 1.65 (m, 4H) 2.64 (d, J=4.53 Hz, 4H) 3.16 (q, J=6.82 Hz, 4H) 3.87 (d, J=7.00 Hz, 2H) 6.27 (ddd, J=15.23, 7.48, 7.20 Hz, 1H) 6.60 (d, J=8.10 Hz, 1H) 6.94 (d, J=8.23 Hz, 1H) 7.47 (m, 1H) 7.55 (d, J=15.51 Hz, 1H) 7.64 (m, 1H) 7.78 (m, 2H) 9.53 (s, 1H) 9.80 (s, 1H).

EXAMPLE 565

2-[({2-[4-(diethylamino)butyl]phenyl}sulfonyl)amino]-5,6,7,8-tetrahydro-1-naphthalenecarboxylic acid

EXAMPLE 565A methyl 2-[({2-[4-(diethylamino)butyl]phenyl}sulfonyl)amino]-5,6,7,8-tetrahydro-1-naphthalenecarboxylate A mixture of Example 529D (300 mg, 0.64 mmol) in methanol (12 mL) was hydrogenated with $H_2$ over 90 mg (30 wt %) of 10% Pd/C. After 4.5 hours the reaction was filtered through diatomaceous earth (Celite®). The pad was washed with methanol and the filtrates were combined with those from a 50 mg scale (0.11 mmol) reaction and concentrated to provide 332 mg (94%) of the desired product. MS (ESI(+)) m/e 473 $(M+H)^+$; $^1$H NMR (400 MHz, $CDCl_3$) δ 1.00 (t, J=7.14 Hz, 6H) 1.58 (m, 2H) 1.68 (m, 6H) 2.53 (m, 6H) 2.69 (m, 4H) 2.95 (m, 2H) 3.72 (s, 3H) 6.99 (d, J=8.51 Hz, 1H) 7.05 (d, J=8.37 Hz, 1H) 7.21 (t, J=7.68 Hz, 1H) 7.30 (d, J=7.55 Hz, 1H) 7.42 (t, J=7.14 Hz, 1H) 7.85 (d, J=7.82 Hz, 1H).

EXAMPLE 565B

2-[({2-[4-(diethylamino)butyl]phenyl}sulfonyl)amino]-5,6,7,8-tetrahydro-1-naphthalenecarboxylic acid The method of Example 529E was followed using Example 565A (306 mg, 0.65 mmol), and LiI (348 mg, 4 equiv.) in 6 mL of pyridine. The desired product was obtained in 210 mg (71%) yield. MS (ESI(+)) m/e 459 $(M+H)^+$; MS (ESI(−)) m/e 457 $(M-H)^-$; $^1$H NMR (400 MHz, DMSO-$d_6$) δ 1.17 (t, J=7.27 Hz, 6H) 1.64 (m, 8H) 2.64 (m, 4H) 2.96 (m, 2H) 3.03 (m, 2H) 3.09 (q, J=7.23 Hz, 4H) 6.69 (d, J=8.37 Hz, 1H) 6.96 (d, J=8.37 Hz, 1H) 7.32 (td, J=7.65, 1.30 Hz, 1H) 7.42 (dd, J=7.75, 1.17 Hz, 1H) 7.55 (td, J=7.55, 1.37 Hz, 1H) 7.75 (dd, J=8.03, 1.30 Hz, 1H) 9.26 (s, 1H) 9.76 (s, 1H).

EXAMPLE 566

2-[({2-[(1Z)-3-(diethylamino)-1-propenyl]phenyl}sulfonyl)amino]-5,6,7,8-tetrahydro-1-naphthalenecarboxylic acid

EXAMPLE 566A methyl 2-[({2-[(1Z)-3-(diethylamino)-1-propenyl]phenyl}sulfonyl)amino]-5,6,7,8-tetrahydro-1-naphthalenecarboxylate The desired product was prepared from Example 564B (245 mg, 0.6 mmol), methyl 2-[({2-bromophenyl}sulfonyl)amino]-5,6,7,8-tetrahydro-1-naphthalenecarboxylate (212 mg, 0.5 mmol), and bis(tri-tert-butylphosphine)palladium (50 mg, 0.1 mmol) in 1 mL of toluene for 2 days according to the procedure described in Example 529D (153 mg, 67%). $^1$H NMR (400 MHz, $CDCl_3$) δ 0.87 (t, J=7.14 Hz, 6H) 1.70 (m, 4H) 2.41 (q, J=7.09 Hz, 4H) 2.70 (m, 4H) 3.01 (d, J=6.59 Hz, 2H) 3.83 (s, 3H) 5.97 (m, 1H) 6.97 (m, 3H) 7.31 (d, J=7.27 Hz, 1H) 7.37 (t, J=7.62 Hz, 1H) 7.50 (t, J=7.48 Hz, 1H) 8.02 (d, J=7.96 Hz, 1H).

EXAMPLE 566B

2-[({2-[(1Z)-3-(diethylamino)-1-propenyl]phenyl}sulfonyl)amino]-5,6,7,8-tetrahydro-1-naphthalenecarboxylic acid The method of Example 529E was followed using Example 566A (116 mg, 0.25 mmol), and LiI (134 mg, 4 equiv.) in 2.5 mL of pyridine. The desired product was obtained in 85 mg (77%) yield, contaminated with about 1/3 equiv. of t-$Bu_3$PO. MS (ESI(+)) m/e 443 $(M+H)^+$; MS (ESI (−)) m/e 441 $(M-H)^-$; $^1$H NMR (400 MHz, DMSO-$d_6$) δ 1.02 (t, J=7.20 Hz, 6H) 1.65 (m, 4H) 2.66 (m, 4H) 3.05 (q, J=7.23 Hz, 4H) 3.80 (d, J=6.45 Hz, 2H) 5.89 (dt, J=11.66, 6.93 Hz, 1H) 6.66 (d, J=8.37 Hz, 1H) 6.97 (d, J=8.23 Hz, 1H) 7.33 (m, 2H) 7.51 (t, J=7.34 Hz, 1H) 7.66 (td, J=7.55, 1.10 Hz, 1H) 7.81 (dd, J=7.89, 1.17 Hz, 1H) 9.53 (s, 1H) 9.75 (s, 1H).

EXAMPLE 567

2-[({2-[(1Z)-4-(diethylamino)-1-butenyl]phenyl}sulfonyl)amino]-5,6,7,8-tetrahydro-1-naphthalenecarboxylic acid

EXAMPLE 567A methyl 2-[({2-[(1Z)-4-(diethylamino)-1-butenyl]phenyl}sulfonyl)amino]-5,6,7,8-tetrahydro-1-naphthalenecarboxylate The method of Example 529D was followed, employing Example 529C (330 mg, 0.8 mmol), methyl 2-[({2-bromophenyl}sulfonyl)amino]-5,6,7,8-tetrahydro-1-naphthalenecarboxylate (212 mg, 0.5 mmol) and bis(tri-tert-butylphosphine)palladium (51 mg, 0.1 mmol) in 1 mL of toluene for 2 days (143 mg, 61%). $^1$H NMR (400 MHz, $CDCl_3$) δ 0.90 (t, J=7.14 Hz, 6H) 1.68 (m, 4H) 2.09 (ddd, J=15.61, 7.58, 1.65 Hz, 2H) 2.37 (q, J=7.09 Hz, 6H) 2.69 (m, 4H) 3.85 (s, 3H) 5.81 (dt, J=11.53, 7.41 Hz, 1H) 6.88 (d, J=11.53 Hz, 1H) 6.94 (d, J=8.37 Hz, 1H) 7.00 (d, J=8.50 Hz, 1H) 7.31 (d, J=7.55 Hz, 1H) 7.37 (m, 1H) 7.49 (m, 1H) 8.06 (dd, J=7.96, 1.23 Hz, 1H).

EXAMPLE 567B

2-[({2-[(1Z)-4-(diethylamino)-1-butenyl]phenyl}sulfonyl)amino]-5,6,7,8-tetrahydro-1-naphthalenecarboxylic acid The method of Example 529E was followed using Example 567A (120 mg, 0.25 mmol), and LiI (134 mg, 4 equiv.) in 2.5 mL of pyridine. The desired product was obtained in 82 mg (72%) yield, contaminated with about 1/3 equiv. of t-$Bu_3$PO. MS (ESI(+)) m/e 457 $(M+H)^+$; MS (ESI (−)) m/e 455 $(M-H)^-$; $^1$H NMR (400 MHz, DMSO-$d_6$) δ 1.09 (t, J=7.27 Hz, 6H) 1.64 (m, J=3.02, 3.02 Hz, 4H) 2.40 (m, 2H) 2.65 (m, 4H) 3.02 (q, J=7.18 Hz, 4H) 3.09 (m, 2H) 5.73 (m, 1H) 6.73 (d, J=8.10 Hz, 1H) 6.97 (m, 2H) 7.39 (d, J=7.55 Hz, 1H) 7.45 (t, J=7.75 Hz, 1H) 7.62 (t, J=8.16 Hz, 1H) 7.83 (d, J=7.82 Hz, 1H).

EXAMPLE 568

2-({[2-({3-[3-methyl-1-piperidinyl]propyl}amino)phenyl]sulfonyl}amino)-5,6,7,8-tetrahydro-1-naphthalenecarboxylic acid The desired product was prepared by substituting 3-(3-methyl-1-piperidinyl)-1-propanamine for 3-(N,N-diethylamino)propylamine in Example 229B. MS (ESI) m/e 486 $(M+H)^+$; $^1$H NMR (400 MHz, $CD_3OD$) δ 7.54 (dd, J=7.96, 1.65 Hz, 1H), 7.11 (m, 1H) 7.37 (m, 1H), 7.01 (d, J=8.23 Hz, 1H), 6.63 (m, 1H) 6.80 (m, 1H), 3.43-3.55 (m, 2H), 3.32 (m, 2H), 2.68-2.87 (m, 5H), 2.45-2.55 (m, 1H), 2.00-2.10 (m, 4H), 1.75-2.0 (m, 4H), 1.65-1.75(m, 4H), 1.1-1.25 (m, 1H) 0.99 (d, J=6.31 Hz, 3H).

EXAMPLE 569

2-({[2-({3-[cyclohexyl(methyl)amino]propyl}amino)phenyl]sulfonyl}amino)-5,6,7,8-tetrahydro-1-naphthalenecarboxylic acid The desired product was prepared by substituting N-(3-aminopropyl)-N-cyclohexyl-N-methylamine for 3-(N,N-diethylamino)propylamine in Example 229B. MS (ESI) m/e 500 $(M+H)^+$; $^1$H NMR (400 MHz, $CD_3OD$) δ 7.54 (dd, J=7.96, 1.51 Hz, 1H), 7.38 (m, 1H), 7.08 (m, 1H), 7.01 (d, J=8.51 Hz, 1H), 6.82 (d, J=8.10 Hz, 1-H), 6.64 (m, 1H), 3.5-3.1 (m, 5H), 2.79 (s, 3H), 2.77-2.67 (m, 4H), 2.15-1.95 (m, 4H), 1.95-1.80 (m, 2H), 1.75-1.60 (m, 5H), 1.6-1.1 (m, 5H).

EXAMPLE 570

2-{[(2-{[3-(3,4-dihydro-2(1H)-isoquinolinyl)propyl]amino}phenyl)sulfonyl]amino}-5,6,7,8-tetrahydro-1-naphthalenecarboxylic acid The desired product was prepared by substituting 3-(3,4-dihydro-2(1H)-isoquinolinyl)-1-propanamine for 3-(N,N-diethylamino)propylamine in Example 229B. MS (ESI) m/e 520 $(M+H)^+$; $^1H$ NMR (400 MHz, $CD_3OD$) δ 7.54 (dd, J=7.96, 1.51 Hz, 1H), 7.36 (m, 1H), 7.27 (m, 2H), 7.16 (d, J=8.37 Hz, 1H), 6.97 (d, J=8.37 Hz, 1H), 6.82 (d, J=8.23 Hz, 1H), 6.61 (m, 1H), 4.43 (m, 2H), 3.56 (m, 2H) 3.46 (m, 2H), 3.36 (t, J=6.11 Hz, 2H), 3.34 (m, 2H), 3.17 (t, J=6.17 Hz, 2H), 2.66 (m, 4H), 2.15 (m, 2H), 1.66 (m, 4H).

EXAMPLE 571

3,5-diethyl-2-{[(2-fluorophenyl)sulfonyl]amino}-6-methoxybenzoic acid

EXAMPLE 571A methyl 2-amino-3,5-dibromo-6-methoxybenzoate

The desired product, which was one of two isolated from this reaction, was prepared by using Example 470A in Example 470B. MS (ESI(−)) m/e 336, 338, 340 $(M-H)^-$; $^1H$ NMR (300 MHz, DMSO-$d_6$) δ 7.77 (s, 1H), 5.80 (s, 2H), 3.86 (s, 3H), 3.73 (s, 3H).

EXAMPLE 571B methyl 2-amino-6-methoxy-3,5-divinylbenzoate

The desired product was prepared by substituting Example 571A for Example 226E in Example 226F using double the amount of the appropriate reagents. MS (ESI(+)) m/e 234 $(M+H)^+$, 256 $(M+Na)^+$; (ESI(−)) m/e 232 $(M-H)^-$; $^1H$ NMR (300 MHz, DMSO-$d_6$) δ 7.59 (s, 1H), 6.88 (dd, 1H), 6.74 (dd, 1H), 5.70 (m, 3H), 5.64 (d, 1H), 5.23 (dd, 1H), 5.12 (dd, 1H), 3.83 (s, 3H), 3.64 (s, 3H).

EXAMPLE 571C methyl 2-{[(2-fluorophenyl)sulfonyl]amino}-6-methoxy-3,5-divinylbenzoate The desired product was prepared by substituting Example 571B for Example 126B and substituting 2-fluorobenzenesulfonyl chloride for 3-fluorobenzenesulfonyl chloride in Example 126C. MS (ESI(+)) m/e 392 $(M+H)^+$, 409 $(M+NH_4)^+$, 414 $(M+Na)^+$; (ESI(−)) m/e 390 $(M-H)^-$; $^1H$ NMR (300 MHz, DMSO-$d_6$) δ 10.19 (s, 1H), 7.87 (s, 1H), 7.70 (m, 1H), 7.58 (m, 1H), 7.42 (m, 1H), 7.31 (m, 1H), 6.85 (dd, 1H), 6.72 (dd, 1H), 6.05 (dd, 1H), 5.74 (dd, 1H), 5.47 (dd, 1H), 5.08 (dd, 1H), 3.65 (s, 3H), 3.52 (s, 3H).

EXAMPLE 571D methyl 3,5-diethyl-2-{[(2-fluorophenyl)sulfonyl]amino}-6-methoxybenzoate The desired product was prepared by substituting Example 571C for Example 226F in Example 226G. MS (DCI) m/e 396 $(M+H)^+$; $^1H$ NMR (300 MHz, DMSO-$d_6$) δ 9.87 (s, 1H), 7.68 (m, 1H), 7.63 (m, 1H), 7.44 (m, 1H), 7.32 (m, 1H), 7.21 (s, 1H), 3.61 (s, 3H), 3.39 (s, 3H), 2.58 (q, 2H), 2.48 (q, 2H), 1.16 (t, 3H), 1.01 (t, 3H).

EXAMPLE 571E 3,5-diethyl-2-{[(2-fluorophenyl)sulfonyl]amino}-6-methoxybenzoic acid The desired product was prepared by substituting Example 571D for Example 470F in Example 470G. MS (ESI(+)) m/e 382 $(M+H)^+$, 399 $(M+NH_4)^+$, 404 $(M+Na)^+$; (ESI(−)) m/e 380 $(M-H)^-$; $^1H$ NMR (300 MHz, DMSO-$d_6$) δ 12.69 (br s, 1H), 9.75 (s, 1H), 7.66 (m, 2H), 7.40 (m, 1H), 7.29 (m, 1H), 7.15 (s, 1H), 3.65 (s, 3H), 2.58 (q, 2H), 2.40 (q, 2H), 1.16 (t, 3H), 0.95 (t, 3H).

EXAMPLE 572

2-{[(2-{[2-methyl-3-(4-methyl-1-piperidinyl)propyl]amino}phenyl)sulfonyl]amino}-5,6,7,8-tetrahydro-1-naphthalenecarboxylic acid The desired product was prepared by substituting 2-methyl-3-(4-methyl-1-piperidinyl)-1-propanamine for 3-(N,N-diethylamino)propylamine in Example 229B. MS (ESI) m/e 500 $(M+H)^+$; $^1H$ NMR (400 MHz, $CD_3OD$) δ 7.57 (dd, J=8.03, 1.58 Hz, 1H), 7.38 (m, 1H), 7.09 (m, 1H), 7.01 (d, J=8.37 Hz, 1H), 6.81 (m, 1H), 6.66 (m, 1H), 3.49 (m, 2H), 3.14 (m, 3H), 2.96 (m, 2H), 2.73 (m, 5H), 2.68 (m, 2H), 2.37 (m, 1H), 1.83 (m, 2H), 1.72 (m, 4H), 1.63 (m, 1H), 1.48 (m, 2H), 1.13 (d, 3H). 0.98 (d, 3H).

EXAMPLE 573

2-({[2-({3-[2,6-dimethyl-1-piperidinyl]propyl}amino)phenyl]sulfonyl}amino)-5,6,7,8-tetrahydro-1-naphthalenecarboxylic acid The desired product was prepared by substituting 3-(2,6-dimethyl-1-piperidinyl)-1-propanamine for 3-(N,N-diethylamino)propylamine in Example 229B. MS (ESI) m/e 500 $(M+H)^+$; Mixture of cis/trans: $^1H$ NMR (400 MHz, $CD_3OD$) δ 7.54 (dd, J=7.96, 1.37 Hz, 1H), 7.37 (m, 1H), 6.64 (t, J=7.62 Hz, 1H), 3.33 (m, 5H), 2.69 (m, 4H), 2.00 (m, 4H), 1.69 (m, 9H), 1.31 (d, J=6.45 Hz, 3H), 1.28 (d, J=6.72 Hz, 3H).

EXAMPLE 574

6-[({2-[(E)-2-(4-chlorophenyl)vinyl]phenyl}sulfonyl)amino]-3-ethyl-2-methoxybenzoic acid

EXAMPLE 574A methyl 6-amino-3-bromo-2-methoxybenzoate

A solution of Example 385B (6.83 g, 25.2 mmol) in anhydrous methanol (300 mL) was refluxed for 48 hours. The solution was concentrated and the residue was purified by chromatography on a silica gel column eluting with 20% ethyl acetate/hexane to give the desired product 5.7 g, 87.2% yield. $^1H$ NMR (DMSO-$d_6$) δ 3.70 (s, 3H), 3.82 (s, 3H), 5.92 (s, 2H), 6.45 (d, 1H), 7.30 (d, 1H); MS (ESI(−)) m/e 258, 260 $(M-H)^-$.

EXAMPLE 574B methyl 6-amino-2-methoxy-3-vinylbenzoate

The title compound was prepared from Example 574A (2.6 g, 10 mmol) according to the procedure of Example 230B, yielding 1.2 g, 100%. $^1$H NMR (DMSO-$d_6$) δ 3.62 (s, 3H), 3.80 (s, 3H), 5.03 (d, 1H), 5.52 (d, 1H), 5.90 (s, 2H), 6.50 (d, 1H), 6.75 (dd, 1H), 7.40 (d, 1H); MS (ESI(+)) m/e 208 $(M+H)^+$.

EXAMPLE 574C methyl 6-amino-3-ethyl-2-methoxybenzoate

Example 574B was hydrogenated in methanol (100 mL) over 10% Pd/C (0.5 g) at ambient temperature for 3 hours under one atmosphere of hydrogen. Filtration and evaporation of the solvent gave a mixture of the title compound and Example 576A (2.0 g, 95.6%). $^1$H NMR (DMSO-$d_6$) δ 1.08 (t, 3H), 2.42 (q, 2H), 3.62 (s, 3H), 3.80 (s, 3H), 5.50 (s, 2H), 6.44 (d, 1H), 7.00 (d, 1H); MS (DCI/$NH_3$) m/e 210 $(M+H)^+$.

EXAMPLE 574D methyl 6-{[(2-bromophenyl)sulfonyl]amino}-3-ethyl-2-methoxybenzoate The title compound was prepared from Example 574C (2.0 g, 9.7 mmol) and 2-bromobenzenesulfonyl chloride according to the procedure of Example 385F, yielding 3.04 g, 71.0%. $^1$H NMR (DMSO-$d_6$) δ 1.10 (t, 3H), 2.52 (q, 2H), 3.62 (s, 3H), 3.70 (s, 3H), 6.84 (d, 1H), 7.25 (d, 1H), 7.53 (m, 2H), 7.80-7.94 (m, 2H), 9.95 (s, 1H); MS (ESI(−)) m/e 426, 428, $(M-H)^-$.

EXAMPLE 574E methyl 6-[({2-[(E)-2-(4-chlorophenyl)vinyl]phenyl}sulfonyl)amino]-3-ethyl-2-methoxybenzoate The title compound-was prepared from Example 574D (0.215 g, 0.5 mmol) and trans-2-(4-chlorophenyl)vinyl boronic acid according to the procedure of Example 230B, yielding 0.252 g, 100%. $^1$H NMR (DMSO-$d_6$) δ 1.02 (t, 3H), 2.42 (q, 2H), 3.52 (s, 3H), 3.54 (s, 3H), 6.90 (d, 1H), 7.16 (d, 1H), 7.22 (d, 1H), 7.40-7.70 (m, 7H), 7.80 (d, 1H), 7.90 (d, 1H), 10.00 (s, 1H); MS (ESI(−)) m/e 484 $(M-H)^-$.

EXAMPLE 574F

6-[({2-[(E)-2-(4-chlorophenyl)vinyl]phenyl}sulfonyl)amino]-3-ethyl-2-methoxybenzoic acid The title compound was prepared from Example 574E (70 mg, 0.144 mmol) according to the procedure of Example 385I, yielding 20 mg, 9.4%. $^1$H NMR (DMSO-$d_6$) δ 1.02 (t, 3H), 2.42 (q, 2H), 3.62 (s, 3H), 6.74 (d, 1H), 7.12 (d, 1H), 7.15 (d, 1H), 7.40-7.50 (m, 3H), 7.52 (d, 2H), 7.63 (t, 1H), 7.70 (d, 1H), 7.85 (d, 1H), 7.90 (d, 1H), 9.90 (s, 1H), 13.10 (br s, 1H); MS (ESI(−)) m/e 470 $(M-H)^-$.

EXAMPLE 575

3-ethyl-2-methoxy-6-({[2-(2-phenylethyl)phenyl]sulfonyl}amino)benzoic acid

EXAMPLE 575A methyl 3-ethyl-2-methoxy-6-({[2-(2-phenylethyl)phenyl]sulfonyl}amino)benzoate Example 574E (125 mg, 0.25 mmol) was hydrogenated over 10% Pd/C (50 mg) in methanol at ambient temperature for 3 hours under one atmosphere of hydrogen. Filtration and evaporation of the solvent gave a mixture of the title compound title compound and Example 576A (total 100 mg).

EXAMPLE 575B 3-ethyl-2-methoxy-6-({[2-(2-phenylethyl)phenyl]sulfonyl}amino)benzoic acid A mixture of Example 575A and Example 576A (0.10 g) was treated with LiOH according to the procedure of Example 385I, giving the title compound, 12.4 mg, and Example 576B, 42 mg. $^1$H NMR (DMSO-$d_6$) δ 1.06 (t, 3H), 2.42 (q, 2H), 2.84 (t, 2H), 3.15 (t, 2H), 3.62 (s, 3H), 6.74 (d, 1H), 7.18-7.22 (m, 2H), 7.14-7.30 (m, 4H), 7.35 (t, 1H), 7.45 (d, 1H), 7.55 (t, 1H), 7.80 (d, 1H), 9.95 (s, 1H), 13.20 (br s, 1H); MS (ESI(−)) m/e 438 $(M-H)^-$.

EXAMPLE 576

6-[({2-[2-(4-chlorophenyl)ethyl]phenyl}sulfonyl)amino]-3-ethyl-2-methoxybenzoic acid

EXAMPLE 576A methyl 6-[({2-[2-(4-chlorophenyl)ethyl]phenyl}sulfonyl)amino]-3-ethyl-2-methoxybenzoate Example 574E (125 mg, 0.25 mmol) was hydrogenated over-10% Pd/C (50 mg) in methanol at ambient temperature for 3 h, giving a mixture of Example 575A and the title compound (total 100 mg).

EXAMPLE 576B

6-[({2-[2-(4-chlorophenyl)ethyl]phenyl}sulfonyl)amino]-3-ethyl-2-methoxybenzoic acid A mixture of Example 575A and Example 576A (0.10 g) was treated with LiOH according to the procedure of Example 385I, giving Example 575B, 12.4 mg, and the title compound, 42 mg. $^1$H NMR (DMSO-$d_6$) δ 1.06 (t, 3H), 2.50 (q, 2H), 2.84 (t, 2H), 3.15 (t, 2H), 3.62 (s, 3H), 6.74 (d, 1H), 7.16 (d, 1H), 7.20-7.40 (m, 5H), 7.44 (d, 1H), 7.55 (t, 1H), 7.80 (d, 1H), 9.83 (s, 1H), 13.20 (br s, 1H); MS (ESI(−)) m/e 472 $(M-H)^-$.

EXAMPLE 577

3-ethyl-2-methoxy-6-{[(1-methyl-1H-imidazol-4-yl)sulfonyl]amino}benzoic acid

EXAMPLE 577A methyl 3-ethyl-2-methoxy-6-{[(1-methyl-1H-imidazol-4-yl)sulfonyl]amino}benzoate The title compound was prepared from Example 574C (0.08 g, 0.38 mmol) and 1-methyl-1H-imidazole-4-sulfonyl chloride according to the procedure of Example 385F, yielding 0.13 g, 96.3%. MS (ESI(+)) m/e-354 $(M+H)^+$.

EXAMPLE 577B;

3-ethyl-2-methoxy-6-{[(1-methyl-1H-imidazol-4-yl)sulfonyl]amino}benzoic acid

The title compound was prepared from Example 577A (130 mg, 0.37 mmol) according to the procedure of Example 385I, yielding 91 mg, 72.6%. $^1$H NMR (DMSO-$d_6$) δ 1.10 (t, 3H), 2.55 (q, 2H), 3.62 (s, 3H), 3.64 (s, 3H), 7.05 (d, 1H), 7.23 (d, 1H), 7.74 (s, 1H), 7.76 (s, 1H), 9.45 (s, 1H); MS (ESI(−)) m/e 338 $(M-H)^-$.

EXAMPLE 578

6-{[(1,2-dimethyl-1H-imidazol-4-yl)sulfonyl]amino}-3-ethyl-2-methoxybenzoic acid

EXAMPLE 578A methyl 6-{[(1,2-dimethyl-1H-imidazol-4-yl)sulfonyl]amino}-3-ethyl-2-methoxybenzoate The title compound was prepared from Example 574C (0.08 g, 0.38 mmol) and 1,2-dimethyl-1H-imidazole-4-sulfonyl chloride according to the procedure of Example 385F, yielding 0.14 g, 96.6%. $^1$H NMR (DMSO-$d_6$) δ 1.10 (t, 3H), 2.28 (s, 3H), 2.55 (q, 2H), 3.55 (s, 3H), 3.64 (s, 3H), 3.78 (s, 3H), 7.00 (d, 1H), 7.23 (d, 1H), 7.60 (s, 1H), 9.35 (s, 1H); MS (ESI(−)) m/e 366 $(M-H)^-$.

EXAMPLE 578B

6-{[(1,2-dimethyl-1H-imidazol-4-yl)sulfonyl]amino}-3-ethyl-2-methoxybenzoic acid The title compound was prepared from Example 578A (136 mg, 0.37 mmol) according to the procedure of Example 385I, yielding 92 mg, 70.4%. $^1$H NMR (DMSO-$d_6$) δ 1.12 (t, 3H), 2.28 (s, 3H), 2.55 (q, 2H), 3.55 (s, 3H), 3.64 (s, 3H), 7.06 (d, 1H), 7.23 (d, 1H), 7.68 (s, 1H), 9.42 (s, 1H); MS (ESI(−)) m/e 352 $(M-H)^-$.

EXAMPLE 579

2-(2-aminoethoxy)-6-{[(2-bromo-4-fluorophenyl)sulfonyl]amino}-3-ethylbenzoic acid

EXAMPLE 579A methyl 6-{[(2-bromo-4-fluorophenyl)sulfonyl]amino}-2-[2-(1,3-dioxo-1,3-dihydro-2H-isoindol-2-yl)ethoxy]-3-ethylbenzoate The title compound was prepared from Example 523C (0.85 g, 2.3 mmol) and 2-bromo-4-fluorobenzenesulfonyl chloride according to the procedure of Example 385F, yielding 1.1 g, 78.3%. $^1$H NMR (DMSO-$d_6$) δ 0.98 (t, 3H), 2.42 (q, 2H), 3.50 (s, 3H), 3.88 (t, 2H), 3.95 (t, 2H), 6.80 (d, 1H), 7.20 (d, 1H), 7.38 (t, 1H), 7.80-7.95 (m, 6H), 10.00 (s, 1H); MS (ESI(−)) m/e 603 $(M-H)^-$.

EXAMPLE 579B 2-(2-aminoethoxy)-6-{[(2-bromo-4-fluorophenyl)sulfonyl]amino}-3-ethylbenzoic acid The title compound was prepared from Example 579A (80 mg, 0.13 mmol) according to the procedure of Example 385I, yielding 18 mg, 70.4%. $^1$H NMR (DMSO-$d_6$) δ 1.10 (t, 3H), 2.42 (q, 2H), 3.10 (m, 2H), 4.00 (m, 2H), 6.90 (d, 1H), 7.22 (s, 1H), 7.27 (d, 1H), 7.68 (d, 1H), 7.85 (d, 1H), 8.16 (s, 3H), 9.85 (s, 1H), 11.10 (s, 1H); MS (ESI(−)) m/e 457, 459, $(M-H)^-$.

EXAMPLE 580

2-(3-aminopropoxy)-6-{[(2-bromo-4-fluorophenyl)sulfonyl]amino}-3-ethylbenzoic acid

EXAMPLE 580A methyl 6-amino-3-bromo-2-[3-(1,3-dioxo-1,3-dihydro-2H-isoindol-2-yl)propoxy]benzoate The title compound was prepared from Example 385D (2.5 g, 10.2 mmol) and N-(3-bromopropyl)phthalimide according to the procedure of Example 385E, yielding 3.0 g, 69.4%. $^1$H NMR (DMSO-$d_6$) δ 2.05 (m, 2H), 3.75 (t, 2H), 3.76 (s, 3H), 3.92 (t, 2H), 5.92 (s, 2H), 6.47 (d, 1H), 7.30 (d, 1H), 7.80-7.92 (m, 4H); MS (ESI(−)) m/e 430, 432, $(M-H)^-$.

EXAMPLE 580B methyl 6-amino-2-[3-(1,3-dioxo-1,3-dihydro-2H-isoindol-2-yl)propoxy]-3-vinylbenzoate The title compound was prepared from Example 580A (3.0 g, 6.9 mmol) according to the procedure of Example 230B, yielding 1.92 g, 72.7%. $^1$H NMR (DMSO-$d_6$) δ 1.90-2.01 (m, 2H), 3.68-3.80 (m, 7H), 5.00 (d, 1H), 5.48 (d, 1H), 5.90 (s, 2H), 6.50 (d, 1H), 6.72 (dd, 1H), 7.38 (d, 1H), 7.80-7.92 (m, 4H); MS (ESI(+)) m/e 381 $(M+H)^+$.

EXAMPLE 580C methyl 6-amino-2-[3-(1,3-dioxo-1,3-dihydro-2H-isoindol-2-yl)propoxy]-3-ethylbenzoate Example 580B (1.92 g, 5.0 mmol) was hydrogenated in methanol over 10% Pd/C (0.5 g) at ambient temperature, under one atmosphere of hydrogen for 6 hours. Filtration and evaporation of the solvent gave the title compound, (1.0 g, 52.4%). $^1$H NMR (DMSO-$d_6$) δ 1.06 (t, 3H), 1.90-2.01 (m, 2H), 2.42 (q, 2H), 3.68-3.80 (m, 7H), 5.50 (s, 2H), 6.42 (d, 1H), 7.00 (d, 1H), 7.80-7.92 (m, 4H); MS (ESI(+)) m/e 383 $(M+H)^+$.

EXAMPLE 580D methyl 6-{[(2-bromo-4-fluorophenyl)sulfonyl]amino}-2-[3-(1,3-dioxo-1,3-dihydro-2H-isoindol-2-yl)propoxy]-3-ethylbenzoate The title compound was prepared from Example 580C (1.0 g, 2.6 mmol) and 2-bromo-4-fluorobenzenesulfonyl chloride according to the procedure of Example 385F, yielding 1.15 g, 71.5%. $^1$H NMR (DMSO-$d_6$) δ 1.05 (t, 3H), 1.90-2.01 (m, 2H), 2.55 (q, 2H), 3.65 (s, 3H), 3.66 (t, 2H), 3.80 (t, 2H), 6.82 (d, 1H), 7.23 (d, 1H), 7.40 (t, 2H), 7.80-7.95 (m, 6H); MS (ESI(−)) m/e 617 and 619, $(M-H)^-$.

EXAMPLE 580E 2-(3-aminopropoxy)-6-{[(2-bromo-4-fluorophenyl)sulfonyl]amino}-3-ethylbenzoic acid The title compound was prepared from Example 580D (80 mg, 0.13 mmol) according to the procedure of Example 385I, yielding 6 mg, 10.0%. $^1$H NMR (DMSO-$d_6$) δ 1.10 (t, 3H), 1.93-2.02 (m, 2H), 2.55 (q, 2H), 2.90-3.00 (m, 2H), 3.85 (t, 2H), 6.82 (d, 1H), 7.23 (d, 1H), 7.42 (t, 1H), 7.65-7.75 (m, 1H), 7.83 (d, 1H), 7.90 (br s, 3H), 8.05 (t, 1H); MS (ESI(−)) m/e 459 and 461, $(M-H)^-$.

EXAMPLE 581

3,5-diethyl-2-methoxy-6-{[(2-{[3-(4-morpholinyl)propyl]amino}phenyl)sulfonyl]amino}benzoic acid The desired product was prepared by substituting Example-571E for Example 389B, substituting 4-(3-aminopropyl)morpholine for 4-(N,N-dimethylamino)butylamine, and increasing the temperature to 100° C. in Example 389C. MS (ESI(+)) m/e 506 $(M+H)^+$, 528 $(M+Na)^+$; (ESI(−)) m/e 504 $(M-H)^-$; $^1H$ NMR (300 MHz, DMSO-$d_6$) δ 7.30 (m, 2H), 7.04 (s, 1H), 6.74 (d, 1H), 6.51 (t, 1H), 6.00 (br s, 1H), 3.71 (br s, 6H), 3.65 (s, 3H), 3.61 (m, 6H), 3.15 (t, 2H), 2.55 (q, 2H), 2.31 (q, 2H), 1.71 (m, 2H), 1.13 (t, 3H), 0.89 (t, 3H).

EXAMPLE 582

3,5-diethyl-2-methoxy-6-({[2-({3-[2-methyl-1-piperidinyl]propyl}amino)phenyl]sulfonyl}amino)benzoic acid The desired product was prepared by substituting Example 571E for Example 389B, substituting 3-[(2R)-2-methyl-1-piperidinyl]-1-propanamine for 4-(N,N-dimethylamino)butylamine, and increasing the temperature to 100° C. in Example 389C. MS (ESI(+)) m/e 518 $(M+H)^+$, 540 $(M+Na)^+$; (ESI(−)) m/e 516 $(M-H)^-$; $^1H$ NMR (300 MHz, DMSO-$d_6$) δ 7.26 (t, 1H), 7.07 (m, 1H), 6.99 (s, 1H), 6.69 (d, 1H), 6.39 (t, 1H), 6.35 (br s, 1H), 3.54 (s, 3H), 3.42 (br s, 2H), 3.30 (m, 2H), 3.17 (m, 2H), 3.04 (m, 1H), 2.81 (m, 2H), 2.72 (m, 2H), 2.49 (q, 2H), 1.91 (m, 2H), 1.76 (m, 1H), 1.62 (m, 3H), 1.51 (m, 1H), 1.41 (m, 1H), 1.24 (d, 3H), 1.11 (t, 6H).

EXAMPLE 583

2-{[(2-{[3-(1,4'-bipiperidin-1'-yl)propyl]amino}phenyl)sulfonyl]amino}-5,6,7,8-tetrahydro-1-naphthalenecarboxylic acid

EXAMPLE 584

3,5-diethyl-2-methoxy-6-({[2-({2-[1-methyl-2-pyrrolidinyl]ethyl}amino)phenyl]sulfonyl}amino)benzoic acid The desired product was prepared by substituting Example 571E for Example 389B, substituting 2-(2-aminoethyl)-1-methylpyrrolidine for 4-(N,N-dimethylamino)butylamine, and increasing the temperature to 100° C. in Example 389C. MS (ESI(+)) m/e 490 $(M+H)^+$, 512 $(M+Na)^+$; (ESI(−)) m/e 488 $(M-H)^-$; $^1H$ NMR (500 MHz, $CDCl_3$) δ 7.24 (t, 1H), 7.19 (m, 1H), 7.01 (s, 1H), 6.63 (d, 1H), 6.42 (t, 1H), 3.59 (s, 3H), 3.45 (m, 2H), 3.37 (br s, 2H), 3.22 (m, 2H), 3.06 (br s, 1H), 2.82 (m, 1H), 2.69 (s, 3H), 2.54 (q, 2H), 2.32 (m, 2H), 2.09 (m, 2H), 1.97 (m, 2H), 1.82 (m, 2H), 1.19 (t, 3H), 1.14 (t, 3H).

EXAMPLE 585

2-{[(2-{[3-(diethylamino)propyl]amino}phenyl)sulfonyl]amino}-3,5-diethyl-6-methoxybenzoic acid The desired product was prepared by substituting Example 571E for Example 389B, substituting 1-(N,N-diethylamino)propylamine for 4-(N,N-dimethylamino)butylamine, and increasing the temperature to 100° C. in Example 389C. MS (ESI(+)) m/e 492 $(M+H)^+$, 514 $(M+Na)^+$; (ESI(−)) m/e 490 $(M-H)^-$; $^1H$ NMR (300 MHz, DMSO-$d_6$) δ 7.26 (t, 1H), 7.05 (m, 1H), 6.99 (s, 1H), 6.69 (d, 1H), 6.38 (t, 1H), 3.51 (s, 3H), 3.39 (br s, 3H), 3.23 (m, 2H), 3.08 (m, 2H), 2.96 (m, 2H), 2.76 (m, 2H), 2.48 (q, 4H), 1.90 (m, 2H), 1.13 (m, 12H).

EXAMPLE 586

2-{[(2-{[4-(N,N-dimethylamino)butyl]amino}phenyl)sulfonyl]amino}-3,5-diethyl-6-methoxybenzoic acid The desired product was prepared by substituting Example 571E for Example 389B and increasing the temperature to 100° C. in Example 389C. MS (ESI(+)) m/e 478 $(M+H)^+$, 500 $(M+Na)^+$; (ESI(−)) m/e 476 $(M-H)^-$; $^1H$ NMR (300 MHz, DMSO-$d_6$) δ 7.31 (t, 1H), 7.25 (d, 1H), 7.00 (s, 1H), 6.72 (d, 1H), 6.40 (t, 1H), 6.18 (br s, 1H), 3.59 (s, 3H), 3.45 (br s, 2H), 3.18 (m, 2H), 2.72 (m, 2H), 2.51 (m, 4H), 2.13 (s, 6H), 1.77 (m, 1H), 1.63 (m, 1H), 1.54 (m, 1H), 1.43 (m, 1H), 1.10 (m, 6H).

EXAMPLE 589

3,5-diethyl-2-methoxy-6-{[(1-methyl-1H-imidazol-4-yl)sulfonyl]amino}benzoic acid

EXAMPLE 589A methyl 2-amino-3,5-diethyl-6-methoxybenzoate

The desired compound was prepared by substituting Example 571B for Example 226F in Example 226G. MS (DCI) m/e 238 $(M+H)^+$, 255 $(M+NH_4)^+$; $^1H$ NMR (300 MHz, DMSO-$d_6$) δ 6.91 (s, 1H), 5.18 (s, 2H), 3.81 (s, 3H), 3.61 (s, 3H), 2.44 (q, 2H), 2.43 (q, 2H), 1.10 (t, 3H), 1.09 (t, 3H).

EXAMPLE 589B

3,5-diethyl-2-methoxy-6-{[(1-methyl-1H-imidazol-4-yl)sulfonyl]amino}benzoic acid The desired compound was prepared by substituting Example 589A for Example 126B and 1-methylimidazole-4-sulfonyl chloride for 3-fluorobenzenesulfonyl chloride in Example 126C, then substituting the product directly for Example 470F in Example 470G with purification by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min. MS (ESI(+)) m/e 368 $(M+H)^+$, 390 $(M+Na)^+$; (ESI(−)) m/e 366 $(M-H)^-$; $^1H$ NMR (300 MHz, DMSO-$d_6$) δ 8.98 (s, 1H), 7.66 (s, 1H), 7.42 (s, 1H), 7.05 (s, 1H), 3.58 (s, 3H), 3.57 (s, 3H), 3.35 (br s, 1H), 2.49 (q, 2H), 2.32 (q, 2H), 1.08 (t, 3H), 0.88 (t, 3H).

EXAMPLE 590

2-{[(1,2-dimethyl-1H-imidazol-4-yl)sulfonyl]amino}-3,5-diethyl-6-methoxybenzoic acid The desired compound was prepared by substituting Example 589A for Example 126B and 1,2-dimethylimidazole-4-sulfonyl chloride for 3-fluorobenzenesulfonyl chloride in Example 126C, then substituting the product directly for Example 470F in Example 470G with purification by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min. MS (ESI(+)) m/e 382 $(M+H)^+$, 404 $(M+Na)^+$; (ESI(−)) m/e 380 $(M-H)^-$; $^1H$ NMR (300 MHz, DMSO-$d_6$) δ 9.22 (s, 1H), 7.64 (s, 1H), 7.31 (s, 1H), 3.82 (s, 3H), 3.72 (s, 3H), 3.70 (br s, 1H), 2.74 (q, 2H), 2.61 (q, 2H), 2.49 (s, 3H), 1.32 (t, 3H), 1.12 (t, 3H).

EXAMPLE 591

3,5-diethyl-2-methoxy-6-[(phenylsulfonyl)amino]benzoic acid

The desired compound was prepared by substituting Example 589A for Example 126B and benzenesulfonyl chloride for 3-fluorobenzenesulfonyl chloride in Example 126C, then substituting the product directly for Example 470F in Example 470G with purification by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min. MS (ESI(+)) m/e 364 $(M+H)^+$, 381 $(M+NH_4)^+$, 386 $(M+Na)^+$; (ESI(−)) m/e 362 $(M-H)^-$; $^1H$ NMR (300 MHz, DMSO-$d_6$) δ 12.73 (br s, 1H), 9.43 (s, 1H), 7.72 (m, 2H), 7.63 (m, 1H), 7.56 (m, 2H), 7.13 (s, 1H), 3.69 (s, 3H), 2.60 (q, 2H), 2.23 (q, 2H), 1.17 (t, 3H), 0.90 (t, 3H).

EXAMPLE 592

3,5-diethyl-2-{[(4-fluorophenyl)sulfonyl]amino}-6-methoxybenzoic acid

The desired compound was prepared by substituting Example 589A for Example 126B and 4-fluorobenzenesulfonyl chloride for 3-fluorobenzenesulfonyl chloride in Example 126C, then substituting the product directly for Example 470F in Example 470G with purification by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min. MS (ESI(+)) m/e 382 $(M+H)^+$, 399 $(M+NH_4)^+$, 404 $(M+Na)^+$; (ESI(−)) m/e 380 $(M-H)^-$; $^1H$ NMR (300 MHz, DMSO-$d_6$) δ 12.70 (br s, 1H), 9.47 (br s, 1H), 7.75 (m, 2H), 7.37 (m, 2H), 7.15 (s, 1H), 3.66 (s, 3H), 2.59 (q, 2H), 2.34 (q, 2H), 1.16 (t, 3H), 0.97 (t, 3H).

EXAMPLE 593

3,5-diethyl-2-methoxy-6-[(2-pyridinylsulfonyl)amino]benzoic acid

The desired compound was prepared by substituting Example 589A for Example 126B and 2-pyridinesulfonyl chloride for 3-fluorobenzenesulfonyl chloride in Example 126C, then substituting the product directly for Example 470F in Example 470G with purification by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min. MS (ESI(+)) m/e 365 $(M+H)^+$, 387 $(M+Na)^+$; (ESI(−)) m/e 363 $(M-H)^-$; $^1H$ NMR (300 MHz, DMSO-$d_6$) δ 8.61 (d, 1H), 7.96 (m, 1H), 7.77 (d, 1H), 7.58 (m, 1H), 7.01 (s, 1H), 3.59 (s, 3H), 3.44 (br s, 2H), 2.593 (m, 4H), 1.13 (t, 3H), 0.99 (t, 3H).

EXAMPLE 594

2-[({2-[3-(diethylamino)propyl]phenyl}sulfonyl)amino]-5,6,7,8-tetrahydro-1-naphthalenecarboxylic acid

EXAMPLE 594A methyl 2-[({2-[3-(diethylamino)propyl]phenyl}sulfonyl)amino]-5,6,7,8-tetrahydro-1-naphthalenecarboxylate The method of Example 565A was followed, employing Example 564C (350 mg, 0.77 mmol), and 10% Pd/C (105 mg) in 14 mL of methanol to provide a ~1:1 mixture of the title product. (MS (ESI(+)) m/e 459 $(M+H)^+$) and methyl 2-[2-propylphenylsulfonylamino]-5,6,7,8-tetrahydro-1-naphthalenecarboxylate (MS (ESI(+)) m/e 388 $(M+H)^+$).

EXAMPLE 594B

2-[({2-[3-(diethylamino)propyl]phenyl}sulfonyl)amino]-5,6,7,8-tetrahydro-1-naphthalenecarboxylic acid The method of Example 529E was followed using Example 594A (360 mg), and LiI (429 mg, 4 equiv.) in 8 mL of pyridine. The desired product was obtained in 0.11 g (32% for 2 steps) yield. MS (APCI(+)) m/e 445 $(M+H)^+$; MS (APCI(−)) m/e 443 $(M-H)^-$; $^1H$ NMR (400 MHz, DMSO-$d_6$) δ 1.18 (t, J=7.21 Hz, 6H) 1.57 (m, 4H) 1.75 (m, 2H) 2.57 (m, 2H) 2.84 (m, 2H) 3.01 (m, 8H) 6.85 (d, J=8.31 Hz, 1H) 7.29 (m, 2H) 7.40 (d, J=7.58 Hz, 1H) 7.50 (m, 1H) 7.88 (dd, J=7.83, 1.22 Hz, 1H).

EXAMPLE 595

2-[({2-[(1Z)-5-(diethylamino)-1-pentenyl]phenyl}sulfonyl)amino]-5,6,7,8-tetrahydro-1-naphthalenecarboxylic acid

EXAMPLE 595A AND EXAMPLE 595B

N,N-diethyl-N-[(4E)-5-(tributylstannyl)-4-pentenyl]amine compound with N,N-diethyl-N-[(4Z)-5-(tributylstannyl)-4-pentenyl]amine Toluenesulfonyl chloride (2.44 g, 12.8 mmol, 1.2 equiv.) was added to a solution of 5-pentyn-1-ol (1 mL, 10.7 mmol, 1.0 equiv.), triethylamine (2.2 mL, 16.1 mmol, 1.5 equiv.) and DMAP (65 mg, 0.535 mmol, 0.05 equiv.) in 30 mL of $CH_2Cl_2$. The reaction was stirred at room temperature for 1 day, then diluted with 50 mL of $CH_2Cl_2$. This solution was washed consecutively with 40 mL each of water, 1 molar $NaHCO_3$, 2N HCl, and 10% NaCl. Each wash was extracted with 20 mL $CH_2Cl_2$. The combined organic layers were dried over $MgSO_4$, filtered and concentrated to provide the corresponding tosylate. $^1H$ NMR (400 MHz, $CDCl_3$) δ 1.86 (m, 3H) 2.26 (td, J=6.86, 2.61 Hz, 2H) 2.45 (s, 3H) 4.14 (t, J=6.11 Hz, 2H) 7.34 (dd, J=7.96, 0.69 Hz, 2H) 7.78 (d, J=8.23 Hz, 2H).

A mixture of the tosylate, $K_2CO_3$ (1.71 g, 12.4 mmol), and diethylamine (5.2 mL, 50 mmol) in 16 mL of tetrahydrofuran was heated to 70° C. overnight. After cooling to room temperature, the solids were removed by filtration and the solution was concentrated under vacuum then filtered to provide the corresponding amine. $^1H$ NMR (400 MHz, $CDCl_3$) δ 1.02 (t, J=7.14 Hz, 6H) 1.66 (m, 2H) 1.93 (t, J=2.68 Hz, 1H) 2.21 (td, J=7.10, 2.68 Hz, 2H) 2.51 (m, 6H).

A solution of the amine, tributyltin hydride (4.8 mL, 18 mmol) and AIBN (0.10 g, 0.6 mmol) in 60 mL of benzene was heated to 80° C. for 3 hours. After cooling, the reaction was concentrated and purified by silica gel chromatography to provide 607 mg (13%) of Examples 595A and 595B as a 2:1 mixture. $^1H$ NMR for Example 595A (Z isomer) (400 MHz, $CDCl_3$) δ 0.88 (m, 15H) 1.01 (m, 6H) 1.30 (m, 6H) 1.51 (m, 8H) 2.01 (m, 2H) 2.42 (m, 2H) 2.52 (q, J=7.14 Hz, 4H) 5.78 (m, 1H) 6.50 (dt, J=12.42, 7.03 Hz, 1H).

Also isolated was 2.78 g (60%) of Example 595B (E isomer), contaminated with 8% of the Example 595A. $^1H$ NMR (400 MHz, $CDCl_3$) δ 0.86 (m, 15H) 1.02 (t, J=7.14 Hz, 6H) 1.30 (m, 6H) 1.52 (m, 8H) 2.13 (m, 2H) 2.41 (m, 2H) 2.52 (q, J=7.14 Hz, 4H) 5.93 (m, 2H).

EXAMPLE 595C methyl 2-[({2-[(1Z)-5-(diethylamino)-1-pentenyl]phenyl}sulfonyl)amino]-5,6,7,8-tetrahydro-1-naphthalenecarboxylate The method of Example 529D was followed, employing Example 595A (516 mg, 1.2 mmol), methyl-2-[({2-bromophenyl}sulfonyl)amino]-5,6,7,8-tetrahydro-1-naphthalenecarboxylate (424 mg, 1.0 mmol) and bis(tri-tert-butylphosphine)palladium (100 mg, 0.2 mmol) in 2 mL of toluene for 2 days. 228 mg (47%) of the title compound was obtained. $^1H$ NMR (400 MHz, $CDCl_3$) δ 0.95 (t, J=7.14 Hz, 5H) 1.47 (dt, J=15.16, 7.65 Hz, 2H) 1.69 (m, 4H) 1.96 (q, J=7.73 Hz, 2H) 2.31 (m, 2H) 2.43 (q, J=7.09 Hz, 4H) 2.69 (m, 4H) 3.83 (s, 3H) 5.83 (dt, J=11.56, 7.46 Hz, 1H) 6.82 (d, J=11.53 Hz, 1H) 6.96 (d, J=8.51 Hz, 1H) 7.03 (d, J=8.37 Hz, 1H) 7.30 (d, J=7.41 Hz, 1H) 7.34 (m, 1H) 7.48 (td, J=7.55, 1.24 Hz, 1H) 8.02 (dd, J=7.96, 1.23 Hz, 1H).

EXAMPLE 595D

2-[({2-[(1Z)-5-(diethylamino)-1-pentenyl]phenyl}sulfonyl)amino]-5,6,7,8-tetrahydro-1-naphthalenecarboxylic acid A solution of Example 595C (205 mg, 0.4 mmol), and LiI (214 mg, 4 equiv.) in 4 mL of pyridine was reacted in a microwave at 150° C. for 35 minutes, concentrated, and purified by preparative HPLC on a Waters Symmetry C8 column (40 mm×100 mm, 7 μm particle size) using a gradient of 10% to 95% acetonitrile/10 mM aqueous ammonium acetate over 12 minutes (15 minute run time) at a flow rate of 70 mL/min. in 143 mg (76%) yield. MS (ESI(+)) m/e 471 $(M+H)^+$; MS (ESI(−)) m/e 469 $(M-H)^-$; $^1$H NMR (400 MHz, DMSO-$d_6$) δ 0.99 (t, J=7.21 Hz, 6H) 1.56 (m, 6H) 2.10 (m, 2H) 2.58 (m, 4H) 2.68 (q, J=7.09 Hz, 4H) 2.90 (m, 2H) 5.71 (dt, J=11.55, 7.06 Hz, 1H) 6.79 (d, J=8.31 Hz, 1H) 6.93 (d, J=11.74 Hz, 1H) 7.12 (d, J=8.31 Hz, 1H) 7.32 (m, 2H) 7.48 (td, J=7.46, 1.22 Hz, 1H) 7.79 (dd, J=7.83, 1.22 Hz, 1H).

EXAMPLE 596

2-[({2-[(1E)-5-(diethylamino)-1-pentenyl]phenyl}sulfonyl)amino]-5,6,7,8-tetrahydro-1-naphthalenecarboxylic acid

EXAMPLE 596A methyl 2-[({2-[(1E)-5-(diethylamino)-1-pentenyl]phenyl}sulfonyl)amino]-5,6,7,8-tetrahydro-1-naphthalenecarboxylate The method of Example 529D was followed, employing Example 595B (516 mg, 1.2 mmol), methyl 2-[({2-bromophenyl}sulfonyl)amino]-5,6,7,8-tetrahydro-1-naphthalenecarboxylate (424 mg, 1.0 mmol) and bis(tri-tert-butylphosphine)palladium (100 mg, 0.2 mmol) in 2 mL of toluene for 2 days. 441 mg (91%) of the title compound was obtained. $^1$H NMR (400 MHz, $CDCl_3$) δ 1.03 (t, J=7.14 Hz, 6H) 1.66 (m, 6H) 2.21 (m, 2H) 2.48 (m, 2H) 2.54 (q, J=7.14 Hz, 4H) 2.69 (m, 4H) 3.72 (s, 3H) 6.10 (dt, J=15.51, 6.86 Hz, 1H) 7.01 (d, J=8.37 Hz, 1H) 7.09 (d, J=15.64 Hz, 1H) 7.17 (d, J=8.37 Hz, 1H) 7.25 (td, J=7.58, 1.44 Hz, 1H) 7.44 (td, J=7.48, 0.96 Hz, 1H) 7.50 (m, 1H) 7.89 (dd, J=7.96, 1.24 Hz, 1H).

EXAMPLE 596B

2-[({2-[(1E)-5-(diethylamino)-1-pentenyl]phenyl}sulfonyl)amino]-5,6,7,8-tetrahydro-1-naphthalenecarboxylic acid A solution of Example 596A (420 mg, 0.9 mmol), and LiI (482 mg, 4 equiv.) in 9 mL of pyridine was reacted in two vials in a microwave at 150° C. for 35 minutes. After concentration, the crude product was purified by preparative HPLC on a Waters Symmetry C8 column (40 mm×100 mm, 7 μm particle size) using a gradient of 10% to 95% acetonitrile/10 mM aqueous $NH_4OAc$ over 12 minutes (15 minute run time) at a flow rate of 70 mL/min. in 36 mg (8%) yield. MS (ESI(+)) m/e 471 $(M+H)^+$; MS (ESI(−)) m/e 469 $(M-H)^-$; $^1$H NMR (400 MHz, DMSO-$d_6$) δ 1.21 (t, J=6.72 Hz, 6H) 1.55 (m, 4H) 2.01 (s, 2H) 2.28 (q, J=6.11 Hz, 2H) 2.55 (s, 2H) 2.86 (s, 2H) 3.05 (m, 6H) 6.30 (m, 1H) 6.81 (m, 1H) 7.11 (d, J=8.31 Hz, 1H) 7.17 (d, J=15.89 Hz, 1H) 7.35 (m, 1H) 7.51 (t, J=6.97 Hz, 1H) 7.57 (m, 1H) 7.93 (m, 1H).

EXAMPLE 597

2-[({2-[5-(diethylamino)pentyl]phenyl}sulfonyl)amino]-5,6,7,8-tetrahydro-1-naphthalenecarboxylic acid

EXAMPLE 597A methyl 2-[({2-[5-(diethylamino)pentyl]phenyl}sulfonyl)amino]-5,6,7,8-tetrahydro-1-naphthalenecarboxylate A 1:1.2 mixture of Example 595C and Example 596A (408 mg, 0.84 mmol) was hydrogenated over 120 mg of 10% Pd/C in 16 mL of methanol for 1 hour. The reaction mixture was filtered through diatomaceous earth (Celite®), and concentrated to provide 332 mg (81%) of the title compound. $^1$H NMR (400 MHz, $CDCl_3$) δ 1.16 (t, J=7.14 Hz, 6H) 1.42 (m, 2H) 1.67 (m, 8H) 2.62 (m, 2H) 2.72 (m, 8H) 2.88 (m, 2H) 3.75 (s, 3H) 7.03 (d, J=8.51 Hz, 1H) 7.18 (d, J=8.37 Hz, 1H) 7.22 (m, 1H) 7.29 (dd, J=7.75, 1.17 Hz, 1H) 7.44 (td, J=7.48, 1.37 Hz, 1H) 7.84 (dd, J=7.96, 1.37 Hz, 1H).

EXAMPLE 597B

2-[({2-[5-(diethylamino)pentyl]phenyl}sulfonyl)amino]-5,6,7,8-tetrahydro-1-naphthalenecarboxylic acid A solution of Example 597A (310 mg, 0.6 mmol), and LiI (322 mg, 4 equiv.) in 6 mL of pyridine was reacted in two vials in a microwave at 150° C. for 35 minutes and concentrated. The concentrate was purified by preparative HPLC on a Waters Symmetry C8 column (40 mm×100 mm, 7 μm particle size) using a gradient of 10% to 95% acetonitrile/10 mM aqueous ammonium acetate over 12 minutes (15 minute run time) at a flow rate of 70 mL/min. The product was combined with a sample of Example 596B to provide 256 mg of a 5:4 mixture of Example 596B and Example 597B.

The mixture (229 mg) was hydrogenated in the presence of 0.2 mL of 2N HCl and 70 mg of 10% Pd/C in 10 mL of methanol for 2.5 hours. The reaction was filtered through diatomaceous earth (Celite ®) and concentrated to provide 210 mg of the title compound. MS (ESI(+)) m/e 473 $(M+H)^+$; MS (ESI(−)) m/e 471 $(M-H)^-$; $^1$H NMR (400 MHz, DMSO-$d_6$) δ 1.19 (t, J=7.21 Hz, 6H) 1.41 (m, 2H) 1.66 (m, 8H) 2.62 (s, 2H) 2.70 (s, 2H) 2.96 (m, 4H) 3.08 (q, J=7.25 Hz, 4H) 4.09 (s, 1H) 6.81 (d, J=8.07 Hz, 1H) 6.94 (d, J=8.31 Hz, 1H) 7.32 (t, J=7.58 Hz, 1H) 7.42 (d, J=7.58 Hz, 1H) 7.53 (t, J=7.58 Hz, 1H) 7.79 (d, J=7.83 Hz, 1H) 10.31 (s, 1H).

EXAMPLE 598

3-ethyl-2-methyl-6-[(2-pyridinylsulfonyl)amino]benzoic acid

EXAMPLE 598A 2-methyl-6-(pyridine-2-sulfonylamino)-3-vinyl-benzoic acid benzyl ester The title compound was prepared from Example 110A according to the procedure of Example 230B with a yield of 50%. %. $^1$H NMR (DMSO-$d_6$): δ2.12 (s, 3H), 5.26 (s, 2H), 3.68 (t, 2H), 5.34 (d, 1H), 5.65 (d, 1H), 6.89 (dd, 1H), 6.98 (d, 1H), 7.35-7.40 (m, 5H), 7.47 (d, 1H), 7.65 (t, 1H), 7.87 (d, 1H), 8.05 (t, 1H), 8.73 (d, 1H), 10.04 (s, 1H). MS (ESI+): m/z 409, base peak.

EXAMPLE 598

3-ethyl-2-methyl-6-[(2-pyridinylsulfonyl)amino] benzoic acid

Example 598A (0.46 g, 1.12 mmole) was hydrogenated in MeOH (4 mL), THF (4 mL) and water (2 mL) over 10% Pd/C (150 mg) at ambient temperature under one atmosphere of hydrogen for 6 h. Filtration and evaporation of the solvents gave a white solid, 0.36 g, 100%. %. $^1$H NMR (DMSO-$d_6$): δ1.02 (t, 3H), 2.08 (s, 3H), 2.58 (q, 2H), 6.82 (d, 1H), 7.02 (d, 1H), 7.58 (t, 1H), 7.58 (d, 1H), 7.98 (t, 1H), 8.65 (d, 1H), 9.80 (bs, 1H), 13 (bs, 1H). MS (ESI$^-$): m/z 319, base peak.

EXAMPLE 600

2-({[2-({2-[1-methyl-2-pyrrolidinyl]ethyl}amino) phenyl]sulfonyl}amino)-6,7,8,9-tetrahydro-5H-benzo [7]annulene-1-carboxylic acid The desired product was prepared by substituting 2-[(1-methyl-2-pyrrolidinyl]ethylamine for N,N,2,2-tetramethyl-1,3-propanediamine in Example 510I. (ESI(+)) m/e 472 $(M+H)^+$; MS (ESI(−)) m/e 470 $(M-H)^-$; $^1$H NMR (300 MHz, DMSO-$d_6$) δ 7.57 (d, 1H), 7.42 (t, 1H), 6.98 (d, 1H), 6.85 (t, 1H), 6.67 (t, 1H), 6.53 (d, 1H), 2.86 (m, 1H), 2.81 (s, 3H), 2.72 (m, 7H), 2.62 (m, 1H), 2.54 (m, 1H), 1.74 (m, 4H), 1.64 (m, 4H), 1.51 (m, 4H).

EXAMPLE 601

2-(2-aminoethoxy)-3-ethyl-6-{[(2-ethyl-4-fluorophenyl)sulfonyl]amino}benzoic acid

EXAMPLE 601A methyl 2-[2-(1,3-dioxo-1,3-dihydro-2H-isoindol-2-yl)ethoxy]-3-ethyl-6-{[(4-fluoro-2-vinylphenyl)sulfonyl]amino}benzoate The title compound was prepared from Example 579A (0.12 g, 0.2 mmol) according to the procedure of Example 230B, yielding 87 mg, 79.1%. MS (ESI(−)) m/e 551 $(M-H)^-$.

EXAMPLE 601B methyl 2-[2-(1,3-dioxo-1,3-dihydro-2H-isoindol-2-yl)ethoxy]-3-ethyl-6-{[(2-ethyl-4-fluorophenyl)sulfonyl]amino}benzoate Example 601A (80 mg) was hydrogenated in methanol (3 mL) and THF (3 mL) over 10% Pd/C at ambient temperature under one atmosphere of hydrogen for 6 h. Filtration and evaporation of the solvent provided the title compound, 80 mg.

EXAMPLE 601C 2-(2-aminoethoxy)-3-ethyl-6-{[(2-ethyl-4-fluorophenyl)sulfonyl]amino}benzoic acid The title compound was prepared from Example 601B (80 mg, 0.14 mmol) according to the procedure of Example 385I, yielding 15.2 mg, 26%. $^1$H NMR (DMSO-$d_6$) δ 1.08 (t, 3H), 1.13 (t, 3H), 2.48 (q, 2H), 2.98 (q, 2H), 3.09 (t, 2H), 3.93 (t, 2H), 6.96 (d, 1H), 7.04 (d, 1H), 7.14 (t, 1H), 7.25 (d, 1H), 7.95 (t, 1H), 8.16 (s, 3H). MS (ESI(−)) m/e 409 $(M-H)^-$.

EXAMPLE 602

2-(2-aminoethoxy)-3-ethyl-6-{[(4-fluoro-2-propylphenyl)sulfonyl]amino}benzoic acid

EXAMPLE 602A methyl 2-[2-(1,3-dioxo-1,3-dihydro-2H-isoindol-2-yl)ethoxy]-3-ethyl-6-[({4-fluoro-2-[(1E)-1-propenyl] phenyl}sulfonyl)amino]benzoate The title compound was prepared from Example 579A (0.12 g, 0.2 mmol) and trans-1-propenylboronic acid according to the procedure of Example 230B, yielding 75 mg, 66.4%. $^1$H NMR (DMSO-$d_6$) δ 0.95 (t, 3H), 1.76 (d, 3H), 2.42 (q, 2H), 3.48 (s, 3H), 3.90 (t, 2H), 3.98 (t, 2H), 6.26-6.40 (m, 1H), 6.78 (d, 1H), 6.87 (d, 1H), 7.12 (t, 1H), 7.18 (d, 1H), 7.46 (d, 1H), 7.72 (d, 1H), 7.80-7.94 (m, 4H), 9.80 (s, 1H); MS (ESI(−)) m/e 565 $(M-H)^-$.

EXAMPLE 602B methyl 2-[2-(1,3-dioxo-1,3-dihydro-2H-isoindol-2-yl)ethoxy]-3-ethyl-6-{[(4-fluoro-2-propylphenyl) sulfonyl]amino}benzoate Example 602A (75 mg) was hydrogenated in methanol (3 mL) and THF (3 mL) over 10% Pd/C at ambient temperature under one atmosphere of hydrogen. Filtration and evaporation of the solvent gave the title compound, 73 mg.

EXAMPLE 602C 2-(2-aminoethoxy)-3-ethyl-6-{[(4-fluoro-2-propylphenyl)sulfonyl]amino}benzoic acid The title compound was prepared from Example 602B (75 mg, 0.13 mmol) according to the procedure of Example 385I, yielding 18.2 mg, 33.0%. $^1$H NMR (DMSO-$d_6$) δ 0.92 (t, 3H), 1.08 (t, 3H), 1.50-1.60 (m, 2H), 2.48 (q, 2H), 2.92 (t, 2H), 3.09 (t, 2H), 3.93 (t, 2H), 6.96 (d, 1H), 7.02 (d, 1H), 7.15 (t, 1H), 7.23 (d, 1H), 7.95 (t, 1H), 8.00-8.40 (br s, 3H). MS (ESI(−)) m/e 423 $(M-H)^-$.

EXAMPLE 603

2-(2-aminoethoxy)-3-ethyl-6-({[4-fluoro-2-(2-phenylethyl)phenyl]sulfonyl}amino)benzoic acid

EXAMPLE 603A methyl 2-[2-(1,3-dioxo-1,3-dihydro-2H-isoindol-2-yl)ethoxy]-3-ethyl-6-[({4-fluoro-2-[(E)-2-phenylvinyl]phenyl}sulfonyl)amino]benzoate The title compound was prepared from Example 579A (0.12 g, 0.2 mmol) and trans-2-phenylvinylboronic acid according to the procedure of Example 230B, yielding 93 mg, 73.8%. $^1$H NMR (DMSO-$d_6$) δ0.82 (t, 3H), 2.28 (q, 2H), 3.36 (s, 3H), 3.84 (s, 4H), 6.90 (d, 1H), 7.14-7.30 (m, 4H), 7.35 (t, 2H), 7.45 (d, 2H), 7.52 (d, 1H), 7.74 (d, 1H), 7.80-7.95 (m, 5H), 9.98 (s, 1H); MS (ESI(−)) m/e 627 $(M-H)^-$.

EXAMPLE 603B methyl-2-[2-(1,3-dioxo-1,3-dihydro-2H-isoindol-2-yl)ethoxy]-3-ethyl-6-({[4-fluoro-2-(2-phenylethyl)phenyl]sulfonyl}amino)benzoate Example 603A (90 mg) was hydrogenated in methanol (3 mL) and THF (3 mL) over 10% Pd/C at ambient temperature under one atmosphere of hydrogen. Filtration and evaporation of the solvent gave the title compound, 85 mg.

EXAMPLE 603C 2-(2-aminoethoxy)-3-ethyl-6-({[4-fluoro-2-(2-phenylethyl)phenyl]sulfonyl}amino)benzoic acid The title compound was prepared from Example 603B (90 mg, 0.14 mmol) according to the procedure of Example 385I, yielding 20.4 mg, 30.0%. $^1$H NMR ($CD_3OD$) δ 1.14 (t, 3H), 2.58 (q, 2H), 2.93 (m, 2H), 3.18 (t, 2H), 3.26 (m, 2H), 4.00 (t, 2H), 6.97-7.00 (m, 2H), 7.08 (d, 1H), 7.17-7.27 (m, 6H), 7.94 (t, 1H); MS (ESI(−)) m/e 485 $(M-H)^-$.

EXAMPLE 604

2-({[2-({3-[4-(tert-butoxycarbonyl)-1-piperazinyl]-3-oxopropyl}amino)phenyl]sulfonyl}amino)-8-methyl-5,6,7,8-tetrahydro-1-naphthalenecarboxylic acid

EXAMPLE 604A tert-butyl 4-(cyanoacetyl)-1-piperazinecarboxylate

A mixture of 1-tert-butoxycarbonylpiperazine (7.44 g, 40 mmol) and ethyl cyanoacetate (8.53 mL, 80 mmol) was gently stirred in 20 mL of toluene at 90° C. for 2 days. The mixture was concentrated and purified by silica gel column chromatography, eluting with 30% ethyl acetate in n-hexane to provide the title compound (3.68 g). MS (ESI(−)) m/e 252 $(M-H)^-$; $^1$H NMR (300 MHz, DMSO-$d_6$) δ 3.41 (m, 4H), 3.27-3.35 (m, 4H), 2.72 (m, 2H), 2.38 (m, 2H), 1.41 (s, 9H).

EXAMPLE 604B tert-butyl 4-β-alanyl-1-piperazinecarboxylate

A mixture of Example 604A (500 mg) was hydrogenated in the presence of Raney® nickel (5 g) in 10 mL of 20% ammonium hydroxide in methanol at room temperature for 16 hours under 60 psi pressure. Insoluble was filtered off and the filtrate was evaporated to dryness and the residue was redissolved in ether. The ethereal solution was passed through membrane filter. The title compound was obtained after ether was removed. 330 mg. MS (ESI(+)) m/e 258 $(M+H)^-$; $^1$H NMR (300 MHz, DMSO-$d_6$) δ 4.04 (s, 2H), 3.42-3.45 (m, 4H), 3.26-3.33 (m, 42H), 1.41 (s, 9H).

EXAMPLE 604C 2-({[2-({3-[4-(tert-butoxycarbonyl)-1-piperazinyl]-3-oxopropyl}amino)phenyl]sulfonyl}amino)-8-methyl-5,6,7,8-tetrahydro-1-naphthalenecarboxylic acid The title compound was prepared from the compound of Example 275F (50 mg, 0.13 mmol) and Example 604B (205 mg, 0.8 mmol) according to the procedure described in Example 275G. MS (ESI(−)) m/e 599 $(M-H)^-$; $^1$H NMR (300 MHz, DMSO-$d_6$) δ 9.25 (s, 1H), 8.70 (s, 1H), 7.47 (dd, 1H), 7.40 (dt, 1H), 6.94 (d, 1H), 6.83 (d, 1H), 6.56-6.65 (m, 2H), 6.04 (s, 1H), 3.35-3.45 (m, 4H), 3.22-3.30 (m, 3H), 3.07 (m, 1H), 2.61-2.70 (m, 2H), 1.57-1.75 (m, 3H), 1.40 (s, 9H), 1.09 (d, 3H).

EXAMPLE 605

2-({[2-({3-[4-(tert-butoxycarbonyl)-1-piperazinyl]-2,2-dimethyl-3-oxopropyl}amino)phenyl]sulfonyl}amino)-8-methyl-5,6,7,8-tetrahydro-1-naphthalenecarboxylic acid

EXAMPLE 605A tert-butyl 4-(3-amino-2,2-dimethylpropanoyl)-1-piperazinecarboxylate A mixture of 60% sodium hydride in oil (0.74 g, 16.5 mmol) in 10 mL of N,N-dimethylformamide at room temperature was treated with Example 604A (1.90 g, 7.5 mmol), then treated dropwise with a solution of iodomethane (1.17 mL, 18.75 mmol) in 10 mL of N,N-dimethylformamide over 1 hour. The mixture was stirred overnight, treated with 10 mL of saturated ammonium chloride, and treated with 50 mL of ethyl acetate. The organic layer was washed with brine (5×), dried ($MgSO_4$), filtered, concentrated, and purified by silica gel column chromatography, eluting with 20% ethyl acetate in n-hexane. The purified product was hydrogenated following the procedure described in Example 604B to provide the desired product. MS (ESI(+)) m/e 286 $(M+H)^-$; $^1$H NMR (300 MHz, DMSO-$d_6$) δ 3.48-3.52 (m, 4H), 3.24-3.35 (m, 4H), 2.60 (s, 2H), 1.41 (s, 9H), 1.14 (s, 6H).

EXAMPLE 605B 2-({[2-({3-[4-(tert-butoxycarbonyl)-1-piperazinyl]-2,2-dimethyl-3-oxopropyl}amino)phenyl]sulfonyl}amino)-8-methyl-5,6,7,8-tetrahydro-1-naphthalenecarboxylic acid The title compound was prepared from the compound of Example 275F and Example 605A according to the procedure described in Example 275G MS (ESI(−)) m/e 627 $(M-H)^-$; $^1$H NMR (300 MHz, DMSO-$d_6$) δ 9.06 (s, 1H), 8.72 (s, 1H), 7.51 (dd, 1H), 7.36 (dt, 1H), 6.90-6.97 (m, 2H), 6.58-6.66 (m, 2H), 6.33 (m, 1H), 3.71-3.75 (m, 2H), 3.22-3.30 (m, 4H), 3.07 (m, 1H), 2.61-2.74 (m, 2H), 1.61-1.75 (m, 3H), 1.40 (s, 9H), 1.21 (s, 3H), 1.20 (s, 3H), 1.09 (d, 3H).

EXAMPLE 606

8-methyl-2-{[(2-{[3-(4-morpholinyl)-3-oxopropyl]amino}phenyl)sulfonyl]amino}-5,6,7,8-tetrahydro-1-naphthalenecarboxylic acid The title compound was prepared by a similar method describing in example 605, except morpholine was employed instead of tert-butoxycarbonylpiperazine; MS (ESI(−)) m/e 500 $(M-H)^-$; $^1$H NMR (300 MHz, DMSO-$d_6$) δ 9.65 (s, 1H), 9.27 (s, 1H), 7.67 (dd, 1H), 7.45 (dt, 1H), 7.32 (dt, 1H), 7.00 (dd, 1H), 6.80 (t, 1H), 6.60 (m, 1H), 3.402-3.44 (m, 4H), 3.27 (m, 2H), 2.59-2.66 (m, 2H), 1.61-1.75 (m, 4H), 1.09 (d, 3H).

EXAMPLE 607

8-methyl-2-{[(2-{[3-oxo-3-(1-piperazinyl)propyl]amino}phenyl)sulfonyl]amino}-5,6,7,8-tetrahydro-1-naphthalenecarboxylic acid The title compound was prepared by treating Example 604C (30 mg) with 4N HCl in dioxane (5 ml). After stirring at room temperature for 1 hour, the solvent was removed and the residue was treated with anhydrous ether. Solid was collected by filtration, washed with ether and dried to provide the desired product. MS (ESI(−)) m/e 499 (M−H)$^-$.

EXAMPLE 608

2-{[(2-{[2,2-dimethyl-3-oxo-3-(1-piperazinyl)propyl]amino}phenyl)sulfonyl]amino}-8-methyl-5,6,7,8-tetrahydro-1-naphthalenecarboxylic acid The title compound was prepared by treating Example 605B (25 mg) with 4N HCl in dioxane (5 ml). The reaction was carried out at room temperature for 1 hour with stirring. After solvent was removed, the residue was treated with anhydrous ether. The solid was collected by filtration, washed with ether and dried to provide the desired product. MS (ESI (−)) m/e 527 (M−H)$^-$.

EXAMPLE 615

3-ethyl-6-[({4-fluoro-2-[4-(2-methyl-1-pyrrolidinyl)butyl]phenyl}sulfonyl)amino]-2-methoxybenzoic acid

EXAMPLE 615A methyl 6-{[(2-bromo-4-fluorophenyl)sulfonyl]amino}-3-ethyl-2-methoxybenzoate The title compound was prepared from Example 574C (3.97 g, 19 mmol) and 2-bromo-4-fluorobemzenesulfonyl chloride according to the procedure of Example 385F, yielding 6.49 g, 76.6%. $^1$H NMR (DMSO-$d_6$) δ 1.13 (t, 3H), 2.55 (q, 2H), 3.62 (s, 3H), 3.72 (s, 3H), 6.84 (d, 1H), 7.25 (d, 1H), 7.40 (dd, 1H), 7.82-7.94 (m, 2H), 10.02 (s, 1H); MS (ESI(−)) m/e 444, 446, (M−H)$^-$.

EXAMPLE 615B methyl 3-ethyl-6-({[4-fluoro-2-(4-hydroxy-1-butynyl)phenyl]sulfonyl}amino)-2-methoxybenzoate A solution of Example 615A (0.446 g, 1.0 mmol), bis (triphenylphosphine))palladium dichloride (35 mg, 0.05 mmol), triphenylphosphine (6.5 mg, 0.025 mmol), 4-hydroxy-1-butyne (0.14 g, 2.0 mmol) and trimethylamine (0.2 mL, 1.5 mmol) in anhydrous THF (6 mL) in a scintillation vial was shaken at ambient temperature for 20 minutes. Copper (I) iodide (5 mg, 0.025 mmol) was added. The mixture was purged with argon, sealed and shaken at 75° C. for 8 hours, treated with ethyl acetate (30 mL), washed with brine (2×10 mL), dried ($MgSO_4$), filtered, and concentrated. The residue was purified on a silica gel column eluting with 30% ethyl acetate in hexanes to provide the desired product, 304 mg, 69.9%. $^1$H NMR (DMSO-$d_6$) δ 1.11 (t, 3H), 2.55 (q, 2H), 2.61 (t, 2H), 3.63 (t, 2H), 3.73 (s, 3H), 5.25 (t, 1H), 6.86 (d, 1H), 7.25 (d, 1H), 7.32 (t, 1H), 7.52 (d, 2H), 7.82 (dd, 1H), 9.59 (s, 1H); MS (ESI(−)) m/e 434 (M−H)$^-$.

EXAMPLE 615C methyl 3-ethyl-6-({[4-fluoro-2-(4-hydroxybutyl)phenyl]sulfonyl}amino)-2-methoxybenzoate Example 615B (304 mg, 0.70 mmol) was hydrogenated in methanol (15 mL) over 10% Pd/C (100 mg) under one atmosphere of hydrogen at ambient temperature overnight and Filtration and evaporation of the solvent gave the desired product, 288 mg, 93.7%. $^1$H NMR (DMSO-$d_6$) δ 1.12 (t, 3H), 1.46 (m, 2H), 1.55 (m, 2H), 2.55 (q, 2H), 2.83 (t, 2H), 3.43 (t, 2H), 3.62 (s, 3H), 3.68 (s, 3H), 6.80 (d, 1H), 7.10-7.30 (m, 3H), 7.80 (d, 1H), 9.85 (s, 1H); MS (ESI(−)) m/e 438 (M−H)$^-$.

EXAMPLE 615D methyl 3-ethyl-6-{[(4-fluoro-2-{4-[(methylsulfonyl)oxyl]butyl}phenyl)sulfonyl]amino}-2-methoxybenzoate A solution of Example 615C (288 mg, 0.66 mmol), methanesulfonyl chloride (188 mg, 1.64 mmol) and pyridine (104 mg, 1.32 mmol) in dichloromethane (5 mL) was stirred at ambient temperature overnight. Dichloromethane (20 mL) was added and the solution was washed with 1N HCl (2×10 mL) and brine (2×10 mL). The solution was then dried ($MgSO_4$), filtered, and concentrated to provide the desired product (0.33 g, 97%).

EXAMPLE 615E methyl 3-ethyl-6-[({4-fluoro-2-[4-(2-methyl-1-pyrrolidinyl)butyl]phenyl}sulfonyl)amino]-2-methoxybenzoate A solution of Example 615D (0.165 g, 0.31 mmol) and 2-methylpyrrolidine (70 mg, 0.8 mmol) in anhydrous $CH_3CN$ (3.0 mL) was heated at 50° C. for 10 hours. The mixture was directly purified on a silica gel column, eluting with ethyl acetate, then 5% methanol in $CH_2Cl_2$, giving the desired product. 85 mg, 52.7%. MS (ESI(−)) m/e 505 (M−H)$^-$.

EXAMPLE 615F 3-ethyl-6-[({4-fluoro-2-[4-(2-methyl-1-pyrrolidinyl)butyl]phenyl}sulfonyl)amino]-2-methoxybenzoic acid The title compound was prepared from Example 615E (83 mg, 0.16 mmol) according to the procedure of Example 385I, yielding 36 mg, 32.2%. $^1$H NMR (DMSO-$d_6$) δ 0.96 (d, 3H), 1.02 (t, 3H), 1.20-1.30 (m, 2H), 1.55-1.63 (m, 4H), 1.90-2.05 (m, 2H), 2.15-2.25 (m, 1H), 2.40 (q, 2H), 2.90-3.05 (m, 4H), 3.62 (s, 3H), 6.80 (d, 1H), 6.88 (d, 1H), 7.09 (t, 1H), 7.15 (d, 1H), 7.93 (dd, 1H); MS (ESI(−)) m/e 491 (M−H)$^-$.

EXAMPLE 616

6-[({2-[4-(diethylamino)butyl]-4-fluorophenyl}sulfonyl)amino]-3-ethyl-2-methoxybenzoic acid

EXAMPLE 616A methyl 6-[({2-[4-(diethylamino)butyl]-4-fluorophenyl}sulfonyl)amino]-3-ethyl-2-methoxybenzoate The title compound was prepared from Example 615D (0.165 g, 0.31 mmol) and dimethylamine (60 mg, 0.8 mmol) according to the procedure of Example 615E, yielding 15 mg, 9.5%.

EXAMPLE 616

6-[({2-[4-(diethylamino)butyl]-4-fluorophenyl}sulfonyl)amino]-3-ethyl-2-methoxybenzoic acid The title compound was prepared from Example 616A (15 mg, 0.03 mmol) according to the procedure of Example 385I, yielding 4 mg, 27.8%. $^1$H NMR ($CD_3OD$) δ 1.10 (t, 3H), 1.30 (t, 6H), 1.70-1.80 (m, 2H), 1.80-1.90 (m, 2H), 2.54 (q, 2H), 3.10 (t, 2H), 3.15-3.25 (m, 6H), 3.72 (s, 3H), 6.9 (t, 1H), 7.04 (d, 1H), 7.14 (d, 1H), 7.24 (d, 1H), 7.96 (dd, 1H); MS (ESI(−)) m/e 479 $(M-H)^-$.

EXAMPLE 617

2-{[(2-{[2-(4-pyridinyl)ethyl]amino}phenyl)sulfonyl]amino}-5,6,7,8-tetrahydro-1-naphthalenecarboxylic acid The desired product was prepared by substituting 4-(2-aminoethyl)pyridine for 3-(N,N-diethylamino)propylamine in Example 229B. MS (ESI(+)) m/e 452 $(M+H)^+$; MS (ESI (−)) m/e 450 $(M-H)^-$; $^1H$ NMR (300 MHz, DMSO-$d_6$) δ 9.48 (s, 1H), 8.63 (d, 2H), 7.66 (d, 2H), 7.49 (dd, 1H), 7.40 (t, 1H), 6.95 (d, 1H), 6.89 (d, 1H), 6.65 (d, 1H), 6.59 (d, 1H), 5.97 (bds, 1H), 3.01 (t, 2H), 2.66 (m, 4H), 2.55 (m, 2H), 1.66 (m, 4H).

EXAMPLE 618

2-{[(4-bromo-2-fluorophenyl)sulfonyl]amino}-5,6,7,8-tetrahydro-1-naphthalenecarboxylic acid The desired product was prepared by substituting 4-bromo-2-fluorobenzenesulfonyl chloride for 4-fluorobenzenesulfonyl chloride in Example 128D. MS (ESI(+)) m/e 444, 446 $(M+NH_4)^+$; MS (ESI(−)) m/e 426, 428 $(M-H)^-$; $^1H$ NMR (300 MHz, DMSO-$d_6$) δ 7.68 (d, 1H), 7.62 (d, 1H), 7.50 (dd, 1H), 6.98 (d, 1H), 6.91 (d, 1H), 2.86 (m, 2H), 2.62 (m, 2H), 1.62 (m, 4H).

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (III)

(III)

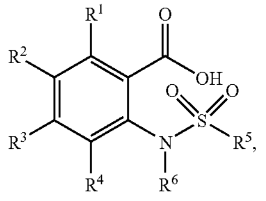

or a therapeutically acceptable salt thereof, wherein $R^1$ is selected from the group consisting of hydrogen, $C_1$-$C_4$ alkyl, $C_2$-$C_4$ alkenyl, $C_1$-$C_4$ alkoxy, $R_aR_bN$— and $R_aR_b$Nalkoxy, wherein $R_a$ and $R_b$ are each independently selected from the group consisting of hydrogen and alkyl;

$R^2$ is selected from the group consisting of alkoxy, alkoxyalkyl, $C_1$-$C_{10}$ alkyl, alkylsulfanyl, alkylsulfanylalkyl, alkylsulfonyl, alkylsulfonylalkyl, amino, aminoalkyl, cycloalkyl and (cycloalkyl)alkyl;

$R^3$ is selected from the group consisting of hydrogen and alkyl;

$R^4$ is selected from the group consisting of hydrogen, alkenyl, alkoxy, alkoxyalkyl, alkoxycarbonyl, alkyl, alkylcarbonyl, alkylsulfonyl, alkylsulfanyl, alkylsulfanylalkyl, carboxy, cyano, cyanoalkyl, cycloalkyl, (cycloalkyl)alkyl, heteroaryl, heterocycle, heterocyclealkyl, heterocyclealkenyl, hydroxy, hydroxyalkyl, nitro, phenyl, phenylsulfonyl, $R_{c4}R_{d4}N$—, $R_{c4}R_{d4}$Nalkyl, $R_{c4}R_{d4}$Nalkenyl, $R_{c4}R_{d4}$Nalkynyl, $R_{c4}R_{d4}$Nalkoxy, $R_{c4}R_{d4}$Nalkoxycarbonyl, $R_{c4}R_{d4}$Ncarbonyl, $R_{c4}R_{d4}$Ncycloalkyl, $R_{c4}R_{d4}$Nalkylcycloalkyl, $R_{c4}R_{d4}$N(cycloalkyl)alkyl, $R_{c4}R_{d4}$Nsulfinyl, $R_{e4}R_{f4}$Nalkyl($R_{c4}$)N—, $R_{e4}R_{f4}$Nalkyl ($R_{c4}$)Ncarbonyl, $R_{e4}R_{f4}$Nalkyl($R_{c4}$)Ncarbonylalkenyl, $R_{e4}R_{f4}$Nalkylcarbonyl($R_{c4}$)N—, $R_{e4}R_{f4}$Nalkoxycarbonyl($R_{c4}$)N—, $R_{c4}R_{d4}$Nalkylsulfanyl, $R_{c4}R_{d4}$Nalkylsulfinyl, $R_{c4}R_{d4}$Nalkylsulfonyl, $R_{g4}R_{j4}$Nalkyl($R_{c4}$)Ncarbonyl ($R_{c4}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano and nitro; and wherein $R_{c4}$, $R_{d4}$, $R_{e4}$, $R_{f4}$, $R_{g4}$ and $R_{j4}$ are each independently selected from the group consisting of hydrogen, alkoxyalkyl, alkyl, alkylcarbonyl, aminoalkyl, cycloalkyl, (cycloalkyl)alkyl, heterocycle and phenyl, or each individual pair of $R_{c4}$ and $R_{d4}$, or $R_{e4}$ and $R_{f4}$, or $R_{g4}$ and $R_{j4}$ taken together with the nitrogen atom they are each attached form a heterocycle;

$R^5$ is selected from the group consisting of alkyl, amino, aminoalkyl, aryl, arylalkenyl, arylalkyl, heteroaryl, heteroarylalkenyl, heteroarylalkyl, heterocycle, heterocyclealkyl and heterocyclealkenyl, wherein aryl, the aryl group of arylalkenyl, the aryl group of arylalkyl, the heteroaryl, the heteroaryl of heteroarylalkenyl, the heteroaryl of heteroarylalkyl, and the heterocycle of $R^5$ may be optionally substituted with 1, 2 or 3 substituents independently selected from the group consisting of alkenyl, alkoxy, alkoxycarbonyl, alkyl, alkylcarbonyl, alkylsulfonyl, aminoalkyl, phenyl, phenylsulfonyl, carboxy, cyano, cyanoalkyl, heteroaryl, heterocycle, heterocyclealkyl, heterocyclealkenyl, hydroxy, nitro, $R_{c5}R_{d5}N$—, $R_{c5}R_{d5}$Nalkyl, $R_{c5}R_{d5}$Nalkenyl, $R_{c5}R_{d5}$Nalkynyl, $R_{c5}R_{d5}$Nalkoxy, $R_{c5}R_{d5}$Nalkoxycarbonyl, $R_{c5}R_{d5}$Ncarbonyl, $R_{c5}R_{d5}$Ncycloalkyl, $R_{c5}R_{d5}$Nalkylcycloalkyl, $R_{c5}R_{d5}$Ncycloalkylalkyl, $R_{c5}R_{d5}$Nsulfinyl, $R_{e5}R_{f5}$Nalkyl($R_{c5}$)N—, $R_{e5}R_{f5}$Nalkyl($R_{c5}$)Ncarbonyl, $R_{e5}R_{f5}$Nalkyl($R_{e5}$)Ncarbonylalkenyl, $R_{e5}R_{f5}$Nalkylcarbonyl($R_{c5}$)N—, $R_{e5}R_{f5}$Nalkoxycarbonyl($R_{c5}$)N—, $R_{c5}R_{d5}$Nalkylsulfanyl, $R_{c5}R_{d5}$Nalkylsulfinyl, $R_{c5}R_{d5}$Nalkylsulfonyl, $R_{g5}R_{j5}$Nalkyl($R_{e5}$)Ncarbonyl ($R_{c5}$)N—; wherein the phenyl group, the phenyl group of phenylsulfonyl, the heteroaryl, the heterocycle, the heterocycle of heterocyclealkyl, the heterocycle of heterocyclealkenyl may be optionally substituted with 1, 2 or 3 substituents selected from the group consisting of alkoxy, alkyl, cyano, and nitro; and wherein $R_{c5}$, $R_{d5}$, $R_{e5}$, $R_{f5}$, $R_{g5}$ and $R_{j5}$ are each independently selected from the group consisting of hydrogen, alkoxyalkyl, alkyl, alkylcarbonyl, aminoalkyl, cycloalkyl, (cycloalkyl)alkyl, heterocycle and phenyl; and $R^6$ is selected from the group consisting of hydrogen, alkyl, alkylsulfanylalkyl, aryl, and arylalkyl.

2. A pharmaceutical composition comprising a compound of claim 1 or a therapeutically acceptable salt thereof in combination with a therapeutically acceptable carrier.

3. A compound of claim 1 selected from the group consisting of 5-ethyl-2-[(phenylsulfonyl)amino]benzoic acid, 5-isopropyl-2-[(phenylsulfonyl)amino]benzoic acid, 5-isobutyl-2-[(phenylsulfonyl)amino]benzoic acid,
2-[(phenylsulfonyl)amino]-5-propylbenzoic acid,
5-cyclopentyl-2-[(phenylsulfonyl)amino]benzoic acid,
5-cyclohexyl-2-[(phenylsulfonyl)arnino]benzoic acid,
5-butyl-2-[(phenylsulfonyl)amino]benzoic acid,
5-(3-methylbutyl)-2-[(phenylsulfonyl)amino]benzoic acid,
5-(2-methylbutyl)-2-[(phenylsulfonyl)amino]benzoic acid,
5-pentyl-2-[(phenylsulfonyl)amino]benzoic acid,
5-(2-ethylbutyl)-2-[(phenylsulfonyl)amino]benzoic acid,
5-hexyl-2-[(phenylsulfonyl)amino]benzoic acid,
5-ethyl-2-{[(3-methylphenyl)sulfonyl]amino}benzoic acid,
5-ethyl-2-{[(3-fluorophenyl)sulfonyl]amino}benzoic acid,
2-{[(2-chlorophenyl)sulfonyl]amino}-5-ethylbenzoic acid,
2-{[(3,4-difluorophenyl)sulfonyl]amino}-5-ethylbenzoic acid,
5-ethyl-2-({[3-(trifluoromethyl)phenyl]sulfonyl}amino) benzoic acid,
5-ethyl-2-{[(4-methylphenyl)sulfonyl]amino}benzoic acid,
2-{[(3-cyanophenyl)sulfonyl]amino}-5-ethylbenzoic acid,
2-{[(4-cyanophenyl)sulfonyl]amino}-5-ethylbenzoic acid,
2-{[(2,5-dimethylphenyl)sulfonyl]amino}-5-ethylbenzoic acid,
5-ethyl-2-{[(3-methoxyphenyl)sulfonyl]amino}benzoic acid,
2-{[(2,5-dimethoxyphenyl)sulfonyl]amino}-5-ethylbenzoic acid,
5-ethyl-2-({[2-(methylsulfonyl)phenyl]sulfonyl}amino) benzoic acid,
5-ethyl-2-({[2-(trifluoromethoxy)phenyl]sulfonyl}amino)benzoic acid and
2-({[3,5-bis(trifluoromethyl)phenyl]sulfonyl}amino)-5-ethylbenzoic acid.

* * * * *

UNITED STATES PATENT AND TRADEMARK OFFICE

CERTIFICATE OF CORRECTION

PATENT NO. : 7,491,718 B2
APPLICATION NO. : 10/681784
DATED : February 17, 2009
INVENTOR(S) : Comess et al.

It is certified that error appears in the above-identified patent and that said Letters Patent is hereby corrected as shown below:

Column 232, line 14, in claim 1, delete "($R_{c4}$)" and insert -- ($R_{e4}$) --.

Column 233, line 4, in claim 3, delete "arnino]" and insert -- amino] --.

Column 233, line 6, in claim 3, delete "(phenylsulfonyl )" and insert -- (phenylsulfonyl) --.

Column 233, line 20, in claim 3, delete "2-( {" and insert -- 2-({ --.

Column 233, line 20, in claim 3, delete "sulfonyl }" and insert -- sulfonyl} --.

Column 234, line 1, in claim 3, delete "amino }" and insert -- amino} --.

Column 234, line 14, in claim 3, delete "sulfonyl }" and insert -- sulfonyl} --.

Column 234, lines 16-17, in claim 3, delete "sulfonyl }" and insert -- sulfonyl} --.

Signed and Sealed this

Eleventh Day of May, 2010

David J. Kappos
*Director of the United States Patent and Trademark Office*